United States Patent
Igawa et al.

(10) Patent No.: US 11,912,989 B2
(45) Date of Patent: Feb. 27, 2024

(54) ANTIGEN-BINDING MOLECULES, THE ANTIGEN-BINDING ACTIVITY OF WHICH VARIES ACCORDING TO THE CONCENTRATION OF COMPOUNDS, AND LIBRARIES OF SAID MOLECULES

(71) Applicant: CHUGAI SEIYAKU KABUSHIKI KAISHA, Tokyo (JP)

(72) Inventors: Tomoyuki Igawa, Shizuoka (JP); Shigero Tamba, Shizuoka (JP); Shun Shimizu, Shizuoka (JP); Kanako Tatsumi, Shizuoka (JP); Shojiro Kadono, Kanagawa (JP); Hiroki Kawauchi, Kanagawa (JP); Kazuhiro Ohara, Kanagawa (JP); Masayuki Matsushita, Kanagawa (JP); Takashi Emura, Shizuoka (JP); Masaki Kamimura, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 231 days.

(21) Appl. No.: 17/182,331

(22) Filed: Feb. 23, 2021

(65) Prior Publication Data
US 2021/0180049 A1    Jun. 17, 2021

Related U.S. Application Data

(62) Division of application No. 15/100,934, filed as application No. PCT/JP2014/082060 on Dec. 4, 2014, now Pat. No. 10,961,530.

(30) Foreign Application Priority Data

Dec. 4, 2013   (JP) .............................. JP2013-251537

(51) Int. Cl.
*C40B 40/10*     (2006.01)
*C12N 15/10*     (2006.01)
(Continued)

(52) U.S. Cl.
CPC .......... *C12N 15/1093* (2013.01); *C07K 16/00* (2013.01); *C07K 16/005* (2013.01);
(Continued)

(58) Field of Classification Search
None
See application file for complete search history.

(56) References Cited

U.S. PATENT DOCUMENTS

| 5,998,588 A | 12/1999 | Hoffman et al. |
| 10,961,530 B2 | 3/2021 | Igawa et al. |

(Continued)

FOREIGN PATENT DOCUMENTS

| CA | 2850041 | 4/2013 |
| CA | 2850322 | 4/2013 |

(Continued)

OTHER PUBLICATIONS

U.S. Appl. No. 17/266,024, Igawa et al., filed Feb. 4, 2021.
(Continued)

*Primary Examiner* — Christian C Boesen
(74) *Attorney, Agent, or Firm* — Fish & Richardson P.C.

(57) ABSTRACT

An objective of the present invention is to provide target tissue-specific antigen-binding molecules, antigen-binding molecules whose antigen-binding activity varies depending on the concentration of an unnatural compound, libraries comprising a plurality of the antigen-binding molecules which are different from one another, pharmaceutical compositions comprising the antigen-binding molecules, methods of screening for the antigen-binding molecules, and methods for producing the antigen-binding molecules. The
(Continued)

Absence of the small-molecule switch
unable to bind to the antigen

+ Small-molecule switch

Presence of the small-molecule switch
binds to the antigen present inventors created antigen-binding domains whose antigen-binding activity varies depending on the concentration of a small molecule compound or antigen-binding molecules containing an antigen-binding domain, and libraries comprising a plurality of the antigen-binding domains which are different from one another or antigen-binding domains, and demonstrated that the above-noted objective could be achieved by using the libraries. Various diseases originating from target tissues can be treated in a target tissue-specific manner by using the antigen-binding molecules of the present invention.

14 Claims, 49 Drawing Sheets

Specification includes a Sequence Listing.

(51) Int. Cl.
  *C07K 16/28* (2006.01)
  *C07K 16/24* (2006.01)
  *C07K 16/00* (2006.01)
  *C07K 16/42* (2006.01)
  *C07K 16/44* (2006.01)
  *C40B 50/06* (2006.01)
  *C07K 16/30* (2006.01)

(52) U.S. Cl.
  CPC ........ *C07K 16/248* (2013.01); *C07K 16/2809* (2013.01); *C07K 16/2863* (2013.01); *C07K 16/2866* (2013.01); *C07K 16/30* (2013.01); *C07K 16/4283* (2013.01); *C07K 16/44* (2013.01); *C40B 50/06* (2013.01); *C07K 2317/21* (2013.01); *C07K 2317/24* (2013.01); *C07K 2317/31* (2013.01); *C07K 2317/55* (2013.01); *C07K 2317/92* (2013.01)

(56) References Cited

U.S. PATENT DOCUMENTS

| | | | |
|---|---|---|---|
| 11,673,947 | B2 | 6/2023 | Igawa et al. |
| 2004/0241759 | A1 | 12/2004 | Tozer et al. |
| 2006/0141456 | A1 | 6/2006 | Edwards et al. |
| 2007/0009523 | A1 | 1/2007 | Presta |
| 2008/0292637 | A1 | 11/2008 | Fishman |
| 2009/0155255 | A1 | 6/2009 | Glaser et al. |
| 2010/0158909 | A1 | 6/2010 | McDonagh et al. |
| 2010/0172868 | A1 | 7/2010 | Morrison et al. |
| 2010/0183621 | A1 | 7/2010 | Jure-Kunkel et al. |
| 2010/0216159 | A1 | 8/2010 | Dulgar-Tulloch et al. |
| 2011/0076284 | A1 | 3/2011 | Corbin et al. |
| 2011/0111406 | A1 | 5/2011 | Igawa et al. |
| 2011/0229489 | A1 | 9/2011 | Pons et al. |
| 2011/0236372 | A1 | 9/2011 | Villa et al. |
| 2011/0245108 | A1 | 10/2011 | Crea et al. |
| 2011/0305714 | A1 | 12/2011 | Stavenhagen et al. |
| 2012/0237498 | A1 | 9/2012 | Ahrens et al. |
| 2013/0203609 | A1 | 8/2013 | Horn |
| 2014/0255398 | A1 | 9/2014 | Igawa et al. |
| 2014/0271617 | A1 | 9/2014 | Igawa et al. |
| 2015/0166654 | A1 | 6/2015 | Igawa et al. |
| 2016/0304862 | A1 | 10/2016 | Igawa et al. |
| 2019/0359704 | A1 | 11/2019 | Igawa et al. |
| 2021/0324099 | A1 | 10/2021 | Igawa et al. |
| 2022/0153875 | A1 | 5/2022 | Mizuno et al. |
| 2023/0020377 | A1 | 1/2023 | Katada et al. |

FOREIGN PATENT DOCUMENTS

| | | |
|---|---|---|
| CN | 101098890 | 1/2008 |
| CN | 102405278 | 4/2012 |
| CN | 104487457 | 4/2015 |
| EP | 2 275 443 A | 1/2011 |
| EP | 2 305 710 A | 4/2011 |
| EP | 2 409 990 A | 1/2012 |
| EP | 2 552 955 A | 2/2013 |
| EP | 2 679 681 A | 1/2014 |
| EP | 2 762 564 A | 8/2014 |
| EP | 2 857 420 A | 4/2015 |
| EP | 3 156 072 A | 4/2017 |
| JP | 2007-531724 | 11/2007 |
| JP | 2007-532139 | 11/2007 |
| JP | 2010-110330 | 5/2010 |
| JP | 2011-097869 | 5/2011 |
| JP | 2011-137838 | 7/2011 |
| JP | 2011-184418 | 9/2011 |
| JP | 2012-518613 | 8/2012 |
| JP | 2013-521772 | 6/2013 |
| JP | 2018-517674 | 7/2018 |
| JP | 2018-537473 | 12/2018 |
| TW | 2014/00503 | 1/2014 |
| WO | WO 01/48480 | 7/2001 |
| WO | WO 02/081646 | 10/2002 |
| WO | WO 03/105757 | 12/2003 |
| WO | WO 2005/096706 | 10/2005 |
| WO | WO 2005/115452 | 12/2005 |
| WO | WO 2006/020114 | 2/2006 |
| WO | WO 2006/053301 | 5/2006 |
| WO | WO 2007/053718 | 5/2007 |
| WO | WO 2008/092117 | 7/2008 |
| WO | WO 2009/015284 | 1/2009 |
| WO | WO 2009/086320 | 7/2009 |
| WO | WO 2009/097017 | 8/2009 |
| WO | WO 2009/125825 | 10/2009 |
| WO | WO 2010/081173 | 7/2010 |
| WO | WO 2010/094698 | 8/2010 |
| WO | WO 2010/104821 | 9/2010 |
| WO | WO 2010/107109 | 9/2010 |
| WO | WO 2010/107110 | 9/2010 |
| WO | WO 2010/127284 | 11/2010 |
| WO | WO 2011/038302 | 3/2011 |
| WO | WO 2011/111007 | 9/2011 |
| WO | WO 2011/122011 | 10/2011 |
| WO | WO 2012/033953 | 3/2012 |
| WO | WO 2012/044831 | 4/2012 |
| WO | WO 2013/046722 | 4/2013 |
| WO | WO 2013/047729 | 4/2013 |
| WO | WO 2013/180200 | 12/2013 |
| WO | WO 2013/190127 | 12/2013 |
| WO | WO 2014/030750 | 2/2014 |
| WO | WO 2014/163101 | 10/2014 |
| WO | WO 2015/083764 | 6/2015 |
| WO | WO 2015/190538 | 12/2015 |
| WO | WO 2016/170176 | 10/2016 |
| WO | WO 2016/194992 | 12/2016 |
| WO | WO 2017/046994 | 3/2017 |
| WO | WO 2017/096165 | 6/2017 |
| WO | WO 2017/104783 | 6/2017 |
| WO | WO 2020/032230 | 2/2020 |
| WO | WO 2020/189748 | 9/2020 |
| WO | WO 2021/131021 | 7/2021 |
| WO | WO 2021/162020 | 8/2021 |
| WO | WO 2022/270611 | 12/2022 |
| WO | WO 2022/270612 | 12/2022 |

OTHER PUBLICATIONS

U.S. Appl. No. 17/438,993, Mizuno et a., filed Sep. 14, 2021.
Enomoto et al., "Development of high-throughput spermidine synthase activity assay using homogeneous time-resolved fluorescence," Anal Biochem, Apr. 15, 2006, 351(2):229-240.
Limm et al., "The metabolite 5'-methylthioadenosine signals through the adenosine receptor A2B in melanoma," Eur J Cancer, Oct. 2014, 50(15):2714-2724.
Stevens et al., "Quantitative analysis of 5'-deoxy-5'methylthioadenosine in melanoma cells by liquid chromatography-stable isotope ratio tandem mass spectrometry," J Chromatogr B Analyt Technol Biomed Life Sci, Dec. 1, 2008, 876(1):123-128.
U.S. Appl. No. 14/402,574, Igawa et al., filed Nov. 20, 2014.
U.S. Appl. No. 15/100,934, Igawa et al., filed Jun. 1, 2016.

(56) References Cited

OTHER PUBLICATIONS

U.S. Appl. No. 18/138,888, Igawa et al., filed Apr. 25, 2023.
U.S. Appl. No. 16/539,765, filed Aug. 13, 2019, Igawa et al.
Alley et al., "Antibody-drug conjugates: targeted drug delivery for cancer," Curr Opin Chem Biol, Aug. 2010, 14(4):529-537. doi: 10.1016/j.cbpa.2010.06.170. Epub Jul. 17, 2010.
Ascierto et al., "Clinical Experiences With Anti-CD 137 and Anti-PD1 Therapeutic Antibodies," Semin Oncol, Oct. 2010, 37(5):508-516. doi: 10.1053/j.seminoncol. Sep. 8, 2010.
Baeuerle et al., "BiTE: Teaching antibodies to engage T-cells for cancer therapy," Curr Opin Mol Ther, Feb. 2009, 11(1):22-30.
Carreno et al., "2E8 binds to the high affinity I-domain in a metal ion-dependent manner: a second generation monoclonal antibody selectively targeting activated LFA-1," J Biol Chem, Oct. 22, 2010, 285(43):32860-32868. doi: 10.1074/jbc.M110.111591. Epub Aug. 19, 2010.
Chen et al., "Kynurenine Pathway Metabolites in Humans: Disease and Healthy States," Int J Tryptophan Res, Jan. 8, 2009, 2:1-19. Epub Jan. 8, 2009.
Chockalingam et al., "Design and application of stimulus-responsive peptide systems," Protein Eng Des Sel, Apr. 2007, 20(4):155-161. Epub Mar. 21, 2007.
Clayton et al., "Cancer Exosomes Express CD39 and CD73, Which Suppress T Cells through Adenosine Production," J Immunol, Jul. 15, 2011, 187(2):676-683. doi:10.4049/jimmunol.1003884.
Dall'Acqua et al., "Increasing the affinity of a human IgG1 for the neonatal Fc receptor: biological consequences," J Immunol, Nov. 1, 2002, 169(9):5171-5180.
Dall'Acqua et al., "Properties of human IgG1s engineered for enhanced binding to the neonatal Fc receptor (FcRn)," J Biol Chem, Aug. 18, 2006, 281(33):23514-23524. Epub Jun. 21, 2006.
De Bono et al., "ING-1, a monoclonal antibody targeting Ep-CAM in patients with advanced adenocarcinomas," Clin Cancer Res, Nov. 15, 2004, 10(22):7555-6575.
Desjarlais et al., "Optimizing engagement of the immune system by anti-tumor antibodies: an engineer's perspective," Drug Discov Today, Nov. 2007, 12(21-22):898-910. Epub Oct. 22, 2007.
Diamond et al., "Somatic mutation of the T15 heavy chain gives rise to an antibody with autoantibody specificity," Proc Natl Acad Sci USA, Sep. 1984, 81(18):5841-5844.
Dubrot et al., "Treatment with anti-CD137 mAbs causes intense accumulations of liver T cells without selective antitumor immunotherapeutic effects in this organ," Cancer Immunol Immunother, Aug. 2010, 59(8):1223-1233. doi: 10. 1007/s00262-010-0846-9. Epub Mar. 25, 2010.
Fanning et al., "A combinatorial approach to engineering a dual-specific metal switch antibody," Biochemistry, Jun. 14, 2011, 50(23):5093-5095. doi: 10.1021/bi2003845. Epub May 18, 2011.
Fanning et al., "Structural basis of an engineered dual-specific antibody: conformational diversity leads to a hypervariable loop metal-binding site," Protein Eng Des Sel, Oct. 2014, 27(10):391-397.
Finkelstein et al., Protein physics: Lecture course with colored and stereoscope illustrations and tasks: study guide, 2012, p. 23 (with English translation).
Forster et al., "Programming peptidomimetic syntheses by translating genetic codes designed de novo," Proc Natl Acad Sci USA, May 27, 2003, 100(11):6353-6357. Epub May 16, 2003.
Hamid et al., "Anti-programmed death-1 and anti-programmed death-ligand 1 antibodies in cancer therapy," Expert Opin Biol Ther, Jun. 2013, 13(6):847-861. doi:10.1517/14712598.2013.770836. Epub Feb. 19, 2013.
Hanahan et al., "Hallmarks of Cancer: The Next Generation," Cell, Mar. 4, 2011, 144(5):646-674. doi: 10.1016/j.oell.2011.02.013.
Hardie et al., "Isolation of Specific Antibody Under Conditions of Low Ionic Strength," J Immunol Methods, May 1977, 15(4):305-314.
Hasemann et al., "Mutational Analysis of Arsonate Binding by a $CRI_{A+}$ Antibody-$V_H$ and $V_L$ Junctional Diversity are Essential for Binding Activity," J Biol Chem, Apr. 25, 1991, 266(12):7626-7632.
Hogenesch et al., "Challenges in pre-clinical testing of anti-cancer drugs in cell culture and in animal models," J Control Release, Dec. 10, 2012, 164(2):183-186.
Houot et al., "Therapeutic effect of CD137 immunomodulation in lymphoma and its enhancement by $T_{reg}$ depletion," Blood, Oct. 15, 2009, 114(16):3431-3438. doi: 10.1182/blood-2009-05-223958. Epub Jul. 29, 2009.
Hu et al., "Combinatorial libraries against libraries for selecting neoepitope activation-specific antibodies," Proc Natl Acad Sci USA, Apr. 2010, 107(14):6252-6257.
Igawa et al., "Antibody recycling by engineered pH-dependent antigen binding improves the duration of antigen neutralization," Nat Biotechnol, Nov. 2010, 28(11):1203-1207. doi: 10.1038/nbt. 1691. Epub Oct. 17, 2010.
Juszczak et al., "Ipilimumab: a novel immunomodulating therapy causing autoimmune hypophysitis: a case report and review," Eur J Endocrinol, Jul. 2012, 167(1):1-5. doi: 10.1530/EJE-12-0167. Epub Apr. 10, 2012.
Kim et al., "Antibody Engineering for the Development of Therapeutic Antibodies," Mol Cells, Aug. 31, 2005, 20(1):17-29.
Kunkel et al., "Rapid and efficient site-specific mutagenesis without phenotypic selection," Proc Natl Acad Sci USA, Jan. 1985, 82(2):488-492.
Lewis et al., "Differential responses of human tumor cell lines to anti-p185HER2 monoclonal antibodies," Cancer Immunol Immunother, Sep. 1993, 37(4):255-263.
Li et al., "Antitumor activities of agnostic anti-TNFR antibodies require differential FcγRIIB coengagement in vivo," Proc Natl Acad Sci USA, Nov. 26, 2013, 110(48):19501-19506. doi: 10.1073/pnas.1319502110. Epub Nov. 11, 2013.
Lowder et al., "Monoclonal Antibodies-Therapeutic and Diagnostic Uses in Malignancy," West J Med, Dec. 1985, 143(6):810-818.
Lukashev et al., "Hypoxia-dependent anti-inflammatory pathways in protection of cancerous tissues," Cancer Metastasis Rev, Apr. 3, 2007, 2026:273-279.
Lutterbuese et al., "T cell-engaging BiTE antibodies specific for EGFR potently eliminate KRAS- and BRAF-mutated colorectal cancer cells," Proc Natl Acad Sci USA, Jul. 13, 2010, 107(28):12605-12610. doi: 10.1073/pnas.1000976107. Epub Jun. 28, 2010.
Luttrell et al., "Reaction Coupling of Chelation and Antigen Binding in the Calcium Ion-dependent Antibody Binding of Cyclic AMP," J Biol Chem, Nov. 15, 1991, 266(32):21626-21630.
Maurer et al., "Antigenicity of polypeptides (PolyαAmino acids): Calcium-Dependent and Independent Antibodies," J Immunol, Sep. 1970, 105(3):567-573.
Mimoto et al., "Engineered antibody Fc variant with selectively enhanced FcγRIIb binding over both FcγRIIaR$^{131}$ and FcγRIIaH$^{131}$," Protein Eng Des Sel, Jun. 5, 2013, 26(10):589-598. doi: 10.1093/protein/gzt022.
Misawa et al., "Rapid and High-Sensitivity Cell-Based Assays of Protein-Protein Interactions Using Split Click Beetle Luciferase Complementation: An Approach to the Study of G-Protein-Coupled Receptors," Anal Chem, Mar. 15, 2010, 82(6):2552-2560. doi: 10.1021/ac100104Q.
Nam et al., "Current evidence for the management of rheumatoid arthritis with biological disease-modifying antirheumatic drugs: a systematic literature review informing the EULAR recommendations for the management of RA," Ann Rheum Dis, Jun. 2010, 69(6):976-986. doi: 10.1136/ard.2009.126573. Epub May 6, 2010.
Ohno et al., "Antigen-binding specificities of antibodies are primarily determined by seven residues of VH," Proc Natl Acad Sci USA, May 1985, 82(9):2945-2949.
Pace et al., "How to measure and predict the molar absorption coefficient of a protein," Protein Sci, Nov. 1995, 4(11):2411-2423.
Paul, Chapter 12 "Antigen-Antibody Interactions and Monoclonal Antibodies," Fundamental Immunology, Third Edition, 1984, pp. 421-424.
Paul, Chapter 12 "Antigen-Antibody Interactions and Monoclonal Antibodies," Fundamental Immunology, M.: Mir, 1987-1989, vol. 3, pp. 6-10 (with the corresponding pages from an English version of Fundamental Immunology).
Pavlou et al., "The therapeutic antibodies market to 2008," Eur J Pharm Biopharm, Apr. 2005, 59:389-396.

(56) References Cited

OTHER PUBLICATIONS

Pedroza et al., "Interleukin-6 Contributes to Inflammation and Remodeling in a Model of Adenosine Mediated Lung Injury," PLoS One, Jul. 2011, 6(7):e22667, pp. 1-13.
Petkova et al., "Enhanced half-life of genetically engineered human IgG1 antibodies in a humanized FcRn mouse model: potential application in humorally mediated autoimmune disease," Int Immunol, Dec. 2006, 18(12):1759-1769. Epub Oct. 31, 2006.
Prieto et al., "CTLA-4 Blockade with Ipilimumab: Long-term Follow-up of 177 Patients with Metastatic Melanoma," Clin Cancer Res, Apr. 1, 2012, 18(7):2039-2047. doi: 10.1158/1078-0432.CCR-11-1823. Epub Jan. 23, 2012.
Reichert et al., "Monoclonal antibody successes in the clinic," Nat. Biotechnol, Sep. 2005, 23(9):1073-1078.
Reverberi et al., "Factors affecting the antigen-antibody reaction," Blood Transfus, Nov. 2007, 5(4):227-240. doi: 10.2450/2007.0047-07.
Richard et al., "Adenosine upregulates CXCR4 and enhances the proliferative and migratory responses of human carcinoma cells to CXCL12/SDF-1α," Jul. 5, 2006, Int J Cancer, 119:2044-2053.
Riechelmann et al., "Phase I trial with the CD44v6-targeting immunoconjugate bivatuzumab mertansine in head and neck squamous cell carcinoma," Oral Oncol, Sep. 2008, 44(9):823-829. doi: 10.1016/j.oraloncology.2007.10.009. Epub Jan. 18, 2008.
Roitt et al., Immunology, M:Mir, 2000, p. 110 (with English translation).
Roopenian et al., "FcRn: the neonatal Fc receptor comes of age," Nat Rev Immunol, Sep. 2007, 7(9):715-725. Epub Aug. 17, 2007.
Rudikoff et al., "Single amino acid substitution altering antigen-binding specificity," Proc Natl Acad Sci USA, Mar. 1982, 79(6):1979-1983.
Satoh et al., "Non-fucosylated therapeutic antibodies as next-generation therapeutic antibodies," Expert Opin Biol Ther, Nov. 2006, 6(11):1161-1173.
Schabowsky et al., "A Novel Form of 4-1BBL Has Better Immunomodulatory Activity than an Agonistic Anti-4-1BB Ab without A Associated Severe Toxicity," Vaccine, Dec. 11, 2009, 28(2):512-522. doi: 10.1016/j.vaccine.2009.09.127. Epub Oct. 29, 2009.
Shields et al., "High resolution mapping of the binding site on human IgG11 for Fc gamma RI, Fc gamma RII, Fc gamma RIII, and FcRn and design of IgG1 variants with improved binding to the Fc gamma R," J Biol Chem, Mar. 2, 2001, 276(9):6591-6604. Epub Nov. 28, 2000.
Stepanov, Chapter 6.12 "About a relationship between primary and spatial structures of the protein," Molecular biology. Structure and Functions of Proteins, M:Nauka, 2005, pp. 144-146 (with English translation).
Summers et al., "Fine-tuning of dendritic cell biology by the TNF superfamily," Nat Rev Immunol, Apr. 10, 2012, 12(5):339-351. doi: 10.1038/nri3193.
Suzuki, Nibs Letter, Research and Development of Antibody Pharmaceuticals, 2010, 56(4):45-51 (with English translation).
Takeuchi et al., "The Japanese experience with biologic therapies for rheumatoid arthritis," Nat Rev Rheumatol, Nov. 2010, 6(11):644-652. doi: 10.1038/nrrheum.2010.154. Epub Sep. 28, 2010.
Tang et al., "Immunotherapy and tumor microenvironment," Cancer Letters, Jan. 1, 2016, 370:85-90.
Trinh et al., "Ipilimumab in the treatment of melanoma," Expert Opin Biol Ther, Jun. 2012, 12(6):773-782. doi: 10.1517/14712598.2012.675325. Epub Apr. 14, 2012.
Vaccaro et al., "Engineering the Fc region of immunoglobulin G to modulate in vivo antibody levels," Nat Biotechnol, Oct. 2005, 23(10):1283-1288. Epub Sep. 25, 2005.
Vengelen-Tyler et al., "Two Examples of Antibodies Dependent upon the Presence of Inosine," Transfusion, May-Jun. 1981, 21(2):315-319.
Vinay et al., "4-1BB signaling beyond T cells," Cell Mol Immunol, Jul. 2011, 8(4):281-284. doi: 10.1038/cmi.2010.82.Epub Jan. 10, 2011.
Wang et al., "Expanding the Genetic Code," Annu Rev Biophys Biomol Struct, Jun. 2006, 35:225-249.
Weiner et al., "Monoclonal antibodies: versatile platforms for cancer immunotherapy," Nat Rev Immunol, May 2010, 10(5):317-327. doi: 10.1038/nri2744.
Yarilin, Fundamentals of Immunology, M:Medicina, 1999, pp. 172-174 (with English translation).
Zalevsky et al., "Enhanced antibody half-life improves in vivo activity," Nat Biotechnol, Feb. 2010, 28(2):157-159. doi: 10.1038/nbt.1601. Epub Jan. 17, 2010.
USPTO Restriction Requirement in U.S. Appl. No. 14/402,574, dated Feb. 11, 2016, 10 pages.
Fish & Richardson P.C., Response to Restriction Requirement in U.S. Appl. No. 14/402,574 dated Feb. 11, 2016, filed Apr. 11, 2016, 1 page.
USPTO Office Action in U.S. Appl. No. 14/402,574, dated May 6, 2016, 31 pages.
Fish & Richardson P.C., Response to Office Action in U.S. Appl. No. 14/402,574 dated May 6, 2016, filed Oct. 6, 2016, 35 pages.
USPTO Final Office Action in U.S. Appl. No. 14/402,574, dated Oct. 31, 2016, 16 pages.
Fish & Richardson P.C., Response to Office Action in U.S. Appl. No. 14/402,574 dated Oct. 31, 2016, filed Jan. 30, 2017, 31 pages.
USPTO Advisory Action in U.S. Appl. No. 14/402,574, dated Feb. 16, 2017, 3 pages.
USPTO Office Action in U.S. Appl. No. 14/402,574, dated Jan. 16, 2018, 24 pages.
USPTO Applicant-Initiated Interview Summary in U.S. Appl. No. 14/402,574, dated, May 4, 2018, 27 pages.
USPTO Final Office Action in U.S. Appl. No. 14/402,574, dated Jul. 16, 2018, 10 pages.
International Search Report for App. Ser. No. PCT/JP2013/064975, dated Aug. 6, 2013, 3 pages.
International Preliminary Report on Patentability for App. Ser. No. PCT/JP2013/064975, dated Dec. 2, 2014, 6 pages.
International Search Report for App. Ser. No. PCT/JP2014/082060, dated Mar. 10, 2015, 2 pages.
International Preliminary Report on Patentability for App. Ser. No. PCT/JP2014/082060, dated Jun. 7, 2016, 7 pages.
U.S. Appl. No. 17/788,998, Katada et al., filed Jun. 24, 2022.
U.S. Appl. No. 17/798,686, Sakurai et al., filed Aug. 10, 2022.
USPTO Non-Final Office Action in U.S. Appl. No. 16/539,765, dated Nov. 18, 2021, 31 pages.
USPTO Final Office Action in U.S. Appl. No. 16/539,765, dated Jul. 12, 2022, 16 pages.
U.S. Appl. No. 17/848,983, Katada et al., filed Jun. 24, 2022.
USPTO Restriction Requirement in U.S. Appl. No. 15/100,934, dated Apr. 20, 2018, 15 pages.
USPTO Non-Final Office Action in U.S. Appl. No. 15/100,934, dated Nov. 2, 2018, 20 pages.
USPTO Final Office Action in U.S. Appl. No. 15/100,934, dated Aug. 2, 2019, 21 pages.
USPTO Non-Final Office Action in U.S. Appl. No. 15/100,934, dated Apr. 2, 2020, 7 pages.
USPTO Notice of Allowance in U.S. Appl. No. 15/100,934, dated Nov. 19, 2020, 9 pages.
USPTO Supplemental Notice of Allowability in U.S. Appl. No. 15/100,934, dated Dec. 24, 2020, 5 pages.
Binyamin et al., "Probing ATP-dependent conformational changes in the multidrug resistance protein 1 (MRP1/ABCC1) in live tumor cells with a novel recombinant single-chain Fv antibody targeted to the extracellular N-terminus," Int J Cancer, Sep. 20, 2005, 116(5):703-709.
Fish & Richardson P.C., Reply to Restriction Requirement in U.S. Appl. No. 15/100,934, filed Oct. 12, 2018, 1 page.
Fish & Richardson P.C., Reply to Action dated Nov. 2, 2018 in U.S. Appl. No. 15/100,934, filed Apr. 26, 2019, 6 pages.
Fish & Richardson P.C., Amendment in Reply to Final Action in U.S. Appl. No. 15/100,934, filed Jan. 31, 2020, 13 pages.
Fish & Richardson P.C., Amendment and Reply of Action dated Apr. 2, 2020 in U.S. Appl. No. 15/100,934, filed Aug. 27, 2020, 9 pages.

ANTIGEN-BINDING MOLECULES, THE ANTIGEN-BINDING ACTIVITY OF WHICH VARIES ACCORDING TO THE CONCENTRATION OF COMPOUNDS, AND LIBRARIES OF SAID MOLECULES

CROSS-REFERENCE TO RELATED APPLICATIONS

This application is a divisional of U.S. application Ser. No. 15/100,934, filed on Jun. 1, 2016, which is the National Stage of International Application No. PCT/JP2014/082060, filed on Dec. 4, 2014, which claims the benefit of Japanese Application No. 2013-251537, filed on Dec. 4, 2013.

TECHNICAL FIELD

The present invention relates to libraries of antigen-binding domains or antigen-binding molecules comprising an antigen-binding domain, of which antigen-binding activity varies depending on the concentration of a small molecule compound. The present invention also relates to antigen-binding domains or antigen-binding molecules comprising an antigen-binding domain, of which antigen-binding activity varies depending on the concentration of an unnatural compound, production methods and screening methods for the antigen-binding molecules, and pharmaceutical compositions comprising the antigen-binding molecules.

BACKGROUND ART

Antibodies are drawing attention as pharmaceuticals as they are highly stable in plasma and have few side effects. In particular, a number of IgG-type antibody pharmaceuticals are available on the market, and many antibody pharmaceuticals are currently under development (Non-Patent Documents 1 and 2).

As cancer therapeutic agents using antibody pharmaceuticals, Rituxan against a CD20 antigen, cetuximab against an EGFR antigen, herceptin against a HER2 antigen, and such have been approved so far (Non-Patent Document 3). These antibody molecules bind to antigens expressed on cancer cells, and exhibit cytotoxic activity against cancer cells by ADCC and such. Such cytotoxic activity by ADCC and etc. are known to depend on the number of antigens expressed on cells targeted by the therapeutic antibodies (Non-Patent Document 4); therefore, high expression level of the target antigen is preferable from the stand point of the effects of the therapeutic antibodies. However, even if the antigen expression level is high, when antigens are expressed in normal tissues, cytotoxic activity mediated by ADCC etc. will be exerted against normal cells, and therefore side-effects will become a major problem. Therefore, antigens targeted by therapeutic antibodies used as therapeutic agents for cancer are preferably antigens specifically expressed in cancer cells. For example, antibody molecules against the EpCAM antigen which is known as a cancer antigen have been considered to be promising as therapeutic agents for cancer. However, the EpCAM antigen is known to be expressed in the pancreas as well, and in practice, administration of anti-EpCAM antibodies in clinical trials has been reported to cause pancreatitis as a side-effect due to cytotoxic activity towards the pancreas (Non-Patent Document 5).

Following the success of antibody pharmaceuticals that exert cytotoxic activity by ADCC activity, a second generation of improved antibody molecules that exert strong cytotoxic activity through enhancement of ADCC activity by removing fucose of N-type sugar chains in the native human IgG1 Fc region (Non-Patent Document 6), enhancement of ADCC activity by enhancing the binding toward FcγRIIIa by substitution of amino acids in the native human IgG1 Fc region (Non-Patent Document 7), and such have been reported. As antibody pharmaceuticals that exert cytotoxic activity against cancer cells through a mechanism other than the above-mentioned ADCC activity mediated by NK cells, improved antibody molecules that exert a stronger cytotoxic activity, such as an antibody-drug conjugate (ADC) in which an antibody is conjugated with a drug having potent cytotoxic activity (Non-Patent Document 8), and a low molecular weight antibody that exerts toxic activity against cancer cells by recruiting T cells to cancer cells (Non-Patent Document 9), have been reported as well.

Such antibody molecules exerting a stronger cytotoxic activity can exert cytotoxic activity against cancer cells that do not have much antigen expression, but on the other hand, they will exert similar cytotoxic activity against normal tissues with low antigen expression. In fact, in comparison to cetuximab which is a natural human IgG1 against an EGFR antigen, EGFR-BiTE, which is a bispecific antibody against CD3 and EGFR, can exert a potent cytotoxic activity against cancer cells by recruiting T cells to cancer cells and exert antitumor effects. On the other hand, since EGFR is expressed also in normal tissues, when EGFR-BiTE is administered to cynomolgus monkeys, serious side effects have appeared (Non-Patent Document 10). Furthermore, bivatuzumab mertansine, an ADC formed by linking mertansine to an antibody against CD44v6 which is highly expressed in cancer cells, has been shown to cause severe skin toxicity and liver toxicity in clinical practice because CD44v6 is expressed also in normal tissues (Non-Patent Document 11).

When antibodies that can exert a potent cytotoxic activity against cancer cells having low antigen expression are used as such, the target antigen needs to be expressed in a highly cancer-specific manner. However, since HER2 and EGFR, which are target antigens of herceptin and cetuximab, respectively, are also expressed in normal tissues, the number of cancer antigens expressed in a highly cancer-specific manner is thought to be limited. Therefore, while it is possible to strengthen the cytotoxic activity against cancer, the side effects occurring due to cytotoxic actions against normal tissues may become problematic.

Furthermore, recently, ipilimumab which enhances tumor immunity by inhibiting CTLA4 which contributes to immunosuppression in cancer was shown to prolong overall survival of metastatic melanoma (Non-Patent Document 12). However, since ipilimumab inhibits CTLA4 systemically, while tumor immunity is enhanced, the emergence of autoimmune disease-like severe side effects due to systemic activation of the immune system is becoming a problem (Non-Patent Document 13).

On the other hand, as antibody pharmaceuticals against diseases besides cancer, antibody pharmaceuticals that exert therapeutic effects by inhibiting inflammatory cytokines in inflammatory/autoimmune diseases are known (Non-Patent Document 14). For example, Remicade and Humira which target TNF, and Actemra which targets IL-6R exhibit high therapeutic effects against rheumatoid arthritis, but on the other hand, systemic neutralization of these cytokines has led to the observation of infection as side effects (Non-Patent Document 15).

Various techniques have been developed as techniques that can be applied to second-generation antibody pharmaceuticals. While techniques for improving effector functions, antigen-binding ability, pharmacokinetics, and stability, or techniques for reducing immunogenic risks have been reported (Non-Patent Document 16), there are hardly any reports on techniques that enable target tissue-specific action of antibody pharmaceuticals to overcome such side effects. For example, regarding lesions such as cancer tissues and inflammatory tissues, pH-dependent antibodies that make use of the acidic pH condition at these target tissues have been reported (Patent Documents 1 and 2). However, the decrease of pH (that is, increase in hydrogen ion concentration) in cancer tissues and inflammatory tissues as compared to normal tissues is slight, and since it is difficult to produce antibodies that act by detecting a slight increase in the concentration of hydrogen ions which have an extremely small molecular weight, and also because acidic pH conditions may be found in normal tissues such as osteoclastic bone resorption region or in tissues other than the lesion of interest, use of pH conditions as a lesion-specific environmental factor was considered to face many challenges. On the other hand, methods for producing antibodies that exert antigen-binding activity only after they are cleaved by a protease expressed at lesion sites such as cancer tissues and inflammatory tissues have been reported (Patent Document 3). However, since cleavage of antibodies by proteases is irreversible, when the antibodies that have been cleaved at the lesion site enter the blood stream and return to normal tissues, they can bind to the antigens in normal tissues as well, and this is considered to be a problem. Furthermore, cancer specificity of such proteases is also thought to have problems that need to be addressed. Therefore, techniques that enable reversible action at sites of inflammation or cancer (lesion sites) without systemic action in normal tissues and blood for exerting drug efficacy while avoiding side effects are not known. Further, methods for controlling antibody activities and pharmacological effects by non-invasive administrations of exogenous compounds are not known.

PRIOR ART DOCUMENTS

Patent Documents

[Patent document 1] WO 2003/105757
[Patent document 2] WO 2012/033953
[Patent document 3] WO 2010/081173

Non-Patent Documents

[Non-patent document 1] Monoclonal antibody successes in the clinic. Janice M Reichert, Clark J Rosensweig, Laura B Faden & Matthew C Dewitz, Nat. Biotechnol. (2005) 23, 1073-1078
[Non-patent document 2] The therapeutic antibodies market to 2008. Pavlou A K, Belsey M J., Eur. J. Pharm. Biopharm. (2005) 59 (3), 389-396
[Non-patent document 3] Monoclonal antibodies: versatile platforms for cancer immunotherapy. Weiner L M, Surana R, Wang S., Nat. Rev. Immunol. (2010) 10 (5), 317-327
[Non-patent document 4] Differential responses of human tumor cell lines to anti-p185HER2 monoclonal antibodies. Lewis G D, Figari I, Fendly B, Wong W L, Carter P, Gorman C, Shepard H M, Cancer Immunol. Immunotherapy (1993) 37, 255-263
[Non-patent document 5] ING-1, a monoclonal antibody targeting Ep-CAM in patients with advanced adenocarcinomas. de Bono J S, Tolcher A W, Forero A, Vanhove G F, Takimoto C, Bauer R J, Hammond L A, Patnaik A, White M L, Shen S, Khazaeli M B, Rowinsky E K, LoBuglio A F, Clin. Cancer Res. (2004) 10 (22), 7555-7565
[Non-patent document 6] Non-fucosylated therapeutic antibodies as next-generation therapeutic antibodies. Satoh M, Iida S, Shitara K., Expert Opin. Biol. Ther. (2006) 6 (11), 1161-1173
[Non-patent document 7] Optimizing engagement of the immune system by anti-tumor antibodies: an engineer's perspective. Desjarlais J R, Lazar G A, Zhukovsky E A, Chu S Y, Drug Discov. Today (2007) 12 (21-22), 898-910
[Non-patent document 8] Antibody-drug conjugates: targeted drug delivery for cancer. Alley S C, Okeley N M, Senter P D., Curr. Opin. Chem. Biol. (2010) 14 (4), 529-537
[Non-patent document 9] BiTE: Teaching antibodies to engage T-cells for cancer therapy. Baeuerle P A, Kufer P, Bargou R., Curr. Opin. Mol. Ther. (2009) 11 (1), 22-30
[Non-patent document 10] T cell-engaging BiTE antibodies specific for EGFR potently eliminate KRAS- and BRAF-mutated colorectal cancer cells. Lutterbuese R, Raum T, Kischel R, Hoffmann P, Mangold S, Rattel B, Friedrich M, Thomas O, Lorenczewski G, Rau D, Schaller E, Herrmann I, Wolf A, Urbig T, Baeuerle P A, Kufer P., Proc. Natl. Acad. Sci. U.S.A. (2010) 107 (28), 12605-12610
[Non-patent document 11] Phase I trial with the CD44v6-targeting immunoconjugate bivatuzumab mertansine in head and neck squamous cell carcinoma. Riechelmann H, Sauter A, Golze W, Hanft G, Schroen C, Hoermann K, Erhardt T, Gronau S., Oral Oncol. (2008) 44 (9), 823-829
[Non-patent document 12] Ipilimumab in the treatment of melanoma. Trinh V A, Hwu W J., Expert Opin. Biol. Ther., (2012) April 14 (doi:10.1517/14712598.2012.675325)
[Non-patent document 13] IPILIMUMAB—A NOVEL IMMUNOMODULATING THERAPY CAUSING AUTOIMMUNE HYPOPHYSITIS: A CASE REPORT AND REVIEW. Juszczak A, Gupta A, Karavitaki N, Middleton M R, Grossman A., Eur. J. Endocrinol. (2012) April 10 (doi: 10.1530/EJE-12-0167)
[Non-patent document 14] The Japanese experience with biologic therapies for rheumatoid arthritis. Takeuchi T, Kameda H., Nat. Rev. Rheumatol. (2010) 6 (11), 644-652
[Non-patent document 15] Current evidence for the management of rheumatoid arthritis with biological disease-modifying antirheumatic drugs: a systematic literature review informing the EULAR recommendations for the management of RA. Nam J L, Winthrop K L, van Vollenhoven R F, Pavelka K, Valesini G, Hensor E M, Worthy G, Landewe R, Smolen J S, Emery P, Buch M E I., Ann. Rheum. Dis. (2010) 69 (6), 976-986
[Non-patent document 16] Antibody engineering for the development of therapeutic antibodies. Kim S J, Park Y, Hong H J., Mol. Cells. (2005) 20 (1), 17-29

SUMMARY OF THE INVENTION

Problems to be Solved by the Invention

In view of the above-described background, if it is possible to obtain antibodies whose binding to a target antigen is regulated by the concentration of a small molecule produced or specifically present in a target tissue (hereinafter may be referred to as "small-molecule switch antibodies"), such antibodies will be very useful because they can act reversibly on lesions such as tumor sites and inflammatory sites, and side-effects can be avoided. Furthermore, if it is possible to obtain antibodies whose antigen binding is regulated by the concentration of an unnatural compound, such antibodies will be very useful since they can be controlled by the administration of an exogenous compound that activates antibody activities and pharmacological actions at the lesions, or an exogenous compound that can be administered non-invasively.

However, there are no reports that such antibodies have been obtained by conventional methods such as methods of immunizing non-human animals with antigens, or methods of using a library of human-derived or non-human animal-derived antibodies.

Therefore, there has been a strong desire to provide antibodies (small-molecule switch antibodies) whose binding to a discretionary target antigen is regulated by the concentration of a small molecule produced or specifically present in the target tissue or an unnatural compound, and methods for efficiently obtaining such antibodies in a short period of time.

Means for Solving the Problems

The present inventors conducted dedicated studies to achieve the above-described objectives. As a result, they generated antigen-binding molecules comprising an antigen-binding domain whose antigen-binding activity varies depending on the concentration of the target tissue-specific compound. Furthermore, the present inventors discovered that the antigen-binding molecules or pharmaceutical compositions comprising the antigen-binding molecules are useful for treating diseases that originate from a target tissue, and that they are also useful for treatment of diseases originating from target tissues that includes administering the antigen-binding molecules. They also discovered that the antigen-binding molecules are useful in the production of pharmaceuticals for treating diseases that originate from target tissues.

The present inventors also successfully produced a library comprising a plurality of antigen-binding molecules having different sequences from one another, wherein the molecules have an antigen-binding domain that comprises amino acid residues involved in binding with a small molecule that may cause the antigen-binding activity of the antigen-binding molecule to vary according to differences in the in vivo environmental factors or depending on administration of an unnatural compound. They also created methods for screening and producing the antigen-binding molecules using the library, and thereby completed the present invention.

The present invention is based on such findings, and specifically includes embodiments exemplified below.

Embodiment 1

A library that comprises mainly:
(i) a plurality of antigen-binding domains or antigen-binding molecules comprising an antigen-binding domain, which have different sequences from one another; or
(ii) nucleic acids that encode the plurality of antigen-binding domains or antigen-binding molecules comprising an antigen-binding domain, which have different sequences from one another;
wherein the aforementioned antigen-binding domains or antigen-binding molecules are antigen-binding domains or antigen-binding molecules comprising an antigen-binding domain whose antigen-binding activity varies depending on the concentration of a small molecule compound.

Embodiment 2

The library of Embodiment [1], which is produced by a method comprising the steps of:
(a) identifying amino acid sites that fulfill any one or more of (i) to (iii) below in antigen-binding domains whose antigen-binding activity varies depending on the concentration of a small molecule compound or in antigen-binding domains that have binding activity to a small molecule compound:
  (i) one or more amino acid sites that are not involved in the binding to the small molecule compound;
  (ii) one or more amino acid sites that show diversity of amino acid occurrence frequency in the antibody repertoire of the animal species to which the parent antigen-binding domain belongs; and
  (iii) one or more amino acid sites that are not important for canonical structure formation; and
(b) designing a library that comprises nucleic acids encoding unmodified antigen-binding domains/molecules, and nucleic acids that encode individually a plurality of variants of the aforementioned antigen-binding domains or antigen-binding molecules comprising an antigen-binding domain which have different sequences from one another and have modifications at one or more of the amino acid sites identified in step (a).

Embodiment 3

The library of Embodiment [2] which is produced by a method comprising the steps of:
(a) identifying amino acid sites that fulfill any one or more of (i) to (iii) below in antigen-binding domains whose antigen-binding activity varies depending on the concentration of a small molecule compound or in antigen-binding domains that have binding activity to a small molecule compound:
  (i) one or more amino acid sites that are not involved in the binding to the small molecule compound;
  (ii) one or more amino acid sites that show diversity of amino acid occurrence frequency in the antibody repertoire of the animal species to which the parent antigen-binding domain belongs; and
  (iii) one or more amino acid sites that are not important for canonical structure formation;
(b) producing a plurality of variants of the aforementioned antigen-binding domains or antigen-binding molecules comprising an antigen-binding domain, which have different sequences from one another and have modifications at one or more of the amino acid sites identified in step (a);
(c) identifying one or more amino acid modifications that do not substantially change the binding activity of each of the aforementioned variants to the small molecule compound; and
(d) producing a library comprising nucleic acids that encode unmodified antigen-binding domains/molecules, and nucleic acids that encode a plurality of variants of the aforementioned antigen-binding domains or antigen-binding molecules comprising an antigen-binding domain, which have different sequences from one another and have one or more of the amino acid modifications identified in step (c).

Embodiment 4

The library of Embodiment [1] produced by a method comprising the steps of:
1) contacting a library comprising a plurality of antigen-binding molecules having binding activity to a small molecule compound with the small molecule compound; and
2) concentrating from the library, nucleic acids that encode a plurality of variants of antigen-binding molecules having binding activity to the small molecule compound.

Embodiment 5

The library of Embodiment [4], wherein the aforementioned antigen-binding molecules are antigen-binding molecules that comprise heavy-chain variable regions and light-chain variable regions of an antibody, and wherein the library is produced by a method comprising any one of the steps of:
1) designing a library by concentrating nucleic acids that encode a plurality of variants of antigen-binding molecules having binding activity to a small molecule compound from the library of Embodiment [4] which comprises nucleic acids encoding one or more variants produced by modifying amino acids positioned in the heavy chain variable regions;
2) designing a library by concentrating nucleic acids that encode a plurality of variants of antigen-binding molecules having binding activity to a small molecule compound from the library of Embodiment [4] which comprises nucleic acids encoding one or more variants produced by modifying amino acids positioned in the light chain variable regions; and
3) designing a library by combining the antigen-binding molecule-encoding nucleic acids concentrated from each of the variable region libraries of steps 1) and 2).

Embodiment 6

The library of any one of Embodiments [1] to [5], wherein the aforementioned antigen-binding molecules are fusion polypeptides formed by fusing an antigen-binding domain with at least a portion of a virus coat protein.

Embodiment 7

The library of any one of Embodiments [1] to [5], wherein the aforementioned antigen-binding molecules are antigen-binding molecules comprising antibody heavy chains and light chains, and the library further comprises a step of designing a synthetic library of the heavy chains and/or light chains.

Embodiment 8

The library of Embodiment [7], wherein the antibody heavy chains and/or light chains comprise a germline-derived framework sequence.

Embodiment 9

The library of any one of Embodiments [1] to [8], wherein the aforementioned small molecule compound is a target tissue-specific compound or an unnatural compound.

Embodiment 10

The library of any one of Embodiments [1] to [9], wherein the aforementioned target tissue is a cancer tissue or an inflammatory tissue.

Embodiment 11

The library of Embodiment [10], wherein the cancer tissue-specific compound is at least one compound selected from the group consisting of nucleosides that have a purine ring structure, amino acids and their metabolites, lipids and their metabolites, primary metabolites from sugar metabolism, and nicotinamide and its metabolites.

Embodiment 12

The library of any one of Embodiments [1] to [11], wherein the small molecule compound is kynurenine, adenosine, adenosine monophosphate, adenosine diphosphate, or adenosine triphosphate.

Embodiment 13

The library of any one of Embodiments [1] to [12], wherein the amino acid sites not involved in binding with the small molecule compound are sites other than any one or more of the amino acids selected from below:
H chain: 97, 100c, 101, 94, 95, 100d, 100e, 33, 50, 52, 56, 57, 58, 99, 100, 100a, 54, 55 (Kabat Numbering); and
L chain: 49, 55, 95c, 96, 95a, 95b (Kabat Numbering).

Embodiment 14

A method for producing an antigen-binding molecule comprising an antigen-binding domain whose antigen-binding activity varies depending on the concentration of a small molecule compound, which comprises the steps of:
(a) contacting the library of any one of Embodiments [1] to [13] with an antigen in the absence of a small molecule compound;
(b) selecting an antigen-binding domain that does not bind to the antigen in step (a) above;
(c) contacting the antigen-binding domain selected in step (b) above with the antigen in the presence of the small molecule compound;
(d) selecting the antigen-binding domain that binds to the antigen in step (c) above;
(e) linking the polynucleotide that encodes the antigen-binding domain selected in step (d) above with a polynucleotide that encodes a polypeptide comprising an Fc region;
(f) culturing a cell introduced with a vector in which the polynucleotide obtained in step (e) above is operably linked; and
(g) collecting the antigen-binding molecule from the culture solution of the cell cultured in step (f) above.

Embodiment 15

A method for producing an antigen-binding molecule comprising an antigen-binding domain whose antigen-binding activity varies depending on the concentration of a small molecule compound, which comprises the steps of:
(a) contacting the library of any one of Embodiments [1] to [13] with an antigen in the presence of a small molecule compound;
(b) collecting an antigen-binding domain by dissociating it using the small molecule compound at a lower concentration than in step (a) above;
(c) linking the polynucleotide that encodes the antigen-binding domain collected in step (b) above with a polynucleotide that encodes a polypeptide comprising an Fc region;
(d) culturing a cell introduced with a vector in which the polynucleotide obtained in step (c) above is operably linked; and
(e) collecting the antigen-binding molecule from the culture solution of the cell cultured in step (d) above.

Embodiment 16

The method of Embodiment [14] or [15] for producing an antigen-binding molecule that comprises an antigen-binding domain whose antigen-binding activity varies depending on the concentration of a small molecule compound, which further comprises the steps of:
(a) contacting the library of any one of Embodiments [1] to [13] with a small molecule compound; and
(b) selecting antigen-binding domains collected in step (a) above.

Embodiment 17

The method of any one of Embodiments [14] to [16] for producing an antigen-binding molecule, wherein the small molecule compound is kynurenine, adenosine, adenosine monophosphate, adenosine diphosphate, or adenosine triphosphate.

Embodiment 18

An antigen-binding molecule comprising an antigen-binding domain whose antigen-binding activity varies depending on the concentration of an unnatural compound.

Embodiment 19

A pharmaceutical composition that comprises the antigen-binding molecule of Embodiment [18].

Those skilled in the art will naturally understand that the present invention includes any combination of one or more embodiments described above, as long as it is not technically inconsistent with common technical knowledge of those skilled in the art.

Effects of the Invention

The antigen-binding domains or antigen-binding molecules comprising an antigen-binding domain of the present invention, whose antigen-binding activity varies depending on the concentration of a small molecule compound, and pharmaceutical compositions comprising thereof do not act systemically in the blood or in normal tissues; however, by acting reversibly at lesions such as cancers or inflamed sites in target tissues, they show drug efficacy while avoiding side-effects, and can treat diseases originated at the target tissues.

Furthermore, by using libraries of the present invention comprising a plurality of antigen-binding domains or antigen-binding molecules that comprise an antigen-binding domain and have different sequences from one another, and whose antigen-binding activity varies depending on the concentration of a small molecule compound, various antigen-binding molecules useful for treating tissue-specific diseases such as those described above can be obtained efficiently in a short period of time.

In an embodiment of the libraries of the present invention, amino acid sites in antigen-binding molecule domains that are not involved in the binding to a small molecule compound are identified, and a library is designed to comprise nucleic acids that encode antigen-binding domains having different sequences from one another so that the amino acids at the identified sites become one to several types of amino acids. This provides a library that can yield antigen-binding molecules whose antigen-binding ability varies in the presence of the compound more efficiently than using a library of antibodies derived from humans or non-human animals or a method of immunizing non-human mammals.

Figure 9:
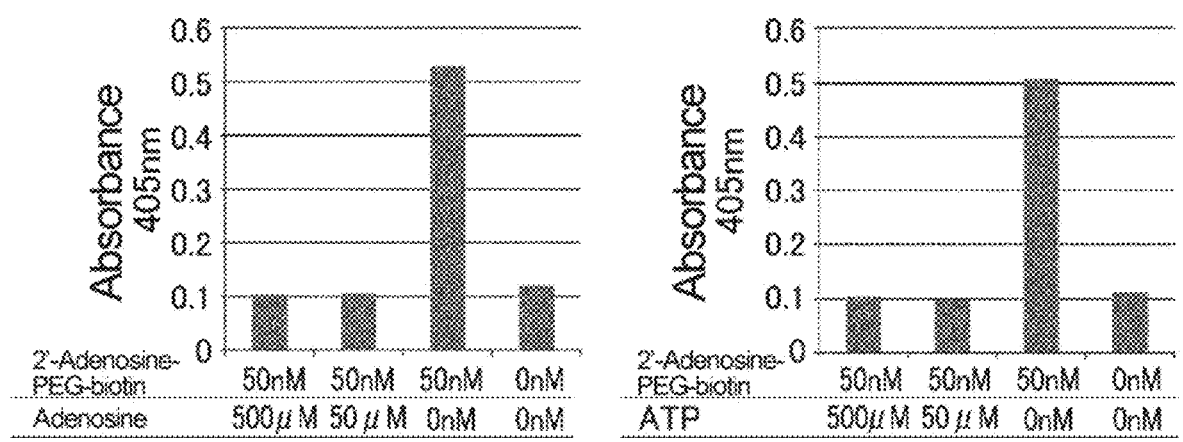

FIG. 9 shows results of competitive ELISA demonstrating that clone SMB0002 binds to adenosine and ATP.

Figure 10A:
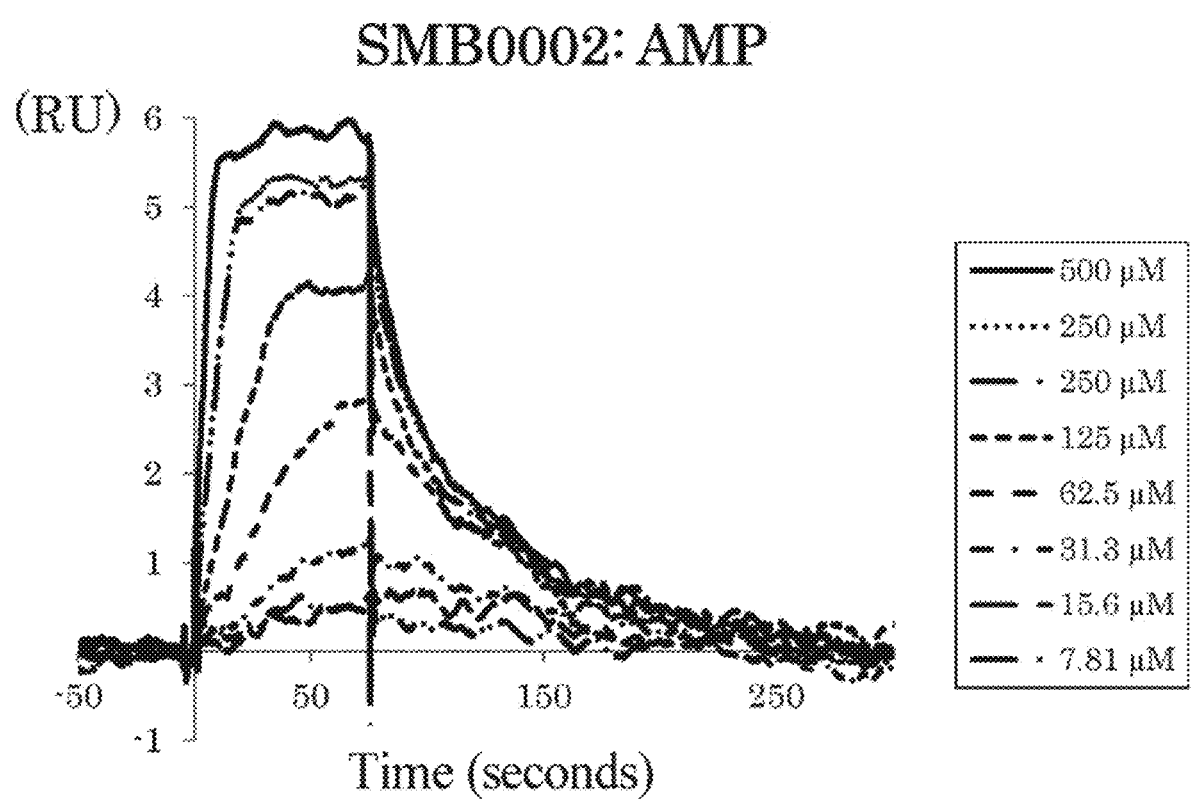

FIG. 10A shows sensorgrams of surface plasmon resonance-based analysis demonstrating that clone SMB0002 binds to (interacts with) AMP. The sensorgrams show interactions between SMB0002 and AMP at 500, 250 (in duplicate), 125, 62.5, 31.3, 15.6, and 7.81 µM in order from the top.

Figure 10B:
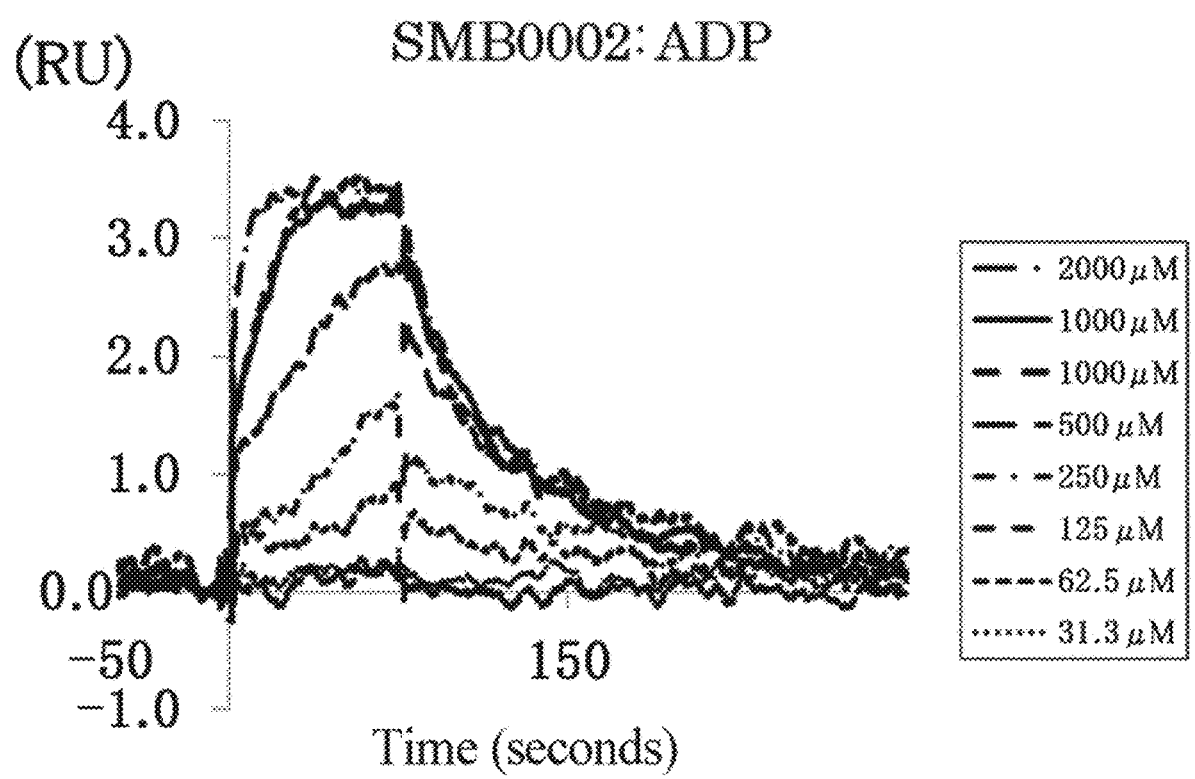

FIG. 10B shows sensorgrams of surface plasmon resonance-based analysis demonstrating that clone SMB0002 binds to (interacts with) ADP. The sensorgrams show interactions between SMB0002 and ADP at 2000, 1000 (in duplicate), 500, 250, 125, 62.5, and 31.3 µM in order from the top.

Figure 11A:
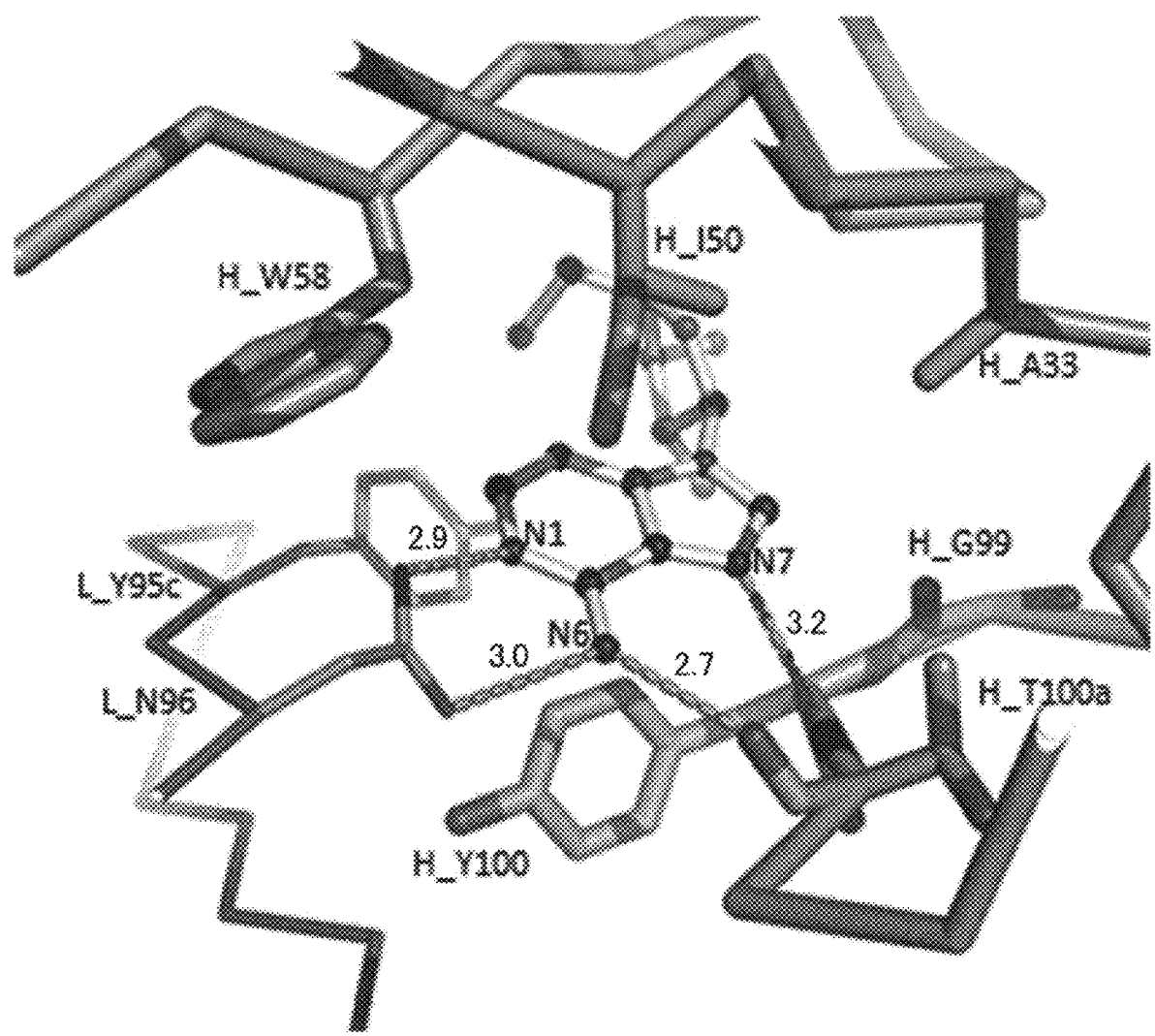

FIG. 11A shows the mode of binding between the SMB0002 antibody and the adenine ring portion of adenosine. In the figure, thick lines show the H chain and thin lines show the L chain of the antibody, and adenosine is shown by a ball-and-stick model. The amino acid residues at distances of 3.8 Å or less from the adenine ring are shown by a stick model. The dashed lines show hydrogen bonds having a distance of 3.2 Å or less between the antibody and the adenine ring portion.

Figure 11B:
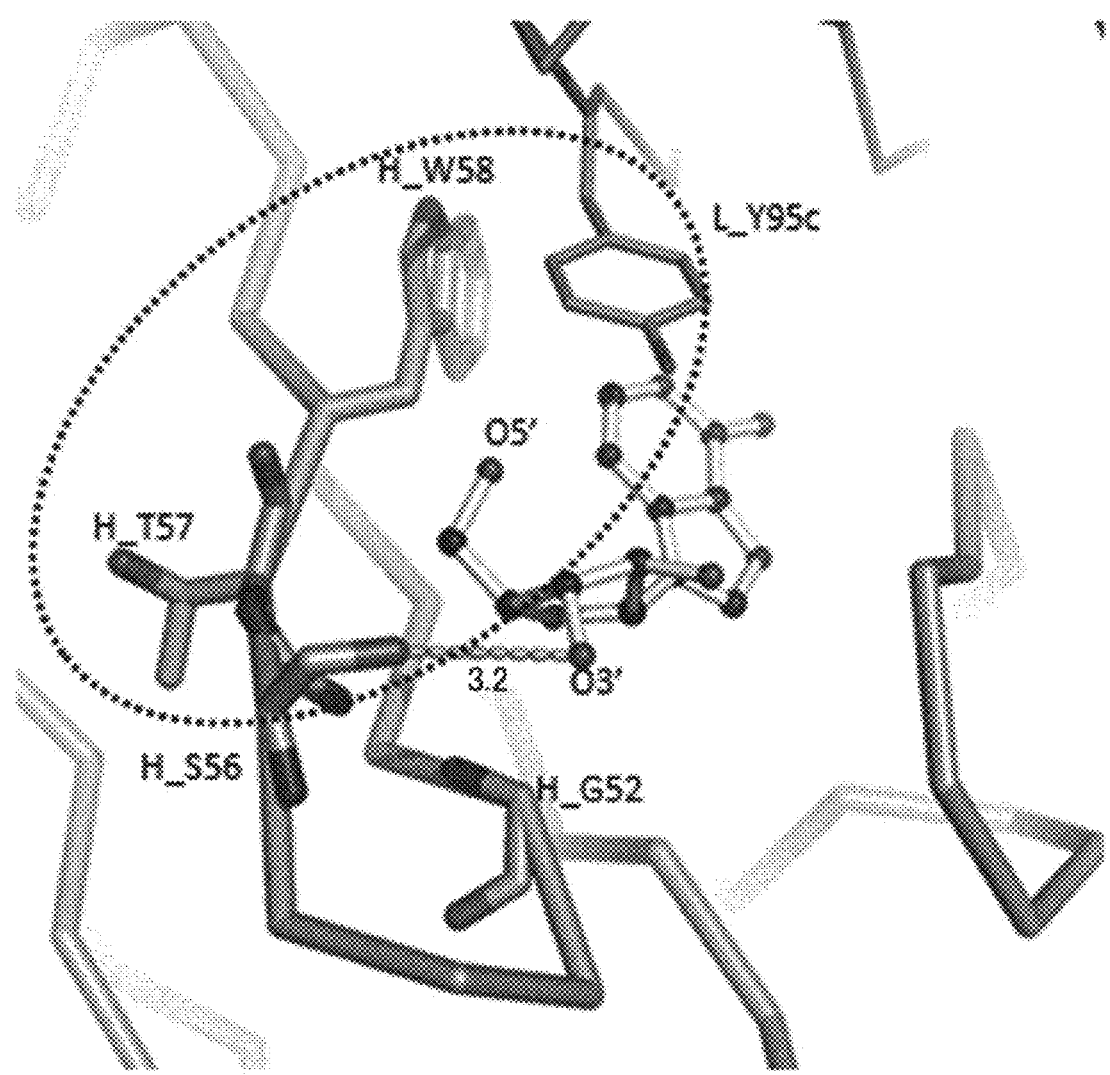

FIG. 11B shows the mode of binding between the SMB0002 antibody and the ribose portion of adenosine. In the figure, thick lines show the H chain and thin lines show the L chain of the antibody, and adenosine is shown by a ball-and-stick model. The amino acid residues at distances of 3.8 Å or less from the ribose portion are shown by a stick model. The dashed lines show hydrogen bonds having a distance of 3.2 Å or less between the antibody and the ribose portion. The area within the dotted lines shows the region of the predicted presence of the phosphate group when bound to AMP.

Figure 12:
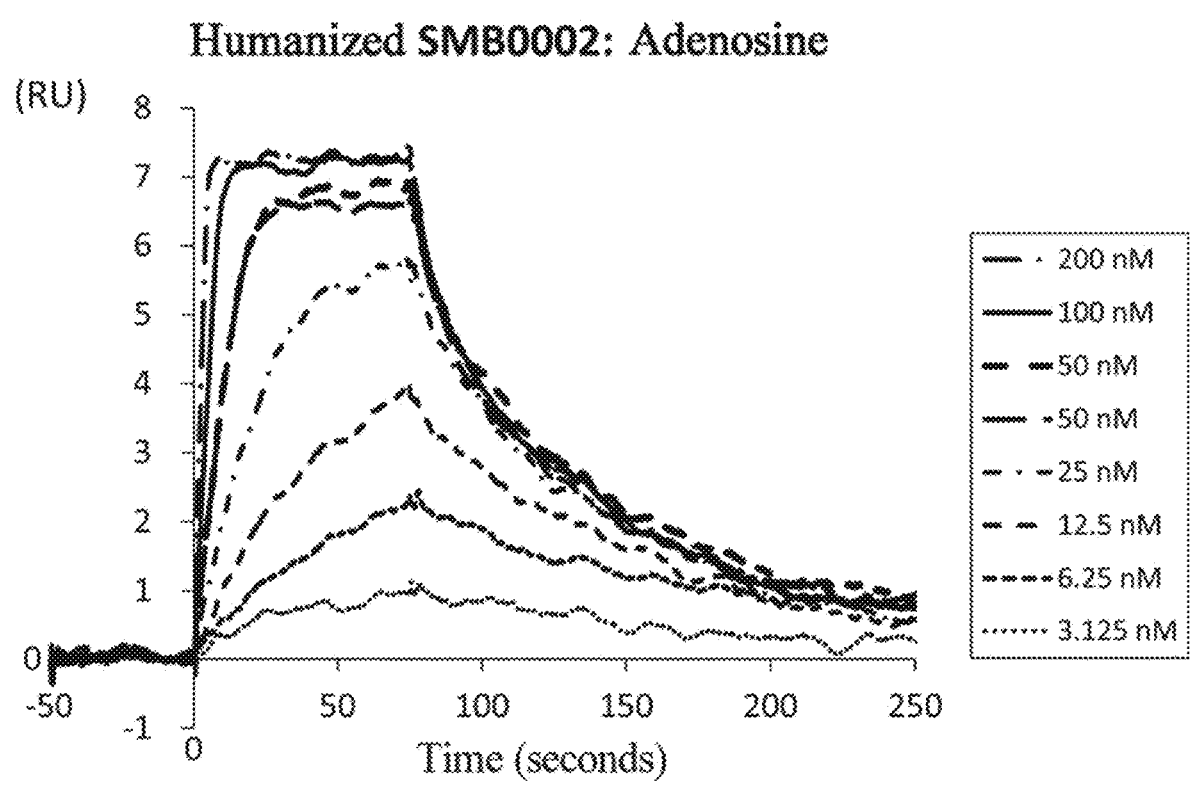

FIG. 12 shows sensorgrams of surface plasmon resonance-based analysis demonstrating that humanized SMB0002 binds to (interacts with) adenosine. The sensorgrams show interactions between humanized SMB0002 and adenosine at 200, 100, 50 (in duplicate), 25, 12.5, 6.25, and 3.125 nM in order from the top.

Figure 13:
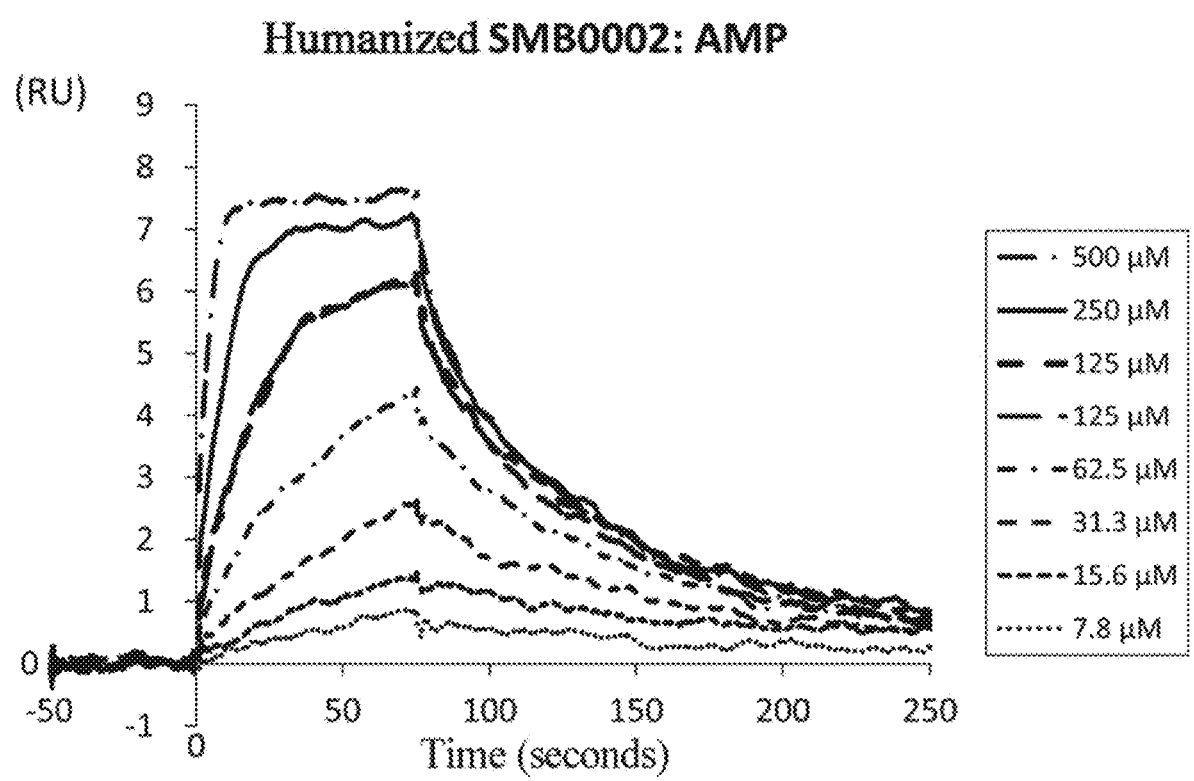

FIG. 13 shows sensorgrams of surface plasmon resonance-based analysis demonstrating that humanized SMB0002 binds to (interacts with) AMP. The sensorgrams show interactions between humanized SMB0002 and AMP at 500, 250, 125 (in duplicate), 62.5, 31.3, 15.6, and 7.8 µM in order from the top.

Figure 14:
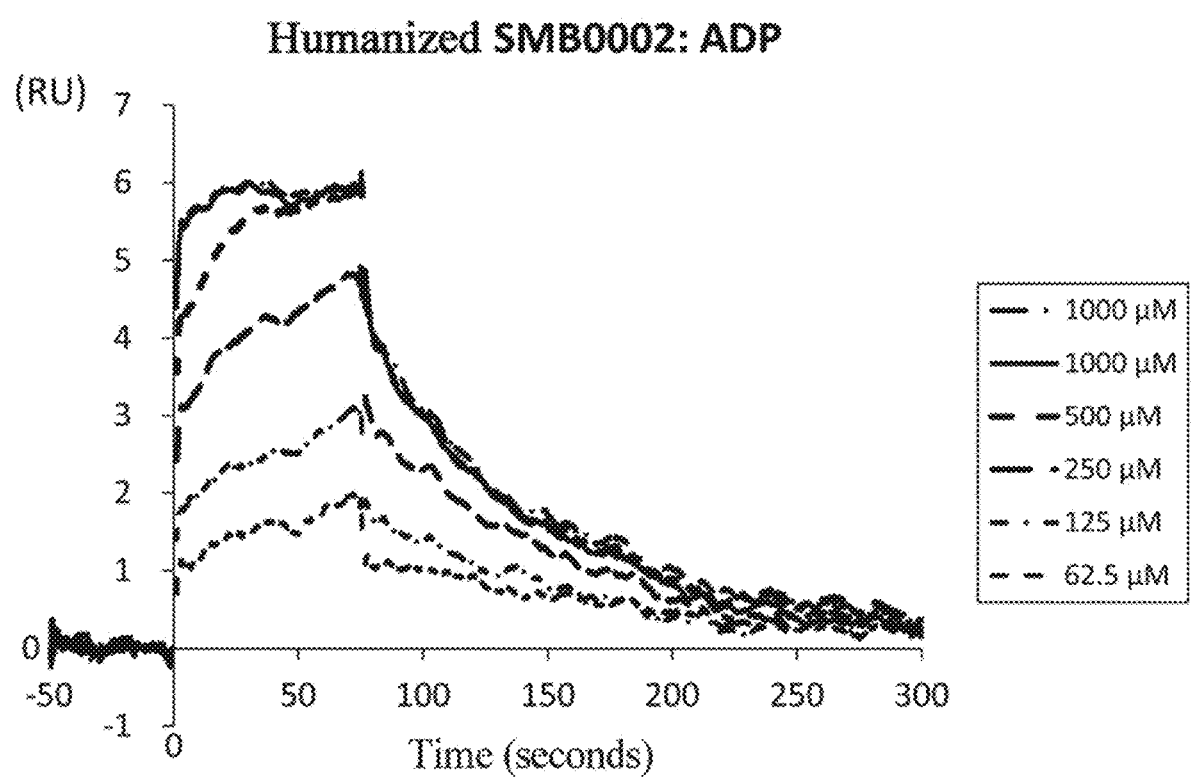

FIG. 14 shows sensorgrams of surface plasmon resonance-based analysis demonstrating that humanized SMB0002 binds to (interacts with) ADP. The sensorgrams show interactions between humanized SMB0002 and ADP at 1000 (in duplicate), 500, 250, 125, and 62.5 µM in order from the top.

Figure 15:
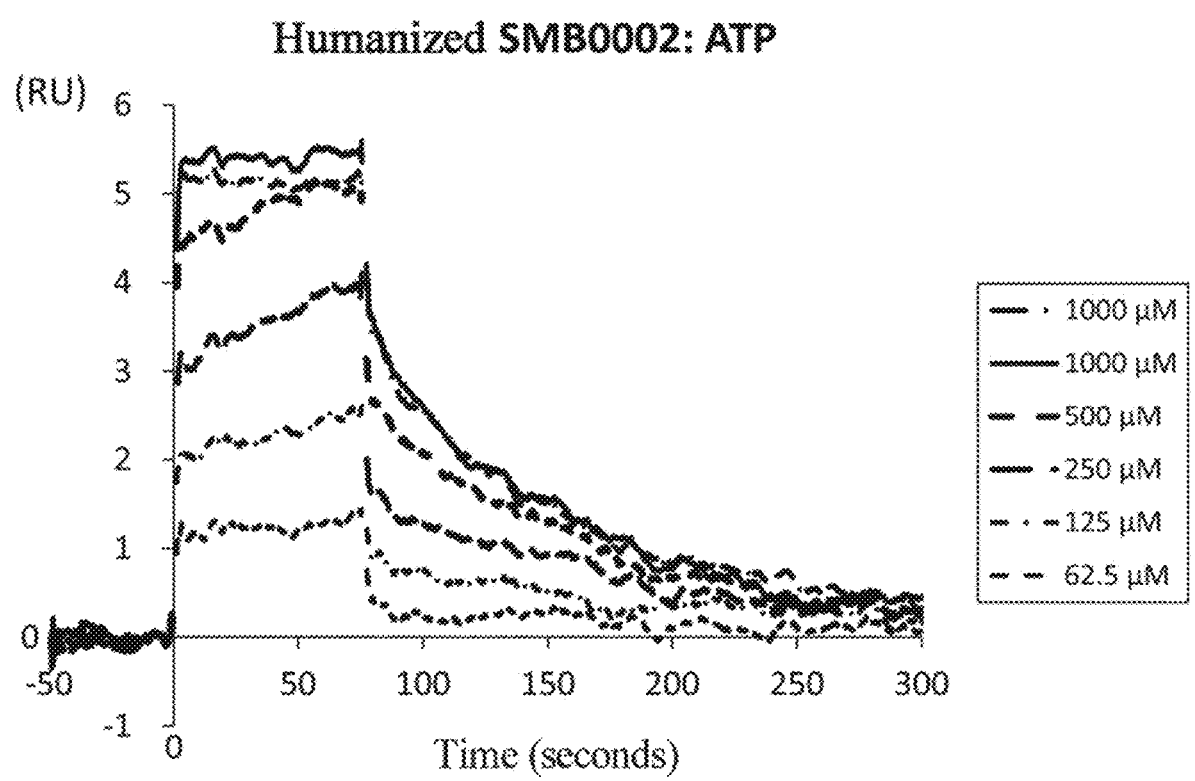

FIG. 15 shows sensorgrams of surface plasmon resonance-based analysis demonstrating that humanized SMB0002 binds to (interacts with) ATP. The sensorgrams show interactions between humanized SMB0002 and ATP at 1000 (in duplicate), 500, 250, 125, and 62.5 µM in order from the top.

Figure 16:
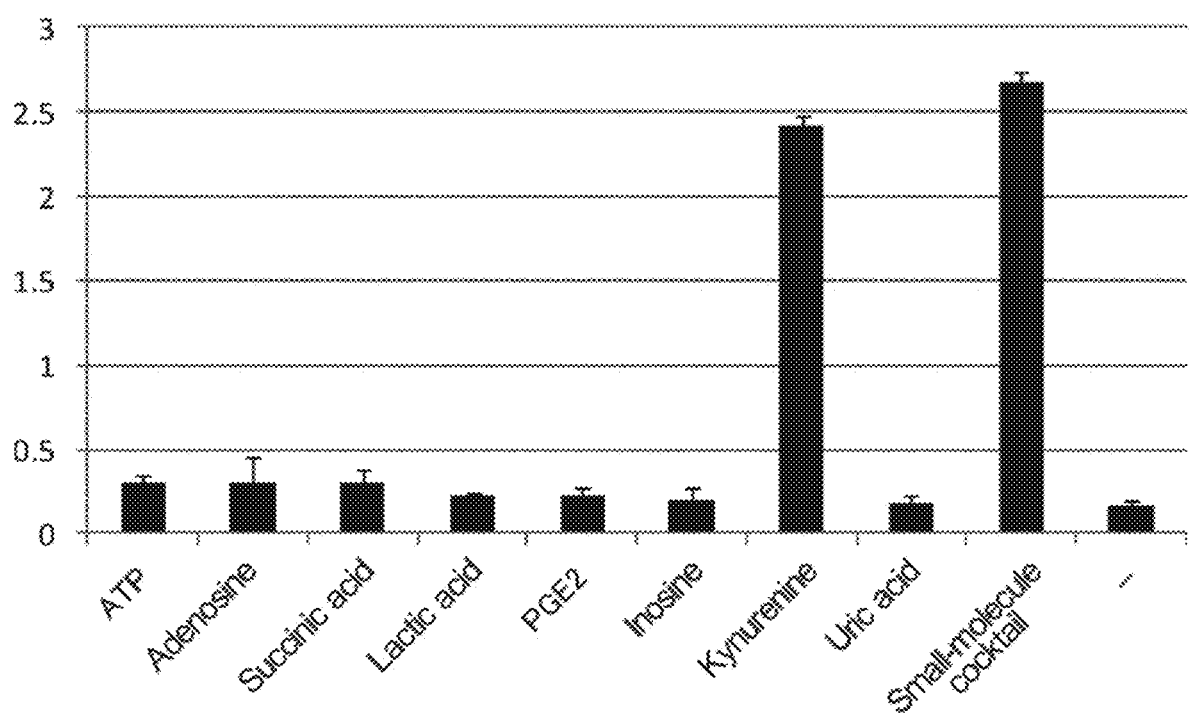

FIG. 16 is a figure showing the result of ELISA for binding of clone 6RNMSC1-2_F02 to human IL-6R. The vertical axis shows the absorbance values which assess the binding activity of the antibody to human IL-6R in the presence or absence of each small molecule.

Figure 17:
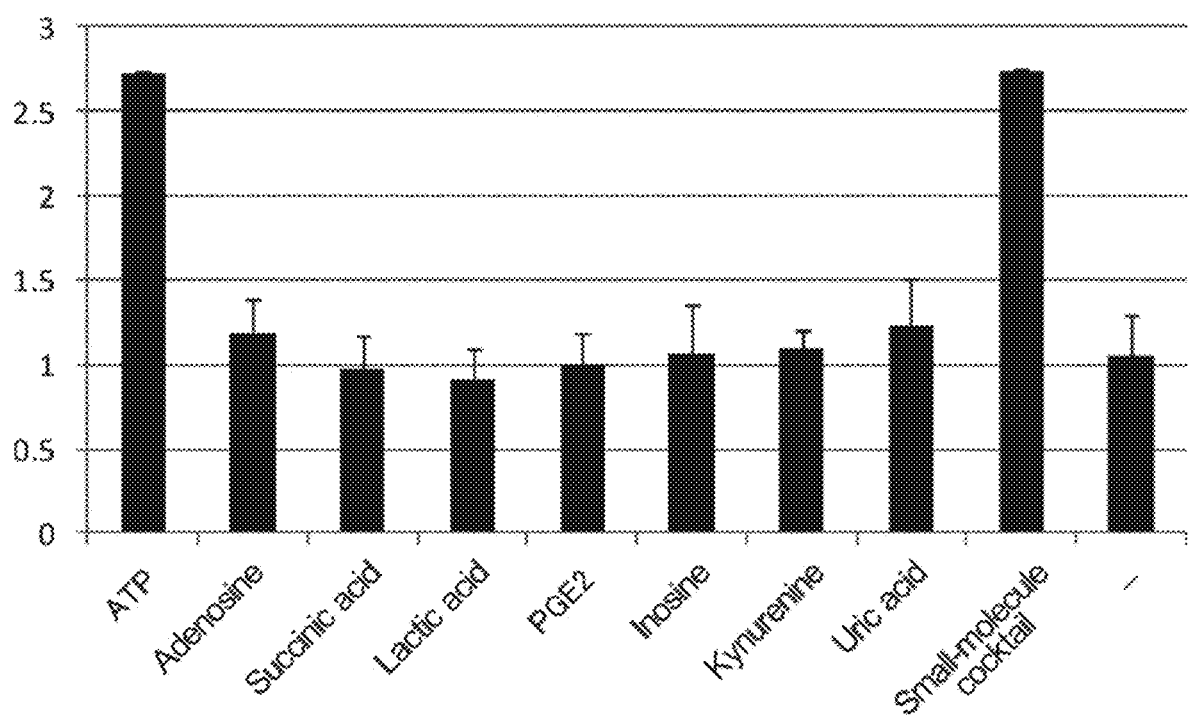

FIG. 17 is a figure showing the result of ELISA for binding of clone 6RNMSC1-3_G02 to human IL-6R. The vertical axis shows the absorbance values which assess the binding activity of the antibody to human IL-6R in the presence or absence of each small molecule.

Figure 18:
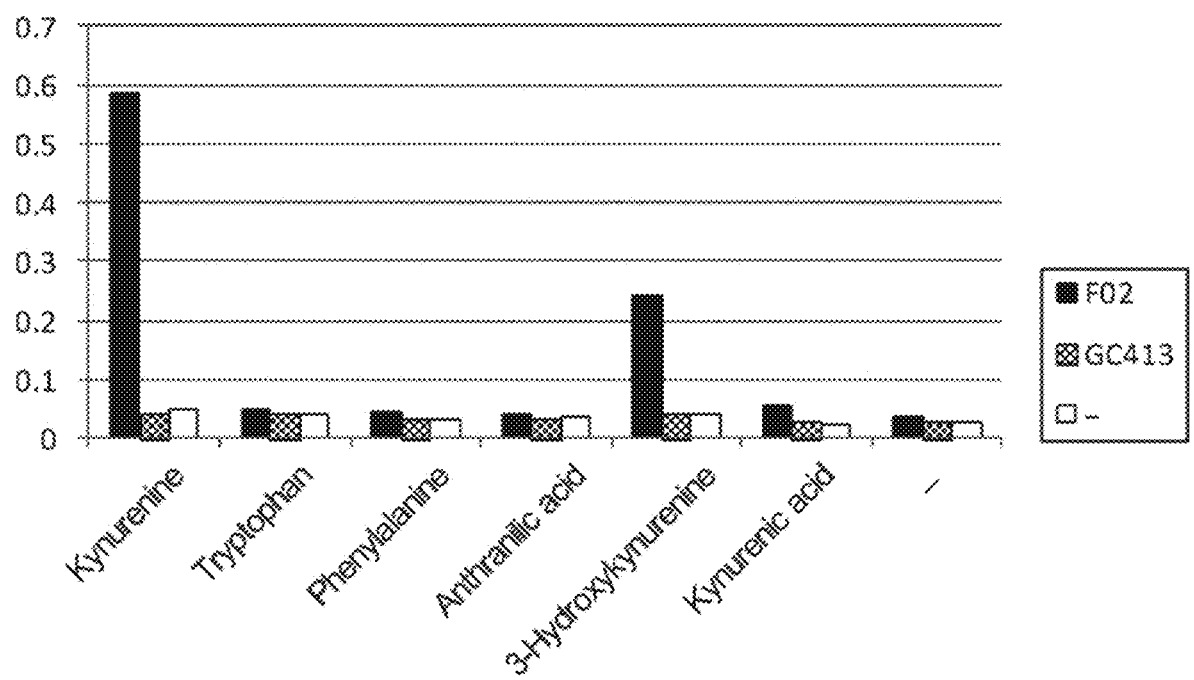

FIG. 18 is a figure showing the result of ELISA for binding of an antibody to human IL-6R. The vertical axis shows the absorbance values which assess the binding activity of the antibody to human IL-6R in the presence or absence of each amino acid or amino acid metabolite.

Figure 19:
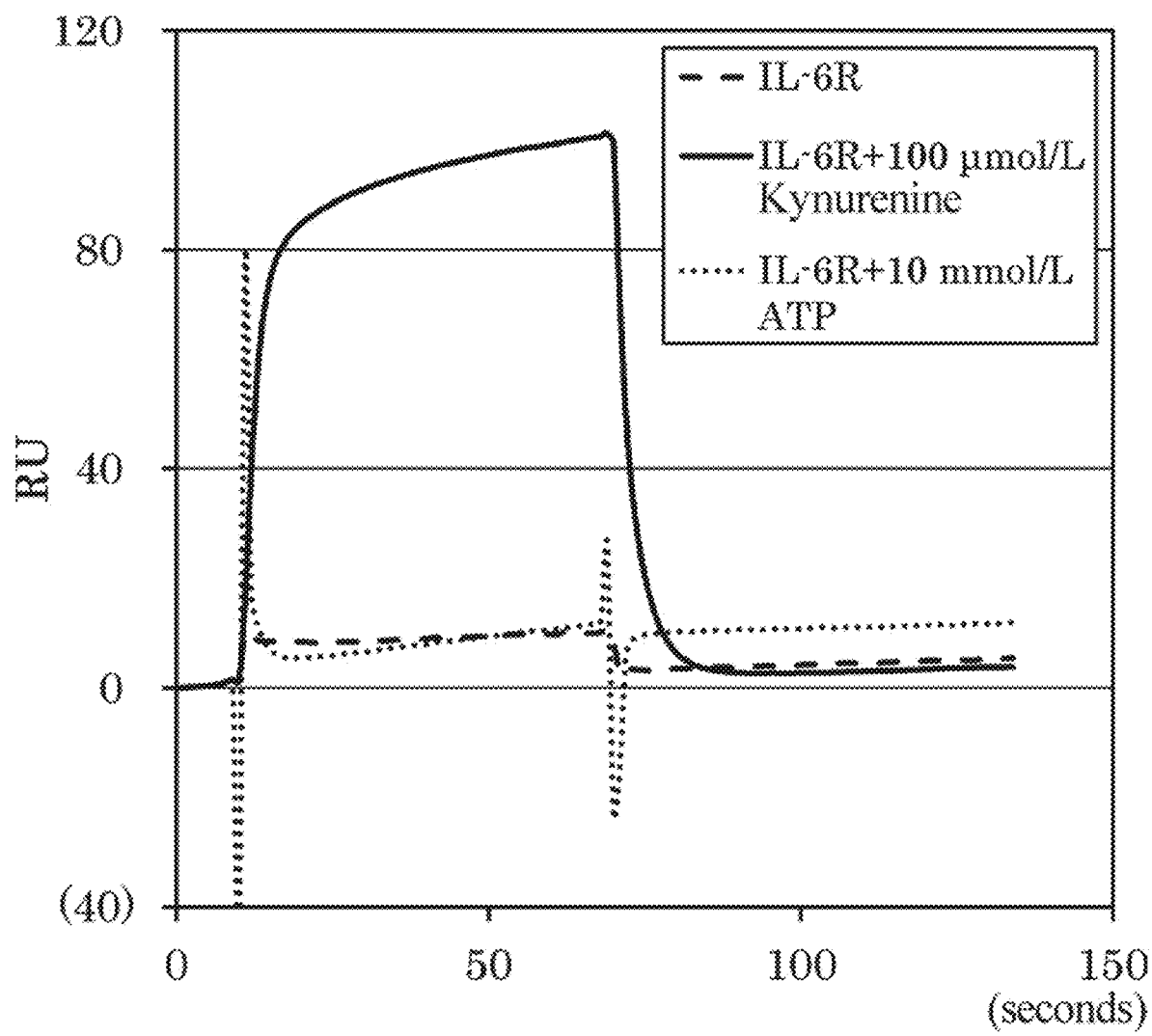

FIG. 19 presents sensorgrams showing the interaction between 6RNMSC1-2_F02 and 1 µmol/L IL-6R in the presence of 100 µmol/L kynurenine, in the presence of 10 mmol/L ATP, and in the absence of kynurenine and ATP. The solid line indicates the interaction in the presence of kynurenine, the dotted line indicates the interaction in the presence of ATP, and the dashed line indicates the interaction in their absence.

Figure 20:
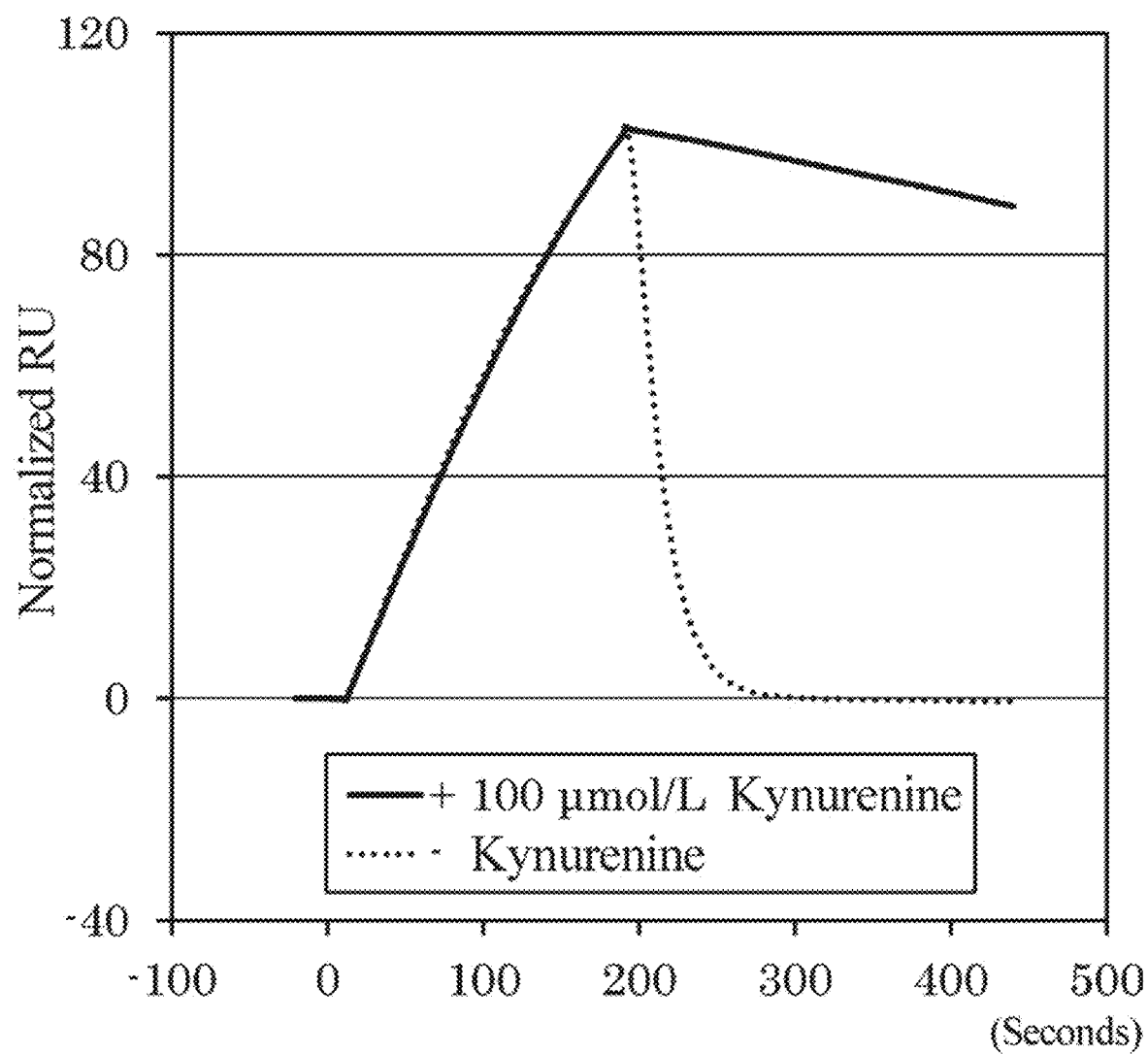

FIG. 20 is a graph obtained by allowing 6RNMSC1-2_F02 to interact with IL-6R immobilized on Sensor chip CM5 in the presence of 100 µmol/L kynurenine, and then observing the dissociation of 6RNMSC1-2_F02 from IL-6R under conditions of a buffer containing 100 µmol/L kynurenine or a buffer that does not contain kynurenine. In the figure, the vertical axis shows values normalized by defining the amount of 6RNMSC1-2_F02 bound in the presence of 100 µmol/L kynurenine as 100, and the horizontal axis shows the passage of time (in seconds) from the start of the interaction. The solid line shows the dissociation of 6RNMSC1-2_F02 from IL-6R in the presence of kynurenine, and the dotted line shows the dissociation of 6RNMSC1-2_F02 from IL-6R in the absence of kynurenine.

Figure 21:
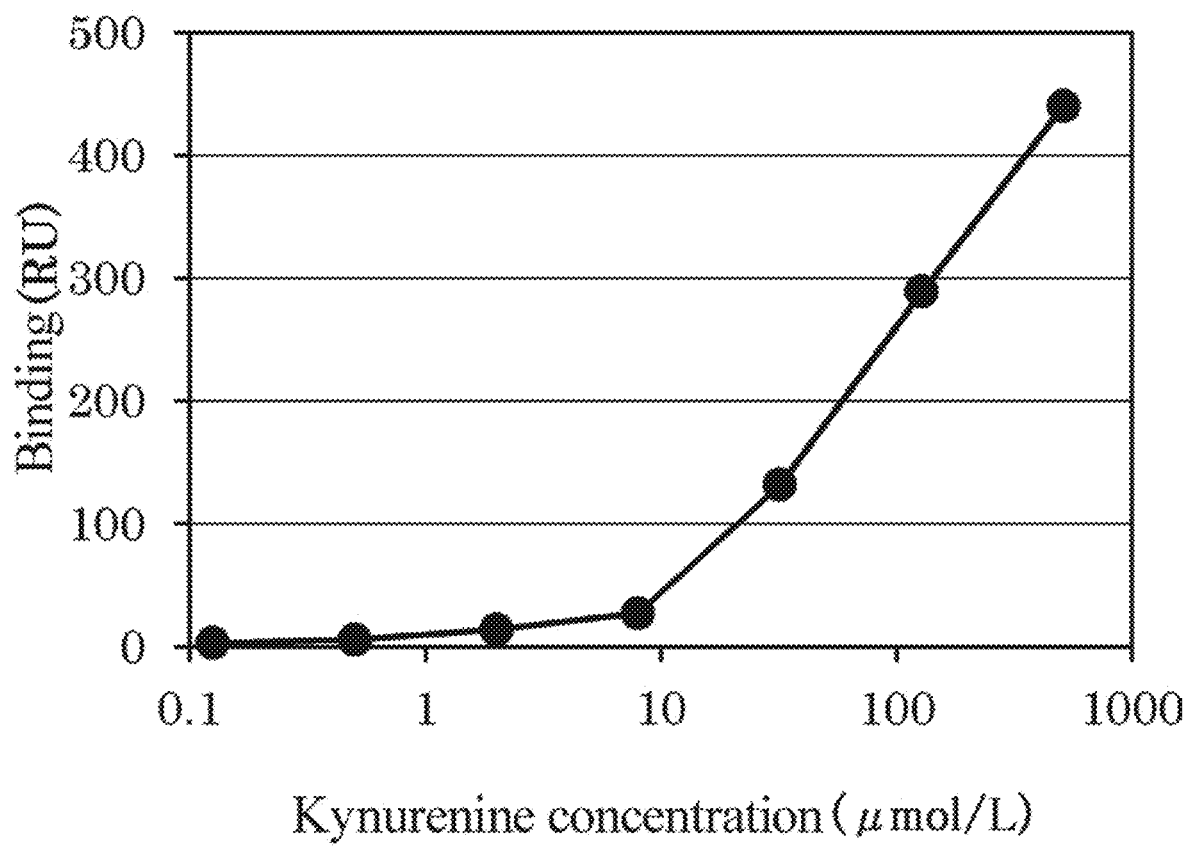

FIG. 21 is a graph produced by allowing 5 µg/L of 6RNMSC1-2_F02 to interact as an analyte for 180 seconds, and assessing the response to IL-6R immobilized onto Sensor chip CM5. The vertical axis shows change in the response (RU) before and after 6RNMSC1-2_F02 interaction, and the horizontal axis shows the concentration (µmol/L) of kynurenine contained in the solution.

Figure 22:
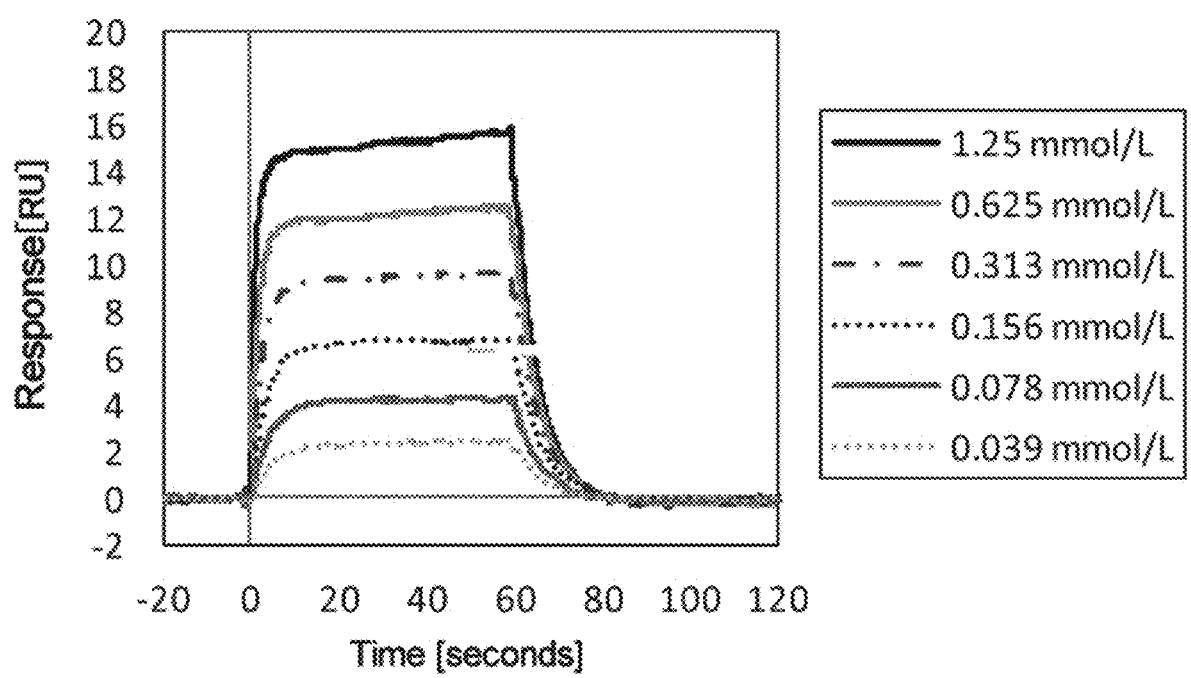

FIG. 22 shows sensorgrams of surface plasmon resonance-based analysis demonstrating that clone 6RNMSC1-2_F02 binds to (interacts with) kynurenine. The sensorgrams show interactions between 6RNMSC1-2_F02 and kynurenine at 1.25, 0.625, 0.313, 0.156, 0.078, and 0.039 mM in order from the top. The kinetic parameters are ka=709 (1/s), kd=0.17 (1/s), and KD=0.239 (mmol/L).

Figure 23:
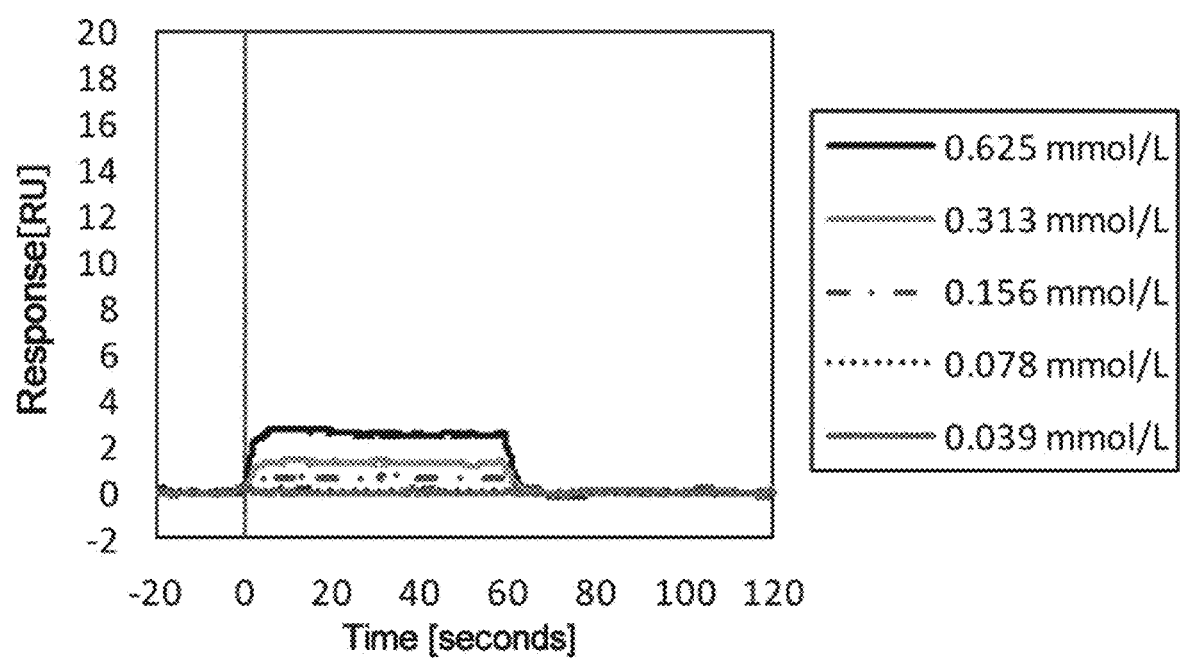

FIG. 23 shows sensorgrams of surface plasmon resonance-based analysis demonstrating that clone 6RNMSC1-2_F02 binds to (interacts with) 3-hydroxy-DL-kynurenine. The sensorgrams show interactions between 6RNMSC1-2_F02 and 3-hydroxy-DL-kynurenine at 0.625, 0.313, 0.156, 0.078, and 0.039 mM in order from the top.

Figure 24:
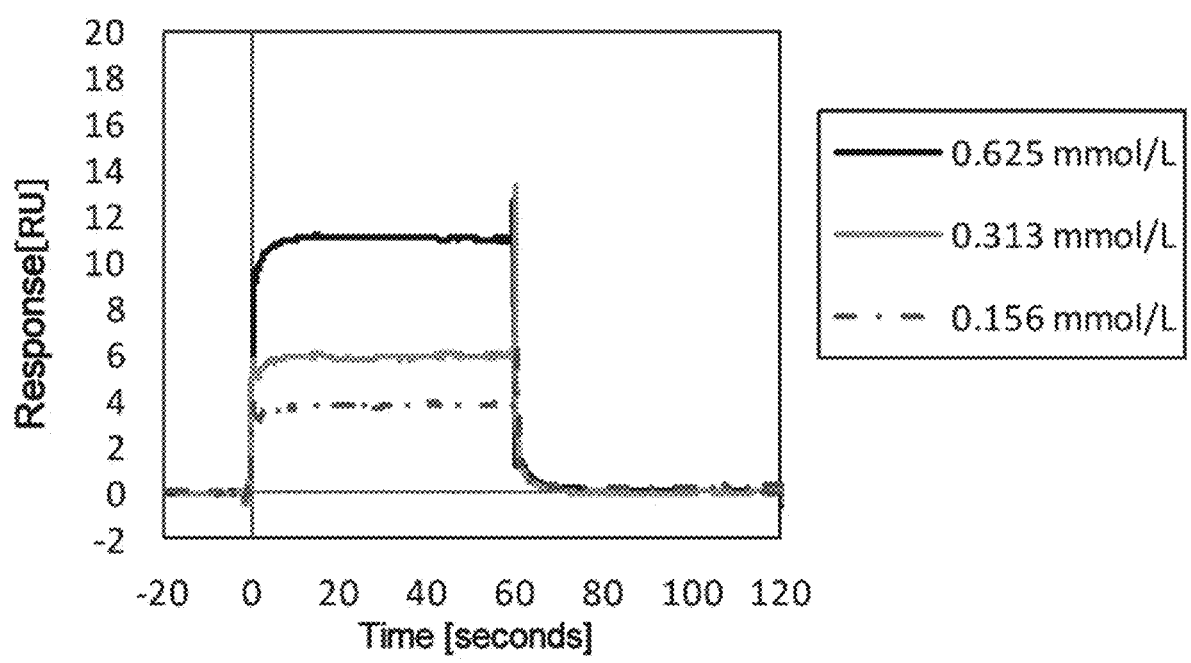

FIG. 24 shows sensorgrams of surface plasmon resonance-based analysis demonstrating that clone 6RNMSC1-2_F02 binds to (interacts with) the compound RO0635389-000-001. The sensorgrams show interactions between 6RNMSC1-2_F02 and the compound RO0635389-000-001 at 0.625, 0.313, and 0.156 mM in order from the top.

Figure 25:
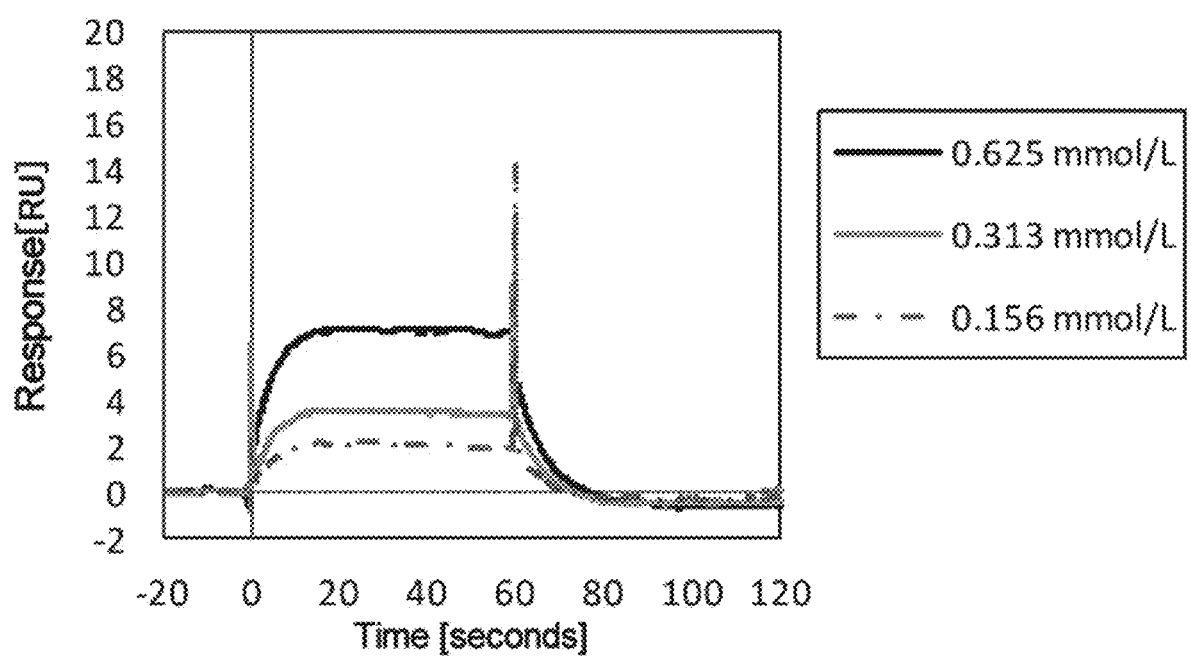

FIG. 25 shows sensorgrams of surface plasmon resonance-based analysis demonstrating that clone 6RNMSC1-2_F02 binds to (interacts with) the compound RO0635390-000-001. The sensorgrams show interactions between 6RNMSC1-2_F02 and the compound RO0635390-000-001 at 0.625, 0.313, and 0.156 mM in order from the top.

Figure 26:
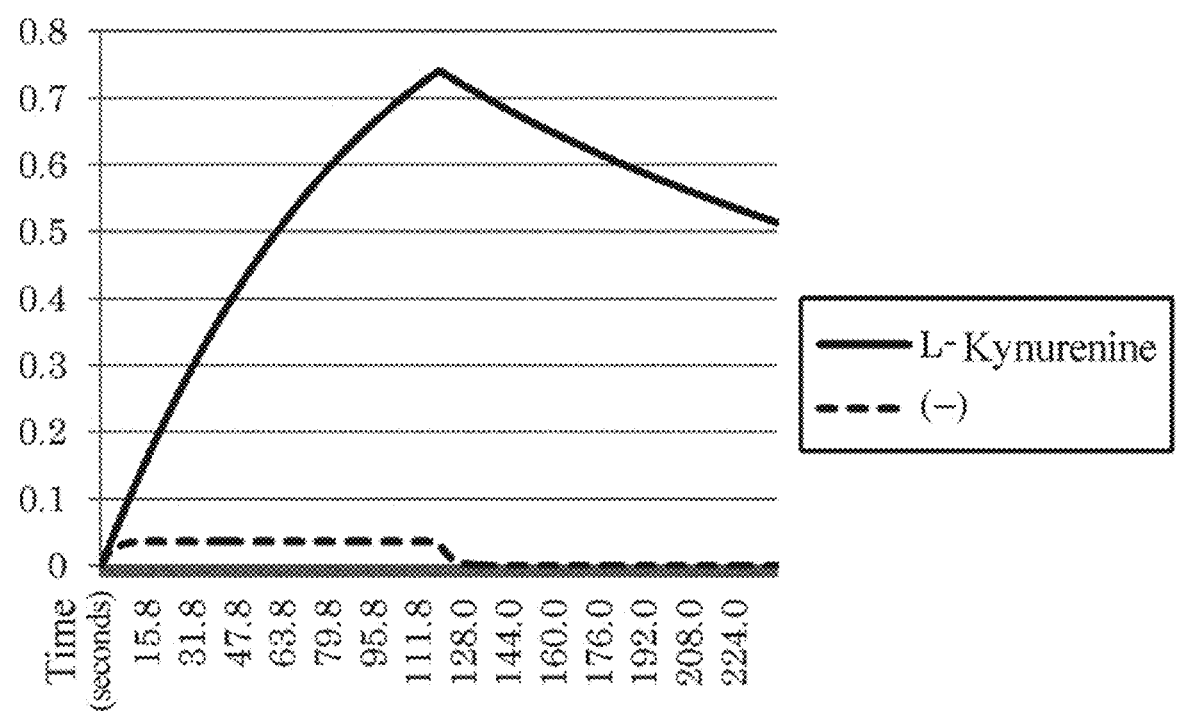

FIG. 26 shows Octet sensorgrams demonstrating that the binding (interaction) of clone 6RNMSC1-2_F02 with IL6R varies depending on the presence (solid line) or absence (dashed line) of kynurenine. The vertical axis shows the response to IL6R.

Figure 27:
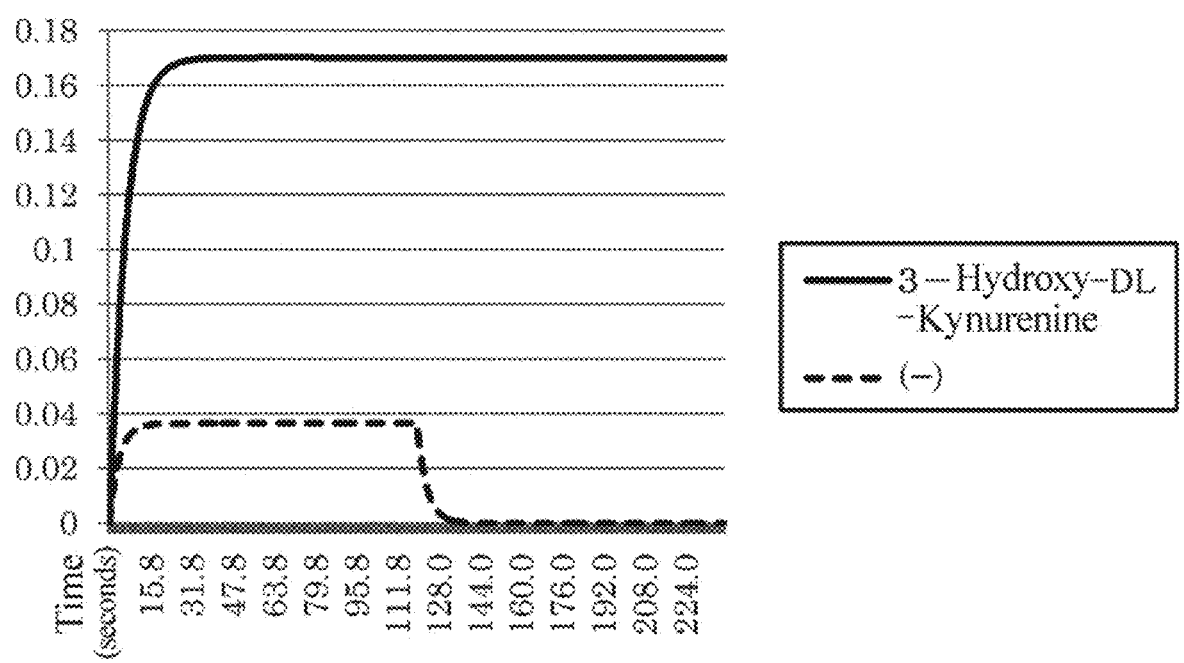

FIG. 27 shows Octet sensorgrams demonstrating that the binding (interaction) of clone 6RNMSC1-2_F02 with IL6R varies depending on the presence (solid line) or absence (dashed line) of 3-hydroxy-DL-kynurenine. The vertical axis shows the response to IL6R.

Figure 28:
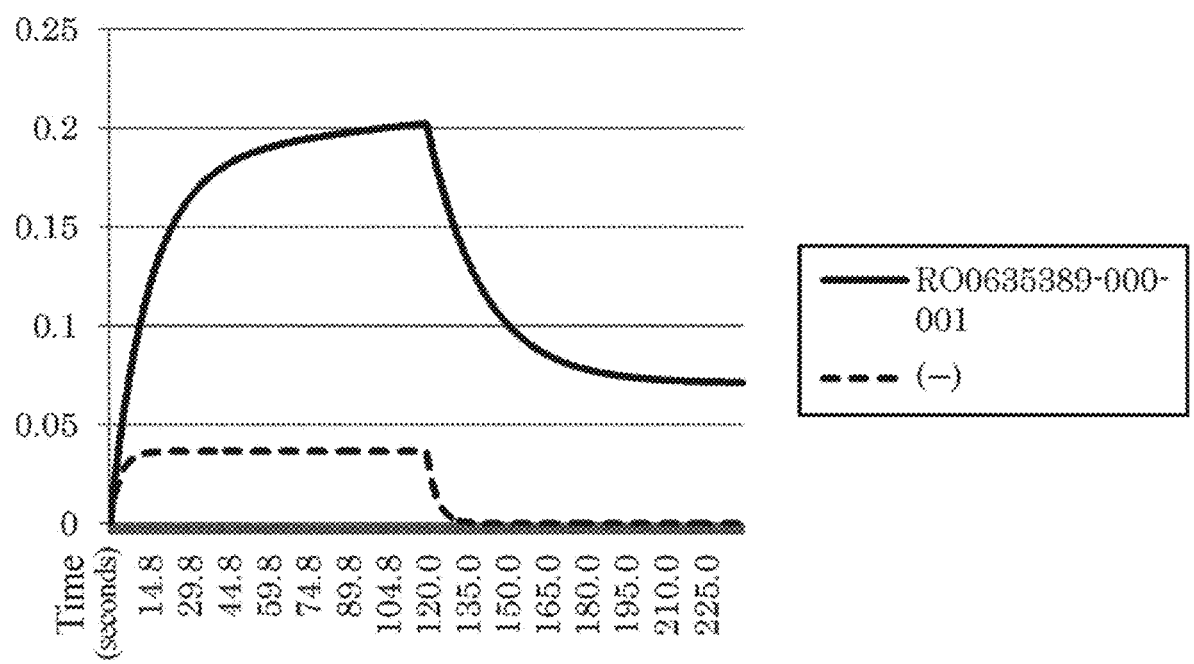

FIG. 28 shows Octet sensorgrams demonstrating that the binding (interaction) of clone 6RNMSC1-2_F02 with IL6R varies depending on the presence (solid line) or absence (dashed line) of the compound RO0635389-000-001. The vertical axis shows the response to IL6R.

Figure 29:
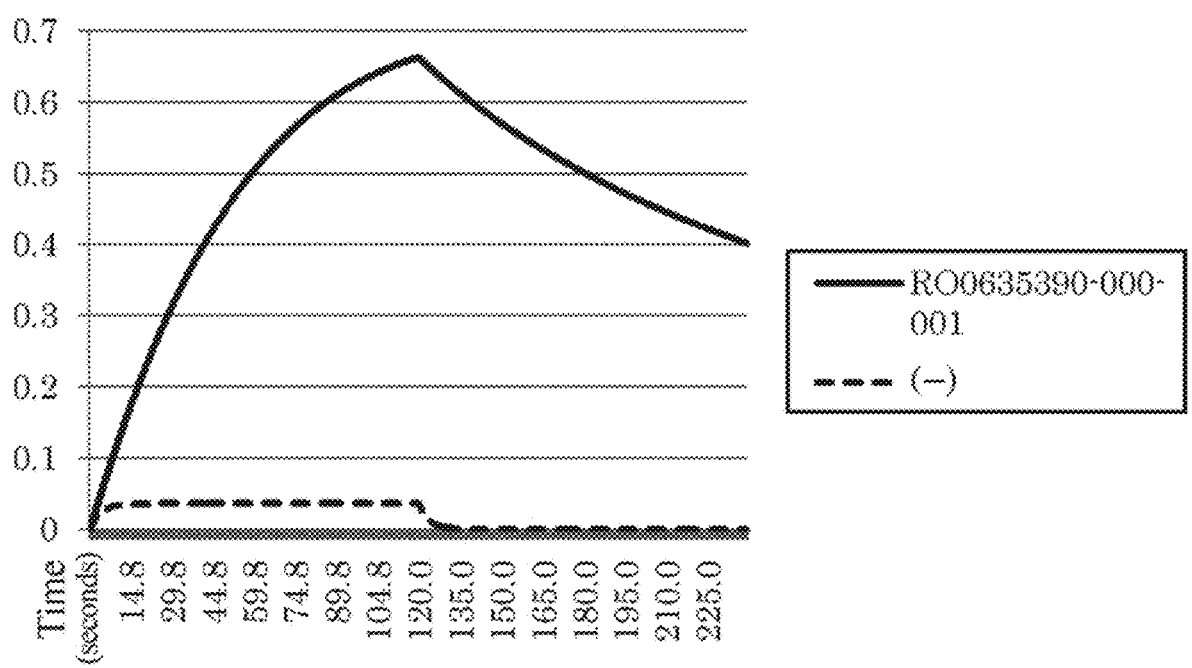

FIG. 29 shows Octet sensorgrams demonstrating that the binding (interaction) of clone 6RNMSC1-2_F02 with IL6R varies depending on the presence (solid line) or absence (dashed line) of the compound RO0635390-000-001. The vertical axis shows the response to IL6R.

Figure 30:
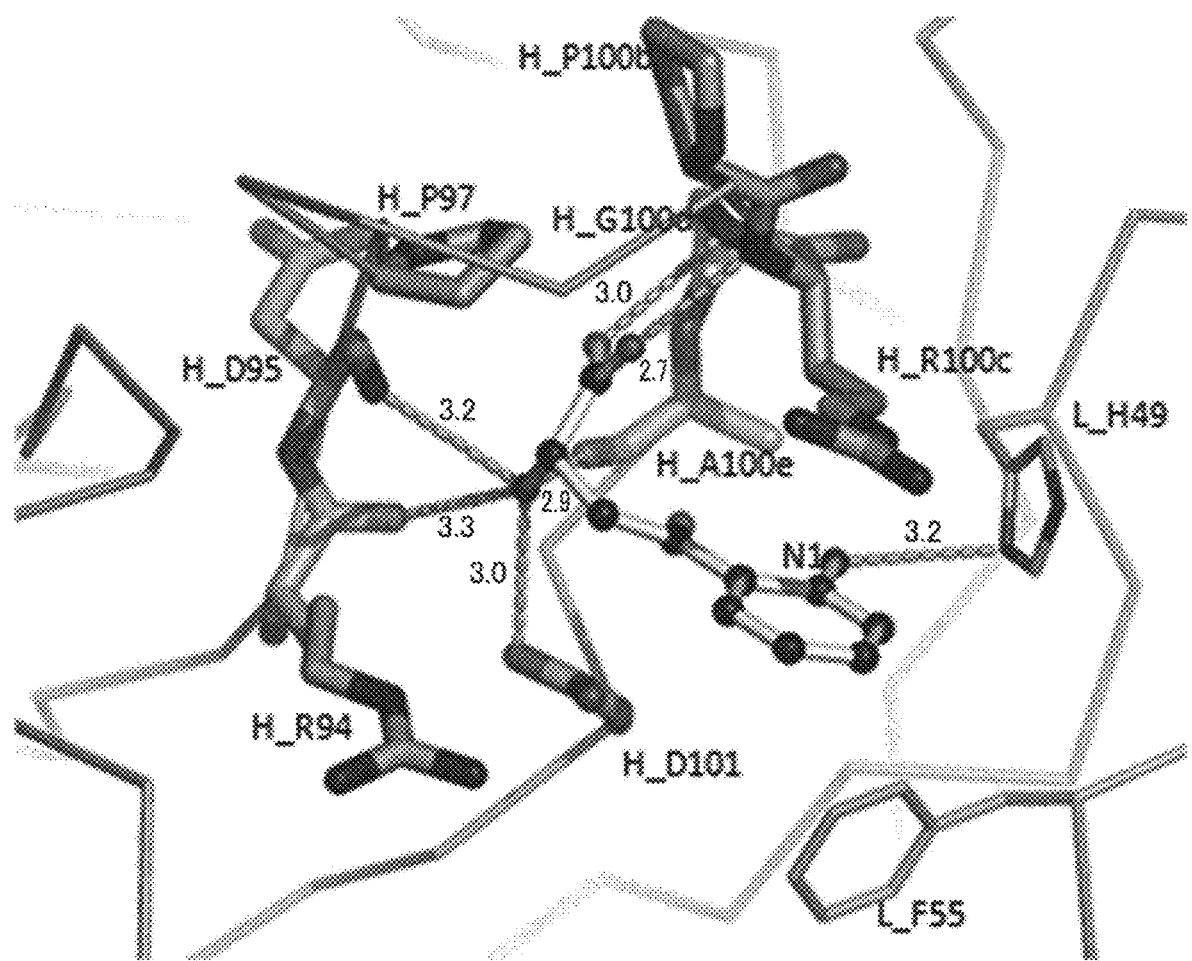

FIG. 30 shows the mode of binding between the 6RNMSC1-2_F02 Fab fragment and kynurenine. In the figure, thick lines show the H chain and thin lines show the L chain of the antibody, and kynurenine is shown by a ball-and-stick model. The amino acid residues at distances of 3.8 Å or less from kynurenine are shown by a stick model. The dashed lines indicate hydrogen bonds or electrostatic interactions having a distance of 3.3 Å or less between the antibody and kynurenine.

Figure 31:
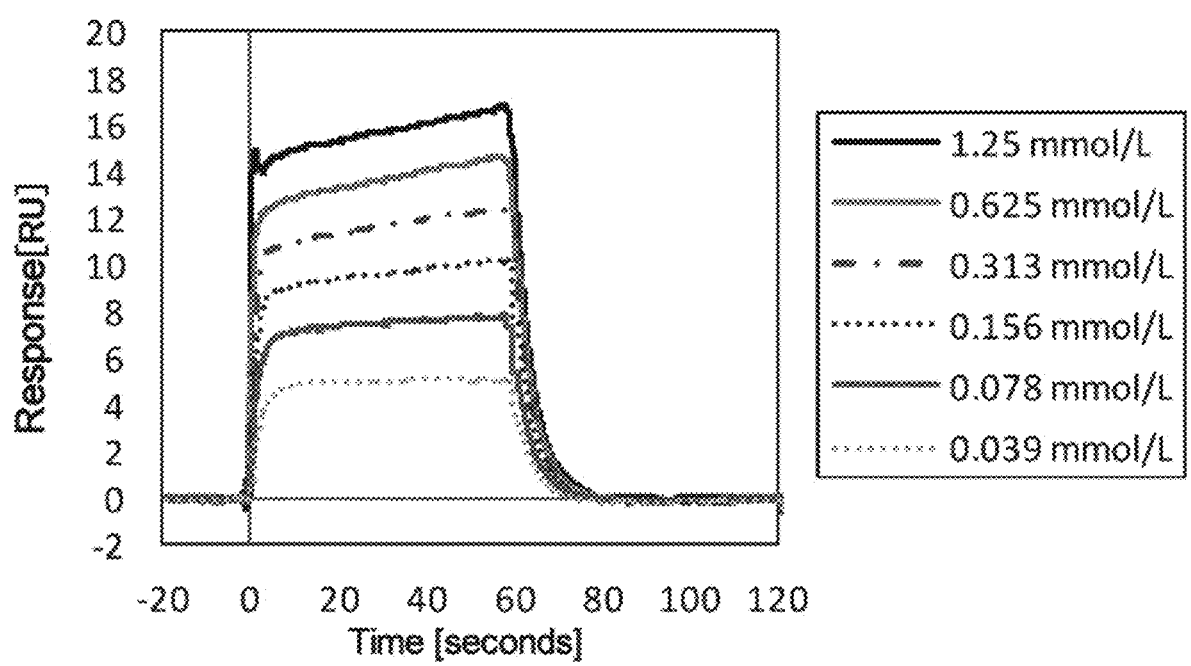

FIG. 31 shows sensorgrams of surface plasmon resonance-based analysis demonstrating that the H49Y variant of clone 6RNMSC1-2_F02 binds to (interacts with) kynurenine. The sensorgrams show interactions between 6RNMSC1-2_F02H49Y and kynurenine at 1.25, 0.625, 0.313, 0.156, 0.078, and 0.039 mM in order from the top. The kinetic parameters are ka=2543 (1/s), kd=0.24 (1/s), KD=0.095 (mmol/L).

Figure 32:
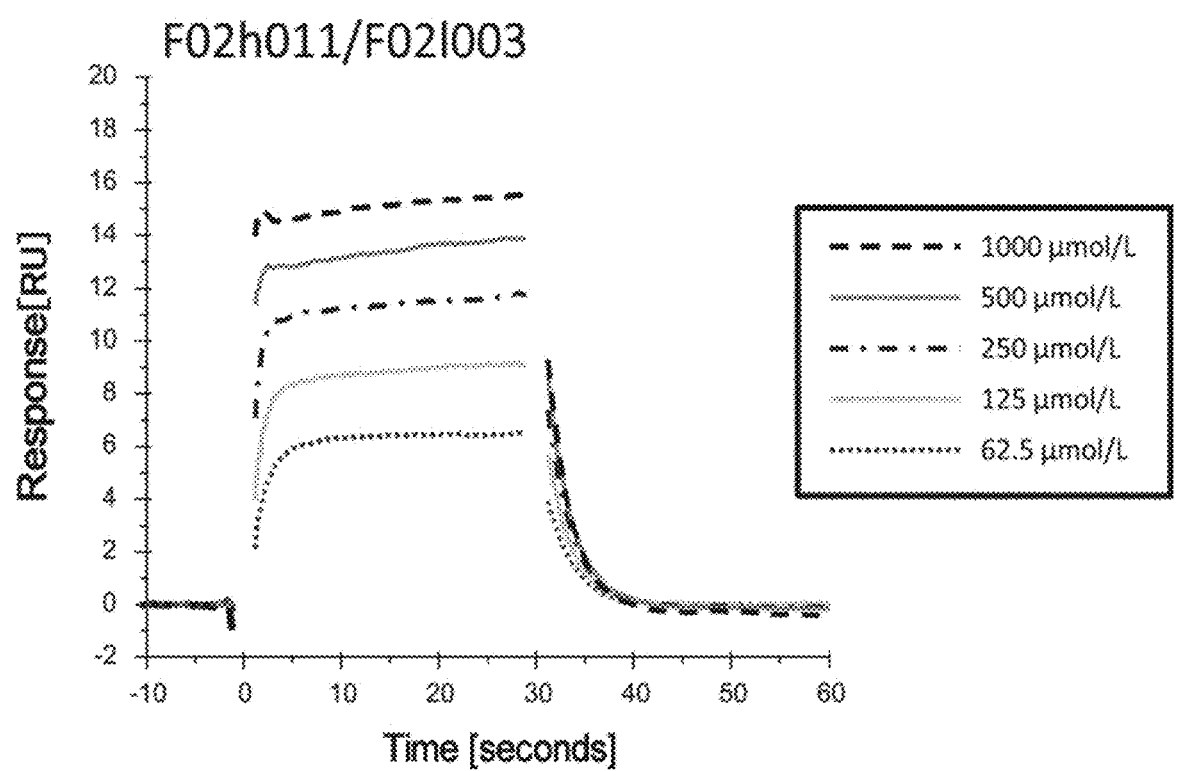

FIG. 32 shows sensorgrams of surface plasmon resonance-based analysis demonstrating that clone F02h011/F021003, which is produced by introducing mutations into the framework sequence of 6RNMSC1-2_F02 to restore the germline sequence, binds to (interacts with) kynurenine. The sensorgrams show the interactions between F02h011/F021003 and kynurenine at 1000, 500, 250, 125, and 62.5 µM in order from the top.

Figure 33:
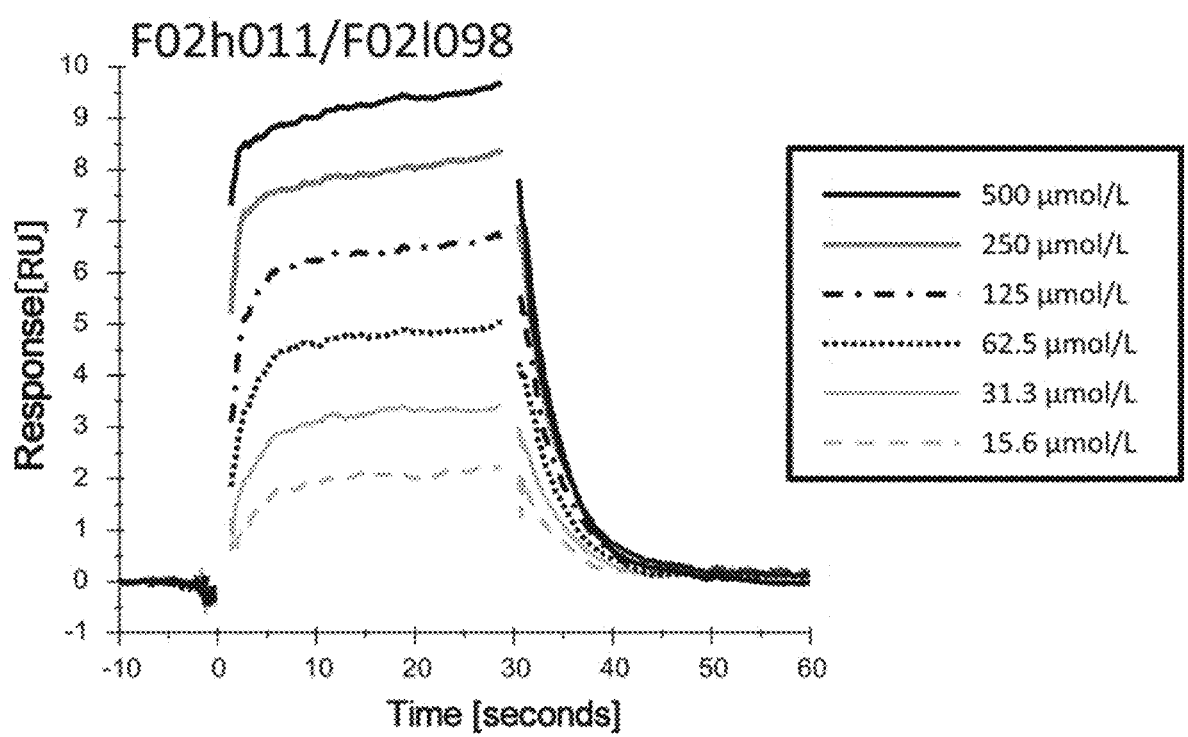

FIG. 33 shows sensorgrams of surface plasmon resonance-based analysis demonstrating that clone F02h011/F021098, which is produced by introducing modifications that enhance kynurenine binding into F02h011/F021003, binds to (interacts with) kynurenine. The sensorgrams show interactions between F02h011/F021098 and kynurenine at 500, 250, 125, 62.5, 31.3, and 15.6 µM in order from the top.

Figure 34:
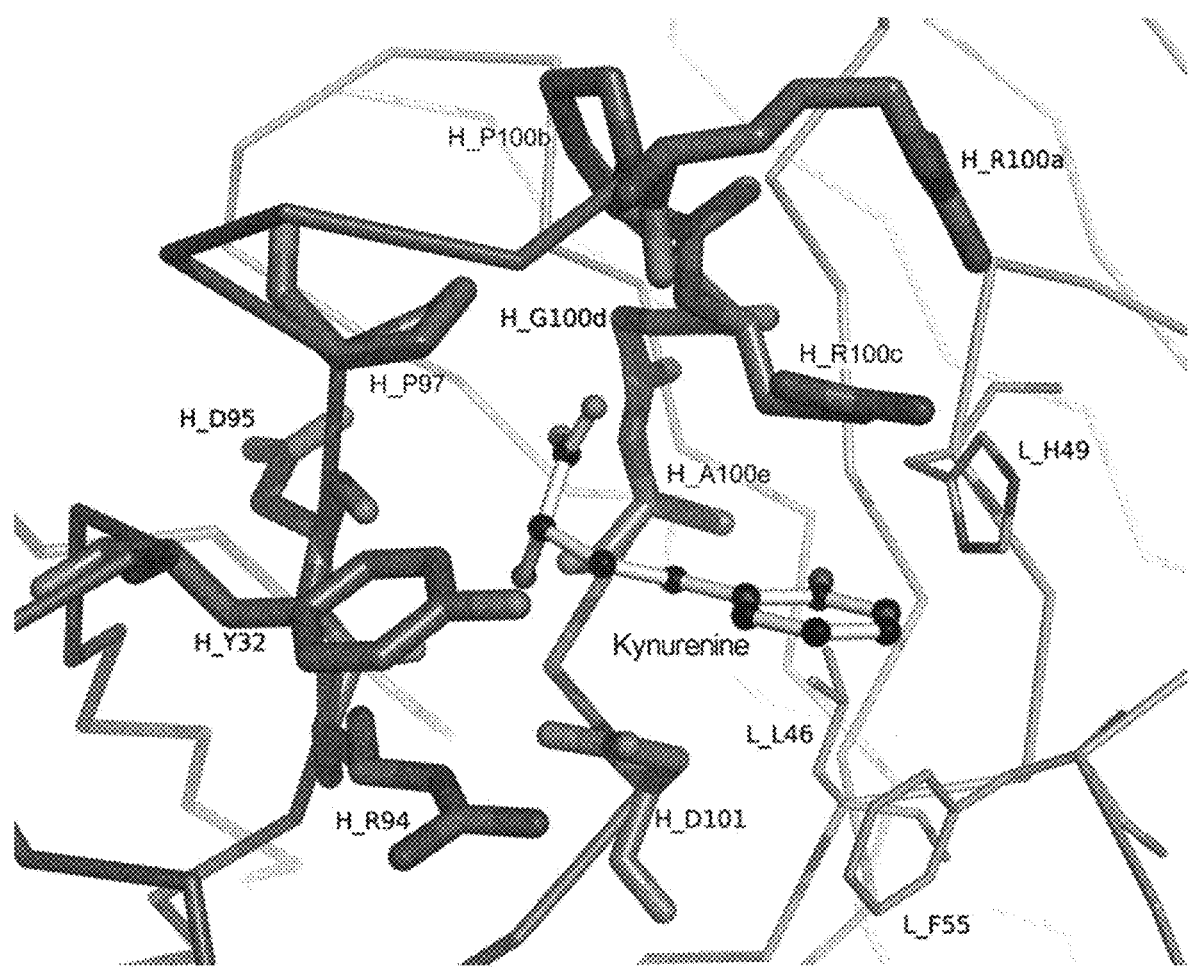

FIG. 34 shows the mode of binding between the 6RNMSC1-2_F02 Fab fragment and kynurenine. In the figure, thick black lines show the heavy chain and thin grey lines show the light chain of the antibody, and kynurenine is shown by a ball-and-stick model. The amino acid residues at a distance of 4.2 Å or less from kynurenine are shown by a stick model.

Figure 35:
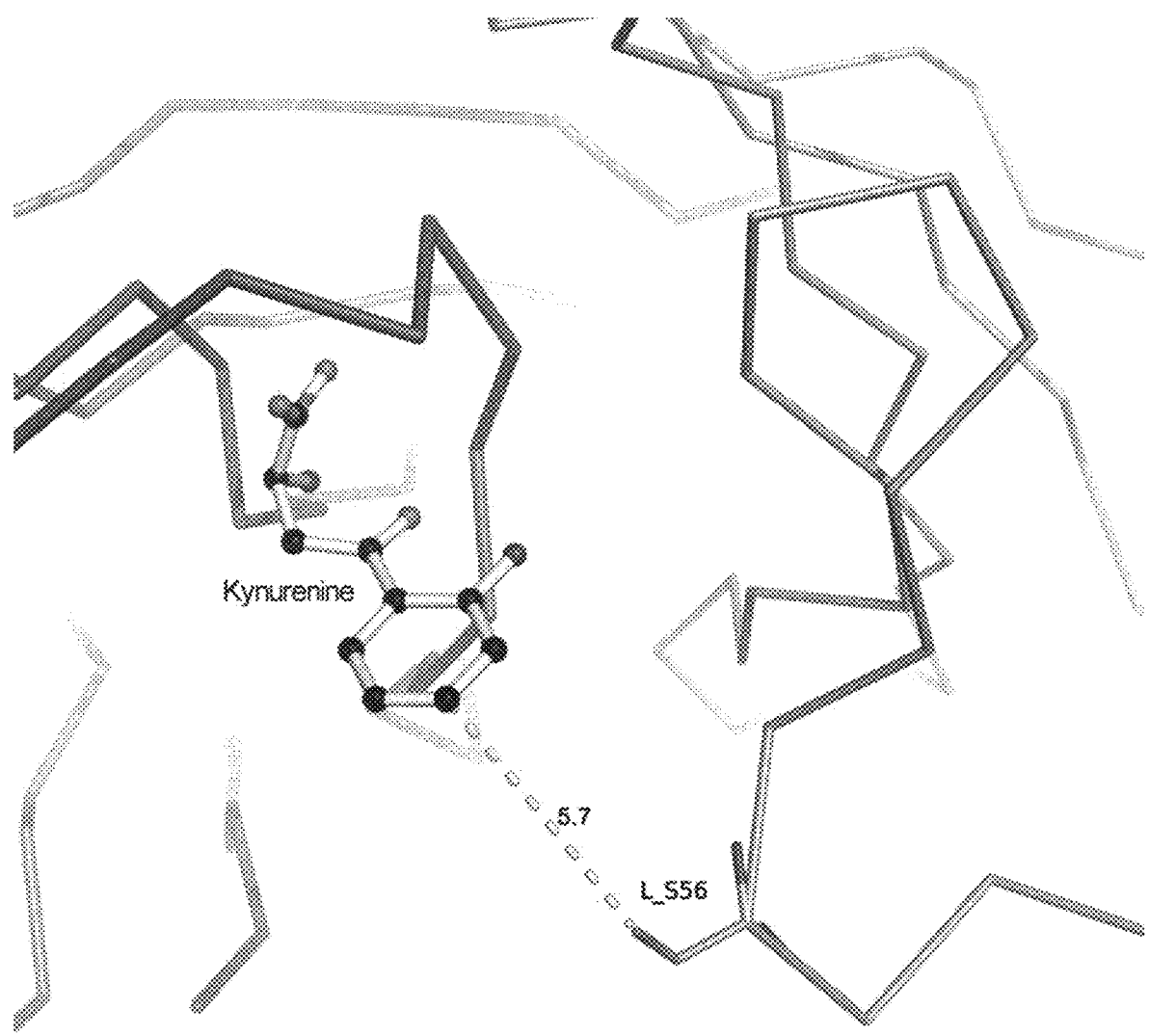

FIG. 35 shows the mode of binding between the 6RNMSC1-2_F02 Fab fragment and kynurenine. In the figure, thick black lines show the heavy chain and thin grey lines show the light chain of the antibody, and kynurenine is shown by a ball-and-stick model. The light chain Ser56 (Kabat numbering) is shown by a stick model. The dashed line and the number on the dashed line show the shortest distance between the non-hydrogen atoms of light chain Ser56 and kynurenine.

Figure 36:
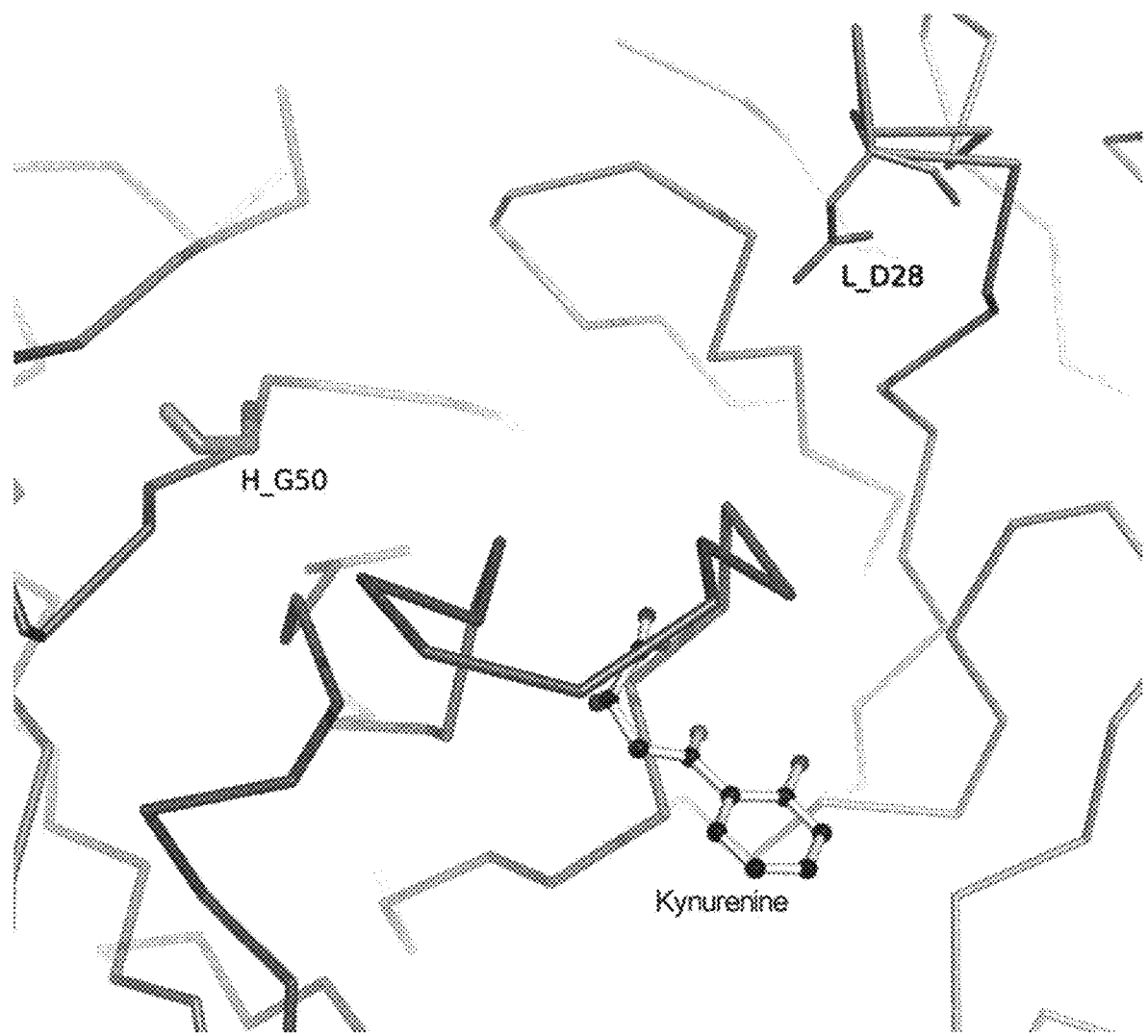

FIG. 36 shows the mode of binding between the 6RNMSC1-2_F02 Fab fragment and kynurenine. In the figure, thick black lines show the heavy chain and thin grey lines show the light chain of the antibody, and kynurenine is shown by a ball-and-stick model. The heavy chain Gly50 and the light chain Asp28 (Kabat numbering) are shown by a stick model.

Figure 37:
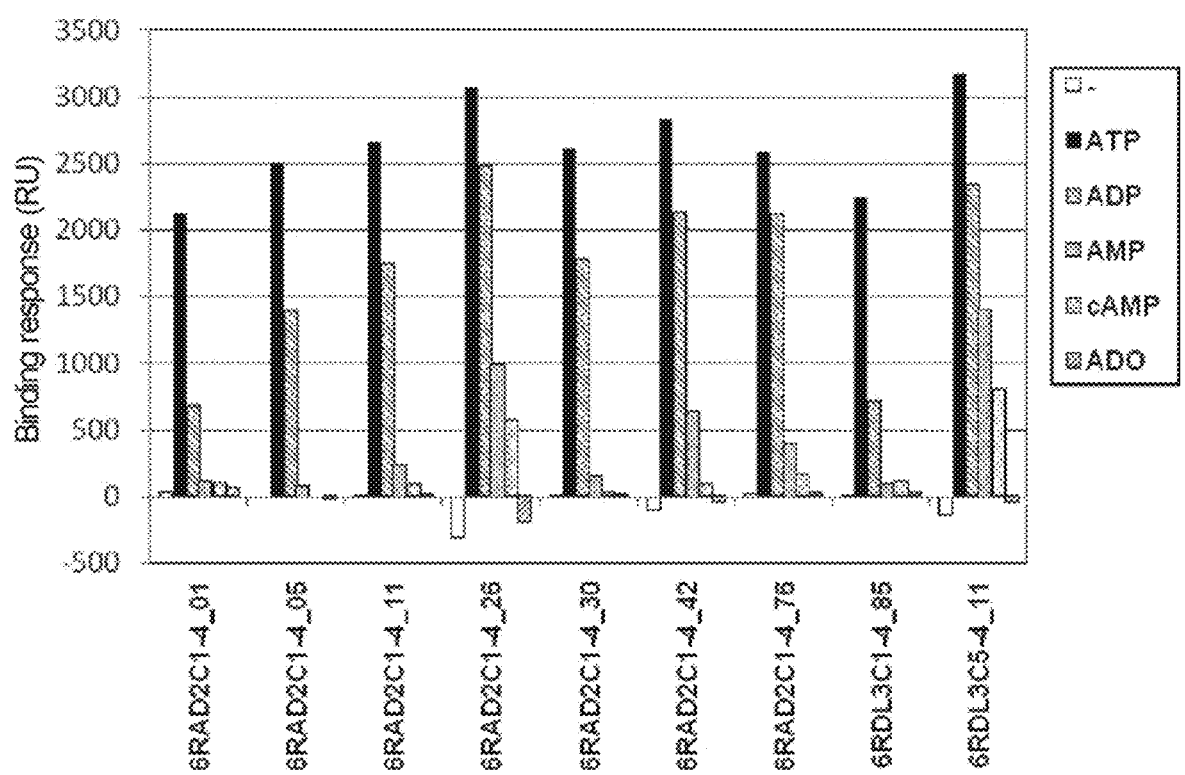

FIG. 37 is a graph showing the level of binding (binding response (RU)) when 1 µM of each clone was interacted with IL-6R immobilized on Sensor chip CM5 for 120 seconds in the presence or absence of each of the small molecules at 1 mM.

Figure 38:
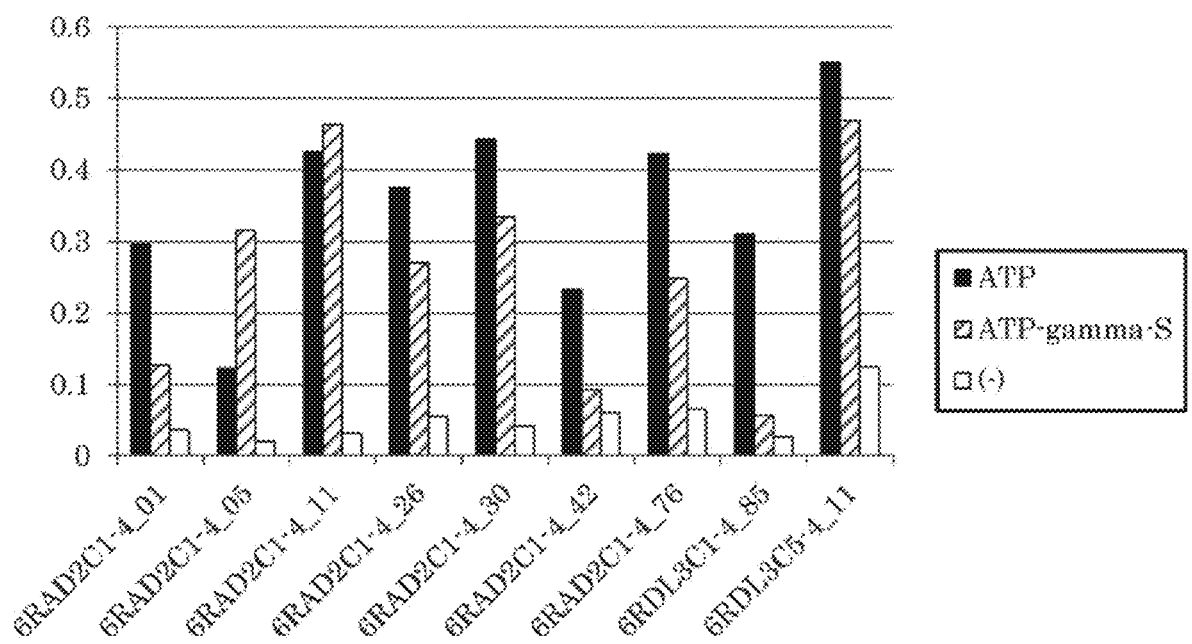

FIG. 38 is a graph showing the level of binding (binding response (RU)) when 10 µg/mL of each clone was interacted with IL-6R immobilized on Octet sensors for 120 seconds in the presence or absence of each of the small molecules at 1 mM.

Figure 39:
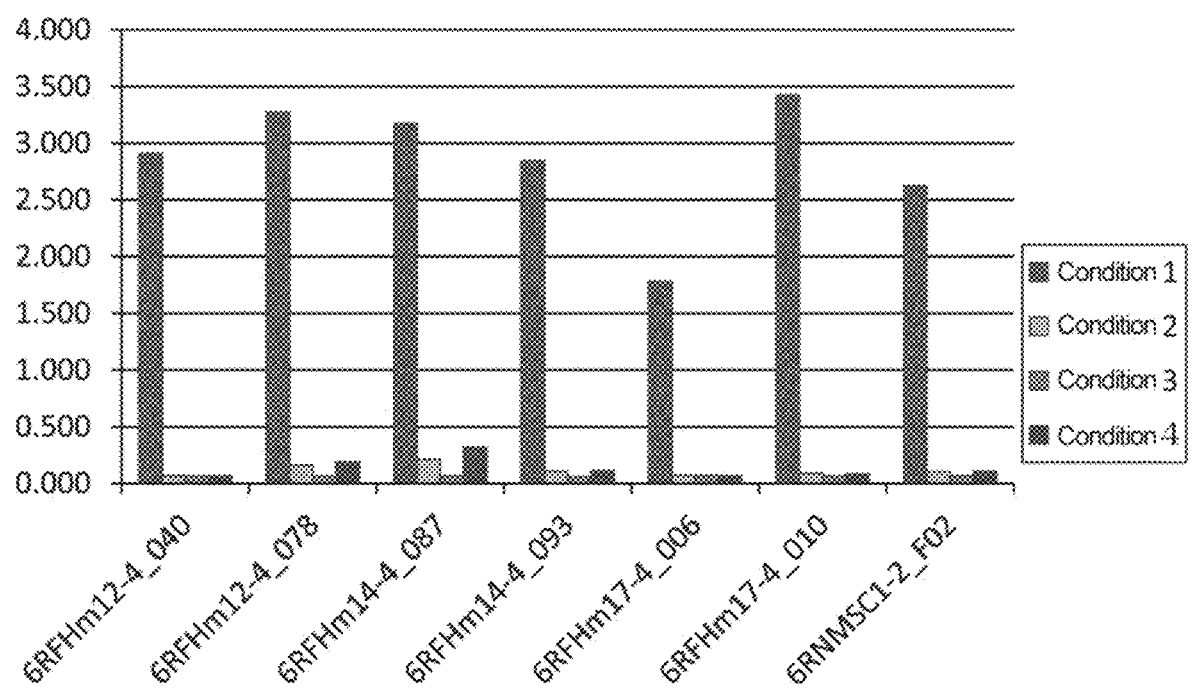

FIG. 39 shows results of ELISA performed on clones obtained from the Ver. A kynurenine library, 6RFHm12-4_040, 6RFHm12-4_078, 6RFHm14-4_087, 6RFHm14-4_093, 6RFHm17-4_006, and 6RFHm17-4_010, against hIL-6R under the respective conditions. 6RNMSC1-2_F02 was used as the positive control. The vertical axis shows the absorbance values for assessing the hIL-6-binding activity of the antibodies. Details of the respective conditions are shown in Table 38.

Figure 40:
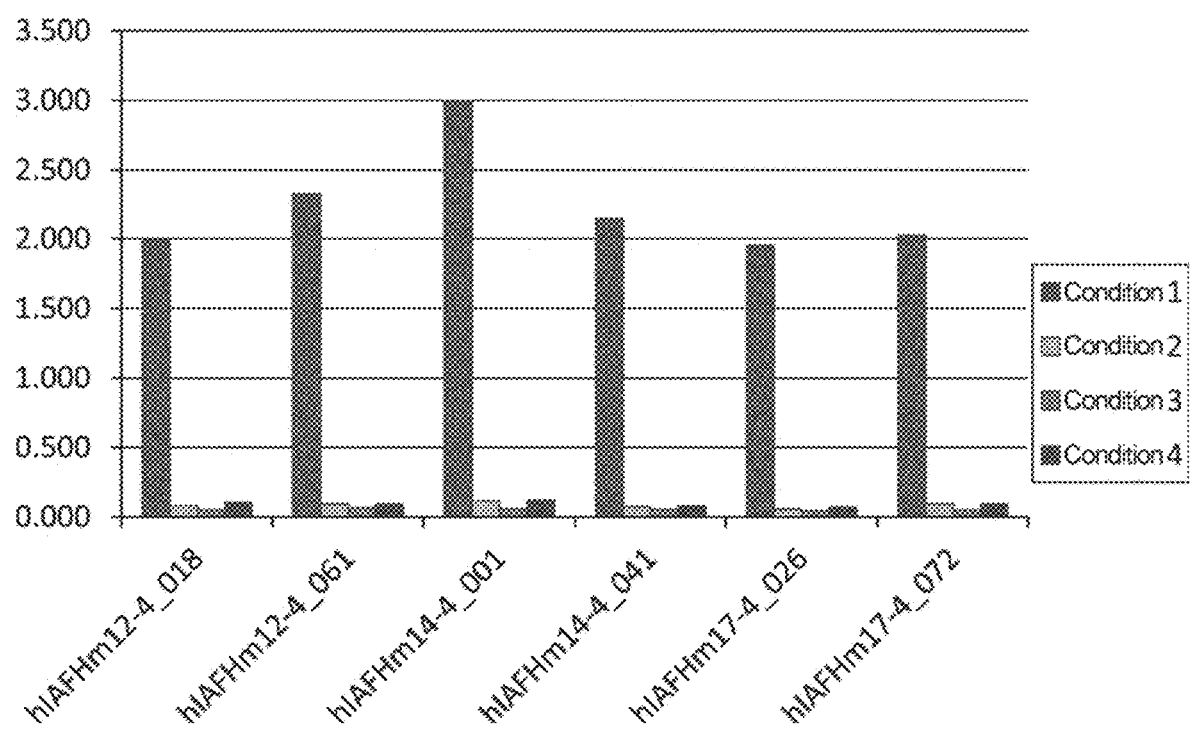

FIG. 40 shows results of ELISA performed on clones obtained from the Ver. A kynurenine library, hIAFHm12-4_018, hIAFHm12-4_061, hIAFHm14-4_001, hIAFHm14-4_041, hIAFHm17-4_026, and hIAFHm17-4_072, against hIgA-Fc under the respective conditions. The vertical axis shows the absorbance values for assessing the hIgA-Fc-binding activity of the antibodies. Details of the respective conditions are shown in Table 41.

Figure 41:
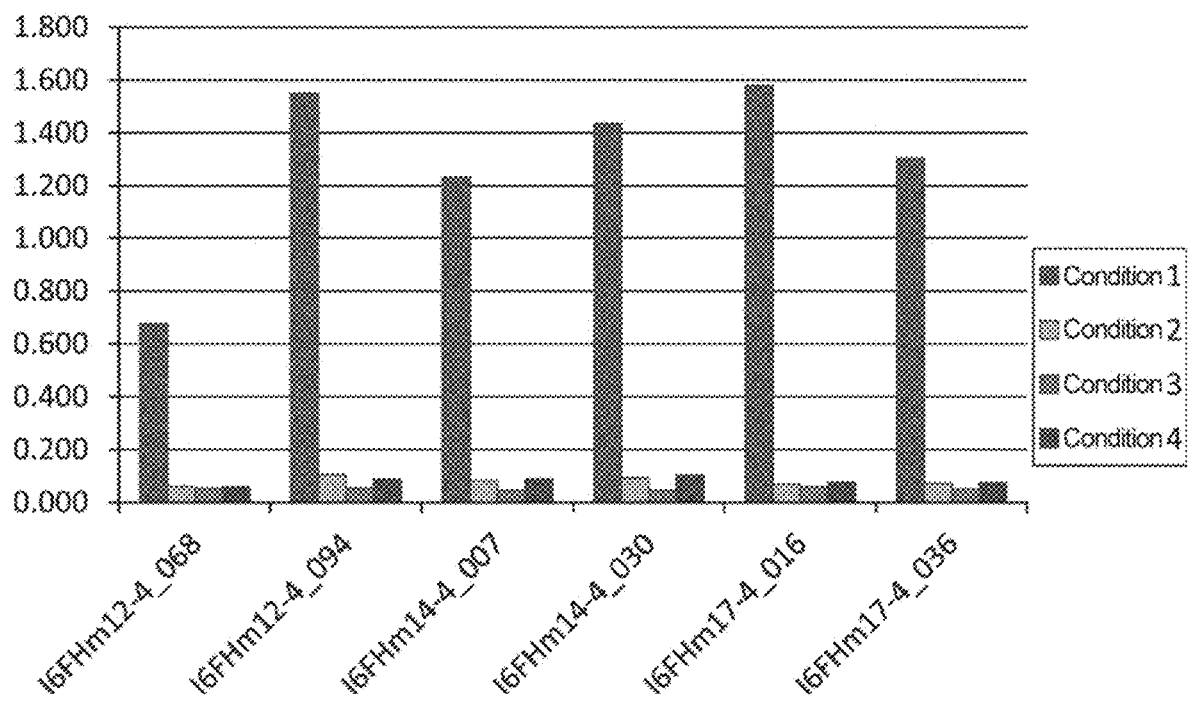

FIG. 41 shows results of ELISA performed on clones obtained from the Ver. A kynurenine library, I6FHm12-4_068, I6FHm12-4_094, I6FHm14-4_007, I6FHm14-4_030, I6FHm17-4_016, and I6FHm17-4_036, against hIL-6 under the respective conditions. The vertical axis shows the absorbance value for assessing the hIL-6-binding activity of the antibodies. Details of the respective conditions are shown in Table 44.

Figure 42:
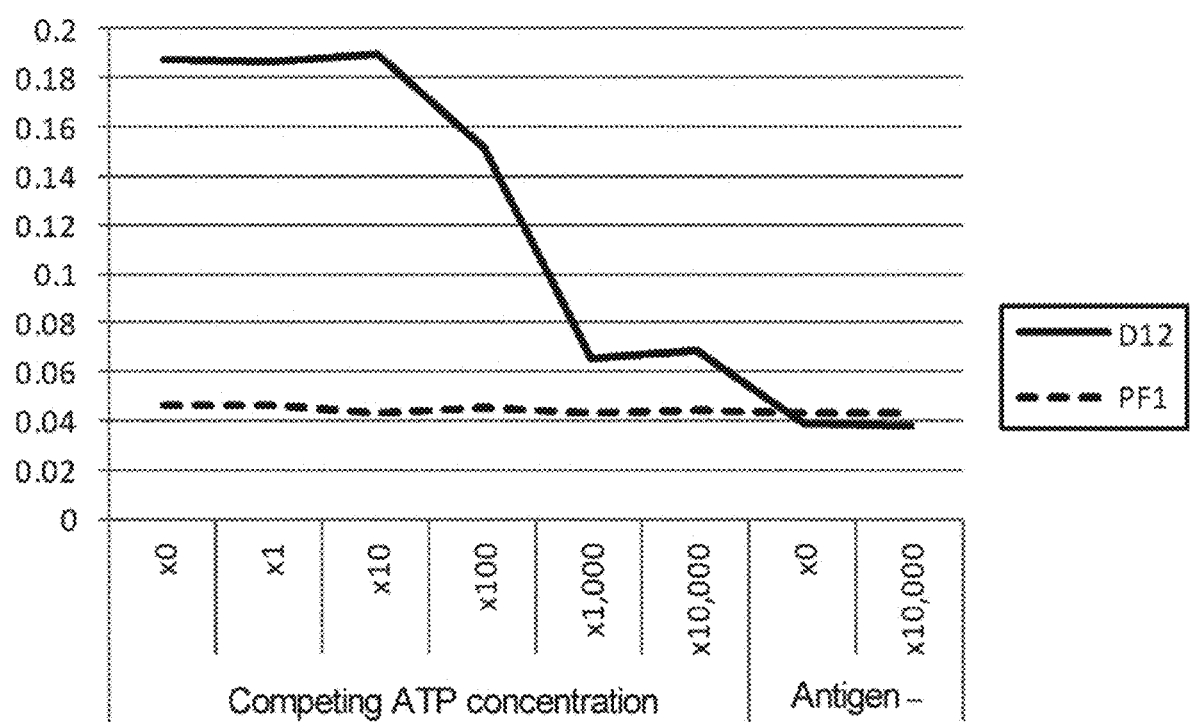

FIG. 42 is a graph that assesses the ability of ATP to inhibit binding of ATNLSA1-4_D12 to the biotin-labeled antigen (a mixture of 5'-Adenosine-PEG-biotin and ATP-PEG-biotin).

Figure 43:
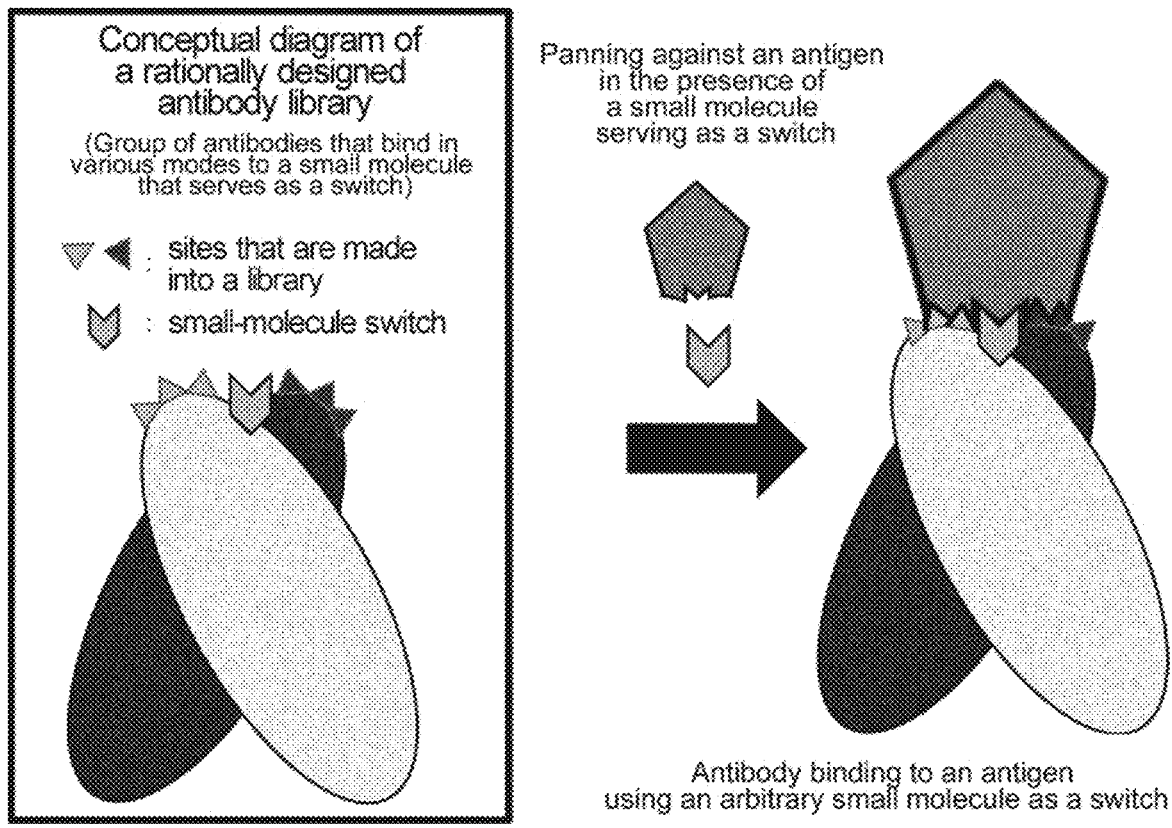

FIG. 43 is a figure for showing the concept of a rationally designed antibody library that can yield small-molecule-switch antibodies against any antigen, wherein the library is made from antibody variable region portions that are in contact with the antigen, and the small molecule is positioned between the antibodies and the antigen as a switch.

Figure 44:
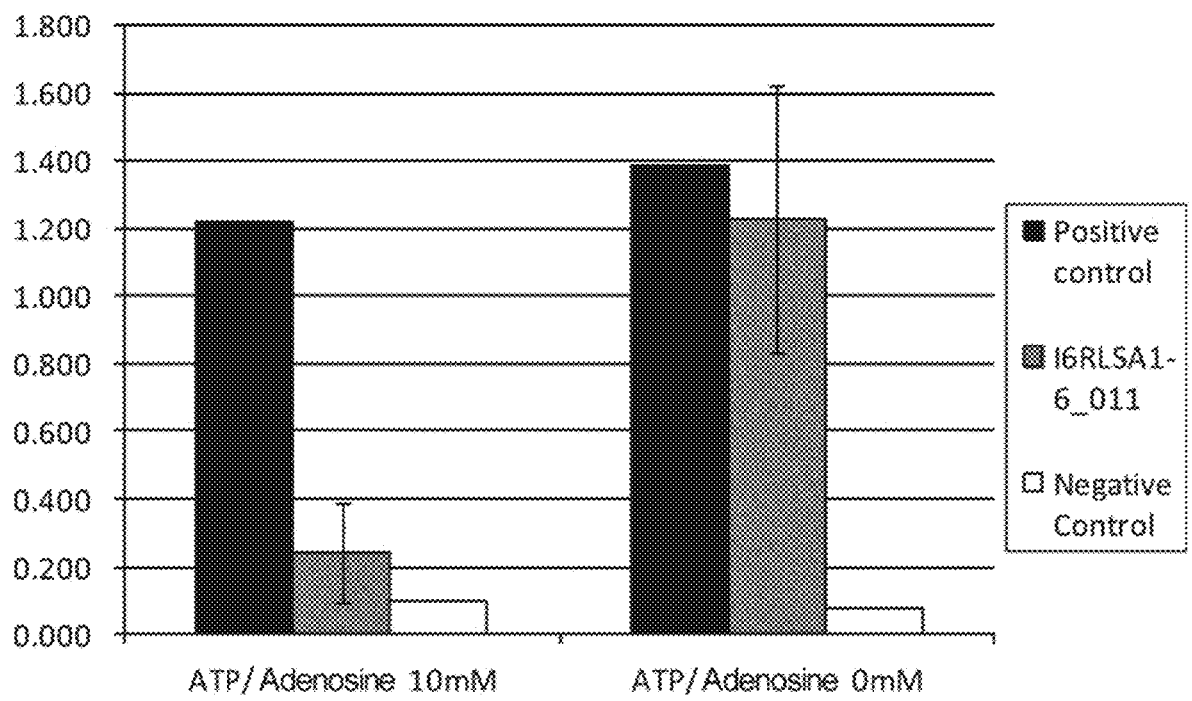

FIG. 44 is a figure showing results of ELISA performed on clone I6RLSA1-6_011, which was obtained from the rationally designed antibody library using ATP/Adenosine-binding antibodies as the template, against human IL-6 in the presence or absence of ATP and adenosine at 10 mM. The vertical axis shows the absorbance value for evaluating the human IL-6-binding activity of the antibody. The clone that shows human IL-6-binding activity regardless of the presence or absence of a small molecule, which was obtained from the rationally designed antibody library, was used as the positive control. M13KO7 Helper Phage was used as the negative control.

Figure 45:
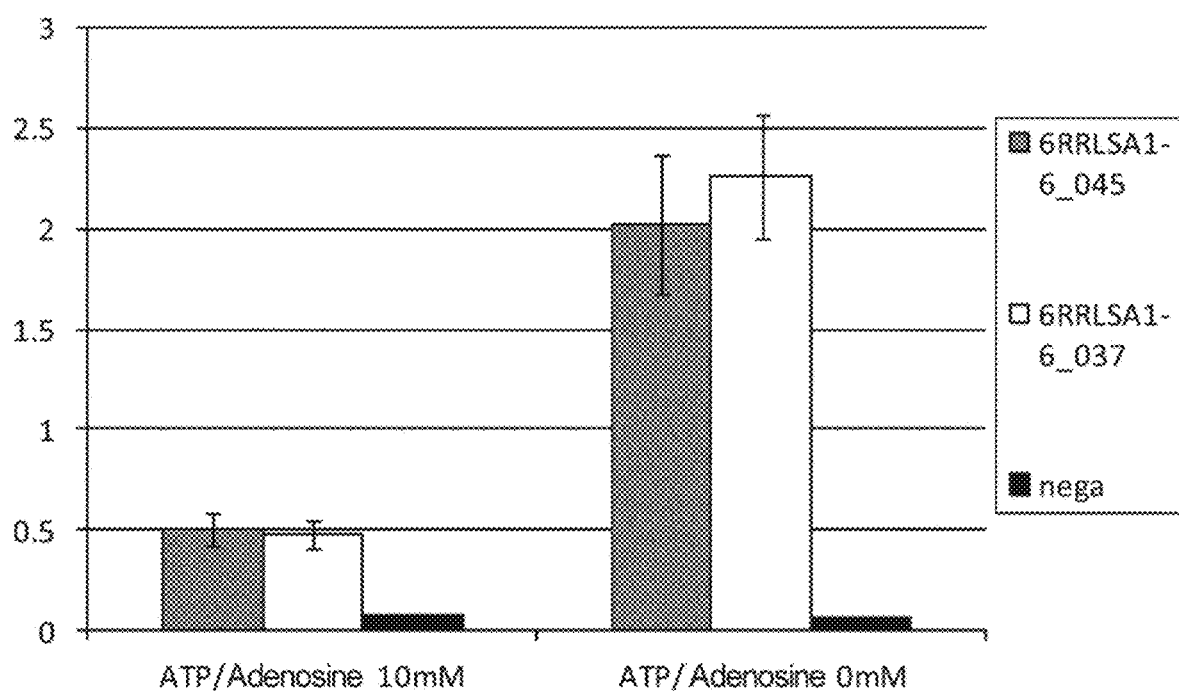

FIG. 45 is a figure showing results of ELISA performed on clones 6RRLSA1-6_037 and 6RRLSA1-6_045, which were obtained from the rationally designed antibody library using ATP/Adenosine-binding antibodies as the template, against human IL-6 receptor in the presence or absence of ATP and adenosine at 10 mM. The vertical axis shows the absorbance value for evaluating the binding activity of the antibodies to the human IL-6 receptor. M13KO7 Helper Phage was used as the negative control (shown as nega in the figure).

Figure 46:
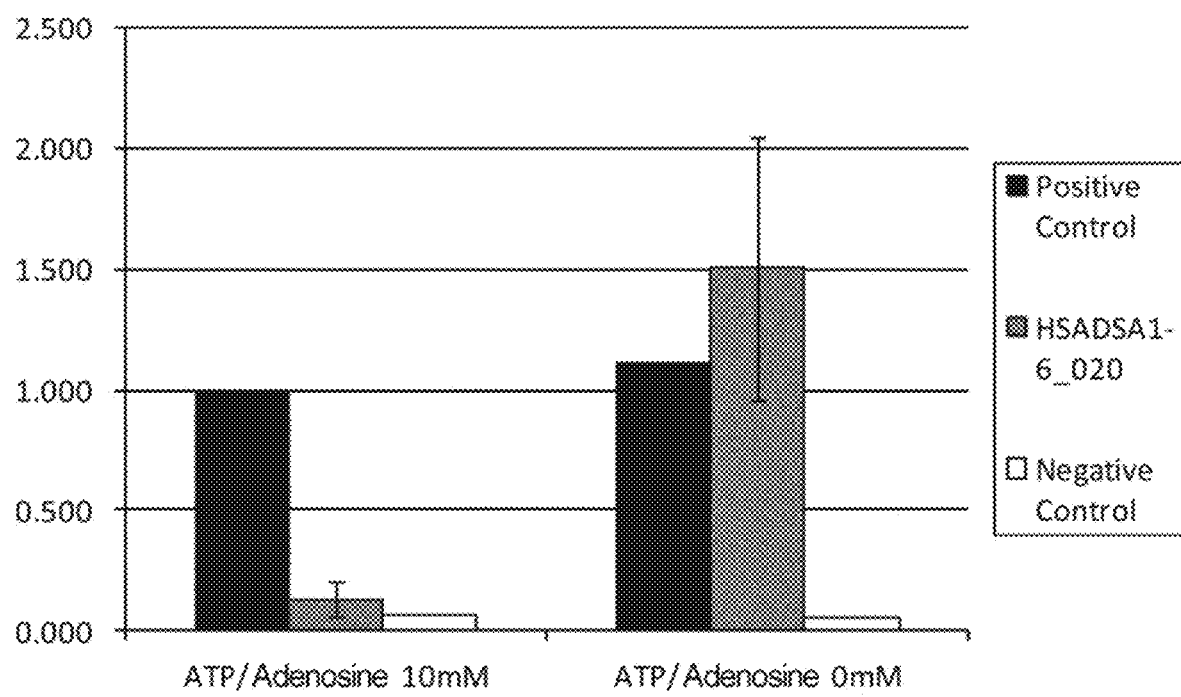

FIG. 46 is a figure showing the result of ELISA performed on clone HSADSA1-6_020 obtained from the rationally designed antibody library, which library uses as a template antibodies that bind ATP/Adenosine, against HSA in the presence or absence of ATP and adenosine at 10 mM. The vertical axis shows the absorbance value which evaluates binding activity of the antibody to HSA. A clone obtained from the rationally designed antibody library and showing binding activity toward HSA regardless of the presence of small molecules was used as the positive control. M13KO7 Helper Phage was used as the negative control.

MODE FOR CARRYING OUT THE INVENTION

The definitions and detailed description below are provided to facilitate understanding of the present invention illustrated herein.

Amino Acids

Herein, amino acids are described by one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Alteration of Amino Acids

For amino acid alteration in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately employed. Furthermore, several known methods may also be employed as amino acid alteration methods for substitution to unnatural amino acids (Annu. Rev. Biophys. Biomol. Struct. (2006) 35, 225-249; and Proc. Natl. Acad. Sci. U.S.A. (2003) 100 (11), 6353-6357). For example, it is suitable to use a cell-free translation system (Clover Direct (Protein Express)) containing a tRNA which has an unnatural amino acid bound to a complementary amber suppressor tRNA of one of the stop codons, the UAG codon (amber codon).

In the present specification, the meaning of the term "and/or" when describing the site of amino acid alteration includes every combination where "and" and "or" are suitably combined. Specifically, for example, "the amino acids at positions 33, 55, and/or 96 are substituted" includes the following variation of amino acid alterations:
amino acid(s) at (a) position 33, (b) position 55, (c) position 96, (d) positions 33 and 55, (e) positions 33 and 96, (f) positions 55 and 96, and (g) positions 33, 55, and 96.

Furthermore, herein, as an expression showing alteration of amino acids, an expression that shows before and after a number indicating a specific position, one-letter or three-letter codes for amino acids before and after alteration, respectively, may be used appropriately. For example, the alteration N100bL or Asn100bLeu used when substituting an amino acid contained in an antibody variable region indicates substitution of Asn at position 100b (according to Kabat numbering) with Leu. That is, the number shows the amino acid position according to Kabat numbering, the one-letter or three-letter amino-acid code written before the number shows the amino acid before substitution, and the one-letter or three-letter amino-acid code written after the number shows the amino acid after substitution. Similarly the alteration P238D or Pro238Asp used when substituting an amino acid of the Fc region contained in an antibody constant region indicates substitution of Pro at position 238 (according to EU numbering) with Asp. That is, the number shows the amino acid position according to EU numbering, the one-letter or three-letter amino-acid code written before the number shows the amino acid before substitution, and the one-letter or three-letter amino-acid code written after the number shows the amino acid after substitution.

Antigens

Herein, "antigens" are not particularly limited in their structure, as long as they comprise epitopes to which antigen-binding domains bind. In other words, antigens can be inorganic or organic substances. Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIAALK-2, activin RIB ALK-4, activin RIIA, activin RIIB, ADAM, ADAM10, ADAM12, ADAM15, ADAM17/TACE, ADAMS, ADAMS, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Ax1, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, PD1, PDL1, LAG3, TIM3, galectin-9, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gash, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, 1-309, TAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-21, IL-23, IL-27, interferon (INF)-alpha, INF-beta, INF-gamma, inhibin, iNOS, insulin A chain, insulin B chain, insulin-like growth factorl, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bpl, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, WIC (HLA-DR), MIF, MIG, MIP, MIP-1-alpha, MK, MMACI, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGGI, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGD2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRl (ALK-5), TGF-betaRII, TGF-betaR11b, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alphabeta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TLR1 (Toll-like receptor 1), TLR2, TLR3, TLR4, TLR5, TLR6, TLR7, TLR8, TLR9, TLR10, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (fit-1), VEGF, VEGFR, VEGFR-3 (fit-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3 a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and S1P; and receptors for hormone and growth factors. Preferred antigens are antigens that are expressed in cancer cells, immune cells, stromal cells, or such present in cancer tissues or inflammatory tissues.

While receptors are recited as examples of the above-mentioned antigens, when these receptors exist in soluble forms in biological fluids, they may also be used as antigens that bind to the antigen-binding molecule of the present invention, which contains an antigen-binding domain whose antigen-binding activity varies depending on the concentration of the small molecule compound (e.g., target tissue-specific compound). An example of a non-limiting embodiment of such a soluble receptor is the soluble IL-6R, which is a protein consisting of the amino acids at positions 1 to 357 in the IL-6R polypeptide sequence of SEQ ID NO: 1 as described in Mullberg et al. (J. Immunol. (1994) 152 (10), 4958-4968).

Membrane-type molecules expressed on cell membranes and soluble molecules secreted from cells to the outside of the cells are included in the examples of the above-mentioned antigens. When the antigen-binding molecule of the present invention, which contains an antigen-binding domain whose antigen-binding activity varies depending on the concentration of the target tissue-specific compound, binds to a soluble molecule secreted from cells, it is preferable that the antigen-binding molecule has neutralizing activity as described later.

The fluids in which the soluble molecules exist are not limited, and the soluble molecules may exist in biological fluids, or more specifically in all fluids filling the space between tissues and cells or vessels in organisms. In a non-limiting embodiment, the soluble molecules to which antigen-binding molecules of the present invention bind may be present in the extracellular fluid. In vertebrates, extracellular fluid is a general term for plasma, interstitial fluid, lymph, compact connective tissue, cerebrospinal fluid, spinal fluid, puncture fluid, synovial fluid, or such components in the bone and cartilage, alveolar fluid (bronchoalveolar lavage fluid), peritoneal fluid, pleural fluid, pericardial effusion, cyst fluid, aqueous humor (hydatoid), or such transcellular fluids (various fluids in the glandular cavities and fluids in the digestive tract cavity and other body cavity fluids produced as a result of active transport/secretory activities of cells).

When an antigen-binding molecule of the present invention comprising an antigen-binding domain whose antigen-binding activity varies depending on the concentration of a small molecule compound (e.g., target tissue-specific compound) binds to a membrane-type molecule expressed on a cell membrane, suitable examples of the antigen-binding molecule include antigen-binding molecules which have cytotoxic activity, bind to a cytotoxic substance, or have the ability to bind to a cytotoxic substance, as described later. Furthermore, antigen-binding molecules having a neutralizing activity instead of the properties of having a cytotoxic activity, binding to a cytotoxic substance, or having the ability to bind to a cytotoxic substance; or in addition to these properties are also suitable examples of a non-limiting embodiment.

Epitopes

"Epitope" means an antigenic determinant in an antigen, and refers to an antigen site to which the antigen-binding domain of an antigen-binding molecule disclosed herein binds. Thus, for example, the epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence has been recognized. Such a linear epitope typically contains at least three and most commonly at least five, for example, about 8 to about 10 or 6 to 20 amino acids in a specific sequence.

In contrast to the linear epitope, a "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

The structure of the antigen-binding domain which binds to an epitope is called a paratope. An epitope and a paratope bind with stability through the action of hydrogen bonds, electrostatic force, van der Waals force, hydrophobic bonds, and such between the epitope and the paratope. This strength of binding between the epitope and paratope is called affinity. The total sum of binding strength when a plurality of antigens and a plurality of antigen-binding molecules bind is referred to as avidity. When an antibody comprising a plurality of antigen-binding domains (i.e., multivalent antibody) or such binds to a plurality of epitopes, the affinity acts synergistically, and therefore avidity becomes higher than affinity.

Binding Activity

Examples of a method for assessing the epitope binding by a test antigen-binding molecule containing an IL-6R antigen-binding domain are described below. According to the examples below, methods for assessing the epitope binding by a test antigen-binding molecule containing an antigen-binding domain for an antigen other than IL-6R, can also be appropriately conducted.

For example, whether a test antigen-binding molecule containing an IL-6R antigen-binding domain recognizes a linear epitope in the IL-6R molecule can be confirmed for example as mentioned below. A linear peptide comprising an amino acid sequence forming the extracellular domain of IL-6R is synthesized for the above purpose. The peptide can be synthesized chemically, or obtained by genetic engineering techniques using a region encoding the amino acid sequence corresponding to the extracellular domain in an IL-6R cDNA. Then, a test antigen-binding molecule containing an IL-6R antigen-binding domain is assessed for its binding activity towards a linear peptide comprising the amino acid sequence forming the extracellular domain. For example, an immobilized linear peptide can be used as an antigen by ELISA to evaluate the binding activity of the antigen-binding molecule towards the peptide. Alternatively, the binding activity towards a linear peptide can be assessed based on the level that the linear peptide inhibits the binding of the antigen-binding molecule to IL-6R-expressing cells. These tests can demonstrate the binding activity of the antigen-binding molecule towards the linear peptide.

Whether a test antigen-binding molecule containing an IL-6R antigen-binding domain recognizes a conformational epitope can be assessed as follows. IL-6R-expressing cells are prepared for the above purpose. A test antigen-binding molecule containing an IL-6R antigen-binding domain can be determined to recognize a conformational epitope when it strongly binds to IL-6R-expressing cells upon contact, but does not substantially bind to an immobilized linear peptide comprising an amino acid sequence forming the extracellular domain of IL-6R. Herein, "not substantially bind" means that the binding activity is 80% or less, generally 50% or less, preferably 30% or less, and particularly preferably 15% or less compared to the binding activity towards cells expressing human IL-6R.

Methods for assaying the binding activity of a test antigen-binding molecule containing an IL-6R antigen-binding domain towards IL-6R-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using IL-6R-expressing cells as antigen.

In the ELISA format, the binding activity of a test antigen-binding molecule containing an IL-6R antigen-binding domain towards IL-6R-expressing cells can be assessed quantitatively by comparing the levels of signal generated by enzymatic reaction. Specifically, a test polypeptide complex is added to an ELISA plate onto which IL-6R-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody binding titer for IL-6R-expressing cells can be determined to compare the binding activity of the test antigen-binding molecule towards IL-6R-expressing cells.

The binding of a test antigen-binding molecule towards an antigen expressed on the surface of cells suspended in buffer or the like can be detected using a flow cytometer. Known flow cytometers include, for example, the following devices:
FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity of a test antigen-binding molecule containing an IL-6R antigen-binding domain towards an antigen include, for example, the following method. First, IL-6R-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule, which is represented by the quantity of the test antigen-binding molecule bound, can be determined by measuring the Geometric Mean value.

Whether a test antigen-binding molecule containing an IL-6R antigen-binding domain shares a common epitope with another antigen-binding molecule can be assessed based on the competition between the two molecules for the same epitope. The competition between antigen-binding molecules can be detected by cross-blocking assay or the like. For example, the competitive ELISA assay is a preferred cross-blocking assay.

Specifically, in cross-blocking assay, the IL-6R protein immobilized to the wells of a microtiter plate is pre-incubated in the presence or absence of a candidate competitor antigen-binding molecule, and then a test antigen-binding molecule is added thereto. The quantity of test antigen-binding molecule bound to the IL-6R protein in the wells is indirectly correlated with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the IL-6R protein-coated wells.

The quantity of the test antigen-binding molecule bound to the wells via the IL-6R protein can be readily determined by labeling the antigen-binding molecule in advance. For example, a biotin-labeled antigen-binding molecule is measured using an avidin/peroxidase conjugate and appropriate substrate. In particular, cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding by a test antigen-binding molecule containing an IL-6R antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or compete for the binding to the same epitope.

When the structure of an epitope bound by a test antigen-binding molecule containing an IL-6R antigen-binding domain has already been identified, whether the test and control antigen-binding molecules share a common epitope can be assessed by comparing the binding activities of the two antigen-binding molecules towards a peptide prepared by introducing amino acid mutations into the peptide forming the epitope.

To measure the above binding activities, for example, the binding activities of test and control antigen-binding molecules towards a linear peptide into which a mutation is introduced are compared in the above ELISA format. Besides the ELISA methods, the binding activity towards the mutant peptide bound to a column can be determined by flowing test and control antigen-binding molecules in the column, and then quantifying the antigen-binding molecule eluted in the elution solution. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, IL-6R-expressing cells and cells expressing IL-6R with a mutation introduced into the epitope are prepared. The test and control antigen-binding molecules are added to a cell suspension prepared by suspending these cells in an appropriate buffer such as PBS. Then, the cell suspensions are appropriately washed with a buffer, and an FITC-labeled antibody that recognizes the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 μg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules, which are represented by the quantity of labeled antibody bound, can be determined by measuring the Geometric Mean value.

In the above method, whether an antigen-binding molecule does "not substantially bind to cells expressing mutant IL-6R" can be assessed, for example, by the following method. First, the test and control antigen-binding molecules bound to cells expressing mutant IL-6R are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the polypeptide complex, the comparison value (ΔGeo–Mean) can be calculated according to Formula 1 below to determine the ratio of increase in fluorescence intensity as a result of the binding by the antigen-binding molecule.

$$\Delta Geo\text{--}Mean = Geo\text{--}Mean \text{ (in the presence of the polypeptide complex)}/Geo\text{--}Mean \text{ (in the absence of the polypeptide complex)} \quad \text{Formula 1:}$$

The Geometric Mean comparison value (ΔGeo–Mean value for the mutant IL-6R molecule) determined by the above analysis, which reflects the quantity of a test antigen-binding molecule bound to cells expressing mutant IL-6R, is compared to the ΔGeo–Mean comparison value that reflects the quantity of the test antigen-binding molecule bound to IL-6R-expressing cells. In this case, the concentrations of the test antigen-binding molecule used to determine the ΔGeo–Mean comparison values for IL-6R-expressing cells and cells expressing mutant IL-6R are particularly preferably adjusted to be equal or substantially equal. An antigen-binding molecule that has been confirmed to recognize an epitope in IL-6R is used as a control antigen-binding molecule.

If the ΔGeo–Mean comparison value of a test antigen-binding molecule for cells expressing mutant IL-6R is smaller than the ΔGeo–Mean comparison value of the test antigen-binding molecule for IL-6R-expressing cells by at least 80%, preferably 50%, more preferably 30%, and particularly preferably 15%, then the test antigen-binding molecule "does not substantially bind to cells expressing mutant IL-6R". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules can be determined to be the same.

Target Tissue

The term "target tissue" as used herein refers to a tissue containing cells carrying antigens to which the antigen-binding molecules of the present invention bind depending on the concentration of small molecule compounds. It is a tissue that yields positive pharmacological effects for the organism carrying the tissue, when the antigen-binding molecules bind to a membrane-type molecule expressed on the cells or bind to a soluble molecule present in the tissue. In this case, the phrase "positive pharmacological effects" refers to effects that relieve, alleviate, ameliorate, or cure symptoms brought about by pathological sites containing the target tissue for the organism carrying the tissue. When the symptoms are brought about by malignant tumors such as cancer, a non-limiting embodiment of a mechanism that yields such a pharmacological effect is, for example, cytotoxic activity and growth inhibition against cancer cells, and immunostimulation in cancer tissues. In the case of inflammatory diseases, examples of such a non-limiting embodiment of the mechanism include immunosuppression and activity to block actions of inflammatory cytokines in inflammatory tissues.

Cancer Tissue-Specific Compounds

The term "compound specific to a cancer tissue (cancer tissue-specific compound)" as used herein refers to a compound differentially present in cancer tissues as compared to non-cancerous tissues. Herein, the term "cancer" is generally used to describe malignant neoplasms, which may be metastatic or non-metastatic. Non-limiting examples of carcinomas developed from epithelial tissues such as skin or digestive tract include brain tumor, skin cancer, head and neck cancer, esophageal cancer, lung cancer, stomach cancer, duodenal cancer, breast cancer, prostate cancer, cervical cancer, endometrial cancer, pancreatic cancer, liver cancer, colorectal cancer, colon cancer, bladder cancer, and ovarian cancer. Non-limiting examples of sarcomas developed from non-epithelial (interstitial) tissues such as muscles include osteosarcoma, chondrosarcoma, rhabdomyosarcoma, leiomyosarcoma, liposarcoma, and angiosarcoma. Non-limiting examples of hematological cancer derived from hematopoietic organs include malignant lymphomas including Hodgkin's lymphoma and non Hodgkin's lymphoma; leukemia including acute myelocytic leukemia or chronic myelocytic leukemia, and acute lymphatic leukemia or chronic lymphatic leukemia; and multiple myeloma. The term "neoplasm" widely used herein refers to any newly formed diseased tissue tumor. In the present invention, neoplasms cause formation of tumors, which are partly characterized by angiogenesis. Neoplasms may be benign such as hemangioma, glioma, or teratoma, or malignant such as carcinoma, sarcoma, glioma, astrocytoma, neuroblastoma, or retinoblastoma.

The term "cancer tissue" refers to a tissue containing at least one cancer cell. Therefore, as cancer tissues contain cancer cells and blood vessels, it refers to all cell types contributing to the formation of a tumor mass containing cancer cells and endothelial cells. Herein, "tumor mass"

refers to a foci of tumor tissue. The term "tumor" is generally used to mean a benign neoplasm or a malignant neoplasm.

For example, in several embodiments, cancer tissue-specific compounds may be compounds defined by qualitative properties of cancer tissues such as being present in cancer tissues but absent in non-cancer tissues, or being absent in cancer tissues but present in non-cancer tissues. In other embodiments, cancer tissue-specific compounds may be compounds defined by quantitative properties of cancer tissues such as being present in cancer tissues at a concentration different (for example, higher concentration or lower concentration) from that in non-cancer tissues. For example, cancer tissue-specific compounds are present differentially at arbitrary concentrations. Generally, cancer tissue-specific compounds can be present at a concentration increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 2-fold, at least 5-fold, at least 10-fold, at least 50-fold, at least 100-fold, at least $10^3$-fold, at least $10^4$-fold, at least $10^5$-fold, at least $10^6$-fold, or more, or up to infinity (i.e., when the compound is absent in non-cancerous tissues). Alternatively, they can generally be present at a concentration decreased by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or at least 100% (i.e., absent). Preferably, cancer tissue-specific compounds are differentially present at statistically significant concentrations (that is, as determined using either Welch's t-test or Wilcoxon rank sum test, the p value is less than 0.05 and/or the q value is less than 0.10). Examples of a non-limiting embodiment of a cancer tissue-specific compound include compounds which are cancer tissue-specific metabolites produced by metabolic activities characteristic of cancer cells, immune cells, or stromal cells contained in cancer tissues, such as those described below (cancer tissue-specific metabolites, cancer cell-specific metabolites, metabolites specific to immune cells that infiltrated into cancer tissues, and cancer stromal cell-specific metabolites).

The term "unnatural compound" as used herein refers to an unnaturally derived chemical substance and its metabolites. An embodiment of the invention is an unnaturally derived chemical substance that has the property of accumulating at the target tissue after being administered to a living body from outside the body, and metabolites thereof. Examples of an unnatural compound include (1) Capecitabine (Xeloda) and its metabolite 5-FU (fluorouracil), and (2) TH-302 and bromo-isophosphoramide mustard (Br-IPM). 5-FU is a metabolite of Capecitabine (Xeloda), and is known to be metabolized by cytidine deaminase and thymidine phosphorylase which are metabolic enzymes specific in cancer tissues (Desmoulin F. et al. Drug Metab Dispos. 2002). TH-302 is known to be converted to Br-IPM by reduction under a low-oxygen condition as in the periphery of cancer tissues (Duan J X, et al. J Med Chem. 2008). For example, when Capecitabine (Xeloda) is administered, it is metabolized into 5-FU by cancer-specific metabolic enzymes, and therefore, the concentration of 5-FU becomes high at the cancer site (Desmoulin F. et al. Drug Metab Dispos. 2002). Accordingly, antibodies that use 5-FU as their switch may be able to bind selectively to the target antigen only at the cancer site. Furthermore, besides metabolic enzymes, molecules formed in a low-oxygen environment or an acidic environment specific to cancers may also be used as the switch. For example, TH-302 (Duan J X, et al. J Med Chem. 2008) is metabolized into Br-IPM under a low-oxygen condition, and therefore, antibodies that use Br-IPM as their switch may be able to bind selectively to the target antigen only at the cancer site. Examples of administration methods of the unnatural compound to a living body include known administration methods such as oral administration, administration through instillation, transdermal administration, transnasal administration, intravenous administration, and transpulmonary administration, but are not limited thereto.

Besides chemical substances that have the property of accumulating at the target tissue and metabolites thereof, another embodiment of the term "unnatural compound" used herein also includes chemical substances and such, which is an unnatural compound that serves as a switch that can control the action of antibodies through intake of oral agents, for example, by oral administration. More specifically, they are chemical substances and such, which is an unnatural compound that can be administered non-invasively such as orally and serves as a switch that can control the antibody action, when a switch antibody that binds to a certain antigen is initially administered invasively such as intravenously or subcutaneously; and then an exogenous compound that serves as a switch is administered non-invasively such as orally. Examples of such compounds include ATPγS and kynurenine metabolites, but are not limited thereto. The problem with antibody pharmaceuticals is that since they have a long half-life, side-effects are lasting when these effects occur; however, if effects of such antibodies can be controlled by non-invasive administration such as oral administration of an unnatural compound, effects of the pharmaceuticals can be stopped by terminating administration of the switch molecule when side effects occur. Furthermore, by preliminary administration of a switch antibody, administration of the switch molecule only when symptoms due to the disorder occur, and pharmacological effects exertion by non-invasive administration such as oral administration only when necessary, are allowed.

The "antigen-binding molecules comprising an antigen-binding domain whose antigen-binding activity varies depending on the concentration of an unnatural compound" of the present invention may yield positive pharmacological effects when administered to a living body.

Cancer Tissue-Specific Metabolites

The term "metabolism" refers to chemical changes that take place in biological tissues and includes "anabolism" and "catabolism". Anabolism refers to biosynthesis or accumulation of molecules, and catabolism refers to degradation of molecules. "Metabolites" are intermediates or products that arise from metabolism. "Primary metabolites" refers to metabolites directly involved in the process of growth or proliferation of cells or organisms. "Secondary metabolites" refer to products that are not directly involved in such process of growth or proliferation, and are products such as pigments or antibiotics that are produced as a result of metabolism which biosynthesizes substances that are not directly involved in biological phenomena common to cells and organisms. The metabolites may be metabolites of "biopolymers", or they may be metabolites of "small molecules". "Biopolymers" are polymers comprising one or more types of repeating units. Biopolymers are generally found in biological systems, and examples include cells forming the organism and intercellular matrices that adhere to them, molecules having a molecular weight of approximately 5000 or more which form structures such as interstitial matrices, particularly polysaccharides (carbohydrates and such), peptides (this term is used so as to include polypeptides and proteins), and polynucleotides, and similarly their analogs such as compounds composed of or including amino acid analogs or non-amino acid groups.

As used herein, the term "small molecules" refers to natural chemical substances other than "biopolymers" that exist in vivo or unnatural chemical substances, and are preferably target tissue-specific compounds or unnatural compounds but are not limited thereto. Suitable examples of a non-limiting embodiment of a cancer tissue-specific metabolite described herein include cancer cell-specific small-molecule metabolites (Eva Gottfried, Katrin Peter and Marina P. Kreutz, From Molecular to Modular Tumor Therapy (2010) 3 (2), 111-132). In addition, metabolites that are highly produced by immune cells that infiltrate into cancer tissues, and metabolites that are highly produced by stromal cells that support the survival and/or growth of cancer cells (cancer stromal cells or cancer associated stromal fibroblasts (CAF)) are also included. Infiltrating immune cells are, for example, dendritic cells, inhibitory dendritic cells, inhibitory T cells, exhausted T cells, and myeloma derived suppressor cells (MDSC). Furthermore, metabolites of the present invention include compounds released from inside the cells to outside the cells when cells present in cancer tissues (cancer cells, immune cells, or stromal cells) die due to apoptosis, necrosis, or such.

To identify cancer cell-specific metabolites, metabolomic analyses focused on metabolic profiling can be suitably used, in addition to transcriptome-level analyses (for example, Dhanasekaran et al. (Nature (2001) 412, 822-826), Lapointe et al. (Proc. Natl. Acad. Sci. U.S.A. (2004) 101, 811-816) or Perou et al. (Nature (2000) 406, 747-752)) and proteome-level analyses (for example, Ahram et al. (Mol. Carcinog. (2002) 33, 9-15), Hood et al. (Mol. Cell. Proteomics (2005) 4, 1741-1753)). More specifically, to identify metabolites in test samples, metabolic profiling that uses high-pressure liquid chromatography (HPLC), nuclear magnetic resonance (NMR) (Brindle et al. (J. Mol. Recognit. (1997) 10, 182-187), mass spectrometry (Gates and Sweeley (Clin. Chem. (1978) 24, 1663-1673) (GC/MS and LC/MS)), and ELISA or such individually and/or in combination may be used appropriately.

These studies elucidated heterogeneity within the constituted tumors which results from changing the concentration gradient of growth factors and metabolites (glucose, oxygen, or such) that enable cancer cell growth under low oxygen pressure conditions (Dang and Semenza (Trends Biochem. Sci. (1999) 24, 68-72)). In these studies, cell line models are also used to understand the change in energy utilization pathway depending on the different malignancy levels of tumors (Vizan et al. (Cancer Res. (2005) 65, 5512-5515)). Examples of a non-limiting embodiment of the technical components of the metabolomics platform include sample extraction, separation, detection, spectroscopic analysis, data normalization, description of class-specific metabolites, pathway mapping, confirmation, and functional characterization of candidate metabolites described by Lawton et al. (Pharmacogenomics (2008) 9, 383). These methods enable identification of cancer cell-specific metabolites in desired cancer tissues.

Examples of a non-limiting embodiment of cancer tissue-specific compounds or cancer tissue-specific metabolites used in the present invention preferably include at least one compound selected from the compounds below. At least one compound means that in addition to cases where the antigen-binding activity of a same antigen-binding domain described below depends on one type of cancer tissue-specific compound or metabolite, cases where it depends on several types of cancer tissue-specific compounds or metabolites are included.

(1) Primary Metabolites of the Krebs Cycle or of the Glycolytic System Such as Lactic Acid, Succinic Acid, and Citric Acid Preferable examples of a non-limiting embodiment of a cancer tissue-specific compound, particularly a cancer cell-specific metabolite, used in the present invention include primary metabolites such as lactic acid, succinic acid, and citric acid, which are produced as a result of glucose metabolism, and are present at higher concentrations in cancer tissues as compared to in the surrounding non-cancerous tissues. The glycolytic system phenotype, which is characterized as an up-regulation of enzymes of the glycolytic system (Embden-Meyerhof pathway) such as pyruvate kinase, hexokinase, and lactic acid dehydrogenase (LDH), has been conventionally known to be a characteristic of solid tumors as Warburg effect.

That is, in tumor cells, high expression of the pyruvate kinase isoform M2 which is necessary for anaerobic glycolysis, and not isoform Ml, is considered to be working advantageously for the growth of tumor cells in vivo (Christofk et al. (Nature (2008) 452, 230-233). Pyruvic acid produced by pyruvate kinase is subjected to feedback inhibition by lactic acid produced as a result of equilibrium reaction by lactic acid dehydrogenase (LDH) under anaerobic conditions. Since the feedback inhibition causes promotion of respiration in mitochondria (Krebs cycle) and cell growth inhibition, up regulation of LDH, hexokinase, and glucose transporter (GLUT) is said to play an important role in the proliferation of cancer cells (Fantin et al. (Cancer Cell (2006) 9, 425-434)). Glucose is metabolized by the glycolytic system, and the final metabolite lactic acid is transported together with protons to the tumor surrounding, and as a result, the pH of the tissues surrounding the tumor is said to become acidic. Lactic acid, which is the final product of the glycolytic pathway, as well as succinic acid and citric acid produced by promotion of respiration in mitochondria are known to be accumulated in cancer tissues (Teresa et al. (Mol. Cancer (2009) 8, 41-59)). Examples of a non-limiting embodiment of cancer tissue-specific compounds, particularly cancer cell-specific metabolites, used in the present invention preferably include such primary metabolites such as lactic acid, succinic acid, and citric acid produced by metabolism by the glycolytic pathway. Furthermore, succinic acid which is present at high concentration in cells is known to leak out to the outside of the cells upon cell death (Nature Immunology, (2008) 9, 1261-1269). Therefore, succinic acid concentration is thought to be increased in cancer tissues in which cell death occurs frequently.

(2) Amino Acids Such as Alanine, Glutamic Acid, and Aspartic Acid

Besides the above-mentioned glucose metabolism, the amino acid metabolism is also known to be altered in tumor cells which require continuous supply of essential amino acids and non-essential amino acids that are necessary for the biosynthesis of biopolymers under anaerobic conditions. Glutamine which contains two nitrogens in its side chain acts as a nitrogen transporter, and is an amino acid that is most widely distributed in an organism. Tumor cells, in which the rate of glutamine uptake into cells is increased, is said to be functioning as a glutamine trap. Such increase in the uptake of glutamine and activity of converting into glutamic acid and lactic acid is called "glutaminolysis", and is considered to be a characteristic of transformed (tumor) cells (Mazurek and Eigenbrodt (Anticancer Res. (2003) 23, 1149-1154); and Mazurek et al. (J. Cell. Physiol. (1999) 181, 136-146)). As a result, cancer patients show an increase in glutamic acid concentration while showing a decrease in plasma glutamine level (Droge et al. (Immunobiology (1987) 174, 473-479)). Furthermore, correlation was observed between concentrations of $^{13}$C-labeled succinic acid, $^{13}$C-labeled alanine, $^{13}$C-labeled glutamic acid, and $^{13}$C-labeled citric acid in studies on $^{13}$C-radiolabeled glucose metabolism in lung cancer tissues. Suitable examples of a non-limiting embodiment of cancer tissue-specific compounds used in this invention include alanine, glutamic acid, and aspartic acid which accumulate at high concentrations in cancer tissues through such glutaminolysis and the like.

(3) Amino Acid Metabolite Such as Kynurenine

Indolamine 2,3-dioxygenase (DO) is a tryptophan-metabolizing enzyme which is highly expressed in many cancers such as melanoma, colon cancer, and kidney cancer (Uyttenhove et al. (Nat. Med. (2003) 9, 1269-127)); and it is known to have two isoforms (Lob et al. (Cancer Immunol. Immunother. (2009) 58, 153-157)). DO catalyzes the conversion of tryptophan to kynurenine (shown as Compound 1), and is the first enzyme in the nicotinamide nucleotide (NAD) de novo pathway. Furthermore, in glioma which does not express DO, kynurenine is produced from tryptophan by tryptophan 2,3-dioxygenase (TDO) in the liver (Opitz et al. (Nature (2011) 478, 7368, 197-203)). DO is also expressed in dendritic cells infiltrated into cancer tissues, and dendritic cells also produce kynurenine (J. Immunol. (2008) 181, 5396-5404). DO is also expressed in myeloid-derived suppressor cells (MDSC) in cancer tissues, and MDSC also produces kynurenine (Yu et al. (J. Immunol. (2013) 190, 3783-3797)).

[Compound 1]

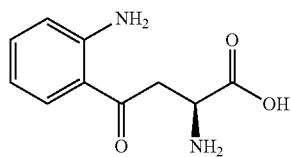

Kynurenine is known to suppress the same type of T cell response (Frumento et al. (J. Exp. Med. (2002) 196, 459-468); and a mechanism has been suggested, in which tumor cells evade antitumor immune responses through such inhibition, and proliferation of glioma cells is promoted through an autocrine proliferation mechanism in which kynurenine acts as an endogenous ligand for the aryl hydrocarbon receptor expressed on gliomas (Optiz et al. (mentioned above)). Kynurenine is converted to anthranilic acid (shown as Compound 2) by kynurenidase, and to 3-hydroxykynurenine (shown as Compound 3) by kynurenine 3-hydroxylase. Anthranilic acid and 3-hydroxykynurenine are both converted to 3-hydroxyanthranilic acid, the precursor of NAD.

[Compound 2]

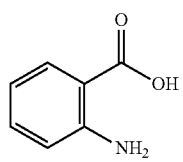

[Compound 3]

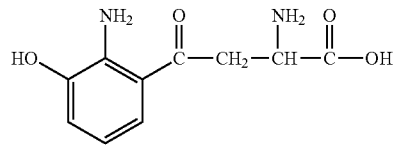

Kynurenine is converted to kynurenic acid (shown as Compound 4) by kynurenine aminotransferase. Examples of a non-limiting embodiment of cancer tissue-specific compounds, particularly cancer cell-specific metabolites, used in the present invention preferably include such amino acid metabolites such as kynurenine and its metabolites such as anthranilic acid, 3-hydroxykynurenine, and kynurenic acid.

[Compound 4]

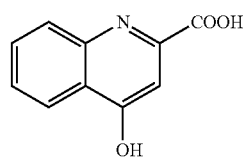

(4) Arachidonic Acid Metabolites Such as Prostaglandin E2

Prostaglandin E2 (PGE2) (Compound 5) is an arachidonic acid metabolite called a prostanoid, which includes thromboxane and prostaglandin synthesized by cyclooxygenase (COX)-1/2 (Warner and Mitchell (FASEB J. (2004) 18, 790-804)). PGE2 promotes the proliferation of colon cancer cells and suppresses their apoptosis (Sheng et al. (Cancer Res. (1998) 58, 362-366)). Cyclooxygenase expression is known to be altered in many cancer cells. More specifically, while COX-1 is expressed constitutively in almost all tissues, COX-2 has been found to be mainly induced by certain types of inflammatory cytokines and cancer genes in tumors (Warner and Mitchell (mentioned above)). In addition, COX-2 overexpression has been reported to be related to bad prognosis for breast cancer (Denkert et al. (Clin. Breast Cancer (2004) 4, 428-433)), and rapid disease progression for ovarian cancer (Denker et al. (Mod. Pathol. (2006) 19, 1261-1269)). Inhibitory T cells that have infiltrated into cancer tissues also produce prostaglandin E2 (Curr. Med. Chem. (2011) 18, 5217-5223). Small molecules such as the arachidonic acid metabolites prostaglandin and leukotriene are known to act as a stimulating factor that regulates autocrine and/or paracrine growth of cancer (Nat. Rev. Cancer (2012) 12 (11) 782-792). Examples of a non-limiting embodiment of cancer tissue-specific compounds used in the present invention, particularly cancer cell-specific metabolites and immune cell-specific metabolites that have infiltrated into cancer tissues, preferably include such arachidonic acid metabolites such as prostaglandin E2. Besides prostaglandin E2, production of thromboxane A2 (TXA2) is enhanced in cancer tissues such as colorectal cancer tissues (J. Lab. Clin. Med. (1993) 122, 518-523), and thromboxane A2 can be suitably presented as a non-limiting embodiment of an arachidonic acid metabolite of the present invention.

[Compound 5]

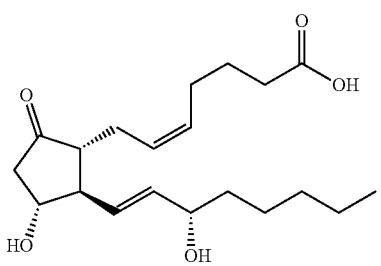

(5) Nucleosides Carrying a Purine Ring Structure Such as Adenosine, Adenosine Triphosphate (ATP), Adenosine Diphosphate (ADP), and Adenosine Monophosphate (AMP)

When cancer cells undergo cell death, a large amount of ATP in the cell is known to leak out to the outside of the cells. Therefore, the ATP concentration is remarkably higher in cancer tissues than in normal tissues (PLoS One. (2008) 3, e2599). Multiple types of cells release adenine nucleotides in the form of ATP, ADP, and AMP. Metabolism takes place through an extracellular enzyme on the cell surface such as extracellular 5'-nucleotidase (ecto-5'-nucleotidase) (CD73) (Resta and Thompson (Immunol. Rev. (1998) 161, 95-109) and Sadej et al. (Melanoma Res. (2006) 16, 213-222)). Adenosine is a purine nucleoside that exists constitutively at low concentration in the extracellular environment, but in hypoxic tissues found in solid cancers, a remarkable increase in the extracellular adenosine concentration has been reported (Blay and Hoskin (Cancer Res. (1997) 57, 2602-2605). CD73 is expressed on the surface of immune cells and tumors (Kobie et al. (J. Immunol. (2006) 177, 6780-6786)), and its activity has been found to be increased in breast cancer (Canbolat et al. (Breast Cancer Res. Treat. (1996) 37, 189-193)), stomach cancer (Durak et al. (Cancer Lett. (1994) 84, 199-202)), pancreatic cancer (Flocke and Mannherz (Biochim. Biophys. Acta (1991) 1076, 273-281), and glioblastoma (Bardot et al. (Br. J. Cancer (1994) 70, 212-218)). It has been proposed that the accumulation of adenosine in cancer tissues may be caused by an increase in the intracellular adenosine production through dephosphorylation of AMP by 5'-nucleotidase in the cytoplasm (Headrick and Willis (Biochem. J. (1989) 261, 541-550)). Furthermore, inhibitory T cells and such that have infiltrated into cancer tissues also express ATPase and produce adenosine (Proc. Natl. Acad. Sci. (2006) 103 (35), 13132-13137; Curr. Med. Chem. (2011) 18, 5217-5223). The produced adenosine is considered to be rendering the cancer tissue an immunosuppressive environment through adenosine receptors such as the A2A receptor (Curr. Med. Chem. (2011), 18, 5217-23). Examples of a non-limiting embodiment of the cancer tissue-specific compound used in the present invention preferably include ATP, ADP, AMP, and adenosine which accumulate at high concentration in cancer tissues through such metabolism of purine nucleotides such as ATP. Furthermore, since adenosine is degraded to inosine by adenosine deaminase, inosine accumulates at high concentration.

(6) Uric Acid

Uric acid is a product of the metabolic pathway of purine nucleosides in vivo, and is released to the outside of cells such as the interstitial space and blood. In recent years, it has been found to be released from dead cells that are present at sites of lesions such as cancer tissues (Nat. Med. (2007) 13, 851-856). Examples of a non-limiting embodiment of cancer tissue-specific compounds used in the present invention preferably include such uric acid which accumulates at high concentration in cancer tissues due to metabolism of purine nucleotides such as ATP.

(7) 1-Methyl Nicotinamide

The enzyme nicotinamide N-methyl transferase is known to be highly expressed in several human cancer tissues. When this enzyme produces the stable metabolite 1-methylnicotinamide from nicotinamide, the methyl group of S-adenosylmethionine (SAM) which serves as a methyl donor is consumed; therefore, the high expression of nicotinamide N-methyltransferase has been suggested to contribute to tumorigenesis through a mechanism that impairs the DNA methylation ability accompanying a decrease in the SAM concentration in cancer cells (Ulanovskaya et al (Nat. Chem. Biol. (2013) 9 (5) 300-306)). The stable metabolite of this enzyme, 1-methylnicotinamide is known to be secreted to the outside of cancer cells (Yamada et al (J. Nutr. Sci. Vitaminol. (2010) 56, 83-86)), and preferable examples of a non-limiting embodiment of cancer tissue-specific compounds used in the present invention include 1-methylnicotinamide and such which accumulate at high concentration in cancer tissues through nicotinamide metabolism.

Inflammatory Tissue-Specific Compounds

The term "compound specific to inflammatory tissue (inflammatory tissue-specific compound)" as used herein refers to a compound that is present differentially in inflammatory tissues as compared to non-inflammatory tissues. Herein, examples of "inflammatory tissues" include:

joints with rheumatoid arthritis or osteoarthritis;
lungs (alveoli) with bronchial asthma or COPD;
digestive organs of inflammatory bowel disease, Crohn's disease, or ulcerative colitis;
fibrotic tissues of fibrosis of the liver, kidney, or lung;
tissues undergoing rejection reaction in organ transplantation;
blood vessels and heart (myocardium) in arteriosclerosis or heart failure;
visceral fat in metabolic syndrome;
skin tissues in atopic dermatitis or other dermatitis; and
spinal nerves in disk herniation or chronic low back pain.

Inflammatory Tissue-Specific Metabolites

"Inflammatory tissue-specific metabolite" refers to metabolites highly produced by immune cells that have infiltrated into inflammatory tissues, and metabolites highly produced by specifically normal cells that have been damaged in inflammatory tissues. Examples of infiltrating immune cells include effector T cells, mature dendritic cells, neutrophils, granule cells (mast cells), and basophils. Furthermore, metabolites in the present invention include compounds that are released from inside the cells to the outside of the cells when the cells that are present in inflammatory tissues (immune cells and normal cells) die by apoptosis, necrosis, or such.

Examples of a non-limiting embodiment of the inflammatory tissue-specific compounds or inflammatory tissue-specific metabolites used in the present invention preferably include at least one compound selected from the compounds below. At least one compound means including cases where the antigen-binding activity of a same antigen-binding domain described below depends on one type of inflammatory tissue-specific compound or metabolite, as well as cases where it depends on several types of inflammatory tissue-specific compounds or metabolites.

(1) Arachidonic Acid Metabolites Such as Prostaglandin E2

The PGE2 concentration has been known to be high in rheumatoid arthritis and osteoarthritis (Eur. J. Clin. Pharmacol. (1994) 46, 3-7.; Clin. Exp. Rheumatol. (1999) 17, 151-160; Am. J. Vet. Res. (2004) 65, 1269-1275). Examples of a non-limiting embodiment of inflammatory tissue-specific compounds, particularly inflammatory tissue-specific metabolites and metabolites specific to immune cells that infiltrate into inflammatory tissues used in the present invention preferably include such arachidonic acid metabolites such as prostaglandin E2.

(2) Nucleosides Carrying a Purine Ring Structure Such as Adenosine, Adenosine Triphosphate (ATP), Adenosine Diphosphate (ADP), and Adenosine Monophosphate (AMP)

ATP concentration is known to be high in pulmonary alveoli where inflammation caused by bronchial asthma is taking place (Nat. Med. (2007) 13, 913-919). ATP concentration is also known to be high in pulmonary alveoli where inflammation caused by COPD is taking place (Am. J. Respir. Crit. Care Med. (2010) 181, 928-934). Furthermore, adenosine concentration has been observed to be high in the joint fluid of rheumatoid arthritis patients (Journal of Pharmaceutical and Biomedical Analysis (2004) 36, 877-882). Furthermore, ATP concentration is known to be high in tissues where a rejection reaction is taking place due to GVHD (Nat. Med. (2010) 16, 1434-1438). Adenosine concentration is known to be enhanced in fibrotic tissues of the liver, kidney, and lung (FASEB J. (2008) 22, 2263-2272; J. Immunol. (2006) 176, 4449-4458; J. Am. Soc. Nephrol. (2011) 22 (5), 890-901; PLoS ONE J. (2010) 5 (2), e9242). Furthermore, ATP concentration has been observed to be increased in fibrotic tissues of pulmonary fibrosis patients (Am. J. Respir. Crit. Care Med. (2010) 182, 774-783). Examples of a non-limiting embodiment of an inflammatory tissue-specific compound used in the present invention suitably include ATP, ADP, AMP, adenosine and such which accumulate at high concentration in inflammatory tissues by metabolism of such purine nucleotides such as ATP. In addition, inosine accumulates at a high concentration due to degradation of adenosine by adenosine deaminase to produce inosine.

(3) Uric Acid

Uric acid is a product of the metabolic pathway of purine nucleosides in vivo, and is released to the outside of cells such as the interstitial space and blood. In recent years, uric acid released from cells undergoing necrosis has been found to promote inflammatory response (J. Clin. Invest. (2010) 120 (6), 1939-1949). Examples of a non-limiting embodiment of inflammatory tissue-specific compounds to be used in the present invention suitably include such uric acid which accumulates at high concentration in inflammatory tissues due to metabolism of purine nucleotides such as ATP.

Antigen-Binding Domain

Herein, an "antigen-binding domain" may be of any structure as long as it binds to an antigen of interest. Such domains preferably include, for example:
antibody heavy-chain and light-chain variable regions;
a module of about 35 amino acids called A domain which is contained in the in vivo cell membrane protein Avimer (International Publication No. WO 2004/044011, International Publication No. WO 2005/040229);
Adnectin containing the 10Fn3 domain which binds to the protein moiety of fibronectin, a glycoprotein expressed on cell membrane (International Publication No. WO 2002/032925);
Affibody which is composed of a 58-amino acid three-helix bundle based on the scaffold of the IgG-binding domain of Protein A (International Publication No. WO 1995/001937);
Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (International Publication No. WO 2002/020565);
Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (International Publication No. WO 2003/029462); and
the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lamprey and hagfish (International Publication No. WO 2008/016854).

Suitable examples of the antigen-binding domains of the present invention include antigen-binding domains comprising antibody heavy-chain and light-chain variable regions. Examples of such antigen-binding domains are suitably "single chain Fv (scFv)", "single chain antibody", "Fv", "single chain Fv 2 (scFv2)", "Fab", or "F(ab')2".

The antigen-binding domains of antigen-binding molecules of the present invention can bind to an identical epitope. Such identical epitope can be present, for example, in a protein comprising the amino acid sequence of SEQ ID NO: 1. Alternatively, each of the antigen-binding domains of antigen-binding molecules of the present invention can bind to a different epitope. Herein, the different epitope can be present in, for example, a protein comprising the amino acid sequence of SEQ ID NO: 1.

Specificity

"Specific" means that one of the molecules that specifically bind does not substantially bind to molecules other than the single or plurality of partner molecules it binds to. Furthermore, "specific" is also used when an antigen-binding domain is specific to a particular epitope among multiple epitopes in an antigen. When an epitope bound by an antigen-binding domain is contained in multiple different antigens, antigen-binding molecules containing the antigen-binding domain can bind to various antigens that have the epitope. Here, "does not substantially bind" is determined according to the method described in the above-mentioned section on binding activity, and refers to the binding activity of a molecule that specifically binds to a molecule other than the partner molecule, where the binding activity is not more than 80%, normally not more than 50%, preferably not more than 30%, or particularly preferably not more than 15% of the binding activity to its partner molecule.

Cytotoxic Activity

In a non-limiting embodiment, the present invention provides antigen-binding molecules that comprise an antigen-binding domain whose antigen-binding activity varies depending on the concentration of a small molecule compound (e.g., cancer tissue-specific compound, inflammatory tissue-specific compound, or metabolites thereof) and which have cytotoxic activity against cells expressing a membrane-type molecule on their cell membrane; and pharmaceutical compositions comprising these antigen-binding molecules as an active ingredient. In the present invention, cytotoxic activity includes, for example, antibody-dependent cell-mediated cytotoxicity (ADCC) activity, complement-dependent cytotoxicity (CDC) activity, and cytotoxic activity by T cells. In the present invention, CDC activity refers to cytotoxic activity by the complement system. On the other hand, ADCC activity refers to the activity of immune cells to damage target cells when the immune cells and such bind to the Fc region of antigen-binding molecules comprising an antigen-binding domain that binds to a membrane-type molecule expressed on the cell membrane of target cells via an Fcγ receptor expressed on the immune cells. Whether an antigen-binding molecule of interest has an ADCC activity or whether it has a CDC activity can be determined using known methods (for example, Current Protocols in Immunology, Chapter 7. Immunologic studies in humans, Editor, Coligan et al, (1993)).

Specifically, effector cells, complement solution, and target cells are first prepared. (1) Preparation of effector cells Spleen is removed from a CBA/N mouse or the like, and spleen cells are dispersed in an RPMI1640 medium (Invitrogen). After the cells are washed in the same medium containing 10% fetal bovine serum (FBS, HyClone), effector cells are prepared by adjusting the spleen cell concentration to $5 \times 10^6$/mL.

(2) Preparation of Complement Solution

Baby Rabbit Complement (CEDARLANE) is diluted 10-fold in a culture medium (Invitrogen) containing 10% FBS to prepare a complement solution.

(3) Preparation of Target Cells

The target cells can be radioactively labeled by culturing cells expressing the antigen with 0.2 mCi of $^{51}$Cr-sodium chromate-(GE Healthcare Bio-Sciences) in a DMEM medium containing 10% FBS for one hour at 37° C. After radioactive labeling, cells are washed three times in an RPMI1640 medium containing 10% FBS, and the target cells can be prepared by adjusting the cell concentration to $2 \times 10^5$/mL.

ADCC activity or CDC activity can be measured by the method described below. In the case of ADCC activity measurement, 50 μL each of the target cell and antigen-binding molecule are added to a 96-well U-bottom plate (Becton Dickinson), and allowed to react for 15 minutes at room temperature. Then, 100 μL of effector cells are added to the plate and this plate is placed in a carbon dioxide incubator for four hours. The final concentration of the antigen-binding molecule may be set, for example, to 0 μg/mL or 10 μg/mL. After incubation, 100 μL of the supernatant is collected from each well, and the radioactivity is measured with a gamma counter (COBRAII AUTO-GAMMA, MODEL D5005, Packard Instrument Company). The cytotoxic activity (%) can be calculated using the measured values according to the equation: $(A-C)/(B-C) \times 100$. A represents the radioactivity (cpm) in each sample, B represents the radioactivity (cpm) in a sample to which 1% NP-40 (Nacalai Tesque) has been added, and C represents the radioactivity (cpm) of a sample containing the target cells alone.

Meanwhile, in the case of CDC activity measurement, 50 μL of target cell and 50 μL of an antigen-binding molecule are added to a 96-well flat-bottomed plate (Becton Dickinson), and allowed to react for 15 minutes on ice. Then, 100 μL of a complement solution is added to the plate, and this plate is placed in a carbon dioxide incubator for four hours. The final concentration of the antigen-binding molecule may be set, for example, to 0 μg/mL or 3 μg/mL. After incubation, 100 μL of supernatant is collected from each well, and the radioactivity is measured with a gamma counter. The cytotoxic activity can be calculated in the same way as in the determination of ADCC activity.

The later-described modified antigen-binding molecules to which cytotoxic substances such as chemotherapeutic agents, toxic peptides, or radioactive chemical substances have been ligated can also be suitably used as the antigen-binding molecules of the present invention having cytotoxic activity. Such modified antigen-binding molecules (hereinafter referred to as "antigen-binding molecule-drug conjugate") can be obtained by chemically modifying the obtained antigen-binding molecules. Methods that have been already established in the field of antibody-drug conjugates and such may be used appropriately as a method for modifying antigen-binding molecules. Furthermore, a modified antigen-binding molecule with a linked toxic peptide can be obtained by expressing in an appropriate host cell a fusion gene produced by linking a gene encoding the toxic peptide in frame with a gene encoding an antigen-binding molecule of the present invention, and then isolating the molecule from the culture solution of the cells.

Neutralizing Activity

The present invention provides in a non-limiting embodiment a pharmaceutical composition that induces an immune response, comprising as an active ingredient an antigen-binding molecule that contains an antigen-binding domain whose antigen-binding activity varies depending on the concentration of a small molecule compound (e.g., a cancer tissue-specific compound, inflammatory tissue-specific compound, metabolites thereof, and such) and has a neutralizing activity against a membrane-type molecule. In another non-limiting embodiment, the present invention provides a pharmaceutical composition that induces an immune response, comprising as an active ingredient an antigen-binding molecule that contains an antigen-binding domain whose antigen-binding activity varies depending on the concentration of a small molecule compound (e.g., a cancer tissue-specific compound, inflammatory tissue-specific compound, metabolites thereof, and such) and has a neutralizing activity against a membrane-type molecule in addition to a cytotoxic activity against cells expressing the membrane-type molecule on their cell membrane. Generally, a neutralizing activity refers to an activity of inhibiting the biological activity of a ligand which has a biological activity towards cells, such as viruses and toxins. Thus, a substance having a neutralizing activity refers to a substance that binds to a ligand or a receptor to which the ligand binds and inhibits the binding between the ligand and the receptor. A receptor whose binding to the ligand has been blocked by the neutralizing activity will not be able to exhibit the biological activity through the receptor. When the antigen-binding molecule is an antibody, the antibody having such a neutralizing activity is generally called a neutralizing antibody. The neutralizing activity of a test substance may be measured by comparing the biological activities in the presence of a ligand between conditions when the test substance is present or absent.

A suitable example of a major ligand for the IL-6 receptor is IL-6, which is shown in SEQ ID NO: 27. The IL-6 receptor, which is an I-type membrane protein whose amino terminus forms the extracellular domain, forms a heterotetramer with the gp130 receptor which was induced by IL-6 to dimerize (Heinrich et al. (Biochem. J. (1998) 334, 297-314)). Formation of the heterotetramer activates Jak associated with the gp130 receptor. Jak carries out autophosphorylation and receptor phosphorylation. The phosphorylation sites of the receptor and of Jak serve as binding sites for molecules belonging to the Stat family having SH2 such as Stat3, and for the MAP kinases, PI3/Akt, and other proteins and adapters having SH2. Next, Stat that bound to the gp130 receptor is phosphorylated by Jak. The phosphorylated Stat dimerizes and translocates to the nucleus, and regulates transcription of target genes. Jak and Stat can also be involved in the signaling cascade through receptors of other classes. A deregulated IL-6 signaling cascade is observed in inflammation and pathological conditions of autoimmune diseases, and cancers such as prostate cancer and multiple myeloma. Stat3 which may act as an oncogene is constitutively activated in many cancers. In prostate cancer and multiple myeloma, there is a crosstalk between the signaling cascade from the IL-6 receptor and the signaling cascade from members of the epidermal growth factor receptor (EGFR) family (Ishikawa et al. (J. Clin. Exp. Hematopathol. (2006) 46 (2), 55-66)).

Such intracellular signaling cascades are different for each cell type; therefore, an appropriate target molecule can be set according to each of the target cells of interest, and the target molecule is not limited to the above-mentioned factors. The neutralization activity can be evaluated by measuring the in vivo signal activation. Furthermore, activation of in vivo signals can also be detected by using as an indicator the transcription-inducing action on a target gene that exists downstream of the in vivo signaling cascade. A change in the transcription activity of a target gene can be detected by the principle of a reporter assay. Specifically, a reporter gene such as the green fluorescence protein (GFP) or luciferase is placed downstream of a transcription factor or a promoter region of the target gene; and a change in transcription activity can be measured in terms of reporter activity by measuring the reporter activity. Commercially available kits for measuring in vivo signal activation can be suitably used (for example, the Mercury Pathway Profiling Luciferase System (Clontech)).

Furthermore, as a method for measuring the neutralization activity on a receptor ligand in the EGF receptor family and such which acts on a signaling cascade that typically works toward enhancing cell proliferation, neutralization activity of an antigen-binding molecule can be evaluated by measuring the proliferation activity of the target cells. For example, the following method is suitably used as a method for measuring or evaluating inhibitory effects based on the neutralization activity of an anti-HB-EGF antibody against the proliferation of cells whose proliferation is promoted by EGF family growth factors such as HB-EGF. As a method for evaluating or measuring the activity of inhibiting cell proliferation in a test tube, a method that measures the incorporation by living cells of [$^3$H]-labeled thymidine added to the culture medium as an index of the DNA replication ability is used. As a more convenient method, a dye exclusion method that measures under a microscope the ability of a cell to release a dye such as trypan blue to the outside of the cell, or the MTT method is used. The latter makes use of the ability of living cells to convert 3-(4,5-dimethylthiazol-2-yl)-2,5-diphenyl tetrazolium bromide (MTT), which is a tetrazolium salt, to a blue formazan product. More specifically, a test antibody is added along with a ligand to the culture solution of a test cell; and after a certain period of time has elapsed, an MTT solution is added to the culture, and this is left to stand for a certain amount of time to let the cell incorporate MTT. As a result, MTT which is a yellow compound is converted to a blue compound by succinate dehydrogenase in the mitochondria of the cell. After this blue product is dissolved for coloration, its absorbance is measured and used as an indicator of the number of viable cells. Besides MTT, reagents such as MTS, XTT, WST-1, and WST-8 are also commercially available (Nacalai Tesque, and such), and can be suitably used. For measurement of the activity, a binding antibody that has the same isotype as the anti-HB-EGF antibody but does not have the cell proliferation-inhibiting activity can be used as a control antibody in the same manner as the anti-HB-EGF antibody, and the anti-HB-EGF antibody is judged to have the activity when it shows a stronger cell proliferation-inhibiting activity than the control antibody.

As cells for evaluating activity, for example, cells showing HB-EGF-promoted proliferation such as the RMG-1 cell line which is an ovarian cancer cell line may be suitably used; and mouse Ba/F3 cells transformed with a vector in which a gene encoding hEGFR/mG-CSFR, which is a fusion protein of the extracellular domain of human EGFR fused in frame with the intracellular domain of the mouse G-CSF receptor, is linked so as to allow expression, may also be suitably used. This way, those skilled in the art may appropriately select cells for evaluating activity to measure the cell proliferation activity mentioned above.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4. A number of allotype sequences of human IgG1, human IgG2, human IgG3, and human IgG4 constant regions due to gene polymorphisms are described in "Sequences of proteins of immunological interest", NIH Publication No. 91-3242. Any of such sequences may be used in the present invention. In particular, for the human IgG1sequence, the amino acid sequence at positions 356 to 358 as indicated by EU numbering may be DEL or EEM. Several allotype sequences due to genetic polymorphisms have been described in "Sequences of proteins of immunological interest", NIH Publication No. 91-3242 for the human Igκ (Kappa) constant region and human IgX, (Lambda) constant region, and any of the sequences may be used in the present invention.

Methods for producing an antibody with desired binding activity are known to those skilled in the art. Below is an example that describes a method for producing an antibody that binds to IL-6R (anti-IL-6R antibody). Antibodies that bind to an antigen other than IL-6R can also be produced according to the example described below.

Anti-IL-6R antibodies can be obtained as polyclonal or monoclonal antibodies using known methods. The anti-IL-6R antibodies preferably produced are monoclonal antibodies derived from mammals. Such mammal-derived monoclonal antibodies include antibodies produced by hybridomas or host cells transformed with an expression vector carrying an antibody gene by genetic engineering techniques. "Humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an IL-6R protein as a sensitizing antigen. Resulting immune cells are fused with known parental cells by conventional cell fusion methods. Then, hybridomas producing an anti-IL-6R antibody can be selected by screening for monoclonal antibody-producing cells using conventional screening methods.

Specifically, monoclonal antibodies are prepared as mentioned below. First, the IL-6R gene whose nucleotide sequence is disclosed in SEQ ID NO: 2 can be expressed to produce an IL-6R protein shown in SEQ ID NO: 1, which will be used as a sensitizing antigen for antibody preparation. That is, a gene sequence encoding IL-6R is inserted into a known expression vector, and appropriate host cells are transformed with this vector. The desired human IL-6R protein is purified from the host cells or their culture supernatants by known methods. In order to obtain soluble IL-6R from culture supernatants, for example, a protein consisting of the amino acids at positions 1 to 357 in the IL-6R polypeptide sequence of SEQ ID NO: 1, such as described in Mullberg et al. (J. Immunol. (1994) 152 (10), 4958-4968), is expressed as a soluble IL-6R, instead of the IL-6R protein of SEQ ID NO: 1. Purified natural IL-6R protein can also be used as a sensitizing antigen.

The purified IL-6R protein can be used as a sensitizing antigen for immunization of mammals. A partial IL-6R peptide may also be used as a sensitizing antigen. In this case, a partial peptide can be prepared by chemical synthesis based on the amino acid sequence of human IL-6R, or by inserting a partial IL-6R gene into an expression vector for expression. Alternatively, a partial peptide can be produced by degrading an IL-6R protein with a protease. The length and region of the partial IL-6R peptide are not limited to particular embodiments. A preferred region can be arbitrarily selected from the amino acid sequence at amino acid positions 20 to 357 in the amino acid sequence of SEQ ID NO: 1. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the IL-6R protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing IL-6R to be used as a sensitizing antigen, and immunization methods using IL-6R are specifically described in WO 2003/000883, WO 2004/022754, WO 2006/006693, and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection administration of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as IL-6R; and
there is no need to purify the antigen for immunization.

In order to prepare a monoclonal antibody of the present invention using DNA immunization, first, a DNA expressing an IL-6R protein is administered to an animal to be immunized. The IL-6R-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized IL-6R can also be produced by the methods described in WO 2003/104453.

After immunizing a mammal as described above, an increase in the titer of an IL-6R-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3x63Ag8.653) (J. Immunol. (1979) 123 (4), 1548-1550);

P3x63Ag8U.1 (Current Topics in Microbiology and Immunology (1978)81, 1-7);

NS-1 (C. Eur. J. Immunol. (1976)6 (7), 511-519);

MPC-11 (Cell (1976) 8 (3), 405-415);

SP2/0 (Nature (1978) 276 (5685), 269-270);

FO (J. Immunol. Methods (1980) 35 (1-2), 1-21);

S194/5.XX0.BU.1 (J. Exp. Med. (1978) 148 (1), 313-323);

R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, an IL-6R-binding monoclonal antibody can bind to IL-6R expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, IL-6R-expressing cells are first prepared. Cells preferably used for screening are mammalian cells in which IL-6R is forcedly expressed. As control, the activity of an antibody to bind to cell-surface IL-6R can be selectively detected using non-transformed mammalian cells as host cells. Specifically, hybridomas producing an anti-IL-6R monoclonal antibody can be isolated by selecting hybridomas that produce an antibody which binds to cells forced to express IL-6R, but not to host cells.

Alternatively, the activity of an antibody to bind to immobilized IL-6R-expressing cells can be assessed based on the principle of ELISA. For example, IL-6R-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-IL-6R antibody is prepared from hybridoma cells expressing the anti-IL-6R antibody. For this purpose, total RNA is first extracted from hybridomas. Methods used for extracting mRNAs from cells include, for example:

the guanidine ultracentrifugation method (Biochemistry (1979) 18(24), 5294-5299), and the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. U.S.A. (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the IL-6R-binding activity of a reshaped immunoglobulin as an indicator. For example, when the objective is to isolate an antibody against IL-6R, it is more preferred that the binding of the antibody to IL-6R is specific. An IL-6R-binding antibody can be screened, for example, by the following steps:

(1) contacting an IL-6R-expressing cell with an antibody comprising the V region encoded by a cDNA isolated from a hybridoma;
(2) detecting the binding of the antibody to the IL-6R-expressing cell; and
(3) selecting an antibody that binds to the IL-6R-expressing cell.

Methods for detecting the binding of an antibody to IL-6R-expressing cells are known. Specifically, the binding of an antibody to IL-6R-expressing cells can be detected by the above-described techniques such as FACS. Immobilized samples of IL-6R-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-IL-6R antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-IL-6R antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region. A chimeric antibody expression vector is constructed by fusing in frame the two genes digested with the same combination of restriction enzymes.

To produce an anti-IL-6R monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples below, a peptide having the amino acid sequence MGWSCI-ILFLVATATGVHS (SEQ ID NO: 3) is used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-IL-6R antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 1994/011523).

There are various known host cell/expression vector combinations for antibody preparation by introducing isolated antibody genes into appropriate hosts. All of these expression systems are applicable to isolation of the antigen-binding domains of the present invention. Appropriate eukaryotic cells used as host cells include animal cells, plant cells, and fungal cells. Specifically, the animal cells include, for example, the following cells.

(1) mammalian cells: CHO (Chinese hamster ovary cell line), COS (Monkey kidney cell line), myeloma (Sp2/0, NS0, etc.), BHK (baby hamster kidney cell line), HeLa, Vero, HEK293 (human embryonic kidney cell line with sheared adenovirus (Ad)5 DNA), PER.C6 cell (human embryonic retinal cell line transformed with the Adenovirus Type 5 (Ad5) E1A and E1B genes) and such (Current Protocols in Protein Science (May, 2001, Unit 5.9, Table 5.9.1));
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:
yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Bio/Technology (1994) 12 (7), 699-702).

When an antigen-binding molecule described herein is administered to human, an antigen-binding domain derived from a genetically recombinant antibody that has been artificially altered to reduce the heterologous antigenicity against human and such, can be appropriately used as the antigen-binding domain of the antigen-binding molecule. Such genetically recombinant antibodies include, for example, humanized antibodies. These altered antibodies are appropriately produced by known methods.

An antibody variable region used to produce the antigen-binding domain of an antigen-binding molecule described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

Besides the phage display method, techniques of using a cell-free translation system, techniques of displaying antigen-binding molecules on the surface of cells or viruses, techniques of using emulsions, and such are known as techniques for obtaining human antibodies by panning using a human antibody library. As techniques of using a cell-free translation system, for example, the ribosome display method where a complex is formed between an mRNA and the translated protein via the ribosome by removing the stop codon and such, the cDNA display method where a gene sequence and the translated protein are covalently linked using a compound such as puromycin, the mRNA display method, the CIS display method where a complex is formed between a gene and the translated protein using a nucleic acid-binding protein, or such may be used. For techniques of presenting an antigen-binding molecule on the surface of cells or viruses, the E. coli display method, Gram-positive bacterium display method, yeast display method, mammalian cell display method, virus display method, and such may be used besides the phage display method. As techniques that use emulsions, the in vitro virus display method which involves incorporating genes and translation-related molecules into an emulsion, and such may be used. These methods are already publicly known (Nat Biotechnol. 2000 December; 18(12):1287-92, Nucleic Acids Res. 2006; 34(19):e127, Proc Natl Acad Sci USA. 2004 Mar. 2; 101 (9):2806-10, Proc Natl Acad Sci USA. 2004 Jun. 22; 101 (25):9193-8, Protein Eng Des Sel. 2008 April; 21(4):247-55, Proc Natl Acad Sci USA. 2000 Sep. 26; 97(20):10701-5, MAbs. 2010 September-October; 2(5):508-18, Methods Mol Biol. 2012; 911:183-98).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bernasconi et al. (Science (2002) 298: 2199-2202) or in WO 2008/081008 can be appropriately used to isolate antibody genes.

A non-limiting embodiment of antibodies in the present invention includes but is not limited to chimeric antigen receptors that are incorporated into T-cells, which are fusions of an antibody or fragments thereof that recognize antigens instead of a T-cell receptor and T-cell signal domains, as well as T-cells into which the chimeric antigen receptor has been incorporated.

EU Numbering and Kabat Numbering

According to the methods used in the present invention, amino acid positions assigned to antibody CDR and FR are specified according to Kabat's numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated by Kabat numbering, while constant region amino acids are indicated by EU numbering based on Kabat's amino acid positions.

Antigen-Binding Domain Whose Binding Activity Varies Depending on the Concentration of a Small Molecule Compound Examples of a small molecule compound include target tissue-specific compounds and unnatural compounds. Examples of a method for selecting antigen-binding domains dependently on a target tissue-specific compound are shown below; and methods such as those for selecting antigen-binding domains dependently on a small molecule compound other than target tissue-specific compounds, and the like, may also be carried out appropriately according to the examples below. To obtain an antigen-binding domain (or an antigen-binding molecule containing the domain) whose antigen-binding activity varies depending on the concentration of a target tissue-specific compound, the methods indicated in the above section on binding activity may be appropriately applied. As a non-limiting embodiment, some specific examples of the methods are presented below. For example, to confirm that the antigen-binding activity of an antigen-binding domain (or an antigen-binding molecule containing the domain) in the presence of a target tissue-specific compound becomes higher than the antigen-binding activity of an antigen-binding domain (or an antigen-binding molecule containing the domain) in the absence of the compound, the antigen-binding activities of the antigen-binding domain (or the antigen-binding molecule containing the domain) in the presence and absence of the target tissue-specific compound or in the presence of high and low concentrations of the compound are compared. In another non-limiting embodiment, for example, to confirm that the antigen-binding activity of an antigen-binding domain (or an antigen-binding molecule containing the domain) in the presence of a high concentration of a target tissue-specific compound becomes higher than the antigen-binding activity of an antigen-binding domain (or an antigen-binding molecule containing the domain) in the presence of a low concentration of the compound, the antigen-binding activities of the antigen-binding domain (or the antigen-binding molecule containing the domain) in the presence of high and low concentrations of the target tissue-specific compound are compared.

Furthermore, in the present invention, the phrase "the antigen-binding activity in the presence of a target tissue-specific compound is higher than the antigen-binding activity in the absence of the compound" can be alternatively expressed as "the antigen-binding activity of an antigen-binding domain (or an antigen-binding molecule containing the domain) in the absence of a target tissue-specific compound is lower than the antigen-binding activity in the presence of the compound". Furthermore, in the present invention, "the antigen-binding activity of an antigen-binding domain (or an antigen-binding molecule containing the domain) in the absence of a target tissue-specific compound is lower than the antigen-binding activity in the presence of the compound" may be alternatively described as "the antigen-binding activity of an antigen-binding domain (or an antigen-binding molecule containing the domain) in the absence of a target tissue-specific compound is weaker than the antigen-binding activity in the presence of the compound".

Furthermore, in the present invention, the phrase "the antigen-binding activity in the presence of a high concentration of a target tissue-specific compound is higher than the antigen-binding activity in the presence of a low concentration of the compound" can be alternatively expressed as "the antigen-binding activity of an antigen-binding domain (or an antigen-binding molecule containing the domain) in the presence of a low concentration of a target tissue-specific compound is lower than the antigen-binding activity in the presence of a high concentration of the compound". In the present invention, "the antigen-binding activity of an antigen-binding domain (or an antigen-binding molecule containing the domain) in the presence of a low concentration of a target tissue-specific compound is lower than the antigen-binding activity in the presence of a high concentration of the compound" may be alternatively described as "the antigen-binding activity of an antigen-binding domain (or an antigen-binding molecule containing the domain) in the presence of a low concentration of a target tissue-specific compound is weaker than the antigen-binding activity in the presence of a high concentration of the compound".

Conditions when measuring antigen-binding activity other than the concentration of a target tissue-specific compound are not particularly limited, and can be selected appropriately by those skilled in the art. For example, it is possible to measure under conditions of HEPES buffer and 37° C. For example, Biacore (GE Healthcare) or such can be used for measurement. When the antigen is a soluble molecule, the activity of an antigen-binding domain (or an antigen-binding molecule containing the domain) to bind to the soluble molecule can be determined by loading the antigen as an analyte onto a chip immobilized with the antigen-binding domain (or an antigen-binding molecule containing the domain). Alternatively, when the antigen is a membrane-type molecule, the binding activity towards the membrane-type molecule can be determined by loading the antigen-binding domain (or an antigen-binding molecule containing the domain) as an analyte onto a chip immobilized with the antigen.

As long as the antigen-binding activity of an antigen-binding domain (or an antigen-binding molecule containing the domain) contained in antigen-binding molecules of the present invention in the absence of a target tissue-specific compound is weaker than the antigen-binding activity in the presence of the target tissue-specific compound, the ratio between the antigen-binding activity in the absence of the compound and the antigen-binding activity in the presence of the compound is not particularly limited. However, the value of KD (in the absence of the compound)/KD (in the presence of the compound), which is a ratio of dissociation constant (KD) against an antigen in the absence of the target tissue-specific compound to KD in the presence of the compound, is preferably 2 or greater, more preferably 10 or greater, and still more preferably 40 or greater. The upper limit of the value of KD (in the absence of the compound)/KD (in the presence of the compound) is not particularly limited, and may be any value, for example, 400, 1,000, or 10,000, as long as it can be provided by the technologies of those skilled in the art. When antigen-binding activity is not observed in the absence of the target tissue-specific compound, the value of the upper limit is infinity.

As long as the antigen-binding activity of an antigen-binding domain (or an antigen-binding molecule containing the domain) contained in antigen-binding molecules of the present invention in the presence of a low concentration of a target tissue-specific is weaker than the antigen-binding activity in the presence of a high concentration of the target tissue-specific compound, the ratio between the antigen-binding activity in the presence of a low concentration of the compound and the antigen-binding activity in the presence of a high concentration of the compound is not particularly limited. However, the value of KD (in the presence of a low concentration of the compound)/KD (in the presence of a high concentration of the compound), which is a ratio of dissociation constant (KD) against an antigen in the presence of a low concentration of the target tissue-specific compound to KD in the presence of a high concentration of the compound, is preferably 2 or greater, more preferably 10 or greater, and still more preferably 40 or greater. The upper limit of the value of KD (in the presence of a low concentration of the compound)/KD (in the presence of a high concentration of the compound) is not particularly limited, and may be any value, for example, 400, 1,000, or 10,000, as long as it can be provided by the technologies of those skilled in the art. When antigen-binding activity is not observed in the presence of a low concentration of the target tissue-specific compound, the value of the upper limit is infinity.

For the value of antigen-binding activity, if the antigen is a soluble molecule, dissociation constant (KD) can be used; and if the antigen is a membrane-type molecule, apparent dissociation constant (apparent KD) can be used. The dissociation constant (KD) and apparent dissociation constant (apparent KD) can be determined by methods known to those skilled in the art, for example, using Biacore (GE Healthcare), a Scatchard plot, a flow cytometer, or such.

As another indicator that shows the ratio between the antigen-binding activity of an antigen-binding domain (or an antigen-binding molecule containing the domain) of the present invention in the absence of a target tissue-specific compound and the antigen-binding activity in the presence of the compound, for example, dissociation rate constant kd can be suitably used. When the dissociation rate constant (kd) is used instead of the dissociation constant (KD) as an indicator that shows the binding activity ratio, the value of kd (in the absence of the compound)/kd (in the presence of the compound), which is a ratio between kd (dissociation rate constant) for an antigen in the absence of a target tissue-specific compound and kd in the presence of the compound, is preferably 2 or greater, more preferably 5 or greater, even more preferably 10 or greater, and still more preferably 30 or greater. The upper limit of the value of kd (in the absence of the compound)/kd (in the presence of the compound) is not particularly limited, and may be any value, for example, 50, 100, or 200, as long as it can be provided by the common technical knowledge of those skilled in the art. When antigen-binding activity is not observed in the absence of the tissue-specific compound, there is no dissociation and the value of the upper limit becomes infinity.

As another indicator that shows the ratio between the antigen-binding activity of an antigen-binding domain (or an antigen-binding molecule containing the domain) of the present invention in the presence of a low concentration of a target tissue-specific compound and the antigen-binding activity in the presence of a high concentration of the compound, for example, dissociation rate constant kd can be suitably used. When the dissociation rate constant (kd) is used instead of the dissociation constant (KD) as an indicator showing the binding activity ratio, the value of kd (in the presence of a low concentration of the compound)/kd (in the presence of a high concentration of the compound), which is a ratio between kd (dissociation rate constant) for an antigen in the presence of a low concentration of a target tissue-specific compound and kd in the presence of a high concentration of the compound, is preferably 2 or greater, more preferably 5 or greater, even more preferably 10 or greater, and still more preferably 30 or greater. The upper limit of the value of kd (in the presence of a low concentration of the compound)/kd (in the presence of a high concentration of the compound) is not particularly limited, and may be any value, for example, 50, 100, or 200, as long as it can be provided by the common technical knowledge of those skilled in the art. When antigen-binding activity is not observed in the presence of a low concentration of the target tissue-specific compound, there is no dissociation and the value of the upper limit becomes infinity.

For the value of antigen-binding activity, if the antigen is a soluble molecule, dissociation rate constant (kd) can be used; and if the antigen is a membrane-type molecule, apparent dissociation rate constant (apparent kd) can be used. The dissociation rate constant (kd) and apparent dissociation rate constant (apparent kd) can be determined by methods known to those skilled in the art, for example, using Biacore (GE Healthcare), a flow cytometer, or such. In the present invention, when measuring the antigen-binding activity of an antigen-binding domain (or an antigen-binding molecule containing the domain) at a certain concentration of the target tissue-specific compound, conditions other than the concentration of the compound concentration are preferably the same.

For example, in an embodiment provided by the present invention, an antigen-binding domain (or an antigen-binding molecule containing the domain) with lower antigen-binding activity in the absence of a target tissue-specific compound than in the presence of the compound, may be obtained by screening of antigen-binding domains (or antigen-binding molecules) that comprises the steps of:
  (a) determining antigen-binding activity of antigen-binding domains (or antigen-binding molecules) in the absence of a target tissue-specific compound;
  (b) determining antigen-binding activity of the antigen-binding domains (or antigen-binding molecules) in the presence of the target tissue-specific compound; and
  (c) selecting an antigen-binding domain (or an antigen-binding molecule) with lower antigen-binding activity in the absence of the target tissue-specific compound than in the presence of the compound.

For example, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by screening of antigen-binding domains (or antigen-binding molecules) that comprises the steps of:
  (a) determining antigen-binding activity of antigen-binding domains (or antigen-binding molecules) in the presence of a low concentration of a target tissue-specific compound;
  (b) determining antigen-binding activity of the antigen-binding domains (or antigen-binding molecules) in the presence of a high concentration of the target tissue-specific compound; and
  (c) selecting an antigen-binding domain (or an antigen-binding molecule) with lower antigen-binding activity in the presence of a low concentration of the target tissue-specific compound than in the presence of a high concentration of the compound.

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by screening of antigen-binding domains (or antigen-binding molecules) or a library thereof that comprises the steps of:
  (a) contacting antigen-binding domains (or antigen-binding molecules) or a library thereof with an antigen in the presence of a target tissue-specific compound;
  (b) placing antigen-binding domains (or antigen-binding molecules) that bind to the antigen in said step (a) in the absence of the compound;
  (c) isolating an antigen-binding domain (or an antigen-binding molecule) that dissociated in said step (b).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by screening of antigen-binding domains (or antigen-binding molecules) or a library thereof that comprises the steps of:
  (a) contacting antigen-binding domains (or antigen-binding molecules) or a library thereof with an antigen in the presence of a high concentration of a target tissue-specific compound;
  (b) placing antigen-binding domains (or antigen-binding molecules) that bind to the antigen in said step (a) in the presence of a low concentration of the compound;
  (c) isolating an antigen-binding domain (or an antigen-binding molecule) that dissociates in said step (b).

Alternatively, in an embodiment provided by the present invention, an antigen-binding domain (or an antigen-binding molecule containing the domain) with lower antigen-binding activity in the absence of a target tissue-specific compound than in the presence of the compound, may be obtained by screening of antigen-binding domains (or antigen-binding molecules) or a library thereof that comprises the steps of:
  (a) contacting a library of antigen-binding domains (or antigen-binding molecules) with an antigen in the absence of a target tissue-specific compound;

(b) selecting antigen-binding domains (or antigen-binding molecules) that do not bind to the antigen in said step (a);

(c) allowing the antigen-binding domains (or antigen-binding molecules) selected in said step (b) to bind to the antigen in the presence of the compound; and (d) isolating an antigen-binding domain (or an antigen-binding molecule) that binds to the antigen in said step (c).

Alternatively, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by screening of antigen-binding domains (or antigen-binding molecules) or a library thereof that comprises the steps of:
(a) contacting a library of antigen-binding domains (or antigen-binding molecules) with an antigen in the presence of a low concentration of a target tissue-specific compound;
(b) selecting antigen-binding domains (or antigen-binding molecules) that do not bind to the antigen in said step (a);

(c) allowing the antigen-binding domains (or antigen-binding molecules) selected in said step (b) to bind to the antigen in the presence of a high concentration the compound; and (d) isolating an antigen-binding domain (or an antigen-binding molecule) that binds to the antigen in said step (c).

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by a screening method comprising the steps of:

(a) contacting a library of antigen-binding domains (or antigen-binding molecules) with an antigen-immobilized column in the presence of a target tissue-specific compound;

(b) eluting an antigen-binding domain (or antigen-binding molecule) that binds to the column in said step (a) from the column in the absence of the compound; and (c) isolating the antigen-binding domain (or antigen-binding molecule) eluted in said step (b).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by a screening method comprising the steps of:

(a) contacting a library of antigen-binding domains (or antigen-binding molecules) with an antigen-immobilized column in the presence of a high concentration of a target tissue-specific compound;

(b) eluting an antigen-binding domain (or antigen-binding molecule) that binds to the column in said step (a) from the column in the presence of a low concentration of the compound; and (c) isolating the antigen-binding domain (or antigen-binding molecule) eluted in said step (b).

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by a screening method comprising the steps of:

(a) allowing a library of antigen-binding domains (or antigen-binding molecules) to pass through an antigen-immobilized column in the absence of a target tissue-specific compound;

(b) collecting an antigen-binding domain (or antigen-binding molecule) eluted without binding to the column in said step (a);

(c) allowing the antigen-binding domain (or antigen-binding molecule) collected in said step (b) to bind to the antigen in the presence of the compound; and (d) isolating an antigen-binding domain (or antigen-binding molecule) that binds to the antigen in said step (c).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by a screening method comprising the steps of:

(a) allowing a library of antigen-binding domains (or antigen-binding molecules) to pass through an antigen-immobilized column in the presence of a low concentration of a target tissue-specific compound;

(b) collecting an antigen-binding domain (or antigen-binding molecule) eluted without binding to the column in said step (a);

(c) allowing the antigen-binding domain (or antigen-binding molecule) collected in said step (b) to bind to the antigen in the presence of a high concentration of the compound; and (d) isolating an antigen-binding domain (or antigen-binding molecule) that binds to the antigen in said step (c).

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by a screening method comprising the steps of:

(a) contacting an antigen with a library of antigen-binding domains (or antigen-binding molecules) in the presence of a target tissue-specific compound;

(b) obtaining an antigen-binding domain (or antigen-binding molecule) that binds to the antigen in said step (a);

(c) placing the antigen-binding domain (or antigen-binding molecule) obtained in said step (b) in the absence of the compound; and (d) isolating an antigen-binding domain (or antigen-binding molecule) whose antigen-binding activity in said step (c) is weaker than that of the reference selected in said step (b).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by a screening method comprising the steps of:

(a) contacting an antigen with a library of antigen-binding domains (or antigen-binding molecules) in the presence of a high concentration of a target tissue-specific compound;

(b) obtaining an antigen-binding domain (or antigen-binding molecule) that binds to the antigen in said step (a);

(c) placing the antigen-binding domain (or antigen-binding molecule) obtained in said step (b) in the presence of a low concentration of the compound; and (d) isolating an antigen-binding domain (or antigen-binding molecule) whose antigen-binding activity in said step (c) is weaker than that of the reference selected in said step (b).

The above-mentioned steps may be repeated two or more times. Thus, the present invention provides an antigen-binding domain (or an antigen-binding molecule containing the domain) with lower antigen-binding activity in the absence of a target tissue-specific compound than in the presence of the compound, or an antigen-binding domain (or an antigen-binding molecule containing the domain) with lower antigen-binding activity in the presence of a low concentration of a target tissue-specific compound than in the presence of a high concentration of the compound, obtained by screening methods that further comprise the step of repeating steps (a) to (c) or (a) to (d) two or more times in the above-mentioned screening methods. The number of repeats of steps (a) to (c) or (a) to (d) is not particularly limited, and it is generally ten or less.

In the screening methods of the present invention, a target tissue-specific compound may be a compound defined by quantitative target tissue specificity such as presence in the target tissue at a concentration (for example, high concentration or low concentration) different from the concentration in non-target tissues. For example, a target tissue-specific compound is differentially present at any concentrations. However, generally, a target tissue-specific compound can be present at a concentration increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 2-fold, at least 5-fold, at least 10-fold, at least 50-fold, at least 100-fold, at least $10^3$-fold, at least $10^4$-fold, at least $10^5$-fold, at least $10^6$-fold, or more, or up to infinity (when the compound is absent in non-target tissues).

The threshold differentiating low and high concentrations can be set appropriately according to the compound. For example, in a non-limiting embodiment of the threshold of ATP or adenosine, the threshold for a low-concentration condition may be selected appropriately from the values of 10 nM, 1 nM, 100 pM, 10 pM, 1 pM, and 0 M. Depending on the predetermined threshold, the high-concentration condition may be set appropriately at a value selected from at least 110%, at least 120%, at least 130%, at least 140%, at least 150%, at least twice, at least five-fold, at least 10-fold, at least 50-fold, at least 100-fold, at least $10^3$-fold, at least $10^4$-fold, at least $10^5$-fold, and at least $10^6$-fold the value of each threshold. Furthermore, in a non-limiting embodiment of PGE2, the threshold for a low-concentration condition may be selected appropriately from the values of 10 pM, 1 pM, 100 fM, 10 fM, 1 fM, and 0 M. Depending on the predetermined threshold, the high-concentration condition may be set appropriately at a value selected from at least 110%, at least 120%, at least 130%, at least 140%, at least 150%, at least twofold, at least five-fold, at least 10-fold, at least 50-fold, at least 100-fold, at least $10^3$-fold, at least $10^4$-fold, at least $10^5$-fold, and at least $10^6$-fold the value of each threshold. Furthermore, in a non-limiting embodiment of Kynurenine, the threshold for a low-concentration condition may be selected appropriately from the values of 10 µM, 1 µM, 100 nM, 10 nM, and 1 nM, and 0 M. Depending on the predetermined threshold, the high-concentration condition may be set appropriately at a value selected from at least 110%, at least 120%, at least 130%, at least 140%, at least 150%, at least twofold, at least five-fold, at least 10-fold, at least 50-fold, at least 100-fold, at least $10^3$-fold, at least $10^4$-fold, at least $10^5$-fold, and at least $10^6$-fold the value of each threshold.

The antigen-binding activity of an antigen-binding domain (or an antigen-binding molecule) may be measured by a method known to those skilled in the art, and conditions other than the concentration of a target tissue-specific compound can be set appropriately by one skilled in the art. The antigen-binding activity of an antigen-binding domain (or an antigen-binding molecule) can be assessed as dissociation constant (KD), apparent dissociation constant (apparent KD), dissociation rate constant (kd), apparent dissociation rate constant (apparent kd), etc. They can be determined by methods known to those skilled in the art, for example, using Biacore (GE Healthcare), the Scatchard plot, FACS, or such.

In the present invention, the step of selecting an antibody or an antigen-binding domain with higher antigen-binding activity in the presence of a target tissue-specific compound than in the absence of the compound has the same meaning as the step of selecting an antibody or an antigen-binding domain with lower antigen-binding activity in the absence of a target tissue-specific compound than in the presence of the compound.

In the present invention, the step of selecting an antibody or an antigen-binding domain with higher antigen-binding activity in the presence of a high concentration of a target tissue-specific compound than in the presence of a low concentration of the compound has the same meaning as the step of selecting an antibody or an antigen-binding domain with lower antigen-binding activity in the absence of a target tissue-specific compound than in the presence of the compound.

As long as antigen-binding activity in the absence of a target tissue-specific compound is lower than the antigen-binding activity in the presence of the compound, the difference between antigen-binding activity in the presence of the compound and antigen-binding activity in the absence of the compound is not particularly limited, but preferably, the antigen-binding activity in the presence of the compound relative to the antigen-binding activity in the absence of the compound is twofold or more, more preferably 10-fold or more, and even more preferably 40-fold or more. The upper limit of the difference between the antigen-binding activities is not particularly limited, and as long as it can be produced by the techniques of those skilled in the art, any value such as 400-fold, 1000-fold, or 10000-fold is possible. In the absence of a target tissue-specific compound, when antigen-binding activity is not observed, this upper limit becomes infinity.

The antigen-binding domains (or antigen-binding molecules containing the domains) of the present invention which are to be screened by the aforementioned screening methods may be any antigen-binding domains (or antigen-binding molecules); and for example, the above-mentioned antigen-binding domains (or antigen-binding molecules) can be screened. For example, antigen-binding domains (or antigen-binding molecules) having naturally-occurring sequences can be screened, and antigen-binding domains (or antigen-binding molecules) with substituted amino acid sequences may be screened.

Library

According to one embodiment, the antigen-binding domain (or an antigen-binding molecule comprising this domain) of the present invention may be obtained from a library comprising mainly a plurality of antigen-binding molecules having sequences different from one another, in which the antigen-binding domain comprises at least one amino acid residue that changes the antigen-binding activity of the antigen-binding molecule depending on the concentration of a small molecule compound. A non-limiting embodiment of the small molecule compound is, for example, a target tissue-specific compound or an unnatural compound. Examples of a target tissue-specific compound include (1) primary metabolites of the Krebs cycle or the glycolytic pathway such as lactic acid, succinic acid, or citric acid, (2) amino acids such as alanine, glutamic acid, or aspartic acid, (3) amino acid metabolites such as kynurenine and metabolites thereof such as anthranilic acid, 3-hydroxykynurenine, and kynurenic acid, (4) arachidonic acid metabolites such as prostaglandin E2, and (5) nucleosides carrying a purine ring structure such as adenosine, adenosine triphosphate (ATP), adenosine diphosphate (ADP), and adenosine monophosphate (AMP). Below are examples of a library that comprises mainly a plurality of such antigen-binding molecules having different sequences from one another, in which the antigen-binding domain comprises at least one amino acid residue that changes the binding activity of the antigen-binding molecule toward an antigen depending on adenosine and/or ATP which are target tissue-specific compounds. Libraries of antigen-binding molecules whose antigen-binding activity varies depending on the concentration of a small molecule compound other than adenosine and/or ATP may also be applied appropriately according to the examples described below.

Herein, a "library" refers to a set of a plurality of antigen-binding molecules or a plurality of fusion polypeptides comprising antigen-binding molecules that have different sequences from one another, or nucleic acids or polynucleotides encoding these molecules or polypeptides. Sequences of a plurality of antigen-binding molecules or a plurality of fusion polypeptides comprising antigen-binding molecules in a library are not uniform sequences, and the antigen-binding molecules or fusion polypeptides comprising antigen-binding molecules have sequences that are different from one another.

Embodiments of the "library" in the present specification can provide not only libraries that can efficiently yield antigen-binding molecules which bind to a target antigen in the presence of a small molecule but do not bind to the target antigen in the absence of the small molecule (small-molecule dependence), but also libraries that can efficiently yield antibodies which bind to a target antigen in the absence of a small molecule and do not bind to the target antigen in the presence of the small molecule (inverse small-molecule dependence).

In one embodiment of the present invention, a fusion polypeptide of the antigen-binding molecule of the present invention and a heterologous polypeptide can be prepared. In a certain embodiment, the fusion polypeptide can be formed by fusion with at least a portion of a viral coat protein selected from the group consisting of, for example, viral coat proteins pIII, pVIII, pVII, pIX, Soc, Hoc, gpD, and pVI, and mutants thereof.

In one embodiment, the antigen-binding molecule of the present invention may be ScFv, a Fab fragment, F(ab)$_2$, or F(ab')$_2$. Therefore, in another embodiment, the present invention provides a library that comprises mainly a plurality of fusion polypeptides having different sequences from one another, in which the fusion polypeptides are formed by fusing these antigen-binding molecules with a heterologous polypeptide. Specifically, the present invention provides a library that comprises mainly a plurality of fusion polypeptides having different sequences from one another, in which the fusion polypeptides are formed by fusing these antigen-binding molecules with at least a portion of a viral coat protein selected from the group consisting of, for example, viral coat proteins pIII, pVIII, pVII, pIX, Soc, Hoc, gpD, and pVI, and mutants thereof. The antigen-binding molecule of the present invention may further comprise a dimerization domain. In one embodiment, the dimerization domain can be located between the heavy or light chain variable region of the antibody and at least a portion of the viral coat protein. This dimerization domain may comprise at least one dimerization sequence and/or one or more sequences comprising cysteine residue(s). This dimerization domain may be preferably linked to the C terminus of the heavy chain variable region or constant region. The dimerization domain can assume various structures, depending on whether the antibody variable region is prepared as a fusion polypeptide component with the viral coat protein component (an amber stop codon following the dimerization domain is absent) or depending on whether the antibody variable region is prepared predominantly without containing the viral coat protein component (e.g., an amber stop codon following the dimerization domain is present). When the antibody variable region is prepared predominantly as a fusion polypeptide with the viral coat protein component, bivalent display is achieved by one or more disulfide bonds and/or a single dimerization sequence.

Herein, the phrase "sequences are different from one another" in the expression "a plurality of antigen-binding molecules whose sequences are different from one another" means that the sequences of antigen-binding molecules in a library are different from one another. Specifically, in a library, the number of sequences different from one another reflects the number of independent clones with different sequences, and may also be referred to as "library size". The library size of a conventional phage display library ranges from $10^6$ to $10^{12}$. The library size can be increased up to $10^{14}$ by the use of known techniques such as ribosome display. However, the actual number of phage particles used in panning selection of a phage library is in general 10 to 10,000 times greater than the library size. This excess multiplicity is also referred to as "the number of library equivalents", and means that there are 10 to 10,000 individual clones that have the same amino acid sequence. Thus, in the present invention, the phrase "sequences are different from one another" means that the sequences of independent antigen-binding molecules in a library, excluding library equivalents, are different from one another. More specifically, the above means that there are $10^6$ to $10^{14}$ antigen-binding molecules whose sequences are different from one another, preferably $10^7$ to $10^{12}$ molecules, more preferably $10^8$ to $10^{11}$ molecules, and particularly preferably $10^8$ to $10^{10}$ molecules whose sequences are different from one another.

Herein, the phrase "a plurality of" in the expression "a library mainly composed of a plurality of antigen-binding domains or antigen-binding molecules containing an antigen-binding domain" generally refers to, in the case of, for example, antigen-binding molecules, fusion polypeptides, polynucleotide molecules, vectors, or viruses of the present invention, a group of two or more types of the substance. For example, when two or more substances are different from one another in a particular characteristic, this means that there are two or more types of the substance. Such examples may include, for example, mutant amino acids observed at specific amino acid positions in an amino acid sequence. For example, when there are two or more antigen-binding molecules of the present invention whose sequences are substantially the same or preferably the same except for flexible residues or except for particular mutant amino acids at hypervariable positions exposed on the surface, there are a plurality of antigen-binding molecules of the present invention. In another example, when there are two or more polynucleotide molecules whose sequences are substantially the same or preferably the same except for nucleotides encoding flexible residues or nucleotides encoding mutant amino acids of hypervariable positions exposed on the surface, there are a plurality of polynucleotide molecules of the present invention.

In addition, herein, the phrase "mainly composed of" in the expression "a library mainly composed of a plurality of antigen-binding molecules" reflects the number of antigen-binding molecules whose antigen-binding activity varies depending on the concentration of a small molecule compound (e.g., a target tissue-specific compound), among independent clones with different sequences in a library. Specifically, it is preferable that there are at least $10^4$ antigen-binding molecules having such binding activity in a library. More preferably, antigen-binding domains of the present invention can be obtained from a library containing at least $10^5$ antigen-binding molecules having such binding activity. Still more preferably, antigen-binding domains of the present invention can be obtained from a library containing at least $10^6$ antigen-binding molecules having such binding activity. Particularly preferably, antigen-binding domains of the present invention can be obtained from a library containing at least $10^7$ antigen-binding molecules having such binding activity. Yet more preferably, antigen-binding domains of the present invention can be obtained from a library containing at least $10^8$ antigen-binding molecules having such binding activity. Alternatively, this may also be preferably expressed as the ratio of the number of antigen-binding molecules in which antigen-binding activity of the antigen-binding domain varies depending on the presence or absence of adenosine and/or ATP with respect to the number of independent clones having different sequences in a library. Specifically, antigen-binding domains of the present invention can be obtained from a library in which antigen-binding molecules having such binding activity account for $10^{-6}\%$ to 80%, preferably $10^{-5}\%$ to 60%, more preferably $10^{-4}\%$ to 40% of independent clones with different sequences in the library. In the case of fusion polypeptides, polynucleotide molecules, or vectors, similar expressions may be possible using the number of molecules or the ratio to the total number of molecules. In the case of viruses, similar expressions may also be possible using the number of virions or the ratio to total number of virions. As a non-limiting embodiment of the present invention, when a plurality of antigen-binding molecules bind to a single type of antigen, preferably, at least 10, 100, 1000, $10^4$, $10^5$, $10^6$, $10^7$, or $10^8$ molecules are present in a library of antigen-binding molecules showing such binding activity. More preferably, antigen-binding domains of the present invention may be obtained from a library in which at least ten antigen-binding molecules showing such binding activity are present. More preferably, the antigen-binding domains of the present invention may be obtained from a library in which at least 100 antigen-binding molecules showing such binding activity are present. Particularly preferably, the antigen-binding domains of the present invention may be obtained from a library in which at least 1000 antigen-binding molecules showing such binding activity are present.

An embodiment of the present invention provides a library produced by a method that comprises the steps of:
(a) identifying amino acid sites that fulfill any one or more of (i) to (iii) below in antigen-binding domains whose antigen-binding activity varies depending on the concentration of a small molecule compound or in antigen-binding domains that have binding activity to a small molecule compound:
(i) one or more amino acid sites that are not involved in the binding to the small molecule compound;
(ii) one or more amino acid sites that show diversity of amino acid occurrence frequency in the antibody repertoire of the animal species to which the parent antigen-binding domain belongs; and
(iii) one or more amino acid sites that are not important for canonical structure formation; and
(b) designing a library that comprises nucleic acids encoding unmodified antigen-binding domains/molecules, and nucleic acids that encode individually a plurality of variants of the aforementioned antigen-binding domains or antigen-binding molecules comprising an antigen-binding domain, which have different sequences from one another and have modifications at one or more of the amino acid sites identified in step (a).

In the present invention, "one or more amino acid sites that are not involved in the binding to the small molecule compound" can be identified by methods such as crystal structure analysis of a complex formed by a small molecule compound and an antibody, three-dimensional structure analysis using NMR, or introduction of amino acid mutations. In a non-limiting embodiment of the present invention, antibody residues that are not involved in the binding to the small molecule can be identified from crystal structure analysis of the complex formed by the small molecule and the antibody. The phrase "involved in the binding to the small molecule" as used herein refers to a condition where intermolecular interactions are taking place between the atoms of the main chain or side chains of the amino acids forming the antibody H chain or L chain and the atoms of the small molecule compound at a distance that may have an effect on the binding activity; or a condition where certain amino acid residues are involved in the binding of the small molecule compound, including an indirect effect of stabilizing the three-dimensional structure of the CDR loop and such to the conformation when bound to the small molecule compound; and a condition that satisfies both of those conditions.

The "condition where intermolecular interactions are taking place" in the present specification can be determined based on the interatomic distances, for example, between non-hydrogen atoms constituting the main chain or side chains of the amino acids that form the antibody H chain or L chain and the non-hydrogen atoms constituting the small molecule compound obtained from crystal structure analysis of the complex formed by the small molecule and the antibody. For example, the above-mentioned interatomic distances are preferably 3.0 Å, 3.2 Å, 3.4 Å, 3.6 Å, 3.8 Å, 4.0 Å, 4.2 Å, 4.4 Å, 4.6 Å, 4.8 Å, or 5.0 Å or less, but are not limited thereto. More preferably, examples of the interatomic distance are 3.6 Å, 3.8 Å, 4.0 Å, or 4.2 Å or less.

More specifically, the possibility of a direct interaction can be determined based on information on the interatomic distances in the three-dimensional structure and the types of intermolecular interactions that take place, and information on the types of atoms. The determination can be done with more accuracy by, without being limited thereto, observing the effect of introducing amino acid residue mutations such as modification to Ala or Gly on the activities of small molecule compounds.

With respect to the "indirectly influenced condition" in the present specification, whether there is an indirect effect on the binding to a small molecule can be estimated, for example, by analyzing in detail conditions of the conformation of each amino acid residue and intermolecular interactions with the surrounding residues from the three-dimensional structure of the small-molecule-antibody complex. The determination can be done more accurately by observing the effect of introducing amino acid residue mutations such as modification to Ala or Gly on the activities of small molecule compounds.

In one embodiment of the present invention, one can select amino acids that are capable of maintaining an appropriate level of binding to the compound, even when residues that are identified not to be involved in small-molecule-binding are substituted with those amino acids. Accordingly, one can design a library in which selected amino acids appear at the selected residues. In this case, one can design a library to comprise mainly a plurality of antigen-binding molecules, which is an assembly of antigen-binding molecules whose residues identified to be not involved in binding of the small molecule compound have been substituted with amino acids that are different from one another.

In another embodiment, amino acid sites that are not involved in binding to a small molecule compound can be considered as amino acid sites other than any one or more amino acid sites selected from among the amino acid sites involved in binding to a small molecule compound.

In a non-limiting embodiment of the present invention, "one or more amino acid sites not involved in binding to a small molecule compound" can be identified by methods of introducing amino acid mutations. For example, amino acids of the variable region are comprehensively modified, and the binding of each variant to the small molecule is measured by known methods that use Biacore and such. The binding activity (affinity) of each variant to the small molecule is calculated as a KD value. This KD value is compared with the KD value of an unmodified antigen-binding domain/ molecule which is the parent sequence, and the modified positions that show binding greater than a certain standard are determined as amino acid sites not involved in binding to the small molecule compound. For example, as a result of performing measurements using known methods such as Biacore, the binding activity (affinity) of the individual variants to the small molecule is calculated as a KD value; and sites of the heavy chain where alteration does not reduce the binding capacity to the small molecule to less than $1/100$, $1/50$, $1/10$, $1/9$, $1/8$, $1/7$, $1/6$, $1/5$, $1/4$, $1/3$, or $1/2$ of the unmodified antigen-binding domain/molecule, and sites of the light chain where alteration does not reduce the binding capacity to the small molecule to less than $1/100$, $1/50$, $1/10$, $1/9$, $1/8$, $1/7$, $1/6$, $1/5$, $1/4$, $1/3$, or $1/2$ of the unmodified antigen-binding domain/ molecule are determined as amino acid sites not involved in binding to the small molecule compound, but the above-mentioned standards are non-limiting. Alternatively, instead of comparing with the KD value of the unmodified antigen-binding domain/molecule which is the parent sequence, the binding activity (affinity) of individual variants to the small molecule is calculated as a KD value, and heavy chain sites having binding capacity not lower than 10 mM, 1 mM, 100 uM, 10 uM, 1 uM, 100 nM, 10 nM, 1 nM, 100 pM, 10 pM, or 1 pM, and light chain sites having binding capacity not lower than 10 mM, 1 mM, 100 uM, 10 uM, 1 uM, 100 nM, 10 nM, 1 nM, 100 pM, 10 pM, or 1 pM are determined as amino acid sites not involved in binding to the small molecule compound, but the above-mentioned standards are non-limiting. The binding activity of the unmodified antigen-binding domain/molecule and variants to the small molecule can be measured by appropriately selecting methods known to those skilled in the art (Biacore, ELISA, ECL, and such).

In another embodiment, amino acid sites that are not involved in binding to a small molecule compound can be considered as amino acid sites other than any one or more amino acid sites selected from among the amino acid sites involved in binding to the small molecule compound.

"Designing a library comprising nucleic acids that encode individually a plurality of variants of the aforementioned antigen-binding domains or antigen-binding molecules comprising an antigen-binding domain, which have different sequences from one another" in the present invention includes designing a library that comprises a plurality of variants of antigen-binding domains or antigen-binding molecules comprising an antigen-binding domain whose amino acids at specified sites have been modified to desired amino acids using known library techniques such as NNK and TRIM libraries (Gonzalez-Munoz A et al. MAbs 2012; Lee C V et al. J Mol Biol. 2004; Knappik A. et al. J Mol Biol. 2000; Tiller T et al. MAbs 2013), but is not particularly limited to this embodiment.

"One or more amino acids" in the present invention does not particularly limit the number of amino acids, and may be two or more types of amino acids, five or more types of amino acids, ten or more types of amino acids, 15 or more types of amino acids, or 20 or more types of amino acids.

"Amino acid sites showing diversity of amino acid occurrence frequency" in the present invention refers to amino acid sites where two or more types of amino acids are found to be present at an occurrence frequency of 1% or higher in the antibody repertoire of the animal species to which the parent antibody (parent antigen-binding domain) belongs.

"Parent antigen-binding domain" in the present invention refers to an antigen-binding domain whose antigen-binding activity varies depending on the concentration of a small molecule compound or an antigen-binding domain having binding activity to a small molecule compound, which will serve as a template for library production.

"Antibody repertoire of the animal species to which the parent antigen-binding domain belongs" in the present invention refers to a repertoire of antibody gene sequences found in the genes of animal species from which the corresponding parent antigen-binding domain is derived. Without being limited thereto, as an example, when the corresponding parent antigen-binding domain is derived from a human, the antibody repertoire of the animal species to which the parent antigen-binding domain belongs refers to a repertoire of antibody gene sequences found in human genes, and when the corresponding parent antigen-binding domain is derived from a rabbit, the antibody repertoire of the animal species to which the parent antigen-binding domain belongs refers to a repertoire of antibody gene sequences found in the genes of rabbits. However, it must be noted that sequences that are actually not expressed as antibodies due to frame shift or presence of termination/initiation codons are not included even if they are present in the genes.

When the corresponding parent antigen-binding domain is derived from a non-human animal, it can be humanized according to conventional methods, and such techniques are widely known to those skilled in the art (for example, European patent publication EP239400, international publications WO1996/002576, WO1993/012227, WO1992/003918, WO1994/002602, WO1994/025585, WO1996/034096, WO1996/033735, WO1992/001047, WO1992/020791, WO1993/006213, WO1993/011236, WO1993/019172, WO1995/001438, and WO1995/015388, Cancer Res., (1993) 53, 851-856, and BBRC., (2013) 436(3):543-50). When a corresponding parent antigen-binding domain is humanized according to conventional methods and then made into a library, in the "antibody repertoire of the animal species to which the parent antigen-binding domain belongs" of the present invention, the antigen-binding domain prior to humanization and the humanized antigen-binding domain can be both treated as the parent antigen-binding domain. Accordingly, the human repertoire and the repertoire of the animal species from which the pre-humanization antigen-binding domains are derived can be both applied as a repertoire of the same animal species. Without being limited thereto, as an example, when the antigen-binding domains prior to humanization are derived from rabbits, the antibody repertoire of the animal species to which the parent antigen-binding domain belongs refers to the repertoire of antibody gene sequences found in the genes of humans and/or rabbits. However, it must be noted that sequences that are not actually expressed as antibodies due to frame shift or presence of termination/initiation codons are not included even if they are present in the genes.

As an example, the antibody repertoire of the animal species to which the parent antigen-binding domain belongs can be investigated by referring to a known database, without being limited thereto. The site where there is diversity of the amino acid occurrence frequency is generally in the CDR region. In one embodiment, when determining the hypervariable positions of known and/or naturally-occurring antibodies, the data provided by Kabat, Sequences of Proteins of Immunological Interest (National Institute of Health Bethesda Md., 1987 and 1991) are useful. Furthermore, multiple databases on the Internet (http://vbase.mrc-cpe.cam.ac.uk/ and http://www.bioinf.org.uk/abs/index.html) provide many collected sequences of human light chains and heavy chains, and their locations. Information on the sequences and their locations is useful for determining the hypervariable positions in the present invention.

In another embodiment, the antibody repertoire of the animal species to which the parent antigen-binding domain belongs can be examined by cloning antibody genes obtained from the corresponding animal species and analyzing their sequences. Without being limited thereto, as an example, a human antibody repertoire is constructed from antibody genes derived from lymphocytes of healthy individuals and may be examined by analyzing the sequences of a naïve library comprising naïve sequences which are unbiased antibody sequences in their repertoire (Gejima et al. (Human Antibodies (2002) 11, 121-129); Cardoso et al. (Scand. J. Immunol. (2000) 51, 337-344)). When examining a repertoire, it is desirable to analyze at least 100 types of sequences, preferably 200 types of sequences, and more preferably 400 types of sequences or more.

With respect to "the antibody repertoire of the animal species to which the parent antigen-binding domain belongs" in the present invention, more preferably it is desirable to examine subgroups of the germline to which the parent antigen-binding domain belongs, without being limited thereto. Examples of a framework include sequences of currently known completely human-type framework regions listed in a website such as V-Base (http://vbase.mrc-cpe.ca-m.ac.uk/). Any of the sequences of these framework regions may be appropriately used as a germline sequence contained in the antigen-binding molecule of the present invention. The germline sequences may be classified into subgroups based on their similarity (Tomlinson et al., J. Mol. Biol. (1992) 227, 776-798; Williams and Winter, Eur. J. Immunol. (1993) 23, 1456-1461; and Cox et al., Nat. Genetics (1994) 7, 162-168). In one example, seven subgroups for the heavy-chain variable region in human antibodies, seven subgroups for Vic, and ten types of subgroups for VX, have been reported; and without being particularly limited to this embodiment, each of the amino acid sites may be examined by analyzing the amino acid repertoire in the subgroup to which the parent antigen-binding domain belongs.

In the "amino acid sites that are not important for canonical structure formation" of the present invention, an antibody canonical structure shows clustering of the three-dimensional structures of mainly CDR1 and CDR2 of the antibody heavy chains and light chains, and the structures can be classified according to the antibody subgroups and the length or sequence of CDRs. In each canonical structure, residues important for maintaining the structure are already known, and by referring to the reports of Chothia et al. (J. Mol. Biol. (1992) 227, 799-817), A1-Lazikani et al. (J. Mol. Biol. (1997) 273, 927-948), Tomlinson et al. (J. Mol. Biol. (1992) 227, 776-798) and such, it is possible to identify the canonical structure that the corresponding parent antigen-binding molecule is classified to, and the residues important for that structure.

Furthermore, even in antigen-binding domains other than those of antibodies, it is known that there are residues important for maintaining the structure; and while not being limited thereto, amino acid sites not important for formation of the canonical structure in each antigen-binding domain can be identified by structural analysis and such of produced mutants.

Another embodiment of the library of the present invention is, for example, the library below.

A library which is produced by a method comprising the steps of:
(a) identifying amino acid sites that fulfill any one or more of (i) to (iii) below in antigen-binding domains whose antigen-binding activity varies depending on the concentration of a small molecule compound or in antigen-binding domains that have binding activity to a small molecule compound:
(i) one or more amino acid sites that are not involved in the binding to the small molecule compound;
(ii) one or more amino acid sites that show diversity of amino acid occurrence frequency in the antibody repertoire of the animal species to which the parent antigen-binding domain belongs; and
(iii) one or more amino acid sites that are not important for canonical structure formation;
(b) producing a plurality of variants of the aforementioned antigen-binding domains or antigen-binding molecules comprising an antigen-binding domain, which have different sequences from one another and have modifications at one or more of the amino acid sites identified in step (a);
(c) identifying one or more amino acid modifications that do not substantially change the binding activity of each of the aforementioned variants to the small molecule compound; and
(d) producing a library comprising nucleic acids that encode unmodified antigen-binding domains/molecules, and nucleic acids that encode a plurality of variants of the aforementioned antigen-binding domains or antigen-binding molecules comprising the antigen-binding domain, which have different sequences from one another and have one or more of the amino acid modifications identified in step (c).

In the "step of producing a plurality of variants of the aforementioned antigen-binding domains or antigen-binding molecules comprising an antigen-binding domain, which have different sequences from one another" of the present invention, among the amino acid sites identified in step (a), the sites in CDR1 and CDR2 can be substituted with amino acids having an occurrence frequency of 10% or more, 9% or more, 8% or more, 7% or more, 6% or more, 5% or more, 4% or more, 3% or more, 2% or more, or 1% or more in the germline, and the sites in CDR3 can be substituted with amino acids having an occurrence frequency of 10% or more, 9% or more, 8% or more, 7% or more, 6% or more, 5% or more, 4% or more, 3% or more, 2% or more, or 1% or more in the germline to produce the individual variants, but the production is not limited thereto.

"Plurality of variants" in the present invention refers to individually different variants of antigen-binding domains produced by substituting at least one or more amino acids in the unmodified antigen-binding domain which is the parent sequence.

The "step of identifying one or more amino acid modifications that do not substantially change the binding activity of each of the aforementioned variants to the small molecule compound" in the present invention has the meaning below. For example, the binding of each variant to a small molecule is measured by a known method using Biacore or such, and the binding activity (affinity) of each variant to the small molecule is calculated as a KD value. This KD value is compared to the KD value of the unmodified antigen-binding domain/molecule which is the parent sequence, and the modified positions that show binding greater than a certain standard are determined as sites that can be changed; and without being limited thereto, amino acids substituted at these sites can be determined as amino acids that can be made into a library (flexible residues made to appear in the library). Alternatively, rather than comparing the KD value of an individual variant with the KD value of the unmodified antigen-binding domain/molecule which is the parent sequence, one can determine the modified positions that show binding greater than a certain standard as sites that can be changed; and without being limited thereto, amino acids substituted at these sites can be determined as amino acids that can be made into a library (flexible residues made to appear in the library).

In the present invention, in determining amino acids that can be made into a library, "modified positions that show binding greater than a certain standard" has the meaning below. For example, as a result of performing measurements using known methods such as Biacore, the binding activity (affinity) of each variant to a small molecule is calculated as a KD value, and sites of the heavy chain where alteration does not reduce the binding capacity to the small molecule to less than 1/100, 1/50, 1/10, 1/9, 1/8, 1/7, 1/6, 1/5, 1/4, 1/3, or 1/2 of the unmodified antigen-binding domain/molecule, and sites of the light chain where alteration does not reduce the binding capacity to the small molecule to less than 1/100, 1/50, 1/10, 1/9, 1/8, 1/7, 1/6, 1/5, 1/4, 1/3, or 1/2 of the unmodified antigen-binding domain/molecule are determined as sites that can be changed; and amino acids substituted at these sites can be determined as amino acid sites that can be made into a library, but the above-mentioned standards are non-limiting. Alternatively, rather than comparing with the KD value of the unmodified antigen-binding domain/molecule which is the parent sequence, the binding activity (affinity) of an individual variant to a small molecule is calculated as a KD value, and heavy chain sites having binding capacity not lower than 10 mM, 1 mM, 100 uM, 10 uM, 1 uM, 100 nM, 10 nM, 1 nM, 100 pM, 10 pM, or 1 pM, and light chain sites having binding capacity not lower than 10 mM, 1 mM, 100 uM, 10 uM, 1 uM, 100 nM, 10 nM, 1 nM, 100 pM, 10 pM, or 1 pM are determined as sites that can be changed; and amino acids substituted at these sites can be determined as amino acid positions that can be made into a library, but the above-mentioned standards are non-limiting.

The binding activity of the unmodified antigen-binding domain/molecule and variants to a small molecule can be measured by appropriately selecting methods known to those skilled in the art (Biacore, ELISA, ECL, and such).

In another embodiment, amino acid sites not involved in binding to a small molecule compound may be considered as amino acid sites other than any one or more amino acid sites selected from among the amino acid sites involved in binding to a small molecule compound.

In the present invention, "the step of producing a library comprising nucleic acids that encode unmodified antigen-binding domains/molecules, and a plurality of variants of the aforementioned antigen-binding domains or antigen-binding molecules comprising an antigen-binding domain, which have different sequences from one another and have one or more of the amino acid modifications identified in step (d)" includes but is not limited to embodiments of constructing a library so that the occurrence frequency of each amino acid identified in step (d) at specific site will become equivalent (for example, when the amino acid repertoire is ten, the occurrence of each amino acid will be adjusted to 10%).

Another embodiment of the library of the present invention is, for example, the library below.

A library produced by a method that comprises the steps of:

1) contacting a library that comprises a plurality of antigen-binding molecules having binding activity to a small molecule compound with the small molecule compound; and
2) concentrating from the library, nucleic acids that encode a plurality of variants of antigen-binding molecules having binding activity to the small molecule compound.

Furthermore, in another embodiment, the library is a library in which the antigen-binding molecule is an antigen-binding molecule comprising the heavy-chain variable regions and light-chain variable regions of an antibody, and is produced by a method that comprises any one of the steps of:

1) designing a library by concentrating nucleic acids that encode a plurality of variants of antigen-binding molecules having binding activity to a small molecule compound from the library which comprises nucleic acids encoding one or more variants produced by modifying amino acids positioned in the heavy chain variable regions;
2) designing a library by concentrating nucleic acids that encode a plurality of variants of antigen-binding molecules having binding activity to a small molecule compound from the library which comprises nucleic acids encoding one or more variants produced by modifying amino acids positioned in the light chain variable regions; and
3) designing a library by combining the antigen-binding molecule-encoding nucleic acids concentrated from each of the variable region libraries of steps 1) and 2).

"Concentrate" in the present invention refers to increasing the ratio of nucleic acids encoding variants having the desired activity present in the library relative to the ratio in the library before the concentration operation is performed. Without being limited thereto, as an example, concentrating nucleic acids that encode variants of antigen-binding molecules having binding activity to a small molecule compound can be accomplished by increasing the ratio of presence of nucleic acids encoding the variants of antigen-binding molecules having binding activity to the small molecule compound by panning. More specifically, without being limited thereto, as an example, it is possible to increase the ratio of presence of nucleic acids that encode variants of antigen-binding molecules having binding activity to a small molecule compound by panning, which involves contacting the small molecule compound with phages presenting a library that comprises a plurality of antigen-binding molecules on their surface by the phage display method, removing phages presenting molecules that do not have binding activity and phages not presenting the molecules by a washing operation, and then collecting only the phages that present antigen-binding molecules which maintain binding. More specifically, the ratio of presence of nucleic acids that encode variants having the desired activity increases preferably 1.1-times or more relative to that of the library before the concentration operation is performed. More preferably, the library of the present invention can be produced by increasing the ratio of presence of nucleic acids encoding variants having the desired activity by 1.2 times or more, 1.5 times or more, 2 times or more, 4 times or more, 10 times or more, 25 times or more, or 100 times or more.

Library Production Method

The invention of the present application also relates to methods for producing various embodiments of "libraries" included in the invention of this application described above.

The "library production method" of the invention of the present application is not limited to any of the specific methods shown as examples below, and includes any method that can produce the above-described "libraries" of the invention of the present application.

For example, "library production method" in the invention of the present application include the methods shown as examples below.

Each of the specific matters in the "library production method" shown as examples below has technical significance as described in detail above with regard to the "library" in the invention of the present application.

Example 1

A method for producing a library that comprises mainly
(i) a plurality of antigen-binding domains or antigen-binding molecules comprising an antigen-binding domain, which have different sequences from one another; or
(ii) nucleic acids that encode the plurality of antigen-binding domains or antigen-binding molecules comprising an antigen-binding domain, which have different sequences from one another;

wherein the aforementioned antigen-binding domains or antigen-binding molecules are antigen-binding domains or antigen-binding molecules comprising an antigen-binding domain whose antigen-binding activity varies depending on the concentration of a small molecule compound;
wherein the method comprises the steps of (a) and (b) below:
(a) identifying amino acid sites that fulfill any one or more of (i) to (iii) below in antigen-binding domains whose antigen-binding activity varies depending on the concentration of a small molecule compound or in antigen-binding domains that have binding activity to a small molecule compound:
  (i) one or more amino acid sites that are not involved in the binding to the small molecule compound;
  (ii) one or more amino acid sites that show diversity of amino acid occurrence frequency in the antibody repertoire of the animal species to which the parent antigen-binding domain belongs; and
  (iii) one or more amino acid sites that are not important for canonical structure formation; and
(b) designing a library comprising nucleic acids that encode unmodified antigen-binding domains/molecules, and nucleic acids that encode individually a plurality of variants of the aforementioned antigen-binding domains or antigen-binding molecules comprising an antigen-binding domain, which have different sequences from one another and have modifications at one or more of the amino acid sites identified in step (a).

Example 2

A method for producing a library that comprises mainly
(i) a plurality of antigen-binding domains or antigen-binding molecules comprising an antigen-binding domain, which have different sequences from one another; or
(ii) nucleic acids that encode the plurality of antigen-binding domains or antigen-binding molecules comprising an antigen-binding domain, which have different sequences from one another;

wherein the aforementioned antigen-binding domains or antigen-binding molecules are antigen-binding domains or antigen-binding molecules comprising an antigen-binding domain whose antigen-binding activity varies depending on the concentration of a small molecule compound;

wherein the method comprises the steps of (a) to (d) below:
(a) identifying amino acid sites that fulfill any one or more of (i) to (iii) below in antigen-binding domains whose antigen-binding activity varies depending on the concentration of a small molecule compound or in antigen-binding domains that have binding activity to a small molecule compound:
(i) one or more amino acid sites that are not involved in the binding to the small molecule compound;
(ii) one or more amino acid sites that show diversity of amino acid occurrence frequency in the antibody repertoire of the animal species to which the parent antigen-binding domain belongs; and
(iii) one or more amino acid sites that are not important for canonical structure formation;
(b) producing a plurality of variants of the aforementioned antigen-binding domains or antigen-binding molecules comprising an antigen-binding domain, which have different sequences from one another and have modifications at one or more of the amino acid sites identified in step (a);
(c) identifying one or more amino acid modifications that do not substantially change the binding activity of each of the aforementioned variants to the small molecule compound; and
(d) producing a library comprising nucleic acids that encode unmodified antigen-binding domains/molecules, and nucleic acids that encode a plurality of variants of the aforementioned antigen-binding domains or antigen-binding molecules comprising an antigen-binding domain, which have different sequences from one another and have one or more of the amino acid modifications identified in step (c).

Example 3

A method for producing a library that comprises mainly
(i) a plurality of antigen-binding domains or antigen-binding molecules comprising an antigen-binding domain, which have different sequences from one another; or
(ii) nucleic acids that encode the plurality of antigen-binding domains or antigen-binding molecules comprising an antigen-binding domain, which have different sequences from one another;
wherein the aforementioned antigen-binding domains or antigen-binding molecules are antigen-binding domains or antigen-binding molecules comprising an antigen-binding domain whose antigen-binding activity varies depending on the concentration of a small molecule compound
wherein the method comprises the steps of 1) and 2) below:
1) contacting a library that comprises a plurality of antigen-binding molecules having binding activity to a small molecule compound with the small molecule compound; and
2) concentrating from the library, nucleic acids that encode a plurality of variants of antigen-binding molecules having binding activity to the small molecule compound.

Example 4

A method for producing a library that comprises mainly
(i) a plurality of antigen-binding domains or antigen-binding molecules comprising an antigen-binding domain, which have different sequences from one another; or
(ii) nucleic acids that encode the plurality of antigen-binding domains or antigen-binding molecules comprising an antigen-binding domain, which have different sequences from one another;
wherein the aforementioned antigen-binding domains or antigen-binding molecules are antigen-binding domains or antigen-binding molecules comprising an antigen-binding domain whose antigen-binding activity varies depending on the concentration of a small molecule compound;
wherein the method comprises any one of steps 1) to 3) below:
1) designing a library by concentrating nucleic acids that encode a plurality of variants of antigen-binding molecules having binding activity to a small molecule compound from the library of (Example 3) which comprises nucleic acids encoding one or more variants produced by modifying amino acids positioned in the heavy chain variable regions;
2) designing a library by concentrating nucleic acids that encode a plurality of variants of antigen-binding molecules having binding activity to a small molecule compound from the library of (Example 3) which comprises nucleic acids encoding one or more variants produced by modifying amino acids positioned in the light chain variable regions; and
3) designing a library by combining the antigen-binding molecule-encoding nucleic acids concentrated from each of the variable region libraries of steps 1) and 2).

Example 5

The library production method of any one of (Example 1) to (Example 4) described above, wherein the antigen-binding molecules are fusion polypeptides formed by fusing an antigen-binding domain with at least a portion of a virus coat protein.

Example 6

The library production method of any one of (Example 1) to (Example 4) described above, wherein the aforementioned antigen-binding molecules are antigen-binding molecules comprising antibody heavy chains and light chains, and the method further comprises the step of designing a synthetic library of the heavy chains and/or light chains.

Example 7

The library production method of (Example 6) described above, wherein the antibody heavy chains and/or light chains include a germline-derived framework sequence.

Example 8

The library production method of any one of (Example 1) to (Example 7) described above, wherein the aforementioned small molecule compound is a target tissue-specific compound or an unnatural compound.

Example 9

The library production method of any one of (Example 1) to (Example 8) described above, wherein the aforementioned target tissue is a cancer tissue or an inflammatory tissue.

Example 10

The library production method of (Example 9) described above, wherein the cancer tissue-specific compound is at least one compound selected from the group consisting of nucleosides that have a purine ring structure, amino acids and their metabolites, lipids and their metabolites, primary metabolites from sugar metabolism, and nicotinamide and its metabolites.

Example 11

The library production method of any one of (Example 1) to (Example 10) described above, wherein the small molecule compound is kynurenine, adenosine, adenosine monophosphate, adenosine diphosphate, or adenosine triphosphate.

Example 12

The library production method of any one of (Example 1) to (Example 11) described above, wherein the amino acid sites not involved in binding with the small molecule compound are sites other than any one or more of the amino acids selected from below:
H chain: 97, 100c, 101, 94, 95, 100d, 100e, 33, 50, 52, 56, 57, 58, 99, 100, 100a, 54, 55 (Kabat Numbering); and
L chain: 49, 55, 95c, 96, 95a, 95b (Kabat Numbering).

Library (Other Embodiments)

An embodiment of a library of the present invention that can yield antigen-binding domains whose antigen-binding ability varies depending on the concentration of a small molecule compound is, for example, the library below.

A library that comprises mainly:
(i) a plurality of antigen-binding domains or antigen-binding molecules comprising an antigen-binding domain, which have different sequences from one another; or
(ii) nucleic acids that encode a plurality of antigen-binding domains or antigen-binding molecules comprising an antigen-binding domain, which have different sequences from one another;

wherein the antigen-binding domains or antigen-binding molecules are antigen-binding domains or antigen-binding molecules comprising an antigen-binding domain having binding activity to a small molecule compound. A library of this embodiment preferably has diversity 20 of $1.2 \times 10^8$ or higher.

The term "comprises mainly" in the description of a library that comprises mainly a plurality of antigen-binding molecules in this embodiment reflects the number of antigen-binding molecules having binding activity to a small molecule compound (for example, a target tissue-specific compound) among the number of independent clones that differ in sequence in the library. Specifically, presence of at least $10^4$ antigen-binding molecules that exhibit such binding activity in the library is preferred. In other words, the term may be suitably expressed as the ratio of antigen-binding molecules in which the antigen-binding activity of the antigen-binding domain differs depending on the presence or absence of the small molecule to the number of the independent clones that differ in sequence in the library. Specifically, the antigen-binding domains of the present invention can be obtained from a library that comprises antigen-binding molecules that exhibit such binding activity at a ratio of $10^{-6}\%$ to 80%, or $10^{-5}\%$ to 60%, preferably $10^{-4}\%$ to 40%, more preferably $10^{-3}\%$ to 40%, and even more preferably $10^{-2}\%$ to 40% to the number of the independent clones that differ in sequence in the library. Similar to the case above, fusion polypeptides, polynucleotide molecules, or vectors can also be presented as the number of molecules or the ratio to all molecules. In addition, viruses can also be presented as the number of individual viruses or the ratio to all viruses as in the above case.

An embodiment of a library of the present invention that can yield antigen-binding domains whose antigen-binding activity varies depending on the concentration of a small molecule compound is, for example, the library below.

A library that comprises mainly:
(i) a plurality of antibody molecules having different sequences from one another; or
(ii) nucleic acids that encode a plurality of antibody molecules having different sequences from one another;

wherein the antibody molecules have binding activity to a small molecule compound and have a diversity that fulfills any one of (i) to (vi) below:
(i) heavy chain CDR1 diversity of 13 or higher;
(ii) heavy chain CDR2 diversity of 129 or higher;
(iii) heavy chain CDR3 diversity of 5 or higher;
(iv) light chain CDR1 diversity of 193 or higher;
(v) light chain CDR2 diversity of 7 or higher; and
(vi) light chain CDR3 diversity of 17 or higher.

The term "comprises mainly" in the description of a library that comprises mainly a plurality of antigen-binding molecules in this embodiment reflects the number of antigen-binding molecules having binding activity to a small molecule compound (for example, a target tissue-specific compound) among the number of independent clones that differ in sequence in the library. Specifically, presence of at least $10^4$ antigen-binding molecules that exhibit such binding activity in the library is preferred. In other words, the term may be suitably expressed as the ratio of antigen-binding molecules in which the antigen-binding activity of the antigen-binding domain differs depending on the presence or absence of the small molecule to the number of independent clones that differ in sequence in the library. Specifically, the antigen-binding domains of the present invention can be obtained from a library comprising antigen-binding molecules that exhibit such binding activity at a ratio of $10^{-6}\%$ to 80%, or $10^{-5}\%$ to 60%, preferably $10^{-4}\%$ to 40%, more preferably $10^{-3}\%$ to 40%, and even more preferably $10^{-2}\%$ to 40% to the number of independent clones that differ in sequence in the library. As in the case above, fusion polypeptides, polynucleotide molecules, or vectors can also be presented as the number of molecules or the ratio to all molecules. In addition, similar to the case above, viruses can also be presented as the number of individual virus individuals or the ratio to all viruses.

An embodiment of a library of the present invention that can yield antigen-binding domains whose antigen-binding ability varies depending on the concentration of a small molecule compound is, for example, the library below.

A library that comprises mainly:
(i) a plurality of antigen-binding domains or antigen-binding molecules comprising an antigen-binding domain, which have different sequences from one another; or
(ii) nucleic acids that encode a plurality of antigen-binding domains or antigen-binding molecules comprising an antigen-binding domain, which have different sequences from one another;

wherein the antigen-binding domains or antigen-binding molecules are antigen-binding domains or antigen-binding molecules comprising an antigen-binding domain that have binding activity to a small molecule compound, and the library is for obtaining antigen-binding domains or antigen-binding molecules comprising an antigen-binding domain whose antigen-binding activity varies depending on the concentration of a small molecule compound.

The term "comprises mainly" in the description of a library that comprises mainly a plurality of antigen-binding molecules in this embodiment reflects the number of antigen-binding molecules having binding activity to a small molecule compound (for example, a target tissue-specific compound) among the number of independent clones that differ in sequence in the library. Specifically, presence of at least $10^4$ antigen-binding molecules that exhibit such binding activity in the library is preferred. In other words, the term may be suitably expressed as the ratio of antigen-binding molecules in which the antigen-binding activity of the antigen-binding domain differs depending on the presence or absence of the small molecule to the number of independent clones that differ in sequence in the library. Specifically, the antigen-binding domains of the present invention can be obtained from a library comprising antigen-binding molecules that exhibit such binding activity at a ratio of $10^{-6}\%$ to 80%, or $10^{-5}\%$ to 60%, preferably $10^{-4}\%$ to 40%, more preferably $10^{-3}\%$ to 40%, and even more preferably $10^{-2}\%$ to 40% to the number of independent clones that differ in sequence in the library. As in the above case, fusion polypeptides, polynucleotide molecules, or vectors can also be presented as the number of molecules or the ratio to all molecules. In addition, viruses can also be presented as the number of individual viruses or the ratio to all viruses as in the above case.

Amino Acids that Change the Antigen-Binding Activity of an Antigen-Binding Domain Depending on the Presence or Absence of a Small Molecule With respect to methods for obtaining (methods of screening for) templates (antigen-binding domains whose antigen-binding activity varies depending on the concentration of a small molecule compound, or antigen-binding domains having binding activity to a small molecule compound) to be used when producing a library of the present invention, these antigen-binding domains and such may be prepared in any manner. It is possible to use pre-existing antigen-binding domains or antibodies, and pre-existing libraries (phage libraries, etc.), antibodies or libraries prepared from hybridomas obtained by immunizing animals or from B cells of immunized animals, for example, antibodies or libraries prepared from immune cells such as B cells of animals immunized with a conjugate in which adenosine or ATP, which is an embodiment of the small molecule compound, is suitably linked to an adjuvant agent such as a highly immunogenic T cell epitope peptide, without being limited thereto. A non-limiting example of the T cell epitope peptide suitably includes a Tetanus toxin-derived p30 helper peptide (shown in SEQ ID NO: 4, and also referred to as Fragment C (FrC)).

In a non-limiting embodiment of a method for preparing antigen-binding domains or antibodies of the present invention obtained by the aforementioned screening method, it is possible to use a library that comprises, for example, a module of about 35 amino acids called the A domain which is contained in the in vivo cell membrane protein Avimer; Adnectin containing the 10Fn3 domain which binds to the protein in fibronectin, a glycoprotein expressed on cell membranes; Affibody which has as scaffold the IgG-binding domain composed of a 58-amino acid three-helix bundle of Protein A; Designed Ankyrin Repeat proteins (DARPins) which are regions exposed on the molecular surface of ankyrin repeats (AR) having a structure of repeatedly stacked subunits consisting of a turn containing 33 amino acid residues, two antiparallel helices, and a loop; Anticalins and such, in which four loop regions support one side of a barrel structure formed by eight antiparallel strands twisted toward the center, which are highly conserved in lipocalin molecules such as neutrophil gelatinase-associated lipocalin (NGAL); and the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the acquired immune system in jawless vertebrates such as lamprey and hagfish.

Preferred antigen-binding domains of the present invention include, for example, antigen-binding domains containing antibody heavy-chain and light-chain variable regions. Preferred examples of such antigen-binding domains include "single chain Fv (scFv)", "single chain antibody", "Fv", "single chain Fv 2 (scFv2)", "Fab", "F(ab')2", and IgG, and a library comprising thereof may also be used.

Furthermore, as a non-limiting embodiment of a method for preparing antigen-binding domains or antibodies of the present invention obtained by the aforementioned screening method, it is possible to use a technique for preparing antigen-binding domains or antibodies having binding activity to a small molecule compound by panning using an above-mentioned library. As a library, it is possible to use, for example, but without being limited thereto, a phage display library, a ribosome display library, an mRNA display library, a cDNA display library, a CIS display library, an *E. coli* display library, a Gram-positive bacterium display library, an yeast display library, a mammalian cell display library, a virus display library, and an in vitro virus display library.

In an embodiment of the aforementioned technique for preparing antigen-binding domains or antibodies having binding activity to a small molecule compound by panning, small molecule compounds fixed onto a carrier such as beads can be used. The fixed small molecule compounds can be produced by, for example, without being limited thereto, a method of contacting small molecule compounds synthesized to be chemically linked to biotin via a linker with beads or a plate onto which streptavidin or NeutrAvidin has been fixed, or a method of adhering the small molecule compounds covalently linked to an adjuvant such as bovine serum albumin (BSA) to beads or plates by hydrophobic interaction. These methods are already publicly known (J. Immunol. Methods. 2003 September, 280 (1-2): 139-55; BMC Biotechnol. 2009 Jan. 29; 9: 6. doi: 10.1186/1472-6750-9-6). Antigen-binding domains or antibodies having binding activity to the small molecule compounds can be prepared by collecting antigen-binding domains or antibodies that have binding activity to the fixed small molecule compounds.

Alternatively, in another embodiment of the aforementioned technique for preparing antigen-binding domains or antibodies having binding activity to a small molecule compound by panning, a fluorescence-labeled small molecule compound, or a biotin-labeled small molecule compound and fluorescence-labeled streptavidin (or NeutrAvidin or avidin) may be used. Antigen-binding domains or antibodies having binding activity to the small molecule compound can be prepared by contacting the fluorescence-labeled small molecule compound, or the biotin-labeled small molecule compound and fluorescence-labeled streptavidin (or NeutrAvidin or avidin), with a library presented on the cell surface or such, and then using the fluorescence-activated cell sorting (FACS) method. These methods are already publicly known (Proc Natl Acad Sci USA. 2000 Sep. 26; 97 (20): 10701-5).

Furthermore, in a non-limiting embodiment of a method for preparing antigen-binding domains or antibodies of the present invention obtained by the aforementioned screening method, pre-existing antigen-binding domains having binding activity to the small molecule compound may be used. For example, when adenosine and/ATP are used as an example, without being limited thereto, molecules belonging to the kinase family having ATP-binding activity can be used as the antigen-binding domain, and molecules belonging to the adenosine deaminase family having adenosine-binding activity can be used as the antigen-binding domain. By producing a library of portions in these molecules that are not involved in the binding to ATP and/or adenosine, it is possible to obtain antigen-binding molecules that show antigen binding in a manner dependent on the ATP and/or adenosine concentration.

As a method for obtaining antigen-binding domains using non-antibody-like proteins, a library produced by using the loop-forming sites and surface residues of the a-helix of the non-antibody-like protein can be used, without being limited thereto. Methods for constructing such libraries are already known (Nat Biotechnol. 2004 May; 22 (5): 575-82; J Mol Biol. 1998 Dec. 11; 284 (4): 1141-51; and Nat Biotechnol. 1997 August; 15 (8): 772-7). Furthermore, techniques for obtaining antigen-binding domains that have binding activity to a small molecule compound by panning using a library constructed as described above are publicly known. In one example, the constructed library is expressed on the surface of phages by the phage display method. Phages expressing binding domains that bind to a small molecule compound linked to bovine serum albumin, biotin, or such may be selected using beads, immunotubes, plates, and such. Such methods for obtaining non-antibody-like antigen-binding domains that have binding activity to a small molecule compound are already known (Proc Natl Acad Sci USA. 1999 Mar. 2; 96 (5): 1898-903). Furthermore, amino acid sites not involved in the binding to the small molecule compound and amino acid sites not important for canonical structure formation can be identified by, without being limited thereto, performing a crystal structure analysis on these antigen-binding domains which have binding activity to the small molecule compound, or by producing variants and evaluating their binding activities (J Mol Biol. 2003 Jul. 4; 330 (2): 385-96, Proteins. 2003 Oct. 1; 53 (1): 121-9). The libraries described in the present invention can be constructed by introducing diversity to the amino acid sites identified in this manner. Furthermore, in another embodiment of the present invention, a library of limited amino acid sites can also be used. Anticalin has been reported as a non-antibody-like antigen-binding domain, and is a four-loop region that supports one side of a barrel structure formed by eight antiparallel strands twisted toward the center, which are highly conserved in lipocalin molecules such as neutrophil gelatinase-associated lipocalin (NGAL). In Anticalin, the amino acid sites used for binding to a small molecule compound are known to be different from the amino acid sites used for protein binding; and as an example, without being limited thereto, it is known that mutually different libraries, in which amino acid sites that can be involved in binding to the small molecule and amino acid sites that can be involved in binding to the protein are mutated respectively, can be used (FEBS Lett. 2014 Jan. 21; 588(2):213-8). Therefore, it is possible to construct a library of the present invention by obtaining antigen-binding domains having binding activity to a small molecule compound from a library that can yield binding domains for the small molecule compound, and then introducing diversity at the amino acid sites used to obtain antigen-binding domains having protein-binding activity to the obtained antigen-binding domains having binding activity to the small molecule compound. More specifically, it is known that in human lipocalin2 (Lcn2), each of the amino acid sites, V33, L36, 141, Y52, T54, S68, L70, W79, R81, K134, T136, and Y138, can be used as a site for introducing diversity in a library for obtaining small molecule compound-binding domains (J Am Chem Soc. 2009 Mar. 18; 131(10):3565-76); and similarly, each of the amino acid sites, A40, L42, E44, K46, D47, Q49, K50, L70, R72, K73, D77, W79, P101, G102, L103, K125, S127, Q128, R130, and Y132, can be used as a site for introducing diversity in a library for obtaining protein-binding domains (Proc Natl Acad Sci USA. 2009 May 19; 106(20):8198-203). Therefore, without being limited thereto, it is possible to construct a library of the present invention by first using a library that comprises antigen-binding domains made to have diversity at each of the amino acid sites, V33, L36, 141, Y52, T54, S68, L70, W79, R81, K134, T136, and Y138, to obtain antigen-binding domains having binding activity to a small molecule compound, and then introducing diversity to the obtained antigen-binding domains having binding activity to the small molecule compound at each of the amino acid sites, A40, L42, E44, K46, D47, Q49, K50, R72, K73, D77, P101, G102, L103, K125, S127, Q128, R130, and Y132. For antibodies and non-antibody-like antigen-binding domains other than lipocalin molecules, those skilled in the art can also construct libraries of the present invention by appropriately referring to the above-described library construction methods. In another embodiment, antigen-binding domains having binding activity to a small molecule compound can be used. As an example, *Rhodnius prolixus* aggregation inhibitor 1 (RPAI-1) belonging to the lipocalin family, which is known to have binding activity to ATP, ADP, AMP, and adenosine, can be used (J Biol Chem. 2000 Apr. 28; 275 (17): 12639-50 and Biochemistry, 2002 Mar. 19; 41 (11): 3810-8). Amino acid sites not involved in the binding to the small molecule compound and amino acid sites not important for canonical structure formation can be identified by analyzing the crystal structure of the antigen-binding domains, or by producing variants and then evaluating their binding activities, without being limited thereto. Libraries of the present invention can be constructed by introducing diversity at the amino acid sites identified in this manner. Presence of antigen-binding domains belonging to the lipocalin family having binding activity to various small molecule compounds besides ATP, ADP, AMP, and adenosine, such as histamine, serotonin, adrenaline, and noradrenalin, are known (J Biol Chem. 2003 Feb. 14; 278 (7): 4611-7 and Expert Rev Clin Immunol. 2007 July; 3 (4): 491-501); and without being limited thereto, they can be used to construct libraries of the present invention that use antigen-binding domains having binding activity to various small molecule compounds. For other non-antibody-like antigen-binding domains and antibodies, libraries of the present invention can also be produced by those skilled in the art by appropriately referring to the above-described library construction methods.

As a non-limiting embodiment of the present invention, detailed description will be made using adenosine and/or ATP as examples, but the following examples are also appropriately applied to small molecules besides adenosine and/or ATP. Examples of amino acids that change the antigen-binding activity of the antigen-binding molecule depending on the presence or absence of adenosine and/or ATP as described above may include amino acids that form an adenosine- and/or ATP-binding motif. The amino acid positions where the above-mentioned amino acids are contained in the antigen-binding domain are not limited to any specific position, and as long as the antigen-binding activity of the antigen-binding domain changes depending on the presence or absence of adenosine and/or ATP, any position in the heavy chain variable region or light chain variable region forming the antigen-binding domain is possible. More specifically, the antigen-binding domains of the present invention may be obtained from a library comprising mainly antigen-binding molecules that have different sequences from one another, in which amino acids that change the antigen-binding activity of the antigen-binding molecule depending on the presence or absence of adenosine and/or ATP are contained in the antigen-binding domain of the heavy chain. In a non-limiting embodiment, antigen-binding domains of the present invention may be obtained from a library comprising mainly antigen-binding molecules that have different sequences from one another, in which amino acids that change the antigen-binding activity of the antigen-binding molecule depending on the presence or absence of adenosine and/or ATP are contained in CDR1, CDR2, and/or CDR3 of the heavy chain. In another non-limiting embodiment, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in FR1, FR2, FR3 and/or FR4 of the heavy chain.

Furthermore, in an embodiment of the present invention, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in the antigen-binding domain of the heavy chain and/or light chain. In a non-limiting embodiment, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in CDR1, CDR2, and/or CDR3 of the heavy chain and/or light chain. In another non-limiting embodiment, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in FR1, FR2, FR3 and/or FR4 of the heavy chain and/or light chain.

In a non-limiting embodiment, examples of such amino acids include any one or more amino acids selected from amino acids at positions 52, 52a, 53, 96, 100a, and 100c contained in the heavy chain variable region. Also, in a non-limiting embodiment, examples of such amino acids include one or more amino acids selected from amino acids including Ser at position 52, Ser at position 52a, Arg at position 53, Gly at position 96, Leu at position 100a, and Trp at position 100c contained in the heavy chain variable region.

Any framework sequence can be used as the framework sequence of the light-chain and/or heavy-chain variable regions of an antigen-binding molecule as long as the amino acids that change the antigen-binding activity of the antigen-binding molecule depending on the presence or absence of adenosine and/or ATP are contained in the antigen-binding domain of the heavy chain and/or light chain. The origin of the framework sequences is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In a particularly preferred embodiment, the framework sequences of the light chain and/or heavy chain variable region of an antigen-binding molecule preferably have human germ-line framework sequences. Thus, in an embodiment of the present invention, if the entire framework sequences are human sequences, it is thought that an antigen-binding molecule of the present invention induces little or no immunogenic response when it is administered to humans (for example, to treat diseases). In the above sense, the phrase "containing a germ line sequence" in the present invention means that a part of the framework sequences of the present invention is identical to a part of any human germ line framework sequences. Specifically, the framework sequence of the present invention is at least 50% or more, 60% or more, 70% or more, 80% or more, 90% or more, or 100% or more identical to the germ line sequence. For example, when the heavy chain FR2 sequence of an antigen-binding molecule of the present invention is a combination of heavy chain FR2 sequences of different human germ line framework sequences, such a molecule is also an antigen-binding molecule "containing a germ line sequence" in the present invention. Even when the framework sequences of antigen-binding molecules of the present invention are sequences with substitutions, they are antigen-binding molecules "containing a germ line sequence" of the present invention. Examples of such sequences with substitutions include, in particular, sequences in which amino acids of part of human germ line framework sequences have been substituted with amino acids that change the antigen-binding activity of the antigen-binding molecule depending on the presence or absence of adenosine and/or ATP.

Preferred examples of the frameworks include, for example, fully human framework region sequences currently known, which are included in the website of V-Base (http://vbase.mrc-cpe.cam.ac.uk/) or others. Those framework region sequences can be appropriately used as a germ line sequence contained in an antigen-binding molecule of the present invention. The germ line sequences may be categorized according to their similarity (Tomlinson et al. (J. Mol. Biol. (1992) 227, 776-798); Williams and Winter (Eur. J. Immunol. (1993) 23, 1456-1461); Cox et al. (Nat. Genetics (1994) 7, 162-168)). Appropriate germ line sequences can be selected from Vκ, which is grouped into seven subgroups; Vλ, which is grouped into ten subgroups; and VH, which is grouped into seven subgroups.

Fully human VH sequences preferably include, but are not limited to, for example, VH sequences of:
  subgroup VH1 (for example, VH1-2, VH1-3, VH1-8, VH1-18, VH1-24, VH1-45, VH1-46, VH1-58, and VH1-69);
  subgroup VH2 (for example, VH2-5, VH2-26, and VH2-70);
  subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);
  subgroup VH4 (VH4-4, VH4-28, VH4-31, VH4-34, VH4-39, VH4-59, and VH4-61);
  subgroup VH5 (VH5-51);
  subgroup VH6 (VH6-1); and
  subgroup VH7 (VH7-4 and VH7-81).

These are also described in known documents (Matsuda et al. (J. Exp. Med. (1998) 188, 1973-1975)) and such, and thus persons skilled in the art can appropriately design antigen-binding molecules of the present invention based on the information of these sequences. It is also preferable to use other fully human frameworks or framework sub-regions.

Fully human Vκ sequences preferably include, but are not limited to, for example:
  A20, A30, L1, L4, L5, L8, L9, L11, L12, L14, L15, L18, L19, L22, L23, L24, O2, O4, O8, O12, O14, and O18 grouped into subgroup Vk1;
  A1, A2, A3, A5, A7, A17, A18, A19, A23, O1, and O11, grouped into subgroup Vk2;
  A11, A27, L2, L6, L10, L16, L20, and L25, grouped into subgroup Vk3;
  B3, grouped into subgroup Vk4;
  B2 (herein also referred to as Vk5-2), grouped into subgroup Vk5; and
  A10, A14, and A26, grouped into subgroup Vk6

(Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).

Fully human VX, sequences preferably include, but are not limited to, for example:

V1-2, V1-3, V1-4, V1-5, V1-7, V1-9, V1-11, V1-13, V1-16, V1-17, V1-18, V1-19, V1-20, and V1-22, grouped into subgroup VL1;

V2-1, V2-6, V2-7, V2-8, V2-11, V2-13, V2-14, V2-15, V2-17, and V2-19, grouped into subgroup VL1;

V3-2, V3-3, and V3-4, grouped into subgroup VL3;

V4-1, V4-2, V4-3, V4-4, and V4-6, grouped into subgroup VL4; and

V5-1, V5-2, V5-4, and V5-6, grouped into subgroup VL5 (Kawasaki et al. (Genome Res. (1997) 7, 250-261)).

Normally, these framework sequences are different from one another at one or more amino acid residues. These framework sequences can be used in combination with "at least one amino acid residue that alters the antigen-binding activity of an antigen-binding domain depending on the presence or absence of adenosine and/or ATP" of the present invention. Other examples of the fully human frameworks used in combination with "at least one amino acid residue that alters the antigen-binding activity of an antigen-binding domain depending on the presence or absence of adenosine and/or ATP" of the present invention include, but are not limited to, for example, KOL, NEWM, REI, EU, TUR, TEI, LAY, and POM (for example, Kabat et al. (1991) supra; Wu et al. (J. Exp. Med. (1970) 132, 211-250)).

Without being bound by a particular theory, one reason for the expectation that the use of germ line sequences precludes adverse immune responses in most individuals is believed to be as follows. As a result of the process of affinity maturation during normal immune responses, somatic mutation occurs frequently in the variable regions of immunoglobulin. Such mutations mostly occur around CDRs whose sequences are hypervariable, but also affect residues of framework regions. Such framework mutations do not exist on the germ line genes, and also they are less likely to be immunogenic in patients. On the other hand, the normal human population is exposed to most of the framework sequences expressed from the germ line genes. As a result of immunotolerance, these germ line frameworks are expected to have low or no immunogenicity in patients. To maximize the possibility of immunotolerance, variable region-encoding genes may be selected from a group of commonly occurring functional germ line genes.

Known methods such as site-directed mutagenesis (Kunkel et al. (Proc. Natl. Acad. Sci. USA (1985) 82, 488-492)) and overlap extension PCR can be appropriately employed to produce the antigen-binding molecules of the present invention in which the above-described variable region sequences, heavy or light chain variable region sequences, CDR sequences, or framework sequences contain amino acids that alter the antigen-binding activity of the antigen-binding domain depending on the presence or absence of adenosine and/or ATP.

For example, a library which contains a plurality of antigen-binding molecules of the present invention whose sequences are different from one another can be constructed by combining heavy chain variable regions prepared as a randomized variable region sequence library with a light chain variable region selected as a CDR sequence and/or framework sequence originally containing at least one amino acid residue that alters the antigen-binding activity of the antigen-binding domain depending on the presence or absence of adenosine and/or ATP.

Alternatively, a heavy chain and/or light chain variable region sequence selected as a CDR sequence and/or a framework sequence originally containing at least one amino acid residue that changes the antigen-binding activity of an antigen-binding domain depending on the presence or absence of adenosine and/or ATP as mentioned above, can be designed to contain various amino acid residues other than the above amino acid residue(s). Herein, such residues are referred to as "flexible residues". The number and position of flexible residues are not particularly limited as long as the antigen-binding activity of the antigen-binding molecule of the present invention varies depending on the concentration of a tissue-specific compound. Specifically, the CDR sequences and/or FR sequences of the heavy chain and/or light chain may contain one or more flexible residues. One can identify the flexible residues and the amino acids that those residues can be substituted with for library production by introducing mutations or by crystal structure analysis of complexes formed by an antibody and adenosine and/or ATP. For example, from crystal structure analysis of complexes formed by an antibody and adenosine and/or ATP, one can identify residues in the antibody that are not involved in binding to adenosine and/or ATP. One can select amino acids that can maintain binding to the compounds at an appropriate level even when the residues that have been identified as not being involved in binding to adenosine and/or ATP are substituted with those amino acids. Accordingly, it is possible to design a library that has the selected amino acids for the identified residues. In this case, one can design a library mainly comprising multiple antigen-binding molecules to be an assembly of antigen-binding molecules in which residues identified as not being involved in binding to adenosine and/or ATP have been substituted with amino acids that are different from one another. That is, the combination of individual flexible residues substituted with amino acids that are different from one another can provide sequence diversity in antigen-binding molecules containing the flexible residues.

Antigen-binding molecules can be designed to include residues wherein at least one of the residues that are identified to be involved in binding to adenosine and/or ATP binding becomes any residue selected from that residue and other residues that are different from that residue. In a non-limiting embodiment, examples of amino acids that are identified as being involved in binding to adenosine and/or ATP may include one or more amino acids selected from amino acids at positions 52, 52a, 53, 96, 100a, and 100c in the heavy chain variable region. In a non-limiting embodiment, examples of such amino acids include one or more amino acids selected from amino acids including Ser at position 52, Ser at position 52a, Arg at position 53, Gly at position 96, Leu at position 100a, and Trp at position 100c contained in the heavy chain variable region. For example, when Leu at position 100a mentioned above is identified to be involved in binding to adenosine and/or ATP, the amino acid residue at position 100a in the antigen-binding molecules included in the library may be any amino acid residue selected from the flexible residues of His, Met, Leu, Arg, Trp, or Tyr, in addition to Leu.

In a non-limiting embodiment, examples of the flexible residues may include amino acids at positions 31, 32, 33, 35, 50, 55, 56, 57, 58, 59, 95, 96, 97, 98, 99, 100, 100a, and 100b contained in the heavy chain variable region. In another non-limiting embodiment, examples of such amino acids may include amino acids at positions 26, 27, 27a, 27b, 27c, 28, 29, 31, 32, 50, 51, 52, 53, 54, 55, 89, 90, 91, 92, 93, 94, 95a, 96, and 97 contained in the light chain variable region.

In a non-limiting embodiment, examples of the aforementioned flexible residues may include the following amino acids contained in the heavy chain variable region:

Asp, Gly, Asn, Ser, Arg, or Thr for the amino acid at position 31;
Ala, Phe, His, Asn, Ser, or Tyr for the amino acid at position 32;
Ala, Glu, Asp, Gly, Phe, Ile, His, Lys, Met, Leu, Asn, Gln, Pro, Ser, Arg, Trp, Val, Tyr, or Thr for the amino acid at position 33;
His, Ser, Thr, Tyr, or Asn for the amino acid at position 35;
Ala, Glu, Asp, Gly, Phe, Ile, His, Lys, Met, Leu, Asn, Gln, Pro, Arg, Thr, Trp, Val, Tyr, or Ser for the amino acid at position 50;
Ala, Glu, Asp, Gly, Leu, Thr, Ser, Arg, or Asn for the amino acid at position 55;
Ala, Glu, Asp, Gly, Phe, Ile, His, Lys, Met, Leu, Gln, Pro, Ser, Thr, Trp, Val, or Tyr for the amino acid at position 56;
Ala, Lys, Arg, Thr, or Ile for the amino acid at position 57;
Asp, Gly, Phe, His, Ser, Thr, Tyr, or Asn for the amino acid at position 58;
Leu, or Tyr for the amino acid at position 59;
Ala, Ile, Lys, Met, Leu, Arg, Trp, Val, Tyr, or Phe for the amino acid at position 95;
Ala, Asp, Asn, or Ser for the amino acid at position 96;
Ala, Asp, Gly, Ile, His, Lys, Met, Leu, Asn, Ser, Val, Tyr, or Arg for the amino acid at position 97;
Ala, Glu, Asp, Gly, Phe, Ile, His, Met, Leu, Asn, Gln, Pro, Ser, Arg, Thr, Trp, Val, Tyr, or Lys for the amino acid at position 98;
Ala, Glu, Asp, Phe, His, Lys, Asn, Gln, Ser, Arg, Trp, Val, Tyr, or Gly for the amino acid at position 99;
Ala, Glu, Gly, Phe, Ile, His, Lys, Met, Leu, Asn, Gln, Pro, Ser, Arg, Thr, Trp, Val, Tyr, or Asp for the amino acid at position 100;
Ala, Phe, Ile, His, Lys, Met, Arg, Trp, Val, or Tyr for the amino acid at position 100a; or
Ala, Glu, Asp, Gly, Phe, Ile, His, Lys, Met, Leu, Gln, Pro, Ser, Arg, Thr, Trp, Val, Tyr, or Asn for the amino acid at position 100b.

In a non-limiting embodiment, examples of the aforementioned flexible residues may include the following amino acids contained in the light chain variable region:

Ala, Ser, or Thr for the amino acid at position 26;
Thr or Ser for the amino acid at position 27;
Gly, Asn, Thr, or Ser for the amino acid at position 27a;
Asn or Asp for the amino acid at position 27b;
Ile or Val for the amino acid at position 27c;
Asp or Gly for the amino acid at position 28;
Ala, Asp, Phe, Ser, Arg, Thr, Tyr, or Gly for the amino acid at position 29;
Glu, Asp, Lys, or Asn for the amino acid at position 31;
Ala, Asp, Ser, Thr, or Tyr for the amino acid at position 32;
Asp, Gly, Lys, Asn, Gln, Ser, Arg, Tyr, or Glu for the amino acid at position 50;
Asp, Gly, Lys, Asn, Thr, or Val for the amino acid at position 51;
Ala, Asp, Asn, Thr, or Ser for the amino acid at position 52;
Glu, Asp, His, Asn, Gln, Ser, Tyr, or Lys for the amino acid at position 53;
Lys or Arg for the amino acid at position 54;
Leu or Pro for the amino acid at position 55;
Ala, Gly, Phe, Leu, Asn, Gln, Thr, Val, Tyr, or Ser for the amino acid at position 89;
Ala, Leu, Thr, Val, or Ser for the amino acid at position 90;
Ala, Asp, Phe, His, Lys, Asn, Ser, Arg, Thr, Trp, Val, or Tyr for the amino acid at position 91;
Glu, Asp, Ser, Arg, Thr, Val, Tyr, or Ala for the amino acid at position 92;
Ala, Asp, Ile, Asn, Ser, Arg, Thr, Val, Tyr, or Gly for the amino acid at position 93;
Ala, Asp, Gly, Ile, Asn, Arg, Thr, or Ser for the amino acid at position 94;
Ala, Glu, Asp, Gly, Phe, Ile, His, Lys, Met, Leu, Gln, Pro, Ser, Arg, Thr, Trp, Val, Tyr, or Asn for the amino acid at position 95;
Ala, Glu, Asp, Gly, Ile, His, Lys, Leu, Gln, Pro, Ser, Arg, Thr, Tyr, or Asn for the amino acid at position 95a;
Ala, Asp, Gly, Phe, His, Lys, Leu, Asn, Gln, Pro, Ser, Thr, Trp, Tyr, or Val for the amino acid at position 96; or
Ala, Gly, Ile, Met, Leu, Ser, or Val for the amino acid at position 97.

In an embodiment of the present invention, when the small molecule compound is kynurenine, one can identify the flexible residues and the amino acids that those residues can be substituted with for library production by introduction of mutations and crystal structure analysis of complexes formed by an antibody and kynurenine. For example, from crystal structure analysis of complexes formed by an antibody and kynurenine, residues of the antibody that are not involved in kynurenine binding can be identified. One can select amino acids that can maintain an appropriate level of binding to the compound even when the residues that have been identified as not being involved in kynurenine binding are substituted with those amino acids. Accordingly, it is possible to design a library to have selected amino acids at the identified residues. In this case, one can design a library to comprise mainly a plurality of antigen-binding molecules that is an assembly of antigen-binding molecules in which residues identified as not being involved in kynurenine binding have been substituted with amino acids that are different from one another. That is, combining each of the flexible residues that have been substituted with mutually different amino acids can provide sequence diversity in antigen-binding molecules containing the flexible residues.

Antigen-binding molecules can be designed to include residues wherein at least one of the residues that are identified to be involved in kynurenine binding becomes any residue selected from that residue and residues different from that residue. In a non-limiting embodiment of amino acids identified as being involved in kynurenine binding, examples of amino acid residues whose side chains are involved in kynurenine binding may include any one or more amino acids selected from amino acids at positions P97, R100c, and D101 (Kabat numbering) in the H chain and at positions H49 and F55 (Kabat numbering) in the L chain. Examples of amino acid residues greatly involved in the binding with kynurenine at the main chain portion may include any one or more amino acids selected from amino acids at positions R94, D95, R100c, G100d, and A100e in the H chain. Examples of residues important for maintaining the structure of the H-chain CDR3 in a kynurenine-bound conformation as determined by X-ray crystallography may include any one or more amino acids selected from amino acids at positions P97, P100b, and G100d in the H chain.

In the present invention, a non-limiting embodiment of flexible residues when the small molecule is kynurenine may include, for example, amino acids at positions 24, 26, 27, 28, 29, 30, 31, 32, 33, 50, 51, 52, 52a, 53, 54, 55, 56, 58, 73, 95, 96, 97, 98, 99, 100, 100a, 100b, 100c, 100d, 100e, 100f, and 102 contained in the heavy chain variable region. In another non-limiting embodiment, examples of such amino acids may include amino acids at positions 27d, 27e, 28, 29, 32, 46, 49, 50, 51, 52, 53, 54, 55, 92, 93, and 94 contained in the light chain variable region.

A non-limiting embodiment of the aforementioned flexible residues is an amino acid contained in the heavy chain variable region, which is any of:

Ala, Asp, Glu, Phe, Gly, His, Ile, Lys, Leu, Met, Asn, Pro, Gln, Arg, Ser, Thr, Val, Trp, or Tyr for the amino acid at position 24;

Gly, Ala, Asp, Glu, Phe, His, Ile, Lys, Leu, Pro, Gln, Arg, Ser, Thr, Val, Trp, or Tyr for the amino acid at position 26;

Gly, Ala, Asp, Glu, Phe, His, Ile, Lys, Leu, Asn, Pro, Gln, Arg, Ser, Thr, Val, Trp, or Tyr for the amino acid at position 27;

Thr, Ala, Asp, Glu, Phe, Gly, His, Ile, Lys, Leu, Pro, Gln, Arg, Ser, Val, Trp, or Tyr for the amino acid at position 28;

Phe, Ile, Leu, Trp, or Tyr for the amino acid at position 29;

Ser, Ala, Asp, Glu, Phe, Gly, His, Ile, Lys, Leu, Met, Asn, Pro, Gln, Arg, Thr, Val, Trp, or Tyr for the amino acid at position 30;

Ser, Ala, Asp, Glu, Phe, Gly, His, Ile, Lys, Leu, Asn, Gln, Arg, Thr, Val, Trp, or Tyr for the amino acid at position 31;

Tyr, Phe, or His for the amino acid at position 32;

Ala, Gly, Ile, Lys, Gln, Arg, Ser, Thr, Val, or Trp for the amino acid at position 33;

Gly, Ala, Phe, His, Ile, Lys, Leu, Met, Asn, Gln, Arg, Ser, Thr, Val, Trp, or Tyr for the amino acid at position 50;

Ile, Ala, Gly, Lys, Leu, Gln, Arg, Ser, Thr, Val, Trp, or Tyr for the amino acid at position 51;

Ile, Ala, Glu, Phe, His, Lys, Leu, Asn, Pro, Gln, Arg, Ser, Thr, Val, Trp, or Tyr for the amino acid at position 52;

Pro, Ala, Gly, Ser, Thr, or Trp for the amino acid at position 52a;

Ile, Ala, Asp, Glu, Phe, Gly, His, Lys, Leu, Asn, Pro, Gln, Arg, Ser, Thr, Val, Trp, or Tyr for the amino acid at position 53;

Phe, Ala, Asp, Glu, Gly, His, Ile, Lys, Leu, Pro, Gln, Arg, Ser, Thr, Val, Trp, or Tyr for the amino acid at position 54;

Gly, Ala, Asp, Glu, Phe, His, Ile, Lys, Leu, Asn, Pro, Gln, Arg, Ser, Thr, Val, Trp, or Tyr for the amino acid at position 55;

Thr, Ala, Asp, Glu, Phe, Gly, His, Ile, Lys, Leu, Asn, Pro, Gln, Arg, Ser, Val, Trp, or Tyr for the amino acid at position 56;

Asn, Ala, Asp, Glu, Phe, Gly, His, Lys, Pro, Gln, Arg, Ser, Thr, Val, Trp, or Tyr for the amino acid at position 58;

Glu, Ala, Asp, Phe, Gly, His, Ile, Lys, Leu, Met, Pro, Gln, Arg, Ser, Thr, Val, or Tyr for the amino acid at position 73;

Asp or Gly for the amino acid at position 95;

Ala, Glu, Phe, His, Ile, Lys, Asn, Gln, Arg, Ser, Thr, Val, Trp, or Tyr for the amino acid at position 96;

Pro, Ala, Asn, or Ser for the amino acid at position 97;

Val, Leu, or Thr for the amino acid at position 98;

Val, Ala, Asp, Phe, His, Ile, Lys, Leu, Asn, Gln, Arg, Ser, Thr, Val, Trp, or Tyr for the amino acid at position 99;

Ala, Asp, Glu, Phe, Gly, His, Ile, Lys, Leu, Met, Asn, Gln, Arg, Ser, Val, Trp, or Tyr for the amino acid at position 100;

Arg, Ala, Asp, Glu, Ile, Lys, Leu, Asn, Pro, Gln, Ser, Thr, or Val for the amino acid at position 100a;

Pro, Ala, Lys, Asn, Gln, Arg, or Ser for the amino acid at position 100b;

Arg, His, Lys, or Gln for the amino acid at position 100c;

Gly or Asn for the amino acid at position 100d;

Ala, Gly, or Ser for the amino acid at position 100e;

Phe or Leu for the amino acid at position 100f; or

Ile, Ala, Asp, Glu, Phe, His, Leu, Met, Asn, Gln, Arg, Thr, Val, Trp, or Tyr for the amino acid at position 102.

A non-limiting embodiment of the aforementioned flexible residues is an amino acid contained in the light chain variable region, which is any of:

His, Ala, Asp, Glu, Phe, Gly, Ile, Lys, Leu, Asn, Pro, Gln, Arg, Ser, Thr, Val, Trp, or Tyr for the amino acid at position 27d;

Ser, Ala, Asp, Glu, Phe, Gly, His, Ile, Lys, Leu, Asn, Pro, Gln, Arg, Thr, Val, Trp, or Tyr for the amino acid at position 27e;

Asp, Ala, Glu, Phe, Gly, His, Ile, Lys, Met, Asn, Pro, Gln, Arg, Ser, Thr, Val, Trp, or Tyr for the amino acid at position 28;

Gly, Ala, Asp, Glu, Phe, His, Ile, Lys, Leu, Pro, Gln, Arg, Ser, Thr, Val, Trp, or Tyr for the amino acid at position 29;

Tyr, Ala, Phe, Gly, His, Lys, Leu, Pro, Gln, Arg, Val, or Trp for the amino acid at position 32;

Leu, Ile, Met, Asn, or Val for the amino acid at position 46;

Tyr, Phe, His, or Trp for the amino acid at position 49;

Glu, Ala, Phe, Gly, Ile, Lys, Leu, Met, Gln, Ser, Thr, Val, or Tyr for the amino acid at position 50;

Ile, Ala, Asp, Glu, Phe, Gly, Lys, Leu, Met, Gln, Arg, Ser, Thr, Val, Trp, or Tyr for the amino acid at position 51;

Ser, Ala, Asp, Glu, Phe, Gly, His, Ile, Lys, Leu, Asn, Gln, Arg, Thr, Val, Trp, or Tyr for the amino acid at position 52;

Asn, Ala, Asp, Glu, Phe, Gly, His, Ile, Lys, Leu, Pro, Gln, Arg, Ser, Thr, Val, Trp, or Tyr for the amino acid at position 53;

Arg, Ala, Asp, Glu, Phe, Gly, His, Ile, Lys, Leu, Asn, Pro, Gln, Ser, Thr, Val, Trp, or Tyr for the amino acid at position 54;

Phe, Leu, Met, Arg, or Tyr for the amino acid at position 55;

Thr, Ala, Asp, Glu, Phe, Gly, His, Ile, Lys, Leu, Asn, Gln, Arg, Ser, Val, Trp, or Tyr for the amino acid at position 92;

Gln, Ala, Asp, Glu, Phe, Gly, Ile, Lys, Leu, Asn, Arg, Ser, Thr, Val, or Tyr for the amino acid at position 93; or Phe, His, Ile, Lys, Asn, Gln, Arg, Ser, Thr, Val, Trp, or Tyr for the amino acid at position 94.

In the present invention, another non-limiting embodiment of the flexible residues when the small molecule is kynurenine may include, for example, amino acids at positions 28, 31, 33, 50, 51, 52, 54, 55, 56, 58, 96, 97, 99, 100, 100a, 100b, and 100c contained in the heavy chain variable region. In another non-limiting embodiment, examples of such amino acids may include amino acids at positions 27d, 27e, 28, 29, 32, 52, 53, 54, 56, 92, and 93 contained in the light chain variable region.

In an embodiment of the present invention, when the small molecule compound is adenosine, one can identify the flexible residues and the amino acids that those residues can be substituted with for library production by introduction of mutations and crystal structure analysis of complexes formed by an antibody and adenosine. For example, residues of the antibody that are not involved in adenosine binding can be identified by crystal structure analysis of complexes formed by an antibody and adenosine. One can select amino acids that can maintain an appropriate level of binding to the compound even when the residues that have been identified as not being involved in adenosine binding are substituted with those amino acids. Accordingly, it is possible to design a library to have selected amino acids at the identified residues. In this case, one can design a library to comprise mainly multiple antigen-binding molecules to be an assembly of antigen-binding molecules in which residues identified as not being involved in adenosine binding have been substituted with amino acids that are different from one another. That is, combining each of the flexible residues that have been substituted with mutually different amino acids can provide sequence diversity in antigen-binding molecules containing the flexible residues.

Antigen-binding molecules may be designed to include residues wherein at least one of the residues that are identified to be involved in adenosine binding becomes any residue selected from that residue and residues different from that residue. In a non-limiting embodiment of amino acids that are identified as being involved in adenosine binding, examples may include any one or more amino acids selected from amino acids at positions A33, 150, G52, S56, T57, W58, G99, Y100, and T100a (Kabat numbering) in the H chain and at positions Y95c and N96 (Kabat numbering) in the L chain.

In the present invention, a non-limiting embodiment of flexible residues when the small molecule is adenosine may include, for example, amino acids at positions 31, 32, 53, 54, 55, 56, 57, 59, 61, 62, 65, 96, 97, 98, 100, 100a, 101, and 102 contained in the heavy chain variable region. In another non-limiting embodiment, examples of such amino acids may include amino acids at positions 28, 29, 32, 93, 94, 95, 95a, 95b, and 95c contained in the light chain variable region.

A non-limiting embodiment of the aforementioned flexible residues is an amino acid contained in the heavy chain variable region, which is any of:
Asn, Ala, Asp, Glu, Phe, Gly, His, Ile, Lys, Leu, Pro, Gln, Arg, Ser, Thr, Val, Trp, or Tyr for the amino acid at position 31;
Tyr, Phe, Gly, His, Ile, Lys, Asn, Pro, Gln, Arg, Thr, Val, or Trp for the amino acid at position 32;
Ala, Asp, Glu, Phe, Gly, Ile, Lys, Leu, Pro, Gln, Arg, Ser, Thr, Val, or Tyr for the amino acid at position 53;
Asp, Glu, Phe, Gly, His, Ile, Leu, Gln, Ser, Thr, Val, or Tyr for the amino acid at position 54;
Ser, Ala, Asp, Glu, Phe, Gly, His, Ile, Lys, Leu, Gln, Arg, Thr, Val, or Tyr for the amino acid at position 55;
Ser, Ala, Asp, Glu, Phe, Gly, His, Ile, Lys, Leu, Asn, Gln, Arg, Thr, or Val for the amino acid at position 56;
Thr, Ala, Ile, Lys, Leu, Asn, Gln, Arg, Ser, or Val for the amino acid at position 57;
Tyr, Ala, Asp, Glu, Phe, Gly, His, Ile, Lys, Leu, Gln, Arg, Ser, Thr, Val, or Trp for the amino acid at position 59;
Ser, Ala, Phe, His, Lys, Leu, Asn, Pro, Gln, Arg, Thr, Val, Trp, or Tyr for the amino acid at position 61;
Trp, Ala, Asp, Glu, Phe, or Gly for the amino acid at position 62;
Gly, Ala, Asp, Glu, Phe, Ile, Lys, Leu, Asn, Gln, Arg, Thr, Val, or Trp for the amino acid at position 65;
Arg, Ala, Asp, Glu, Phe, Gly, His, Lys, Leu, Asn, Gln, Ser, Thr, Val, Trp, or Tyr for the amino acid at position 96;
Phe, Ala, Asp, Glu, Gly, His, Ile, Lys, Leu, Asn, Gln, Arg, Ser, Thr, Val, Trp, or Tyr for the amino acid at position 97;
Val, Ala, Asp, Glu, Phe, Gly, His, Ile, Lys, Leu, Asn, Pro, Gln, Arg, Ser, or Thr for the amino acid at position 98;
Tyr or Phe for the amino acid at position 100;
Thr, Ser, or Val for the amino acid at position 100a;
Asp, Ala, Glu, Phe, Gly, His, Ile, Lys, Leu, Asn, Gln, Arg, Ser, Thr, Val, Trp, or Tyr for the amino acid at position 101; or
Pro, Asp, or Asn for the amino acid at position 102.

A non-limiting embodiment of the aforementioned flexible residues is an amino acid contained in the light chain variable region, which is any of:
Trp, Ala, Phe, His, Lys, Asn, Ser, Thr, Val, or Tyr for the amino acid at position 28;
Asn, Ala, Asp, Glu, Phe, Gly, His, Ile, Lys, Leu, Pro, Gln, Arg, Ser, Thr, Val, Trp, or Tyr for the amino acid at position 29;
Tyr, Ala, Asp, Phe, Gly, or His for the amino acid at position 32;
Ala, Asp, Glu, Phe, Gly, His, Leu, Gln, Arg, Ser, Thr, Val, or Tyr for the amino acid at position 93;
Asn, Ala, Asp, Glu, Phe, Gly, His, Ile, Lys, Leu, Pro, Gln, Arg, Ser, Thr, Val, Trp, or Tyr for the amino acid at position 94;
Ser, Ala, Asp, Glu, Phe, Gly, His, Ile, Lys, Leu, Asn, Pro, Gln, Arg, Thr, Val, Trp, or Tyr for the amino acid at position 95;
Gly, Ala, Asp, Glu, Phe, His, Ile, Lys, Leu, Asn, Pro, Gln, Arg, Val, Trp, or Tyr for the amino acid at position 95a;
Trp, Ala, Asp, Glu, Phe, Gly, His, Ile, Lys, Leu, Asn, Pro, Gln, Arg, Ser, Thr, Val, or Tyr for the amino acid at position 95b; or
Tyr, Phe, His, Lys, Leu, Asn, or Val for the amino acid at position 95c.

In an embodiment of the present invention, when the small molecule compound is adenosine monophosphate, one can identify the flexible residues and the amino acids that those residues can be substituted with for library production by crystal structure analysis of complexes formed by an antibody and adenosine monophosphate, and by introduction of mutations and modeling based on the crystal structure of a complex formed by an antibody and adenosine which is an analogous compound. For example, residues of the antibody that are not involved in the binding to adenosine monophosphate can be identified by modeling using the crystal structure analysis of complexes formed by the antibody and adenosine. One can select amino acids that can maintain an appropriate level of binding to the compound even when the residues that have been identified as not being involved in adenosine monophosphate binding are substituted with those amino acids. Accordingly, it is possible to design a library to have selected amino acids at the identified residues. In this case, one can design a library to comprise mainly a plurality of antigen-binding molecules that is an assembly of antigen-binding molecules in which residues identified as not being involved in adenosine monophosphate binding have been substituted with amino acids that are different from one another. That is, combining each of the flexible residues that have been substituted with mutually different amino acids can provide sequence diversity in antigen-binding molecules containing the flexible residues.

Antigen-binding molecules may be designed to include residues wherein at least one of the residues that are identified to be involved in adenosine monophosphate binding becomes any residue selected from that residue and residues different from that residue. In a non-limiting embodiment of amino acids identified as being involved in the binding to the ribose moiety and adenine ring moiety of adenosine monophosphate, examples may include any one or more amino acids selected from amino acids at positions A33, I50, G52, S56, T57, W58, G99, Y100, and T100a (Kabat numbering) in the H chain and at positions Y95c and N96 (Kabat numbering) in the L chain. In a non-limiting embodiment, examples of amino acids identified as being involved in binding to the phosphate moiety of adenosine monophosphate may include any one or more amino acids selected from amino acids at positions D54, S55, S56, T57, and W58 in the H chain CDR2 and at positions G95a, W95b, and Y95c (Kabat numbering) in the L chain CDR3.

A non-limiting embodiment of the aforementioned flexible residues is an amino acid contained in the heavy chain variable region, which is any of:

Asn, Ala, Asp, Glu, Phe, Gly, His, Ile, Lys, Leu, Pro, Gln, Arg, Ser, Thr, Val, Trp, or Tyr for the amino acid at position 31;

Tyr, Phe, Gly, His, Ile, Lys, Asn, Pro, Gln, Arg, Thr, Val, or Trp for the amino acid at position 32;

Ala, Asp, Glu, Phe, Gly, Ile, Lys, Leu, Pro, Gln, Arg, Ser, Thr, Val, or Tyr for the amino acid at position 53;

Asp, Glu, Phe, Gly, His, Ile, Leu, Gln, Ser, Thr, Val, or Tyr for the amino acid at position 54;

Ser, Ala, Asp, Glu, Phe, Gly, His, Ile, Lys, Leu, Gln, Arg, Thr, Val, or Tyr for the amino acid at position 55;

Ser, Ala, Asp, Glu, Phe, Gly, His, Ile, Lys, Leu, Asn, Gln, Arg, Thr, or Val for the amino acid at position 56;

Thr, Ala, Ile, Lys, Leu, Asn, Gln, Arg, Ser, or Val for the amino acid at position 57;

Tyr, Ala, Asp, Glu, Phe, Gly, His, Ile, Lys, Leu, Gln, Arg, Ser, Thr, Val, or Trp for the amino acid at position 59;

Ser, Ala, Phe, His, Lys, Leu, Asn, Pro, Gln, Arg, Thr, Val, Trp, or Tyr for the amino acid at position 61;

Trp, Ala, Asp, Glu, Phe, or Gly for the amino acid at position 62;

Gly, Ala, Asp, Glu, Phe, Ile, Lys, Leu, Asn, Gln, Arg, Thr, Val, or Trp for the amino acid at position 65;

Arg, Ala, Asp, Glu, Phe, Gly, His, Lys, Leu, Asn, Gln, Ser, Thr, Val, Trp, or Tyr for the amino acid at position 96;

Phe, Ala, Asp, Glu, Gly, His, Ile, Lys, Leu, Asn, Gln, Arg, Ser, Thr, Val, Trp, or Tyr for the amino acid at position 97;

Val, Ala, Asp, Glu, Phe, Gly, His, Ile, Lys, Leu, Asn, Pro, Gln, Arg, Ser, or Thr for the amino acid at position 98;

Tyr or Phe for the amino acid at position 100;

Thr, Ser, or Val for the amino acid at position 100a;

Asp, Ala, Glu, Phe, Gly, His, Ile, Lys, Leu, Asn, Gln, Arg, Ser, Thr, Val, Trp, or Tyr for the amino acid at position 101; or Pro, Asp, or Asn for the amino acid at position 102.

A non-limiting embodiment of the aforementioned flexible residues is an amino acid contained in the light chain variable region, which is any of:

Trp, Ala, Phe, His, Lys, Asn, Ser, Thr, Val, or Tyr for the amino acid at position 28;

Asn, Ala, Asp, Glu, Phe, Gly, His, Ile, Lys, Leu, Pro, Gln, Arg, Ser, Thr, Val, Trp, or Tyr for the amino acid at position 29;

Tyr, Ala, Asp, Phe, Gly, or His for the amino acid at position 32;

Ala, Asp, Glu, Phe, Gly, His, Leu, Gln, Arg, Ser, Thr, Val, or Tyr for the amino acid at position 93;

Asn, Ala, Asp, Glu, Phe, Gly, His, Ile, Lys, Leu, Pro, Gln, Arg, Ser, Thr, Val, Trp, or Tyr for the amino acid at position 94;

Ser, Ala, Asp, Glu, Phe, Gly, His, Ile, Lys, Leu, Asn, Pro, Gln, Arg, Thr, Val, Trp, or Tyr for the amino acid at position 95;

Gly, Ala, Asp, Glu, Phe, His, Ile, Lys, Leu, Asn, Pro, Gln, Arg, Val, Trp, or Tyr for the amino acid at position 95a;

Trp, Ala, Asp, Glu, Phe, Gly, His, Ile, Lys, Leu, Asn, Pro, Gln, Arg, Ser, Thr, Val, or Tyr for the amino acid at position 95b; or Tyr, Phe, His, Lys, Leu, Asn, or Val for the amino acid at position 95c.

In an embodiment of the present invention, when the small molecule compound is adenosine diphosphate or adenosine triphosphate, one can identify the flexible residues and the amino acids that those residues can be substituted with for library production by crystal structure analysis of complexes formed by an antibody and adenosine diphosphate or adenosine triphosphate, and introduction of mutations and modeling based on the crystal structure of a complex formed by an antibody and adenosine which is an analogous compound. For example, residues of the antibody that are not involved in the binding to adenosine diphosphate or adenosine triphosphate can be identified by modeling using crystal structure analysis of complexes formed by an antibody and adenosine diphosphate or adenosine triphosphate. One can select amino acids that can maintain an appropriate level of binding to the compounds even when the residues that have been identified as not being involved in the binding to adenosine diphosphate or adenosine triphosphate are substituted with those amino acids. Accordingly, it is possible to design a library to have selected amino acids at the identified residues. In this case, one can design a library mainly comprising a plurality of antigen-binding molecules that is an assembly of antigen-binding molecules in which residues identified as not being involved in the binding to adenosine diphosphate or adenosine triphosphate have been substituted with amino acids that are different from one another. That is, combining each of the flexible residues that have been substituted with mutually different amino acids can provide sequence diversity in antigen-binding molecules containing the flexible residues.

Antigen-binding molecules may be designed to include residues wherein at least one of the residues that are identified to be involved in the binding to adenosine diphosphate or to adenosine triphosphate becomes any residue selected from that residue and residues different from that residue. In a non-limiting embodiment, amino acids that are identified as being involved in the binding to the ribose moiety and adenine ring moiety of adenosine diphosphate or adenosine triphosphate are similar to those for adenosine, and examples may include any one or more amino acids selected from amino acids at positions A33, I50, G52, S56, T57, W58, G99, Y100, and T100a (Kabat numbering) in the H chain and at positions Y95c and N96 (Kabat numbering) in the L chain. For the amino acids identified as being involved in the binding to the phosphate moiety of adenosine diphosphate or adenosine triphosphate, one can predict modifications that can enhance binding to adenosine diphosphate or adenosine triphosphate through examinations based on crystal structures similar to those described above.

Herein, "flexible residues" refers to amino acid residue variations present at hypervariable amino acid positions of light-chain and heavy-chain variable regions at which several different amino acids exist, when the amino acid sequences of known and/or native antibodies or antigen-binding domains are compared. The hypervariable positions are generally located in the CDR regions. In an embodiment, the data provided by Kabat, Sequences of Proteins of Immunological Interest (National Institute of Health Bethesda Md., 1987 and 1991) is useful for determining the hypervariable positions in known and/or native antibodies. Furthermore, databases on the Internet (http://vbase.mrc-cpe.cam.ac.uk/, and http://www.bioinf.org.uk/abs/index.html) provide many collected sequences of human light chains and heavy chains, and their locations. The information of those sequences and locations is useful for determining the hypervariable positions in the present invention. According to the present invention, when a certain amino acid position has preferably about 2 to about 20, preferably about 3 to about 19, preferably about 4 to about 18, preferably 5 to 17, preferably 6 to 16, preferably 7 to 15, preferably 8 to 14, preferably 9 to 13, and preferably 10 to 12 possible amino acid residue variants, the position can be considered to be hypervariable. In some embodiments, a certain amino acid position may have preferably at least about 2, preferably at least about 4, preferably at least about 6, preferably at least about 8, preferably about 10, and preferably about 12 possible amino acid residue variants.

A library of the present invention that contains a plurality of antigen-binding molecules having different sequences from one another can be constructed by combining heavy chain variable regions produced as a randomized variable region sequence library with the aforementioned light chain variable regions introduced with at least one amino acid residue that changes the antigen-binding activity of the antigen-binding domains depending on the presence or absence of small molecules. Similarly, a library of the present invention that contains a plurality of antigen-binding molecules having different sequences from one another can also be produced by combining with the heavy-chain variable regions introduced with at least one amino acid residue that changes the antigen-binding activity of the antigen-binding domains depending on the presence or absence of small molecules, and having the other amino acid residues designed as flexible residues.

When heavy chain variable regions produced as a randomized variable region sequence library, and light chain variable regions into which at least one amino acid residue that alters the antigen-binding activity of an antigen-binding molecule depending on the concentration of the small molecule compound has been introduced, are combined as described above, the sequences of the light chain variable regions can be designed to contain flexible residues in the same manner as described above. The number and position of such flexible residues are not particularly limited to particular embodiments as long as the antigen-binding activity of antigen-binding molecules of the present invention varies depending on the presence or absence of adenosine and/or ATP. Specifically, the CDR sequences and/or FR sequences of heavy chain and/or light chain can contain one or more flexible residues.

The preferred heavy chain variable regions to be combined include, for example, randomized variable region libraries. Known methods are combined as appropriate to produce a randomized variable region library. In a non-limiting embodiment of the present invention, an immune library constructed based on antibody genes derived from lymphocytes of animals immunized with a specific antigen, patients with infections, persons with an elevated antibody titer in blood as a result of vaccination, cancer patients, or auto immune disease patients, may be preferably used as a randomized variable region library.

In another non-limiting embodiment of the present invention, a synthetic library produced by replacing the CDR sequences of V genes in genomic DNA or functional reshaped V genes with a set of synthetic oligonucleotides containing sequences encoding codon sets of an appropriate length can also be preferably used as a randomized variable region library. In this case, since sequence diversity is observed in the heavy chain CDR3 sequence, it is also possible to replace the CDR3 sequence only. A criterion of giving rise to diversity in amino acids in the variable region of an antigen-binding molecule is that diversity is given to amino acid residues at surface-exposed positions in the antigen-binding molecule. The surface-exposed position refers to a position that is considered to be able to be exposed on the surface and/or contacted with an antigen, based on structure, ensemble of structures, and/or modeled structure of an antigen-binding molecule. In general, such positions are CDRs. Preferably, surface-exposed positions are determined using coordinates from a three-dimensional model of an antigen-binding molecule using a computer program such as the InsightII program (Accelrys). Surface-exposed positions can be determined using algorithms known in the art (for example, Lee and Richards (J. Mol. Biol. (1971) 55, 379-400); Connolly (J. Appl. Cryst. (1983) 16, 548-558)). Determination of surface-exposed positions can be performed using software suitable for protein modeling and three-dimensional structural information obtained from an antibody. Software that can be used for these purposes preferably includes SYBYL Biopolymer Module software (Tripos Associates). Generally or preferably, when an algorithm requires a user input size parameter, the "size" of a probe which is used in the calculation is set at about 1.4 Angstrom or smaller in radius. Furthermore, methods for determining surface-exposed regions and areas using software for personal computers are described by Pacios (Comput. Chem. (1994) 18 (4), 377-386; J. Mol. Model. (1995) 1, 46-53).

Furthermore, in a non-limiting embodiment of the present invention, amino acids of the variable region including the CDR region and/or the framework region may be altered appropriately to improve antibody stability. In a non-limiting embodiment, examples of such amino acids may include the amino acids of positions 1, 5, 10, 30, 48, and 58. More specifically, examples may include Gln at position 1, Gln at position 5, Asp at position 10, Asn at position 30, Leu at position 48, and Asn at position 58. For the improvement of antibody stability, these amino acids can be substituted with corresponding amino acids contained in a germ-line sequence. In a non-limiting embodiment, an example of such a germ line sequence may be the VH3-21 sequence. In this case, Gln of position 1 may be substituted with Glu, Gln of position 5 may be substituted with Val, Asp of position 10 may be substituted with Gly, Asn of position 30 may be substituted with Ser, Leu of position 48 may be substituted with Val, and Asn of position 58 may be substituted with Tyr.

In another non-limiting embodiment of the present invention, a naïve library which is constructed from antibody genes derived from lymphocytes of healthy individuals and consists of naïve sequences which are antibody sequences that do not have bias in their repertoire, can also be particularly preferably used as a randomized variable region library (Gejima et al. (Human Antibodies (2002) 11, 121-129); Cardoso et al. (Scand. J. Immunol. (2000) 51, 337-344)). Herein, "an amino acid sequence comprising a naïve sequence" refers to an amino acid sequence obtained from such a naïve library.

Fc Region

An Fc region contains an amino acid sequence derived from the heavy chain constant region of an antibody. An Fc region is a portion of the antibody heavy chain constant region that includes the N terminal end of the hinge region, which is the papain cleavage site, at an amino acid around position 216 (indicated by EU numbering), and the hinge, CH2, and CH3 domains. Fc regions can be obtained from human IgG1; however, they are not limited to any specific IgG subclass. Preferred examples of the Fc regions include Fc regions having FcRn-binding activity in an acidic pH range as described below. Preferred examples of the Fc regions include Fc regions having Fcγ receptor-binding activity as described below. In a non-limiting embodiment, examples of such Fc regions include the Fc regions of human IgG1 (SEQ ID NO: 5), IgG2 (SEQ ID NO: 6), IgG3 (SEQ ID NO: 7), or IgG4 (SEQ ID NO: 8).

Fcγ receptor (FcγR)

"Fcγ receptor" (also called "FcγR") refers to a receptor capable of binding to the Fc region of monoclonal IgG1, IgG2, IgG3, or IgG4 antibodies; and means all members belonging to the family of proteins substantially encoded by Fcγ receptor genes. In humans, the family includes FcγRI (CD64) including isoforms FcγRIa, FcγRIb, and FcγRIc; FcγRII (CD32) including isoforms FcγRIIa (including allotype H131 and R131, i.e., FcγRIIa(H) and FcγRIIa(R)), FcγRIIb (including FcγRIIb-1 and FcγRIIb-2), and FcγRIIc; and FcγRIII (CD16) including isoform FcγRIIIa (including allotype V158 and F158, i.e., FcγRIIIa(V) and FcγRIIIa(F)) and FcγRIIIb (including allotype FcγRIIIb-NA1 and FcγRIIIb-NA2); as well as all unidentified human FcγRs, FcγR isoforms, and allotypes thereof; but the family is not limited to these examples. Without being limited thereto, FcγRs include those derived from humans, mice, rats, rabbits, and monkeys. FcγRs may be derived from any organism. Mouse FcγRs include FcγRI (CD64), FcγRII (CD32), FcγRIII (CD16), and FcγRIII-2 (FcγRIV, CD16-2), as well as all unidentified mouse FcγRs, FcγR isoforms, and allotypes thereof, but they are not limited to these examples. Preferred examples of such Fcγ receptors include, human FcγRI (CD64), FcγRIIa (CD32), FcγRIIb (CD32), FcγRIIIa (CD16), and/or FcγRIIIb (CD16). The polynucleotide sequence and amino acid sequence of human FcγRI are shown in SEQ ID NOs: 9 (NM_000566.3) and 10 (NP 000557.1), respectively; the polynucleotide sequence and amino acid sequence of human FcγRIIa (allotype H131) are shown in SEQ ID NOs: 11 (BC020823.1) and 12 (AAH20823.1), respectively (allotype R131 is a sequence in which the amino acid at position 166 of SEQ ID NO: 12 is substituted with Arg); the polynucleotide sequence and amino acid sequence of FcγIIb are shown in SEQ ID NOs: 13 (BC146678.1) and 14 (AAI46679.1), respectively; the polynucleotide sequence and amino acid sequence of FcγRIIIa are shown in SEQ ID NOs: 15 (BC033678.1) and 16 (AAH33678.1), respectively; and the polynucleotide sequence and amino acid sequence of FcγRIIIb are shown in SEQ ID NOs: 17 (BC128562.1) and 18 (AAI28563.1), respectively (RefSeq accession number or such is shown in parentheses). Whether an Fcγ receptor has binding activity to the Fc region of a monoclonal IgG1, IgG2, IgG3, or IgG4 antibody can be assessed by ALPHA (Amplified Luminescent Proximity Homogeneous Assay) screen, surface plasmon resonance (SPR)-based BIACORE methods, and others (Proc. Natl. Acad. Sci. USA (2006) 103(11), 4005-4010), in addition to the above-described FACS and ELISA formats.

In FcγRI (CD64) including FcγRIa, FcγRIb, and FcγRIc, and FcγRIII (CD16) including isoforms FcγRIIIa (including allotypes V158 and F158) and FcγRIIIb (including allotypes FcγRIIIb-NA1 and FcγRIIIb-NA2), a chain that binds to the Fc region of IgG is associated with common γ chain having ITAM responsible for transduction of intracellular activation signal. Meanwhile, the cytoplasmic domain of FcγRII (CD32) including isoforms FcγRIIa (including allotypes H131 and R131) and FcγRIIc contains ITAM. These receptors are expressed on many immune cells such as macrophages, mast cells, and antigen-presenting cells. The activation signal transduced upon binding of these receptors to the Fc region of IgG results in enhancement of the phagocytic activity of macrophages, inflammatory cytokine production, mast cell degranulation, and the enhanced function of antigen-presenting cells. Fcγ receptors having the ability to transduce the activation signal as described above are herein referred to as activating Fcγ receptors.

Meanwhile, the intracytoplasmic domain of FcγRllb (including FcγRllb-1 and FcγRllb-2) contains ITIM responsible for transduction of inhibitory signals. The crosslinking between FcγRIIb and B cell receptor (BCR) on B cells suppresses the activation signal from BCR, which results in suppression of antibody production via BCR. The crosslinking of FcγRIII and FcγRIIb on macrophages suppresses the phagocytic activity and inflammatory cytokine production. Fcγ receptors having the ability to transduce the inhibitory signal as described above are herein referred to as inhibitory Fcγ receptor.

FcγR-Binding Activity of Fc Region

As mentioned above, Fc regions having an Fcγ receptor-binding activity are examples of Fc regions comprised in the antigen-binding molecules of the present invention. A non-limiting embodiment of such an Fc region includes the Fc region of human IgG1 (SEQ ID NO: 5), IgG2 (SEQ ID NO: 6), IgG3 (SEQ ID NO: 7), or IgG4 (SEQ ID NO: 8). Whether an Fcγ receptor has binding activity to the Fc region of a monoclonal IgG1, IgG2, IgG3, or IgG4 antibody can be assessed by ALPHA screen (Amplified Luminescent Proximity Homogeneous Assay), surface plasmon resonance (SPR)-based BIACORE method, and others (Proc. Natl. Acad. Sci. U.S.A. (2006) 103(11), 4005-4010), in addition to the above-described FACS and ELISA formats.

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule comprising Fc region is immobilized to the donor beads and glutathione S-transferase (GST)-tagged Fcγ receptor is immobilized to the acceptor beads. In the absence of an antigen-binding molecule comprising a competitive Fc region variant, Fcγ receptor interacts with an antigen-binding molecule comprising a native Fc region, inducing a signal of 520 to 620 nm as a result. The antigen-binding molecule having a non-tagged Fc region variant competes with the antigen-binding molecule comprising a native Fc region for the interaction with Fcγ receptor. The relative binding affinity can be determined by quantifying the reduction of fluorescence as a result of competition. Methods for biotinylating the antigen-binding molecules such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector to which the gene is operably linked, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these constants. Inhibition assay is preferably used in the BIACORE methods. Examples of such inhibition assay are described in Proc. Natl. Acad. Sci. U.S.A. (2006) 103(11), 4005-4010.

Fc Regions with Altered Fcγ Receptor (FcγR) Binding

In addition to the Fc region of human IgG1 (SEQ ID NO: 5), IgG2 (SEQ ID NO: 6), IgG3 (SEQ ID NO: 7), or IgG4 (SEQ ID NO: 8), an Fc region with altered FcγR binding, which has a higher Fcγ receptor-binding activity than an Fc region of a native human IgG may be appropriately used as an Fc region included in the present invention. Herein, "Fc region of a native human IgG" refers to an Fc region in which the sugar chain bonded to position 297 (EU numbering) of the Fc region of human IgG1, IgG2, IgG3, or IgG4 shown in SEQ ID NOs: 5, 6, 7, or 8 is a fucose-containing sugar chain. Such Fc regions with altered FcγR binding may be produced by altering amino acids of the Fc region of a native human IgG. Whether the FcγR-binding activity of an Fc region with altered FcγR binding is higher than that of an Fc region of a native human IgG can be determined appropriately using methods described in the abovementioned section on binding activity.

In the present invention, "alteration of amino acids" or "amino acid alteration" of an Fc region includes alteration into an amino acid sequence which is different from that of the starting Fc region. The starting Fc region may be any Fc region, as long as a variant modified from the starting Fc region can bind to human Fcγ receptor in a neutral pH range. Furthermore, an Fc region altered from a starting Fc region which had been already altered can also be used preferably as an Fc region of the present invention. The "starting Fc region" can refer to the polypeptide itself, a composition comprising the starting Fc region, or an amino acid sequence encoding the starting Fc region. Starting Fc regions can comprise known Fc regions produced via recombination described briefly in the section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG class. This means that an Fc region of human IgG1, IgG2, IgG3, or IgG4 can be used appropriately as a starting Fc region, and herein also means that an Fc region of an arbitrary IgG class or subclass derived from any organisms described above can be preferably used as a starting Fc region. Examples of native IgG variants or altered forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; International Publication Nos. WO 2009/086320, WO 2008/092117, WO 2007/041635, and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between an FcγR-binding altered Fc region of the present invention and its starting Fc region. Amino acid difference between an FcγR-binding altered Fc region of the present invention and its starting Fc region can also be preferably specified based on the specific amino acid differences at the above-described specific amino acid positions by EU numbering. Examples of methods of preparing such variants are shown in the section "Alteration of amino acids".

Included in the antigen-binding molecules of the present invention, an Fc region with altered FcγR binding, which has a higher Fcγ receptor-binding activity than that of an Fc region of a native human IgG, (an FcγR binding-altered Fc region) may be obtained by any method. Specifically, the Fc region with altered FcγR binding may be obtained by altering amino acids of an IgG-type human immunoglobulin used as a starting Fc region. Preferred Fc regions of the IgG-type immunoglobulins for alteration include, for example, those of human IgGs shown in SEQ ID NOs: 5, 6, 7, or 8 (IgG1, IgG2, IgG3, or IgG4, respectively, and variants thereof).

Amino acids of any positions may be altered into other amino acids, as long as the binding activity toward the Fcγ receptor is higher than that of the Fc region of a native human IgG. When the antigen-binding molecule contains a human IgG1 Fc region as the human Fc region, it preferably contains an alteration that yields the effect of a higher Fcγ receptor-binding activity than that of the Fc region of a native human IgG, in which the sugar chain bound at position 297 (EU numbering) is a fucose-containing sugar chain. Such amino acid alterations have been reported, for example, in international publications such as WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

For the pH conditions to measure the binding activity of the Fcγ receptor binding domain and the Fcγ receptor contained in the antigen-binding molecule of the present invention, conditions in an acidic pH range or in a neutral pH range may be suitably used. The acidic pH range or neutral pH range, as a condition to measure the binding activity of the Fcγ receptor binding domain and the Fcγ receptor contained in the antigen-binding molecule of the present invention, generally indicates pH 5.8 to pH 8.0. Preferably, it is a range indicated with arbitrary pH values between pH 6.0 and pH 7.4; and preferably, it is selected from pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, and pH 7.4; and particularly preferably, it is pH 6.15 to 7.4, which is close to the pH of cancer tissues (Vaupel et al., Cancer Res. (1989) 49, 6449-6665). With regard to the temperature used as a measurement condition, the binding affinity between an Fcγ receptor binding domain and a human Fcγ receptor can be evaluated at any temperature between 10° C. and 50° C. Preferably, a temperature between 15° C. and 40° C. is used to determine the binding affinity between a human Fcγ receptor binding domain and Fcγ receptor. More preferably, any temperature between 20° C. and 35° C., such as any single temperature from 20° C., 21° C., 22° C., 23° C., 24° C., 25° C., 26° C., 27° C., 28° C., 29° C., 30° C., 31° C., 32° C., 33° C., 34° C., and 35° C., can be similarly used to determine the binding affinity between an Fcγ receptor binding domain and an Fcγ receptor. A temperature of 25° C. is a non-limiting example in an embodiment of the present invention.

Herein, "Fc region with altered FcγR binding has a higher Fcγ receptor-binding activity than the native Fc region" means that the human Fcγ receptor-binding activity of the Fc region with altered FcγR binding toward any of the human Fcγ receptors of FcγRI, FcγRIIa, FcγRIIb, FcγRIIIa, and/or FcγRIIIb is higher than the binding activity of the native Fc region toward these human Fcγ receptors. For example, it means that based on an above-described analytical method, in comparison to the binding activity of an antigen-binding molecule containing a native human IgG Fc region as a control, the binding activity of the antigen-binding molecule comprising an Fc region with altered FcγR binding is 105% or more, preferably 110% or more, 115% or more, 120% or more, 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, 2-fold or more, 2.5-fold or more, 3-fold or more, 3.5-fold or more, 4-fold or more, 4.5-fold or more, 5-fold or more, 7.5-fold or more, 10-fold or more, 20-fold or more, 30-fold or more, 40-fold or more, 50-fold or more, 60-fold or more, 70-fold or more, 80-fold or more, 90-fold or more, or 100-fold or more. The starting Fc region may be used as a native Fc region, and native Fc regions of antibodies of the same subclass may also be used.

In the present invention, an Fc region of a native human IgG in which the sugar chain bonded to the amino acid at position 297 (EU numbering) is a fucose-containing sugar chain, is suitably used as a native Fc region of human IgG to be used as a control. Whether or not the sugar chain bonded to the amino acid at position 297 (EU numbering) is a fucose-containing sugar chain can be determined using a known technique (Non-fucosylated therapeutic antibodies as next-generation therapeutic antibodies. Satoh M, Iida S, Shitara K., Expert Opin. Biol. Ther. (2006) 6 (11), 1161-1173). For example, it is possible to determine whether or not the sugar chain bonded to the native human IgG Fc region is a fucose-containing sugar chain by a method such as the one below. Sugar chain is dissociated from a native human IgG to be tested, by reacting the test native human IgG with N-Glycosidase F (Roche diagnostics) (Weitzhandler et al. (J. Pharma. Sciences (1994) 83, 12, 1670-1675)). Next, a dried concentrate of a reaction solution from which protein has been removed by reaction with ethanol (Schenk et al. (J. Clin. Investigation (2001) 108 (11) 1687-1695)) is fluorescently labeled with 2-aminopyridine (Bigge et al. (Anal. Biochem. (1995) 230 (2) 229-238)). Reagents are removed by solid extraction using a cellulose cartridge, and the fluorescently labeled 2-AB-modified sugar chain is analyzed by normal-phase chromatography. It is possible to determine whether or not the sugar chain bonded to the native Fc region of a human IgG is a fucose-containing sugar chain by observing the detected chromatogram peaks.

As an antigen-binding molecule containing a native Fc region of an antibody of the same subclass, which is to be used as a control, an antigen-binding molecule having an Fc region of a monoclonal IgG antibody may be suitably used. The structures of the Fc regions are described in SEQ ID NO: 5 (A is added to the N terminus of Database Accession No. AAC82527.1), SEQ ID NO: 6 (A is added to the N terminus of Database Accession No. AAB59393.1), SEQ ID NO: 7 (Database Accession No. CAA27268.1), and SEQ ID NO: 8 (A is added to the N terminus of Database Accession No. AAB59394.1). Further, when an antigen-binding molecule containing an Fc region of a particular antibody isotype is used as the test substance, the effect of the antigen-binding molecule containing the test Fc region on Fcγ receptor-binding activity is tested by using as a control an antigen-binding molecule having an Fc region of a monoclonal IgG antibody of that particular isotype. In this way, antigen-binding molecules containing an Fc region of which Fcγ receptor-binding activity is demonstrated to be high are suitably selected.

Fc Regions Having a Selective Binding Activity Toward an Fcγ Receptor

Examples of Fcγ receptor binding domains suitable for use in the present invention include Fcγ receptor binding domains having a higher binding activity to a particular Fcγ receptor than to other Fcγ receptors (Fcγ receptor binding domains having a selective binding activity to an Fcγ receptor). When an antibody is used as the antigen-binding molecule (when an Fc region is used as the Fcγ receptor binding domain), a single antibody molecule can only bind to a single Fcγ receptor molecule. Therefore, a single antigen-binding molecule cannot bind to other activating FcγRs in an inhibitory Fcγ receptor-bound state, and cannot bind to other activating Fcγ receptors or inhibitory Fcγ receptors in an activating Fcγ receptor-bound state.

Fc Regions with a Higher Binding Activity Toward an Activating Fcγ Receptor than the Binding Activity Toward an Inhibitory Fcγ Receptor As described above, preferable activating Fcγ receptors include FcγRI (CD64) including FcγRIa, FcγRIb, and FcγRIc; FcγRIIa; and FcγRIII (CD16) including FcγRIIIa (including allotypes V158 and F158) and FcγRIIIb (including allotypes FcγRIIIb-NA1 and FcγRIIIb-NA2). Meanwhile, preferred examples of inhibitory Fcγ receptors include FcγRIIb (including FcγRIIb-1 and FcγRIIb-2).

Herein, an example of a case where the binding activity toward a certain Fcγ receptor is higher than the binding activity toward another Fcγ receptor is the case where the binding activity toward an activating Fcγ receptor is higher than the binding activity toward an inhibitory Fcγ receptor. In this case, the binding activity of the Fc region toward any of the human Fcγ receptors of FcγRIa, FcγRIIa, FcγRIIIa, and/or FcγRIIIb is said to be higher than the binding activity toward FcγRIIb. For example, this means that, based on an above-described analytical method, the binding activity of an antigen-binding molecule containing the Fc region toward any of the human Fcγ receptors, FcγRIa, FcγRIIa, FcγRIIIa, and/or FcγRIIIb, is 105% or more, preferably 110% or more, 120% or more, 130% or more, 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10-fold or more, 20-fold or more, 30-fold or more, 40-fold or more, 50-fold or more, 60-fold, 70-fold, 80-fold, 90-fold, or 100-fold or more as compared with the binding activity toward FcγRIIb. The Fc region with a higher binding activity toward activating Fcγ receptors than to inhibitory Fcγ receptors may be favorably included in antigen-binding molecules of the present invention whose antigen-binding domain binds to a membrane-type molecule. IgG1 antibodies containing such Fc regions are known to enhance the ADCC activity mentioned below. Therefore, antigen-binding molecules containing the Fc-region are also useful as antigen-binding molecules to be included in the pharmaceutical compositions of the present invention.

In a non-limiting embodiment of the present invention, examples of the Fc region with a higher binding activity toward activating Fcγ receptors than to inhibitory Fcγ receptors (or having a selective binding activity toward inhibitory Fcγ receptors) preferably include Fc regions in which at least one or more amino acids selected from the group consisting of amino acids at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 indicated by EU numbering mentioned above, have been altered to amino acids different from those of the native Fc region.

Fc Regions Whose Binding Activity Toward an Inhibitory Fcγ Receptor is Higher than the Binding Activity Toward an Activating Fcγ Receptor Herein, an example of a case where the binding activity toward a certain Fcγ receptor is higher than the binding activity toward another Fcγ receptor is the case where the binding activity toward an inhibitory Fcγ receptor is higher than the binding activity toward an activating Fcγ receptor. In this case, the binding activity of the Fc region toward FcγRIIb is said to be higher than the binding activity toward any of the human Fcγ receptors of FcγRIa, FcγRIIa, FcγRIIIa, and/or FcγRIIIb. For example, this means that, based on an above-described analytical method, the binding activity of an antigen-binding molecule containing the Fc region toward FcγRIIb is 105% or more, preferably 110% or more, 120% or more, 130% or more, 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10-fold or more, 20-fold or more, 30-fold or more, 40-fold or more, 50-fold, 60-fold, 70-fold, 80-fold, 90-fold, or 100-fold or more as compared with the binding activity toward any of the human Fcγ receptors of FcγRIa, FcγRIIa, FcγRIIIa, and/or FcγRIIIb. The Fc region with a higher binding activity toward inhibitory Fcγ receptors than to activating Fcγ receptors may be favorably included in antigen-binding molecules of the present invention whose antigen-binding domain binds to a soluble molecule.

In a non-limiting embodiment of the present invention, examples of the Fc region with a higher binding activity toward inhibitory Fcγ receptors than to activating Fcγ receptors (or having a selective binding activity toward inhibitory Fcγ receptors) preferably include Fc regions in which, of the amino acids of the above Fc region, the amino acids at 238 and 328 indicated by EU numbering are altered to amino acids different from those of the native Fc region.

In a non-limiting embodiment of the present invention, examples of the Fc region with a higher binding activity toward inhibitory Fcγ receptors than to activating Fcγ receptors (or having a selective binding activity toward inhibitory Fcγ receptors) preferably include Fc regions altered at any one or more of the amino acids in the above Fc region as indicated by EU numbering: the amino acid at position 238 (indicated by EU numbering) is altered into Asp; and the amino acid at position 328 (indicated by EU numbering) is altered into Glu. Furthermore, as the Fc regions having a selective binding activity toward inhibitory Fcγ receptors, the Fc regions or alterations described in US 2009/0136485 can be suitably selected.

In another non-limiting embodiment of the present invention, preferred examples include Fc regions altered at any one or more of the amino acids in the above Fc region as indicated by EU numbering: the amino acid at position 238 (indicated by EU numbering) to Asp; and the amino acid at position 328 (indicated by EU numbering) to Glu.

In still another non-limiting embodiment of the present invention, preferred examples include Fc regions that have one or more of the alterations exemplified in PCT/JP2012/054624: substitution of Pro at position 238 (indicated by EU numbering) with Asp; alteration of the amino acid at position 237 (indicated by EU numbering) to Trp; alteration of the amino acid at position 237 (indicated by EU numbering) to Phe; alteration of the amino acid at position 267 (indicated by EU numbering) to Val; alteration of the amino acid at position 267 (indicated by EU numbering) to Gln; alteration of the amino acid at position 268 (indicated by EU numbering) to Asn; alteration of the amino acid at position 271 (indicated by EU numbering) to Gly; alteration of the amino acid at position 326 (indicated by EU numbering) to Leu; alteration of the amino acid at position 326 (indicated by EU numbering) to Gln; alteration of the amino acid at position 326 (indicated by EU numbering) to Glu; alteration of the amino acid at position 326 (indicated by EU numbering) to Met; alteration of the amino acid at position 239 (indicated by EU numbering) to Asp; alteration of the amino acid at position 267 (indicated by EU numbering) to Ala; alteration of the amino acid at position 234 (indicated by EU numbering) to Trp; alteration of the amino acid at position 234 (indicated by EU numbering) to Tyr; alteration of the amino acid at position 237 (indicated by EU numbering) to Ala; alteration of the amino acid at position 237 (indicated by EU numbering) to Asp; alteration of the amino acid at position 237 (indicated by EU numbering) to Glu; alteration of the amino acid at position 237 (indicated by EU numbering) to Leu; alteration of the amino acid at position 237 (indicated by EU numbering) to Met; alteration of the amino acid at position 237 (indicated by EU numbering) to Tyr; alteration of the amino acid at position 330 (indicated by EU numbering) to Lys; alteration of the amino acid at position 330 (indicated by EU numbering) to Arg, alteration of the amino acid at position 233 (indicated by EU numbering) to Asp, alteration of the amino acid at position 268 (indicated by EU numbering) to Asp, alteration of the amino acid at position 268 (indicated by EU numbering) to Glu, alteration of the amino acid at position 326 (indicated by EU numbering) to Asp, alteration of the amino acid at position 326 (indicated by EU numbering) to Ser, alteration of the amino acid at position 326 (indicated by EU numbering) to Thr, alteration of the amino acid at position 323 (indicated by EU numbering) to Ile, alteration of the amino acid at position 323 (indicated by EU numbering) to Leu, alteration of the amino acid at position 323 (indicated by EU numbering) to Met, alteration of the amino acid at position 296 (indicated by EU numbering) to Asp, alteration of the amino acid at position 326 (indicated by EU numbering) to Ala, alteration of the amino acid at position 326 (indicated by EU numbering) to Asn, and alteration of the amino acid at position 330 (indicated by EU numbering) to Met.

Fc Regions with Modified Sugar Chains

Fc regions contained in the antigen-binding molecules provided by the present invention may include Fc regions that have been modified so that the composition of the sugar-chain-attached Fc regions has a high percentage of fucose-deficient sugar-chain-attached Fc regions, or a high percentage of bisecting N-acetylglucosamine-added Fc regions. Removal of fucose residue from N-acetylglucosamine at the reducing end of N-glycoside linkage complex sugar chains bonded to the antibody Fc region is known to enhance the affinity to FcγRIIIa (Non-Patent Document 6). It is known that for IgG1 antibodies containing such Fc regions, the ADCC activity mentioned below is enhanced; therefore, antigen-binding molecules containing such Fc regions are also useful as antigen-binding molecules to be contained in pharmaceutical compositions of the present invention. Examples of antibodies with fucose residue removed from N-acetylglucosamine at the reducing end of N-glycoside linkage complex sugar chains bonded to the antibody Fc regions are antibodies such as:
antibodies modified by glycosylation (for example, WO 1999/054342); and
antibodies deficient in fucose attached to sugar chains (for example, WO 2000/061739, WO 2002/031140, and WO 2006/067913).

More specifically, to produce antibodies deficient in fucose attached to sugar chains (for example, WO 2000/061739, WO 2002/031140, and WO 2006/067913) as another non-limiting embodiment of antibodies with fucose residue removed from N-acetylglucosamine at the reducing end of N-glycoside linkage complex sugar chains bonded to the antibody Fc regions, host cells having a low ability to add fucose to sugar chains are produced by altering the activity of forming the sugar chain structure of the polypeptide to be glycosylated. Antibodies that lack fucose in their sugar chains can be collected from culture of the host cells by expressing a desired antibody gene in the host cells. Non-limiting suitable examples of the activity to form the sugar chain structure of a polypeptide include the activity of a transporter or an enzyme selected from the group consisting of fucosyltransferase (EC 2.4.1.152), fucose transporter (SLC35C1), GMD (GDP-mannose-4,6-dehydratase) (EC 4.2.1.47), Fx (GDP-keto-6-deoxymannose-3,5-epimerase, 4-reductase) (EC 1.1.1.271), and GFPP (GDP-β-L-fucose pyrophosphorylase (EC 2.7.7.30). As long as these enzymes or transporters can exhibit their activities, their structures are not necessarily specified. Herein, proteins that can exhibit these activities are referred to as "functional proteins". In a non-limiting embodiment, methods for altering these activities include deletion of these activities. To produce host cells deficient in these activities, known methods such as a method for destroying the genes of these functional proteins to make them unable to function may be appropriately employed (for example, WO2000/061739, WO2002/031140, and WO2006/067913). Host cells deficient in such activities can be produced, for example, by a method that destroys the genes of these functional proteins endogenous to CHO cells, BHK cells, NS0 cells, SP2/0 cells, YO myeloma cells, P3X63 mouse myeloma cells, PER cells, PER.C6 cells, HEK293 cells, hybridoma cells, or such, so that the genes are unable to function.

Antibodies that have a sugar chain containing bisecting GlcNAc (WO2002/079255, etc.) are known. In a non-limiting embodiment, host cells for expressing a gene that encodes a functional protein having GnTIII (β-1,4-mannosyl-glycoprotein acetylglucosaminyltransferase) (EC 2.4.1.144) activity or GalT (β-1,4-galactosyltransferase) (EC 2.4.1.38) activity are produced to prepare antibodies that have bisecting GlcNAc-containing sugar chains. In another suitable non-limiting embodiment, host cells that co-express, in addition to the aforementioned functional proteins, a gene encoding a functional protein having human ManII (mannosidase II) (3.2.1.114) activity, a gene encoding a functional protein having GnTI (β-1,2-acetylglucosaminyltransferase I) (EC 2.4.1.94) activity, a gene encoding a functional protein having GnTII (β-1,2-acetylglucosaminyltransferase II) (EC 2.4.1.143) activity, a gene encoding a functional protein having ManI (mannosidase) (EC 3.2.1.113) activity, and a-1,6-fucosyl transferase (EC 2.4.1.68), are produced (WO2004/065540).

Antibodies with fucose residue removed from N-acetylglucosamine at the reducing end of N-glycoside linkage complex sugar chains bonded to the antibody Fc regions and antibodies having sugar chains containing bisecting GlcNAc can be produced, respectively, by transfecting an expression vector containing the antibody gene into host cells with a low ability to add fucose to sugar chains, and into host cells having the activity to form bisecting GlcNAc structure-containing sugar chains. Methods for producing these antibodies can be applied to methods for producing antigen-binding molecules containing altered Fc regions that have been modified so that the composition of the sugar-chain-attached Fc regions of the present invention has a high percentage of fucose-deficient sugar chain-attached Fc regions or a high percentage of bisecting N-acetylglucosamine-added Fc regions. The composition of the sugar-chain-attached Fc regions contained in the antigen-binding molecules of the present invention produced by such production methods can be assessed by the method described in "Fc regions with altered Fcγ receptor (FcγR) binding" above.

Multi Specific Antigen-Binding Molecules or Multiparatopic Antigen-Binding Molecules An antigen-binding molecule comprising at least two antigen-binding domains in which at least one of the antigen-binding domains binds to a first epitope in an antigen molecule, and at least another one of the antigen-binding domains binds to a second epitope in the antigen molecule, is called "multispecific antigen-binding molecule" from the viewpoint of its reaction specificity. When two types of antigen-binding domains contained in a single antigen-binding molecule allow binding to two different epitopes by the antigen-binding molecule, this molecule is called "bispecific antigen-binding molecule". When three types of antigen-binding domains contained in a single antigen-binding molecule allow binding to three different epitopes by the antigen-binding molecule, this antigen-binding molecule is called "trispecific antigen-binding molecule".

A paratope in the antigen-binding domain that binds to the first epitope in the antigen molecule and a paratope in the antigen-binding domain that binds to the second epitope which is structurally different from the first epitope have different structures. Therefore, an antigen-binding molecule comprising at least two antigen-binding domains in which at least one of the antigen-binding domains binds to a first epitope in an antigen molecule, and at least another one of the antigen-binding domains binds to a second epitope in the antigen molecule, is called "multiparatopic antigen-binding molecule" from the viewpoint of the specificity of its structure. When two types of antigen-binding domains contained in a single antigen-binding molecule allow binding to two different epitopes by the antigen-binding molecule, this molecule is called "biparatopic antigen-binding molecule". When three types of antigen-binding domains contained in a single antigen-binding molecule allow binding to three different epitopes by the antigen-binding molecule, this molecule is called "triparatopic antigen-binding molecule".

Multivalent multispecific or multiparatopic antigen-binding molecules comprising one or more antigen-binding domains and methods for preparing them are described in non-patent documents such as Conrath et al., (J. Biol. Chem. (2001) 276 (10) 7346-7350), Muyldermans (Rev. Mol. Biotech. (2001) 74, 277-302), and Kontermann R. E. (2011) Bispecific Antibodies (Springer-Verlag), and in patent documents such as WO1996/034103 and WO1999/023221. Antigen-binding molecules of the present invention can be produced using multispecific or multiparatopic antigen-binding molecules, and their preparation methods described in these documents.

Bispecific Antibodies and Methods for Producing them

In an embodiment, bispecific antibodies and methods for producing them are mentioned below as examples of the aforementioned multispecific or multiparatopic antigen-binding molecules and methods for preparing them. Bispecific antibodies are antibodies comprising two types of variable regions that bind specifically to different epitopes. IgG-type bispecific antibodies can be secreted from a hybrid hybridoma (quadroma) produced by fusing two types of hybridomas that produce IgG antibodies (Milstein et al., Nature (1983) 305, 537-540).

When a bispecific antibody is produced by using recombination techniques such as those described in the above-mentioned section on antibodies, one may adopt a method that introduces genes encoding heavy chains containing the two types of variable regions of interest into cells to co-express them. However, even when only the heavy-chain combination is considered, such a co-expression method will produce a mixture of (i) a combination of a pair of heavy chains in which one of the heavy chains contains a variable region that binds to a first epitope and the other heavy chain contains a variable region that binds to a second epitope, (ii) a combination of a pair of heavy chains which include only heavy chains containing a variable region that binds to the first epitope, and (iii) a combination of a pair of heavy chains which include only heavy chains containing a variable region that binds to the second epitope, which are present at a molecular ratio of 2:1:1. It is difficult to purify antigen-binding molecules containing the desired combination of heavy chains from the mixture of three types of heavy chain combinations.

When producing bispecific antibodies using such recombination techniques, bispecific antibodies containing a heteromeric combination of heavy chains can be preferentially secreted by adding appropriate amino acid substitutions in the CH3 domains constituting the heavy chains. Specifically, this method is conducted by substituting an amino acid having a larger side chain (knob (which means "bulge")) for an amino acid in the CH3 domain of one of the heavy chains, and substituting an amino acid having a smaller side chain (hole (which means "void")) for an amino acid in the CH3 domain of the other heavy chain so that the knob is placed in the hole. This promotes heteromeric heavy chain formation and simultaneously inhibits homomeric heavy chain formation (International Publication No. WO 1996027011; Ridgway et al., Protein Engineering (1996) 9, 617-621; Merchant et al., Nature Biotechnology (1998) 16, 677-681).

Furthermore, there are also known techniques for producing a bispecific antibody by applying methods for controlling polypeptide association, or association of polypeptide-formed heteromeric multimers to the association between heavy chains. Specifically, methods for controlling heavy chain formation may be employed to produce a bispecific antibody (International Publication No. WO 2006/106905), in which amino acid residues forming the interface between the heavy chains are altered to inhibit the association between the heavy chains having the same sequence and to allow the formation of heavy chains of different sequences. Such methods can be used for generating bispecific antibodies.

In a non-limiting embodiment of the present invention, two polypeptides constituting an Fc region derived from a bispecific antibody described above can be suitably used as an Fc region to be included in the antigen-binding molecule. More specifically, it is preferable to use two polypeptides that constitute an Fc region, and which comprise Cys for the amino acid at position 349 and Trp for the amino acid at position 366 according to EU numbering in the amino acid sequence of one of the polypeptides; and Cys for the amino acid at position 356, Ser for the amino acid at position 366, Ala for the amino acid at position 368, and Val for the amino acid at position 407 as indicated by EU numbering in the amino acid sequence of the other polypeptide.

In another non-limiting embodiment of the present invention, two polypeptides that constitute an Fc region and which comprise Asp for the amino acid at position 409 according to EU numbering in the amino acid sequence of one of the polypeptides, and Lys for the amino acid at position 399 according to EU numbering in the amino acid sequence of the other polypeptide, may be suitably used as the Fc region. In the above embodiment, the amino acid at position 409 may be Glu instead of Asp, and the amino acid at position 399 may be Arg instead of Lys. Moreover, in addition to the amino acid Lys at position 399, Asp may be suitably be added as the amino acid at position 360 or Asp may suitably be added as the amino acid at position 392.

In still another non-limiting embodiment of the present invention, two polypeptides that constitute an Fc region, and which comprise Glu for the amino acid at position 370 according to EU numbering in the amino acid sequence of one of the polypeptides, and Lys for the amino acid at position 357 according to EU numbering in the amino acid sequence of the other polypeptide, may be suitably used as the Fc region.

In yet another non-limiting embodiment of the present invention, two polypeptides that constitute an Fc region, and which comprise Glu for the amino acid at position 439 according to EU numbering in the amino acid sequence of one of the polypeptides, and Lys for the amino acid at position 356 according to EU numbering in the amino acid sequence of the other polypeptide, may be suitably used as the Fc region.

In still yet another non-limiting embodiment of the present invention, any of the embodiments indicated below of combinations from the above may be suitably used as the Fc region:

(i) two polypeptides that constitute an Fc region, and which comprise Asp for the amino acid at position 409 and Glu for the amino acid at position 370 according to EU numbering in the amino acid sequence of one of the polypeptides, and Lys for the amino acid at position 399 and Lys for the amino acid at position 357 according to EU numbering in the amino acid sequence of the other polypeptide (in this embodiment, the amino acid at position 370 according to EU numbering may be Asp instead of Glu, and the amino acid Asp at position 392 may be used instead of the amino acid Glu at position 370 according to EU numbering);

(ii) two polypeptides that constitute an Fc region, and which comprise Asp for the amino acid at position 409 and Glu for the amino acid at position 439 according to EU numbering of the amino acid sequence of one of the polypeptides; and Lys for the amino acid at position 399 and Lys for the amino acid at position 356 according to EU numbering in the amino acid sequence of the other polypeptide (in this embodiment, the amino acid Asp at position 360, the amino acid Asp at position 392, or the amino acid Asp at position 439 may be used instead of the amino acid Glu at position 439 according to EU numbering);

(iii) two polypeptides that constitute an Fc region, and which comprise Glu for the amino acid at position 370 and Glu for the amino acid at position 439 according to EU numbering in the amino acid sequence of one of the polypeptides, and Lys for the amino acid at position 357 and Lys for the amino acid at position 356 according to EU numbering in the amino acid sequence of the other polypeptide; or two polypeptides that constitute an Fc region, and which comprise Asp the amino acid at position 409, Glu for the amino acid at position 370, and Glu for the amino acid at position 439 according to EU numbering in the amino acid sequence of one of the polypeptides; and Lys for the amino acid at position 399, Lys for the amino acid at position 357, and Lys for the amino acid at position 356 according to EU numbering in the amino acid sequence of the other polypeptide (in this embodiment, the amino acid at position 370 may not be substituted with Glu, and furthermore, when the amino acid at position 370 is not substituted with Glu, the amino acid at position 439 may be Asp instead of Glu, or the amino acid Asp at position 392 may be used instead of the amino acid Glu at position 439, according to EU numbering).

Further, in another non-limiting embodiment of the present invention, it may also be suitable to use two polypeptides that constitute an Fc region, and which comprise Lys for the amino acid at position 356 according to EU numbering in the amino acid sequence of one of the polypeptides, and Arg for the amino acid at position 435 and Glu for the amino acid at position 439 according to EU numbering in the amino acid sequence of the other polypeptide.

In still another non-limiting embodiment of the present invention, it may also be suitable to use two polypeptides that constitute an Fc region and which comprise Lys for the amino acid at position 356 and Lys for the amino acid at position 357 according to EU numbering in the amino acid sequence of one of the polypeptides, and Glu for the amino acid at position 370, Arg for the amino acid at position 435, and Glu for the amino acid at position 439 according to EU numbering in the amino acid sequence of the other polypeptide.

Furthermore, in addition to the above-mentioned technologies of associating heterologous heavy chains, CrossMab technology which is known as a technology for associating heterologous light chains, in which a light chain forming a variable region that binds to a first epitope and a light chain forming a variable region that binds to a second epitope are respectively associated with a heavy chain forming a variable region that binds to the first epitope and a heavy chain forming a variable region that binds to the second epitope (Scaefer et al. (Proc. Natl. Acad. Sci. U.S.A. (2011) 108, 11187-11192)), may also be used to produce the multispecific or multiparatopic antigen-binding molecules provided by the present invention. Furthermore, Fab-Arm Exchange which is known as a technology for associating heterologous heavy chains, in which a heavy chain forming a variable region that binds to a first epitope and a heavy chain forming a variable region that binds to a second epitope by utilizing that heterologous IgG4 heavy chains exchange each other (Labrijn et al. (Proc. Natl. Acad. Sci. U.S.A. (2013) 110, 5145-5150), WO2008119353), may also be used to produce the multispecific or multiparatopic antigen-binding molecules provided by the present invention.

Effector Cells

In the present invention, the term "effector cells" may be used in the broadest sense including T cells (CD4$^+$ (helper lymphocyte) T cells and/or CD8$^+$ (cytotoxic) T cells), multinuclear leucocytes (neutrophils, eosinophils, basophils, mast cells), monocytes, macrophages, histiocytes, or leukocytes such as natural killer cells (NK cells), NK-like T cells, Kupffer cells, Langerhans cells, or lymphokine-activated killer cells (LAK cells), B-lymphocytes, or antigen-presenting cells such as dendritic cells or macrophages. Preferred examples of effector cells include CD8$^+$ (cytotoxic) T cells, NK cells, or macrophages. Membrane-type molecules expressed on the cell membrane of effector cells may be used as antigens to which at least one antigen-binding domain contained in the antigen-binding molecule of the present invention binds. Non-limiting examples of a preferred membrane-type molecule may be CD3, CD2, CD28, CD44, CD16, CD32, CD64, or NKG2D, NK cell-activating ligands, or polypeptides constituting TCR.

Cytotoxic Substances

In order for antigen-binding molecules of the present invention to bind to cancer cells and exhibit cytotoxic activity, cytotoxic substances may be linked to antigen-binding molecules. The cytotoxic substances may be chemotherapeutic agents exemplified below, or compounds disclosed in Curr Opin Chem Biol (2010) 14, 529-37 and WO 2009/140242; and these compounds are linked to antigen-binding molecules by appropriate linkers and such. When antigen-binding molecules of the present invention are used as pharmaceutical compositions, these cytotoxic substances may be linked to the antigen-binding molecules prior to administration, or they may be administered before, after, or at the same time when the antigen-binding molecules are administered to subjects (test individuals, patients, and such).

The later-described modified antigen-binding molecules to which cytotoxic substances such as chemotherapeutic agents, toxic peptides, or radioactive chemical substances have been linked may also be used preferably as antigen-binding molecules of the present invention having cytotoxic activity. Such modified antigen-binding molecules (hereinafter referred to as antigen-binding molecule-drug conjugate) can be obtained by chemically modifying the obtained antigen-binding molecules. Methods that have been already established in the field of antibody-drug conjugates and such may be used appropriately as methods for modifying antigen-binding molecules. Furthermore, a modified antigen-binding molecule to which a toxic peptide is linked can be obtained by expressing in appropriate host cells a fused gene produced by linking a gene encoding the toxic peptide in frame with a gene encoding an antigen-binding molecule of the present invention, and then isolating it from the cell culture.

Examples of chemotherapeutic agents linked to the antigen-binding molecules of the present invention may include: azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine, and vincristine.

In the present invention, preferred chemotherapeutic agents are low-molecular-weight chemotherapeutic agents. Low-molecular-weight chemotherapeutic agents are unlikely to interfere with the function of antigen-binding molecules even after they bind to antigen-binding molecules of the present invention. In the present invention, low-molecular-weight chemotherapeutic agents usually have a molecular weight of 100 to 2000, preferably 200 to 1000. The chemotherapeutic agents exemplified herein are all low-molecular-weight chemotherapeutic agents. The chemotherapeutic agents of the present invention include prodrugs that are converted into active chemotherapeutic agents in vivo. Prodrug activation may be enzymatic conversion or non-enzymatic conversion.

Moreover, cytotoxic substances that are linked to antigen-binding molecules of the present invention include, for example, toxic peptides (toxins) such as *Pseudomonas* exotoxin A, Saporin-s6, Diphtheria toxin, Cnidarian toxin; radioiodine; and photosensitizers. Suitable examples of the toxic peptides include the following:

Diphtheria toxin A Chain (Langone et al. (Methods in Enzymology (1983) 93, 307-308)); *Pseudomonas* Exotoxin (Nature Medicine (1996) 2, 350-353);

Ricin Chain (Ricin A Chain) (Fulton et al. (J. Biol. Chem. (1986) 261, 5314-5319), Sivam et al. (Cancer Res. (1987) 47, 3169-3173), Cumber et al (J. Immunol. Methods (1990) 135, 15-24), Wawrzynczak et al. (Cancer Res. (1990) 50, 7519-7562), and Gheeite et al. (J. Immunol. Methods (1991) 142, 223-230));

Deglicosylated Ricin A Chain (Thorpe et al. (Cancer Res. (1987) 47, 5924-5931));

Abrin A Chain (Wawrzynczak et al. (Br. J. Cancer (1992) 66, 361-366), Wawrzynczak et al. (Cancer Res. (1990) 50, 7519-7562), Sivam et al. (Cancer Res. (1987) 47, 3169-3173), and Thorpe et al. (Cancer Res. (1987) 47, 5924-5931));

Gelonin (Sivam et al. (Cancer Res. (1987) 47, 3169-3173), Cumber et al. (J. Immunol. Methods (1990) 135, 15-24), Wawrzynczak et al. (Cancer Res., (1990) 50, 7519-7562), and Bolognesi et al. (Clin. exp. Immunol. (1992) 89, 341-346));

PAP-s; Pokeweed anti-viral protein from seeds (Bolognesi et al. (Clin. exp. Immunol. (1992) 89, 341-346));

Briodin (Bolognesi et al. (Clin. exp. Immunol. (1992) 89, 341-346));

Saporin (Bolognesi et al. (Clin. exp. Immunol. (1992) 89, 341-346));

Momordin (Cumber et al. (J. Immunol. Methods (1990) 135, 15-24); Wawrzynczak et al. (Cancer Res. (1990) 50, 7519-7562); and Bolognesi et al. (Clin. exp. Immunol. (1992) 89, 341-346));

Momorcochin (Bolognesi et al. (Clin. exp. Immunol. (1992) 89, 341-346));

Dianthin 32 (Bolognesi et al. (Clin. exp. Immunol. (1992) 89, 341-346));

Dianthin 30 (Stirpe F., Barbieri L. (FEBS letter (1986) 195, 1-8));

Modeccin (Stirpe F., Barbieri L. (FEBS letter (1986) 195, 1-8));

Viscumin (Stirpe F., Barbieri L. (FEBS letter (1986) 195, 1-8));

Volkesin (Stirpe F., Barbieri L. (FEBS letter (1986) 195, 1-8));

Dodecandrin (Stirpe F., Barbieri L. (FEBS letter (1986) 195, 1-8));

Tritin (Stirpe F., Barbieri L. (FEBS letter (1986) 195, 1-8));

Luffin (Stirpe F., Barbieri L. (FEBS letter (1986) 195, 1-8)); and

Trichokirin (Casellas et al. (Eur. J. Biochem. (1988) 176, 581-588), and Bolognesi et al. (Clin. exp. Immunol., (1992) 89, 341-346)).

Antigen-Binding Molecule

In the present invention, "an antigen-binding molecule comprising an antigen-binding domain whose antigen-binding activity in the presence of a small molecule compound (e.g., target tissue-specific compound) is higher than in the absence of the target tissue-specific compound" is used in the broadest sense; and specifically, it includes various types of molecules as long as they show antigen-binding activity. Molecules in which an antigen-binding domain is linked to an Fc region include, for example, antibodies. Antibodies may include single monoclonal antibodies (including agonistic antibodies and antagonistic antibodies), human antibodies, humanized antibodies, chimeric antibodies, and such. Alternatively, when used as antibody fragments, they preferably include antigen-binding domains and antigen-binding fragments (for example, Fab, F(ab')2, scFv, and Fv). Scaffold molecules where three dimensional structures, such as already-known stable α/β barrel protein structure, are used as a scaffold (base) and only some portions of the structures are made into libraries to construct antigen-binding domains are also included in antigen-binding molecules of the present invention.

An antigen-binding molecule of the present invention may contain at least some portions of an Fc region that mediates the binding to Fcγ receptor and/or FcRn. In a non-limiting embodiment, the antigen-binding molecule includes, for example, antibodies and Fc fusion proteins. A fusion protein refers to a chimeric polypeptide comprising a polypeptide having a first amino acid sequence that is linked to a polypeptide having a second amino acid sequence that would not naturally link in nature. For example, a fusion protein may comprise a polypeptide comprising the amino acid sequence of at least a portion of an Fc region (for example, a portion of an Fc region responsible for the binding to Fcγ receptor, and/or a portion of an Fc region responsible for the binding to FcRn). The amino acid sequences may be present in separate proteins that are transported together to a fusion protein, or generally may be present in a single protein; however, they are included in a new rearrangement in a fusion polypeptide. Fusion proteins can be produced, for example, by chemical synthesis, or by genetic recombination techniques to express a polynucleotide encoding peptide regions in a desired arrangement.

Respective domains of the present invention can be linked together via linkers or directly via polypeptide binding. The linkers comprise arbitrary peptide linkers that can be introduced by genetic engineering, synthetic linkers, and linkers disclosed in, for example, Holliger et al., Protein Engineering (1996) 9(3), 299-305. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids.

For example, such peptide linkers preferably include:

```
Ser

Gly Ser

Gly·Gly·Ser

Ser·Gly·Gly

Gly·Gly·Gly.Ser                          (SEQ ID NO: 19)

Ser·Gly·Gly·Gly                          (SEQ ID NO: 20)

Gly·Gly·Gly·Gly·Ser                      (SEQ ID NO: 21)

Ser·Gly·Gly·Gly·Gly                      (SEQ ID NO: 22)

Gly·Gly·Gly·Gly·Gly·Ser                  (SEQ ID NO: 23)

Ser·Gly·Gly·Gly·Gly·Gly                  (SEQ ID NO: 24)

Gly·Gly·Gly·Gly·Gly·Gly·Ser              (SEQ ID NO: 25)

Ser·Gly·Gly·Gly·Gly·Gly·Gly              (SEQ ID NO: 26)

(Gly·Gly·Gly·Gly·Ser (SEQ ID NO: 21))n (Ser·Gly·Gly·Gly·Gly (SEQ ID NO: 22))n
``` where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate (BS³),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), di sulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES). These crosslinking agents are commercially available.

When multiple linkers for linking the respective domains are used, they may all be of the same type, or may be of different types. In addition to the linkers exemplified above, linkers with peptide tags such as His tag, HA tag, myc tag, and FLAG tag may also be suitably used. Furthermore, hydrogen bonding, disulfide bonding, covalent bonding, ionic interaction, and properties of binding with each other as a result of combination thereof may be suitably used. For example, the affinity between CH1 and CL of antibody may be used, and Fc regions originating from the above-described bispecific antibodies may also be used for hetero Fc region association. Moreover, disulfide bonds formed between domains may also be suitably used.

In order to link respective domains via peptide linkage, polynucleotides encoding the domains are linked together in frame. Known methods for linking polynucleotides in frame include techniques such as ligation of restriction fragments, fusion PCR, and overlapping PCR. Such methods can be appropriately used alone or in combination to construct antigen-binding molecules of the present invention. In the present invention, the terms "linked" and "fused", or "linkage" and "fusion" are used interchangeably. These terms mean that two or more elements or components such as polypeptides are linked together to form a single structure by any means including the above-described chemical linking means and genetic recombination techniques. Fusing in frame means, when two or more elements or components are polypeptides, linking two or more units of reading frames to form a continuous longer reading frame while maintaining the correct reading frames of the polypeptides. When two molecules of Fab are used as an antigen-binding domain, an antibody, which is an antigen-binding molecule of the present invention where the antigen-binding domain is linked in frame to a constant region including an Fc region via peptide bond without linker, can be used as a preferred antigen-binding molecule of the present invention.

Low-Molecular-Weight Antibody

The antibodies used in the present invention are not limited to full-length antibody molecules, and can be low-molecular-weight antibodies (minibodies) and modified products thereof. A low-molecular-weight antibody includes an antibody fragment that lacks a portion of a full-length antibody (for example, whole antibody such as whole IgG); and is not particularly limited as long as it has an antigen-binding activity. The low-molecular-weight antibody of the present invention is not particularly limited as long as it is a portion of a full-length antibody, but preferably comprises a heavy-chain variable region (VH) and/or a light-chain variable region (VL). The amino acid sequence of VH or VL may have substitution(s), deletion(s), addition(s), and/or insertion(s). Furthermore, as long as it has an antigen-binding activity, VH and/or VL can be partially deleted. The variable region may be chimerized or humanized. Specific examples of antibody fragments include Fab, Fab', F(ab')2, and Fv. Specific examples of low-molecular-weight antibodies include Fab, Fab', F(ab')2, Fv, scFv (single chain Fv), diabody, and sc(Fv)2 (single chain (Fv)2). Multimers of these antibodies (for example, dimers, trimers, tetramers, and polymers) are also included in the low-molecular-weight antibodies of the present invention.

Antibody fragments can be produced by treating an antibody with an enzyme such as papain and pepsin. Alternatively, genes encoding these antibody fragments can be constructed, inserted into expression vectors, and then expressed in appropriate host cells (see, for example, Co et al, (J. Immunol. (1994) 152, 2968-2976); Better and Horwitz (Methods in Enzymology (1989) 178, 476-496), Plueckthun and Skerra (Methods in Enzymology (1989) 178, 476-496); Lamoyi (Methods in Enzymology (1989) 121, 652-663); Rousseaux (Methods in Enzymology (1989) 121, 663-669); and Bird, et al., TIBTECH (1991) 9, 132-137).

A diabody refers to a bivalent low-molecular-weight antibody constructed by gene fusion (Hollinger et al., (Proc. Natl. Acad. Sci. USA 90, 6444-6448 (1993)); EP 404,097; WO 1993/11161; and such). A diabody is a dimer composed of two polypeptide chains. Generally, in each polypeptide chain constituting the dimer, VL and VH are linked by a linker within the same chain. The linker in a diabody is generally short enough to prevent binding between VL and VH. Specifically, the amino acid residues constituting the linker are, for example, about five residues. A linker between VL and VH that are encoded by the same polypeptide chain is too short to form a single-chain variable region fragment, and a dimer is formed between the polypeptide chains. As a result, diabodies have two antigen binding sites.

scFv can be obtained by linking the H-chain V region and L-chain V region of an antibody. In scFv, the H-chain V region and L-chain V region are ligated via a linker, preferably a peptide linker (Huston, et al, Proc. Natl. Acad. Sci. U.S.A. (1988) 85, 5879-5883). The H-chain V region and L-chain V region of scFv may be derived from any of the antibodies described herein. The peptide linker for ligating the V regions is not particularly limited; and for example, any single-chain peptide consisting of 3 to 25 residues or so, or peptide linkers described later or such can be used as the linker. PCR methods such as those described above can be used for ligating the V regions. DNA encoding scFv can be amplified by a PCR method using as a template either whole DNA or a partial DNA encoding a desired amino acid sequence, which is selected from a DNA sequence encoding the H chain or the H chain V region of the above-mentioned antibody, and a DNA encoding the L chain or the L chain V region of the above-mentioned antibody; and using a pair of primers having sequences corresponding to the sequences of the two ends. Next, a DNA having the desired sequence can be obtained by performing a PCR reaction using a combination of a DNA encoding the peptide linker portion, and a pair of primers having sequences designed so that both ends of the DNA will be ligated to the H chain and the L chain, respectively. Once the scFv-encoding DNA is constructed, expression vectors having the DNA, and recombinant cells transformed with the expression vector can be obtained according to conventional methods. Furthermore, the scFvs can be obtained by culturing the resulting recombinant cells to express the scFv-encoding DNA.

sc(Fv)2 is a low-molecular-weight antibody prepared by linking two VHs and two VLs with linkers or such to form a single chain (Hudson et al (J. Immunol. Methods 1999; 231: 177-189)). sc(Fv)2 can be produced, for example, by linking scFvs with a linker.

Moreover, antibodies in which two VHs and two VLs are arranged in the order of VH, VL, VH, and VL starting from the N-terminal side of a single chain polypeptide ([VH]-linker-[VL]-linker-[VH]-linker-[VL]) are preferred. The order of the two VHs and the two VLs is not particularly limited to the above-mentioned arrangement, and they may be arranged in any order. Examples include the following arrangements:

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

A linker similar to the linker described in the section "Antigen-binding molecules" above may be used as the linker for linking the antibody variable regions. A particularly preferred embodiment of sc(Fv)2 in the present invention includes, for example, the following sc(Fv)2:
[VH]-peptide linker (15 amino acids)-[VL]-peptide linker (15 amino acids)-[VH]-peptide linker (15 amino acids)-[VL]

Typically, three linkers are required to link four antibody variable regions. The linkers to be used may be of the same type or different types. Examples of a non-limiting embodiment of a low-molecular-weight antibody in the present invention include a diabody or sc(Fv)2, wherein the paratopes are different from each other; one of the paratopes binds to an epitope in a membrane-type molecule which binds to a cell membrane of cancer cells, cells infiltrated into inflammatory tissues, and such; and the other paratope binds to an epitope in the membrane-type molecule expressed on the cell membrane of effector cells. In the above-mentioned diabody or sc(Fv)2, the binding activity of one of the paratopes toward an epitope in a membrane-type molecule which binds to a cell membrane of cancer cells, cells infiltrated into inflammatory tissues, and such may depend on a small molecule compound (e.g., cancer tissue-specific compound, inflammatory tissue-specific compound, or unnatural compound), the binding activity of one of the paratopes toward an epitope in a membrane-type molecule which binds to an effector cell membrane may depend on a small molecule compound (e.g., a cancer tissue-specific compound, inflammatory tissue-specific compound, or unnatural compound), or the binding activities of both paratopes may depend on a small molecule compound (e.g., a cancer tissue-specific compound, inflammatory tissue-specific compound, or unnatural compound).

A non-limiting embodiment of a low-molecular-weight antibody in the present invention includes, for example, a diabody or sc(Fv)2, wherein the paratopes are different from each other; one of the paratopes binds to an epitope in a membrane-type molecule which binds to a cell membrane of cancel cells, cells infiltrated into inflammatory tissues, and such; and the other paratope binds to an epitope in a cytotoxic substance. In the diabody or sc(Fv)2 mentioned above, the binding activity of one of the paratopes that binds to an epitope in a membrane-type molecule which binds to a cell membrane of cancel cells, cells infiltrated into inflammatory tissues, and such may depend on a small molecule compound (e.g., a cancer tissue-specific compound, inflammatory tissue-specific compound, or unnatural compound), the binding activity of the other paratope that binds to an epitope in a cytotoxic substance may depend on a small molecule compound (e.g., a cancer tissue-specific compound, inflammatory tissue-specific compound, or unnatural compound), or the binding activities of both paratopes may depend on a cancer tissue-specific compound.

Such low-molecular-weight antibody can be obtained by treating an antibody with an enzyme such as papain or pepsin to generate antibody fragments, or by constructing DNAs that encode these antibody fragments or low-molecular-weight antibodies, inserting them into expression vectors, and then expressing them in appropriate host cells (see, for example, Co, M. S. et Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

FcRn

Unlike Fcγ receptor belonging to the immunoglobulin superfamily, human FcRn is structurally similar to polypeptides of major histocompatibility complex (WIC) class I, exhibiting 22% to 29% sequence identity to class I MHC molecules (Ghetie el a1., Immunol. Today (1997) 18 (12): 592-598). FcRn is expressed as a heterodimer consisting of soluble (3 or light chain ((32 microglobulin) complexed with transmembrane a or heavy chain. Like WIC, FcRn a chain comprises three extracellular domains (a1, a2, and a3) and its short cytoplasmic domain anchors the protein onto the cell surface. a1 and a2 domains interact with the FcRn-binding domain of the antibody Fc region (Raghavan et al., Immunity (1994) 1: 303-315).

FcRn is expressed in maternal placenta and yolk sac of mammals, and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG. Typically, binding of FcRn to IgG molecules is strictly pH dependent. The optimal binding is observed in an acidic pH range below 7.0.

Human FcRn whose precursor is a polypeptide having the signal sequence of SEQ ID NO: 28 (the polypeptide with the signal sequence is shown in SEQ ID NO: 29) forms a complex with human β2-microglobulin in vivo. Soluble human FcRn complexed with β2-microglobulin is produced by using conventional recombinant expression techniques.

Fc regions of the present invention can be assessed for their binding activity to such a soluble human FcRn complexed with β2-microglobulin. Herein, unless otherwise specified, human FcRn refers to a form capable of binding to an Fc region of the present invention. Examples include a complex between human FcRn and human β2-microglobulin.

Embodiments of combining the present invention with techniques for modifying the constant region are, for example, combinations with antibody modification techniques such as Fc-modifying techniques to enhance FcRn binding at acidic pH (WO2002060919, WO2004035752, and WO2000042072), Fc-modifying techniques to enhance FcRn binding at neutral pH (WO2011122011 and WO2012133782), techniques for enhancing inhibitory Fcγ receptor-selective binding (WO2012115241 and WO2013125667), techniques for enhancing activating Fcγ receptor-selective binding (techniques for enhancing ADCC activity) (WO2013002362), and techniques for lowering the binding activity to a Rheumatoid factor (WO2013046704).

A non-limiting embodiment of a combination of the present invention with techniques for modifying the variable region includes, for example, combinations with techniques for modifying pH-dependent antibodies (WO2009125825), calcium-dependent antibodies (WO2012073992), and such.

Heterocomplex Comprising the Four Molecules Including Two Molecules of FcRn and One Molecule of Activating Fcγ Receptor Crystallographic studies on FcRn with IgG antibodies demonstrated that an FcRn-IgG complex is composed of one molecule of IgG for two molecules of FcRn, and the two molecules are thought to bind around the interface of the CH2 and CH3 domains located on both sides of the IgG Fc region (Burmeister et al. (Nature (1994) 372, 336-343)). Meanwhile, as demonstrated in Example 3 of PCT/JP2012/058603, the antibody Fc region was demonstrated to be able to form a complex comprising the four molecules including two molecules of FcRn and one molecule of activating Fcγ receptor (PCT/JP2012/058603). This heterocomplex formation is a phenomenon which was revealed as a result of analyzing the properties of antigen-binding molecules containing an Fc region having an FcRn-binding activity under a neutral pH range condition.

While the present invention is not bound to a particular principle, it can be considered that antigen-binding molecules administered in vivo produce the effects described below on the in vivo pharmacokinetics (plasma retention) of the antigen-binding molecules and an immune response (immunogenicity) to the administered antigen-binding molecules, as a result of the formation of heterocomplexes containing the four molecules including the Fc region contained in the antigen-binding molecules, two molecules of FcRn, and one molecule of activating Fcγ receptor. In addition to the various types of activating Fcγ receptors, FcRn is expressed on immune cells. It is suggested that the formation of such tetrameric complexes on immune cells by antigen-binding molecules promotes incorporation of antigen-binding molecules into immune cells by increasing affinity toward immune cells and by causing association of intracellular domains to enhance the internalization signal. The same also applies to antigen-presenting cells and the possibility that antigen binding-molecules are likely to be incorporated into antigen-presenting cells by formation of tetrameric complexes on the cell membrane of antigen-presenting cells. In general, antigen-binding molecules incorporated into antigen-presenting cells are degraded in the lysosomes of the antigen-presenting cells and are presented to T cells. As a result, plasma retention of antigen-binding molecules may be worsened because incorporation of antigen-binding molecules into antigen-presenting cells is promoted by the formation of the above-described tetrameric complexes on the cell membrane of the antigen-presenting cells. Similarly, an immune response may be induced (aggravated).

For this reason, it is conceivable that when an antigen-binding molecule having lowered ability to form such tetrameric complexes is administered in vivo, plasma retention of the antigen-binding molecules would improve, and induction of in vivo immune response would be suppressed. Preferred embodiments of such antigen-binding molecules which inhibit the formation of these complexes on immune cells including antigen-presenting cells are, for example, the three embodiments described below.

Antigen-Binding Molecules which Inhibit the Formation of Heterocomplexes (Embodiment 1) an Antigen-Binding Molecule Containing an Fc Region Having FcRn-Binding Activity Under a Neutral pH Range Condition and Whose Binding Activity Toward Activating FcγR is Lower than the Binding Activity of a Native Fc Region Toward Activating FcγR The antigen-binding molecule of Embodiment 1 forms a trimeric complex by binding to two molecules of FcRn; however, it does not form any complex containing activating FcγR. An Fc region whose binding activity toward activating FcγR is lower than the binding activity of a native Fc region toward activating FcγR can be prepared by altering the amino acids of the native Fc region as described above. Whether the binding activity toward activating FcγR of the altered Fc region is lower than the binding activity toward activating FcγR of the native Fc region can be appropriately tested using the methods described in the section "Binding Activity" above.

Preferred activating Fcγ receptors include FcγRI (CD64) which includes FcγRIa, FcγRIb, and FcγRIc; FcγRIIa (including allotypes R131 and H131); and FcγRIII (CD16) which includes isoforms FcγRIIIa (including allotypes V158 and F158) and FcγRIIIb (including allotypes FcγRIIIb-NA1 and FcγRIIIb-NA2).

Herein, "a binding activity of the Fc region variant toward an activating Fcγ receptor is lower than the binding activity of the native Fc region toward an activating Fcγ receptor" means that the binding activity of the Fc region variant toward any of the human Fcγ receptors (FcγRI, FcγRIIa, FcγRIIIa, and/or FcγRIIIb) is lower than the binding activity of the native Fc region toward these human Fcγ receptors. For example, it means that based on an above-described analytical method, the binding activity of the antigen-binding molecule containing an Fc region variant as compared to the binding activity of an antigen-binding molecule containing a native Fc region as a control is 95% or less, preferably 90% or less, 85% or less, 80% or less, 75% or less, and particularly preferably 70% or less, 65% or less, 60% or less, 55% or less, 50% or less, 45% or less, 40% or less, 35% or less, 30% or less, 25% or less, 20% or less, 15% or less, 10% or less, 9% or less, 8% or less, 7% or less, 6% or less, 5% or less, 4% or less, 3% or less, 2% or less, or 1% or less. As a native Fc region, a starting Fc region may be used, and Fc regions of wild-type antibodies of different isotypes may also be used.

Meanwhile, the binding activity of the native form toward an activating FcγR is preferably a binding activity toward the Fcγ receptor for human IgG1. Other than performing the above-described alterations, binding activity toward the Fcγ receptor can be lowered by changing the isotype to human IgG2, human IgG3, or human IgG4. Alternatively, besides by performing the above-described alterations, the binding activity toward an Fcγ receptor can also be lowered by expressing the antigen-binding molecule containing an Fc region having a binding activity toward the Fcγ receptor in hosts that do not add sugar chains such as *Escherichia coli*.

For the antigen-binding molecule containing a control Fc region, an antigen-binding molecule having an Fc region of a monoclonal IgG antibody may be appropriately used. The structures of such Fc regions are shown in SEQ ID NO: 5 (A is added to the N terminus of RefSeq Accession No. AAC82527.1), SEQ ID NO: 6 (A is added to the N terminus of RefSeq Accession No. AAB59393.1), SEQ ID NO: 7 (RefSeq Accession No. CAA27268.1), and SEQ ID NO: 8 (A is added to the N terminus of RefSeq Accession No. AAB59394.1). Further, when an antigen-binding molecule containing an Fc region of a particular antibody isotype is used as the test substance, effect on the binding activity of the antigen-binding molecule containing the Fc region toward an Fcγ receptor is tested by using the antigen-binding molecule having an Fc region of a monoclonal IgG antibody of a particular isotype as a control. In this way, antigen-binding molecules containing an Fc region whose binding activity toward the Fcγ receptor was demonstrated to be high are suitably selected.

In a non-limiting embodiment of the present invention, preferred examples of Fc regions whose binding activity toward an activating FcγR is lower than the binding activity of the native Fc region toward an activating FcγR include Fc regions with alteration of one or more amino acids at any of positions 234, 235, 236, 237, 238, 239, 270, 297, 298, 325, 328, and 329 as indicated by EU numbering in the amino acids of an above-described Fc region to be different from those of the native Fc region. The alterations in the Fc region are not limited to the above example, and they may be, for example, modifications such as deglycosylation (N297A and N297Q), IgG1-L234A/L235A, IgG1-A325A/A330S/P331S, IgG1-C226S/C229S, IgG1-C226S/C229S/E233P/L234V/L235A, IgG1-L234F/L235E/P331S, IgG1-S267E/L328F, IgG2-V234A/G237A, IgG2-H268Q/V309L/A330S/A331S, IgG4-L235A/G237A/E318A, and IgG4-L236E described in Cur. Opin. in Biotech. (2009) 20 (6), 685-691; alterations such as G236R/L328R, L235G/G236R, N325A/L328R, and N325L/L328R described in WO 2008/092117; amino acid insertions at positions 233, 234, 235, and 237 according to EU numbering; and alterations at the positions described in WO 2000/042072.

In a non-limiting embodiment of the present invention, examples of a preferred Fc region include Fc regions having one or more of the following alterations as indicated by EU numbering in an aforementioned Fc region:

Ala, Arg, Asn, Asp, Gln, Glu, Gly, His, Lys, Met, Phe, Pro, Ser, Thr, or Trp for the amino acid at position 234;

Ala, Asn, Asp, Gln, Glu, Gly, His, Ile, Lys, Met, Pro, Ser, Thr, Val, or Arg for the amino acid at position 235;

Arg, Asn, Gln, His, Leu, Lys, Met, Phe, Pro, or Tyr for the amino acid at position 236;

Ala, Asn, Asp, Gln, Glu, His, Ile, Leu, Lys, Met, Pro, Ser, Thr, Val, Tyr, or Arg for the amino acid at position 237;

Ala, Asn, Gln, Glu, Gly, His, Ile, Lys, Thr, Trp, or Arg for the amino acid at position 238;

Gln, His, Lys, Phe, Pro, Trp, Tyr, or Arg for the amino acid at position 239;

Ala, Arg, Asn, Gln, Gly, His, Ile, Leu, Lys, Met, Phe, Ser, Thr, Trp, Tyr, or Val for the amino acid at position 265;

Ala, Arg, Asn, Asp, Gln, Glu, Gly, His, Lys, Phe, Pro, Ser, Thr, Trp, or Tyr for the amino acid at position 266;

Arg, His, Lys, Phe, Pro, Trp, or Tyr for the amino acid at position 267;

Ala, Arg, Asn, Gln, Gly, His, Ile, Leu, Lys, Met, Phe, Pro, Ser, Thr, Trp, Tyr, or Val for the amino acid at position 269;

Ala, Arg, Asn, Gln, Gly, His, Ile, Leu, Lys, Met, Phe, Pro, Ser, Thr, Trp, Tyr, or Val for the amino acid at position 270;

Arg, His, Phe, Ser, Thr, Trp, or Tyr for the amino acid at position 271;

Arg, Asn, Asp, Gly, His, Phe, Ser, Trp, or Tyr for the amino acid at position 295;

Arg, Gly, Lys, or Pro for the amino acid at position 296;

Ala for the amino acid at position 297;

Arg, Gly, Lys, Pro, Trp, or Tyr for the amino acid at position 298;

Arg, Lys, or Pro for the amino acid at position 300;

Lys or Pro for the amino acid at position 324;

Ala, Arg, Gly, His, Ile, Lys, Phe, Pro, Thr, Trp, Tyr, or Val for the amino acid at position 325;

Arg, Gln, His, Ile, Leu, Lys, Met, Phe, Pro, Ser, Thr, Trp, Tyr, or Val for the amino acid at position 327;

Arg, Asn, Gly, His, Lys, or Pro for the amino acid at position 328;

Asn, Asp, Gln, Glu, Gly, His, Ile, Leu, Lys, Met, Phe, Ser, Thr, Trp, Tyr, Val, or Arg for the amino acid at position 329;

Pro or Ser for the amino acid at position 330;

Arg, Gly, or Lys for the amino acid at position 331; or

Arg, Lys, or Pro for the amino acid at position 332.

(Embodiment 2) an Antigen-Binding Molecule Containing an Fc Region Having FcRn-Binding Activity Under a Neutral pH Range Condition and Whose Binding Activity Toward an Inhibitory FcγR is Higher than the Binding Activity Toward an Activating Fcγ Receptor By binding to two molecules of FcRn and one molecule of inhibitory FcγR, the antigen-binding molecule of Embodiment 2 can form a complex comprising these four molecules. However, since a single antigen-binding molecule can bind with only one molecule of FcγR, the single antigen-binding molecule in a state bound to an inhibitory FcγR cannot bind to other activating FcγRs. Furthermore, it has been reported that an antigen-binding molecule that is incorporated into cells in a state bound to an inhibitory FcγR is recycled onto the cell membrane, and thus escapes from degradation inside the cells (Immunity (2005) 23, 503-514). More specifically, it is considered that antigen-binding molecules having selective binding activity toward an inhibitory FcγR cannot form heterocomplexes containing an activating FcγR and two molecules of FcRn, which cause an immune response.

Preferred activating Fcγ receptors include FcγRI (CD64) which includes FcγRIa, FcγRIb, and FcγRIc; FcγRIIa (including allotypes R131 and H131); and FcγRIII (CD16) which includes isoforms FcγRIIIa (including allotypes V158 and F158) and FcγRIIIb (including allotypes FcγRIIIb-NA1 and FcγRIIIb-NA2). Meanwhile, examples of preferred inhibitory Fcγ receptors include FcγRIIb (including FcγRIIb-1 and FcγRIIb-2).

Herein, "a binding activity toward an inhibitory FcγR is higher than the binding activity toward an activating Fcγ receptor" means that the binding activity of the Fc region variant toward FcγRIIb is higher than the binding activity toward any of the human Fcγ receptors, FcγRI, FcγRIIa, FcγRIIIa, and/or FcγRIIIb. For example, it means that based on an above-described analytical method, the binding activity toward FcγRIIb of the antigen-binding molecule containing an Fc region variant as compared with the binding activity toward any of the human Fcγ receptors, FcγRI, FcγRIIa, FcγRIIIa, and/or FcγRIIIb is 105% or more, preferably 110% or more, 120% or more, 130% or more, 140% or more, and particularly preferably 150% or more, 160% or more, 170% or more, 180% or more, 190% or more, 200% or more, 250% or more, 300% or more, 350% or more, 400% or more, 450% or more, 500% or more, 750% or more, 10 times or more, 20 times or more, 30 times or more, 40 times or more, 50 times or more.

Most preferably, the binding activity toward FcγRIIb is higher than each of the binding activities toward FcγRIa, FcγRIIa (including allotypes R131 and H131), and FcγRIIIa (including allotypes V158 and F158). FcγRIa shows a markedly high affinity toward native IgG1; thus, the binding is thought to be saturated in vivo due to the presence of a large amount of endogenous IgG1. For this reason, inhibition of complex formation may be possible even if the binding activity toward FcγRIIb is greater than the binding activities toward FcγRIIa and FcγRIIIa, and lower than the binding activity toward FcγRIa.

As a control antigen-binding molecule containing an Fc region, antigen-binding molecules having an Fc region of a monoclonal IgG antibody may be appropriately used. The structures of such Fc regions are shown in SEQ ID NO: 5 (A is added to the N terminus of RefSeq Accession No. AAC82527.1), SEQ ID NO: 6 (A is added to the N terminus of RefSeq Accession No. AAB59393.1), SEQ ID NO: 7 (RefSeq Accession No. CAA27268.1), and SEQ ID NO: 8 (A is added to the N terminus of RefSeq Accession No. AAB59394.1). Further, when an antigen-binding molecule containing an Fc region of a particular antibody isotype is used as the test substance, effect on the binding activity of the Fc region-containing antigen-binding molecule toward an Fcγ receptor is tested by using an antigen-binding molecule having the Fc region of a monoclonal IgG antibody of a particular isotype as a control. In this way, antigen-binding molecules containing an Fc region whose binding activity toward the Fcγ receptor was demonstrated to be high are appropriately selected.

In a non-limiting embodiment of the present invention, preferred examples of Fc regions having a selective binding activity toward an inhibitory FcγR include Fc regions in which among the amino acids of an above-described Fc region, the amino acid at 238 or 328 as indicated by EU numbering is altered to an amino acid different from that of the native Fc region. Furthermore, as an Fc region having a selective binding activity toward an inhibitory Fcγ receptor, the Fc regions or alterations described in US 2009/0136485 can be appropriately selected.

In a non-limiting embodiment of the present invention, a preferred example is an Fc region having one or more of the following alterations as indicated by EU numbering in an aforementioned Fc region: the amino acid at position 238 is Asp; or the amino acid at position 328 is Glu.

In still another non-limiting embodiment of the present invention, examples of a preferred Fc region include Fc regions having a substitution of Pro at position 238 according to EU numbering with Asp and having one or more of the alterations:
alteration of the amino acid at position 237 according to EU numbering to Trp, the amino acid at position 237 according to EU numbering is Phe, the amino acid at position 267 according to EU numbering is Val, the amino acid at position 267 according to EU numbering is Gln, the amino acid at position 268 according to EU numbering is Asn, the amino acid at position 271 according to EU numbering is Gly, the amino acid at position 326 according to EU numbering is Leu, the amino acid at position 326 according to EU numbering is Gln, the amino acid at position 326 according to EU numbering is Glu, the amino acid at position 326 according to EU numbering is Met, the amino acid at position 239 according to EU numbering is Asp, the amino acid at position 267 according to EU numbering is Ala, the amino acid at position 234 according to EU numbering is Trp, the amino acid at position 234 according to EU numbering is Tyr, the amino acid at position 237 according to EU numbering is Ala, the amino acid at position 237 according to EU numbering is Asp, the amino acid at position 237 according to EU numbering is Glu, the amino acid at position 237 according to EU numbering is Leu, the amino acid at position 237 according to EU numbering is Met, the amino acid at position 237 according to EU numbering is Tyr, the amino acid at position 330 according to EU numbering is Lys, the amino acid at position 330 according to EU numbering is Arg, the amino acid at position 233 according to EU numbering is Asp, the amino acid at position 268 according to EU numbering is Asp, the amino acid at position 268 according to EU numbering is Glu, the amino acid at position 326 according to EU numbering is Asp, the amino acid at position 326 according to EU numbering is Ser, the amino acid at position 326 according to EU numbering is Thr, the amino acid at position 323 according to EU numbering is Ile, the amino acid at position 323 according to EU numbering is Leu, the amino acid at position 323 according to EU numbering is Met, the amino acid at position 296 according to EU numbering is Asp, the amino acid at position 326 according to EU numbering is Ala, the amino acid at position 326 according to EU numbering is Asn, and the amino acid at position 330 according to EU numbering is Met.

(Embodiment 3) an Antigen-Binding Molecule Containing an Fc Region, in which One of the Two Polypeptides Constituting the Fc Region has an FcRn-Binding Activity Under a Neutral pH Range Condition and the Other Polypeptide does not have FcRn-Binding Activity Under a Neutral pH Range Condition By binding to one molecule of FcRn and one molecule of FcγR, the antigen-binding molecule of Embodiment 3 can form a trimeric complex; however, it does not form any heterocomplex comprising four molecules including two molecules of FcRn and one molecule of FcγR. As an Fc region in which one of the two polypeptides constituting the Fc region has an FcRn-binding activity under a neutral pH range condition and the other does not have any FcRn-binding activity under a neutral pH range condition contained in the antigen-binding molecule of Embodiment 3, Fc regions derived from bispecific antibodies may be suitably used. Bispecific antibodies are two types of antibodies having specificities toward different antigens. Bispecific antibodies of an IgG type can be secreted from hybrid hybridomas (quadromas) resulting from fusion of two types of hybridomas producing IgG antibodies (Milstein et al. (Nature (1983) 305, 537-540)).

When an antigen-binding molecule of Embodiment 3 described above is produced by using recombination techniques such as those described in the section "Antibodies" above, one can use a method in which genes encoding the polypeptides that constitute the two types of Fc regions of interest are transfected into cells to co-express them. However, the produced Fc regions will be a mixture in which the following will exist at a molecular ratio of 2:1:1: an Fc region in which one of the two polypeptides constituting the Fc region has an FcRn-binding activity under a neutral pH range condition and the other polypeptide does not have any FcRn-binding activity under a neutral pH range condition; an Fc region in which the two polypeptides constituting the Fc region both have an FcRn-binding activity under a neutral pH range condition; and an Fc region in which both of the two polypeptides constituting the Fc region do not have FcRn-binding activity under a neutral pH range condition. It is difficult to purify antigen-binding molecules containing the desired combination of Fc regions from the three types of IgGs.

When producing the antigen-binding molecules of Embodiment 3 using such recombination techniques, antigen-binding molecules comprising a heteromeric combination of Fc regions can be preferentially secreted by adding appropriate amino acid substitutions to the CH3 domains constituting the Fc regions. Specifically, this method is conducted by substituting an amino acid having a larger side chain (knob (which means "bulge")) for an amino acid in the CH3 domain of one of the heavy chains, and substituting an amino acid having a smaller side chain (hole (which means "void")) for an amino acid in the CH3 domain of the other heavy chain so that the knob is arranged in the hole. This promotes heteromeric H chain formation and simultaneously inhibits homomeric H chain formation (WO 1996027011; Ridgway et al., (Protein Engineering (1996) 9, 617-621); Merchant et al., (Nature Biotechnology (1998) 16, 677-681)).

Furthermore, there are also known techniques for producing a bispecific antibody by applying methods for controlling polypeptide association or association of polypeptide-formed heteromeric multimers to the association between two polypeptides that constitute an Fc region. Specifically, methods for controlling polypeptide association may be employed to produce a bispecific antibody (WO 2006/106905), in which amino acid residues forming the interface between two polypeptides that constitute the Fc region are altered to inhibit the association between Fc regions having the same sequence, and to allow the formation of polypeptide complexes formed by two Fc regions of different sequences. Specifically, the methods in the above-described section on bispecific antibodies and methods for producing them can be used as a non-limiting embodiment for preparing the antigen-binding molecule of Embodiment 3 of the present invention.

These antigen-binding molecules of Embodiments 1 to 3 are all expected to be able to reduce immunogenicity and improve plasma retention as compared to antigen-binding molecules capable of forming tetrameric complexes.

Methods for Producing Antigen-Binding Domains

The present invention provides methods for producing antigen-binding domains whose antigen-binding activity in the presence of a small molecule compound is higher than the antigen-binding activity in the absence of the compound.

More specifically, the present invention provides a method for producing an antigen-binding domain, which comprises steps (a) to (e) below:
(a) determining the antigen-binding activity of an antigen-binding domain in the absence of a small molecule compound;
(b) determining the antigen-binding activity of an antigen-binding domain in the presence of the small molecule compound;
(c) selecting an antigen-binding domain whose antigen-binding activity in the absence of a small molecule compound is lower than in the presence of the compound;
(d) culturing cells transfected with a vector to which a polynucleotide encoding the antigen-binding domain selected in (c) is operably linked; and
(e) collecting an antigen-binding domain from a culture medium of the cells cultured in (d).

The present invention also provides a method for producing an antigen-binding domain, which comprises steps (a) to (e) below:
(a) determining the antigen-binding activity of an antigen-binding domain in the presence of a low concentration of a small molecule compound;
(b) determining the antigen-binding activity of an antigen-binding domain in the presence of a high concentration of the small molecule compound;
(c) selecting an antigen-binding domain whose antigen-binding activity in the presence of a low concentration of the small molecule compound is lower than in the presence of a high concentration of the compound;
(d) culturing cells transfected with a vector to which a polynucleotide encoding the antigen-binding domain selected in (c) is operably linked; and
(e) collecting an antigen-binding domain from a culture medium of the cells cultured in (d).

Furthermore, the present invention provides a method for producing an antigen-binding domain, which comprises steps (a) to (e) below:
(a) contacting antigen-binding domains or a library thereof with an antigen in the presence of a small molecule compound;
(b) placing the antigen-binding domains that bound to the antigen in said step (a) in the absence of the compound;
(c) isolating an antigen-binding domain that was dissociated in said step (b);
(d) culturing cells transfected with a vector to which a polynucleotide encoding the antigen-binding domain selected in (c) is operably linked; and
(e) collecting an antigen-binding domain from a culture medium of the cells cultured in (d).

In addition, the present invention provides a method for producing an antigen-binding domain, which comprises steps (a) to (e) below:
(a) contacting antigen-binding domains or a library thereof to an antigen in the presence of a high concentration of a small molecule compound;
(b) placing the antigen-binding domains that bind to the antigen in said step (a) in the presence of a low concentration of the compound;
(c) isolating an antigen-binding domain that dissociates in said step (b);
(d) culturing cells transfected with a vector to which a polynucleotide encoding the antigen-binding domain selected in (c) is operably linked; and
(e) collecting an antigen-binding domain from a culture medium of the cells cultured in (d).

The present invention provides a method for producing an antigen-binding domain, which comprises steps of (a) to (f) below:
(a) contacting a library of antigen-binding domains with an antigen in the absence of a small molecule compound;
(b) selecting antigen-binding domains that do not bind to the antigen in said step (a);
(c) allowing the antigen-binding domains selected in said step (b) to bind to the antigen in the presence of the compound;
(d) isolating an antigen-binding domain that bind to the antigen in said step (c);
(e) culturing cells transfected with a vector to which a polynucleotide encoding the antigen-binding domain selected in (d) is operably linked; and
(f) collecting an antigen-binding domain from a culture medium of the cells cultured in (e).

The present invention provides a method for producing an antigen-binding domain, which comprises steps (a) to (f) below:
(a) contacting a library of antigen-binding domains with an antigen in the presence of a low concentration of a small molecule compound;
(b) selecting antigen-binding domains that do not bind to the antigen in said step (a);
(c) allowing the antigen-binding domains selected in said step (b) to bind to the antigen in the presence of a high concentration of the compound;
(d) isolating an antigen-binding domain that bind to the antigen in said step (c);
(e) culturing cells transfected with a vector to which a polynucleotide encoding the antigen-binding domain selected in (d) is operably linked; and
(f) collecting an antigen-binding domain from a culture medium of the cells cultured in (e).

The present invention provides a method for producing an antigen-binding domain, which comprises steps (a) to (e) below:
(a) contacting a library of antigen-binding domains with an antigen-immobilized column in the presence of a small molecule compound;
(b) eluting antigen-binding domains that bind to the column in said step (a) from the column in the absence of the compound;
(c) isolating the antigen-binding domain eluted in said step (b);
(d) culturing cells transfected with a vector to which a polynucleotide encoding the antigen-binding domain selected in (c) is operably linked; and
(e) collecting an antigen-binding domain from a culture medium of the cells cultured in (d).

The present invention provides a method for producing an antigen-binding domain, which comprises steps (a) to (e) below:
(a) contacting a library of antigen-binding domains with an antigen-immobilized column in the presence of a high concentration of a small molecule compound;
(b) eluting antigen-binding domains that bind to the column in said step (a) from the column in the presence of a low concentration of the compound;
(c) isolating an antigen-binding domain eluted in said step (b);
(d) culturing cells transfected with a vector to which a polynucleotide encoding the antigen-binding domain selected in (c) is operably linked; and (e) collecting an antigen-binding domain from a culture medium of the cells cultured in (d).

The present invention provides a method for producing an antigen-binding domain, which comprises steps (a) to (f) below:
  (a) allowing a library of antigen-binding domains to pass through an antigen-immobilized column in the absence of a small molecule compound;
  (b) collecting antigen-binding domains that are eluted without binding to the column in step (a);
  (c) allowing the antigen-binding domains collected in step (b) to bind to the antigen in the presence of the compound;
  (d) isolating an antigen-binding domain that bind to the antigen in step (c);
  (e) culturing cells transfected with a vector to which a polynucleotide encoding the antigen-binding domain selected in (d) is operably linked; and
  (f) collecting an antigen-binding domain from a culture medium of the cells cultured in (e).

The present invention provides a method for producing an antigen-binding domain, which comprises steps (a) to (f) below:
  (a) allowing a library of antigen-binding domains to pass through an antigen-immobilized column in the presence of a low concentration of a small molecule compound;
  (b) collecting antigen-binding domains that are eluted without binding to the column in said step (a);
  (c) allowing the antigen-binding domains collected in said step (b) to bind to the antigen in the presence of a high concentration of the compound;
  (d) isolating an antigen-binding domain that binds to the antigen in said step (c);
  (e) culturing cells transfected with a vector to which a polynucleotide encoding the antigen-binding domain selected in (d) is operably linked; and
  (f) collecting an antigen-binding domain from a culture medium of the cells cultured in (e).

Furthermore, the present invention provides a method for producing an antigen-binding domain, which comprises steps (a) to (f) below:
  (a) contacting an antigen with a library of antigen-binding domains in the presence of a small molecule compound;
  (b) obtaining antigen-binding domains that bind to the antigen in step (a);
  (c) placing the antigen-binding domain obtained in step (b) in the absence of the compound;
  (d) isolating an antigen-binding domain whose antigen-binding activity in step (c) is weaker than the reference selected in step (b);
  (e) culturing cells transfected with a vector to which a polynucleotide encoding the antigen-binding domain selected in (d) is operably linked; and
  (f) collecting an antigen-binding domain from a culture medium of the cells cultured in (e).

The present invention provides a method for producing an antigen-binding domain, which comprises steps (a) to (f) below:
  (a) contacting an antigen with a library of antigen-binding domains in the presence of a high concentration of a small molecule compound;
  (b) obtaining antigen-binding domains that bind to the antigen in step (a);
  (c) placing the antigen-binding domains obtained in step (b) in the presence of a low concentration of the compound;
  (d) isolating an antigen-binding domain whose antigen-binding activity in step (c) is weaker than the reference selected in step (b);
  (e) culturing cells transfected with a vector to which a polynucleotide encoding the antigen-binding domain selected in (d) is operably linked; and
  (f) collecting an antigen-binding domain from a culture medium of the cells cultured in (e).

The terms "cells", "cell line", and "cell culture" are used synonymously herein, and such naming may include all progenies of the cells or cell line. This way, for example, the terms "transformant" and "transformed cells" include cultures and primary target cells derived from them regardless of the number of passages. Furthermore, it is understood that due to intentional or accidental mutations, the DNA content is not always exactly the same in all progenies. Progenies of mutants having substantially the same function or biological activity such as those screened for in the initially transformed cells may also be included. When the description is intended to refer to a different naming, that intention may become obvious from the context of the description. Cells that are appropriate for use are suitably selected from cells described in the section "Antibodies" above.

When referring to the expression of a coding sequence, the term "control sequences" refers to DNA nucleotide sequences necessary for the expression of an operably linked coding sequence in a particular host organism. The control sequences that are suitable for prokaryotes include, for example, a promoter, optionally an operator sequence, a ribosome binding site, and possibly, other as yet poorly understood sequences. Eukaryotic cells are known to utilize promoters, polyadenylation signals, and enhancers for the expression of a coding sequence.

For a nucleic acid, the term "operably linked" means that the nucleic acid is placed into a functional relationship with another nucleic acid sequence. For example, DNA for a presequence or secretory leader is operably linked to DNA for a polypeptide if it is expressed as a precursor protein that participates in the secretion of the polypeptide. A promoter or enhancer is operably linked to a coding sequence if it affects the transcription of the sequence. A ribosome binding site is operably linked to a coding sequence if it is positioned so as to facilitate translation. Generally, "operably linked" means that the DNA sequences being linked are contiguous and, in the case of a secretory leader, contiguous and in reading frame. However, enhancers do not have to be contiguous. Linking is accomplished by ligation at suitable restriction sites. If such sites do not exist, the synthetic oligonucleotide adaptors or linkers are used in accordance with conventional practice. Furthermore, linked nucleic acids may be produced by the above-mentioned overlap extension PCR technique.

"Ligation" refers to the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates.

The DNA is then purified by phenol-chloroform extraction and ethanol precipitation, or by silica purification. The DNA fragments that are to be ligated together are put in solution in equimolar amounts. The solution will contain ATP, ligase buffer, and a ligase such as T4 DNA ligase at about 10 units per 0.5 μg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation of the fragment during the ligation step.

In the production methods of the present invention, an antigen-binding domain which has a higher antigen-binding activity in the presence of a small molecule compound than in its absence, which has been selected by the method described in the above section "Antigen-binding domain dependent on a small molecule compound" is isolated. For example, when an antigen-binding domain isolated in this manner has been selected from a library, the polynucleotide encoding the antigen-binding domain is isolated by general gene amplification from a virus such as a phage, as described in the Examples below. Furthermore, when an antigen-binding domain or an antibody isolated in this manner has been selected from culture media of cells such as hybridomas, the antibody gene or such can be isolated by general gene amplification from the cells as shown in the section "Antibodies" above.

Methods for Producing Antigen-Binding Molecules

The present invention provides methods for producing antigen-binding molecules whose antigen-binding activity in the presence of a small molecule compound is higher than the antigen-binding activity in the absence of the compound.

More specifically, the present invention provides a method for producing antigen-binding molecules, which comprises the steps of:
(a) determining the antigen-binding activity of an antigen-binding domain in the absence of a small molecule compound;
(b) determining the antigen-binding activity of the antigen-binding domain in the presence of the small molecule compound;
(c) selecting an antigen-binding domain with lower antigen-binding activity in the absence of the small molecule compound than in the presence of the compound;
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting antigen-binding molecules from a culture medium of the cells cultured in (e).

The present invention also provides a method for producing an antigen-binding molecule, which comprises the steps of:
(a) determining the antigen-binding activity of an antigen-binding domain in the presence of a low concentration of a small molecule compound;
(b) determining the antigen-binding activity of the antigen-binding domain in the presence of a high concentration of the small molecule compound;
(c) selecting an antigen-binding domain with lower antigen-binding activity in the presence of a low concentration of the small molecule compound than in the presence of a high concentration of the compound;
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting antigen-binding molecules from a culture medium of the cells cultured in (e).

Furthermore, the present invention provides a method for producing an antigen-binding molecule, which comprises the steps of:
(a) contacting antigen-binding domains or a library thereof with an antigen in the presence of a small molecule compound;
(b) placing the antigen-binding domains that bind to the antigen in said step (a) in the absence of the compound;
(c) isolating an antigen-binding domain that dissociates in said step (b);
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting an antigen-binding molecule from a culture medium of the cells cultured in (e).

In addition, the present invention provides a method for producing an antigen-binding molecule, which comprises the steps of:
(a) contacting antigen-binding domains or a library thereof with an antigen in the presence of a high concentration of a small molecule compound;
(b) placing the antigen-binding domains that bind to the antigen in said step (a) in the presence of a low concentration of the compound;
(c) isolating an antigen-binding domain that dissociates in said step (b);
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting antigen-binding molecules from a culture medium of the cells cultured in (e).

The present invention provides a method for producing an antigen-binding molecule, which comprises the steps of:
(a) contacting a library of antigen-binding domains with an antigen in the absence of a small molecule compound;
(b) selecting antigen-binding domains that do not bind to the antigen in said step (a);
(c) allowing the antigen-binding domains selected in said step (b) to bind to the antigen in the presence of the compound;
(d) isolating an antigen-binding domain that binds to the antigen in said step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:
(a) contacting a library of antigen-binding domains with an antigen in the presence of a low concentration of a small molecule compound;
(b) selecting antigen-binding domains that do not bind to the antigen in said step (a);

(c) allowing the antigen-binding domains selected in said step (b) to bind to the antigen in the presence of a high concentration of the compound;
(d) isolating an antigen-binding domain that binds to the antigen in said step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:
(a) contacting a library of antigen-binding domains with an antigen-immobilized column in the presence of a small molecule compound;
(b) eluting antigen-binding domains that bind to the column in said step (a) from the column in the absence of the compound;
(c) isolating an antigen-binding domain eluted in said step (b);
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting antigen-binding molecules from a culture medium of the cells cultured in (e).

The present invention provides a method for producing an antigen-binding molecule, which comprises the steps of:
(a) contacting a library of antigen-binding domains with an antigen-immobilized column in the presence of a high concentration of a small molecule compound;
(b) eluting antigen-binding domains that bind to the column in said step (a) from the column in the presence of a low concentration of the compound;
(c) isolating an antigen-binding domain eluted in said step (b);
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting antigen-binding molecules from a culture medium of the cells cultured in (e).

The present invention provides a method for producing an antigen-binding molecule, which comprises the steps of:
(a) allowing a library of antigen-binding domains to pass through an antigen-immobilized column in the absence of a small molecule compound;
(b) collecting antigen-binding domains that are eluted without binding to the column in said step (a);
(c) allowing the antigen-binding domains collected in step (b) to bind to the antigen in the presence of the compound;
(d) isolating an antigen-binding domain that binds to the antigen in step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:
(a) allowing a library of antigen-binding domains to pass through an antigen-immobilized column in the presence of a low concentration of a small molecule compound;
(b) collecting antigen-binding domains that are eluted without binding to the column in said step (a);
(c) allowing the antigen-binding domains collected in said step (b) to bind to the antigen in the presence of a high concentration of the compound;
(d) isolating an antigen-binding domain that binds to the antigen in said step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

Furthermore, the present invention provides a method for producing an antigen-binding molecule, which comprises the steps of:
(a) contacting a library of antigen-binding domains with an antigen in the presence of a small molecule compound;
(b) obtaining antigen-binding domains that bind to the antigen in said step (a);
(c) placing the antigen-binding domains obtained in said step (b) in the absence of the compound;
(d) isolating an antigen-binding domain whose antigen-binding activity in said step (c) is weaker than the reference selected in step (b);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:
(a) contacting a library of antigen-binding domains with an antigen in the presence of a high concentration of a small molecule compound;
(b) obtaining antigen-binding domains that bind to the antigen in said step (a);
(c) placing the antigen-binding domains obtained in step (b) in the presence of a low concentration of the compound;
(d) isolating an antigen-binding domain whose antigen-binding activity in step (c) is weaker than the reference selected in step (b);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention also provides a method for producing an antigen-binding molecule that comprises an antigen-binding domain whose antigen-binding activity varies depending on the concentration of a small molecule compound, which comprises the steps of:
(a) contacting a library of the present invention with an antigen in the absence of a small molecule compound;

(b) selecting an antigen-binding domain that does not bind to the antigen in step (a) above;
(c) contacting the antigen-binding domain selected in step (b) above with the antigen in the presence of the small molecule compound;
(d) selecting an antigen-binding domain that binds to the antigen in step (c) above;
(e) linking a polynucleotide encoding the antigen-binding domain selected in step (d) above with a polynucleotide encoding a polypeptide comprising an Fc region;
(f) culturing cells introduced with a vector in which the polynucleotide obtained in step (e) above is operably linked; and
(g) collecting the antigen-binding molecule from the culture solution of cells cultured in step (f) above.

The present invention also provides a method for producing an antigen-binding molecule that comprises an antigen-binding domain whose antigen-binding activity varies depending on the concentration of a small molecule compound, which further comprises in addition to the above-mentioned embodiment the steps of:
(a) contacting a library of the present invention with a small molecule compound; and
(b) selecting an antigen-binding domain collected in step (a) above.

Further, the present invention provides a method for producing an antigen-binding molecule that comprises an antigen-binding domain whose antigen-binding activity varies depending on the concentration of a small molecule compound, which comprises the steps of:
(a) contacting a library of the present invention with an antigen in the presence of a small molecule compound;
(b) collecting an antigen-binding domain by dissociation using a lower concentration of the small molecule compound than in step (a) above;
(c) linking a polynucleotide encoding the antigen-binding domain collected in step (b) above with a polynucleotide encoding a polypeptide comprising an Fc region;
(d) culturing cells introduced with a vector in which the polynucleotide obtained in step (c) above is operably linked; and
(e) collecting an antigen-binding molecule from the culture solution of cells cultured in step (d) above.

The present invention also provides a method for producing an antigen-binding molecule that comprises an antigen-binding domain whose antigen-binding activity varies depending on the concentration of a small molecule compound, which further comprises in addition to the above-mentioned embodiment, the steps of:
(a) contacting a library of the present invention with the small molecule compound; and
(b) selecting an antigen-binding domain collected in step (a) above.

A non-limiting embodiment of the Fc region whose polynucleotide sequence is linked to a polynucleotide encoding an antigen-binding domain is, for example, the Fc region contained in the constant region of a human IgG1 (SEQ ID NO: 5), IgG2 (SEQ ID NO: 6), IgG3 (SEQ ID NO: 7), or IgG4 (SEQ ID NO: 8) antibody. An Fc region is a portion of the heavy chain constant region of an antibody, starting from the N terminal end of the hinge region, which corresponds to the papain cleavage site at an amino acid around position 216 according to EU numbering, and contains the hinge, CH2, and CH3 domains. The Fc region may be obtained from human IgG1, but it is not limited to any particular subclass of IgG.

A non-limiting embodiment of the Fc region whose polynucleotide sequence is linked to a polynucleotide encoding an antigen-binding domain includes, for example, Fc regions whose binding activity toward an activating FcγR is lower than that of the native Fc region toward an activating FcγR. Another non-limiting embodiment of the Fc region preferably includes, for example, Fc regions in which one or more amino acids at positions 234, 235, 236, 237, 238, 239, 270, 297, 298, 325, 328, and 329 according to EU numbering are altered to amino acids that are different from those of the native Fc region of SEQ ID NO: 5, 6, 7, or 8. The alterations in the Fc region are not limited to the above example, and they may be, for example, alterations such as deglycosylation (N297A and N297Q), IgG1-L234A/L235A, IgG1-A325A/A330S/P331S, IgG1-C226S/C229S, IgG1-C226S/C229S/E233P/L234V/L235A, IgG1-L234F/L235E/P331S, IgG1-S267E/L328F, IgG2-V234A/G237A, IgG2-H268Q/V309L/A330S/A331S, IgG4-L235A/G237A/E318A, and IgG4-L236E described in Cur. Opin. in Biotech. (2009) 20 (6), 685-691; alterations such as G236R/L328R, L235G/G236R, N325A/L328R, and N325L/L328R described in WO 2008/092117; amino acid insertions at positions 233, 234, 235, and 237 according to EU numbering; and alterations at the positions described in WO 2000/042072.

When the Fc region contained in the antigen-binding molecule of the present invention is an Fc region that has been modified so that the percentage of the Fc region to which a fucose-deficient sugar chain has been attached, or bisecting N-acetylglucosamine has been attached, will become higher, the above-mentioned transformed host cells that are suitably used are host cells that have low ability to add fucose to a sugar chain as a result of modification of the activity to form the sugar chain structure of a polypeptide to be modified with a sugar chain (for example, WO 2000/061739, WO 2002/031140, and WO 2006/067913). In a non-limiting embodiment of such host cells, host cells deficient in the activity of an enzyme or transporter selected from the group consisting of fucosyltransferase (EC 2.4.1.152), fucose transporter (SLC35C1), GMD (GDP-mannose-4,6-dehydratase) (EC 4.2.1.47), Fx (GDP-keto-6-deoxymannose-3,5-epimerase, 4-reductase) (EC 1.1.1.271), and GFPP (GDP-β-L-fucose pyrophosphorylase (EC 2.7.7.30), may be suitably used (for example, WO 2000/061739, WO 2002/031140, and WO 2006/067913). Host cells deficient in such activity can be produced, for example, by a method that destroys the genes of these functional proteins endogenous to CHO cells, BHK cells, NS0 cells, SP2/0 cells, YO myeloma cells, P3X63 mouse myeloma cells, PER cells, PER.C6 cells, HEK293 cells, hybridoma cells, or such so that they are unable to function.

When the Fc region contained in the antigen-binding molecule of the present invention is an Fc region having a sugar chain containing a bisecting GlcNAc, the above-described transformed cells that are suitably used are host cells expressing a gene encoding a functional protein having GnTIII (β-1,4-mannosyl-glycoprotein 4-β-N-acetylglucosaminyltransferase) (EC2.4.1.144) activity or GalT (β-1, 4-galactosyltransferase) (EC 2.4.1.38) activity to produce antibodies which have bisecting GlcNAc-containing sugar chains (WO2002/079255 and such). In another suitable non-limiting embodiment, host cells that co-express, in addition to the aforementioned functional proteins, a gene encoding a functional protein having human ManII (mannosidase II) (3.2.1.114) activity, a gene encoding a functional protein having GnTI (β-1,2-acetylglucosaminyltransferase I) (EC 2.4.1.94) activity, a gene encoding a functional protein having GnTII (β-1,2-acetylglucosaminyltransferase II) (EC 2.4.1.143) activity, a gene encoding a functional protein having Manl (mannosidase) (EC 3.2.1.113) activity, and a-1,6-fucosyl transferase (EC 2.4.1.68), are suitably used (WO2004/065540).

Antigen-binding molecules of the present invention are produced using methods that follow the methods for producing antibodies, such as isolation from culture media of the above-mentioned cells, which are described in the section "Antibodies" above. A non-limiting embodiment of the aforementioned polypeptides containing an Fc region includes, for example, the antibody constant region of SEQ ID NO: 5, 6, 7, or 8. A non-limiting embodiment of the antigen-binding molecules of the present invention is for example, a full-length antibody molecule.

Pharmaceutical Compositions

The present invention provides pharmaceutical compositions comprising an antigen-binding molecule that does not act systemically in the blood or normal tissues, but acts on lesions such as cancer and inflamed sites, to exhibit drug efficacy while avoiding side effects. The binding of the antigen-binding molecule contained in the pharmaceutical composition of the present invention to target antigen is regulated depending on the concentration of target tissue-specific compounds that are specifically present or produced in a target tissue and/or unnatural compounds that accumulate in the tissue. Thus, for example, when the antigen-binding molecule targets an antigen in a cancer tissue or inflammatory tissue, it binds to an antigen expressed in cancer cells, immune cells, stromal cells, or such in cancer tissues; an antigen secreted in cancer tissues; or an antigen expressed by immune cells or such in inflammatory tissues; and an antigen secreted in inflammatory tissues; and cannot bind to antigens expressed in normal tissues; therefore, side effects due to cytotoxic activity, neutralizing activity, or such against normal tissues are avoided; and at the same time, potent cytotoxic effects, growth suppressing effects, and immunity-enhancing action on cancers, or immunosuppressive effects against inflammatory cells in inflammatory tissues, are exhibited. For example, a bispecific or biparatopic antigen-binding molecule containing an antigen-binding domain that binds to EGFR expressed on cancer cells and an antigen-binding domain that binds to CD3 expressed on T cells in a manner dependent on a cancer tissue-specific compound, does not bind to EGFR expressed on normal tissues but bind to EGFR expressed on cancer cells; thereby exhibiting potent antitumor effects while avoiding side effects. Specifically, while the antigen-binding molecule binds to CD3 expressed on T cells in the vicinity of cancer cells in a manner dependent on a cancer tissue-specific compound, the molecule does not bind to CD3 expressed on T cells that are not in the vicinity of cancer cells. Therefore, the molecule activates T cells in the vicinity of cancer cells, exhibiting potent antitumor effects while avoiding side effects.

Such antigen-binding molecules that bind to an antigen in target tissues but not in other normal tissues and blood exhibit drug efficacy while avoiding side effects. Antigen-binding molecules provided by the present invention, which bind to an antigen by using a small molecule present at high concentrations in target tissues in vivo as a switch, namely, small molecule switch antigen-binding molecules, do not bind to the antigen in a normal environment where the small molecule is not present, but can bind to the antigen in target tissues where the small molecule is present at high concentrations.

A non-limiting embodiment of such small molecule switch antigen-binding molecules includes cancer tissue-specific compound-dependent or inflammatory tissue-specific compound-dependent antigen-binding molecules, in which a cancer tissue-specific or inflammatory tissue-specific compound such as adenosine, adenosine 5'-triphosphate (ATP), inosine, kynurenine, prostaglandin E2 (PGE2), succinic acid, and lactic acid, which are present at a high concentration in cancer tissues or inflammatory tissues and capable of functioning as a switch, provides a switch function by being sandwiched between the antigen-binding molecule of the present invention (the paratope contained therein) and the antigen (the epitope contained therein), or by binding with the antigen-binding molecule of the present invention to thereby change the structure of the paratope of the antigen-binding molecule for the antigen. In the absence of the compound, the interaction between the paratope in the antigen-binding molecule of the present invention and the epitope in the antigen is not sufficient for the antigen-binding molecule of the present invention to be able to bind to the antigen. In the presence of the compound, the compound interposes between the paratope in the antigen-binding molecule of the present invention and the epitope in the antigen, or changes the structure of the paratope; and the antigen-binding molecule that has bound to the antigen in a target tissue such as cancer tissue or inflammatory tissue, where the compound is present at a high concentration, can exhibit drug efficacy on cells expressing the antigen. Moreover, since this binding of the switch compound is reversible, the binding of an antigen-binding molecule of the present invention to an antigen by means of these switch compounds may be controlled in a reversible manner. Thus, antigen-binding molecules of the present invention which can exhibit drug efficacy in a lesion site such as cancer tissue or inflammatory tissue by binding to pathogenic cells such as cancer cells or immune cells in a cancer tissue or inflammatory tissue or by binding to an antigen secreted in a cancer tissue or inflammatory tissue are useful as pharmaceutical compositions. The pharmaceutical compositions of the present invention may comprise a pharmaceutically acceptable carrier.

In the present invention, pharmaceutical compositions generally refer to pharmaceutical agents for treating or preventing, or testing and diagnosing diseases. Furthermore, in the present invention, the phrase "pharmaceutical composition containing an antigen-binding molecule whose antigen-binding activity varies depending on the concentration of a small molecule compound" (in this regard, a small molecule compound includes a target tissue-specific compound, unnatural compound, and such) can be rephrased as "method for treating a disease which comprises administering to a subject to be treated an antigen-binding molecule whose antigen-binding activity varies depending on the concentration of a small molecule compound", or rephrased as "use of an antigen-binding molecule whose antigen-binding activity varies depending on the concentration of a small molecule compound in the production of a pharmaceutical for treating a disease". Furthermore, the phrase "pharmaceutical composition containing an antigen-binding molecule whose antigen-binding activity varies depending on the concentration of a small molecule compound" can be rephrased as "use of an antigen-binding molecule whose antigen-binding activity varies depending on the concentration of a small molecule compound, for treating a disease".

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions can be formulated by mixing in the form of unit dose required in the generally approved medicine manufacturing practice, by appropriately combining with pharmacologically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice. Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80™, HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions in the dosage form for injections, transnasal administration, transpulmonary administration, or transdermal administration are administered. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule can be, for example, from 0.0001 to 1,000 mg/kg for each administration. Alternatively, the dose can be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

Those skilled in the art will naturally understand that any arbitrary combination of one or more of the embodiments described herein are included in the present invention, as long as it is not technically inconsistent with the common general knowledge of those skilled in the art.

All prior art documents cited in this specification are incorporated herein by reference.

Herein below, the present invention will be specifically described with the Examples; however, the present invention should not be limited thereto.

EXAMPLES

[Example 1] Concept of and Strategy for Obtaining Switch Antibodies that Bind to Antigens Using Small Molecules which are Present at High Concentrations in Target Tissues as a Switch (1-1) Concept of Switch Antibodies Whose Antigen-Binding Ability Varies in the Presence of Target Tissue-Specific Compounds In order to exert drug efficacy while avoiding adverse effects, there is a need for drug discovery technology that works in lesions such as cancer or inflammatory sites without acting systemically in normal tissues or blood. Antibody molecules that can bind to antigens expressed on cancer cells but are incapable of binding to the antigens expressed on normal tissues after administration can exert strong cytotoxic effects against cancer while avoiding adverse effects on normal tissues as a result of cytotoxic action. For example, antigen-binding molecules that have been altered from the above-described EGFR-BiTE (Non-patent Document 9), which cannot bind to EGFR expressed on normal tissues but are capable of binding to EGFR expressed on cancer cells, can exert strong an antitumor effect while avoiding adverse effects. Meanwhile, BiTE exerts an antitumor effect by recruiting and activating T cells via CD3 (Non-patent Document 8); and if it is possible to confer EGFR-BiTE with the property of binding to CD3 expressed on T cells in the vicinity of cancer cells but not to CD3 expressed on T cells outside the vicinity of cancer cells, EGFR-BiTE altered to have the property can activate T cells in cancer and thus can exert strong antitumor effects while avoiding adverse effects.

However, this is not limited to only antibody pharmaceuticals against cancer. When an antibody molecule binds and inhibits cytokines in the synovial fluid of inflamed joints in rheumatoid arthritis but does not systemically inhibit the cytokines, the molecule can exert potent therapeutic effects against inflammatory/autoimmune diseases such as rheumatoid arthritis while avoiding increased risks of infection due to systemic neutralization of cytokines.

Figure 1:
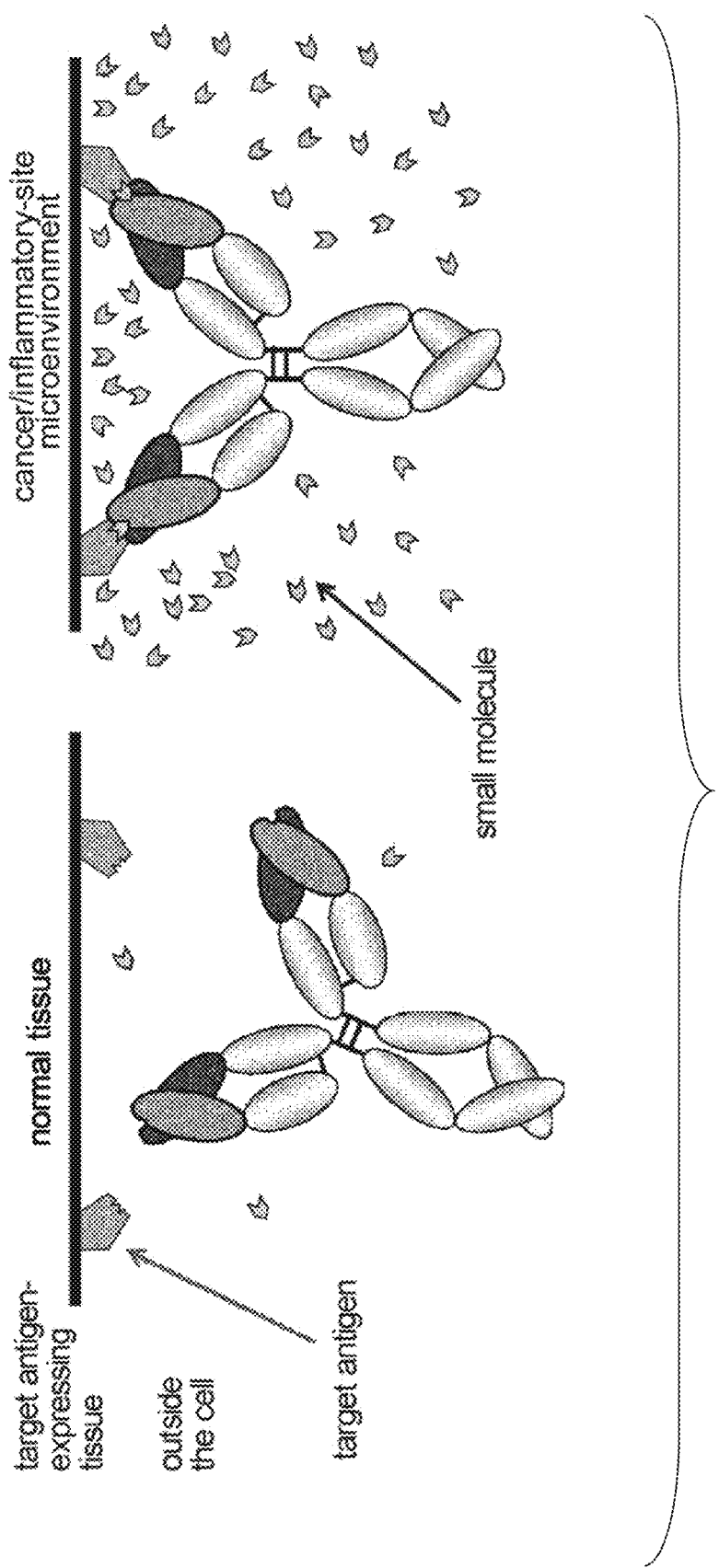
FIG. 1 shows that a small-molecule-switch antibody does not bind to antigens in a normal environment where the small molecules are not present, but binds to the antigens in the target tissue where the small molecules are present at a high concentration.

As described above, antibodies that bind to antigens in cancer tissues but not to antigens in other tissues such as normal tissues and blood can exert drug efficacy while avoiding adverse effects. However, ideal antibodies having such properties have not been reported so far. Meanwhile, as shown in FIG. 1, antibody molecules that bind to antigens via small molecules, as a switch, that are present at high concentrations in cancer tissues in vivo or via compounds that have a property of accumulating in cancer tissues after being administered in vivo (i.e., small molecule switch antibodies), do not bind to antigens in environments in the absence of such small molecules; and they can bind to antigens in target tissues where the small molecules are present at high concentrations.

In developing such small-molecule switch antibodies, first it was to search for small molecules that are present at high concentration in cancer tissues and are considered to be usable as a switch. The result suggested that adenosine, adenosine triphosphate (adenosine 5'-triphosphate (ATP)), inosine, kynurenine, prostaglandin E2 (PGE2), succinic acid, and lactic acid were promising as a switch. Each of these small molecules is either produced by cancer cells, or released from cancer cells after cell death, or produced by immune cells etc. infiltrating cancer tissues, and thus they are present at high concentrations in cancer tissues; however, they are present at lower concentrations in normal tissues and blood in comparison to cancer tissues.

Next, a search was carried out for molecules having the property to accumulate in cancer tissues following in vivo administration. Prodrugs such as Xeloda and TH302 when administered in vivo are metabolized by metabolic enzymes expressed in cancer tissues and produce small molecules that can serve as a switch. Thus, 5-fluorouracil (5-FU), Br-IPM, and such were expected to be useful as a switch. 5-FU is a metabolic product of Capecitabine (Xeloda) and is known to be metabolized by the cancer tissue-specific metabolic enzymes cytidine deaminase and thymidine phosphorylase (Desmoulin F. et al., Drug Metab Dispos. 2002). Meanwhile, TH-302 is known to be converted into Br-IPM by reduction under hypoxic conditions such as around cancer tissues (Duan J X, et al., J Med Chem. 2008). Thus, after in vivo administration, the prodrugs are thought to be metabolized by metabolic enzymes expressed in cancer tissues and to exist at high concentrations, while in normal tissues and blood, they are thought to exist at low concentrations as compared to in cancer tissues.

Figure 2:
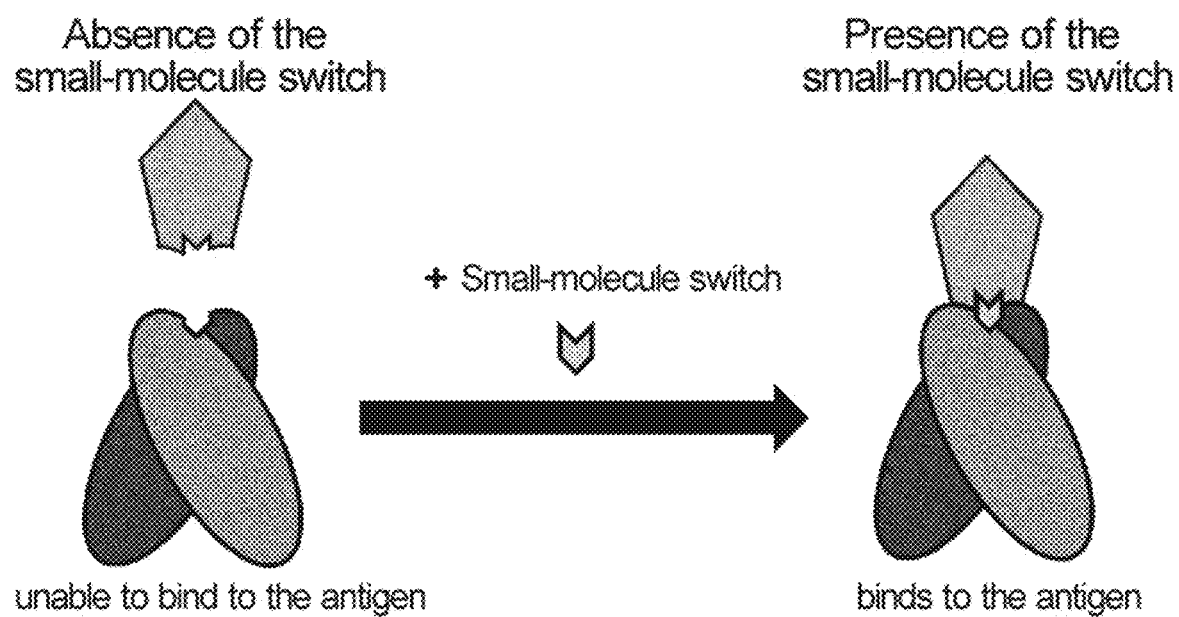
FIG. 2 shows that the small molecule functions as a switch by fitting between the anti-small-molecule antibody and the antigen. If the small molecule is absent, the antibody-antigen interaction is insufficient and the antibody cannot bind to the antigen, but if the small molecule is present, the antibody can bind to the antigen by having the small molecule placed between the antibody and the antigen.

If these small molecules can be sandwiched in the complex between the antigen and the antibody as shown in FIG. 2, the molecules could fulfill the function as a switch. Alternatively, if these small molecules can alter the antigen-binding ability of an antibody by binding to it and changing the conformation of the antigen-binding site of the antibody, these small molecules could fulfill the function as a switch. Specifically, in the absence of the small molecules, the interaction between the antigen and the antibody is insufficient and the antibody cannot bind to the antigen; however, in the presence of the small molecules, the antibody can bind to the antigen. In other words, in the presence of a low concentration of the small molecules, the interaction between the antigen and the antibody is insufficient and the antibody cannot bind to the antigen; however, in the presence of a high concentration of the small molecules, the antibody can bind to the antigen. Furthermore, since the binding of the small molecules that become a switch is reversible, the regulation of antigen binding by these small molecule switches is reversible.

Alternatively, the action of the antibody can be regulated through administration of an oral agent, by oral administration of an exogenous compound serving as a switch. Specifically, when a switch antibody that binds to an antigen using an exogenous compound as a switch, which compound can be administered non-invasively such as by oral administration, is invasively administered e.g. intravenously or subcutaneously, the action of the antibody can be regulated by non-invasively administering the exogenous compound that becomes a switch by oral administration or such. Antibody pharmaceuticals have long half-lives; thus, if adverse effects occur, the effect will be prolonged, and this is a disadvantage. However, if the action of the antibody can be regulated in this way by non-invasively administering exogenous compounds such as by oral administration, the action of the pharmaceutical can be discontinued by interrupting the administration of the switch molecule when adverse effects occurred. Moreover, by preliminarily administering a switch antibody, pharmacological effects could be exerted only when necessary by non-invasive administration such as oral administration by administering switch molecules only when symptoms occurred due to the disease.

(1-2) Strategy for Obtaining Switch Antibodies Whose Antigen-Binding Ability Varies in the Presence of Target Tissue-Specific Compounds Methods for more efficiently producing switch antibodies that bind to antigens in a reversible manner depending on the presence of target tissue-specific compounds include methods that use library techniques. When, using as a template an antibody that maintains binding with a tissue-specific compound, its variable region that is not involved in the binding with the compound is made into a library, antibodies capable of binding to the compound appear at a higher frequency than in ordinary antibody libraries, suggesting that antigen-binding molecules having desired properties could be obtained efficiently. Thus, to first obtain an antibody for use as template sequence for the library, acquisition of antibodies that bind to adenosine or ATP, which are known to be present at high concentrations in cancer cells, was attempted.

Figure 3:
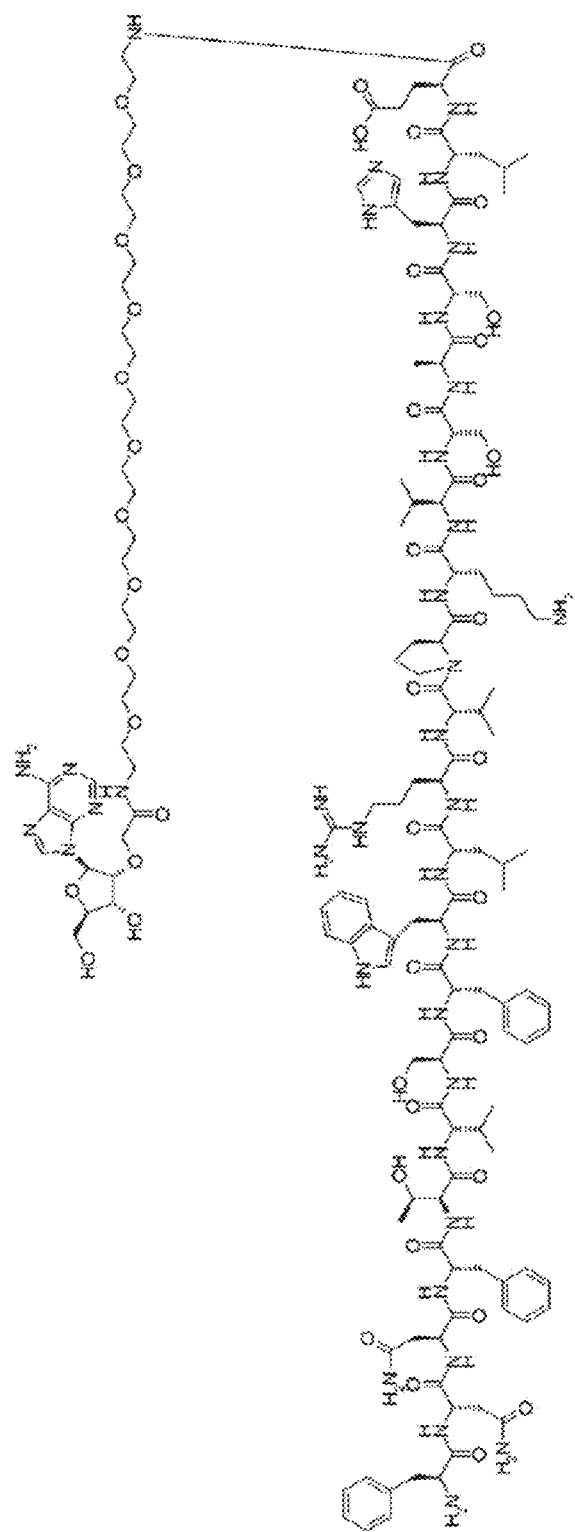
FIG. 3 shows the structure of 2'-Adenosine-PEG-peptide which is an adenosine analog used for immunization of rabbits.
Figure 4:
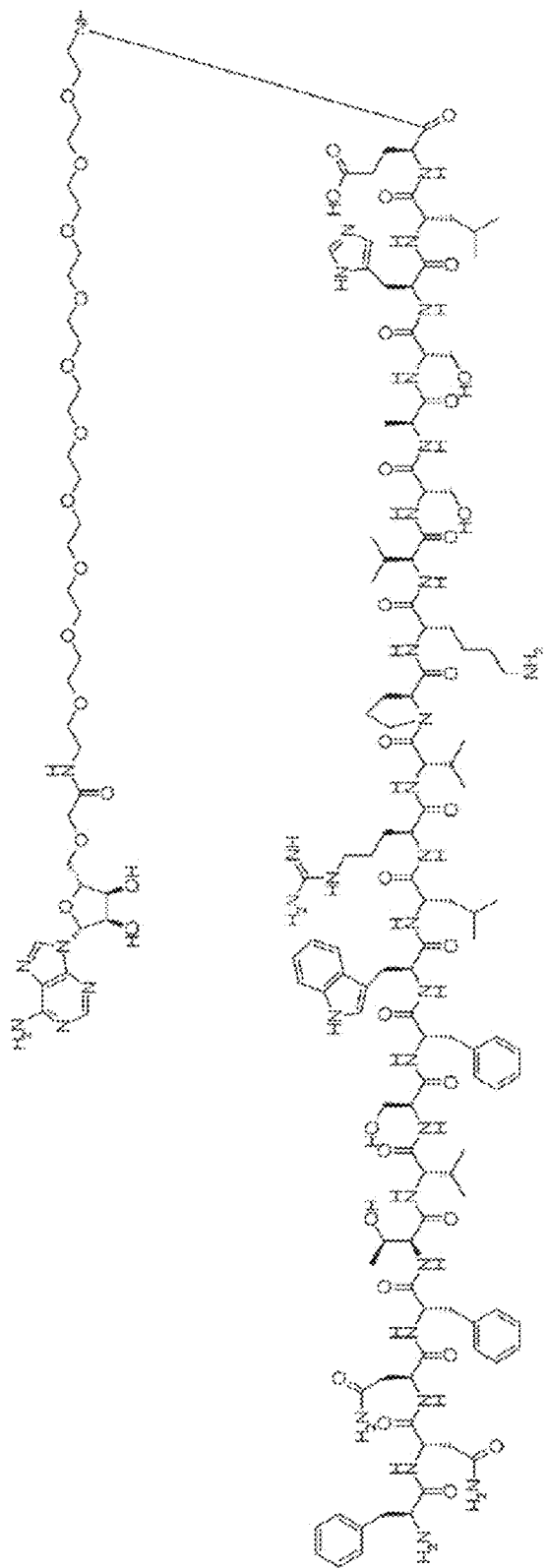
FIG. 4 shows the structure of 5'-Adenosine-PEG-peptide which is an adenosine analog used for immunization of rabbits.
Figure 5:
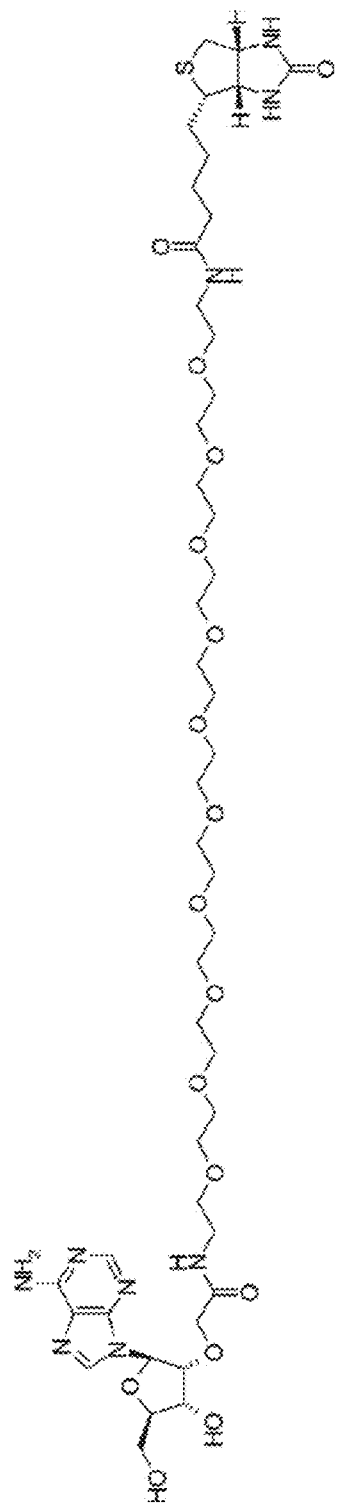
FIG. 5 shows the structure of 2'-Adenosine-PEG-biotin formed by substituting biotin for the peptide portion of the adenosine analog used for immunization of rabbits.

[Example 2] Acquisition of Anti-Adenosine Antibodies by Rabbit B Cell Cloning (2-1) Design of Immunogen to Construct Adenosine-Binding Library The immunogens used in immunizing rabbits were 2'-Adenosine-PEG-Tetanus toxin p30 helper peptide (2'-Adenosine-PEG-peptide) shown in FIG. 3 and 5'-Adenosine-PEG-Tetanus toxin p30 helper peptide (5'-Adenosine-PEG-peptide) shown in FIG. 4. The Tetanus toxin p30 helper peptide consists of the amino acid sequence FNNFTVSFWLRVPKVSASHLE (SEQ ID NO: 4), and is a peptide identified as an epitope of T cell receptor expressed on helper T cells (Eur. J. Immunol. (1989) 19, 2237-2242). The peptide is known to activate antibody production (J. Immunol. (1992) 149, 717-721). When linked to adenosine, the peptide serves as an adjuvant and thus is expected to enhance the production of antibodies against adenosine. The linkage between adenosine and the Tetanus toxin p30 helper peptide was designed to be through PEG so that epitopes of antibodies against adenosine can hardly contain the Tetanus toxin p30 helper peptide. Adenosine is an ATP metabolite, and since the phosphate groups of ATP are attached to the 5' hydroxyl group of adenosine, antibodies that do not recognize the 5' hydroxyl group of adenosine as an epitope may also bind to ATP in addition to adenosine. That is, it would be easier to obtain antibodies that can bind to both adenosine and ATP by using as an immunogen the 5'-Adenosine-PEG-Tetanus toxin p30 helper peptide, while it would be easier to obtain antibodies that bind to adenosine but not to ATP by using as an immunogen the 2'-Adenosine-PEG-Tetanus toxin p30 helper peptide. For this reason, the two types of immunogens which contain the Tetanus toxin p30 helper peptide linked to the 2' or 5' position of adenosine were prepared in the manner described in (2-2).

Figure 6:
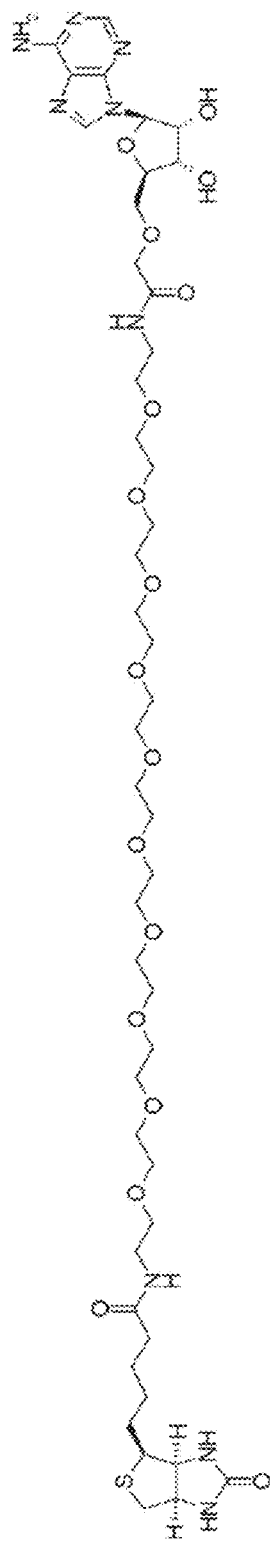
FIG. 6 shows the structure of 5'-Adenosine-PEG-biotin formed by substituting biotin for the peptide portion of the adenosine analog used for immunization of rabbits.

In addition, 2'-Adenosine-PEG-biotin (FIG. 5) and 5'-Adenosine-PEG-biotin (FIG. 6), in which biotin is conjugated instead of the Tetanus toxin p30 helper peptide, were produced as described below. By assessing the binding to these two types of Adenosine-PEG-biotin, antibodies can be tested to demonstrate that their epitopes do not contain the Tetanus toxin p30 helper peptide.

(2-2) Synthesis of Immunogens to Prepare Adenosine-Binding Library

2'-Adenosine-PEG-peptide (adenosine 2'-PEG-peptide conjugate or 2'-(PEG-peptide)adenosine) and 2'-Adenosine-PEG-biotin (adenosine 2'-PEG-biotin conjugate or 2'-(PEG-biotin)adenosine) were synthesized in the manner described below. The synthesized 2'-Adenosine-PEG-peptide and 2'-Adenosine-PEG-biotin were analyzed or fractionated under the conditions below.

The conditions of LCMS analysis are noted as below.

TABLE 1

| Analysis condition | Apparatus | Column (length, mm) | Mobile phase | Gradient (A/B) | Flow rate (ml/min) | Column temperature (C. °) | Wavelength |
|---|---|---|---|---|---|---|---|
| SQDAA05 | Acquity UPLC/SQD | Aldrich Ascentis Express C18 (2.1 × 50) | A) 10 mM AcONH4, H2O B) MeOH | 95/5 => 0/100 (1.0 min) => 0/100 (0.4 min) | 1.0 | 35 | 210-400 nm PDA total |
| SQDAA50 | Acquity UPLC/SQD | Aldrich Ascentis Express C18 (2.1 × 50) | A) 10 mM AcONH4, H2O B) MeOH | 50/50 => 0/100 (0.7 min) => 0/100 (0.7 min) | 1.0 | 35 | 210-400 nm PDA total |
| SQDFA05 | Acquity UPLC/SQD | Aldrich Ascentis Express C18 (2.1 × 50) | A) 0.1% FA, H2O B) 0.1% FA CH3CN | 95/5 => 0/100 (1.0 min) => 0/100 (0.4 min) | 1.0 | 35 | 210-400 nm PDA total |
| SQDFA50 | Acquity UPLC/SQD | Aldrich Ascentis Express C18 (2.1 × 50) | A) 0.1% FA, H2O B) 0.1% FA CH3CN | 50/50 => 0/100 (0.7 min) => 0/100 (0.7 min) | 1.0 | 35 | 210-400 nm PDA total |

The conditions of preparative HPLC are described as below.

TABLE 2

| Preparative condition | Apparatus | Column (length, mm) | Mobile phase | Gradient (A/B) | Flow rate (ml/min) | Column temperature (C. °) | Wavelength |
|---|---|---|---|---|---|---|---|
| A | Preparative HPLC system with injection/fractionation (Gilson, inc.) | Aldrich Ascentis RP-Amide (21.2 × 150 mm 5 μm) | A) 0.1% FA H2O B) 0.1% FA MeCN | isocratic (A/B): 15/85 | 20.0 | 40 | 254, 258 nm |
| B | Preparative HPLC system with injection/fractionation (Gilson, Inc.) | YMC Actus ODS-A (20 × 100 mm 5 μm) | A) 20 mM AcONH4 H2O B) 20 mM AcONH4 MeOH/MeCN(1/1) | isocratic (A/B): 47/53 | 20.0 | 40 | 254, 258 nm |

(2-2-1) Synthesis of Compound 006 (Boc-Phe-Asn-Asn-Phe-Thr (tBu)-Val-Ser (tBu)-Phe-Trp (Boc)-Lue-Arg (Pbf)-Val-Pro-Lys (Boc)-Val-Ser (tBu)-Ala-Ser (tBu)-His (Trt)-Leu-Glu (tBu)-OH)

[Compound 6]

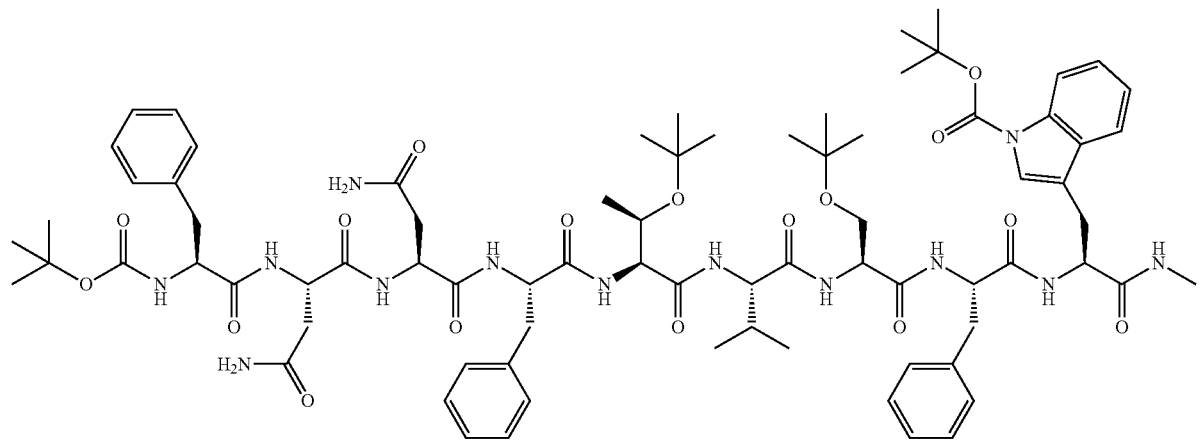

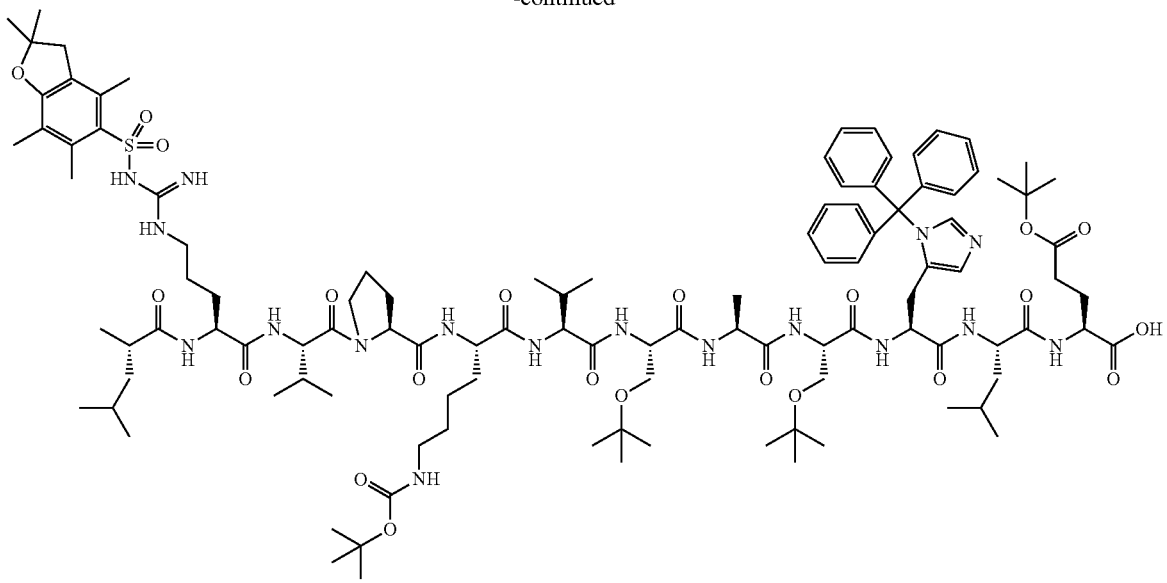

Peptide synthesis was performed by the Fmoc method using a peptide synthesizer (Multipep RS; Intavis). All Fmoc amino acids were purchased from WATANABE CHEMICAL INDUSTRIES, LTD. The detailed procedure of the treatment was in the manual attached to the synthesizer.

Fmoc-Glu(tBu)-OH linked at its C terminus to 2-chlorotrityl resin (250 mg/column, 30 columns, 11.7 mmol), an N,N-dimethylformamide solution containing various Fmoc amino acids (0.6 mol/1) and 1-hydroxy-7-azabenzotriazole (0.375 mol/1), and an N,N-dimethylformamide solution (10% v/v) of diisopropylcarbodiimide were loaded in the synthesizer. The synthesis reaction was performed using as an Fmoc-deprotection solution, an N,N-dimethylformamide solution (20% v/v) containing piperidine and 5% (wt/v) urea. After the resin was washed with N,N-dimethylformamide, Fmoc deprotection was carried out, followed by one cycle of Fmoc amino acid condensation reaction. This cycle was repeated to elongate peptides on the resin surface. After elongation, the resin was washed with trifluoroethanol. Peptides were cleaved off from the resin by adding trifluoroethanol/dichloromethane (=1/1). Thus, compound 006 (7.2 g) was obtained as a crude product.

LCMS (ESI) m/z=1185(M+3H)3+
Retention time: 1.24 minute (Analysis condition, SQDAA05)

(2-2-2) Synthesis of Compound 007

[Compound 7]

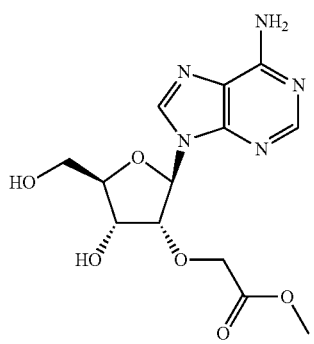

A suspension of adenosine (2.00 g, 7.48 mmol) in N,N-dimethylformamide (40 ml) was cooled down to 0° C., and 60% sodium hydride (0.42 g, 10.48 mol) was added thereto. The reaction mixture was stirred for one hour at 0° C. After adding methyl bromoacetate (0.76 ml, 8.01 mmol), the resulting reaction mixture was stirred for five hours at room temperature, and acetic acid (1 ml) and methanol (3 ml) were added thereto. The reaction mixture was concentrated under reduced pressure. The resulting residue was purified by normal phase silica gel column chromatography (dichloromethane/methanol). Thus, compound 007 (0.93 g, 37%) was obtained.

LCMS(ESI) m/z=340(M+H)+
Retention time: 0.27 minute (Analysis condition, SQDFA05)

(2-2-3) Synthesis of Compound 008

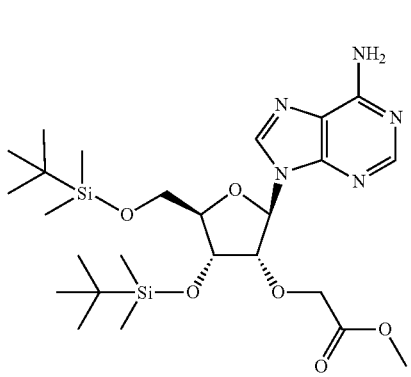

[Compound 8]

t-Butyldimethylsilyl chloride (999 mg, 6.63 mol) and imidazole (722 mg, 10.61 mol) were added to a pyridine solution (8 ml) of compound 007 (900 mg, 2.65 mmol). The reaction mixture was stirred for four hours at room temperature, and extracted with ethyl acetate/water. The extracted organic layer was washed with a saturated sodium chloride solution, and dried over anhydrous sodium sulfate. After filtration, the organic layer was concentrated under reduced pressure. The resulting residue was purified by normal phase silica gel column chromatography (dichloromethane/methanol). Thus, compound 008 (1.17 g, 78%) was obtained.

LCMS (ESI) m/z=568(M+H)+

Retention time: 1.10 minute (Analysis condition, SQDFA05)

(2-2-4) Synthesis of Compound 009

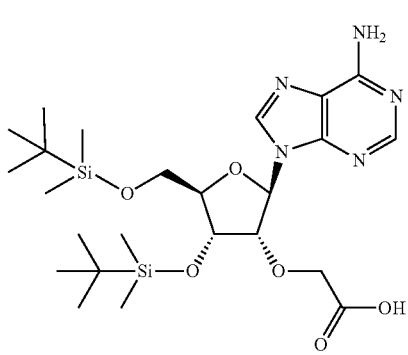

[Compound 9]

Lithium hydroxide (61 mg, 2.55 mol) dissolved in water (0.17 ml) was added to a solution of compound 008 (290 mg, 0.511 mmol) in methanol (0.34 ml)/tetrahydrofuran (0.34 ml). The reaction mixture was stirred for 30 minutes at room temperature. The mixture was neutralized with 1 M hydrochloric acid, and concentrated under reduced pressure. The concentrated residue was extracted with ethyl acetate/water. The resulting organic layer was washed with a saturated sodium chloride solution, and dried over anhydrous sodium sulfate. After filtration, the organic layer was concentrated under a reduced pressure. Thus, compound 009 (319 mg, 90%) was obtained.

LCMS (ESI) m/z=552(M−H)−

Retention time: 0.97 minute (Analysis condition, SQDFA05)

(2-2-5) Synthesis of Compounds 010 and 011

[Compound 10]

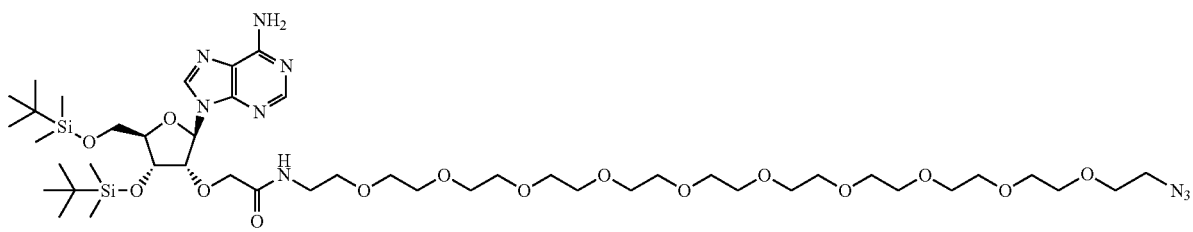

[Compound 11]

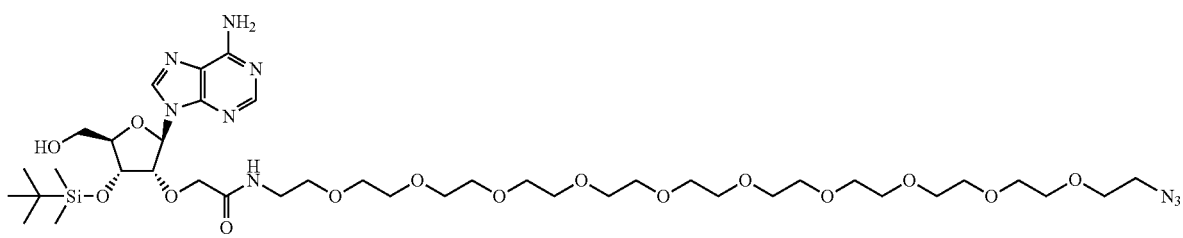

1-Hydroxybenzotriazole (75 mg, 0.553 mol) and 1-ethyl-3-(3-dimethylaminopropyl) carbodiimide hydrochloride (106 mg, 0.553 mol) were added to an N,N-dimethylformamide (1.5 ml) solution of compound 009 (255 mg, 0.460 mmol), and it was stirred for three minutes at room temperature. 0-(2-aminoethyl)-0'-2-azidoethyl) nonaethylene glycol (291 mg, 0.553 mmol) was added to the reaction mixture, and it was stirred for three hours at room temperature. The reaction mixture was concentrated under a reduced pressure, and the resulting residue was purified by reverse phase silica gel column chromatography (aqueous 10 mM ammonium acetate solution/methanol. Compounds 010 (177 mg, 42%) and 011 (72 mg, 19%) were obtained.

Compound 010
LCMS (ESI) m/z=1063(M+H)+
Retention time: 0.98 minute (Analysis condition, SQDFA05)

Compound 011
LCMS (ESI) m/z=949(M+H)+
Retention time: 0.67 minute (Analysis condition, SQDFA05)

(2-2-6) Synthesis of Compound 012

[Compound 12]

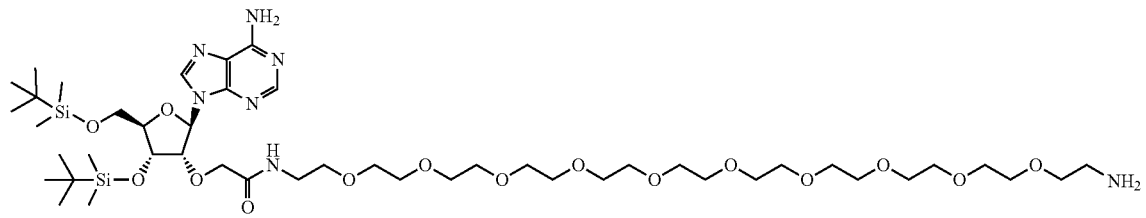

10% palladium carbon (34 mg) was added to a solution of compound 010 (170 mg, 0.160 mmol) in ethanol (1 ml). The reaction mixture was stirred for two hours under hydrogen atmosphere, and again 10% palladium carbon (34 mg) was added thereto. The reaction mixture was stirred for two hours under a hydrogen atmosphere to complete the reaction. The filtrate of the reaction solution was concentrated under a reduced pressure. Compound 012 (34 mg, 95%) was obtained.

LCMS (ESI) m/z=1037(M+H)+
Retention time: 0.70 minute (Analysis condition, SQDFA05)

(2-2-7) Synthesis of Compounds 013 and 014

[Compound 13]

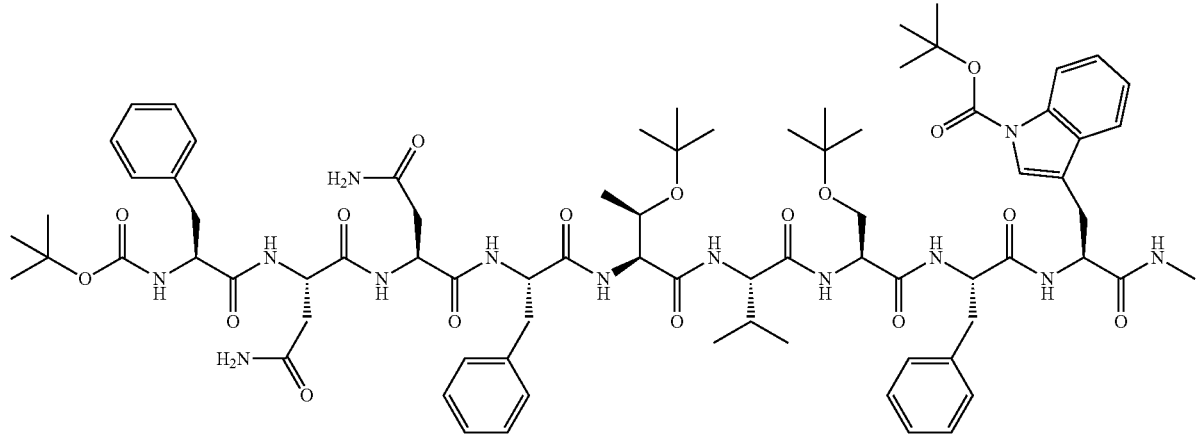

-continued
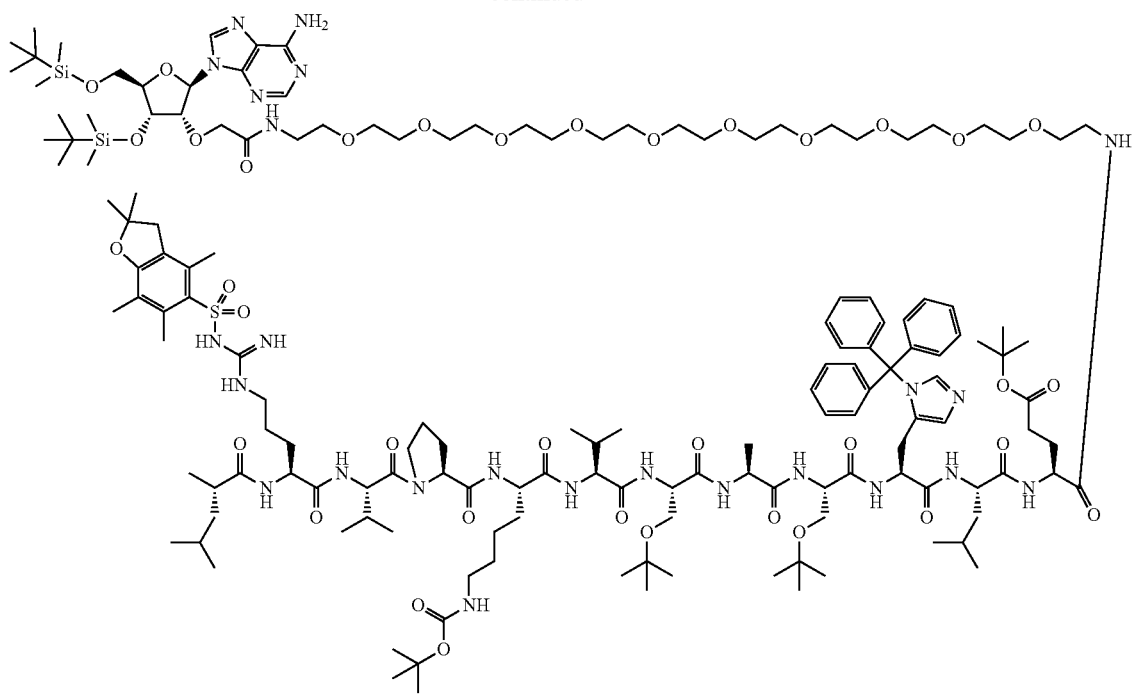
[Compound 14]
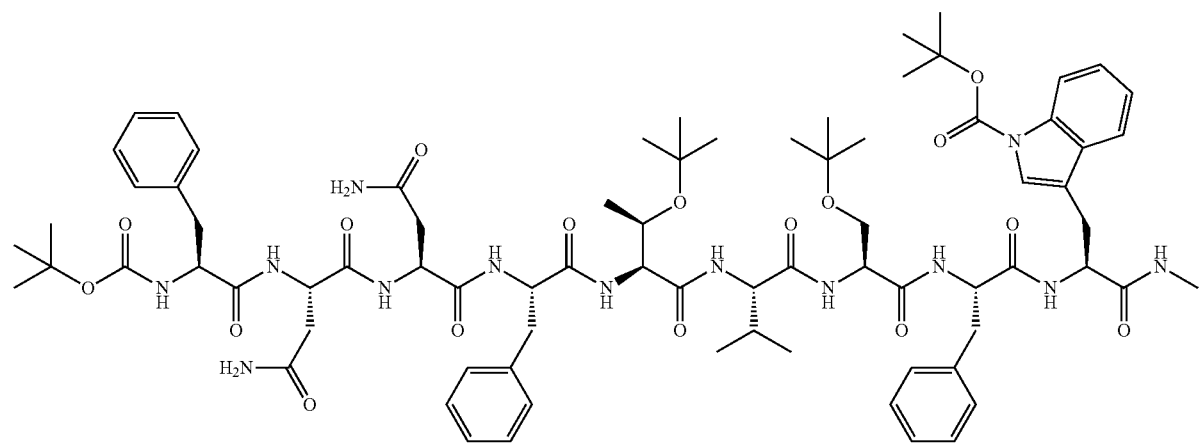

-continued

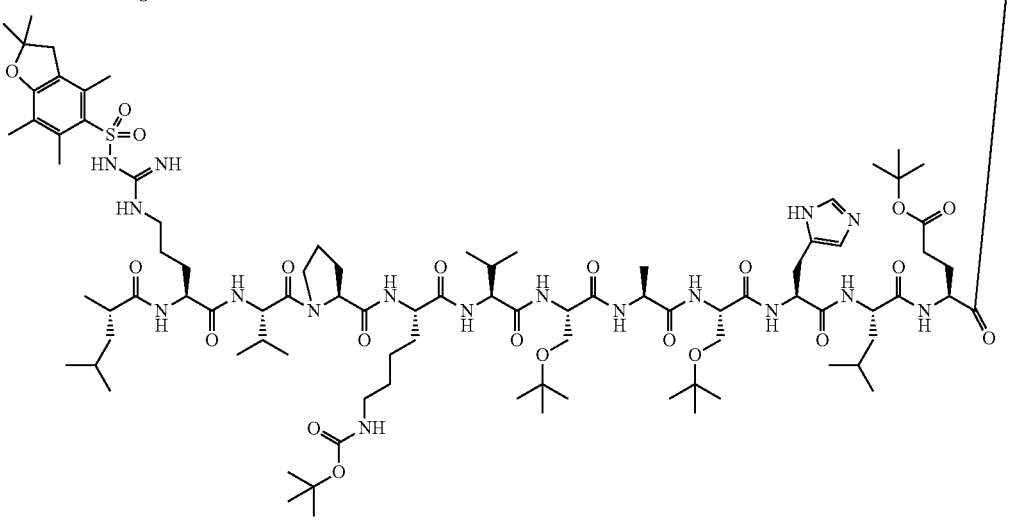

Compound 006 (354 mg, 0.110 mmol), 1-hydroxybenzotriazole (13 mg, 0.100 mol), and 1-ethyl-3-(3-dimethylaminopropyl) carbodiimide hydrochloride (19 mg, 0.100 mol) were added to a solution of compound 012 (86 mg, 0.083 mmol) in N,N-dimethylformamide (1.5 ml), and it was stirred for two hours at room temperature. The filtrate of the reaction mixture was purified by preparative condition A described in Table 2. A mixture of compounds 013 and 014 (72 mg) was obtained.

Compound 013
LCMS (ESI) m/z=1525(M+3H)3+, 1144(M+4H)4+
Retention time: 1.13 minute (Analysis condition, SQDAA50)

Compound 014
LCMS (ESI) m/z=1444(M+3H)3+, 1083(M+4H)4+
Retention time: 1.02 minute (Analysis condition, SQDAA50)

(2-2-8) Synthesis of 2'-Adenosine-PEG-Peptide (Adenosine 2'-PEG-Peptide Conjugate or 2'-(PEG-Peptide)Adenosine) (Compound 015)

[Compound 15]

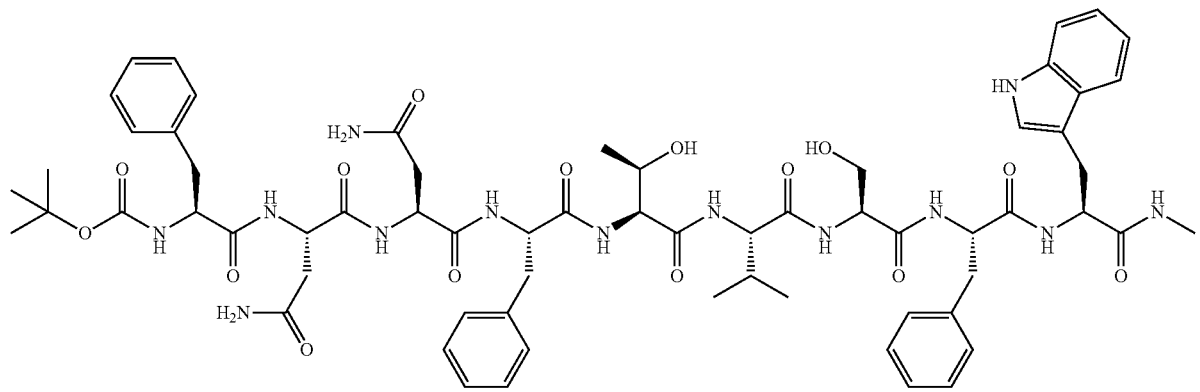

-continued

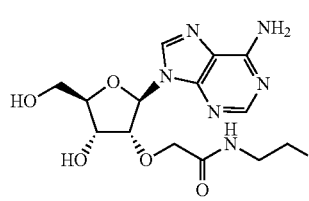
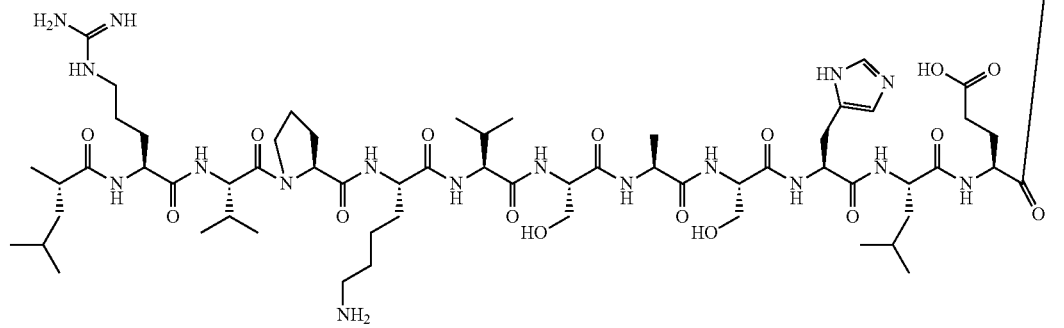

Trifluoroacetic acid (16 ml), dichloromethane (8 ml), water (1.3 ml), and tetraisopropylsilane (1.3 ml) were added to the mixture of compounds 013 and 014 (42 mg), and it was stirred for six hours at room temperature. The residue obtained by concentrating the reaction mixture under reduced pressure was purified by preparative condition B described in Table 2. Thus, compound 015 (10 mg) was obtained.

LCMS (ESI) m/z=1090(M+3H)3+, 818(M+4H)4+

Retention time: 0.52 minute (Analysis condition, SQDAA50)

(2-2-9) Synthesis of Compound 016

[Compound 16]

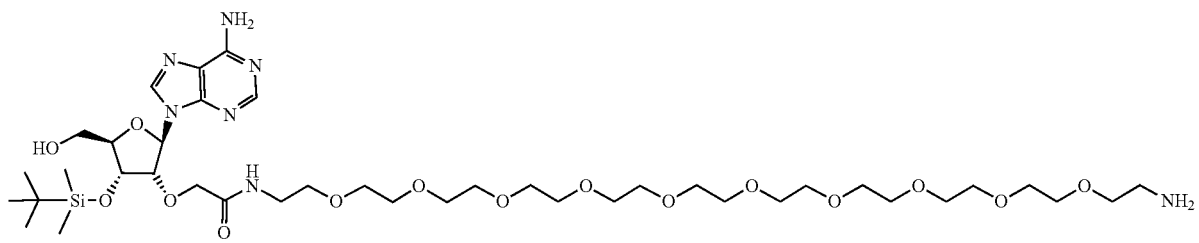

10% palladium carbon (34 mg) was added to a solution of compound 011 (70 mg, 0.074 mmol) in ethanol (1 ml), and the reaction mixture was stirred for five hours under hydrogen atmosphere. The filtrate of the reaction mixture was concentrated under reduced pressure. Thus, compound 016 (58 mg, 85%) was obtained.

LCMS (ESI) m/z=923(M+H)+

Retention time: 0.50 minute (Analysis condition, SQDFA05)

(2-2-10) Synthesis of Compound 017

[Compound 17]

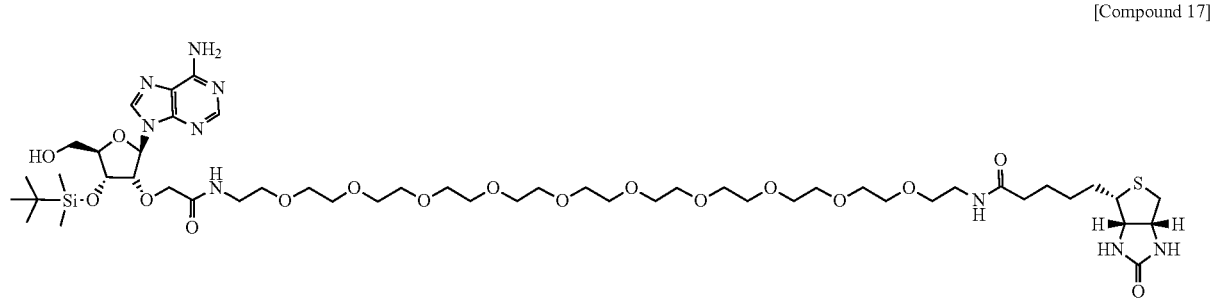

D-biotin N-succinimidyl (24 mg, 0.069 mmol) and triethylamine (13 μl, 0.094 mol) were added to a solution of compound 016 (58 mg, 0.063 mmol) in N,N-dimethylformamide (1 ml), and it was stirred for two hours at room temperature. Then, after D-biotin N-succinimidyl (5 mg, 0.015 mmol) was added, the reaction was completed upon 1.5 hours of stirring at room temperature. The reaction mixture was purified by reverse phase silica gel column chromatography (aqueous 10 mM ammonium acetate solution/methanol. Compound 017 (50 mg, 69%) was obtained.

LCMS (ESI) m/z=1149(M+H)+

Retention time: 1.04 minute (Analysis condition, SQDFA05)

(2-2-11) Synthesis of 2'-Adenosine-PEG-Biotin (Adenosine 2'-PEG-Biotin Conjugate or 2'-(PEG-Biotin)Adenosine) (Compound 018)

[Compound 18]

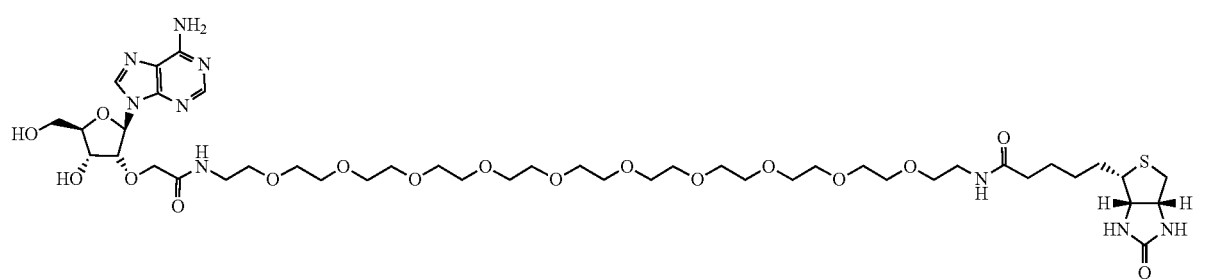

A solution of 1 M tetra-n-butylammonium fluoride in tetrahydrofuran (65 µl, 0.065 mmol) was added to a solution of compound 017 (62 mg, 0.054 mmol) in tetrahydrofuran (2 ml), and it was stirred at room temperature for one hour. Then, 1 M tetra-n-butylammonium fluoride in tetrahydrofuran solution (20 µl, 0.020 mmol) was added, and the reaction was completed by stirring at room temperature for one hour. The reaction mixture was concentrated under a reduced pressure, and the residue was purified by reverse phase silica gel column chromatography (aqueous 0.1% formic acid solution/0.1% formic acid in acetonitrile). Compound 018 (12 mg, 21%) was obtained.

LCMS (ESI) m/z=1035(M+H)+

Retention time: 0.71 minute (Analysis condition, SQDAA05)

Furthermore, 5'-Adenosine-PEG-peptide and 5'-Adenosine-PEG-biotin were also synthesized by the same reaction.

(2-3) Production of Adenosine-Binding Antibodies in Animals and Antibody Screening Rabbits were immunized with 2'-Adenosine-PEG-peptide and/or 5'-Adenosine-PEG-peptide by a conventional method. Candidates for cells with adenosine-binding activity were selected from suspensions of cells collected from blood of the immunized rabbits, by using autoMACS Pro Separator and FACSAria (BD) which uses Adenosine-PEG-biotin-binding activity and rabbit IgG expression as indicators. Then, screening was carried out with antibodies secreted in the culture supernatants of the selected cells. In the screening, ELISA was performed to assess the presence of binding activity to Adenosine-PEG-biotin. ELISA was also performed to assess whether adenosine, when added in combination with Adenosine-PEG-biotin at a level 1000 times or more of that of Adenosine-PEG-biotin, suppresses the binding to Adenosine-PEG-biotin. The H-chain and L-chain variable regions were isolated by PCR from cells selected using as an indicator the presence of the Adenosine-PEG-biotin-binding activity as well as suppression of the binding to Adenosine-PEG-biotin by adenosine added in combination with Adenosine-PEG-biotin. The obtained variable regions were expressed in combination with a human IgG1 heavy chain constant region and a human light chain constant region.

[Example 3] Assessment of Clones Obtained by Rabbit B Cell Cloning (3-1) Assessment of Clones Obtained by Rabbit B Cell Cloning for their Binding Activity to 2'-Adenosine-PEG-Biotin Clones obtained by rabbit B cell cloning were assessed for their binding activity to adenosine by the SPR method. Antigen-antibody reaction between the clones and 2'-Adenosine-PEG-Biotin was kinetically analyzed using Biacore 4000 (GE Healthcare). Sensor chip CM5 (GE Healthcare) was immobilized with an appropriate amount of protein A/G (Invitrogen) by amine coupling. Antibodies of interest were captured by the chip. Then, after 100 nmol/l 2'-adenosine-PEG-Biotin was interacted as an analyte for 60 seconds, the dissociation of the analyte was monitored and measured for 60 seconds. The running buffer used was HBS-P+(GE Healthcare). All measurements were carried out at 25° C. The analyte was diluted using the running buffer.

Figure 7:
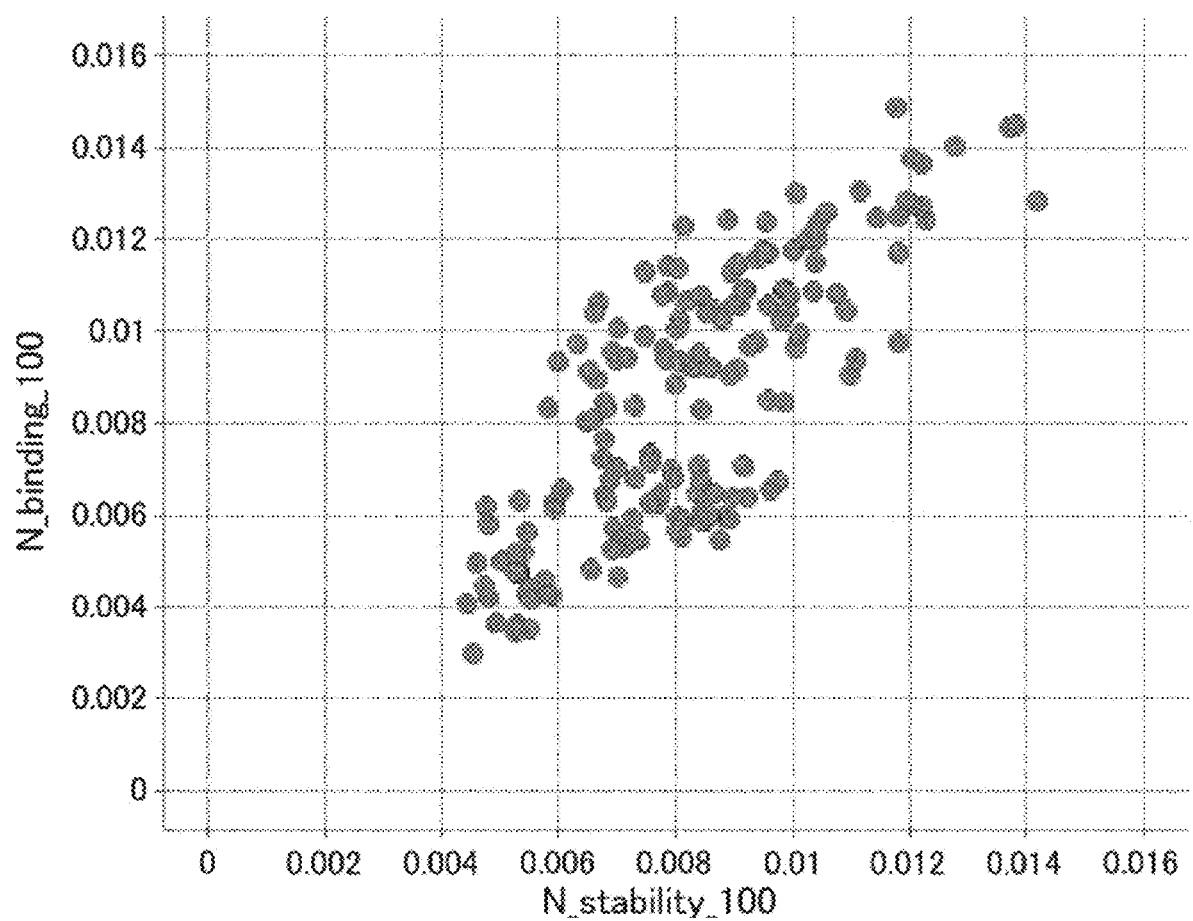
FIG. 7 shows results of comparing the 2'-Adenosine-PEG-Biotin-binding activities of the individual antibodies obtained by rabbit B cells cloning. The vertical axis shows the value (N_binding_100) obtained by dividing the amount of each antibody bound in the interaction with 2'-Adenosine-PEG-biotin by the capture level (RU) of each antibody, and the horizontal axis shows the value (N_stability_100) obtained by dividing the value obtained 60 seconds after dissociation of 2'-Adenosine-PEG-biotin from each antibody after its interaction with 2'-Adenosine-PEG-biotin by the capture level (RU) of each antibody.

The respective antibodies were compared for their binding activity to 2'-Adenosine-PEG-Biotin using as an indicator the value (N_binding_100) of dividing the amount of binding upon interaction with 2'-Adenosine-PEG-Biotin by the amount of capture (RU) for each antibody, and the value (N_stability_100) of dividing the amount of dissociation of 2'-Adenosine-PEG-Biotin from each antibody for 60 seconds after interaction with 2'-Adenosine-PEG-Biotin by the amount of capture (RU) for each antibody. Regarding antibodies for which the amount of capture was 1500 RU or less, their binding was not sufficiently detectable and thus they were excluded from the subjects to be tested. The result is shown in FIG. 7. The result shown in FIG. 7 demonstrates that the B cell cloning method yielded adenosine-binding clones with various affinity.

(3-2) Assessment of 2'-Adenosine-PEG-Biotin-Binding Clones for their Binding Activity to Adenosine and ATP, and Sequence Analysis of the Clones Clones which were demonstrated to bind to 2'-Adenosine-PEG-Biotin were assessed for their binding to adenosine and ATP by SPR and competitive ELISA.

(3-2-1) Assessment by SPR of 2'-Adenosine-PEG-Biotin-Binding Clones for their Binding to Adenosine Using Biacore T200 (GE Healthcare), the antibody SMB0002 obtained by the B cell cloning method was analyzed for its interaction with adenosine in antigen-antibody reaction. Sensor chip CM5 (GE Healthcare) was immobilized with an appropriate amount of protein A (Invitrogen) by amine coupling. Antibodies of interest were captured by the chip to allow interaction to adenosine as an antigen. The running buffer used was 50 mmol/l TrisHCl, 150 mmol/l NaCl, 0.02% (w/v) Tween20, pH 7.6. All measurements were carried out at 25° C. The antigens were diluted using the running buffer.

Regarding SMB0002, the diluted antigen solutions and the running buffer which is the blank were loaded at a flow rate of 30 µL/min for 75 seconds to allow each of the antigens to interact with the antibody captured on the sensor chip. Then, running buffer was run at a flow rate of 30 µL/min for four minutes and dissociation of the antigen from the antibody was observed. Next, 10 mmol/L glycine-HCl, pH 1.5, was loaded at a flow rate of 30 µL/min for 30 seconds to regenerate the sensor chip. Kinetic parameters such as the association rate constant ka (1/Ms) and the dissociation rate constant kd (l/s) were calculated based on the sensorgrams obtained by the measurements. The dissociation constant KD (M) was calculated from these constants. Each parameter was calculated using the Biacore T200 Evaluation Software (GE Healthcare).

The result showed that SMB0002 bound to adenosine. The clone was assessed for its binding at adenosine concentrations of 100 (duplicate), 50, 25, 12.5, 6.25, and 3.13 nM. The observed sensorgrams are summarized in FIG. 8A. KD of SMB0002 toward adenosine was $1.5 \times 10^{-8}$ (mol/L).

(3-2-2) Assessment of 2'-Adenosine-PEG-Biotin-Binding Clones for ATP Binding by the SPR Method Biacore T200 (GE Healthcare) was used to analyze interaction in the antigen-antibody reaction with ATP. The antibody of interest was captured onto protein A/G (Invitrogen) immobilized in an appropriate amount onto Sensor chip CM5 (GE Healthcare) by the amine coupling method, and ATP which is the antigen was allowed to interact. The running buffer used was 10 mmol/L ACES, 150 mmol/L NaCl, 0.05% (w/v) Tween 20, pH 7.4. All measurements were carried out at 25° C. The antigen was diluted with running buffer.

Regarding SMB0002, the diluted antigen solutions and the running buffer which is the blank were loaded at a flow rate of 20 μL/min for two minutes to allow each of the antigens to interact with the antibody captured on the sensor chip. Then, running buffer was run at a flow rate of 20 μL/min for three minutes and dissociation of the antigen from the antibody was observed. Next, 10 mmol/L glycine-HCl, pH 1.5, was injected at a flow rate of 30 μL/min for 30 seconds to regenerate the sensor chip. Kinetic parameters such as the association rate constant ka (1/Ms) and the dissociation rate constant kd (1/s) were calculated based on the sensorgrams obtained by the measurements. The dissociation constant KD (M) was calculated from these constants. Each parameter was calculated using the Biacore T200 Evaluation Software (GE Healthcare).

Figure 8A:
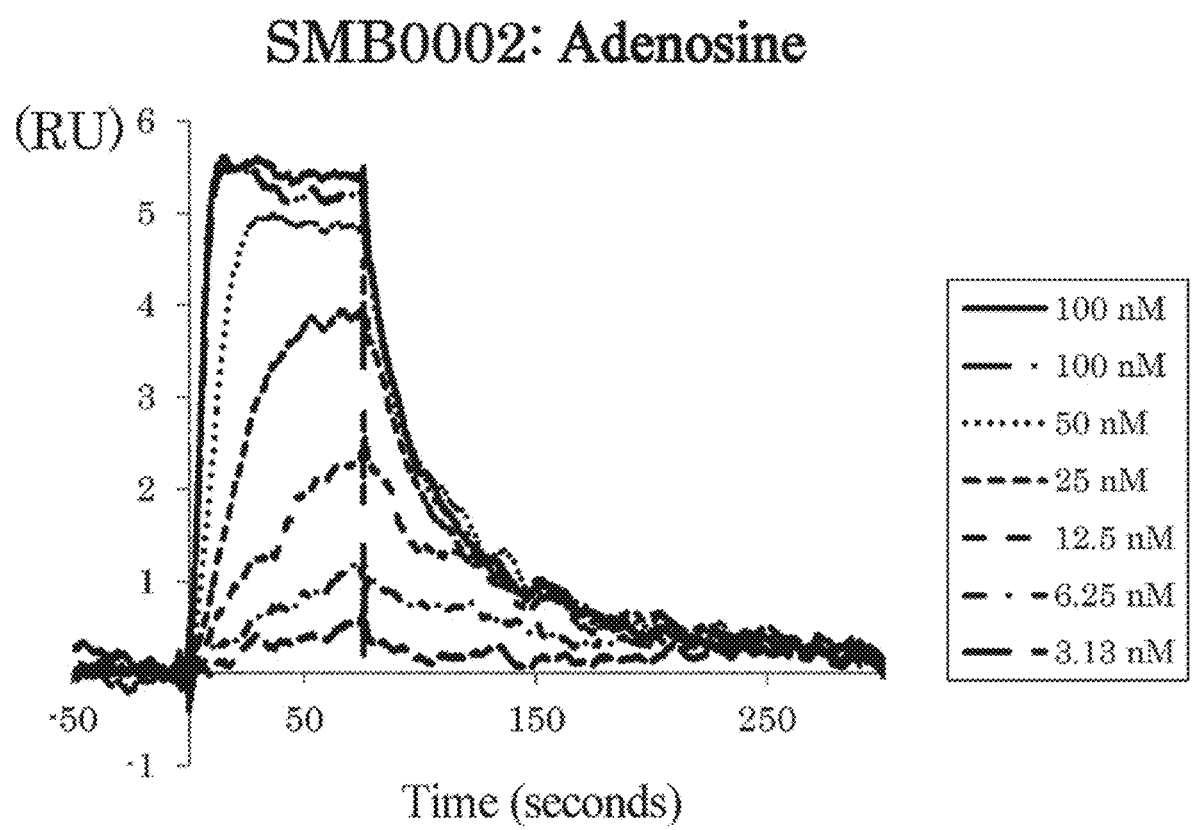
FIG. 8A shows sensorgrams of surface plasmon resonance-based analysis demonstrating that clone SMB0002 binds to (interacts with) adenosine. The sensorgrams show interactions between SMB0002 and adenosine at 100 (in duplicate), 50, 25, 12.5, 6.25, and 3.13 nM in order from the top.
Figure 8B:
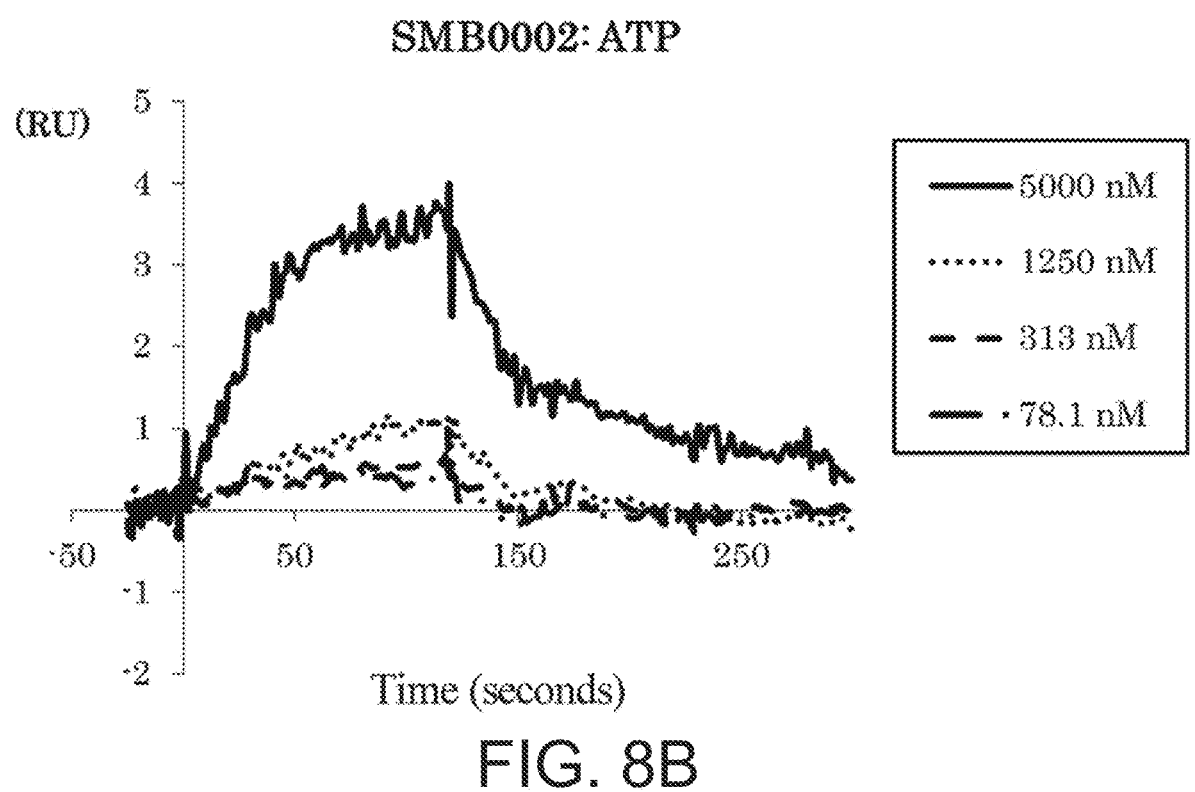
FIG. 8B shows sensorgrams of surface plasmon resonance-based analysis demonstrating that clone SMB0002 binds to (interacts with) ATP. The sensorgrams show interactions between SMB0002 and ATP at 5000, 1250, 313, and 78.1 nM in order from the top.

The result showed that SMB0002 also bound to ATP. Each clone was assessed for its binding at ATP concentrations of 5000, 1250, 313, and 78.1 nM. The observed sensorgrams are summarized in FIG. 8B. As shown in FIGS. 8A and 8B, SMB0002 bound to both adenosine and ATP. The KD of SMB0002 toward adenosine was $1.5E^{-8}$ (mol/L) and the KD of SMB0002 toward ATP was $1.0E^{-5}$ (mol/L).

(3-2-3) Assessment of 2'-Adenosine-PEG-Biotin-Binding Clones for their Binding to Adenosine and ATP by Competitive ELISA Antibodies demonstrated to bind to 2'-Adenosine-PEG-Biotin were diluted to 1 μg/ml with PBS, and added to each well of a 384-well MAXISorp (Nunc). To immobilize the antibodies, the plate was allowed to stand for one hour or more at room temperature. After the antibodies diluted with PBS were removed from each well, TBS containing 1% BSA was added thereto and the plate was allowed to stand for one hour or more. Then, the TBS (pH 7.4) containing 1% BSA was removed from the plate. 2'-Adenosine-PEG-Biotin diluted to 50 nM with PBS, a mixture of 2'-Adenosine-PEG-Biotin and adenosine diluted to 50 nM and 500 μM respectively with PBS, a mixture of 2'-Adenosine-PEG-Biotin and ATP diluted to 50 nM and 500 μM respectively with PBS, or PBS alone was added to the plate. The plate was allowed to stand at room temperature for one hour, and then washed three times with 80 μl of PBS containing 0.05% Tween-20. Then, Streptavidin-HRP (Thermo fisher scientific) diluted 20000 times with PBS was added to each well, and the plate was allowed to stand for one hour or more at room temperature. After the plate was washed three times with 80 μl of PBS containing 0.05% Tween-20, a chromogenic substrate (ABTS peroxidase substrate) was added to each well. After the plate was incubated for one hour, color development in the solution of each well was assessed by measuring absorbance at 405 nm using SpectraMax from Molecular Device.

As shown in FIG. 9, the result showed that the binding of SMB0002 to 2'-Adenosine-PEG-Biotin was inhibited by adding excess amounts of adenosine and ATP. Thus, the antibody clones were demonstrated to bind not only to 2'-Adenosine-PEG-Biotin but also to both adenosine and ATP.

(3-2-4) Sequence Analysis of the Adenosine- and ATP-Binding Clone

The amino acid sequence of clone SMB0002, which bound to both adenosine and ATP, is shown in Table 3.

TABLE 3

| Clone name | Heavy chain SEQ ID NO | Light chain SEQ ID NO |
|---|---|---|
| SMB0002 | SEQ ID NO: 30 | SEQ ID NO: 31 |

[Example 4] Design of Library for Obtaining AMP/ADP/ATP/Adenosine-Switch Antibodies Based on Comprehensive Alteration Using an Anti-ATP/Adenosine Antibody Adenosine and ATP are known to be present at high concentrations in cancer tissues and inflamed tissues. Many antibodies showing antigen-binding ability only in the presence of ATP were obtained from a rational design library constructed using an ATP-binding antibody as a template in Reference Example 2 described below. This suggested that antibodies showing antigen-binding ability only in the presence of adenosine, AMP, ADP, or ATP could similarly be obtained by constructing a library using an antibody that shows binding ability to adenosine, AMP, ADP, or ATP as a template.

(4-1) Assessment of the Binding of the Adenosine-Binding Antibody SMB0002 to AMP and ADP Binding by the SPR Method SMB0002 expressed and purified by the method described in Reference Example 1 described below was assayed for AMP binding by a method similar to the measurement method using Biacore described in Example 3-2. Binding of SMB0002 was assessed at AMP concentrations of 500, 250 (duplicate), 125, 62.5, 31.25, 15.625, and 7.8125 μM. The observed sensorgrams are shown in FIG. 10A. As shown in FIG. 10A, binding of SMB0002 to AMP was observed. The KD of SMB0002 toward AMP was $5.9 \times 10^{-5}$ (mol/L).

Binding to ADP was assessed by a method similar to the measurement method using Biacore described in Example 3-2, except that the NaCl concentration was changed to 600 mM. Binding of SMB0002 was assessed at ADP concentrations of 2000, 1000 (duplicate), 500, 250, 250, 125, 62.5, and 31.3 μM. The observed sensorgrams are shown in FIG. 10B. As shown in FIG. 10B, binding of SMB0002 to ADP was observed. The KD of SMB0002 toward ADP was $2.4 \times 10^{-4}$ (mol/L).

(4-2) X-Ray Crystallographic Analysis of the Adenosine-Binding Antibody SMB0002

The three-dimensional structure of the complex of adenosine and the adenosine-binding antibody SMB0002 obtained from immunized rabbits in Example 3 was revealed by X-ray crystallographic analysis.

(4-2-1) Preparation of Full-Length SMB0002 Antibody for Crystallization

The full-length SMB0002 antibody for crystallization was prepared and purified by a method known to those skilled in the art.

(4-2-2) Preparation of SMB0002 Fab Fragments from the Full-Length Antibody

After the obtained full-length SMB0002 antibody was concentrated with a 10000 molecular weight cutoff (MWCO) ultrafiltration membrane, a sample was prepared by diluting to 1.5 mg/ml with 4 mM L-cysteine, 5 mM EDTA, 25 mM MES, pH 6.5. Papain (Roche Applied Science) was added to the sample at an amount of 1/100 to the full-length antibody by mass ratio, and this was allowed to stand at 35° C. for 2 hours. Then, the reaction was terminated by adding 20 ml of 25 mM sodium acetate buffer, pH 5.0, in which a tablet of protease inhibitor cocktail mini, EDTA-free (Roche Applied Science) was dissolved. Next, this sample was loaded onto a 1-ml size cation-exchange column HiTrap SP HP (GE Healthcare) to whose downstream 1-ml size Protein A-carrying column HiTrap Mab Select Sure (GE Healthcare) was tandemly connected and which was equilibrated with 25 mM sodium acetate buffer, pH 5.0. Elution was performed by linearly increasing the concentration of NaCl in the buffer, and a purified fraction of Fab fragments of the SMB0002 antibody was obtained. Then, the obtained purified fraction was concentrated with a 5000 MWCO ultrafiltration membrane and loaded onto the gel filtration column Superdex 200 16/60 prep grade (GE Healthcare) equilibrated with 25m M HEPES buffer, pH 7.0, 100 mM NaCl. The column was eluted with the same buffer to obtain Fab fragments of SMB0002 for crystallization. All column operations were carried out at low temperature.

(4-2-3) Crystallization of the Complex of Adenosine and SMB0002 Fab Fragment A sample of SMB0002 Fab for crystallization purified by the above-described method was concentrated with a 5000 MWCO ultrafiltration membrane to A280=22.3. Then, adenosine was added at a final concentration of 0.9 mM, and crystallization was carried out using the sitting drop vapor diffusion method. Using a reservoir solution of 20% PEG3350 and 0.2M ammonium citrate dibasic, crystallization drops were prepared by mixing at reservoir solution: crystallization sample=0.2 µl:0.2 µl by Hydra II Plus One (MATRIX). The drops were allowed to stand at 20° C. and plate-like crystals were successfully obtained.

(4-2-4) Measurement of X-Ray Diffraction Data from the Crystal of the Complex of SMB0002 Fab Fragment and Adenosine An obtained single crystal of the complex of SMB0002 Fab fragment and adenosine was immersed in a solution of 0.2 M ammonium citrate dibasic, 0.025 M HEPES pH 7, 25% PEG3350, 0.1 M NaCl, 1 mM Adenosine, and 16% Glycerol. Then, the single crystal was scooped together with the solution using a pin equipped with a minute nylon loop, and frozen in liquid nitrogen. X-ray diffraction data were measured at BL-17A of the synchrotron radiation facility Photon Factory of the High Energy Accelerator Research Organization. The frozen state was maintained through the measurement by placing in a stream of nitrogen gas at −178° C. A total of 300 X ray diffraction images were collected using the CCD detector Quantum 315r (ADSC) attached to the beamline by rotating the crystal by 0.6°. Lattice constant determination, diffraction spot indexing, and diffraction data processing from the obtained diffraction images were performed using the programs Xia2 (J. Appl. Cryst. (2010) 43, 186-190), XDS Package (Acta Cryst. (2010) D66, 125-132), and Scala (Acta Cryst. (2006) D62, 72-82). Ultimately, this successfully yielded diffraction intensity data of up to 1.76 angstrom resolution. This crystal belonged to space group P1 with lattice constants a=49.960 angstrom, b=105.730 angstrom, c=106.166 angstrom, α=62.58°, β3=77.29°, γ=77.49°.

(4-2-5) X-Ray Crystallographic Analysis of the Complex of Adenosine and SMB0002 Fab Fragment To determine the structure of the SMB0002 Fab fragment and adenosine complex crystal, the molecular replacement method was carried out using the program Phaser (J. Appl. Cryst. (2007) 40, 658-674). The number of complexes in the asymmetrical unit was estimated to be four from the size of the obtained crystal lattice and the molecular weight of the SMB0002 Fab fragment. A homology model of the antibody was constructed using Discovery Studio 3.5 (Accelrys). The model was divided into the variable region and constant region, and using the coordinate of each structure as search model, their orientation and position in the crystal lattices were determined based on the rotation function and translation function. Further, the crystallographic reliability factor R for the diffraction intensity data at 25 to 3.0 angstroms was 46.36% and Free R was 46.10%, when rigid body refinement was carried out on the obtained initial structural model in which the variable region and constant region portions were independently moved. Then, structural model refinement was carried out by repeating the following processes: structural refinement using the program REFMAC5 (Acta Cryst. (2011) D67, 355-367), and revision of the structural model performed using the program Coot (Acta Cryst. (2010) D66, 486-501) by referring to the electron density maps having as coefficients 2Fo-Fc and Fo-Fc, which were calculated based on the experimentally determined structural factor Fo, the structural factor Fc which were calculated from the model, and the phase calculated from the model. Ultimately, with 168160 diffraction intensity data at 25 to 1.76 angstrom resolution, the crystallographic reliability factor R and Free R of the structural model containing 14681 non-hydrogen atoms were 19.82% and 23.15% respectively.

(4-2-6) Identification of the Interaction Sites of SMB0002 and Adenosine

Ultimately, the crystallographic structure of the complex of SMB0002 Fab fragment and adenosine was determined at a resolution of 1.76 angstrom. There were four SMB0002 Fab fragments in the asymmetrical unit of the crystal, adenosine was bound to all of them, and the binding mode was almost the same for all. The crystallographic structure showed that adenosine bound in a pocket formed between the H chain and L chain of the Fab fragment of the antibody, in a manner that the adenine ring is oriented toward the depth of the pocket. As shown in FIG. 11A, the adenine ring moiety of adenosine is recognized by each of the side chains of H-chain A33, I50, W58, and Y100 and L-chain Y95c and N96, as well as by each of the main chains of H-chain G99 and T100a of the antibody. It was revealed that robust recognition was achieved in particular by formation of two hydrogen bonds between the side chain of L-chain N96 and both N at position 1 and NH2 at position 6 of adenosine, as well as by formation of hydrogen bonds between the main chain carbonyl oxygen and amide NH group of H-chain T100a and NH2 at position 6 and N at position 7 of the adenine ring respectively. Furthermore, the adenine ring is surrounded by each of the side chains of H-chain A33, I50, W58, Y100 and L-chain Y95c of the antibody, and forms van der Waals interactions and CH-πc interactions with these residues. Both H-chain G99 and T100a form an interaction with the adenine ring in their main chain moieties. However, since G99 has a φ-Ψ angle characteristic of Gly on the Ramachandran plot, it is thought to be important in maintaining the loop structure of the H-chain CDR3 upon binding to adenosine. Moreover, the side chain of T100a is also thought to play an important role in maintaining the loop structure of the H-chain CDR3 upon binding to adenosine by forming an interaction with other residues in the H-chain CDR3. As shown in FIG. 11B, the ribose moiety of adenosine is recognized by the respective side chains of H-chain S56 and W58 and L-chain Y95c, as well as the T57 main chain and H-chain G52. Interaction with these residues is primarily attributed to van der Waals interaction; however, formation of a hydrogen bond is seen, albeit weak, between the side chain of H-chain S56 and the 3' OH of ribose. H-chain G52, including its Cα atom, forms multiple van der Waals interactions with the ribose moiety, and is thought to play an important role in adenosine recognition. Meanwhile, H-chain T57 forms an interaction with the ribose moiety at its main chain only, and the side chain is not directly involved in the binding.

As shown in Example 4-1, the antibody binds not only to adenosine but also to AMP, though with reduced binding activity. In the crystallographic structure, the 5' OH of ribose in adenosine is forming an intramolecular interaction with N at position 3 of the adenine ring moiety; however, this binding cannot be formed in AMP and the position of the 5' O slightly changes so that, as a result, the phosphate group of AMP is inferred to be present in the region indicated by the dotted line in FIG. 11B. Since this region is in a position that allows interaction with residues in the H-chain CDR2 and L-chain CDR3, binding to AMP can be expected to be increased by introducing appropriate mutations into the H-chain CDR2 and L-chain CDR3.

From the results described above, the mode of adenosine recognition by the antibody has been revealed and the amino acid residues of the antibody variable region that are greatly involved in adenosine binding have been identified. The amino acid residues that are greatly involved in adenosine binding include: A33, I50, G52, S56, T57, W58, G99, Y100, and T100a (Kabat numbering) in the H chain, and Y95c and N96 (Kabat numbering) in the L chain. Moreover, predicted residues that are possibly located close to the 5' phosphate group in AMP were: D54, S55, S56, T57, and W58 of the H-chain CDR2, and G95a, W95b, and Y95c of the L-chain CDR3. Modification of these residues may result in increased binding with AMP.

Furthermore, by performing similar considerations for ADP and ATP based on crystallographic structures, modifications that can increase the binding to ADP and ATP could also be predicted.

(4-3) Humanization of Rabbit-Derived Antibody SMB0002

SMB0002 is a rabbit-derived antibody; thus, to construct a human antibody library, the sequence was humanized by a method known to those skilled in the art (EP Patent Publication No. 239400; International Publication Nos. WO1996/002576; WO1993/012227; WO1992/003918; WO1994/002602; WO1994/025585; WO1996/034096; WO1996/033735; WO1992/001047; WO1992/020791; WO1993/006213; WO1993/011236; WO1993/019172; WO1995/001438; WO1995/015388; Cancer Res., (1993) 53, 851-856; BBRC., (2013) 436 (3):543-50; etc.).

Humanized SMB0002 (heavy chain variable region sequence: SEQ ID NO: 85; light chain variable region sequence: SEQ ID NO: 86) was expressed and purified by the method described in Reference Example 1-1. Binding of humanized SMB0002 to adenosine and AMP was measured and analyzed by a method using Biacore T200 (GE Healthcare). Protein A (Invitrogen) immobilized in an appropriate amount onto a Sensor chip CM5 (GE Healthcare) by the amine coupling method was allowed to capture the antibody of interest, and the interaction with the antigen adenosine, AMP, ADP, or ATP was observed. The running buffer used was 50 mM Tris-HCl, 150 mM NaCl, 0.02% (w/v) Tween 20, pH 7.6, for adenosine and AMP, and 50 mM Tris-HCl, 150 mM NaCl, 0.02% (w/v) Tween 20, 2 mM $MgCl_2$, pH 7.6, for ADP and ATP. All measurements were carried out at 25° C. The antigens were diluted with the running buffer.

Diluted antigen solutions and the running buffer as a blank were added at a flow rate of 30 μL/min for 75 seconds to the antibody captured on the sensor chip, and the binding between the antibody and antigens was observed. Then, the running buffer was run at a flow rate of 30 μL/min for five minutes, and dissociation of the antigens from the antibody was observed. Next, 10 mM glycine-HCl, pH 1.5, was added at a flow rate of 30 μL/min for 30 seconds to regenerate the sensor chip. Kinetic parameters such as the association rate constant ka (1/Ms) and the dissociation rate constant kd (1/s) were calculated based on the sensorgrams obtained by the measurements. The dissociation constant KD (M) was calculated from these constants. Each parameter was calculated using Biacore T200 Evaluation Software (GE Healthcare).

The result showed that humanized SMB0002 bound to adenosine, AMP, ADP, and ATP. Sensorgrams observed when samples with adenosine concentrations of 200, 100, 50 (duplicate), 25, 12.5, 6.25, and 3.125 nM interacted with the clone are summarized in FIG. 12. The KD of humanized SMB0002 toward adenosine was $7.5 \times 10^{-9}$ M. Next, sensorgrams observed when samples with AMP concentrations of 500, 250, 125 (duplicate), 62.5, 31.3, 15.6, and 7.8 μM interacted with the clone are summarized in FIG. 13. The KD of humanized SMB0002 toward AMP was $3.5 \times 10^{-5}$ M. Next, sensorgrams observed when samples with ADP concentrations of 1000 (duplicate), 500, 250, 125, and 62.5 μM interacted with the clone are summarized in FIG. 14. The KD of humanized SMB0002 toward ADP was $7.9 \times 10^{-5}$ M. Finally, sensorgrams observed when samples with ATP concentrations of 1000 (duplicate), 500, 250, 125, and 62.5 μM interacted with the clone are summarized in FIG. 15. The KD of humanized SMB0002 toward ATP was $1.4 \times 10^{-4}$ M. Since humanized SMB0002 had binding activity toward adenosine, AMP, ADP, and ATP, the sequence was used as a template sequence for constructing a human antibody library.

(4-4) Assessment of Comprehensive Variants for Designing a Library Based on the Result of X-Ray Crystallographic Structure Analysis The crystallographic structure of the complex of adenosine and the adenosine-binding antibody SMB0002 was analyzed in Example (4-2). The mode of recognition by which the antibody recognizes adenosine (and AMP) and the amino acid residues of the antibody variable region that are presumed not to be significantly involved in adenosine (and AMP) binding were deduced based on the result of crystallographic structure analysis. It was conceived that, by comprehensively evaluating variants whose residues located close to the adenosine recognition site are substituted with each of the amino acids, the sites that can be made into a library and the amino acids that can be made into a library could be determined. Specifically, it was conceived that, by evaluating the sites that are not greatly involved in the binding toward adenosine, AMP, ADP, or ATP, the sites in which amino acids other than those of the native sequence that may be involved in binding but do not significantly reduce the binding toward adenosine, AMP, ADP, or ATP (do not render the binding to zero) are present, as well as the amino acids, the sites that can be made into a library and the amino acids that can be made into a library could be determined. Several variants were generated by introducing modifications to these residues in the humanized SMB0002 prepared in Example (4-3).

Of the sites in the heavy chain, the modified sites (the sites shown according to Kabat numbering and indicated as "Kabat" in the table), the amino acids before modification at these sites (the amino acids indicated as "native sequence" in the table), and the amino acids after modification (the amino acids indicated as "altered amino acids" in the table) are shown in Table 4.

TABLE 4

| | HCDR1 | | HCDR2 | | | | | | | | | HCDR3 | | | | | | | | | | |
|---|---|---|---|---|---|---|---|---|---|---|---|---|---|---|---|---|---|---|---|---|---|---|
| | \multicolumn{22}{c}{Kabat} | | | | | | | | | | | | | | | | | | | | | |
| | 31 | 32 | 53 | 54 | 55 | 56 | 57 | 59 | 61 | 62 | 65 | 96 | 97 | 98 | 99 | 100 | 100a | 100b | 100c | 100d | 101 | 102 |
| | \multicolumn{22}{c}{Native sequence} | | | | | | | | | | | | | | | | | | | | | |
| | N | Y | A | D | S | S | T | Y | S | W | G | R | F | V | G | Y | T | N | A | F | D | P |
| Altered amino acid | A | A |   | A | A | A | A | A | A | A | A | A | A | A | A | A | A | A |   |   | A | A |
|  | D | D | D | D |   | D | D | D | D | D | D | D | D | D | D | D |   |   |   |   |   | D |
|  | E | E | E | E | E | E | E | E |   | E | E | E | E | E | E | E |   |   |   |   | E | E |
|  | F | F | F | F | F | F | F | F | F | F | F | F |   | F | F | F |   |   |   |   | F | F |
|  | G | G | G | G | G | G | G | G |   | G |   | G | G | G |   | G | G | G | G | G | G | G |
|  | H | H | H | H | H | H | H | H | H | H |   | H | H | H | H | H |   |   |   |   | H | H |
|  | I | I | I | I | I | I | I | I | I |   |   | I | I | I | I | I |   |   |   |   | I | I |
|  | K | K | K | K | K | K | K | K | K | K |   | K | K | K | K | K |   |   |   |   | K | K |
|  | L | L | L | L | L | L | L | L | L |   |   | L | L | L | L | L |   |   |   |   | L | L |
|  | N |   | N |   |   | N | N |   | N |   |   | N | N | N | N |   | N |   |   |   | N | N |
|  | P | P | P | P | P | P | P | P | P | P |   |   | P | P | P | P |   |   |   |   | P | P |
|  | Q | Q | Q | Q | Q | Q | Q | Q | Q | Q |   | Q | Q | Q | Q | Q |   |   |   | Q | Q | Q |
|  | R | R | R | R | R | R | R | R | R |   |   | R |   | R | R | R |   |   |   |   | R | R |
|  | S | S | S | S |   |   | S | S |   |   |   | S | S | S | S | S | S | S |   |   | S | S |
|  | T | T | T | T | T | T |   | T | T |   |   | T | T | T | T | T |   | T |   |   | T | T |
|  | V | V | V | V | V | V | V | V | V | V |   | V | V | V |   | V | V |   |   |   | V | V |
|  | W | W | W | W | W | W | W | W | W |   |   | W | W | W | W | W |   |   |   |   | W | W |
|  | Y | Y |   | Y | Y | Y | Y |   | Y |   |   | Y | Y | Y | Y |   |   |   |   |   | Y | Y |

Of the sites in the light chain, the modified sites (the sites shown according to Kabat numbering and indicated as "Kabat" in the table), the amino acids before modification at these sites (the amino acids indicated as "native sequence" in the table), and the amino acids after modification (the amino acids indicated as "altered amino acids" in the table) are shown in Table 5.

TABLE 5

| | | LCDR1 | | | | | LCDR3 | | |
| --- | --- | --- | --- | --- | --- | --- | --- | --- | --- |
| | | | | | Kabat | | | | |
| | | 28 | 29 | 32 | 93 | 94 | 95 | 95a | 95b | 95c |
| | | | | | Native sequence | | | | |
| | | W | N | Y | A | N | S | G | W | Y |
| Altered amino acid | A | A | A | A | | A | A | A | A | A |
| | D | D | D | D | D | D | D | D | D | D |
| | E | E | E | E | E | E | E | E | E | E |
| | F | F | F | F | F | F | F | F | F | F |
| | G | G | G | G | G | G | G | | G | G |
| | H | H | H | H | H | H | H | H | H | H |
| | I | I | I | I | I | I | I | I | I | I |
| | K | K | K | K | K | K | K | K | K | K |
| | L | L | L | L | L | L | L | L | L | L |
| | N | N | | | | | N | N | N | N |
| | P | P | P | P | P | P | P | P | P | P |
| | Q | Q | Q | Q | Q | Q | Q | Q | Q | Q |
| | R | R | R | R | R | R | R | R | R | R |
| | S | S | S | S | S | S | | | S | S |
| | T | T | T | T | T | T | T | | T | T |
| | V | V | V | V | V | V | V | V | V | V |
| | W | | W | W | W | W | W | W | | W |
| | Y | Y | Y | | Y | Y | Y | Y | Y | |

The binding of each variant expressed and purified by the method described in Reference Example 1 described below to adenosine and AMP was measured by the method using Biacore described in Example 4-3 except that the $MgCl_2$ concentration was 2 mM. As a result of the measurements, the affinity of each variant toward adenosine and AMP was calculated as KD value. The result of the comparison of the KD values for adenosine between each variant of the heavy chain and the parental sequence, humanized SMB0002, is shown in Table 6, and the result of the comparison of the KD values for AMP is shown in Table 7. The result of the comparison of the KD values for adenosine of each variant of the light chain and humanized SMB0002 is shown in Table 8, and the result of the comparison of the KD values for AMP is shown in Table 9.

TABLE 6

| | | HCDR1 | | | | HCDR2 Kabat | | | | | | HCDR3 |
|---|---|---|---|---|---|---|---|---|---|---|---|---|
| | | 31 | 32 | 53 | 54 | 55 | 56 | 57 | 59 | 61 | 62 | 65 | 96 |
| | | | | | | Native sequence | | | | | | |
| | | N | Y | A | D | S | S | T | Y | S | W | G | R |
| Altered amino acid | A | 0.9 | 0.1 | | 0.0 | 0.5 | 0.4 | 0.3 | 0.9 | 1.0 | 0.7 | 0.8 | 0.5 |
| | D | 0.6 | 0.1 | 0.5 | | 0.5 | 0.4 | 0.2 | 0.7 | 0.0 | 1.0 | 0.7 | 0.2 |
| | E | 0.7 | 0.1 | 0.5 | 0.3 | 0.5 | 0.4 | 0.2 | 0.8 | | 0.9 | 0.7 | 1.0 |
| | F | 0.7 | 0.7 | 0.2 | 0.5 | 0.5 | 0.2 | 0.2 | 0.6 | 1.1 | 0.8 | 0.9 | 1.6 |
| | G | 0.5 | 0.3 | 0.8 | 0.3 | 0.6 | 0.3 | 0.2 | 0.7 | | 0.9 | | 0.7 |
| | H | 0.4 | 0.7 | 0.2 | 0.3 | 0.6 | 0.3 | 0.2 | 0.9 | 0.6 | | | 0.7 |
| | I | 1.1 | 0.3 | 0.4 | 0.2 | 0.4 | 0.2 | 0.2 | 0.7 | | | 0.7 | 0.2 |
| | K | 0.9 | 0.5 | 0.8 | 0.1 | 0.3 | 0.4 | 0.2 | 0.6 | 0.5 | | 0.7 | 0.9 |
| | L | 0.9 | 0.2 | 0.2 | 0.4 | 0.3 | 0.6 | 0.2 | 0.6 | 0.6 | | 0.7 | 0.6 |
| | N | | 0.5 | | | | 0.3 | 0.2 | | 0.8 | | 0.7 | 0.4 |
| | P | 0.3 | 1.6 | 0.3 | 0.1 | 0.2 | 0.1 | 0.2 | 0.1 | 0.8 | | | 0.0 |
| | Q | 1.2 | 0.3 | 0.5 | 0.4 | 0.3 | 0.3 | 0.5 | 0.7 | 1.1 | | 0.8 | 0.6 |
| | R | 0.8 | 0.8 | 0.5 | 0.7 | 0.4 | 0.5 | 0.3 | 0.6 | 0.9 | | 0.8 | |
| | S | 1.0 | 0.2 | 0.3 | 0.4 | | | 0.3 | 0.9 | | | | 0.6 |
| | T | 1.0 | 0.3 | 0.4 | 0.5 | 0.3 | 0.5 | | 0.6 | 1.1 | | 0.6 | 0.9 |
| | V | 0.6 | 0.2 | 0.4 | 0.3 | 0.3 | 0.2 | 0.5 | 0.6 | 1.0 | | 0.6 | 0.4 |
| | W | 0.6 | 0.4 | 0.0 | 0.2 | 0.1 | 0.1 | 0.2 | 0.5 | 0.9 | | 0.7 | 0.9 |
| | Y | 0.7 | | 0.2 | 0.2 | 0.3 | 0.2 | 0.2 | | 1.0 | | | 0.9 |

| | | HCDR3 Kabat | | | | | | | | |
|---|---|---|---|---|---|---|---|---|---|---|
| | | 97 | 98 | 99 | 100 | 100a | 100b | 100c | 100d | 101 | 102 |
| | | | | | Native sequence | | | | | | |
| | | F | V | G | Y | T | N | A | F | D | P |
| Altered amino acid | A | 0.3 | 0.7 | 0.4 | 0.0 | 0.2 | 0.1 | | | 0.7 | 0.2 |
| | D | 0.3 | 0.4 | 0.4 | 0.0 | | | | | | 0.3 |
| | E | 0.3 | 0.5 | 0.2 | 0.0 | | | | | 0.6 | 0.2 |
| | F | | 0.6 | 0.1 | 0.9 | | | | | 0.5 | 0.1 |
| | G | 0.2 | 0.4 | | 0.0 | 0.0 | 0.1 | 0.1 | 0.0 | 0.6 | 0.2 |
| | H | 0.5 | 0.6 | 0.2 | 0.2 | | | | | 0.6 | 0.1 |
| | I | 0.4 | 0.9 | 0.1 | 0.0 | | | | | 0.5 | 0.2 |
| | K | 0.4 | 0.7 | 0.1 | 0.0 | | | | | 0.6 | 0.2 |
| | L | 0.3 | 0.7 | 0.1 | 0.0 | | | | | 0.5 | 0.1 |
| | N | 0.4 | 0.6 | | 0.0 | | | | | 0.5 | 0.3 |
| | P | 0.1 | 0.8 | 0.1 | 0.0 | | | | | 0.0 | |
| | Q | 0.4 | 0.8 | 0.1 | 0.0 | | | | 0.1 | 0.5 | 0.2 |

TABLE 6-continued

| | | | | | | | | |
|---|---|---|---|---|---|---|---|---|
| R | 0.3 | 0.9 | 0.1 | 0.0 | | | 0.4 | 0.2 |
| S | 0.3 | 0.9 | 0.3 | 0.0 | 0.2 | 0.1 | 0.7 | 0.2 |
| T | 0.3 | 0.6 | 0.1 | 0.0 | | 0.1 | 0.4 | 0.1 |
| V | 0.4 | | 0.0 | 0.0 | 0.5 | | 0.4 | 0.1 |
| W | 0.5 | 0.5 | 0.0 | 0.1 | | | 0.5 | 0.1 |
| Y | 0.4 | 0.5 | 0.1 | | | | 0.6 | 0.1 |

TABLE 7

| | | HCDR1 | | HCDR2 Kabat | | | | | | | | | HCDR3 |
|---|---|---|---|---|---|---|---|---|---|---|---|---|---|
| | | 31 | 32 | 53 | 54 | 55 | 56 | 57 | 59 | 61 | 62 | 65 | 96 |
| | | | | | | | Native sequence | | | | | | |
| | | N | V | A | D | S | S | I | Y | S | W | G | R |
| Altered Amino Acid | A | 0.9 | 0.3 | | 0.0 | 0.9 | 1.1 | 0.4 | 1.0 | 1.3 | 0.9 | 0.9 | 0.6 |
| | D | 0.6 | 0.2 | 2.1 | | 0.8 | 0.9 | 0.3 | 0.7 | 0.0 | 1.0 | 1.0 | 0.2 |
| | E | 1.1 | 0.2 | 1.6 | 1.2 | 0.6 | 0.8 | 0.2 | 1.0 | | 0.9 | 1.1 | 1.0 |
| | F | 1.1 | 1.1 | 0.3 | 0.8 | 0.6 | 0.2 | 0.2 | 0.9 | 1.3 | 1.0 | 1.1 | 2.0 |
| | G | 0.6 | 0.3 | 2.0 | 1.0 | 0.8 | 0.6 | 0.3 | 0.8 | | 1.2 | | 0.8 |
| | H | 1.1 | 0.9 | 0.2 | 1.1 | 1.0 | 0.6 | 0.2 | 1.1 | 1.3 | | | 0.8 |
| | I | 1.3 | 0.5 | 0.7 | 0.3 | 0.4 | 0.3 | 0.3 | 0.7 | | | 0.8 | 0.3 |
| | K | 1.0 | 1.4 | 2.7 | 0.0 | 0.6 | 0.9 | 0.4 | 0.8 | 1.2 | | 0.9 | 1.3 |
| | L | 1.1 | 0.3 | 0.5 | 0.7 | 0.6 | 0.9 | 0.4 | 0.7 | 1.2 | | 0.9 | 0.8 |
| | N | | 0.8 | | | | 0.7 | 0.3 | | 1.6 | | 0.8 | 0.5 |
| | P | 0.3 | 3.2 | 0.6 | 0.3 | 0.2 | 0.1 | 0.2 | 0.2 | 1.2 | | | 0.0 |
| | Q | 1.2 | 0.3 | 1.2 | 0.8 | 0.5 | 0.6 | 0.6 | 0.9 | 1.6 | | 0.7 | 0.7 |
| | R | 1.2 | 1.4 | 1.2 | 0.0 | 0.6 | 1.2 | 0.4 | 0.9 | 1.2 | | 0.8 | |
| | S | 1.3 | 0.3 | 0.7 | 1.0 | | | 0.4 | 1.0 | | | | 1.0 |
| | T | 1.6 | 0.4 | 0.9 | 1.5 | 0.7 | 1.1 | | 1.0 | 1.2 | | 0.9 | 1.3 |
| | V | 1.5 | 0.6 | 0.6 | 0.4 | 0.4 | 0.3 | 0.6 | 0.8 | 1.3 | | 0.8 | 0.6 |
| | W | 1.4 | 1.2 | 0.0 | 0.4 | 0.0 | 0.1 | 0.2 | 1.1 | 1.1 | | 0.7 | 1.1 |
| | Y | 1.3 | | 0.4 | 0.4 | 0.3 | 0.2 | 0.2 | | 1.1 | | | 1.0 |

| | | HCDR3 Kabat | | | | | | | | | |
|---|---|---|---|---|---|---|---|---|---|---|---|
| | | 97 | 98 | 99 | 100 | 100a | 100b | 100c | 100d | 101 | 102 |
| | | | | | | Native sequence | | | | | |
| | | F | V | G | Y | T | N | A | F | D | P |
| Altered Amino Acid | A | 0.3 | 0.7 | 0.1 | 0.0 | 0.1 | 0.0 | | | 2.5 | 0.2 |
| | D | 0.3 | 0.4 | 0.1 | 0.0 | | | | | | 0.5 |
| | E | 0.3 | 0.6 | 0.2 | 0.0 | | | | | 1.0 | 0.2 |
| | F | | 07 | 0.1 | 1.3 | | | | | 0.8 | 0.2 |

TABLE 7-continued

| | 1 | 2 | 3 | 4 | 5 | 6 | 7 | 8 | 9 |
|---|---|---|---|---|---|---|---|---|---|
| G | 0.3 | 0.4 | 0.0 | 0.0 | 0.0 | 0.1 | 0.0 | 0.7 | 0.3 |
| H | 0.9 | 0.8 | 0.1 | 0.1 | | | | 1.1 | 0.2 |
| I | 0.5 | 1.0 | 0.0 | 0.0 | | | | 0.8 | 0.2 |
| K | 0.6 | 0.8 | 0.1 | 0.0 | | | | 09 | 0.3 |
| L | 0.3 | 0.9 | 0.1 | 0.0 | | | | 0.7 | 0.2 |
| N | 0.4 | 0.7 | | 0.0 | | | | 0.8 | 0.4 |
| P | 0.1 | 0.8 | 0.1 | 0.0 | | | | 0.0 | |
| Q | 0.4 | 09 | 0.1 | 0.0 | | | 0.0 | 0.7 | 0.3 |
| R | 0.4 | 1.0 | 0.1 | 0.0 | | | | 0.7 | 0.3 |
| S | 0.6 | 0.3 | 0.1 | 0.0 | 0.2 | 0.0 | | 0.8 | 0.3 |
| T | 0.5 | 0.8 | 0.0 | 0.0 | | 0.0 | | 0.6 | 0.2 |
| V | 0.3 | | 0.0 | 0.0 | 0.5 | | | 0.5 | 0.2 |
| W | 0.5 | 0.1 | 0.0 | 0.0 | | | | 0.8 | 0.2 |
| Y | 0.5 | 0.1 | 0.0 | | | | | 0.9 | 0.2 |

TABLE 8

| | | LCDR1 | | | | | LCDR3 | | |
|---|---|---|---|---|---|---|---|---|---|
| | | | | | Kabat | | | | |
| | | 28 | 29 | 32 | 93 | 94 | 95 | 95a | 95b | 95c |
| | | | | | Native sequence | | | | |
| | | W | N | Y | A | N | S | G | W | Y |
| Altered amino acid | A | 0.3 | 0.7 | 0.2 | | 0.9 | 0.7 | 0.5 | 0.7 | 0.1 |
| | D | 0.1 | 0.7 | 0.1 | 0.4 | 1.0 | 0.6 | 0.5 | 0.4 | 0.1 |
| | E | 0.1 | 0.7 | 0.2 | 0.4 | 0.7 | 0.7 | 0.5 | 0.6 | 0.1 |
| | F | 0.8 | 0.4 | 0.7 | 0.6 | 0.7 | 0.4 | 0.4 | 0.5 | 0.6 |
| | G | 0.1 | 0.7 | 0.2 | 0.3 | 1.1 | 0.9 | | 0.7 | 0.1 |
| | H | 0.6 | 0.6 | 0.4 | 0.8 | 0.7 | 0.8 | 1.0 | 0.8 | 0.3 |
| | I | 0.1 | 0.4 | 0.0 | 0.1 | 0.6 | 0.8 | 0.5 | 0.7 | 0.2 |
| | K | 0.3 | 0.6 | 0.1 | 0.0 | 0.8 | 0.7 | 0.5 | 0.5 | 0.5 |
| | L | 0.2 | 0.6 | 0.1 | 0.7 | 0.6 | 0.8 | 0.6 | 0.5 | 1.0 |
| | N | 0.3 | | | | | 0.5 | 1.0 | 0.5 | 0.6 |
| | P | 0.1 | 0.3 | 0.1 | 0.1 | 0.3 | 0.6 | 0.3 | 0.4 | 0.1 |
| | Q | 0.1 | 0.8 | 0.1 | 0.8 | 0.6 | 0.6 | 0.7 | 0.8 | 0.0 |
| | R | 0.2 | 0.7 | 0.1 | 1.3 | 0.6 | 0.6 | 0.8 | 1.1 | 0.2 |
| | S | 0.6 | 0.7 | 0.2 | 0.5 | 0.9 | | | 0.8 | 0.1 |
| | T | 0.5 | 0.4 | 0.1 | 0.7 | 0.7 | 0.7 | | 0.9 | 0.1 |
| | V | 0.6 | 0.4 | 0.0 | 0.5 | 0.4 | 0.7 | 0.6 | 0.7 | 0.2 |
| | W | | 0.6 | 0.1 | 0.0 | 0.7 | 0.5 | 0.5 | | 0.1 |
| | Y | 0.7 | 0.7 | | | 0.8 | 0.7 | 0.3 | 0.3 | 1.0 |

TABLE 9

| | | LCDR1 | | | | | LCDR3 | | |
|---|---|---|---|---|---|---|---|---|---|
| | | | | | Kabat | | | | |
| | | 28 | 29 | 32 | 93 | 94 | 95 | 95a | 95b | 95c |
| | | | | | Native sequence | | | | |
| | | W | N | Y | A | N | S | G | W | Y |
| Altered amino acid | A | 0.4 | 0.8 | 0.2 | | 1.3 | 1.4 | 0.8 | 1.2 | 0.2 |
| | D | 0.1 | 1.0 | 0.1 | 0.8 | 1.2 | 1.2 | 0.8 | 1.0 | 0.1 |
| | E | 0.1 | 1.0 | 0.2 | 0.8 | 1.2 | 0.9 | 1.0 | 1.2 | 0.0 |
| | F | 0.9 | 0.6 | 0.9 | 1.0 | 1.3 | 0.3 | 1.1 | 0.9 | 1.1 |
| | G | 0.1 | 1.2 | 0.2 | 0.5 | 1.5 | 1.8 | | 1.0 | 0.1 |
| | H | 0.9 | 0.9 | 0.5 | 1.2 | 1.1 | 1.0 | 0.8 | 1.0 | 0.7 |
| | I | 0.2 | 0.6 | 0.1 | 0.1 | 0.9 | 0.8 | 0.5 | 0.9 | 0.3 |
| | K | 0.4 | 1.0 | 0.1 | 0.0 | 1.1 | 0.7 | 0.6 | 1.5 | 2.2 |
| | L | 0.3 | 1.2 | 0.1 | 0.9 | 1.3 | 1.8 | 1.4 | 1.3 | 1.9 |
| | N | 0.4 | | | | | 1.0 | 0.7 | 1.1 | 1.9 |
| | P | 0.1 | 0.5 | 0.1 | 0.0 | 0.5 | 1.4 | 0.4 | 0.8 | 0.3 |
| | Q | 0.1 | 1.0 | 0.1 | 1.3 | 1.5 | 1.2 | 1.0 | 1.4 | 0.0 |
| | R | 0.2 | 1.0 | 0.1 | 2.5 | 1.0 | 0.9 | 1.0 | 2.2 | 0.4 |
| | S | 0.5 | 1.0 | 0.3 | 1.0 | 1.6 | | | 1.6 | 0.1 |
| | T | 0.5 | 0.6 | 0.1 | 1.2 | 1.0 | 1.1 | | 1.4 | 0.1 |
| | V | 0.5 | 0.8 | 0.0 | 0.8 | 0.6 | 1.0 | 0.5 | 1.2 | 0.4 |
| | W | | 1.0 | 0.2 | 0.0 | 0.8 | 0.7 | 1.0 | | 0.1 |
| | Y | 1.0 | 0.9 | | | 1.3 | 1.4 | 0.5 | 0.4 | 0.9 |

(4-5) Library Design Based on Comprehensive Variant Evaluation

To design a library, sites that meet at least one of the conditions shown below were selected as library-constructible sites based on the information obtained in Example 4-4.

Condition 1: sites that are not greatly involved in the binding toward adenosine, AMP, ADP, or ATP, or sites in which amino acids other than those of the native sequence that may be involved in binding but do not significantly reduce the binding toward adenosine, AMP, ADP, or ATP (do not render the binding to zero) are present;

Condition 2: sites having a certain level of diversity of amino acid occurrence frequency as repertoire of the antibody; and Condition 3: sites that are not important for the formation of canonical structures.

From the evaluation results of Example (4-4), sites for which at least one or more variants exist, which variants have KD values toward adenosine and AMP both indicating more than 20% binding of the parent sequence (humanized SMB0002) toward adenosine and AMP, were judged to be modifiable sites that meet the above-described conditions. Of the amino acids substituted at these sites, the amino acids whose KD values toward adenosine and AMP both indicate more than 20% binding of the parent sequence (humanized SMB0002) toward adenosine and AMP were judged to be library-constructible amino acids (flexible residues that can be made to appear in the library). A library for obtaining ATP/AMP/ADP/adenosine switch antibodies is constructed by designing a library in which at least any one or more amino acids from among the amino acids contained in the amino acid repertoire, which includes the library-constructible amino acids selected from the above-described variant analysis (the flexible residues that can be made to appear in the library) and the amino acids of the non-modified antibody (i.e., the amino acids included in the native sequence of the humanized SMB0002), appear at the determined modifiable sites in the CDRs of the humanized SMB0002. The sites containing an amino acid repertoire in the heavy chain, and the amino acid repertoires at these sites are shown in Table 10. The sites containing an amino acid repertoire in the light chain, and the amino acid repertoires at these sites are shown in Table 11. In the tables, sites shown according to Kabat numbering indicated by "Kabat" represent modifiable sites; amino acids indicated by "native sequence" represent non-modified amino acids at these sites; and amino acids indicated by "library-constructible amino acids" represent library-constructible amino acids at these sites. A library, in which at least any one amino acid from among the amino acids contained in the selected amino acid repertoire appear at each of the modifiable sites, was designed.

TABLE 10

| | | HCDR1 | | HCDR2 | | | | | | | HCDR3 | | | | | | |
|---|---|---|---|---|---|---|---|---|---|---|---|---|---|---|---|---|---|
| | | | | | | | | Kabat | | | | | | | | | |
| | | 31 | 32 | 53 | 54 | 55 | 56 | 57 | 59 | 61 | 62 | 65 | 96 | 97 | 98 | 100 | 100a | 101 | 102 |
| | | | | | | | | Native sequence | | | | | | | | | |
| | | N | Y | A | D | S | S | T | Y | S | W | G | R | F | V | Y | T | D | P |
| Library-constructible amino acid | A | A | | | | A | A | A | A | A | A | A | A | A | A | | | A | |
| | D | D | | D | | D | D | | D | | D | D | D | D | D | | | | D |
| | E | E | | E | E | E | E | | E | | E | E | E | E | E | | | E | |
| | F | F | F | F | F | F | F | | F | F | F | F | F | | F | F | | F | |
| | G | G | G | G | G | G | | | G | | G | | G | G | G | | | G | |
| | H | H | H | | H | H | H | | H | H | | | H | H | H | | | H | |
| | I | I | I | I | I | I | I | I | I | | | I | | I | I | | | I | |
| | K | K | K | K | | K | K | K | K | K | | K | K | K | K | | | K | |
| | L | L | | L | L | L | L | L | L | | | L | L | L | L | | | L | |
| | N | | N | | | N | N | | N | | | N | N | N | N | | | N | N |
| | P | P | P | P | | | | | P | | | | P | | | | | | |
| | Q | Q | Q | Q | Q | Q | Q | Q | Q | | | Q | Q | Q | Q | | | Q | |
| | R | R | R | R | | R | R | R | R | R | | | R | R | R | | | R | |
| | S | S | | S | S | | | S | S | | | S | S | S | | S | S | | |
| | T | T | T | T | T | T | T | | T | T | | T | T | T | T | | | T | |

TABLE 10-continued

| | HCDR1 | | HCDR2 | | | | | | | | | HCDR3 | | | | | | |
|---|---|---|---|---|---|---|---|---|---|---|---|---|---|---|---|---|---|---|
| | | | | | | Kabat | | | | | | | | | | | | |
| | 31 | 32 | 53 | 54 | 55 | 56 | 57 | 59 | 61 | 62 | 65 | 96 | 97 | 98 | 100 | 100a | 101 | 102 |
| | | | | | | | Native sequence | | | | | | | | | | | |
| | N | Y | A | D | S | S | T | Y | S | W | G | R | F | V | Y | T | D | P |
| | V | V | V | V | V | V | V | V | | V | V | | V | V | | V | V | |
| | W | W | | | | | | | W | W | | W | W | | | | W | |
| | Y | Y | | Y | Y | Y | | | | Y | | | Y | Y | | | Y | |

TABLE 11

| | LCDR1 | | | LCDR3 | | | | | |
|---|---|---|---|---|---|---|---|---|---|
| | | | | Kabat | | | | | |
| | 28 | 29 | 32 | 93 | 94 | 95 | 95a | 95b | 95c |
| | | | | Native sequence | | | | | |
| | W | N | Y | A | N | S | G | W | Y |
| Library-constructible amino acid | A | A | A | | A | A | A | A | |
| | D | | D | D | D | D | D | D | |
| | E | | E | | E | E | E | E | |
| | F | F | F | F | F | F | F | F | F |
| | G | | G | G | G | G | | G | |
| | H | H | H | H | H | H | H | H | H |
| | I | | I | | I | I | I | I | |
| | K | K | | | K | K | K | K | K |
| | L | | L | L | L | L | L | L | L |
| | N | N | | | N | N | N | N | |
| | P | | P | | P | P | P | P | |
| | Q | | Q | Q | Q | Q | Q | Q | |
| | R | | R | R | R | R | R | R | |
| | S | S | | S | S | | | S | |
| | T | T | | T | T | T | | T | |
| | V | V | V | V | V | V | V | V | V |
| | W | | W | | W | W | W | | |
| | Y | Y | | Y | Y | Y | Y | Y | |

Genes containing each of the sequences included in the library designed in this manner are synthesized, and using the collection (library) of these individual genes as a template, a gene library is amplified with primers that can amplify each of VH and VL. The amplified gene library of rationally designed human antibody heavy chain variable regions and that of the human antibody light chain variable regions are introduced into appropriate phagemid vectors having both a human IgG-derived CHI sequence and a human IgG-derived light chain constant region sequence. A rationally designed library which enables to obtain antibodies which bind to antigens using adenosine, AMP, ADP or ATP as a switch is constructed by introducing these phagemid vectors into *Escherichia coli* by electroporation and then presenting Fab domains consisting of a human antibody variable region-constant region. Such a rationally designed library composed of diverse H chains and L chains having binding activities to adenosine, AMP, ADP, or ATP is thought to be useful as a library containing human antibodies that enable to efficiently obtain AMP/ADP/ATP/adenosine switch antibodies against arbitrary antigens, where adenosine, AMP, ADP, or ATP is sandwiched between the antibody and antigen as shown in FIG. 43. Moreover, since, as described above, SMB0002 binds not only to adenosine and AMP but also to ADP and ATP, it is also predicted to have binding activity to cAMP and ATP-gamma-S which are structurally similar to AMP, ADP, ATP, and adenosine. Thus, the library is considered to be useful for obtaining switch antibodies whose binding activity toward an arbitrary target antigen varies depending on the presence or absence of any one or more small molecules of ATP, ADP, AMP, cAMP, adenosine, and ATP-gamma-S.

[Example 5] Design of Library for Obtaining AMP/ADP/ATP/Adenosine Switch Antibodies by Panning with Molecules Acting as a Switch A method which involves designing library sites by comprehensive alteration and constructing a library using as template an antibody showing binding ability toward adenosine, AMP, ADP, or ATP was described in Example 4. As a different approach, a method using panning on molecules that act as a switch is also useful as a method for generating a library.

(5-1) X-Ray Crystallographic Structure Analysis of the Adenosine-Binding Antibody SMB0002

The crystallographic structure of the complex of adenosine and the adenosine-binding antibody SMB0002 was revealed in Example 4-2. The mode of recognition by which the antibody recognizes adenosine (and AMP) and the amino acid residues of the antibody variable region that are presumed not to be significantly involved in adenosine (and AMP) binding were deduced based on the result of crystallographic structure analysis.

SMB0002 is a rabbit-derived antibody; thus, to construct a human antibody library, the sequence was humanized by a method known to those skilled in the art (as described above).

To design a library, sites that meet at least one of the following conditions are selected as library-constructible sites.

Condition 1: sites that are not greatly involved in the binding toward adenosine, AMP, ADP, or ATP, or sites in which amino acids other than those of the native sequence are present and which may be involved in binding but which do not significantly reduce the binding toward adenosine, AMP, ADP, or ATP (do not render the binding to zero);

Condition 2: sites having a certain level of diversity of amino acid occurrence frequency as repertoire of the antibody; and Condition 3: sites that are not important for the formation of canonical structures.

First, a library is designed, in which the occurrence of nucleotides for the amino acids at sites in the CDR1, CDR2, or CDR3 among the sites contained in the humanized SMB0002 sequence and fulfilling the above conditions in the heavy chain, and which are not greatly involved in the binding toward adenosine, AMP, ADP, or ATP, are limited to only particular nucleotides. Examples include NNK and TRIM libraries (Gonzalez-Munoz A et al. MAbs 2012; Lee C V et al. J Mol Biol. 2004; Knappik A. et al. J Mol Biol. 2000; Tiller T et al. MAbs 2013). Genes of the collection of designed gene sequences are synthesized (heavy chain variable region library), combined with the light chain variable region sequence of the humanized SMB0002 (the parental sequence, SEQ ID NO: 86), and introduced into appropriate phagemid vectors having a human IgG-derived CH1 sequence and a human IgG-derived light chain constant region sequence. These phagemid vectors are introduced into *Escherichia coli* by electroporation to construct a phage-display library of human antibody heavy chain variable regions capable of binding to antigens using any one of adenosine, AMP, ADP, and ATP as a switch.

Then, a library is designed, in which the occurrence of nucleotides for the amino acids at sites in the CDR1, CDR2, or CDR3 among the sites contained in the humanized SMB0002 sequence and fulfilling the above conditions in the light chain, and which are not greatly involved in the binding toward adenosine, AMP, ADP, or ATP, are limited to only particular nucleotides. Examples include NNK and TRIM libraries. Genes of the collection of designed gene sequences are synthesized (light chain variable region library), combined with the heavy chain variable region sequence of the humanized SMB0002 (the parental sequence, SEQ ID NO: 85), and introduced into appropriate phagemid vectors having a human IgG-derived CH1 sequence and a human IgG-derived light chain constant region sequence. These phagemid vectors are introduced into *Escherichia coli* by electroporation to construct a phage-display library of human antibody light chain variable regions capable of binding to antigens using any one of adenosine, AMP, ADP, and ATP as a switch.

Panning is performed using biotinylated ATP, biotinylated ADP, biotinylated AMP, or biotinylated adenosine to obtain a population of antibodies that specifically bind to ATP, ADP, AMP, or adenosine from each of the constructed phage-display libraries of heavy chain and light chain variable regions.

Biotinylated adenosine was prepared by the method described in Example 2-2-11.

ATP-PEG-biotin can be purchased from JenaBioscience (Catalog No. NU-926-BIO) and used. Like ATP, AMP and ADP have a structure in which a phosphate group is added to the 5' hydroxyl group of adenosine. Thus, it is preferable that an appropriate linker (such as a PEG linker) is attached to the phosphate group and then biotin is added to the end of the linker in the same fashion as in biotinylated ATP.

Phages are produced by *E. coli* retaining the constructed phagemids for phage-display. The phage population precipitated by adding 2.5 M NaCl/10% PEG to the culture solution of *E. coli* producing phages is diluted with TBS to obtain a phage library suspension. Then, BSA is added at a final concentration of 4% to the phage library suspension. Panning is performed using antigens immobilized onto magnetic beads. As magnetic beads, NeutrAvidin coated beads (Sera-Mag SpeedBeads NeutrAvidin-coated) or Streptavidin coated beads (Dynabeads M-280 Streptavidin) can be used.

Phages capable of binding to adenosine, AMP, ADP, or ATP are collected by panning. Specifically, by adding biotin-labeled antigens to the prepared phage library suspension, the phage library is contacted with adenosine, AMP, ADP, or ATP at room temperature for 60 minutes. BSA-blocked magnetic beads are added, and the antigen/phage complex is allowed to bind to the magnetic beads at room temperature for 15 minutes. The beads are washed with 1 mL of TBST and TBS. Then, beads to which TBS containing trypsin at a final concentration of 1 mg/mL has been added are suspended for 15 minutes at room temperature, and a phage suspension is collected from the beads separated immediately thereafter using a magnetic stand. The pIII protein of phages not displaying Fab (helper phage-derived pIII protein) is cleaved by addition of trypsin, resulting in loss of the ability of phages not displaying Fab to infect $E.$ $coli$. Phages eluted with the trypsin solution are added to 10 mL of the $E.$ $coli$ strain ER2738 in a logarithmic growth phase (OD600=0.4-0.7). The $E.$ $coli$ is cultured at 37° C. while gently stirring for one hour to allow phages to infect the $E.$ $coli$. The infected $E.$ $coli$ are seeded on 225 mm×225 mm plates. Then, phages are collected from the culture solution of the seeded $E.$ $coli$ to collect a phage library suspension. Similar panning is performed several times to obtain a population of phages that bind to adenosine, AMP, ADP, or ATP.

Since phages that bind to an antigen (adenosine, AMP, ADP, or ATP) obtained from each of the heavy chain and light chain variable region phage-display libraries are a population that has antigen-binding ability, an Fab-displaying phage library constructed by combining the two is predicted to contain a large number of clones that retain the binding to small molecules serving as a switch. Thus, it is thought that a library that allows isolation of switch antibodies with higher efficiency can be generated.

Genes are extracted by methods known to those skilled in the art from $E.$ $coli$ infected with each of the phage libraries of the heavy chain and light chain. Using as template the collection (library) of each of the genes obtained as described above, gene libraries are amplified with primers capable of amplifying each of VH and VL. The gene library of the amplified human antibody heavy chain variable region and the gene library of the amplified human antibody light chain variable region are introduced into an appropriate phagemid vector having both a human IgG-derived CH1 sequence and a human IgG-derived light chain constant region sequence. The phagemid vectors are introduced into $E.$ $coli$ by electroporation to construct a design library which enables to obtain antibodies presenting Fab domains consisting of a human antibody variable region-constant region and which bind to antigens using adenosine, AMP, ADP, or ATP as a switch. A design library composed of H chains and L chains having such diverse binding activity to adenosine, AMP, ADP, or ATP is thought to be useful as a library containing human antibodies that enable to efficiently obtain AMP/ADP/ATP/adenosine switch antibodies against arbitrary antigens, where adenosine, AMP, ADP, or ATP is sandwiched between the antibody and antigen as shown in FIG. 43. Moreover, since, as described above, SMB0002 binds not only to adenosine and AMP but also to ADP and ATP, it is also predicted to have binding activity to cAMP and ATP-gamma-S which are structurally similar to AMP, ADP, ATP, and adenosine. Thus, the library is considered to be useful for obtaining switch antibodies whose binding activity toward an arbitrary target antigen varies depending on the presence of any one or more small molecules of ATP, ADP, AMP, cAMP, adenosine, and ATP-gamma-S.

[Example 6] Acquisition of Antibodies that Bind to the Human IL-6 Receptor (hIL-6R) in the Presence of Small Molecules from a Human Antibody Library Using the Phage Display Technique (6-1) Acquisition of Antibodies that Bind to hIL-6R in the Presence of Small Molecules from a Naive Human Antibody Library by Bead Panning A naïve human antibody phage-display library constructed as described in Reference Example 1 described below was screened for antibodies showing human IL-6 receptor (hIL-6R)-binding activity in the presence of small molecules. Specifically, phages presenting antibodies showing binding activity toward hIL-6R captured onto beads in the presence of small molecules were collected. Phages were collected from the phage elution solution eluted from the beads in the absence of the small molecules. In this acquisition method, biotin-labeled hIL-6R was used as antigen.

Phages produced by $E.$ $coli$ retaining the constructed phagemids for phage display were purified by a common method. Then, a phage library suspension dialyzed against TBS was obtained. Next, BSA was added at a final concentration of 4% to the phage library suspension. Panning was performed using antigens immobilized onto magnetic beads. The magnetic beads used were NeutrAvidin coated beads (Sera-Mag SpeedBeads NeutrAvidin-coated) or Streptavidin coated beads (Dynabeads M-280 Streptavidin).

To efficiently isolate small molecule switch antibodies dependent on small molecules that can play a role as a switch in cancer tissues, panning was carried out, which concentrates antibodies that bind to antigens in the presence of a mixed solution of the following various small molecules (adenosine, adenosine 5'-triphosphate (ATP), inosine, kynurenine, prostaglandin E2 (PGE2), succinic acid, and lactic acid) (hereinafter referred to as small molecule cocktail (SC)), but do not bind to antigens in the absence of SC.

Specifically, SC was prepared to contain adenosine triphosphate sodium salt (ATP-Na), adenosine, inosine, succinic acid, and lactic acid, each at a final concentration of 1 mM, prostaglandin E2 (PGE2) at a final concentration of 1 μM, and kynurenine at a final concentration of 100 μM, and its pH was adjusted to 7.4 with NaOH. The prepared phage library suspension was contacted with the SC and 250 pmol of biotin-labeled antigens at room temperature for 60 minutes. Then, BSA-blocked magnetic beads were added to the phage library suspension, and the antigen/phage complexes were allowed to bind to the magnetic beads at room temperature for 15 minutes. The beads were washed once with SC/TBS (TBS containing SC). Then, beads to which 0.5 mL of 1 mg/mL trypsin solution has been added were suspended for 15 minutes at room temperature, and a phage suspension was collected from the beads separated immediately thereafter using a magnetic stand. The collected phage suspension was added to 10 ml of $E.$ $coli$ strain ER2738 in a logarithmic growth phase (OD600=0.4-0.7). The $E.$ $coli$ was cultured at 37° C. while gently stirring for one hour to allow phages to infect the $E.$ $coli$. The infected $E.$ $coli$ were seeded on 225 mm×225 mm plates. Then, phages are collected from the culture solution of the seeded E. coli to collect a phage library suspension.

The first panning was carried out to collect phages that can bind in the presence of small molecules, while the second and subsequent pannings were carried out to concentrate phages that can bind to antigens only in the presence of SC. Specifically, 40 pmol of biotin-labeled antigen, SC, and NaOH were added to the prepared phage library suspension to let the phage library contact with the antigen and small molecules at room temperature for 60 minutes. BSA-blocked magnetic beads were added, and the antigen/phage complex was allowed to bind to the magnetic beads at room temperature for 15 minutes. The beads were washed with 1 mL of SC/TBST and SC/TBS. Then, beads to which 0.5 mL of TBS has been added were suspended at room temperature, and a phage suspension was collected from the beads separated immediately thereafter using a magnetic stand. This process was repeated, and then the two phage suspensions separately eluted were combined. 5 μL, of 100 mg/mL trypsin was added to the collected phage suspension to cleave the pIII protein of phages that do not display Fab (helper phage-derived pIII protein), resulting in loss of the ability of phages not displaying Fab to infect E. coli. The phages collected from the trypsin-treated phage suspension were added to 10 mL of E. coli strain ER2738 in a logarithmic growth phase (OD600=0.4-0.7). The E. coli was cultured at 37° C. while gently stirring for one hour to allow phages to infect the E. coli. The infected E. coli was seeded on 225 mm×225 mm plates. Then, phages were collected from the culture solution of the seeded E. coli to collect a phage library suspension. Three rounds of panning were performed in the presence of SC to obtain antibodies having antigen-binding activity.

(6-2) Assessment of Binding Activity in the Presence of Small Molecules by Phage ELISA From a single colony of E. coli obtained in (6-1), a phage-containing culture supernatant was collected according to a conventional method (Methods Mol. Biol. (2002) 178, 133-145). Purified phages that were purified by the method described in Reference Example (1-3) were subjected to ELISA by the procedure described below. A StreptaWell 96 microtiter plate (Roche) was coated overnight with 100 μL of TBS containing biotin-labeled hIL-6R. After removing biotin-labeled hIL-6R that did not bind to the plate by washing each of the wells of the plate with TBST, the wells were blocked with 250 μL of 2% skim milk/TBS for one hour or longer. After removing 2% skim milk/TBS, purified phages were added to each well of the plate, and the plate was left still at room temperature for one hour to allow antibody-presenting phages to bind to biotin-labeled hIL-6R present in each well in the presence/absence of SC. Each well was washed with TBST or SC/TBST, and HRP-conjugated anti-M13 antibody (Amersham Pharmacia Biotech) diluted with TBS or SC/TBS was added thereto, and the plate was incubated for one hour. After washing with TBST or SC/TBST, the chromogenic reaction of TMB single solution (ZYMED) added in each well was terminated by adding sulfuric acid. Then, the color development was measured by absorbance at 450 nm.

Clones 6RNMSC1-2_F02 and 6RNMSC1-3_G02 having binding activity to the antigen hIL-6R in the presence of a small molecule mixture were obtained by carrying out phage ELISA using 960 isolated clones.

(6-3) Expression and Purification of Antibodies that Bind to hIL-6R

Using specific primers (SEQ ID NOs: 78 and 80), genes were amplified from clones 6RNMSC1-2_F02 and 6RNMSC1-3_G02 determined to have binding activity to biotin-labeled hIL-6R in the presence of SC based on the phage ELISA described in (6-2). The nucleotide sequences of the genes were analyzed (6RNMSC1-2_F02: the heavy chain sequence is shown in SEQ ID NO: 32 and the light chain sequence is shown in SEQ ID NO: 33; 6RNMSC1-3_G02: the heavy chain sequence is shown in SEQ ID NO: 34 and the light chain sequence is shown in SEQ ID NO: 35). The genes encoding the variable regions of 6RNMSC1-2_F02, 6RNMSC1-3_G02, and the negative control anti-human glypican 3 antibody GC413 (heavy chain: SEQ ID NO: 36; light chain: SEQ ID NO: 37) were inserted into an animal expression plasmid carrying human IgG1/Kappa. The expressed antibodies were purified by the method described in Reference Example 1 described below.

(6-4) Identification of Small Molecules that are Required for hIL-6R Binding of Isolated Antibodies Three types of obtained antibodies 6RNMSC1-2_F02, 6RNMSC1-3_G02, and GC413 were subjected to ELISA under the nine conditions shown in Table 12. Meanwhile, small molecules were suitably prepared at the concentrations shown in Table 12 using the buffers listed in Table 13. The antigen used was biotin-labeled hIL-6R.

TABLE 12

| Condition | Small molecule | Concentration |
| --- | --- | --- |
| 1 | ATP-Na | 1 mM |
| 2 | Adenosine | 1 mM |
| 3 | inosine | 1 mM |
| 4 | PGE2 | 1 μM |
| 5 | Succinic acid | 1 mM |
| 6 | Lactic acid | 1 mM |
| 7 | Kynurenine | 100 μM |
| 8 | ATP 1 mM, Adenosine 1 mM, Inosine 1 mM, PGE2 1 μM, Succinic acid 1 mM, Lactic acid 1 mM, Kynurenine 100 μM | |
| 9 | — | — |

TABLE 13

| Wash buffer | 10 mM ACES, 150 mM NaCl, 0.05% Tween20, pH7.4 |
| --- | --- |
| Blocking Buffer | 10 mM ACES, 150 mM NaCl, 2% SkimMilk, pH7.4 |
| Sample Buffer | 10 mM ACES, 150 mM NaCl, Small molecule, pH7.4 |

First, a StreptaWell 96 microtiter plate (Roche) was coated with 100 μL of PBS containing biotin-labeled hIL-6R at room temperature for one hour or longer. After removing biotin-labeled hIL-6R that did not bind to the plate by washing each well of the plate with TBST, the wells were blocked with 250 μl of Blocking Buffer (2% skim milk/TBS) for one hour or longer, and Blocking Buffer was removed from each well. 100 μL of each of the purified IgGs prepared at 2.5 μg/mL using Sample Buffer containing small molecules at the final concentrations shown in Table 12 were added to each well, and the plate was let still at room temperature for one hour to allow each IgG to bind to biotin-labeled hIL-6R present in each well. After washing with Wash Buffer containing small molecules at the final concentrations shown in Table 12, HRP-conjugated anti-human IgG antibody (BIOSOURCE) diluted with Sample Buffer containing the same small molecules was added to each well and the plate was incubated for one hour. After washing with Wash Buffer containing respective small molecules, the chromogenic reaction of TMB single solution (ZYMED) added in each well was terminated by adding sulfuric acid. Then, the color development was measured by absorbance at 450 nm. The composition of the Buffer used is shown in Table 13.

The measurement results are shown in FIGS. 16 and 17. When 6RNMSC1-2_F02 and 6RNMSC1-3_G02 were used, the obtained result was that the absorbance under condition 9 (no small molecule) was significantly lower as compared to the absorbance under condition 8 (cocktail solution containing all of the small molecules). It was confirmed from this result that 6RNMSC1-2_F02 and 6RNMSC1-3_G02 had the property that their antigen binding varies depending on the presence or absence of the small molecules. Moreover, the result obtained when 6RNMSC1-2_F02 was used was that the absorbance under condition 7 (100 uM kynurenine) was comparable to that under condition 8, but the absorbance was significantly low under other conditions; thus, it was demonstrated that 6RNMSC1-2_F02 is an antibody that binds to the antigen hIL-6R in the presence of kynurenine (FIG. 16). Further, the result obtained when 6RNMSC1-3_G02 was used was that the absorbance under condition 1 (1 mM ATP-Na) was comparable to that under condition 8, but the absorbance was significantly low under other conditions; thus, it was demonstrated that 6RNMSC1-3_G02 is an antibody that binds to the antigen hIL-6R in the presence of ATP (FIG. 17). It was shown that several antibodies whose antigen-binding ability varies under the presence of different small molecules could be isolated at one time by using a method as described above.

[Example 7] Characterization of Antibody 6RNMSC1-2_F02

(7-1) Assessment by ELISA of hIL-6R-Binding Activity in the Presence of Amino Acids and Amino Acid Metabolites Other than Kynurenine Antibody 6RNMSC1-2_F02 obtained in Example 6, which binds to hIL-6R in the presence of small molecules, is an antibody that binds to hIL-6R in the presence of kynurenine. A series of amino acid metabolites such as tryptophan metabolites were assessed for whether they are appropriate as a non-limiting embodiment of cancer tissue-specific compounds, in particular, cancer cell-specific metabolites, for use in the present invention.

Antibody 6RNMSC1-2_F02 having antigen-binding activity in the presence of kynurenine described in Example 6 and negative control GC413 were subjected to ELISA under the seven conditions described in Table 14. Meanwhile, each of the amino acids and metabolites thereof were appropriately prepared at the concentrations shown in Table 14 using the buffers shown in Table 13. The antigen used was biotin-labeled hIL-6R.

TABLE 14

| Condition | Small Molecule | Concentration |
|---|---|---|
| 1 | Kynurenine | 1 mM |
| 2 | Tryptophan | 1 mM |
| 3 | Phenylalanine | 1 mM |
| 4 | Anthranilic acid | 1 mM |
| 5 | 3-Hydroxykynurenine | 1 mM |
| 6 | Kynurenic acid | 1 mM |
| 7 | — | — |

First, a StreptaWell 96 microtiter plate (Roche) was coated with 100 μL of PBS containing biotin-labeled antigens at room temperature for one hour or longer. After removing antigens that did not bind to the plate by washing each well of the plate with TBST, the wells were blocked with 250 μl of Blocking Buffer (2% skim milk/TBS) for one hour or longer, and Blocking Buffer was removed from each well. 100 μL of each of the purified IgGs prepared at 2.5 μg/mL using Sample Buffer containing small molecules at the final concentrations shown in Table 14 were added to each well, and the plate was let still at room temperature for one hour to allow each IgG to bind to the antigen present in each well. After washing with Wash Buffer containing amino acids and amino acid metabolites at the final concentrations shown in Table 14, HRP-conjugated anti-human IgG antibody (BIOSOURCE) diluted with Sample Buffer containing amino acids and amino acid metabolites was added to each well, and the plate was incubated for one hour. After washing with Wash Buffer containing the respective amino acids and amino acid metabolites, the chromogenic reaction of TMB single solution (ZYMED) added in each well was terminated by adding sulfuric acid. Then, the color development was measured by absorbance at 450 nm. The composition of the Buffer used is shown in Table 13.

The measurement results are shown in FIG. 18. When 6RNMSC1-2_F02 was used, the absorbance under condition 7 (no small molecule) was significantly lower as compared to the absorbance under condition 1 (kynurenine solution). Similarly, the absorbance under condition 5 (3-hydroxy kynurenine solution) showed a high absorbance similarly to that under condition 1; thus, it was shown that 6RNMSC1-2_F02 is an antibody that binds to the antigen hIL-6R not only in the presence of kynurenine but also in the presence of a kynurenine metabolite. Moreover, since the absorbance was significantly low under other conditions, 6RNMSC1-2_F02 was shown to be an antibody that does not bind to the antigen hIL-6R even if tryptophan, a precursor of kynurenine, is present. Since the expression of DO, which is an enzyme that produces kynurenine by metabolizing tryptophan, is elevated in cancer microenvironments, antibodies that bind to antigens in the presence of kynurenine or metabolites thereof but not in the presence of tryptophan are considered to be important as antibodies that bind to antigens only in cancer microenvironments. Furthermore, from the above, it was thought that the same method can be used to obtain antibodies that bind to an antigen of interest not only in the presence of a single type of amino acid metabolite, but also in the presence of multiple types of structurally different amino acid metabolites.

Thus, an antibody which uses as a switch a molecule that is produced locally in cancer via metabolism by cancer-specific enzymes (in this Example, MO and its downstream metabolic enzymes) is thought to be able to selectively bind to target antigens only locally in cancer. In this Example, metabolic products generated from the endogenous molecule tryptophan by cancer-specific metabolic enzymes are used as a switch; however, it is considered that it is possible to use, as a switch, an artificial molecule (unnatural molecule) that is administered exogenously such as by oral or intravenous administration as well as a metabolic product generated from an endogenous molecule by cancer-specific metabolic enzymes. For example, as described in Example 1, capecitabine (xeloda), when administered, is metabolized into 5-FU by cancer-specific metabolic enzymes or such, resulting in an increase of local 5-FU concentration in cancer (Desmoulin F. et al., Drug Metab Dispos. 2002). Thus, it is considered that an antibody that uses 5-FU as a switch can selectively bind to the target antigen only locally in cancer. Alternatively, it is considered possible to use, as a switch, molecules produced due to cancer-specific hypoxic environments or acidic environments, instead of metabolic enzymes. For example, since, under hypoxic conditions, TH-302 (Duan J X, et al., J Med Chem. 2008) is metabolized into Br-IPM, an antibody that uses Br-IPM as a switch could selectively bind to target antigens only locally in cancer.

(7-2) Assessment by Surface Plasmon Resonance for the Effect of Kynurenine on Human IL6 Receptor Binding Biacore T200 (GE Healthcare) was used to analyze the interaction of antigen-antibody reaction between 6RNMSC1-2_F02 and human IL-6 receptor (hIL-6R). An appropriate amount of protein A (Invitrogen) was immobilized onto Sensor chip CM5 (GE Healthcare) by the amine coupling method. The antibody of interest was captured onto the sensor chip, and the antigen hIL-6R was allowed to interact. The running buffer used was 20 mmol/L ACES, 150 mmol/L NaCl, 0.05% (w/v) Tween 20, pH 7.4. The interaction with the antigen hIL-6R was measured at 25° C. hIL-6R was diluted with the running buffer, the running buffer containing 100 µmol/L kynurenine, or, as a control, the running buffer containing 10 mmol/L ATP.

Diluted hIL-6R solutions and the running buffer which is the blank were injected at a flow rate of 10 µL/min for one minute and hIL-6R was allowed to interact with 6RNMSC1-2_F02 captured on the sensor chip. Then, the running buffer was run at a flow rate of 10 µL/min for one minute to observe the dissociation of hIL-6R from the antibody. Next, 10 mmol/L glycine-HCl, pH 1.5, was injected at a flow rate of 30 µL/min for 30 seconds to regenerate the sensor chip. The dissociation constant $K_D$ (M) of 6RNMSC1-2_F02 for hIL-6R was calculated from the kinetic parameters, the association rate constant ka (1/Ms) and the dissociation rate constant kd (1/s), calculated based on the sensorgrams obtained by the measurements. Each parameter was calculated using Biacore T200 Evaluation Software (GE Healthcare).

Sensorgrams obtained by this measurement of the interaction between 6RNMSC1-2_F02 and 1 µmol/L hIL-6R in the presence of 100 µmol/L kynurenine, 10 mmol/L ATP, or in the absence of these are shown in FIG. 19. As shown in FIG. 19, in the presence of 100 µmon kynurenine, 6RNMSC1-2_F02 bound to hIL-6R; however, hIL-6R binding was not detected in the absence of kynurenine. Thus, 6RNMSC1-2_F02 was confirmed to have the property of binding to hIL-6R using kynurenine as a switch. Further, the dissociation constant KD of 6RNMSC1-2_F02 in the presence of 100 µmol/L kynurenine was 1.5 µmon.

(7-3) Effect of Kynurenine as a Switch on Dissociation of the Antibody from hIL-6R Whether 6RNMSC1-2_F02 that bound to hIL-6R in the presence of kynurenine dissociates in the presence of kynurenine in a kynurenine concentration-dependent manner was assessed using Biacore T200 (GE Healthcare). The running buffers used were 20 mmol/L ACES, 150 mmol/L NaCl, 0.05% (w/v) Tween 20, pH 7.4, and 20 mmol/L ACES, 150 mmol/L NaCl, 0.05% (w/v) Tween 20, pH 7.4, 100 µmol/L kynurenine. The measurements were performed at 25° C. As an analyte, 5 µg/mL 6RNMSC1-2_F02 diluted with 20 mmol/L ACES, 150 mmol/L NaCl, 0.05% (w/v) Tween 20, pH 7.4, containing 100 µmol/L kynurenine was allowed to interact for 180 seconds with hIL-6R immobilized onto Sensor chip CM5 by amine coupling. Then, the mode of the dissociation of hIL-6R was observed under each running buffer condition. In order to compare the extent of dissociation under each running buffer condition, the amount of 6RNMSC1-2_F02 bound to hIL-6R in the presence of 100 µmol/L kynurenine was taken as 100 for normalization, and the normalized values were compared. The sensorgram showing the interaction between 6RNMSC1-2_F02 and hIL-6R after normalization is shown in FIG. 20. The result of FIG. 20 revealed that, after binding to hIL-6R in the presence of kynurenine, 6RNMSC1-2_F02 had the property of rapidly dissociating hIL-6R when kynurenine is no more present. Specifically, the regulation by kynurenine on binding of the antibody to hIL-6R was confirmed to be reversible.

(7-4) Assessment of the Effect by Kynurenine Concentration on hIL-6R Binding

Next, the effect of kynurenine concentration on antigen-antibody reaction between 6RNMSC1-2_F02 and hIL-6R was assessed using Biacore T200 (GE Healthcare). The running buffer used was 20 mmol/L ACES, 150 mmol/L NaCl, 0.05% (w/v) Tween 20, pH 7.4. Antigen-antibody reaction between 6RNMSC1-2_F02 and human IL-6R was assayed at 25° C. hIL-6R was immobilized onto Sensor chip CM5 by amine coupling. As an analyte, 1 µg/mL 6RNMSC1-2_F02 diluted with 20 mmol/L ACES, 150 mmol/L NaCl, 0.05% (w/v) Tween 20, pH 7.4, containing kynurenine adjusted to various concentrations were allowed to interact for 180 seconds and changes in the amount of binding were observed. The result is shown in FIG. 21. From this result, it was revealed that the higher the concentration of kynurenine acting as a switch, the greater the amount of 6RNMSC1-2_F02 binding to hIL-6R.

Since, in this assay system, hIL-6R is immobilized on a sensor chip, 6RNMSC1-2_F02 is thought to bind in a divalent manner. The amount of 6RNMSC1-2_F02 that bound to hIL-6R was also observed to increase when the kynurenine concentration increases in this assay system where 6RNMSC1-2_F02 recognizes hIL-6R in a divalent manner. This result showed that, in divalent binding as well, 6RNMSC1-2_F02 has the property of binding to IL-6R using kynurenine as a switch.

The results described above revealed that 6RNMSC1-2_F02 is an antibody which, using kynurenine as a switch, binds to hIL-6R in the presence of kynurenine and dissociates from hIL-6R in the absence of kynurenine. Furthermore, 6RNMSC1-2_F02 was confirmed not to show hIL-6R-binding activity in the absence of kynurenine, enabling a complete ON/OFF regulation, and to fulfill a switch function.

(7-5) Assessment of the Binding Ability of 6RNMSC1-2_F02 for Kynurenine Derivatives Kynurenine-dependent antibody 6RNMSC1-2_F02 obtained from the library was assessed for its binding to kynurenine and derivatives thereof using Biacore T200 (GE Healthcare). The following seven molecules were assessed as derivatives: the kynurenine isomer D-kynurenine and the derivatives 3-hydroxy-DL-kynurenine, 4-(4-methylphenyl)-4-oxobutyric acid, RO0447436-000-001, RO0635389-000-001, RO0438566-001-001, and RO0635390-000-001. The chemical structure of each compound is shown below.

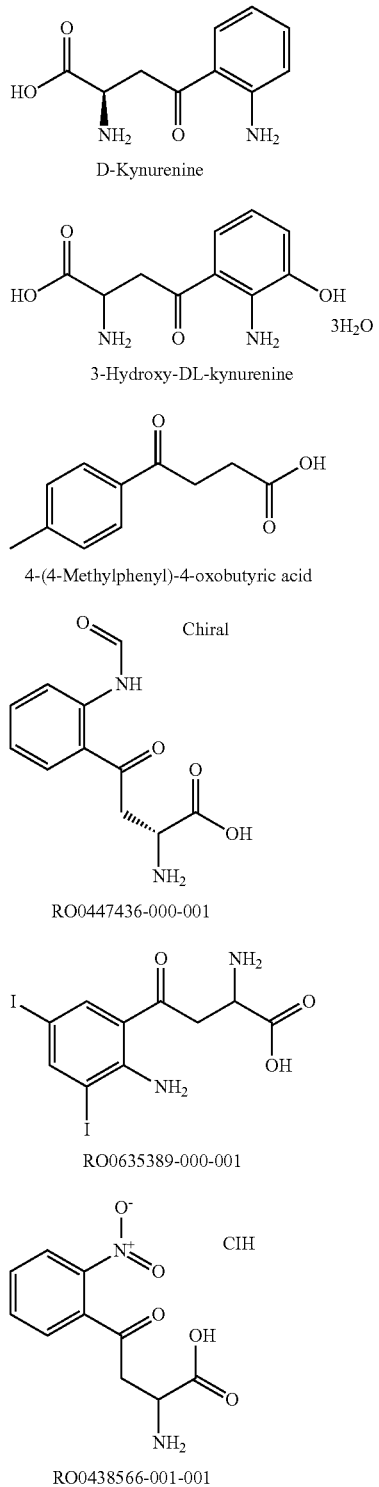

[Compound 19] D-Kynurenine

[Compound 20] 3-Hydroxy-DL-kynurenine · 3H₂O

[Compound 21] 4-(4-Methylphenyl)-4-oxobutyric acid

[Compound 22] RO0447436-000-001

[Compound 23] RO0635389-000-001

[Compound 24] RO0438566-001-001

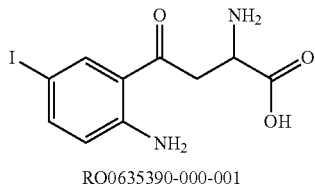

[Compound 25] RO0635390-000-001

An appropriate amount of protein A (Invitrogen) was immobilized onto Sensor chip CM4 (GE Healthcare) by the amine coupling method. The antibody of interest was captured thereon, and the antigen kynurenine and derivatives thereof were allowed to interact. The running buffer used was 50 mmol/L Tris-HCl, 150 mmol/L NaCl, 0.02% (w/v) Tween 20, 5% DMSO, pH 7.6. All measurements were carried out at 15° C. The antigens were diluted with the running buffer.

Regarding 6RNMSC1-2_F02, the diluted antigen solutions and the running buffer as the blank were each added at a flow rate of 30 μL/min for 60 seconds to allow each antigen to interact with the antibody captured on the sensor chip. Then, the running buffer was run at a flow rate of 30 μL/min for 60 seconds to observe the dissociation of antigens from the antibody. Kinetic parameters, the association rate constant ka (1/Ms) and the dissociation rate constant kd (1/s), were calculated based on the sensorgrams obtained by the measurements. The dissociation constant KD (M) was calculated from these constants. Each parameter was calculated using Biacore T200 Evaluation Software (GE Healthcare).

Based on the assessment result, the kinetic parameters of the interaction between kynurenine and 6RNMSC1-2_F02 were determined as: ka=709 (1/s), kd=0.17 (1/s), and KD=0.239 (mmol/L). Sensorgrams obtained as a result of the assessment are shown in FIG. 22. Sensorgrams representing the results of the binding with the derivatives are depicted in: FIG. 23 for 3-hydroxy-DL-kynurenine, FIG. 24 for RO0635389-000-001, and FIG. 25 for RO0635390-000-001. Scrubber2 (Biologic software) and Microsoft Office Excel 2007 were used to show the sensorgrams. These results revealed that 6RNMSC1-2_F02 can not only bind to kynurenine, but also to some kynurenine derivatives such as 3-hydroxy-DL-kynurenine, RO0635389-000-001, and RO0635390-000-001.

(7-6) Assessment of Responsiveness of 6RNMSC1-2_F02 to Unnatural Small Molecules Octet (PRIMETECH) was used to assess the effect of various small molecules on the antigen-antibody reaction between hIL-6R and the kynurenine-switch antibody 6RNMSC1-2_F02 obtained from a library. A total of eight molecules shown in Example (7-5), which are kynurenine and derivatives thereof, were evaluated as small molecules. The assay buffer used was TBS, pH 7.4, and measurements were carried out at 30° C. Biotinylated hIL-6R was immobilized onto a streptavidin sensor chip, the antibody was allowed to interact, and changes in the amount of its binding were observed. The antibody was diluted using the assay buffer or the assay buffer to which either one of the small molecules has been added. The final concentration of each small molecule was adjusted to 100 uM, while the final antibody concentration was adjusted to 10 μg/mL.

The hIL-6R binding activity of 6RNMSC1-2_F02 obtained by this measurement in the presence of each small molecule at 100 uM or in their absence is shown in: FIG. 26 for kynurenine, FIG. 27 for 3-hydroxy-DL-kynurenine, FIG. 28 for RO0635389-000-001, and FIG. 29 for RO0635390-000-001. As shown in FIG. 26, in the presence of 100 uM kynurenine, 6RNMSC1-2_F02 bound to hIL-6R, while in the absence of kynurenine, hIL-6R binding was not observed. Thus, Octet also confirmed that 6RNMSC1-2_F02 had the property of binding to hIL-6R using kynurenine as a switch. Furthermore, as shown in FIGS. 27 to 29, binding to hIL-6R was observed in the presence of the small molecules other than kynurenine such as 3-hydroxy-DL-kynurenine, RO0635389-000-001, and RO0635390-000-001 which are kynurenine derivatives capable of binding to 6RNMSC1-2_F02, while in the absence of these small molecules, binding to hIL-6R was not observed. The above demonstrated that anti-h1L-6R antibodies for which kynurenine and derivatives thereof (unnatural compounds) function as a switch can be isolated from a library.

Example 7-3 showed the utilization of endogenous molecules as a switch. With this Example, it has been shown that artificial molecules (unnatural molecules) can also be used as a switch. Specifically, it has been demonstrated that antibodies can be generated, which use as a switch unnatural metabolites produced by cancer-specific metabolic enzymes from artificial molecules (unnatural molecules) that can be administered exogenously by oral or intravenous routes or such.

[Example 8] Design of Library for Obtaining Kynurenine-Switch Antibodies by Comprehensive Alteration Using a Kynurenine-Switch Anti-h1L-6R Antibody The concentration of kynurenine is known to be high in cancer tissues. Several antibodies showing antigen-binding ability only in the presence of ATP were obtained from a rationally designed library constructed in Reference Example 2 using as a template an ATP-binding antibody. This suggested that antibodies showing antigen-binding ability only in the presence of kynurenine could also be obtained by constructing a library using as a template an antibody that shows binding ability to kynurenine.

(8-1) X-Ray Crystallographic Structure Analysis of the hIL-6R-Binding Antibody 6RNMSC1-2_F02 which Uses Kynurenine as a Switch The three-dimensional structure of the complex of kynurenine and antibody 6RNMSC1-2_F02 that binds to hIL-6R using kynurenine as a switch, which was obtained from a library in Example 7, was revealed by x-ray crystallographic structure analysis.

(8-1-1) Preparation of the Full-Length 6RNMSC1-2_F02 Antibody for Crystallization The full-length 6RNMSC1-2_F02 antibody for crystallization was prepared and purified by a method known to those skilled in the art.

(8-1-2) Preparation of 6RNMSC1-2_F02 Fab Fragment from the Full-Length Antibody

After the obtained antibody 6RNMSC1-2_F02 was concentrated with 10000 molecular weight cutoff (MWCO) ultrafiltration membrane, a sample was prepared by diluting the antibody to 2 mg/ml with 100 mM Tris buffer, pH 8.0, and Endoproteinase Lys-C Sequencing Grade (Roche Applied Science) was added thereto at a mass ratio of 1/400 to the full-length antibody. The mixture was incubated at 35° C. for 45 minutes. Then, the reaction was terminated by adding 20 ml of 25 mM sodium acetate buffer, pH 5.0 into which a tablet of protease inhibitor cocktail mini, EDTA-free (Roche Applied Science) has been dissolved. Next, this sample was added to a 1-ml size cation-exchange column HiTrap SP HP (GE Healthcare) to whose downstream 1-ml size Protein A-carrying column HiTrap MabSelect Sure (GE Healthcare) was tandemly connected and which was equilibrated with 25 mM sodium acetate buffer, pH 5.0. Elution was performed by linearly increasing the concentration of NaCl in the buffer, and a purified fraction of Fab fragments of the 6RNMSC1-2_F02 antibody was obtained. This was added to the gel filtration column Superdex 200 16/60 prep grade (GE Healthcare) equilibrated with 25 mM HEPES buffer, pH 7.5, 100 mM NaCl. The Fab fragments of 6RNMSC1-2_F02 were eluted with the same buffer from this column for crystallization. All column operations were carried out at low temperature.

(8-1-3) Preparation of Crystals of the Complex of Kynurenine and 6RNMSC1-2_F02 Fab Fragment A sample of 6RNMSC1-2_F02 Fab fragment for crystallization purified by the above-described method was concentrated with a 5000 MWCO ultrafiltration membrane to A280=24.1. Then, 50 mM kynurenine dissolved in 100% DMSO was added at a final concentration of 2 mM, and crystallization was carried out using the sitting drop vapor diffusion method. Crystallization was carried out using Hydra II Plus One (MATRIX). Using a reservoir solution of 0.2 M lithium sulfate monohydrate, 30.0% w/v PEG 3350, and 0.1 M Tris, pH 8.5, crystallization drops were prepared by mixing at reservoir solution: crystallization sample=0.2: 0.2 μl. The drops were allowed to stand at 20° C. and thin columnar crystals were successfully obtained. Then, one of the obtained crystals was immersed in a 0.18 M lithium sulfate monohydrate, 27.3% PEG3350, 0.09 M HEPES pH7.5, 18.2% ethylene glycol, 4.5 mM kynurenine, 9% DMSO solution for 30 minutes at room temperature, and a crystal of the complex of 6RNMSC1-2_F02 Fab fragment and kynurenine was obtained.

(8-1-4) Measurement of X-Ray Diffraction Data from the Crystal of the Complex of 6RNMSC1-2_F02 Fab Fragment and Kynurenine A single crystal of the complex of 6RNMSC1-2_F02 Fab fragment and kynurenine prepared by the method described above was scooped together with the solution using a pin equipped with a minute nylon loop, and frozen in liquid nitrogen. X-ray diffraction data were measured using BL-5A at the synchrotron radiation facility Photon Factory of the High Energy Accelerator Research Organization. The frozen state was maintained through the measurement by placing in a stream of nitrogen gas at −178° C. A total of 360 X-ray diffraction images were collected using CCD detector Quantum 315r (ADSC) attached to the beamline by rotating the crystal by 0.5°. Lattice constant determination, diffraction spot indexing, and diffraction data processing from the obtained diffraction images were performed using the programs Xia2 (J. Appl. Cryst. (2010) 43, 186-190), XDS Package (Acta Cryst. (2010) D66, 125-132), and Scala (Acta Cryst. (2006) D62, 72-82). Ultimately, this successfully yielded diffraction intensity data of up to 2.33 angstrom resolution. This crystal belonged to space group P1 with lattice constants a=55.830 angstrom, b=56.040 angstrom, c=80.340 angstrom, α=87.81°, β=82.88°, γ=65.54°.

(8-1-5) X-Ray Crystallographic Analysis of the Complex of Kynurenine and 6RNMSC1-2_F02 Fab Fragment To determine the structure of the complex of kynurenine and 6RNMSC1-2_F02 Fab fragment, the molecular replacement method was carried out using the program Phaser (J. Appl. Cryst. (2007) 40, 658-674). The number of complexes in the asymmetrical unit was estimated to be two from the size of the obtained crystal lattice and the molecular weight of the 6RNMSC1-2_F02 Fab fragment. A homology model of the antibody was constructed using Discovery Studio3.5 (Accelrys). This Fab model was divided into the variable region and constant region, and using the coordinate of each structure as search model, their orientation and position in the crystal lattices were determined based on the rotation function and translation function. Further, the crystallographic reliability factor R for the diffraction intensity data at 25 to 3.0 angstroms was 40.57% and Free R was 38.91%, when rigid body refinement was carried out on the obtained initial structural model in which the variable region and constant region portions were independently moved. Then, structural model refinement was carried out by repeating the following processes: structural refinement using the program REFMAC5 (Acta Cryst. (2011) D67, 355-367), and revision of the structural model performed using the program Coot (Acta Cryst. (2010) D66, 486-501) by referring to the electron density maps having as coefficients 2Fo-Fc and Fo-Fc, which were calculated based on the experimentally determined structural factor Fo, the structural factor Fc calculated from the model, and the phase calculated from the model. Ultimately, with 34135 diffraction intensity data at 25 to 2.33 angstrom resolution, the crystallographic reliability factor R and Free R for the structural model containing 7019 non-hydrogen atoms were 20.4% and 26.56%, respectively.

(8-1-6) Identification of the Interaction Sites of 6RNMSC1-2_F02 and Kynurenine

Ultimately, the crystallographic structure of the complex between kynurenine and the Fab fragment of antibody 6RNMSC1-2-F02 that binds to hIL-6R using kynurenine as a switch, which was obtained from a library in Example 7, was determined at a resolution of 2.33 angstrom.

There were two Fab fragment molecules of the antibody in the asymmetrical unit of the crystal, and kynurenine was bound to only one of them. It was revealed that kynurenine was recognized mainly by the H-chain CDR3 of the antibody, and bound to the antibody at a position slightly deviated from the part usually used in antigen binding.

As shown in FIG. 30, a kynurenine molecule is recognized by the respective side chains of H-chain P97, R100c, and D101, and L-chain H49 and F55, as well as by the respective main chains of H-chain R94, D95, R100c, G100d, and A100e of the antibody. Furthermore, the amino groups in the amino acid backbone of kynurenine are positively charged at neutral pH, and several hydrogen bonds and electrostatic interactions are observed with the main chain carbonyl oxygen of each of the H-chain D95, R94, and A100e, and the side chain carboxy group of D101. Moreover, the negatively charged carboxy group of kynurenine forms several hydrogen bonds with the amide NH group of the main chain of each of the H-chain G100d and R100c. The network of these strong hydrogen bonds and electrostatic interactions is expected to play an important role in recognition of kynurenine by the antibody. Furthermore, the side chain of H-chain R100c forms a cation-π interaction with the benzene ring moiety of kynurenine. In addition, the L-chain H49 and F55 and H-chain D101 surround the benzene ring moiety of kynurenine, and formation of van der Waals interactions with these residues contribute to binding recognition for kynurenine. Further, the side chain of L-chain H49 was confirmed to form a hydrogen bond, though weak, with the NH2 group in the aromatic ring of kynurenine.

The result described above revealed the mode of kynurenine recognition by the antibody and identified the amino acid residues of the antibody variable region that are greatly involved in kynurenine binding. Amino acid residues whose side chains are significantly involved in kynurenine binding include: P97, R100c, and D101 (Kabat numbering) in the H-chain, and H49 and F55 (Kabat numbering) in the L-chain. Moreover, residues whose main chain moieties are significantly involved in kynurenine binding include R94, D95, R100c, G100d, and A100e in the H-chain. Further, based on their structural features, residues such as P97, P100b, and G100d are thought to possibly be significantly contributing indirectly to kynurenine binding by maintaining the structure of the H-chain CDR3 in a conformation necessary for binding to kynurenine.

(8-2) Assessment of 6RNMSC1-2_F02 Variants for Binding Ability to Kynurenine (8-2-1) Assessment of Heavy Chain Variants of 6RNMSC1-2_F02 for Binding Ability to Kynurenine As described above, by crystallographic structure analysis, heavy-chain P97, P100b, R100c, G100d, D101, and such were found as residues that may be playing an important role in kynurenine binding. Thus, regarding some of the residues, variants were actually produced to assess their binding ability for kynurenine. The variants constructed are: P97A, P97G, P100bG, R100cA, G100dA, G100dV, and D101A (Table 15).

TABLE 15

| Clone name | Heavy chain SEQ ID NO | Light chain SEQ ID NO |
| --- | --- | --- |
| 6RNMSC1-2_F02 P97A | SEQ ID NO: 38 | SEQ ID NO: 33 |
| 6RNMSC1-2_F02 P97G | SEQ ID NO: 39 | SEQ ID NO: 33 |
| 6RNMSC1-2_F02 P100bG | SEQ ID NO: 40 | SEQ ID NO: 33 |
| 6RNMSC1-2_F02 R100cA | SEQ ID NO: 41 | SEQ ID NO: 33 |
| 6RNMSC1-2_F02 G100dA | SEQ ID NO: 42 | SEQ ID NO: 33 |
| 6RNMSC1-2_F02 G100dV | SEQ ID NO: 43 | SEQ ID NO: 33 |
| 6RNMSC1-2_F02 D101A | SEQ ID NO: 44 | SEQ ID NO: 33 |

Various 6RNMSC1-2_F02 variants expressed and purified by the method described in Reference Example 1 below were assessed for their kynurenine binding by a similar method as that with Biacore described in Example (7-5). As a result, 6RNMSC1-2_F02 was confirmed once again to bind to kynurenine; however, all the other variants had a reduced or considerably reduced ability to bind to kynurenine. Thus, the residues deduced to be important for kynurenine binding by the crystallographic structure were demonstrated to indeed participate in binding, and this result supported the results from crystallographic structure analysis.

(8-2-2) Assessment of the H49Y Variant of 6RNMSC1-2_F02 for Binding Ability to Kynurenine From the crystallographic structure analysis, it was thought that the light chain amino acid residue that is forming an important interaction with kynurenine is only H49 (Kabat numbering). Moreover, the result of sequence analysis suggested that the framework of 6RNMSC1-2_F02 was derived from VLkappa-2 germline. In VLkappa-2 germline, the amino acid at position 49 by Kabat numbering is Tyr in almost all cases, and is highly conserved. Thus, a variant was generated by substituting His49 with Tyr to assess the degree of contribution of His to the interaction with kynurenine.

The His49Tyr variant (heavy chain SEQ ID NO: 32; light chain SEQ ID NO: 45) of 6RNMSC1-2_F02 expressed and purified by the method of Reference Example 1 described below was assessed for kynurenine binding by a method similar to that with Biacore described in Example (7-5). The result revealed that H49Y retained kynurenine binding. Kinetic parameters were also determined: ka=2543 (1/s), kd=0.24 (1/s), and KD=0.095 (mmol/L). Sensorgrams showing the assessment results are shown in FIG. 31.

(8-2-3) Modification of 6RNMSC1-2_F02 to a Germline Framework Sequence

The result of sequence analysis suggested that the VH framework of 6RNMSC1-2_F02 is derived from a VH1-69 germline while the VL framework of 6RNMSC1-2_F02 is derived from a Vκ2-28 germline. Thus, with the purpose of increasing antibody stability, to restore the framework sequence of 6RNMSC1-2_F02 to the germline framework sequence, the following modifications were introduced into the framework sequence of 6RNMSC1-2_F02: VH_Met108Leu, VL_Thr07Ser, VL_Ser11Leu, VL_Leu15Pro, VL_Gln17Glu, VL_Leu36Tyr, VL_Gln37Leu, VL_Arg39Lys, VL_Pro43Ser, VL_Arg45Gln, VL_His49Tyr, VL_Ala67Ser, and VL_Asn70Asp (numbers indicate Kabat numbering). The variant was named F02h011/F021003 (heavy chain variable region sequence: SEQ ID NO: 95; light chain variable region sequence: SEQ ID NO: 96). The Tm of F02h011/F021003 expressed and purified by the method described in Reference Example 1-1 was measured by DSC. Measurement by DSC was carried out by a method known to those skilled in the art. The Tm of the variant of 6RNMSC1-2_F02 to which these modifications were added increased from 82.9° C. to 85.2° C., demonstrating stabilization of the structure. Furthermore, kynurenine binding of F02h011/F021003 was measured by a Biacore-based method described in Example (7-5), except that the time of adding the diluted antigen solutions and the running buffer as a blank was modified to 30 seconds, and F02h011/F021003 was confirmed to retain kynurenine binding. Kinetic parameters of kynurenine binding were determined: ka=3664 (1/s), kd=0.40 (1/s), and KD=0.11 (mmol/L). Sensorgrams showing the assessment results are shown in FIG. 32. It is sometimes preferable to use highly stable frameworks for antibody libraries; thus, F02h011/F021003 was used as the framework sequence in Examples (8-2-3) and (9-2) described below. The framework sequences are shown in Table 16.

TABLE 16

| Framework | SEQ ID NO | Sequence |
|---|---|---|
| Heavy chain framework 1 | 87 | QVQLVQSGAEVKKPGSSVKVSCKASGGIFS |
| Heavy chain framework 2 | 88 | WVRQAPGQGLEWMG |
| Heavy chain framework 3 | 89 | RVTITADESTSTAYMELSSLRSEDTAVYYCAR |
| Heavy chain framework 4 | 90 | WGQGTLVTVSS |
| Light chain framework 1 | 91 | DIVMTQSPLSLPVTPGEPASISC |
| Light chain framework 2 | 92 | WYLQKPGQSPQLLIY |
| Light chain framework 3 | 93 | GVPDRFSGSGSGTDFTLKISRVEAEDVGVYYC |
| Light chain framework 4 | 94 | WYLQKPGQSPQLLIY |

(8-2-4) Search for Modifications that Increase the Kynurenine Binding of F02h011/F021003

Residues putatively involved in the kynurenine binding of 6RNMSC1-2_F02 were predicted based on the results described in Examples (8-1) and (8-2-1). In addition to these residues, a search was carried out for residues for which an increase in kynurenine binding can be expected through modification.

Specifically, based on the crystallographic structure of the complex of the antibody Fab fragment and kynurenine, amino acid residues present within 4.2 angstrom from kynurenine were selected, as shown in FIG. 34. As a result, heavy-chain Tyr32 and Arg100a (Kabat numbering) and light-chain Leu46 (Kabat numbering) were newly found. Furthermore, since the heavy-chain CDR3 is a CDR loop which most highly contributes to kynurenine binding and modification to residues in this loop may indirectly influence kynurenine binding, amino acid residues were modified at as many residue positions as possible. However, the following residues were ruled out as a candidate for the modified residue sites: heavy-chain Asp95 which forms a strong hydrogen bond with light-chain Arg96 and determines the loop structure; heavy-chain Arg100a which forms a hydrogen bond with light-chain Glu50 and determines the loop structure; and heavy-chain Pro100b whose side chain is oriented in the opposite direction from kynurenine and for which formation of interaction with kynurenine cannot be expected even if a modification is introduced. Meanwhile, light-chain Ser56, though distant from kynurenine as shown in FIG. 35, was chosen as a site of residue modification, since its side chain is oriented in the direction of kynurenine and modification with an amino acid residue longer than Ser may possibly result in formation of an interaction with kynurenine. Furthermore, the result described in Example (9-2) below showed that kynurenine-binding activity was increased by substituting heavy-chain Gly50 and light-chain Asp28 with Ala. Since these residue sites are not positions that can directly interact with kynurenine (FIG. 36), they are speculated to indirectly contribute by stabilizing the conformation of the overall Fab upon kynurenine binding. Moreover, regarding these residue sites, modification into residues other than Ala can possibly result in further increase of the kynurenine binding; thus, these residue positions were also chosen as sites for comprehensive alteration. Whether modifications expected to result in an effect of increasing the kynurenine-binding ability can be identified was examined by exhaustive assessment of variants in which these residues have been modified to various amino acids.

Such modification sites in FO2h011/F021003 constructed in Example (8-2-3) (positions according to Kabat numbering which are indicated by "Kabat" in the table), the amino acids before modification at these sites (amino acids indicated by "native sequence" in the table), and the amino acids after modification (amino acids indicated by "altered amino acids" in the table) are shown in Table 17.

TABLE 17

| | HCDR1 | HCDR2 | HCDR3 | | | | | | | | | | LCDR1 | LFR2 | | LCDR2 | |
|---|---|---|---|---|---|---|---|---|---|---|---|---|---|---|---|---|---|
| Kabat | 32 | 50 | 96 | 97 | 98 | 99 | 100 | 100c | 100d | 100e | 101 | 102 | 28 | 46 | 49 | 55 | 56 |
| Native sequence | Y | G | A | P | V | V | A | R | G | A | D | I | D | L | Y | F | S |
| Altered amino acid | A | A | A | A | A | A | A | A | A | | A | A | A | | A | A | A |
| | D | D | D | | D | | | D | D | D | | D | D | | D | D | D |
| | E | E | E | E | E | | E | E | E | | E | E | E | E | E | E | E |
| | F | F | F | F | F | F | F | F | F | | F | F | F | F | F | F | F |
| | G | | G | G | | | G | G | | | | G | G | | G | G | G |
| | H | H | H | H | H | | H | H | H | | | H | H | H | H | H | H |
| | I | I | I | I | I | I | I | I | I | I | | | | | I | | I |
| | K | K | K | K | K | | K | K | K | | | K | K | | K | K | K |
| | L | L | L | L | L | L | L | L | L | L | | L | L | | L | L | L |
| | M | M | M | M | M | | M | M | M | | | M | M | | M | M | M |
| | N | N | N | N | N | | N | N | N | N | N | N | N | | N | N | N |
| | P | P | P | P | | | P | P | P | | | | | | P | P | P |
| | Q | Q | Q | Q | Q | | Q | Q | Q | Q | Q | Q | Q | | Q | Q | Q |
| | R | R | R | R | R | | R | | | | | R | R | | | R | R |
| | S | S | S | S | S | S | S | S | S | S | S | S | S | | S | | |
| | T | T | T | T | T | | T | T | T | T | | T | T | | T | | |
| | V | V | V | V | | | V | V | V | V | | V | V | | V | V | V |
| | W | W | W | W | W | | W | W | W | | | W | W | | W | W | W |
| | | Y | Y | Y | Y | | Y | Y | Y | | | Y | Y | Y | | Y | Y |

The binding of each variant expressed and purified by the method described in Reference Example 1 described below to kynurenine was measured by the Biacore-based method described in Example (7-5), except that the time of adding the diluted antigen solutions and the running buffer as a blank was modified to 30 seconds. Meanwhile, the type of sensor chip immobilized with Protein A was changed to Sensor chip Series S CM3 (GE Healthcare) to measure some of the variants. When kynurenine dissociation was too fast to determine the dissociation rate constant, a dissociation constant KD (M) was calculated by analysis of equilibrium values based on the degree of binding response during the interaction with each antigen (association phase). In this case also, Biacore T200 Evaluation Software (GE Healthcare) was used to calculate the parameters. Based on the assay result, the affinity of each variant for kynurenine was calculated as KD values. The result of comparing the KD values of each of the variants and F02h011/F021003 for kynurenine is shown in Table 18.

TABLE 18

| | | HCDR1 | HCDR2 | HCDR3 | | | | | | | | LCDR1 | LFR2 | | LCDR2 | |
|---|---|---|---|---|---|---|---|---|---|---|---|---|---|---|---|---|
| | | | | Kabat | | | | | | | | | | | | |
| | | 32 | 50 | 96 | 97 | 98 | 99 | 100 | 100c | 100d | 100e | 101 | 102 | 28 | 46 | 49 | 55 | 56 |
| | | | | Native sequence | | | | | | | | | | | | |
| | | Y | G | A | P | V | V | A | R | G | A | D | I | D | L | Y | F | S |
| Altered amino acid | A | 0.0 | 3.1 | | 0.5 | 0.0 | 0.5 | | 0.1 | 0.1 | | 0.0 | 0.4 | 2.5 | | 0.0 | | 0.9 |
| | D | 0.0 | 0.0 | 0.0 | 0.0 | | | 0.6 | 0.0 | 0.0 | 0.0 | | 0.7 | | | | 0.0 | 0.5 |
| | E | 0.0 | 0.0 | 0.4 | 0.1 | | | 0.8 | 0.0 | 0.0 | | 0.0 | 0.5 | 1.7 | | | 0.0 | 0.5 |
| | F | 0.0 | 1.8 | 0.8 | 0.0 | 0.1 | | 0.9 | 0.0 | 0.0 | | | 0.6 | 2.0 | 0.0 | | 0.7 | 1.3 |
| | G | 0.0 | | 0.0 | 0.0 | | | 1.3 | 0.0 | | | | 0.1 | 1.5 | 0.0 | | 0.0 | 0.9 |
| | H | 0.0 | 0.6 | 1.6 | 0.0 | | | 0.6 | 2.5 | 0.1 | | | 0.7 | 2.6 | | | 1.2 | 1.1 |
| | I | 0.0 | 2.7 | 0.4 | 0.0 | 0.2 | | 1.0 | 0.0 | 0.0 | 0.0 | | | 2.1 | 0.1 | | 0.0 | 1.3 |
| | K | 0.0 | 1.9 | 1.3 | 0.1 | | | 0.6 | 0.7 | 0.0 | | | 0.2 | 1.8 | | | 0.0 | 1.0 |
| | L | 0.0 | 1.0 | 0.1 | 0.0 | 0.2 | | 1.2 | 0.0 | 0.0 | 0.0 | | 0.3 | 0.0 | | | 0.0 | 0.8 |
| | M | 0.0 | 2.3 | 0.1 | 0.0 | | | 0.6 | 0.0 | 0.2 | | | 0.4 | 2.1 | | | 0.0 | 1.0 |
| | N | 0.0 | 1.6 | 0.7 | 0.4 | | | 0.3 | 0.0 | 0.3 | 0.0 | 0.0 | 0.4 | 1.5 | | | 0.2 | 0.7 |
| | P | 0.0 | 0.0 | 0.0 | | | | 0.0 | 0.0 | 0.0 | | | 0.0 | 3.2 | | | 0.0 | 0.7 |
| | Q | 0.0 | 0.3 | 2.1 | 0.0 | | | 0.6 | 0.2 | 0.0 | 0.0 | 0.0 | 0.4 | 1.8 | | | 0.0 | 0.7 |
| | R | 0.0 | 1.0 | 0.3 | 0.0 | | | 0.5 | | 0.0 | | | 0.2 | 1.2 | | | 0.0 | 1.2 |
| | S | 0.0 | 2.7 | 0.5 | 0.4 | | 0.5 | 0.5 | 0.0 | 0.0 | 0.3 | 0.0 | 0.1 | 0.9 | | 0.1 | | |
| | T | 0.0 | 1.5 | 0.5 | 0.0 | 0.3 | | 0.4 | 0.0 | 0.0 | 0.0 | | 0.3 | 1.4 | | 0.0 | | |
| | V | 0.0 | 7.0 | 1.9 | 0.0 | | | 0.6 | 0.0 | 0.0 | 0.0 | | 0.6 | 2.1 | | | 0.0 | 2.8 |
| | W | 0.0 | 1.8 | 6.5 | 0.0 | | | 1.1 | 0.0 | 0.0 | | | 0.7 | 2.2 | | | 0.3 | 1.4 |
| | Y | | 3.3 | 0.3 | 0.0 | 0.2 | | 0.9 | 0.1 | 0.0 | | | 0.6 | 3.2 | 0.0 | | | 1.5 |

Of the modifications expected to result in increased kynurenine binding, the sequence into which the modification Lch_Ser56Tyr was added was named F02h011/F021098 (heavy chain variable region sequence: SEQ ID NO: 95; light chain variable region sequence: SEQ ID NO: 97). The sequence was used as a template sequence for a library. The binding of F02h011/F021098 to kynurenine was measured by the Biacore-based method described in Example (7-5), except that the time of adding the diluted antigen solutions and the running buffer as a blank was modified to 30 seconds and the type of sensor chip immobilized with Protein A was changed to Sensor chip Series S CM3 (GE Healthcare). Kinetic parameters for the kynurenine binding of F02h011/F021098 were determined: ka=3686 (1/s), kd=0.26 (1/s), and KD=0.072 (mmol/L). Sensorgrams showing the assessment results are shown in FIG. 33.

(8-3) Assessment of Comprehensive Variants for Library Design Based on Results of X-Ray Crystallographic Structure Analysis The crystallographic structure of the complex of 6RNMSC1-2_F02 and kynurenine was analyzed in Example (8-1). The mode of recognition by which the antibody recognizes kynurenine and the amino acid residues of the antibody variable region that are presumed not to be significantly involved in kynurenine binding were identified based on the result of crystallographic structure analysis. It was conceived that, by comprehensively evaluating variants whose residues shown below are substituted with each of the amino acids, the sites that can be made into a library and the amino acids that can be made into a library could be determined. Specifically, it was conceived that, by evaluating the sites that are not greatly involved in the binding toward kynurenine, or the sites in which amino acids other than those of the native sequence that may be involved in binding but do not significantly reduce the binding toward kynurenine (do not render the binding to zero) are present, as well as the amino acids, the sites that can be made into a library and the amino acids that can be made into a library could be determined. Several variants were generated by introducing modifications to these residues in FO2h011/F021098, which was generated in Example (8-2-4) and in which a modification that increases kynurenine binding had been added.

Of the sites in the heavy chain, the modified sites (the sites shown according to Kabat numbering and indicated as "Kabat" in the table), the amino acids before modification at these sites (the amino acids indicated as "native sequence" in the table), and the amino acids after modification (the amino acids indicated as "altered amino acids" in the table) are shown in Table 19.

TABLE 19

| | FR1 | | | | | | HCDR1 | | HCDR2 Kabat | | | | | | | | FR3 | HCDR3 | | | | | | | |
|---|---|---|---|---|---|---|---|---|---|---|---|---|---|---|---|---|---|---|---|---|---|---|---|---|---|
| Altered amino acid | 24 | 26 | 27 | 28 | 29 | 30 | 31 | 33 | 51 | 52 | 52a | 53 | 54 | 55 | 56 | 58 | 73 | 95 | 98 | 99 | 100a | 100b | 100e | 100f | 101 |
| Native sequence | A | G | G | T | F | S | S | A | I | I | P | I | F | G | T | N | E | D | V | V | R | P | A | F | D |
| A | | A | A | A | A | A | | | | | | | | | | | A | | | | | | | | |
| D | D | D | D | D | D | D | D | D | D | D | D | D | D | D | D | D | D | | D | D | D | D | D | D | |
| E | E | E | E | E | E | E | E | E | E | E | E | E | E | E | E | E | | E | E | E | E | E | E | E | E |
| F | F | F | F | F | | F | F | F | F | F | F | F | | F | F | F | F | F | F | F | F | F | F | | F |
| G | G | | G | G | G | G | G | G | G | G | G | G | G | | G | G | G | G | G | G | G | G | G | G | G |
| H | H | H | H | H | H | H | H | H | H | H | H | H | H | H | H | H | H | H | H | H | H | H | H | H | H |
| I | I | I | I | I | I | I | I | I | | | I | | I | I | I | I | I | I | I | I | I | I | I | I | I |
| K | K | K | K | K | K | K | K | K | K | K | K | K | K | K | K | K | K | K | K | K | K | K | K | K | K |
| L | L | L | L | L | L | L | L | L | L | L | L | L | L | L | L | L | L | L | L | L | L | L | L | L | L |
| M | M | | | | | M | | | | | | | | | | | M | | | | | | | | |
| N | N | N | N | N | N | N | N | N | N | N | N | N | N | N | N | | N | N | N | N | N | N | N | N | |
| P | P | P | P | P | P | P | P | P | P | P | | P | P | P | P | P | P | P | P | P | P | | P | P | P |
| Q | Q | Q | Q | Q | Q | Q | Q | Q | Q | Q | Q | Q | Q | Q | Q | Q | Q | Q | Q | Q | Q | Q | Q | Q | Q |
| R | R | R | R | R | R | R | R | R | R | R | R | R | R | R | R | R | R | R | R | R | | R | R | R | R |
| S | S | S | S | S | S | | | S | S | S | S | S | S | S | S | S | S | S | S | S | S | S | S | S | S |
| T | T | T | T | | T | T | T | T | T | T | T | T | T | T | | T | T | T | T | T | T | T | T | T | T |
| V | V | V | V | V | V | V | V | V | V | V | V | V | V | V | V | V | V | V | | | V | V | V | V | V |
| W | W | W | W | W | W | W | W | W | W | W | W | W | W | W | W | W | W | W | W | W | W | W | W | W | W |
| Y | Y | Y | Y | Y | Y | Y | Y | Y | Y | Y | Y | Y | Y | Y | Y | Y | Y | Y | Y | Y | Y | Y | Y | Y | Y |

Of the sites in the light chain, the modified sites (the sites shown according to Kabat numbering and indicated as "Kabat" in the table), the amino acids before modification at these sites (the amino acids indicated as "native sequence" in the table), and the amino acids after modification (the amino acids indicated as "altered amino acids" in the table) are shown in Table 20.

TABLE 20

| | LCDR1 | | | | FR2 | LCDR2 | | | | | | LCDR3 | | | |
|---|---|---|---|---|---|---|---|---|---|---|---|---|---|---|---|
| | Kabat | | | | | | | | | | | | | | |
| | 27d | 27e | 29 | 32 | 46 | 50 | 51 | 52 | 53 | 54 | 55 | 92 | 93 | 94 | 96 |
| | Native sequence | | | | | | | | | | | | | | |
| | H | S | G | Y | L | E | I | S | N | R | F | T | Q | F | R |
| Altered amino acid | A | | | | A | | | | | | | | | | |
| | D | D | D | D | D | D | D | D | D | D | D | D | D | D | D |
| | E | E | E | E | E | | E | E | E | E | E | E | E | E | E |
| | F | F | F | F | F | | F | F | F | F | F | | F | F | F |
| | G | G | G | | G | G | G | G | G | G | G | G | G | G | G |
| | H | | H | H | H | | H | H | H | H | H | H | H | H | H |
| | I | I | I | I | I | I | I | | I | I | I | I | I | I | I |
| | K | K | K | K | K | K | K | K | K | K | K | K | K | K | K |
| | L | L | L | L | L | | L | L | L | L | L | L | L | L | L |
| | M | | | | M | M | M | | | | | | | | |
| | N | N | N | | N | | N | N | | N | N | N | N | N | N |
| | P | P | P | P | P | P | P | P | P | P | P | P | P | P | P |
| | Q | Q | Q | Q | Q | Q | Q | Q | Q | Q | Q | Q | Q | Q | Q |
| | R | R | R | R | R | R | R | R | R | | R | R | R | R | |
| | S | S | | S | | S | S | S | | S | S | | S | S | S |
| | T | T | T | T | | T | T | T | T | T | | T | T | T | |
| | V | V | V | V | V | V | V | V | V | V | V | V | V | V | V |
| | W | W | W | W | W | W | W | W | W | W | W | W | W | W | W |
| | Y | Y | Y | Y | | | Y | Y | Y | Y | Y | Y | Y | Y | Y |

The binding of each variant expressed and purified by the method described in Reference Example 1 described below to kynurenine was measured by the method using Biacore described in Example (7-5), except that the time of adding the diluted antigen solutions and the running buffer as a blank was modified to 30 seconds. Meanwhile, the type of sensor chip immobilized with Protein A was changed to Sensor chip Series S CM3 (GE Healthcare) to measure some of the variants. When kynurenine dissociation was too fast to determine the dissociation rate constant, a dissociation constant KD (M) was calculated by analysis of equilibrium values based on the degree of binding response during the interaction with each antigen (association phase). In this case also, Biacore T200 Evaluation Software (GE Healthcare) was used to calculate the parameters. Based on the assay result, the affinity of each variant for kynurenine was calculated as KD values. The result of comparing the KD values of each of the heavy chain variants and FO2h011/F021098, which is the parental sequence, for kynurenine is shown in Table 21. The result of comparing the KD values of each of the light chain variants and FO2h011/F021098, which is the parental sequence, for kynurenine is shown in Table 22.

TABLE 21

|  |  | FR1 | | | | HCDR1 Kabat | | | | HCDR2 | | | | |
|---|---|---|---|---|---|---|---|---|---|---|---|---|---|---|
|  |  | 24 | 26 | 27 | 28 | 29 | 30 | 31 | 33 | 51 | 52 | 52a | 53 | 54 |
|  |  |  |  |  |  | Native sequence | | | | | | | | |
|  |  | A | G | G | T | F | S | S | A | I | I | P | I | F |
| Altered amino acid | A |  | 4.5 | 2.0 | 0.6 | 0.0 | 1.0 |  |  |  |  |  |  |  |
|  | D | 2.1 | 2.5 | 4.6 | 0.7 | 0.0 | 0.8 | 2.6 | 0.0 | 0.0 | 0.1 | 0.0 | 0.3 | 0.6 |
|  | E | 11.0 | 2.0 | 6.0 | 1.1 | 0.0 | 1.1 | 2.4 | 0.0 | 0.1 | 0.4 | 0.0 | 0.2 | 0.4 |
|  | F | 0.4 | 2.6 | 4.9 | 1.2 |  | 1.5 | 1.1 | 0.0 | 0.2 | 0.3 | 0.0 | 0.5 |  |
|  | G | 1.4 |  |  | 0.7 | 0.0 | 0.4 | 1.3 | 0.4 | 0.4 | 0.1 | 0.3 | 0.8 | 0.8 |
|  | H | 1.5 | 2.5 | 3.3 | 0.6 | 0.0 | 1.2 | 1.1 | 0.0 | 0.1 | 0.2 | 0.0 | 0.5 | 0.7 |
|  | I | 0.8 | 4.3 | 2.6 | 1.4 | 0.3 | 0.9 | 0.4 | 2.5 |  |  | 0.1 |  | 0.9 |
|  | K | 1.1 | 7.9 | 3.4 | 0.5 | 0.0 | 1.1 | 1.0 | 0.3 | 0.4 | 0.7 | 0.0 | 0.5 | 0.8 |
|  | L | 0.8 | 5.3 | 4.4 | 1.1 | 0.5 | 2.0 | 1.3 | 0.2 | 0.3 | 0.5 | 0.0 | 0.8 | 0.7 |
|  | M | 1.9 |  |  |  |  | 1.2 |  |  |  |  |  |  |  |
|  | N | 2.6 |  | 4.8 |  |  | 1.1 | 0.9 | 0.0 | 0.2 | 0.4 | 0.0 | 0.4 |  |
|  | P | 0.8 | 11.0 | 1.8 | 0.4 | 0.0 | 0.5 | 0.0 | 0.0 | 0.0 | 0.5 |  | 0.5 | 1.1 |
|  | Q | 1.1 | 4.0 | 3.4 | 0.9 | 0.0 | 1.0 | 1.8 | 0.2 | 0.5 | 0.7 | 0.0 | 0.4 | 0.6 |
|  | R | 0.3 | 9.1 | 4.2 | 0.5 | 0.0 | 1.1 | 08 | 0.4 | 0.7 | 0.3 | 0.0 | 0.5 | 0.8 |
|  | S | 2.1 | 1.6 | 3.4 | 1.0 | 0.0 |  |  | 0.5 | 0.4 | 0.3 | 0.3 | 0.5 | 0.8 |
|  | T | 3.6 | 2.1 | 3.3 |  | 0.0 | 1.5 | 0.5 | 0.4 | 0.3 | 0.6 | 0.2 | 0.8 | 0.9 |
|  | V | 1.0 | 4.9 | 4.4 | 0.8 | 0.2 | 1.0 | 0.5 | 0.7 | 1.8 | 1.0 | 0.0 | 1.2 | 0.8 |
|  | W | 0.5 | 7.6 | 9.7 | 23.6 | 0.3 | 1.5 | 1.2 | 8.3 | 0.2 | 0.5 | 0.2 | 0.3 | 1.0 |
|  | Y | 2.2 | 4.6 | 20.6 | 0.7 | 0.5 | 1.2 | 0.8 | 0.0 | 0.6 | 0.3 | 0.0 | 0.5 | 1.1 |

|  |  | HCDR2 | | FR3 | | HCDR3 Kabat | | | | | | |
|---|---|---|---|---|---|---|---|---|---|---|---|---|
|  |  | 55 | 56 | 58 | 73 | 95 | 98 | 99 | 100a | 100b | 100e | 100f | 101 |
|  |  |  |  |  |  | Native sequence | | | | | | | |
|  |  | G | T | N | E | D | V | V | R | P | A | F | D |
| Altered amino acid | A |  |  |  |  | 1.1 |  |  |  |  |  |  |  |
|  | D | 1.2 | 0.7 | 0.4 | 0.9 |  | 0.0 | 0.2 | 0.4 | 0.0 |  | 0.0 |  |
|  | E | 0.7 | 0.7 | 0.2 |  | 0.0 | 0.0 | 0.2 | 0.3 | 0.0 | 0.0 | 0.0 |  |

TABLE 21-continued

| | c1 | c2 | c3 | c4 | c5 | c6 | c7 | c8 | c9 | c10 | c11 | c12 |
|---|---|---|---|---|---|---|---|---|---|---|---|---|
| F | 0.3 | 1.2 | 0.7 | 0.8 | 0.0 | | 3.4 | 0.1 | 0.0 | 0.0 | | 0.0 |
| G | | 0.3 | 0.8 | 1.1 | 1.2 | 0.0 | 0.1 | 0.0 | 0.1 | 1.4 | 0.0 | 0.0 |
| H | 1.3 | 0.8 | 1.0 | 0.9 | 0.0 | 0.0 | 0.8 | 0.1 | 0.0 | 0.0 | 0.1 | 0.0 |
| I | 0.3 | 1.1 | 0.1 | 1.1 | 0.0 | | 1.0 | 0.5 | 0.0 | | 0.0 | 0.0 |
| K | 0.8 | 0.9 | 1.1 | 1.1 | 0.0 | 0.0 | 0.4 | 0.7 | 1.5 | 0.0 | 0.0 | 0.0 |
| L | 0.5 | 1.6 | 0.1 | 2.0 | 0.0 | | 0.6 | 0.4 | 0.0 | | 2.2 | 0.0 |
| M | | | | 1.6 | | | | | | | | |
| N | 1.8 | 0.6 | | | 0.0 | 0.0 | 0.5 | 0.3 | 0.3 | | 0.0 | |
| P | 0.6 | 0.7 | 0.3 | 1.0 | 0.0 | 0.0 | 0.0 | 1.2 | | 0.0 | 0.0 | 0.0 |
| G | 1.2 | 0.8 | 1.0 | 0.9 | 0.0 | 0.0 | 0.4 | 0.6 | 0.3 | | 0.0 | |
| R | 0.5 | 0.9 | 1.6 | 1.3 | 0.0 | 0.2 | 0.7 | | 0.5 | 0.0 | 0.0 | 0.0 |
| S | 0.9 | 0.8 | 0.7 | 1.0 | 0.0 | 00 | | 0.4 | 0.4 | | 0.0 | |
| T | 0.6 | | 1.1 | 1.3 | 0.0 | | 0.5 | 0.5 | 0.2 | | 0.0 | 0.0 |
| V | 0.4 | 0.8 | 0.6 | 1.4 | 0.0 | | | 0.6 | 0.0 | | 0.0 | 0.0 |
| W | 1.0 | 5.1 | 1.0 | 0.7 | 0.0 | 0.0 | 0.0 | 0.0 | 0.0 | 0.0 | 0.1 | 0.0 |
| Y | 0.5 | 0.9 | 1.5 | 0.4 | 0.0 | | 1.9 | 0.0 | 0.0 | 0.0 | 0.1 | 0.0 |

TABLE 22

| | | LCDR1 | | | | FR2 | | LCDR2 Kabat | | | | | LCDR3 | | |
|---|---|---|---|---|---|---|---|---|---|---|---|---|---|---|---|
| | | 27d | 27e | 29 | 32 | 46 | 50 | 51 | 52 | 53 | 54 | 55 | 92 | 93 | 94 | 96 |
| | | | | | | | Native sequence | | | | | | | | | |
| | | H | S | G | Y | L | E | I | S | N | R | F | T | Q | F | R |
| Altered amino acid | A | | | | | 0.0 | | | | | | | | | | |
| | D | 1.9 | 0.9 | 1.0 | 0.0 | 0.0 | 0.0 | 0.4 | 0.8 | 1.1 | 0.8 | 0.0 | 1.2 | 0.9 | 0.0 | 0.0 |
| | E | 1.3 | 0.9 | 0.9 | 0.2 | | | 0.3 | 1.0 | 0.9 | 0.9 | 0.0 | 0.4 | 1.6 | 0.0 | 0.0 |
| | F | 0.6 | 0.9 | 1.0 | 2.0 | | 0.5 | 0.4 | 1.1 | 1.0 | 0.9 | | 0.9 | 0.5 | | 0.0 |
| | G | 1.1 | 0.9 | | 0.3 | 0.0 | 0.4 | 0.4 | 1.0 | 0.5 | 0.9 | 0.1 | 1.4 | 0.4 | 0.2 | 0.0 |
| | H | | 1.0 | 1.0 | 0.8 | | 0.0 | 0.2 | 0.9 | 0.9 | 1.2 | 0.1 | 1.0 | 0.1 | 0.4 | 0.0 |
| | I | 2.3 | 0.9 | 1.2 | 0.0 | 0.4 | 0.4 | | 1.0 | 1.2 | 0.8 | 0.1 | 2.2 | 0.6 | 0.9 | 0.0 |
| | K | 1.1 | 1.0 | 1.1 | 0.5 | 0.0 | 0.2 | 0.3 | 1.2 | 1.2 | 0.9 | 0.1 | 1.1 | 0.6 | 0.4 | 0.0 |
| | L | 1.8 | 0.9 | 1.0 | 0.4 | | 0.8 | 0.2 | 0.9 | 1.4 | 0.8 | 0.2 | 1.0 | 0.4 | 0.2 | 0.0 |
| | M | | | | | 0.4 | 1.9 | 0.4 | 0.9 | | | | | | | |
| | N | 2.3 | 1.0 | | | 0.3 | | 0.2 | 0.8 | | 0.7 | 0.1 | 1.8 | 1.1 | 0.2 | 0.0 |
| | P | 2.3 | 0.9 | 1.8 | 0.4 | 0.1 | 0.0 | 0.0 | 0.1 | 0.6 | 1.0 | 0.0 | 0.1 | 0.0 | 0.0 | 0.0 |
| | Q | 1.4 | 1.0 | 1.0 | 0.3 | 0.0 | 0.8 | 0.4 | 1.2 | 1.0 | 1.0 | 0.1 | 1.4 | | 0.2 | 0.0 |
| | R | 0.9 | 1.1 | 0.9 | 0.9 | 0.0 | 0.0 | 0.5 | 1.2 | 1.1 | | | 0.1 | 0.9 | 0.7 | 0.3 |
| | S | 1.0 | | 0.9 | | 0.0 | 0.2 | 0.4 | | 0.8 | 0.9 | | 0.9 | 0.8 | 0.2 | 0.0 |
| | T | 2.0 | 1.0 | 0.9 | | 0.0 | 0.3 | 0.4 | 1.0 | 0.7 | 0.6 | | | 1.7 | 0.4 | 0.0 |

TABLE 22 -continued

| | LCDR1 | | FR2 | | | LCDR2 Kabat | | | | | LCDR3 | | | |
|---|---|---|---|---|---|---|---|---|---|---|---|---|---|---|
| 27d | 27e | 29 | 32 | 46 | 50 | 51 | 52 | 53 | 54 | 55 | 92 | 93 | 94 | 96 |
| | | | | | | Native sequence | | | | | | | | |
| H | S | G | Y | L | E | I | S | N | R | F | T | Q | F | R |

| | 27d | 27e | 29 | 32 | 46 | 50 | 51 | 52 | 53 | 54 | 55 | 92 | 93 | 94 | 96 |
|---|---|---|---|---|---|---|---|---|---|---|---|---|---|---|---|
| V | 2.5 | 1.0 | 1.2 | 0.3 | 0.6 | 0.2 | 0.6 | 1.1 | 1.0 | 0.7 | 0.1 | 1.7 | 1.0 | 0.8 | 0.0 |
| W | 0.6 | 1.0 | 1.1 | 0.3 | 0.0 | 0.0 | 0.3 | 1.0 | 1.0 | 0.9 | 0.0 | 0.8 | 0.0 | 0.8 | 0.0 |
| Y | 0.6 | 1.2 | 1.0 | | | 0.2 | 0.3 | 1.1 | 1.1 | 1.2 | 1.3 | 0.9 | 0.5 | 1.1 | 0.0 |

(8-4) Library Design Based on the Result of Assessment of Comprehensive Variants To design a library, sites that meet at least one of the following conditions were selected as library-constructible sites based on the information obtained in Examples (8-2-4) and (8-3) and Example (9-2) described below.

Condition 1: sites that are not greatly involved in the binding toward kynurenine, or sites in which amino acids other than those of the native sequence are present and which may be involved in binding but which do not significantly reduce the binding toward kynurenine;

Condition 2: sites having a certain level of diversity of amino acid occurrence frequency as repertoire of the antibody; and Condition 3: sites that are not important for the formation of canonical structures.

From the evaluation results of Examples (8-2-4) and (8-3) and Example (9-2) described below, when sites for which at least one or more variants, whose KD values toward kynurenine exceed 20% of that of the parent sequence in each evaluation, exist, those were judged to be modifiable sites that meet the above-described conditions. Of the amino acids substituted at these sites, the amino acids, whose KD values toward kynurenine exceed 20% of that of the parent sequence in each evaluation were judged to be library-constructible amino acids (flexible residues that can be made to appear in the library). A library for obtaining kynurenine switch antibodies is constructed by designing a library in which at least any one or more amino acids from among the amino acids contained in the amino acid repertoire, which includes the library-constructible amino acids selected from the variant analysis (the flexible residues that can be made to appear in the library) and the amino acids of the non-modified antibody (i.e., the amino acids included in the native sequence of FO2h011/F021098), appear at the determined modifiable sites in FO2h011/F021098, which was generated in Example (8-2-4) and in which a modification that increases kynurenine binding had been added. The sites containing an amino acid repertoire in the heavy chain, and the amino acid repertoires at these sites are shown in Table 23. The sites containing an amino acid repertoire in the light chain, and the amino acid repertoires at these sites are shown in Table 24. In the tables, sites shown according to Kabat numbering indicated by "Kabat" represent modifiable sites; amino acids indicated by "native sequence" represent non-modified amino acids at these sites; and amino acids indicated by "library-constructible amino acids" represent library-constructible amino acids at these sites. A library, in which at least any one amino acid from among the amino acids contained in the selected amino acid repertoire appears at each of the modifiable sites, was designed.

TABLE 23

| | | FR1 Kabat | | | | | | HCDR1 | | HCDR2 | |
|---|---|---|---|---|---|---|---|---|---|---|---|
| | 24 | 26 | 27 | 28 | 29 | 30 | 31 | 32 | 33 | 50 | 51 |
| | | | | | Native Sequence | | | | | | |
| | A | G | G | T | F | S | S | Y | A | G | I |
| Library-constructible amino acid | A | | A | A | A | | A | A | | A | A |
| | D | | D | D | D | D | | D | D | | | |
| | E | | E | E | E | E | | E | £ | | | |
| | F | | F | F | F | F | | F | F | F | | F |
| | G | G | | | G | | G | G | | G | | G |
| | H | | H | H | H | H | | H | H | H | | H |
| | I | | I | I | I | I | | I | I | | I | I |
| | K | | K | K | K | | | K | K | | K | K | K |
| | L | | L | L | | L | | L | L | | | L | L |

TABLE 23-continued

| | | | | | | | | | |
|---|---|---|---|---|---|---|---|---|---|
| M | M | | | M | | | M | | |
| N | N | N | | N | N | | N | | |
| P | P | P | P | P | | p | | | |
| Q | Q | Q | Q | Q | | Q | Q | Q | Q Q |
| R | R | R | R | R | | R | R | R | R R |
| S | S | S | S | S | | | | S | S S |
| T | T | T | T | | | T | T | T | T T |
| V | V | V | V | V | | V | V | V | V V |
| W | W | W | W | W | W | W | W | W | W W |
| Y | Y | Y | Y | Y | y | Y | Y | | Y Y |

| | HCDR2 | | | | | | FR3 | HCDR3 | | |
|---|---|---|---|---|---|---|---|---|---|---|---|
| | Kabat | | | | | | | | | | |
| | 52 | 52a | 53 | 54 | 55 | 56 | 58 | 73 | 95 | 96 | 97 |
| | Native Sequence | | | | | | | | | | |
| | I | P | I | F | G | T | N | E | D | A | P |
| Library-constructible amino acid | A | A | A | A | A | A | A | A | | | A |
| | D | | D | D | D | D | D | D | | | |
| | E | E | | E | E | E | E | | | E | |
| | F | F | | P | | F | F | F | F | F | |
| | G | | G | G | G | | G | G | G | | |
| | H | H | | H | H | H | H | H | | H | |
| | I | | | I | I | I | | I | | I | |
| | K | K | | K | K | K | K | K | | K | |
| | L | L | | L | L | L | L | | | | |
| | M | | | | | | | | | | |
| | N | N | | N | N | N | | N | | N | N |
| | P | p | | P | P | P | P | P | | | |
| | Q | Q | | Q | Q | Q | Q | Q | Q | Q | |
| | R | R | | R | R | R | R | R | R | R | |
| | S | S | S | S | S | S | s | S | S | S | S |
| | T | T | T | T | T | | | T | T | T | |
| | V | V | | V | V | V | V | V | V | V | |
| | W | W | W | W | W | W | W | W | W | W | |
| | Y | Y | | Y | Y | Y | Y | Y | Y | Y | |

TABLE 23-continued

| | HCDR3 kabat | | | | | | | | | |
|---|---|---|---|---|---|---|---|---|---|---|
| | 98 | 99 | 100 | 100a | 100b | 100c | 100d | 100e | 100f | 102 |
| | | | | | Native Sequence | | | | | |
| | V | V | A | R | P | R | G | A | F | I |
| Library-constructible amino acid | A | A | A | A | | | | | | A |
| | | D | D | D | | | | | | D |
| | | | E | E | | | | | | E |
| | | F | F | | | | | | | F |
| | | | G | | | | | G | | |
| | | H | H | | | H | | | | H |
| | | I | I | I | | | | | | |
| | K | K | K | K | K | K | | | | |
| | L | L | L | L | | | | | L | L |
| | | M | | | | | | | | M |
| | N | N | N | N | N | | N | | | N |
| | P | | | P | | | | | | |
| | | Q | Q | Q | Q | Q | | | | Q |
| | | R | R | | R | | | | | R |
| | | S | S | S | S | | | S | | |
| | T | T | T | T | T | | | | | T |
| | | | V | V | | | | | | V |
| | W | | W | | | | | | | |
| | | Y | Y | | | | | | | Y |

TABLE 24

| | LCDR1 | | | | | FR2 | | LCDR2 | | | | | | LCDR3 | | |
|---|---|---|---|---|---|---|---|---|---|---|---|---|---|---|---|---|
| | 27d | 27e | 28 | 29 | 32 | 46 | 49 | 50 | 51 | 52 | 53 | 54 | 55 | 92 | 93 | 94 |
| | | | | | | | | Native sequence | | | | | | | | |
| | H | S | D | G | Y | L | Y | E | I | S | N | R | F | T | Q | F |
| Library-constructible amino acid | A | A | A | A | A | A | | | A | A | A | A | | A | A | |
| | D | D | | D | | | | | D | D | D | D | | D | D | |
| | E | E | E | E | | | | | E | E | E | E | | E | E | |
| | F | F | F | F | F | F | | | F | F | F | F | | F | F | |
| | G | G | G | G | | G | | | G | G | G | G | | G | G | |
| | H | H | H | H | H | H | H | | | H | H | H | | H | | H |
| | I | I | I | I | | I | I | | | I | I | I | | I | I | |
| | K | K | K | K | K | K | | | K | K | K | K | | K | K | K |

TABLE 24 -continued

| | LCDR1 | | | | FR2 | | LCDR2 | | | | | LCDR3 | | | |
|---|---|---|---|---|---|---|---|---|---|---|---|---|---|---|---|
| | | | | | Kabat | | | | | | | | | | |
| 27d | 27e | 28 | 29 | 32 | 46 | 49 | 50 | 51 | 52 | 53 | 54 | 55 | 92 | 93 | 94 |
| | | | | | | Native sequence | | | | | | | | | |
| H | S | D | G | Y | L | Y | E | I | S | N | R | F | T | Q | F |
| L | L | L | | L | L | | L | L | L | L | L | | L | L | |
| M | | | M | | | M | | M | M | | | M | | | |
| N | N | N | N | | N | | | N | | N | | N | N | N | |
| P | P | P | P | P | P | | | | P | P | | | | | |
| Q | Q | Q | Q | Q | Q | | Q | Q | Q | Q | Q | | Q | | Q |
| R | R | R | R | R | R | | | R | R | R | | R | R | R | |
| S | S | | S | S | | | S | S | | S | S | | S | S | S |
| T | T | T | T | T | | | T | T | T | T | | | T | T | |
| V | V | V | V | V | V | V | | V | V | V | V | | V | V | V |
| W | W | W | W | W | W | W | W | W | W | W | W | W | W | W | W |
| Y | Y | Y | Y | Y | | | Y | Y | Y | Y | Y | Y | Y | Y | Y |

Genes containing each of the sequences included in the library designed in this manner are synthesized, and using the collection (library) of these individual genes as a template, a gene library is amplified with primers that can amplify each of VH and VL. The amplified gene library of rationally designed human antibody heavy chain variable regions and that of the human antibody light chain variable regions are introduced into appropriate phagemid vectors having both a human IgG-derived CH1 sequence and a human IgG-derived light chain constant region sequence. A rationally designed library which enables to obtain antibodies which bind to antigens using kynurenine as a switch are constructed by introducing these phagemid vectors into Escherichia coli by electroporation and then presenting Fab domains consisting of a human antibody variable region-constant region. Such a rationally designed library composed of diverse H chains and L chains having binding activities to kynurenine is thought to be useful as a library containing human antibodies that enable to efficiently obtain kynurenine switch antibodies against arbitrary antigens. Moreover, since, as described in Example (7-6), 6RNMSC1-2_F02 binds not only to kynurenine but also to 3-hydroxykynurenine which is metabolite of kynurenine and kynurenine derivatives including RO0635389-000-001, it is also predicted to have binding activity to other derivatives that are structurally similar to kynurenine. Thus, the library is considered to be useful for obtaining switch antibodies whose binding activity toward an arbitrary target antigen varies depending on the presence or absence of any one or more small molecules of kynurenine, metabolites of kynurenine, and kynurenine derivatives that are exogenous molecules.

[Example 9] Library Design for Obtaining Kynurenine-Switch Antibodies by Panning with a Molecule Acting as a Switch Example 8 describes a method for constructing a library using an antibody having binding activity to kynurenine as a template and designing the sites for making a library by comprehensive modification. As a different approach for producing a library, a method using panning with a molecule that serves as a switch is also useful.

(9-1) X-Ray Crystallographic Analysis of Antibody 6RNMSC1-2_F02 that Binds to hIL-6R with Kynurenine as a Switch The crystal structure of a complex of 6RNMSC1-2_F02 and kynurenine was analyzed as described in Example (8-1). The mode at which kynurenine is recognized by the antibody as well as amino acid residues in the antibody variable region presumably not greatly involved in kynurenine binding were identified based on the results of crystallographic analysis.

(9-2) Assessment for Selecting Library-Constructible Sites, and Library Design

The present inventors conceived that library-constructible sites can be selected through assessment of variants produced by substituting Ala or Val for the various positions selected based on results of the crystallographic analysis of FO2h011/F021003 (heavy chain variable region sequence, SEQ ID NO: 95; light chain variable region sequence, SEQ ID NO: 96) generated as described in Example (8-2-2).

(9-2-1) Assessment for Selecting Library-Constructible Sites in the Heavy Chain Variable Region, and Library Design First, regarding the heavy chain, among the sites contained in the heavy chain sequence of FO2h011/F021003, variants were generated by substituting Ala or Val for the various positions selected based on crystallographic analysis results. The modified sites (positions according to Kabat numbering which are indicated as "Kabat" in the table), amino acids before modification at these sites (amino acids indicated as "native sequence" in the table), and amino acids after modification (amino acids indicated as "altered amino acids" in the table) are shown in Table 25.

TABLE 25

| | HFR1 | HCDR1 | | | | HCDR2 Kabat | | | | | | | | |
|---|---|---|---|---|---|---|---|---|---|---|---|---|---|---|
| | 28 | 31 | 32 | 33 | 35 | 50 | 51 | 52 | 52a | 53 | 54 | 55 | 56 | 58 |
| | | | | | | Native sequence | | | | | | | | |
| | T | S | Y | A | S | G | I | I | P | I | F | G | T | N |
| Altered amino acid | A | A | A | V | A | A | A | A | A | A | A | A | A | A |

| | HCDR3 Kabat | | | | | | | | | | | | | |
|---|---|---|---|---|---|---|---|---|---|---|---|---|---|---|
| | 95 | 96 | 97 | 98 | 99 | 100 | 100a | 100b | 100c | 100d | 100e | 100f | 101 | 102 |
| | | | | | | Native sequence | | | | | | | | |
| | D | A | P | V | V | A | R | P | R | G | A | F | D | I |
| Altered amino acid | A | V | A | A | A | V | A | A | A | A | V | A | A | A |

Each variant expressed and purified by the method described in Reference Example 1 below was assayed for its kynurenine binding by the Biacore-based method described in Example (7-5), except that the period of antigen loading was changed to be 30 seconds. When kynurenine dissociation was too fast to determine the dissociation rate constant, the dissociation constant KD (M) was calculated by analysis of equilibrium values based on the degree of binding response when it is interacted with each antigen (association phase). Also in this case, the Biacore T200 Evaluation Software (GE Healthcare) was used to calculate parameters. Based on the assay results, KD values were calculated to determine the affinity of each variant for kynurenine. Each variant and its parental antibody F02h011/F021003 were compared in terms of the KD value for kynurenine. The results are shown in Table 26.

TABLE 26

| | HFR1 | HCDR1 | | | | HCDR2 Kabat | | | | | | | | |
|---|---|---|---|---|---|---|---|---|---|---|---|---|---|---|
| | 28 | 31 | 32 | 33 | 35 | 50 | 51 | 52 | 52a | 53 | 54 | 55 | 56 | 58 |
| | | | | | | Native sequence | | | | | | | | |
| | T | S | Y | A | S | G | I | I | P | I | F | G | T | N |
| Altered amino acid | A | A | A | V | A | A | A | A | A | A | A | A | A | A |
| F02h011/F021003 ratio | 0.9 | 1.7 | 0.0 | 0.7 | 0.7 | 6.9 | 0.5 | 0.4 | 0.4 | 0.4 | 0.6 | 0.8 | 0.8 | 0.7 |

| | HCDR3 Kabat | | | | | | | | | | | | | |
|---|---|---|---|---|---|---|---|---|---|---|---|---|---|---|
| | 95 | 96 | 97 | 98 | 99 | 100 | 100a | 100b | 100c | 100d | 100e | 100f | 101 | 102 |
| | | | | | | Native sequence | | | | | | | | |
| | D | A | P | V | V | A | R | P | R | G | A | F | D | I |
| Altered amino acid | A | V | A | A | A | V | A | A | A | A | V | A | A | A |
| F02h011/F021003 ratio | 0.0 | 1.9 | 0.5 | 0.1 | 0.5 | 0.6 | 0.3 | 0.2 | 0.1 | 0.2 | 0.0 | 0.0 | 0.0 | 0.4 |

Upon designing a library, sites that meet at least one of the following conditions were selected as library-constructible sites based on information obtained in the above assessment of variants and in the assessment described in Example (8-2-4).

Condition 1: sites that are not greatly involved in the binding toward kynurenine, or sites in which amino acids other than those of the native sequence are present and which may be involved in binding but which do not significantly reduce the binding toward kynurenine (do not render the binding to zero);

Condition 2: sites having a certain level of diversity of amino acid occurrence frequency as repertoire of the antibody; and Condition 3: sites that are not important for the formation of canonical structures.

A library was designed so that the amino acids at positions selected by the conditions described above appear only at certain nucleotides in the heavy chain sequence (SEQ ID NO: 95) of F02h011/F021098 produced as described in Example (8-2-4) by introducing a modification that augments the kynurenine binding. Such libraries include, for example, NNK and TRIM libraries (Gonzalez-Munoz A et al., MAbs 2012; Lee C V et al., J Mol Biol. 2004; Knappik A. et al., J Mol Biol. 2000; Tiller T et al., MAbs 2013). Among the various positions assessed, modification sites in which a KD value for kynurenine indicates more than 20% binding of F02h011/F021003, which is the parental sequence, were judged to be modifiable positions that meet the above-described conditions. However, even if included in such sites, residue positions judged to be structurally important were excluded from the sites to be included in a library, or were included in a library with selected types of occurring amino acids. Sites for library production using NNK codons (indicated by an open circle in the table), sites fixed to the native sequence (indicated by a cross in the table), and amino acids of selected occurring amino acid types are shown in Table 27.

TABLE 27

| | HFR1 | HCDR1 | | | | HCDR2 kabat | | | | | | | |
|---|---|---|---|---|---|---|---|---|---|---|---|---|---|
| | 28 | 31 | 32 | 33 | 35 | 50 | 51 | 52 | 52a | 53 | 54 | 55 | 56 | 58 |
| | | | | | | | Native sequence | | | | | | | |
| | T | S | Y | A | S | G | I | I | P | L | F | G | T | N |
| Library | ○ | ○ | X | ○ | X | ○ | I, F, V, L | ○ | X | X | ○ | G, S | ○ | ○ |

| | HCDR3 kabat | | | | | | | | | | | | |
|---|---|---|---|---|---|---|---|---|---|---|---|---|---|
| | 95 | 96 | 97 | 98 | 99 | 100 | 100a | 100b | 100c | 100d | 100e | 1001 | 101 | 102 |
| | | | | | | Native sequence | | | | | | | | |
| | D | A | P | V | V | A | R | P | R | G | A | F | D | I |
| Library | X | ○ | A, P | X | ○ | ○ | ○ | A, P | R, H | X | X | X | X | X |

The designed gene sequence was synthesized using primers containing at the sites for library production (heavy chain variable region library) NNK codons or codons in which selected amino acids occur; and inserted into an appropriate phagemid vector carrying human IgG-derived CH1 sequence and human IgG-derived light chain constant region sequence in combination with the light chain variable region sequence of F02h011/F021098(parental sequence, SEQ ID NO: 97). A phage-display library of human antibody heavy chain variable regions capable of binding to an antigen via kynurenine as a switch was constructed by introducing the phagemid vector into *E. coli* through electroporation.

(9-2-2) Assessment for Selecting Library-Constructible Sites in the Light Chain Variable Region, and Library Design Next, from the sites comprised in the light chain sequence of F02h011/F021003 in the light chain, various modified variants were generated by substituting Ala or Val for the various positions selected based on the crystallographic analysis results. The modified sites (positions according to Kabat numbering which are indicated as "Kabat" in the table), amino acids before modification at the sites (amino acids indicated as "native sequence" in the table), and amino acids after modification (amino acids indicated as "altered amino acids" in the table) are shown in Table 28.

TABLE 28

| | LCDR1 | | | | | | LCDR2 Kabat | | | | | LCDR3 | | | |
|---|---|---|---|---|---|---|---|---|---|---|---|---|---|---|---|
| | 27d | 27e | 28 | 29 | 30 | 32 | 52 | 53 | 54 | 55 | 56 | 91 | 92 | 93 | 94 | 96 |
| Native sequence | H | S | D | G | N | V | S | N | R | F | S | A | T | Q | F | R |
| Altered amino acid | A | A | A | A | A | A | A | A | A | A | A | V | A | A | A | A |

Each variant expressed and purified by the method described in Reference Example 1 below was assayed for its kynurenine binding by the Biacore-based method described in Example (7-5), except that the period of antigen loading was changed to 30 seconds. When kynurenine dissociation was too fast to determine the dissociation rate constant, the dissociation constant KD (M) was calculated by analyzing equilibrium values based on the degree of binding response when it is interacted with each antigen (association phase). Also in this case, the Biacore T200 Evaluation Software (GE Healthcare) was used to calculate parameters. Based on the assay results, KD values were calculated to determine the affinity of each variant for kynurenine. Each variant and its parental sequence F02h011/F021003 were compared in terms of the KD value for kynurenine. The results are shown in Table 29.

TABLE 29

| | LCDR1 | | | | | | LCDR2 Kabat | | | | | LCDR3 | | | |
|---|---|---|---|---|---|---|---|---|---|---|---|---|---|---|---|
| | 27d | 27e | 28 | 29 | 30 | 32 | 52 | 53 | 54 | 55 | 56 | 91 | 92 | 93 | 94 | 96 |
| Native sequence | H | S | D | G | N | Y | S | N | R | F | S | A | T | Q | F | R |
| Altered amino acid | A | A | A | A | A | A | A | A | A | A | A | V | A | A | A | A |
| F02h011/F021003 ratio | 0.7 | 0.9 | 2.5 | 1.0 | 0.7 | 0.5 | 1.0 | 0.8 | 0.8 | 0.1 | 0.9 | 0.3 | 0.9 | 1.0 | 0.1 | 0.0 |

Upon designing a library, sites that meet at least one of the following conditions were selected as library-constructible sites based on the information obtained in the above assessment of modified variants and in the assessment described in Example (8-2-4).

Condition 1: sites that are not greatly involved in the binding toward kynurenine, or sites in which amino acids other than those of the native sequence are present and which may be involved in binding but which do not significantly reduce the binding toward kynurenine (do not render the binding to zero);

Condition 2: sites having a certain level of diversity of amino acid occurrence frequency as repertoire of the antibody; and Condition 3: sites that are not important for the formation of canonical structures.

A library was designed so that amino acids at positions selected by the conditions described above appear only at certain nucleotides in the light chain sequence (SEQ ID NO: 97) of F02h011/F021098 produced as described in Example (8-2-4) by introducing a modification that augments the kynurenine binding. Such libraries include, for example, NNK and TRIM libraries. Among the various positions assessed, modification sites in which a KD value for kynurenine indicates more than 20% binding of F02h011/F021003, which is the parental sequence, were judged to be modifiable positions that meet the above-described conditions. However, even if included in such sites, residue positions judged to be structurally important were excluded from the sites included in a library or were included in a library with selected types of occurring amino acids. Sites for library production using NNK codons (indicated by an open circle in the table), sites fixed to the native sequence (indicated by a cross in the table), and amino acids of selected occurring amino acid types are shown in Table 30.

TABLE 30

| | LCDR1 | | | | | LCDR2 Kabat | | | | | | LCDR3 | | | | |
|---|---|---|---|---|---|---|---|---|---|---|---|---|---|---|---|---|
| | 27d | 27e | 28 | 29 | 30 | 32 | 52 | 53 | 54 | 55 | 56 | 91 | 92 | 93 | 94 | 96 |
| | | | | | | Native sequence | | | | | | | | | | |
| | H | S | D | G | N | Y | S | N | R | F | S | A | T | Q | F | R |
| Library | O | O | O | O | X | Y, F | O | O | O | X | Y | X | O | O | X | X |

The designed gene sequence was synthesized using primers containing at the sites for library production (light chain variable region library) NNK codons or codons in which selected amino acids occur; and inserted into an appropriate phagemid vector carrying human IgG-derived CH1 sequence and human IgG-derived light chain constant region sequence in combination with the heavy chain variable region sequence of FO2h011/F021098 (parental sequence, SEQ ID NO: 95). A phage-display library of human antibody light chain variable regions capable of binding to an antigen via kynurenine as a switch was constructed by introducing the phagemid vector into *E. coli* through electroporation.

(9-3) Synthesis of Biotinylated Kynurenine to Construct a Kynurenine-Binding Library As shown in Example (7-6), kynurenine derivatives also function as a switch for 6RNMSC1-2_F02. In their structure, the derivatives have a substitution at any of the positions 3, 4, and 5 of kynurenine. Further, the result of crystallographic analysis on the complex of 6RNMSC1-2_F02 and kynurenine allows prediction that biotin introduced at position 3, 4, or 5 of kynurenine does not impede the binding of 6RNMSC1-2_F02 to the antigen hIL-6R. Thus, it is preferable that an appropriate linker (such as PEG linker) is linked at position 3, 4, or 5, and biotin is added to the end of the linker.

An example of biotinylated kynurenine of the present invention is described below. Biotinylated kynurenine of the present invention can be synthesized by various methods. Some of them are illustrated using the schemes below. The schemes are an example, and the present invention is not limited to the chemical reactions and conditions shown herein. The representative compounds of the present invention can be synthesized using appropriate intermediates, known compounds, and reagents.

(9-3-1) Synthesis of Biotinylated Compounds in which a Linker is Linked to Position 4 of Kynurenine Biotinylated kynurenine compounds 028 and 029 can be prepared by the method described below. The biotinylated kynurenine compounds and synthetic intermediates were analyzed under the conditions described below.

The condition of LCMS analysis is as follows.

TABLE 31

| Analysis condition | Apparatus | Column (particle diameter, length, inner diameter) | Mobile phase | Gradient (A/B) | Flow rate (ml/min) | Column temperature (° C.) | Wavelength |
|---|---|---|---|---|---|---|---|
| A | Shimadzu LCMS-2020 | Shim-pack XP-ODS (2.2 um, 50 mm, 3.0 mm) | A: Water/0.05% TFA B: Acetonitrile/0.05% TFA | 95/5 (0.01 min), 0/100 (1.20 min), 0/100 (2.20 min), 95/5 (2.30 min) | 1 | 40 | 190-800 nm, PDA total |
| B | Shimadzu LCMS-2020 | Shim-pack XR-ODS (2.2 um, 50 mm, 3.0 mm) | A: Water/0.05% TFA B: Acetonitrile/0.05% TFA | 95/5 (0.01 min), 0/100 (2.20 min), 0/100 (3.20 min), 95/5 (3.30 min) | 1 | 40 | 190-800 nm, PDA total |
| C | Shimadzu LCMS-2020 | ACQUITY UPLC BEH C18 (1.7 um, 50 mm, 2.1 mm) | A: Water/0.05% TFA B: Acetonitrile/0.05% TFA | 95/5 (0.01 min), 0/100 (1.20 min), 0/100 (1.90 min), 95/5 (2.00 min) | 1 | 45 | 190-800 nm, PDA total |
| D | Shimadzu LCMS-2020 | Shim-pack XR-ODS (2.2 um, 50 mm, 3.0 mm) | A: Water/0.05% TFA B: Acetonitrile/0.05% TFA | 95/5 (0.01 min), 35/65 (4.50 min), 35/65 (5.60 min), 95/5 (5.70 min) | 1 | 40 | 190-800 nm, PDA total |
| E | Shimadzu LCMS-2020 | ACQUITY UPLO BEH C18 (1.7 um, 50 mm, 2.1 mm) | A: Water/0.05% TFA B: Acetonitrile/0.05% TFA | 95/5 (0.01 min), 0/100 (1.00 min), 0/100 (1.80 min), 95/5 (1.90 min) | 1 | 45 | 190-800 nm, PDA total |
| F | Shimadzu LCMS-2020 | Ascentis Express C18 (2.7 um, 50 mm, 3.0 mm) | A: water/0.1% FA B: Acetonitrile/0.05% FA | 90/10 (0.01 min), 0/100 (1.10 min), 0/100 (1.60 min), 90/10 (1.70 min) | 1.5 | 40 | 190-800 nm, PDA total |
| G | Shimadzu LCMS-2020 | Phenomenex kinetex (2.6 um, 50 mm, 3.0 mm) | A: water/0.1% FA B: Acetonitrile/0.05% FA | 90/10 (0.01 min), 0/100 (2.00 min), 0/100 (2.70 min), 90/10 (2.80 min) | 1.5 | 40 | 190-800 nm, PDA total |
| H | Acuity Ultra Performance | Ascentis Express C18 (2.7 um, 50 mm, 2.1 mm) | A: water/0.1% FA B: Acetonitrile/0.05% FA | 60/40 (0.01 min), 0/100 (1.40 min), 0/100 (1.40 min), 60/40 (3.0 min) | 1 | 25 | 190-800 nm, PDA total |

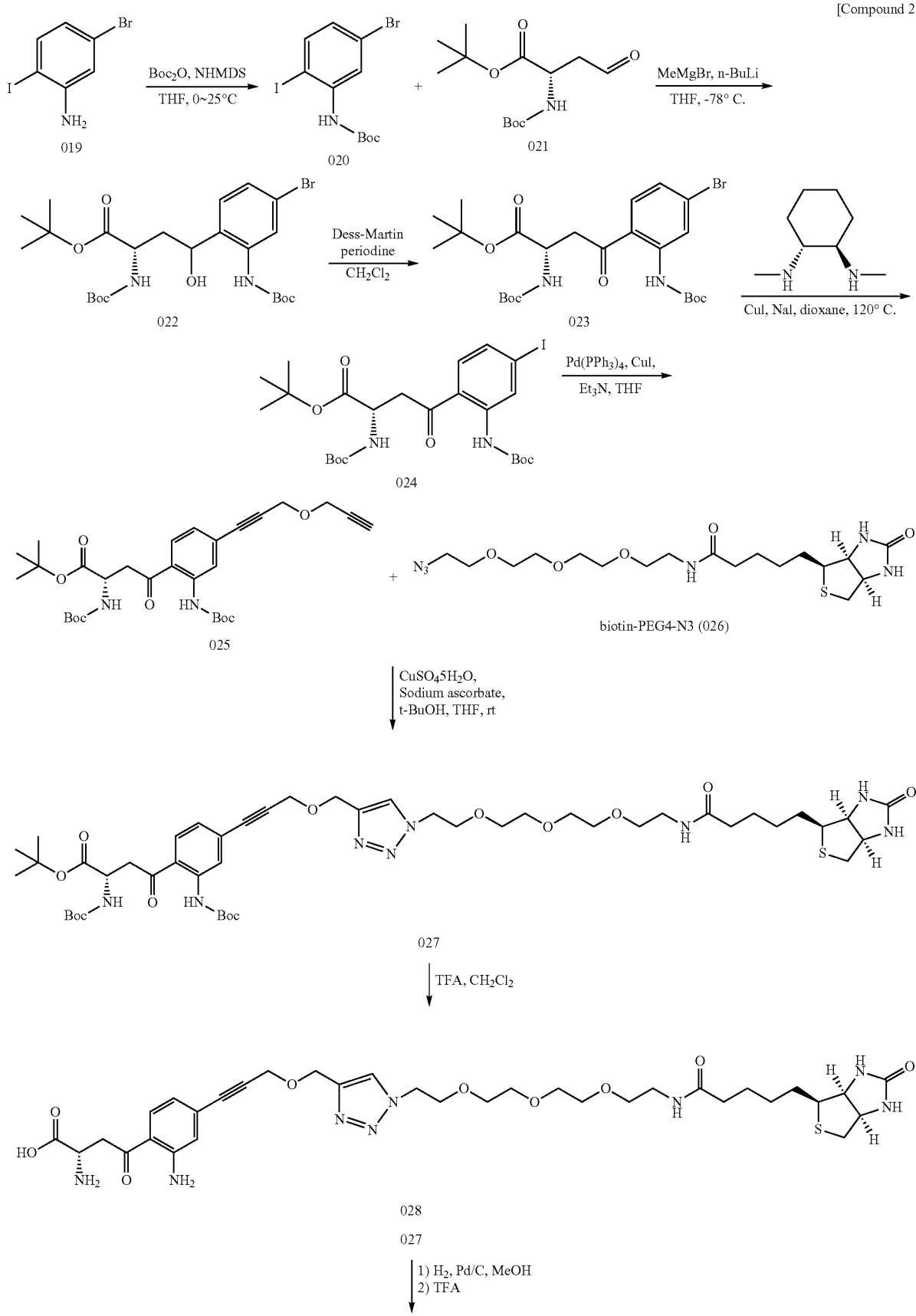

-continued

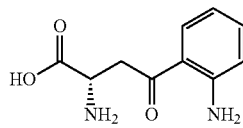
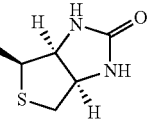

029

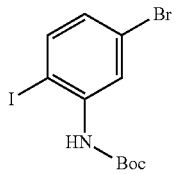

[Compound 27]

Sodium bis(trimethylsilyl)amide (38% tetrahydrofuran solution, 1.9 mol/l, 21.6 ml, 41.1 mmol) was added over 15 minutes to a tetrahydrofuran solution (100 ml) containing 5-bromo-2-iodoaniline (compound 019, 4.90 g, 16.5 mmol, COMBI-BLOCKS) and di-t-butyl dicarbonate (7.54 g, 41.1 mmol) at 0° C. in a nitrogen gas flow. After stirring at 0° C. for 30 minutes and then at room temperature for 18 hours, the reaction solution was diluted with ethyl acetate (300 ml). Following wash with 1 M hydrochloric acid, a saturated aqueous solution of sodium bicarbonate and a saturated saline solution, the mixture was dried over sodium sulfate and concentrated under reduced pressure. The resulting residue was purified by normal phase silica gel column chromatography (ethyl acetate/hexane). This yielded compound 020 (6.14 g, 90%).

LCMS (ESI) m/z=342, 344 (M-Bu+H)+
Retention time: 0.97 minute (analysis condition H)

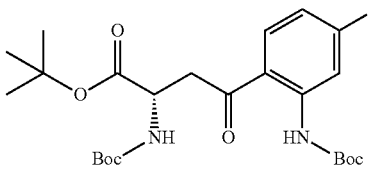

[Compound 28]

Methylmagnesium bromide (1 M, 33.2 ml, 33.2 mmol) was added to a tetrahydrofuran solution (120 ml) of N-t-butoxy-(5-bromo-2-iodophenyl) carbamate (compound 020, 12.0 g, 30.2 mmol) at -78° C. in a nitrogen gas flow, and the mixture was stirred at the same temperature for one hour. Then, after adding n-butyllithium (2.5 M, 13.3 ml, 33.3 mmol), the mixture was stirred at -78° C. for two hours. A tetrahydrofuran solution (15 ml) of (2S)-2-[[t-butoxycarbonyl]amino]-4-oxobutanoate (compound 021, 4.20 g, 15.4 mmol; Roberts et al., Bioorg. Med. Chem. Letters, 13 (2), 265-267 (2003)) was added to the above mixture at -78° C. over 30 minutes, and the mixture was further stirred at the same temperature for two hours. 1 M hydrochloric acid was added to the reaction solution. The reaction solution was extracted three times with ethyl acetate. After washing with 1 M hydrochloric acid, a saturated aqueous solution of sodium bicarbonate and a saturated saline solution, the collected organic layer was concentrated under reduced pressure. The resulting residue was purified by normal phase silica gel column chromatography (ethyl acetate/petroleum ether). This yielded compound 022 (7.50 g, 89%).

LCMS (ESI) m/z=569 (M+Na)+
Retention time: 1.93 minute (analysis condition A)

[Compound 29]

Dess-Martin Periodinane (11.7 g, 27.6 mmol) was added to a dichloromethane solution (100 ml) of compound 022 (7.50 g, 13.8 mmol) at 25° C., and the mixture was stirred for two hours. After diluting with ethyl acetate, the reaction mixture was washed with an aqueous sodium thiosulfate solution, an aqueous sodium hydrogen carbonate solution, and a saturated saline solution, and concentrated under reduced pressure. The resulting residue was purified by normal phase silica gel column chromatography (ethyl acetate/petroleum ether). This yielded compound 023 (5.80 g, 78%).

LCMS (ESI) m/z=565 (M+Na)+
Retention time: 1.78 minute (analysis condition A)

[Compound 30]

A dioxane solution (60 ml) containing compound 023 (2.50 g, 4.58 mmol), copper(I) iodide (438 mg, 2.30 mmol), (1R,2R)-(-)-N,N'-dimethylcyclohexane-1,2-diamine (654 mg, 4.60 mmol), and sodium iodide (1.40 g, 9.34 mmol) was stirred at 120° C. under nitrogen atmosphere for 16 hours. The residue obtained by concentrating the reaction mixture under reduced pressure was purified by normal phase silica gel column chromatography (ethyl acetate/petroleum ether). This yielded compound 024 (1.60 g, 59%).

LCMS (ESI) m/z=613 (M+Na)+

Retention time: 1.95 minute (analysis condition B)

[Compound 31]

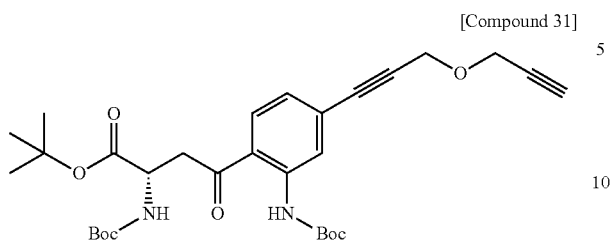

A tetrahydrofuran solution (20 ml) containing compound 024 (1.60 g, 2.71 mmol), tetrakis(triphenylphosphine) palladium (627 mg, 0.54 mmol), copper iodide (103 mg, 0.54 mmol), bis(2-propynyl)ether (893 mg, 9.49 mmol), and triathylamine (960 mg, 9.49 mmol) was stirred at 25° C. under nitrogen atmosphere for 16 hours. The residue obtained by concentrating the reaction mixture under reduced pressure was purified by normal phase silica gel column chromatography (ethyl acetate/petroleum ether). This yielded compound 025 (700 mg, 46%).

LCMS (ESI) m/z=579 (M+Na)+
Retention time: 2.68 minutes (analysis condition B)

[Compound 32]

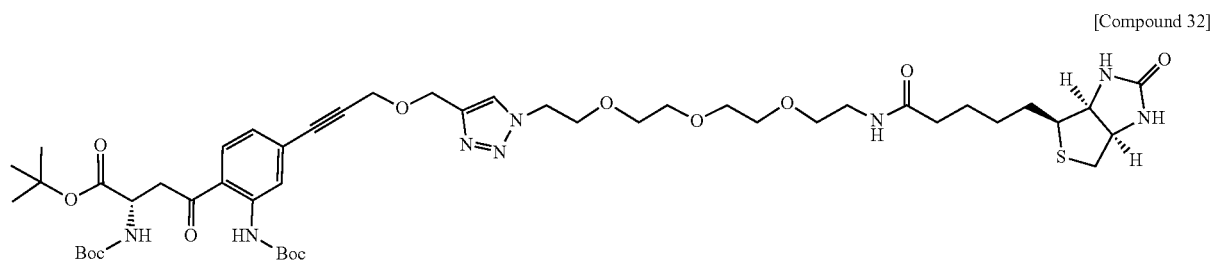 [SMILES: CC(C)(C)OC(=O)Nc1cc(C#CCOCc2cn(CCOCCOCCOCCNC(=O)CCCC[C@@H]3SC[C@@H]4NC(=O)N[C@@H]43)nn2)ccc1C(=O)C[C@H](NC(=O)OC(C)(C)C)C(=O)OC(C)(C)C]

A mixed solution of t-butanol (2.0 ml) and tetrahydrofuran (2.0 ml) containing compound 025 (60.0 mg, 0.11 mmol), biotin-PEG4-N3 (compound 026, 60.0 mg, 0.13 mmol), copper sulfate pentahydrate (10.0 mg, 0.040 mmol), and an aqueous solution of 1 M sodium ascorbate (five drops) was stirred at 25° C. for 16 hours. The residue obtained by concentrating the reaction mixture under reduced pressure was purified by normal phase silica gel column chromatography (methanol/dichloromethane). This yielded compound 027 (100 mg, 91%).

LCMS (ESI) m/z=1001 (M+H)+
Retention time: 1.40 minute (analysis condition C)

[Compound 33]

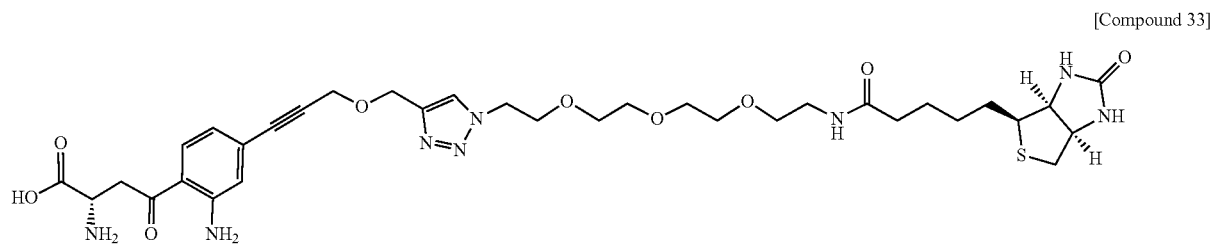 [SMILES: Nc1cc(C#CCOCc2cn(CCOCCOCCOCCNC(=O)CCCC[C@@H]3SC[C@@H]4NC(=O)N[C@@H]43)nn2)ccc1C(=O)C[C@H](N)C(=O)O]

Trifluoroacetic acid (2.0 ml) was added to a dichloromethane solution (10 ml) of compound 027 (100 mg, 0.10 mmol), and the mixture was stirred at 25° C. for two hours. The residue obtained by concentrating the reaction mixture under reduced pressure was purified by high-performance liquid chromatography. This yielded compound 028 (27.8 mg, 37%).

LCMS (ESI) m/z=745 (M+H)+

Retention time: 2.14 minutes (analysis condition D)

[Compound 34]

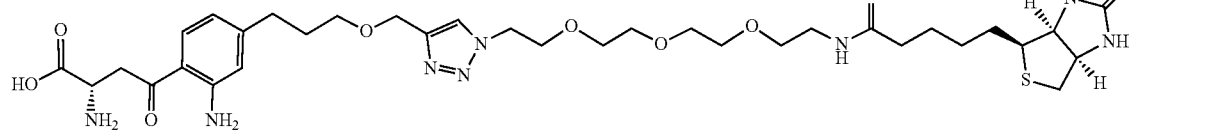

Hydrogen gas was flowed over five hours into a methanol solution (10 ml) containing compound 027 (100 mg, 0.10 mmol) and palladium/carbon (20 mg). After filtration, the reaction mixture was concentrated under reduced pressure. Trifluoroacetic acid (1.0 ml) was added to a dichloromethane solution (10 ml) of the residue. The mixture was stirred at 25° C. for one hour. The residue obtained by concentrating the reaction mixture under reduced pressure was purified by high-performance liquid chromatography. This yielded compound 029 (13.5 mg, 18%).

LCMS (ESI) m/z=749 (M+H)+

Retention time: 1.20 minute (analysis condition B)

(9-3-2) Synthesis of Biotinylated Compounds in which a Linker is Linked to Position 5 of Kynurenine Biotinylated kynurenine compound 036 can be prepared by the method described below.

[Compound 35]

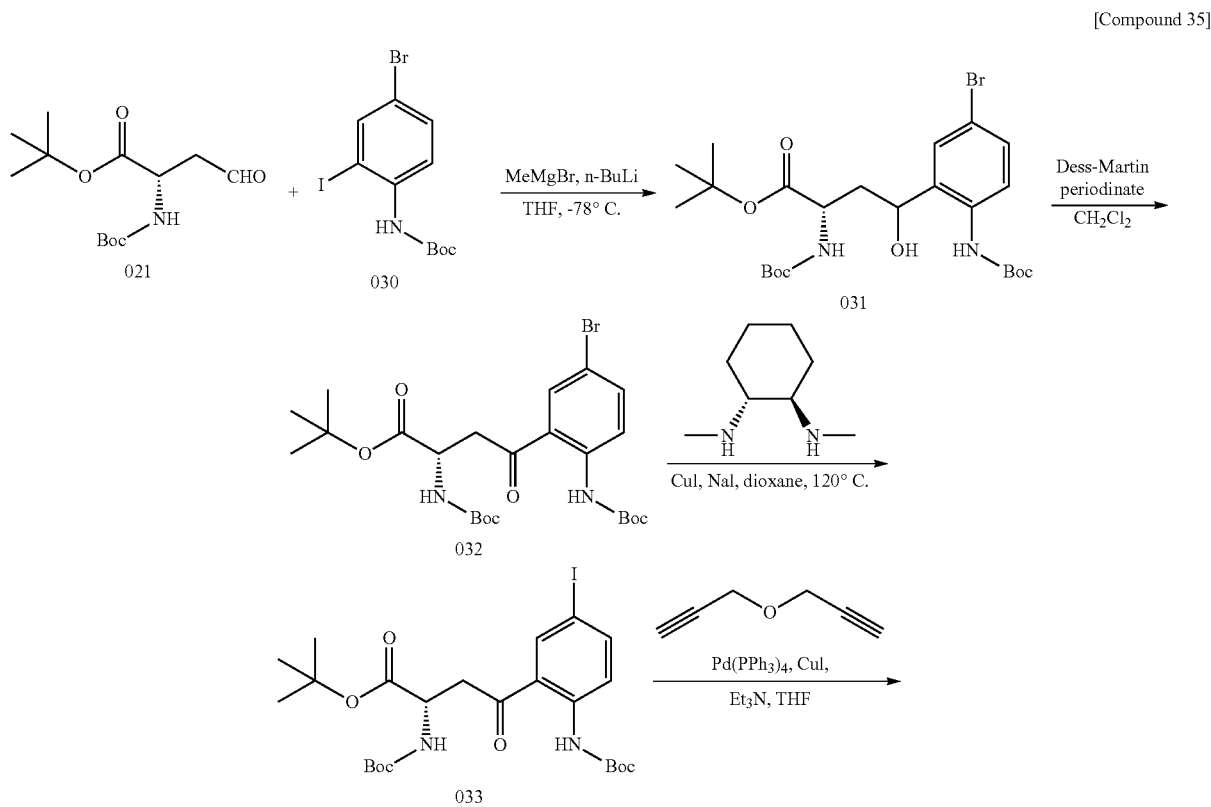

-continued

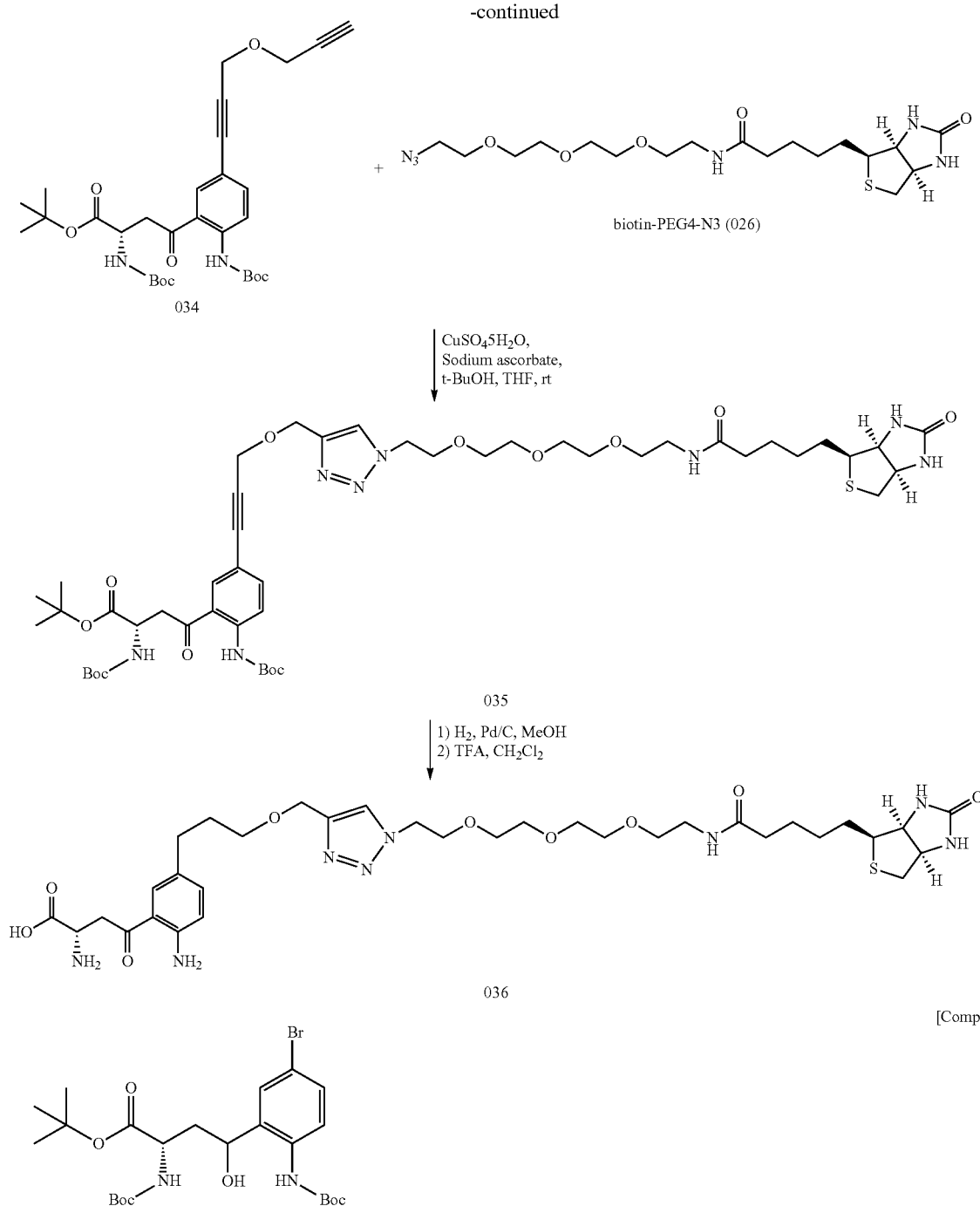

[Compound 36]

Methylmagnesium bromide (1 M, 20 ml, 20 mmol) was added to a tetrahydrofuran solution (80 ml) of N-t-butoxy-(4-bromo-2-iodophenyl) carbamate (Wensbo et al., Tetrahedron, 51 (37), 10323-10342 (1995)) (compound 030, 7.50 g, 18.8 mmol) at −78° C. in a nitrogen gas flow. The mixture was stirred at the same temperature for 20 minutes. Then, after adding n-butyllithium (2.5 M, 10 ml, 25 mmol), the mixture was stirred at −78° C. for 30 minutes. To this solution, a tetrahydrofuran solution (20 ml) of (2S)-2-[[t-butoxycarbonyl] amino]-4-oxobutanoate (compound 021, 2.57 g, 9.40 mmol) was added over 30 minutes at −78° C. The mixture was further stirred for one hour at the same temperature. After adding 1 M hydrochloric acid, the reaction solution was extracted three times with ethyl acetate. The collected organic layer was washed with 1 M hydrochloric acid, a saturated aqueous solution of sodium bicarbonate, and a saturated saline solution, and dried over sodium sulfate. The residue obtained by concentrating under reduced pressure was purified by normal phase silica gel column chromatography (ethyl acetate/petroleum ether). This yielded compound 031 (4.56 g, 89%).

LCMS (ESI) m/z=569 (M+Na)+

Retention time: 1.78 minute (analysis condition A)

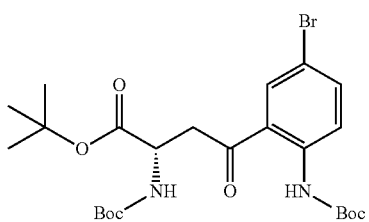
[Compound 37]

Dess-Martin Periodinane (8.89 g, 21.0 mmol) was added to a dichloromethane solution (100 ml) of compound 031 (4.56 g, 8.36 mmol) at 25° C. The mixture was stirred for three hours. After adding an aqueous sodium thiosulfate solution, the reaction mixture was extracted three times with dichloromethane. The combined organic layer was washed with an aqueous sodium hydrogen carbonate solution, and dried over sodium sulfate. The residue obtained by concentrating under reduced pressure was purified by normal phase silica gel column chromatography (ethyl acetate/petroleum ether). This yielded compound 032 (3.60 g, 79%).

LCMS (ESI) m/z=567 (M+H)+
Retention time: 1.90 minute (analysis condition E)

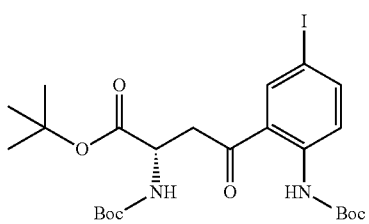
[Compound 38]

A dioxane solution (60 ml) containing compound 032 (3.60 g, 6.62 mmol), copper(I) iodide (650 mg, 3.41 mmol), (1R,2R)-(−)-N,N'-dimethylcyclohexane-1,2-diamine (940 mg, 6.61 mmol), and sodium iodide (1.98 g, 13.2 mmol) was stirred at 120° C. under nitrogen atmosphere for 16 hours. The residue obtained by concentrating the reaction mixture under reduced pressure was purified by normal phase silica gel column chromatography (ethyl acetate/petroleum ether). This yielded compound 033 (3.10 g, 79%).

LCMS (ESI) m/z=613 (M+Na)+
Retention time: 1.33 minute (analysis condition E)

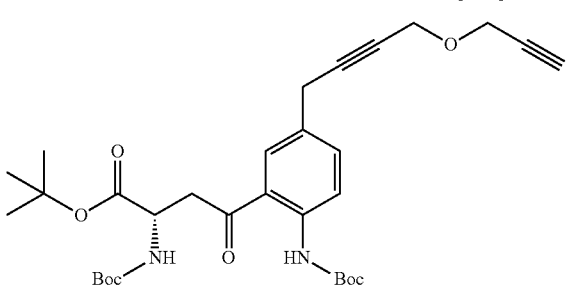
[Compound 39]

A tetrahydrofuran solution (20 ml) of compound 033 (3.10 g, 5.25 mmol), tetrakis(triphenylphosphine) palladium (1.21 g, 1.05 mmol), copper iodide (200 mg, 1.05 mmol), bis(2-propynyl)ether (1.73 mg, 18.4 mmol), and triathylamine (1.86 g, 18.4 mmol) was stirred at 25° C. under nitrogen atmosphere for 16 hours. The residue obtained by concentrating the reaction mixture under reduced pressure was purified by normal phase silica gel column chromatography (ethyl acetate/petroleum ether). This yielded compound 034 (1.00 g, 34%).

LCMS (ESI) m/z=579 (M+Na)+
Retention time: 1.28 minute (analysis condition E)

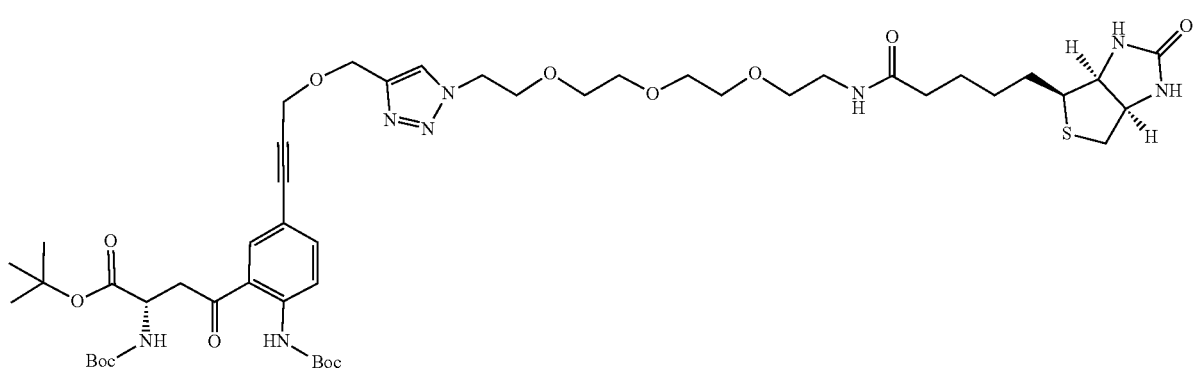
[Compound 40]

A mixed solution of t-butanol (2 ml) and tetrahydrofuran (2 ml) containing compound 034 (90.0 mg, 0.20 mmol), biotin-PEG4-N3 (compounds 026, 90.0 mg, 0.16 mmol), copper sulfate pentahydrate (10 mg, 0.040 mmol), and an aqueous solution of 1 M sodium ascorbate (10 drops) was stirred at 25° C. for 16 hours. The residue obtained by concentrating the reaction mixture under reduced pressure was purified by normal phase silica gel column chromatography (methanol/dichloromethane). This yielded compound 035 (155 mg, 76%).

LCMS (ESI) m/z=1001 (M+H)+
Retention time: 1.13 minute (analysis condition F)

library. Then, BSA was added at a final concentration of 4% to the phage library suspension. Panning was performed with the antigen immobilized on magnetic beads. The magnetic beads used were NeutrAvidin coated beads (Sera-Mag SpeedBeads NeutrAvidin-coated) or Streptavidin coated beads (Dynabeads MyOne StreptAvidin T1).

Panning was carried out using a negative selection method to collect phages that specifically bind to kynurenine. Panning was performed individually for each of the three types of biotinylated kynurenine (compounds 028, 029, and 036) synthesized as described in Example (9-3). Specifically, 0.8 mL of the prepared phage library suspen-

[Compound 41]

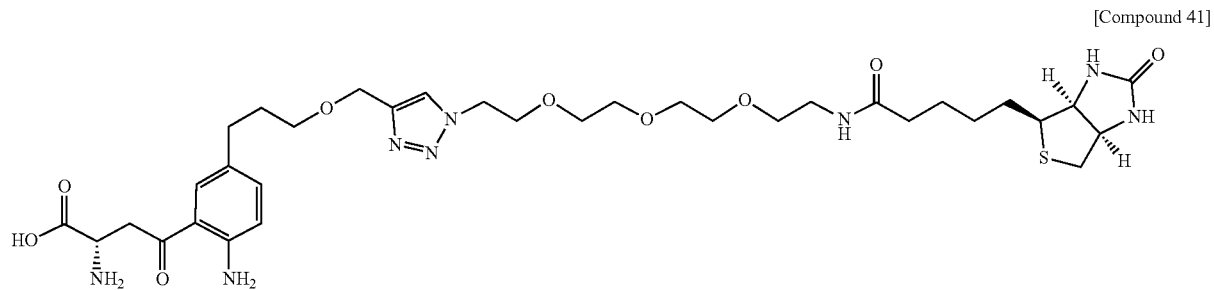 [SMILES: Nc1ccc(CCCOCc2cn(CCOCCOCCOCCNC(=O)CCCC[C@@H]3SC[C@@H]4NC(=O)N[C@@H]43)nn2)cc1C(=O)C[C@H](N)C(=O)O]

Hydrogen gas was flowed over four hours into a methanol solution (10 ml) containing compound 035 (85.0 mg, 0.080 mmol) and palladium/carbon (10 mg). After filtration, the reaction mixture was concentrated under reduced pressure, and trifluoroacetic acid (1.0 ml) was added to a dichloromethane solution (5.0 ml) of the resulting residue. The mixture was stirred at 25° C. for one hour. The residue obtained by concentrating the reaction mixture under reduced pressure was purified by high-performance liquid chromatography. This yielded compound 036 (18.9 mg, 31.6%).

LCMS (ESI) m/z=749 (M+H)+
Retention time: 0.70 minute (analysis condition G)

(9-4) Obtaining a Group of Kynurenine-Binding Antibodies Using Phage-Display Libraries of Heavy Chain and Light Chain Variable Regions With biotinylated kynurenine synthesized as described in Example (9-3), panning was carried out to obtain a group of antibodies that specifically bind to kynurenine from the respective phage-display libraries of the heavy chain and light chain variable regions designed and constructed as described in Examples (9-2-1) and (9-2-2). For the purpose described above, first, phages presenting antibodies that have binding activity to magnetic beads in the absence of biotinylated kynurenine were removed by contacting the antibody-phage-display library with magnetic beads in the absence of biotinylated kynurenine. Then, in the presence of biotinylated kynurenine, panning was performed in the same manner to screen for antibodies that have specific binding activity to biotinylated kynurenine.

E. coli containing the constructed phage-display phagemid vector was infected with M13KO7ΔpIII (PROGEN Biotechnik; referred to as hyperphage), cultured at 30° C. overnight, and phages were collected from the supernatant. To precipitate the group of phages, 2.5 M NaCl/10% PEG was added to the E. coli culture in which phages were produced. The group of phages was diluted with TBS to prepare a solution of an antibody multivalent display phage sion was added to BSA-blocked magnetic beads (Dynabeads MyOne StreptAvidin T1), and allowed to bind for 30 minutes at room temperature and then for another 30 minutes at 4° C. The beads were separated using a magnetic stand to collect phages that did not bind to the beads. This process was repeated. Separately prepared BSA-blocked magnetic beads (Dynabeads MyOne StreptAvidin T1) were allowed to react with 6 nmol of biotinylated kynurenine at room temperature for 30 minutes to immobilize biotinylated kynurenine onto the magnetic beads. The biotinylated kynurenine-immobilized magnetic beads were washed three times with TBST, and the collected phages were added thereto. The phage library was contacted with biotinylated kynurenine for 30 minutes at room temperature and then for another 30 minutes at 4° C. The beads were washed twice with 1 mL of ice-cold TBST, and then once with ice-cold TBS. Then, 0.5 mL of TBS containing trypsin at a final concentration of 1 mg/mL was added to the beads. Immediately after the beads were suspended at room temperature for 15 minutes, the phage suspension was collected from the beads that were separated using a magnetic stand. Phages eluted with the trypsin solution were added to 60 mL of E. coli strain ER2738 in the logarithmic growth phase (OD600=0.4-0.7). The E. coli was gently stirred and incubated at 37° C. for one hour to allow phages to infect the E. coli. The infected E. coli was seeded on three plates of 225 mm×225 mm. Then, E. coli in the seeded culture was infected with hyperphage, and cultured at 30° C. overnight to collect a solution of an antibody multivalent display phage library.

Using the negative selection method in the same way as in the first panning, the second panning was carried out individually for each of the three types of biotinylated kynurenine to collect phages that specifically bind to kynurenine. Specifically, first, magnetic beads (Sera-Mag SpeedBeads NeutrAvidin-coated) were blocked with 2% skim milk-TBS added with 5 μL of 5 mg/mL StreptAvidin recombinant (Roche). The magnetic beads were washed three times with TBST, to which 0.8 mL of a phage library suspension blocked with 4% BSA was added, and allowed to bind at room temperature for 30 minutes. The beads were separated using a magnetic stand to collect phages that did not bind to the beads. This process was repeated. Separately prepared magnetic beads (Sera-Mag SpeedBeads NeutrAvidin-coated) blocked with 2% skim milk-TBS added with 5 µL of 5 mg/mL StreptAvidin recombinant (Roche) were allowed to react with 10 nmol biotinylated kynurenine for 30 minutes at room temperature and then for another 30 minutes at 4° C., to immobilize biotinylated kynurenine onto the magnetic beads. The biotinylated kynurenine-immobilized magnetic beads were washed three times with TBST, and the collected phages were added thereto. The phage library was contacted with biotinylated kynurenine for 30 minutes at room temperature and then for another 30 minutes at 4° C. The beads were washed three times with 1 mL of ice-cold TBST and twice with ice-cold TBS. Then, 0.5 mL of TBS containing trypsin at a final concentration of 1 mg/mL was added to the beads, and immediately after the beads were suspended at room temperature for 15 minutes, the phage suspension was collected from the beads that were separated using a magnetic stand. Of 0.5 mL of phages eluted with the trypsin solution, 50 µL was added to 60 mL of E. coli strain ER2738 in the logarithmic growth phase (OD600=0.4-0.7). The E. coli was gently stirred and incubated at 37° C. for one hour to allow phages to infect the E. coli. The infected E. coli was seeded on three plates of 225 mm×225 mm.

(9-4-2) Assessment of the Binding Activity for Biotinylated Kynurenine by Phage ELISA From a single colony of E. coli obtained as described in Example (9-4-1), a phage-containing culture supernatant was collected according to a conventional method (Methods Mol. Biol. (2002) 178, 133-145). Antibody multivalent display phages were collected using hyperphages as helper phages, and subjected to ELISA. A StreptaWell 96 microtiter plate (Roche) was coated with 80 µL of TBS containing three types of biotinylated kynurenine (a mixture containing an equal amount of compounds 028, 029, and 036) for one or more hours. After biotinylated kynurenine not bound to StreptAvidin was removed by washing each well of the plate with TBST, the wells were blocked with 250 µL of 2% skim milk-TBS for one or more hours. After removal of 2% skim milk-TBS, purified phages were added to each well. The plate was allowed to stand at room temperature for one hour to allow antibody-presenting phages to bind to biotinylated kynurenine in each well. After each well was washed with TBST, an HRP-conjugated anti-M13 antibody (Amersham Pharmacia Biotech) diluted with TBS was added to the wells. The plate was incubated for one hour. After TBST washes, the chromogenic reaction of the solution in each well added with the TMB single solution (ZYMED) was terminated by adding sulfuric acid. Then, color development was measured by absorbance at 450 nm. As a result, several antibodies were confirmed to bind to biotinylated kynurenine. The results of phage ELISA are shown in Table 32.

TABLE 32

| | Library | | | | | |
| --- | --- | --- | --- | --- | --- | --- |
| | Heavy chain library | | | Light chain library | | |
| Panning probe | Compound 028 | Compound 029 | Compound 036 | Compound 028 | Compound 029 | Compound 036 |
| Number of panning rounds | 2 | 2 | 2 | 2 | 2 | 2 |
| Number of clones subjected to ELISA | 96 | 96 | 96 | 96 | 96 | 96 |
| Number of positive clones(Absorbance > 0.2) | 23 | 17 | 33 | 30 | 17 | 63 |
| Number of positive clone sequences | 23 | 17 | 33 | 30 | 17 | 63 |

(9-4-3) Sequence Analysis of Antibodies that Bind to Biotinylated Kynurenine

Using specific primers (SEQ ID NOs: 79 and 80), genes were amplified from clones that are judged to have specific binding activity to kynurenine based on the results of phage ELISA shown in Example (9-4-2). The nucleotide sequences of the genes were analyzed, and the analysis result showed that the sequences of the clones judged to have kynurenine-binding activity were independent of one another.

(9-5) Construction of a Library for Obtaining Kynurenine-Switch Antibodies by Panning with Kynurenine Since antigen (kynurenine)-binding phages obtained from each of the heavy chain and light chain variable region phage-display libraries are a population having kynurenine-binding ability, a Fab-presenting phage library constructed by combining the two was expected to contain a large number of clones that maintain the binding to kynurenine as a switch, implying the possibility of constructing a library that allows more efficient isolation of kynurenine-switch antibodies.

Using a method known to those skilled in the art, genes were extracted from E. coli infected with each of the heavy-chain and light-chain phage libraries obtained as described in Example (9-4). For the heavy chain, a gene library was amplified with primers (SEQ ID NOs: 98 and 99) capable of amplifying the heavy chain variable region using a collection of the obtained genes (heavy chain variable region library) as a template. Regarding the light chain, the heavy chain variable region sequence (library template sequence: SEQ ID NO: 95) of F02h011/F021098 was excised from a collection of the obtained genes (light chain variable region library) by restriction enzyme treatment to construct a phagemid vector carrying the light chain variable region library gene, human IgG-derived light chain constant region sequence, and human IgG-derived CHI sequence. The heavy-chain variable region library gene was inserted into the constructed phagemid vector carrying the light chain variable region library gene to construct a phagemid vector introduced with the human antibody heavy chain/light chain variable region library genes. A designed library that displays a Fab domain composed of the human antibody variable region-constant region, which allows isolation of antibodies that can bind to an antigen via kynurenine as a switch was constructed by introducing the phagemid vector into E. coli by electroporation. Such a designed library composed of various H chains and L chains having kynurenine-binding activity is expected to be useful as a library containing human antibodies that allow efficient isolation of kynurenine-switch antibodies against an arbitrary antigen. Furthermore, as shown in Example (7-6), since 6RNMSC1-2_F02 binds not only to kynurenine, but also to metabolic products thereof: 3-hydroxykynurenine and 3-hydroxy-DL-kynurenine, and to kynurenine derivatives such as RO0635389-000-001 and RO0635390-000-001, the library described above is expected to be useful for isolating switch antibodies whose binding activity to an arbitrary target antigen varies depending on the presence of any one or more small molecules of kynurenine, metabolic products of kynurenine, and kynurenine derivatives.

Example (9-6) Assessment of the Clones in the Library for their Kynurenine-Binding Ability by Phage ELISA Since the library constructed as described in Example (9-5) was obtained via panning with kynurenine, the library was predicted to contain a large number of clones having kynurenine-binding ability. Phage clones isolated from the constructed library were assessed for their binding to biotinylated kynurenine by phage ELISA.

Phages were cultured according to a conventional method (Methods Mol. Biol. (2002) 178, 133-145) from a single colony of E. coli containing genes of the constructed library. Culture supernatants containing the antibody multivalent display phages were collected using hyperphages as helper phages. The collected phage culture supernatants were filtered by ultrafiltration using NucleoFast96 (MACHEREY-NAGEL). 200 µL each of the culture supernatants was applied to each of the wells of NucleoFast96, and centrifuged at 6000 g for 45 minutes. The flow-through fractions were removed. Washing was performed by adding 200 IAL of $H_2O$ to the wells, and centrifugation at 6000 g for 30 minutes. 200 µL of TBS was then added, and after being left to stand at room temperature for five minutes, phage suspensions contained in the supernatants were collected.

After TBS addition, the purified phages were subjected to ELISA by the same method as described in Example (9-4-1). As a result, several antibodies were confirmed to bind to biotinylated kynurenine. Among the analyzed phage clones derived from the primary library, about 49% were found to have kynurenine-binding ability. The results of phage ELISA are shown in Table 33.

TABLE 33

| | |
|---|---|
| Number of clones subjected to ELISA | 192 |
| Number of positive clones (Absorbance > 0.2) | 94 |
| Percentage of positive clones | 48.96% |

[Example 10] Assessment of Proteins that Bind to an Antigen Via a Small Molecule of Non-Biological Origin as a Switch Antibodies (Reference Example 3 described below) that are capable of binding to human IL-6 receptor (hIL-6R) in the presence of ATP or adenosine, which were obtained from a library constructed based on antibody ATNLSA1-4_D12 that binds to ATP and adenosine, were assessed for their human IL-6 receptor-binding ability in the presence of a small molecule of non-biological origin.

(10-1) Preparation of ATP/Adenosine-Switch Antibodies Obtained from a Library

The heavy chain and light chain variable region sequences of clones 6RAD2C1-4_001, 6RAD2C1-4_005, 6RAD2C1-4_011, 6RAD2C1-4_026, 6RAD2C1-4_030, 6RAD2C1-4_042, 6RAD2C1-4_076, 6RDL3C1-4_085, and 6RDL3C5-4_011, which were obtained as described in Reference Example 3 below and judged to have binding activity to biotin-labeled hIL-6R in the presence of ATP or adenosine, were each inserted into a human IgG1/Lambda plasmid for animal expression carrying the antibody heavy chain constant region (SEQ ID NO: 46) or light chain Lambda constant region sequence (SEQ ID NO: 100). The antibodies were expressed using the method described below. Cells of the FreeStyle 293-F line (Invitrogen), which is derived from human embryonic kidney cells, were suspended at a cell density of $1.33 \times 10^6$ cells/mL in the FreeStyle 293 Expression Medium (Invitrogen), and 3-mL of the suspension was seeded in each well of 6-well plates. The prepared plasmid was introduced into the cells by lipofection. After four days of culture in a CO2 incubator (37° C., 8% CO2, 90 rpm), antibodies were purified from culture supernatants by a method known to those skilled in the art using rProtein A Sepharose™ Fast Flow (Amersham Biosciences). Absorbance of solutions of the purified antibodies was measured at 280 nm using a spectrophotometer. From the values obtained by measurement, concentrations of the purified antibodies were calculated using an extinction coefficient determined by the PACE method (Protein Science (1995) 4, 2411-2423).

(10-2) Assessment of Various Small Molecules for their Effect on the Binding to Human IL-6 Receptor by Surface Plasmon Resonance Biacore T200 (GE Healthcare) was used to assess various small molecules for their effect on the antigen-antibody reaction between hIL-6R and nine clones of ATP/adenosine-dependent antibody (6RAD2C1-4_001, 6RAD2C1-4_005, 6RAD2C1-4_011, 6RAD2C1-4_026, 6RAD2C1-4_030, 6RAD2C1-4_042, 6RAD2C1-4_076, 6RDL3C1-4_085, and 6RDL3C5-4_011) isolated from a library. The running buffer used was 20 mmol/L ACES, 150 mmol/L NaCl, 0.05% (w/v) Tween20, pH 7.4. The assay was performed at 25° C. hIL-6R was immobilized onto Sensor chip CM5 by amine coupling, and interacted with the antibodies as an analyte for 120 seconds to observe changes in the amount of binding. Antibodies were diluted with the running buffer or the running buffer added with any one of ATP, ADP, AMP, cAMP, and adenosine (ADO). The final concentration of each small molecule was adjusted to 1 mM, and the final concentration of the antibody was adjusted to 1 µM. Meanwhile, under the 1 mM ATP condition, the assay was carried out with a series of stepwise antibody concentrations. The dissociation constant KD (mol/L) of each clone for hIL-6R was calculated from a plot of equilibrium values against antibody concentration. The parameters were calculated using the Biacore T200 Evaluation Software (GE Healthcare). The dissociation constant KD of each clone in the presence of 1 mM ATP is shown in Table 34.

TABLE 34

| Clone name | Dissociation constant $K_D$ (mol/L) |
|---|---|
| 6RAD2C1-4_01 | 3.0E−07 |
| 6RAD2C1-4_05 | 3.4E−07 |
| 6RAD2C1-4_11 | 2.3E−07 |
| 6RAD2C1-4_26 | 2.1E−07 |
| 6RAD2C1-4_30 | 3.3E−07 |
| 6RAD2C1-4_42 | 2.5E−07 |
| 6RAD2C1-4_76 | 2.5E−07 |
| 6RDL3C1-4_85 | 3.9E−07 |
| 6RDL3C5-4_11 | 1.3E−07 |

The amount of each clone binding to hIL-6R in the absence or presence of each small molecule at 1 mM obtained by this measurement is shown in FIG. 37. As shown in FIG. 37, each clone was bound to hIL-6R in the presence of 1 mM ATP, while binding to hIL-6R was not observed in the absence of ATP. Thus, the clones were confirmed to have the property of binding to hIL-6R using ATP as a switch. Regarding small molecules besides ATP, all clones were revealed to bind in the presence of ADP, and some clones were also found to bind in the presence of AMP and cAMP. In the presence of ADO (adenosine), hIL-6R binding was not observed.

(10-3) Assessment of Various Small Molecules for their Effect on the Binding to Human IL-6 Receptor by Octet Octet (PRIMETECH) was used to assess various small molecules for their effect on the antigen-antibody reaction between hIL-6R and nine ATP/adenosine-dependent antibody clones (6RAD2C1-4_001, 6RAD2C1-4_005, 6RAD2C1-4_011, 6RAD2C1-4_026, 6RAD2C1-4_030, 6RAD2C1-4_042, 6RAD2C1-4_076, 6RDL3C1-4_085, and 6RDL3C5-4_011) obtained from a library. Assay was carried out at 30° C. using TBS, pH 7.4 as an assay buffer. Biotinylated hIL-6R was immobilized onto a streptavidin sensor chip, and interacted with the antibodies to observe changes in the amount of binding. The antibodies were diluted with the assay buffer or the assay buffer added with any one of ATP, ADP, AMP, cAMP, ADO, and ATP-gamma-S. The final concentration of each small molecule was adjusted to 1 mM, and the final antibody concentration was adjusted to 10 μg/mL.

The assessment results on the hIL-6R binding of each clone in the absence or presence of each small molecule at 1 mM obtained by this measurement demonstrated that all clones bound to hIL-6R in the presence of 1 mM ATP. In the absence of ATP, hIL-6R binding was not observed. Thus, Octet also demonstrated that the clones had the property of binding to hIL-6R using ATP as a switch. Furthermore, binding was observed in the presence of ATP-gamma-S for all clones. The amount of IL6R bound in the absence or presence of 1 mM ATP or ATP-gamma-S obtained by the assessment is shown in FIG. 38. The findings described above demonstrate that hIL-6R-binding antibodies, for which ATP and derivatives thereof (ex-vivo molecules) function as a switch, could be isolated from a library.

[Example 11] Obtaining Antibodies that Bind to Human IL-6 Receptor in the Presence of Kynurenine, by Panning with Kynurenine from a Library to Isolate Kynurenine-Switch Antibodies (Ver.A Kynurenine Library)

(11-1) Obtaining Antibodies that have Binding Activity to Human IL-6 Receptor in the Presence of Kynurenine but not in the Absence of Kynurenine from an Antibody Library The phage-display library for obtaining kynurenine-switch antibodies (referred to as the Ver.A kynurenine library), which was constructed as described in Example 9 via panning with kynurenine, was screened for antibodies that have human IL-6 receptor (hIL-6R)-binding activity in the presence of kynurenine. Specifically, phages presenting antibodies that have binding activity to hIL-6R captured on beads in the presence of kynurenine, but are eluted from the beads in the absence of kynurenine were collected. In this isolation method, biotin-labeled hIL-6R was used as an antigen.

E. coli retaining the constructed phage-display phagemid vector was infected with M13KO7ΔpIII (PROGEN Biotechnik; referred to as hyperphage), and cultured at 30° C. overnight. Phages were collected from the supernatant. To precipitate the phage population, 2.5 M NaCl/10% PEG was added to the E. coli culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

The first panning was carried out to enrich phages that can bind to the antigen only in the presence of kynurenine. Specifically, together with 250 pmol of the biotin-labeled antigen, kynurenine was added at a final concentration of 500 μM to 0.5 mL of the prepared phage library suspension, and thus the phage library was contacted with the antigen and kynurenine at room temperature for 15 minutes and then at 4° C. for 45 minutes. BSA-blocked magnetic beads (Sera-Mag SpeedBeads NeutrAvidin-coated) were added, and the antigen/phage complex was allowed to bind to the magnetic beads at 4° C. for 15 minutes. The beads were washed twice with 0.5 mL of ice-cold kynurenine/TBST and once with ice-cold kynurenine/TBS. Immediately after the beads to which 0.25 mL of TBS has been added were suspended at room temperature, the phage suspension was collected from the beads that were separated using a magnetic stand. This process was repeated, and then the two phage suspensions eluted separately were combined together. Five microliter of 100 mg/mL trypsin was added to the collected phage suspension to cleave the Fab. This improved the ability of trypsin-treated phages to infect E. coli. The trypsin-treated phages were added to 10 mL of E. coli strain ER2738 in the logarithmic growth phase (OD600=0.4-0.7). The E. coli was gently stirred and incubated at 37° C. for one hour to allow phages to infect the E. coli. The infected E. coli was seeded on a plate of 225 mm×225 mm. Then, E. coli in the seeded culture was infected with hyperphage, and cultured at 30° C. overnight. Phages were collected from the supernatant to prepare a suspension of antibody multivalent display phage library.

In the second panning, together with kynurenine at a final concentration of 500 μM, 250 pmol of the biotin-labeled antigen was added to 0.4 mL of the prepared phage library suspension, and thus the phage library was contacted with the antigen and kynurenine at room temperature for 60 minutes. BSA-blocked magnetic beads (Sera-Mag Speed-Beads NeutrAvidin-coated) were added, and the antigen/phage complex was allowed to bind to the magnetic beads at room temperature for 15 minutes. The beads were washed twice with 0.5 mL of kynurenine/TBST and once with kynurenine/TBS. Immediately after the beads to which 0.25 mL of TBS has been added were suspended at room temperature, the phage suspension was collected from the beads that were separated using a magnetic stand. This process was repeated, and then the two phage suspensions eluted separately were combined together. Five microliter of 100 mg/mL trypsin was added to the collected phage suspension to cleave the Fab. This improved the ability of trypsin-treated phages to infect E. coli. The trypsin-treated phages were added to 20 mL of E. coli strain ER2738 in the logarithmic growth phase (OD600=0.4-0.7). The E. coli was gently stirred and incubated at 37° C. for one hour to allow phages to infect the E. coli. The infected E. coli was seeded on a plate of 225 mm×225 mm. Then, E. coli in the seeded culture was infected with hyperphage, and cultured at 30° C. overnight. Phages were collected from the supernatant to prepare a suspension of antibody multivalent display phage library.

In the third panning, together with kynurenine at a final concentration of 500 μM, 100 pmol of the biotin-labeled antigen was added to 0.2 mL of the prepared phage library suspension, and thus the phage library was contacted with the antigen and kynurenine at room temperature for 60 minutes. BSA-blocked magnetic beads (Dynabeads MyOne Streptavidin T1) were added, and the antigen/phage complex was allowed to bind to magnetic beads at 4° C. for 30 minutes. The beads were washed three times with 0.4 mL of kynurenine/TBST and twice with kynurenine/TBS. Immediately after the beads to which 0.25 mL of TBS has been added were suspended at room temperature, the phage suspension was collected from the beads that were separated using a magnetic stand. This process was repeated, and then the two phage suspensions eluted separately were combined together. Five microliter of 100 mg/mL trypsin was added to the collected phage suspension to cleave the Fab. This improved the ability of the trypsin-treated phages to infect E. coli. The trypsin-treated phages were added to 20 mL of E. coli strain ER2738 in the logarithmic growth phase (OD600=0.4-0.7). The E. coli was gently stirred and incubated at 37° C. for one hour to allow phages to infect the E. coli. The infected E. coli was seeded on a plate of 225 mm×225 mm. Then, E. coli in the seeded culture was infected with hyperphage, and cultured at 30° C. overnight. Phages were collected from the supernatant to prepare a suspension of antibody multivalent display phage library.

The fourth panning was performed under the same conditions as the third panning.

(11-2) Obtaining Antibodies that Bind to hIL-6R in the Presence of Kynurenine from an Antibody Library by a Negative Selection Method The Ver.A kynurenine library constructed as described in Example 9 was screened for antibodies that have antigen-binding activity in the presence of kynurenine. For screening, the antibody-phage-display library was first contacted with the biotin-labeled antigen-streptavidin in the absence of kynurenine to remove phages presenting antibodies that have antigen-binding activity in the absence of kynurenine. Then, under the condition where kynurenine is present, panning was performed in the same manner to screen for antibodies having antigen-binding activity only under the condition where kynurenine is present.

E. coli retaining the constructed phage-display phagemid vector was infected with M13KO7ΔpIII (PROGEN Biotechnik; referred to as hyperphage), and cultured at 30° C. overnight. Phages were collected from the supernatant. To precipitate the population of phages, 2.5 M NaCl/10% PEG was added to the E. coli culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

In the first panning, phages that can bind to the antigen only in the presence of kynurenine were enriched using a negative selection method. Specifically, 500 pmol of the biotinylated antigen was added to BSA-blocked Sera-Mag SpeedBeads NeutrAvidin-coated, and allowed to bind at room temperature for 15 minutes. After the beads were washed three times with TBS, they were combined with 0.5 mL of phage library suspension blocked with BSA and allowed to bind at room temperature for one hour. The beads were separated using a magnetic stand to collect phages that did not bind to the antigen or beads. Together with 250 pmol of the biotin-labeled antigen, kynurenine was added at a final concentration of 500 μM to the collected phages, and thus the phage library was contacted with the antigen and kynurenine at room temperature for 15 minutes and then at 4° C. for 45 minutes. Then, BSA-blocked magnetic beads were added to the mixed solution of the labeled antigen, kynurenine, and phage library; and the antigen/phage complex was allowed to bind to the magnetic beads at 4° C. for 15 minutes. The beads were washed twice with 0.5 mL of ice-cold kynurenine/TBST and once with ice-cold kynurenine/TBS. Then, 0.5 mL of 1 mg/mL trypsin solution was added to the mixture. The mixture was stirred for 15 minutes at room temperature, and then phages were collected from the beads separated using a magnetic stand. The collected phages were added to 10 mL of E. coli strain ER2738 in the logarithmic growth phase (OD600=0.4-0.7). The E. coli was gently stirred and incubated at 37° C. for one hour to allow phages to infect the E. coli. The infected E. coli was seeded on a plate of 225 mm×225 mm. Then, E. coli in the seeded culture was infected with hyperphage, and cultured at 30° C. overnight. Phages were collected from the supernatant to prepare a suspension of antibody multivalent display phage library.

The second and subsequent panning rounds were carried out to enrich phages that can bind to the antigen only in the presence of kynurenine. Specifically, panning was carried out up to the fourth round by the same method as used in the second and subsequent panning rounds described in Example (11-1).

(11-3) Obtaining Antibodies that Bind to hIL-6R in the Presence of Kynurenine from an Antibody Library by Panning with a Molecule Serving as a Switch The Ver.A kynurenine library constructed as described in Example 9 was screened for antibodies that have antigen-binding activity under the condition where kynurenine is present. For screening, first, panning was carried out with biotinylated kynurenine (compounds 028, 029, and 036) to collect phages presenting antibodies that have kynurenine-binding activity. Then, in the presence of kynurenine, panning was performed with biotin-labeled antigen to screen for antibodies that have antigen-binding activity under the condition where kynurenine is present.

E. coli retaining the constructed phage-display phagemid vector was infected with M13KO7ΔpIII (PROGEN Biotechnik; referred to as hyperphage), and cultured at 30° C. overnight. Phages were collected from the supernatant. To precipitate the population of phages, 2.5 M NaCl/10% PEG was added to the E. coli culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

In the first panning, phages that can bind to biotinylated kynurenine (a mixture of compounds 028, 029, and 036) were enriched. Specifically, 4000 pmol of the biotinylated kynurenine mixture containing equal amounts of compounds 028, 029, and 036 was added to BSA-blocked beads (Dynabeads MyOne Streptavidin T1) and allowed to bind at room temperature for 30 minutes. After the beads were washed three times with TBS, they were combined with 0.8 mL of phage library suspension blocked with BSA, and allowed to contact with biotinylated kynurenine for 30 minutes at room temperature and then for another 30 minutes at 4° C. The beads were washed three times with 1 mL of ice-cold TBST and twice with ice-cold TBS. Then, 0.5 mL of 1 mg/mL trypsin solution was added to the mixed solution. Immediately after suspending the mixture at room temperature for 15 minutes, the phage suspension was collected from the beads that were separated using a magnetic stand. The collected phages were added to 100 mL of E. coli strain ER2738 in the logarithmic growth phase (OD600=0.4-0.7). The E. coli was gently stirred and incubated at 37° C. for one hour to allow phages to infect the E. coli. The infected E. coli was seeded on five plates of 225 mm×225 mm. Then, E. coli in the seeded culture was infected with hyperphage, and cultured at 30° C. overnight. Phages were collected from the supernatant to prepare a suspension of antibody multivalent display phage library.

In the second and subsequent panning rounds, phages that can bind to the antigen only in the presence of kynurenine were enriched. Specifically, panning was carried out up to the fourth round by the same method as used in the second and subsequent panning rounds described in Example (11-1).

(11-4) Assessment of Binding Activity in the Presence of Kynurenine by Phage ELISA Phages were cultured according to a conventional method (Methods Mol. Biol. (2002) 178, 133-145) from a single colony of E. coli obtained as described in (11-1), (11-2), and (11-3). Culture supernatants containing antibody multivalent display phages were collected using hyperphages as helper phages. The collected phage culture supernatants were subjected to ultrafiltration using NucleoFast96 (MACHERY-NAGEL). 200 μL each of the culture supernatants were applied to each well of NucleoFast96. The flowthrough fractions were removed via centrifugation at 6000 g for 45 minutes. 200 μL of H₂O was added and the wells were washed by centrifugation at 6000 g for 30 minutes. Then, 200 μL of TBS was added, and after allowing to stand for five minutes at room temperature, phage suspensions contained in the supernatants were collected.

TBS or 500 μM kynurenine/TBS was added to the purified phages, and they were subjected to ELISA by the procedure described below. A StreptaWell 96 microtiter plate (Roche) was coated with 100 μL of TBS containing biotin-labeled hIL-6R for one or more hours. After removing biotin-labeled hIL-6R not bound to the plate by washing each well of the plate with TBST, the wells were blocked with 250 μL of 2% skim milk-TBS for one or more hours. After removing 2% skim milk-TBS, the prepared purified phages were added to each well of the plate. The plate was allowed to stand at room temperature for one hour to allow antibody-presenting phages to bind to biotin-labeled hIL-6R in each well in the presence/absence of kynurenine. After washing with TBST or kynurenine/TBST, HRP-conjugated anti-M13 antibody (Amersham Pharmacia Biotech) diluted with TBS or kynurenine/TBS was added to each well. The plate was incubated for one hour. After washing with TBST or kynurenine/TBST, the chromogenic reaction of the solution in each well added with TMB single solution (ZYMED) was terminated by adding sulfuric acid. Then, the color development was measured by absorbance at 450 nm. The results revealed several antibodies that bound to human IL-6 receptor in the presence of kynurenine. The results of phage ELISA are shown in Table 35. As described in Example 6 above, antibodies that bind to human IL-6 receptor in the presence of kynurenine were also isolated from the human naïve antibody library; however switch antibodies to human IL-6 receptor could be isolated with much greater efficiency. The results of phage ELISA carried out as described in Example 6-2 are shown in Table 36.

TABLE 35

| Origin | Example (11-1) | Example (11-2) | Example (11-3) |
|---|---|---|---|
| Number of panning rounds | 4 | 4 | 4 |
| Number of clones subjected to ELISA | 96 | 96 | 96 |
| Number of positive clones (absorbance > 0.2) | 96 | 94 | 94 |
| Number of switch clones (kynurenine +/− absorbance ratio > 2) | 93 | 91 | 86 |
| Number of switch clone sequences | 87 | 88 | 77 |

TABLE 36

| | |
|---|---|
| Number of panning rounds | 3 |
| Number of clones subjected to ELISA | 960 |
| Number of positive clones (absorbance > 0.1) | 939 |
| Number of switch clones (kynurenine +/− absorbance ratio > 1.5) | 10 |
| Number of switch clone sequences | 2 |

(11-5) Sequence Analysis of Switch Antibodies Whose Antigen-Binding Activity Varies Depending on the Presence or Absence of Kynurenine Using specific primers (SEQ ID NOs: 79 and 80), genes were amplified from clones judged to have antigen-binding activity under the condition where kynurenine is present based on the phage ELISA results shown in Example (11-4).

The nucleotide sequences of the genes were analyzed. From the analysis results, several clones judged to have binding activity to biotin-labeled hIL-6R in the presence of kynurenine were isolated under all conditions described in Examples (11-1), (11-2), and (11-3). From the isolated clones, six clones were selected, whose amino acid sequences and panning conditions for isolation (indicated as Origin in the table) are shown in Table 37 below.

TABLE 37

| Clone name | Origin | Heavy chain SEQ ID NO | Light chain SEQ ID NO |
|---|---|---|---|
| 6RFHm12-4_040 | Example(11-3) | SEQ ID NO: 101 | SEQ ID NO:102 |
| 6RFHm12-4_078 | Example(11-3) | SEQ ID NO: 103 | SEQ ID NO:104 |
| 6RFHm14-4_087 | Example(11-2) | SEQ ID NO: 105 | SEQ ID NO:106 |
| 6RFHm14-4_093 | Example(11-2) | SEQ ID NO: 107 | SEQ ID NO:108 |
| 6RFHm17-4_006 | Example(11-1) | SEQ ID NO: 109 | SEQ ID NO:110 |
| 6RFHm17-4_010 | Example(11-1) | SEQ ID NO: 111 | SEQ ID NO:112 |

(11-6) Expression and Purification of Antibodies that Bind to hIL-6R

The heavy chain and light chain variable region sequences of the 6 clones described in Example (11-5) were inserted into a plasmid for animal expression having an antibody heavy chain constant region (SEQ ID NO: 113) or light chain kappa constant region sequence (SEQ ID NO: 47). The antibodies were expressed and purified by the method described in Reference Example 1 below.

(11-7) Assessment of the Obtained Antibodies for their hIL-6R-Binding Activity

The selected six types of antibodies and the 6RNMSC1-2_F02 antibody were subjected to ELISA under the conditions indicated in Table 38.

TABLE 38

| | Antigen | Kynurenine | Tryptophan |
|---|---|---|---|
| Condition 1 | hIL6R | 500 uM | — |
| Condition 2 | hIL6R | — | — |
| Condition 3 | — | 500 uM | — |
| Condition 4 | hIL6R | — | 500 uM |

First, a StreptaWell 96 microtiter plate (Roche) was coated with 100 μL of TBS containing biotin-labeled hIL-6R at room temperature for one or more hours. After removing biotin-labeled hIL-6R that are not bound to the plate by washing each well of the plate with TBST, the wells were blocked with 250 μL of Blocking Buffer (2% skim milk/TBS) for one or more hours. Blocking Buffer was removed from each well. 100 μL each of the purified IgGs prepared to 2.5 μg/mL using TBS under the conditions described in Table 38 were added to the wells, and the plate was allowed to stand at room temperature for one hour to allow each IgG to bind to biotin-labeled hIL-6R in each well. TBST was prepared to make the final concentrations shown in Table 38, and each well was washed with the prepared TBST. HRP-conjugated anti-human IgG antibody (BIOSOURCE) diluted with TBS containing the same small molecules was added to each well. The plate was incubated for one hour. After washing with TBST prepared to the final concentrations shown in Table 38, the chromogenic reaction of the solution in each well added with TMB single solution (ZYMED) was terminated by adding sulfuric acid. Then, the color development was measured by absorbance at 450 nm. The measurement results are shown in FIG. 39.

The absorbance under condition 2 or 3 was markedly low as compared to the absorbance under condition 1 in the selected six types of antibodies, similarly to antibody 6RNMSC1-2_F02. This confirmed that the selected six types of antibodies in the form of IgG also have specific binding activity against the biotin-labeled hIL-6R in the presence of kynurenine. Meanwhile, no significant difference was observed for the absorbance under condition 2 as compared to the absorbance under condition 4. Thus, the selected six types of antibodies were also confirmed to not have binding activity to the biotin-labeled hIL-6R in the presence of tryptophan. The results described above shows that multiple hIL-6R-binding antibodies for which kynurenine serves as a switch can be obtained from a library for isolating kynurenine-switch antibodies by using panning with kynurenine (Ver.A kynurenine library). Furthermore, as shown in Reference Example 4 below, antibodies that bind to a target antigen in the absence of ATP but do not bind to a target antigen in the presence of ATP were obtained from the rationally designed library constructed using an ATP-binding antibody as a template as described in Reference Example 2. This suggests that antibodies that bind to a target antigen in the absence of kynurenine but do not bind to a target antigen in the presence of kynurenine can be similarly obtained from a library for obtaining kynurenine-switch antibodies.

[Example 12] Obtaining Antibodies that Bind to Human IgA-Fc (hIgA-Fc) in the Presence of Kynurenine from a Library for Obtaining Kynurenine-Switch Antibodies Using Panning with Kynurenine (Ver.A Kynurenine Library)

(12-1) Obtaining Antibodies that have hIgA-Fc-Binding Activity in the Presence of Kynurenine but not in the Absence of Kynurenine from an Antibody Library The Ver.A kynurenine library constructed as described in Example 9 was screened for antibodies that have human IgA-Fc (hIgA-Fc)-binding activity in the presence of kynurenine. Specifically, phages presenting antibodies that have binding activity to hIgA-Fc captured on beads in the presence of kynurenine but are eluted from the beads in the absence of kynurenine, were collected. In this method, biotin-labeled hIgA-Fc (SEQ ID NO: 146) prepared by the method described in Reference Example 5 was used as an antigen.

E. coli retaining the constructed phage-display phagemid vector was infected with M13KO7ΔpIII (PROGEN Biotechnik; referred to as hyperphage), and cultured at 30° C. overnight. Phages were collected from the supernatant. To precipitate the population of phages, 2.5 M NaCl/10% PEG was added to the E. coli culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

Panning was carried out to enrich phages that can bind to the antigen only in the presence of kynurenine. Specifically, panning was carried out up to the fourth round by a method similar to that indicated in Example (11-1), except that the antigen amount was changed to 500 pmol in the first and second rounds, and 200 pmol in the third and fourth rounds.

(12-2) Obtaining Antibodies that Bind to hIgA-Fc in the Presence of Kynurenine from an Antibody Library by a Negative Selection Method The Ver.A kynurenine library constructed as described in Example 9 was screened for antibodies that have antigen-binding activity under the condition where kynurenine is present. For screening, the antibody-phage-display library was first contacted with biotin-labeled antigen-streptavidin in the absence of kynurenine to remove phages presenting antibodies that have antigen-binding activity in the absence of kynurenine. Then, under the condition where kynurenine is present, panning was performed in the same manner to screen for antibodies having antigen-binding activity only under the condition where kynurenine is present.

*E. coli* retaining the constructed phage-display phagemid vector was infected with M13KO7ΔpIII (PROGEN Biotechnik; referred to as hyperphage), and cultured at 30° C. overnight. Phages were collected from the supernatant. To precipitate the population of phages, 2.5 M NaCl/10% PEG was added to the *E. coli* culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

In the first panning, phages that can bind to the antigen only in the presence of kynurenine were enriched using a negative selection method. Specifically, 1000 pmol of the biotinylated antigen was added to BSA-blocked Sera-Mag SpeedBeads NeutrAvidin-coated and allowed to bind thereto at room temperature for 15 minutes. After the beads were washed three times with TBS, they were combined with 0.5 ml of phage library suspension blocked with BSA and allowed to bind at room temperature for one hour. The beads were separated using a magnetic stand to collect phages that did not bind to the antigen or beads. Together with 500 pmol of the biotin-labeled antigen, kynurenine was added at a final concentration of 500 μM to the collected phages, and thus the phage library was contacted with the antigen and kynurenine at room temperature for 15 minutes and then at 4° C. for 45 minutes. Then, BSA-blocked magnetic beads were added to the mixed solution of the labeled antigen, kynurenine, and phage library, and the antigen/phage complex was allowed to bind to the magnetic beads at 4° C. for 15 minutes. The beads were washed twice with 0.5 ml of ice-cold kynurenine/TBST and once with ice-cold kynurenine/TBS. Then, 0.5 ml of 1 mg/ml trypsin solution was added to the mixed solution. After the mixture was stirred for 15 minutes at room temperature, phages were collected from the beads separated using a magnetic stand. The collected phages were added to 10 ml of *E. coli* strain ER2738 in the logarithmic growth phase (OD600=0.4-0.7). The *E. coli* was gently stirred and incubated at 37° C. for one hour to allow phages to infect the *E. coli*. The infected *E. coli* was seeded on a plate of 225 mm×225 mm. Then, *E. coli* in the seeded culture was infected with hyperphage, and cultured at 30° C. overnight. Phages were collected from the supernatant to prepare a suspension of antibody multivalent display phage library.

The second and subsequent panning rounds were carried out to enrich phages that can bind to the antigen only in the presence of kynurenine. Specifically, panning was carried out up to the fourth round by a method similar to the second and subsequent panning rounds described in Example (11-1), except that the antigen amount was changed to 500 pmol in the second round and 200 pmol in the third and fourth rounds.

(12-3) Obtaining Antibodies that Bind to hIgA-Fc in the Presence of Kynurenine, from an Antibody Library by Panning with a Molecule Serving as a Switch The Ver.A kynurenine library constructed as described in Example 9 was screened for antibodies that have antigen-binding activity under the condition where kynurenine is present. For screening, panning was first carried out with biotinylated kynurenine (compounds 028, 029, and 036) to collect phages presenting antibodies that have kynurenine-binding activity. Then, panning was performed with biotin-labeled antigen in the presence of kynurenine to screen for antibodies that have antigen-binding activity under the condition where kynurenine is present.

*E. coli* retaining the constructed phage-display phagemid vector was infected with M13KO7ΔpIII (PROGEN Biotechnik; referred to as hyperphage), and cultured at 30° C. overnight. Phages were collected from the supernatant. To precipitate a population of phages, 2.5 M NaCl/10% PEG was added to the *E. coli* culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

The first panning was carried out to enrich phages that can bind to biotinylated kynurenine (a mixture of compounds 028, 029, and 036). Specifically, 4000 pmol of a biotinylated kynurenine mixture containing equal amounts of compounds 028, 029, and 036 was added to BSA-blocked beads (Dynabeads MyOne Streptavidin T1) and allowed to bind at room temperature for 30 minutes. After washing the beads three times with TBS, they were combined with 0.8 ml of phage library suspension blocked with BSA, and allowed to contact with biotinylated kynurenine for 30 minutes at room temperature and then for 30 minutes at 4° C. The beads were washed three times with 1 ml of ice-cold TBST and twice with ice-cold TBS. Then, 0.5 ml of 1 mg/ml trypsin solution was added to the mixed solution. Immediately after the mixture was suspended at room temperature for 15 minutes, a phage suspension was collected from the beads that were separated using a magnetic stand. The collected phages were added to 100 ml of *E. coli* strain ER2738 in the logarithmic growth phase (OD600=0.4-0.7). The *E. coli* was gently stirred and incubated at 37° C. for one hour to allow phages to infect the *E. coli*. The infected *E. coli* was seeded on five plates of 225 mm×225 mm. Then, *E. coli* in the seeded culture was infected with hyperphage, and cultured at 30° C. overnight. Phages were collected from the supernatant to prepare a suspension of antibody multivalent display phage library.

The second and subsequent panning rounds were carried out to enrich phages that can bind to the antigen only in the presence of kynurenine. Specifically, panning was carried out up to the fourth round by a method similar to the second and subsequent panning rounds described in Example (11-1), except that the antigen amount was changed to 500 pmol in the second round and 200 pmol in the third and fourth rounds.

(12-4) Assessment of Binding Activity in the Presence of Kynurenine by Phage ELISA Phages were cultured according to a conventional method (Methods Mol. Biol. (2002) 78, 133-145) from a single colony of E. coli obtained as described in (12-1), (12-2), and (12-3). A culture supernatant containing antibody multivalent display phages was collected using hyperphages as helper phages. Phages purified by the method described in Example (11-4) were subjected to ELISA by the procedure described below. A StreptaWell 96 microtiter plate (Roche) was coated with 100 μl of TBS containing biotin-labeled hIgA-Fc for one or more hours. Each well of the plate was washed with TBST to remove biotin-labeled hIgA-Fc that is not bound to the plate, and the wells were blocked with 250 μl of 2% skim milk-TBS for one or more hours. After removing 2% skim milk-TBS, the prepared purified phages were added to each well. The plate was allowed to stand at room temperature for one hour to allow antibody-presenting phages to bind to biotin-labeled hIgA-Fc in each well in the presence/absence of kynurenine. Each well was washed with TBST or kynurenine/TBST, and HRP-conjugated anti-M13 antibody (Amersham Pharmacia Biotech) diluted with TBS or kynurenine/TBS was added thereto. The plate was incubated for one hour. After washing with TBST or kynurenine/TBST, the chromogenic reaction of the solution in each well added with TMB single solution (ZYMED) was terminated by adding sulfuric acid. Then, color development was measured by absorbance at 450 nm. As a result, several antibodies were confirmed to bind to human IgA-Fc in the presence of kynurenine. The results of phage ELISA are shown in Table 39.

TABLE 39

| Origin | Example (12-1) | Example (12-2) | Example (12-3) |
|---|---|---|---|
| Number of panning rounds | 4 | 4 | 4 |
| Number of clones subjected to ELISA | 96 | 96 | 96 |
| Number of positive clones (absorbance > 0.2) | 89 | 90 | 91 |
| Number of switch clones (kynurenine +/− absorbance ratio > 2) | 87 | 90 | 86 |
| Number of switch clone sequences | 67 | 69 | 75 |

(12-5) Sequence Analysis of Switch Antibodies Whose Antigen-Binding Activity Varies Depending on the Presence or Absence of Kynurenine Using specific primers (SEQ ID NOs: 79 and 80), genes were amplified from clones judged to have antigen-binding activity under the condition where kynurenine is present based on the results of phage ELISA shown in Example (12-4). The nucleotide sequences of the genes were analyzed, and as a result, several clones judged to have binding activity to the biotin-labeled hIgA-Fc in the presence of kynurenine were obtained under each condition described in Examples(12-1), (12-2), and (12-3). From the obtained clones, six clones were selected, whose amino acid sequences and panning conditions for obtainment (indicated as Origin in the table) are shown in Table 40 below.

TABLE 40

| Clone name | Origin | Heavy chain SEQ ID NO | Light chain SEQ ID NO |
|---|---|---|---|
| hIA FHm12-4_018 | Example(12-3) | SEQ ID NO: 114 | SEQ ID NO: 115 |
| hIA FHm12-4_061 | Example(12-3) | SEQ ID NO: 116 | SEQ ID NO: 117 |
| hIA FHm14-4_001 | Example(12-2) | SEQ ID NO: 118 | SEQ ID NO: 119 |
| hIA FHm14-4_041 | Example(12-2) | SEQ ID NO: 120 | SEQ ID NO: 121 |
| hIA FHm17-4_026 | Example(12-1) | SEQ ID NO: 122 | SEQ ID NO: 123 |
| hIA FHm17-4_072 | Example(12-1) | SEQ ID NO: 124 | SEQ ID NO: 125 |

(12-6) Expression and Purification of Antibodies that Bind to hIgA-Fc

Each of the heavy chain and light chain variable region sequences of the six clones described in Example (12-5) were inserted into a plasmid for animal expression having an antibody heavy chain constant region (SEQ ID NO: 113) or light chain kappa constant region sequence (SEQ ID NO: 47). Antibodies were expressed and purified by the method described in Reference Example 1 below.

(12-7) Assessment of Obtained Antibodies for their hIgA-Fc-Binding Activity

The obtained six types of antibodies were subjected to ELISA under the conditions described in Table 41.

TABLE 41

| | Antigen | Kynurenine | Tryptophan |
|---|---|---|---|
| Condition 1 | hIgA-Fc | 500 uM | — |
| Condition 2 | hIgA-Fc | — | — |
| Condition 3 | — | 500 uM | — |
| Condition 4 | hIgA-Fc | — | 500 uM |

First, a StreptaWell 96 microtiter plate (Roche) was coated with 100 μl of TBS containing biotin-labeled hIgA-Fc at room temperature for one or more hours. Each well of the plate was washed with TBST to remove biotin-labeled hIgA-Fc not bound to the plate and the wells were blocked with 250 μl of Blocking Buffer (2% skim milk/TBS) for one or more hours. Blocking Buffer was removed from each well. 100 μl each of the purified IgGs prepared to 2.5 μg/ml with TBS under the conditions shown in Table 41 were added to the plate. The plate was left to stand at room temperature for one hour to allow each IgG to bind to the biotin-labeled hIgA-Fc in each well. Each well was washed with TBST prepared at a final concentration shown in Table 41. HRP-conjugated anti-human IgG antibody (BIOSOURCE) diluted with TBS containing the same small molecules was added to the wells. The plate was incubated for one hour. After washing with TBST prepared to the final concentrations shown in Table 41, the chromogenic reaction of the solution in each well added with TMB single solution (ZYMED) was terminated by adding sulfuric acid. Then, color development was measured by absorbance at 450 nm. The measurement results are shown in FIG. 40.

Regarding the selected six types of antibodies, the absorbance under condition 2 or 3 was markedly low as compared to the absorbance under condition 1. This finding confirms that the selected six types of antibodies, in the form of IgG, also have specific binding activity to biotin-labeled hIgA-Fc in the presence of kynurenine. Meanwhile, the absorbance under condition 2 was not markedly different as compared to the absorbance under condition 4. Thus, the selected six types of antibodies were also confirmed to not have binding activity to biotin-labeled hIgA-Fc in the presence of tryptophan. The results described above shows that a number of hIgA-Fc-binding antibodies for which kynurenine functions as a switch can be obtained from a library for obtaining kynurenine-switch antibodies using panning with kynurenine (Ver.A kynurenine library).

[Example 13] Obtaining Antibodies that Bind to Human IL-6 (hIL-6) in the Presence of Kynurenine from a Library for Obtaining Kynurenine-Switch Antibodies Using Panning with Kynurenine (Ver.A Kynurenine Library)

(13-1) Obtaining Antibodies that have Binding Activity to hIL-6 in the Presence of Kynurenine but do not Bind in the Absence of Kynurenine from an Antibody Library The Ver.A kynurenine library constructed as described in Example 9 was screened for antibodies having binding activity to human IL-6 (hIL-6) in the presence of kynurenine. Namely, phages presenting antibodies that have binding activity to hIL-6 captured on beads in the presence of kynurenine, but that are eluted from the beads in the absence of kynurenine, were collected. In this isolation method, biotin-labeled hIL-6 was used as an antigen.

E. coli retaining the constructed phage-display phagemid vector was infected with M13KO7ΔpIII (PROGEN Biotechnik; referred to as hyperphage), and cultured at 30° C. overnight. Phages were collected from the supernatant. To precipitate a population of phages, 2.5 M NaCl/10% PEG was added to the E. coli culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

Panning was carried out to enrich phages that can bind to the antigen only in the presence of kynurenine. Panning was carried out up to the fourth round by a method similar to that described in Example (11-1).

(13-2) Obtaining Antibodies that Bind to hIL-6 in the Presence of Kynurenine Using a Negative Selection Method from an Antibody Library The Ver.A kynurenine library constructed as described in Example 9 was screened for antibodies that have antigen-binding activity under the condition where kynurenine is present. For screening purpose, the antibody-phage-display library was first contacted with biotin-labeled antigen-streptavidin in the absence of kynurenine to remove phages presenting antibodies that have antigen-binding activity even in the absence of kynurenine. Then, panning was similarly performed under the condition where kynurenine is present to screen for antibodies having antigen-binding activity under the condition where kynurenine is present.

E. coli retaining the constructed phage-display phagemid vector was infected with M13KO7ΔpIII (PROGEN Biotechnik; referred to as hyperphage), and cultured at 30° C. overnight. Phages were collected from the supernatant. To precipitate a population of phages, 2.5 M NaCl/10% PEG was added to the E. coli culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

In the first round of panning, phages that can bind to the antigen only in the presence of kynurenine were enriched using a negative selection method. Specifically, 500 pmol of biotinylated antigen was added to BSA-blocked Sera-Mag SpeedBeads NeutrAvidin-coated and allowed to bind at room temperature for 15 minutes. After washing the beads three times with TBS, they were combined with 0.5 ml of phage library suspension blocked with BSA and allowed to bind at room temperature for one hour. The beads were separated using a magnetic stand to collect phages that did not bind to the antigen or beads. Together with 250 pmol of biotin-labeled antigen, kynurenine was added at a final concentration of 500 μM to the collected phages, and the phage library was contacted with the antigen and kynurenine at room temperature for 15 minutes and then at 4° C. for 45 minutes. Then, BSA-blocked magnetic beads were added to the mixed solution of the labeled antigen, kynurenine, and phage library, and the antigen/phage complex was allowed to bind to the magnetic beads at 4° C. for 15 minutes. The beads were washed twice with 0.5 ml of ice-cold kynurenine/TBST and once with ice-cold kynurenine/TBS. Then, 0.5 ml of 1 mg/ml trypsin solution was added to the mixed solution. The mixed solution was stirred for 15 minutes at room temperature, and then phages were collected from the beads separated using a magnetic stand. The collected phages were added to 10 ml of E. coli strain ER2738 in the logarithmic growth phase (OD600=0.4-0.7). The E. coli was gently stirred and incubated at 37° C. for one hour to allow phages to infect the E. coli. The infected E. coli was seeded on a plate of 225 mm×225 mm. Then, E. coli in the seeded culture was infected with hyperphage, and cultured at 30° C. overnight. Phages were collected from the supernatant to prepare a suspension of antibody multivalent display phage library.

In the second and subsequent panning rounds, phages that can bind to the antigen only in the presence of kynurenine were enriched. Specifically, panning was carried out up to the fourth round by a method similar to the second and subsequent panning rounds described in Example (11-1).

(13-3) Obtaining Antibodies that Bind to hIL-6 in the Presence of Kynurenine by Panning with a Molecule Serving as a Switch, from an Antibody Library The Ver.A kynurenine library constructed as described in Example 9 was screened for antibodies that have antigen-binding activity under the condition where kynurenine is present. For screening, panning was first carried out with biotinylated kynurenine (compounds 028, 029, and 036) to collect phages presenting antibodies that have kynurenine-binding activity. Then, panning was performed with biotin-labeled antigen in the presence of kynurenine to screen for antibodies having antigen-binding activity under the condition where kynurenine is present.

E. coli retaining the constructed phage-display phagemid vector was infected with M13KO7ΔpIII (PROGEN Biotechnik; referred to as hyperphage), and cultured at 30° C. overnight. Phages were collected from the supernatant. To precipitate a population of phages, 2.5 M NaCl/10% PEG was added to the E. coli culture in which phages were produced. The phages were diluted with TBS to prepare a suspension of antibody multivalent display phage library. Then, BSA was added at a final concentration of 4% to the phage library suspension. Panning was performed using the antigen immobilized on magnetic beads. The magnetic beads used were NeutrAvidin coated beads (Sera-Mag SpeedBeads NeutrAvidin-coated) or Streptavidin coated beads (Dynabeads MyOne Streptavidin T1).

In the first round of panning, phages that can bind to biotinylated kynurenine (a mixture of compounds 028, 029, and 036) were enriched. Specifically, 4000 pmol of a biotinylated kynurenine mixture containing equal amounts of compounds 028, 029, and 036 was added to BSA-blocked beads (Dynabeads MyOne Streptavidin T1) and allowed to bind at room temperature for 30 minutes. The beads were washed three times with TBS and combined with 0.8 ml of phage library suspension blocked with BSA, and allowed to contact with biotinylated kynurenine for 30 minutes at room temperature and then 30 minutes at 4° C. The beads were washed three times with 1 ml of ice-cold TBST and twice with ice-cold TBS. Then, 0.5 ml of 1 mg/ml trypsin solution was added to the mixed solution. Immediately after the mixture was suspended at room temperature for 15 minutes, a phage suspension was collected from the beads that were separated using a magnetic stand. The collected phages were added to 100 ml of E. coli strain ER2738 in the logarithmic growth phase (OD600=0.4-0.7). The E. coli was gently stirred and incubated at 37° C. for one hour to allow phages to infect the E. coli. The infected E. coli was seeded on five plates of 225 mm×225 mm. Then, E. coli in the seeded culture was infected with hyperphage, and cultured at 30° C. overnight. Phages were collected from the supernatant to prepare a suspension of antibody multivalent display phage library.

In the second and subsequent panning rounds, phages that can bind to the antigen only in the presence of kynurenine were enriched. Specifically, panning was carried out up to the fourth round by a method similar to the second and subsequent panning rounds described in Example (11-1).

(13-4) Assessment of Binding Activity in the Presence of Kynurenine by Phage ELISA Phages were cultured according to a conventional method (Methods Mol. Biol. (2002) 78, 133-145) from a single colony of E. coli obtained as described in (13-1), (13-2), and (13-3). A culture supernatant containing antibody multivalent display phages was collected using hyperphages as helper phages. Phages purified by the method described in Reference Example (11-4) were subjected to ELISA by the procedure described below. A 384-well Microplates Streptavidin-coated (Greiner Bio-One) was coated with 10 μl of TBS containing biotin-labeled hIL-6 for one or more hours. Each well of the plate was washed with TBST to remove biotin-labeled hIL-6 not bound to the plate and the wells were blocked with 80 μl of 2% skim milk-TBS for one or more hours. After removing 2% skim milk-TBS, the prepared purified phages were added to each well of the plate. The plate was left to stand at room temperature for one hour to allow antibody-presenting phages to bind to biotin-labeled hIL-6 in each well in the presence/absence of kynurenine. Each well was washed with TBST or kynurenine/TBST. HRP-conjugated anti-M13 antibody (Amersham Pharmacia Biotech) diluted with TBS or kynurenine/TBS was added to the wells. The plate was incubated for one hour. After washing with TBST or kynurenine/TBST, the chromogenic reaction of the solution in each well added with TMB single solution (ZYMED) was terminated by adding sulfuric acid. Then, the color development was measured by absorbance at 450 nm. As a result, several antibodies were confirmed to bind to hIL-6 in the presence of kynurenine. The results of phage ELISA are shown in Table 42.

TABLE 42

| Origin | Example (13-1) | Example (13-2) | Example (13-3) |
|---|---|---|---|
| Number of panning rounds | 4 | 4 | 4 |
| Number of clones subjected to ELISA | 96 | 96 | 96 |
| Number of positive clones (absorbance > 0.2) | 65 | 59 | 54 |
| Number of switch clones (kynurenine +/− absorbance ratio > 2) | 61 | 58 | 48 |
| Number of switch clone sequences | 42 | 37 | 44 |

(13-5) Sequence Analysis of Switch Antibodies Whose Antigen-Binding Activity Varies Depending on the Presence or Absence of Kynurenine Using specific primers (SEQ ID NOs: 79 and 80), genes were amplified from clones judged to have antigen-binding activity under the condition where kynurenine is present based on the phage ELISA results shown in Example (13-4). The nucleotide sequences of the genes were analyzed. From the analysis results, several clones judged to have binding activity to biotin-labeled hIL-6 in the presence of kynurenine were obtained under each condition described in Examples (13-1), (13-2), and (13-3). From the obtained clones, six clones were selected and their amino acid sequences and panning conditions for isolation (indicated as Origin in the table) are shown in Table 43 below.

TABLE 43

| Clone name | Origin | Heavy chain SEQ ID NO | Light chain SEQ ID NO |
|---|---|---|---|
| I6FHm12-4_068 | Example (13-3) | SEQ ID NO: 126 | SEQ ID NO: 127 |
| I6FHm12-4_094 | Example (13-3) | SEQ ID NO: 128 | SEQ ID NO: 129 |
| I6FHm14-4_007 | Example (13-2) | SEQ ID NO: 130 | SEQ ID NO: 131 |
| I6FHm14-4_030 | Example (13-2) | SEQ ID NO: 132 | SEQ ID NO: 133 |
| I6FHm17-4_016 | Example (13-1) | SEQ ID NO: 134 | SEQ ID NO: 135 |
| I6FHm17-4_036 | Example (13-1) | SEQ ID NO: 136 | SEQ ID NO: 137 |

(13-6) Expression and Purification of Antibodies that Bind to hIL-6

The heavy chain and light chain variable region sequences of the six clones described in Example (13-5) were each inserted into a plasmid for animal expression having an antibody heavy chain constant region (SEQ ID NO: 113) or a light chain kappa constant region sequence (SEQ ID NO: 47). Expression and purification of the antibodies were performed by the method described in Reference Example 1 below.

(13-7) Assessment of the Obtained Antibodies for their hIL-6-Binding Activity

The obtained six types of antibodies were subjected to ELISA under the conditions described in Table 44.

TABLE 44

|  | Antigen | Kynurenine | Tryptophan |
|---|---|---|---|
| Condition 1 | hIL-6 | 500 uM | — |
| Condition 2 | hIL-6 | — | — |
| Condition 3 | — | 500 uM | — |
| Condition 4 | hIL-6 | — | 500 uM |

First, a StreptaWell 96 microtiter plate (Roche) was coated with 100 µl of TBS containing biotin-labeled hIL-6 at room temperature for one or more hours. Each well of the plate was washed with TBST to remove biotin-labeled hIL-6 not bound to the plate and the wells were blocked with 250 µl of Blocking Buffer (2% skim milk/TBS) for one or more hours. Blocking Buffer was removed from each well. 100 µl each of the purified IgGs prepared to 2.5 µg/ml with TBS under the conditions shown in Table 44 were added to the well. The plate was left to stand at room temperature for one hour to allow each IgG to bind to biotin-labeled hIL-6 in each well. Each well was washed with TBST prepared at a final concentration shown in Table 44. HRP-conjugated anti-human IgG antibody (BIOSOURCE) diluted with TBS containing the same small molecules was added to the wells. The plate was incubated for one hour. After washing with TBST prepared at a final concentration shown in Table 44, the chromogenic reaction of the solution in each well added with TMB single solution (ZYMED) was terminated by adding sulfuric acid. Then, the color development was measured by absorbance at 450 nm. The measurement results are shown in FIG. 41.

Regarding the selected six types of antibodies, the absorbance under condition 2 or 3 was markedly low as compared to the absorbance under condition 1. This finding confirms that the selected six types of antibodies, in the form of IgG, also have specific binding activity to biotin-labeled hIL-6 in the presence of kynurenine. Meanwhile, the absorbance under condition 2 was not markedly different as compared to the absorbance under condition 4. Thus, the selected six types of antibodies were also confirmed to not have binding activity to biotin-labeled hIL-6 in the presence of tryptophan. The results described above shows that a number of hIL-6-binding antibodies for which kynurenine functions as a switch can be obtained from a library for obtaining kynurenine-switch antibodies, using panning with kynurenine (Ver.A kynurenine library).

[Reference Example 1] Obtaining Antibodies that Bind to Adenosine and/or ATP, from a Human Antibody Library by Phage Display Techniques (1-1) Preparation of Naïve Human Antibody Phage-Display Library A human antibody phage-display library consisting of multiple phages that present the Fab domains of human antibody sequences that are different from one another was constructed using, as a template, polyA RNA prepared from human PBMC, commercially available human polyA RNA, or such according to a method known to those skilled in the art.

(1-2) Acquisition of Antibodies that Bind to Adenosine and/or ATP from Library by Bead Panning The phage-display library of naïve human antibodies constructed as described in Reference Example (1-1) was screened for antibodies that exhibit antigen-binding activity, specifically, by collecting phages that display antibodies with binding activity to antigens captured by beads. ATP-PEG-Biotin, 2'-Adenosine-PEG-Biotin, and 5'-Adenosine-PEG-Biotin were used as antigens. Regarding ATP-PEG-Biotin, Cat. No. NU-926-BIO was purchased from Jena Bioscience GmbH and used. Regarding 2'-Adenosine-PEG-Biotin and 5'-Adenosine-PEG-Biotin, those constructed in Example (2-2-11) were used.

Phages produced in *E. coli* containing the phagemid vector constructed for phage display were purified by a conventional method, and then dialyzed against TBS to prepare a phage library suspension. Then, BSA was added at a final concentration of 4% to the suspension. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin).

Next, 250 pmol of biotinylated ATP, 2'-adenosine-PEG-Biotin, and 5'-adenosine-PEG-Biotin were added to the prepared phage library suspension. Thus, the phage library suspension was contacted with adenosine and ATP for 60 minutes at room temperature. Then, BSA-blocked magnetic beads were added to the phage library suspension, and the complex of phage with adenosine and/or ATP was allowed to bind to the magnetic beads at room temperature for 15 minutes. The beads were washed once with TBS. Then, the beads were combined with 0.5 ml of 1 mg/ml trypsin solution. Immediately after the beads were suspended at room temperature for 15 minutes, a phage suspension was collected from the beads that were separated using a magnetic stand. The collected phage suspension was added to 10 ml of *E. coli* cells of strain ER2738 at the logarithmic growth phase (OD600=0.4 to 0.7). The *E. coli* was incubated at 37° C. for one hour under gentle stirring to be infected by phage. The infected *E. coli* was seeded in a 225 mm×225 mm plate. Then, phages were collected from the culture medium of the seeded *E. coli* to prepare a liquid stock of phage library.

A second round of panning was performed to also enrich phages that are capable of binding to adenosine and/or ATP. The prepared phage library suspension was contacted with adenosine and ATP for 60 minutes at room temperature by adding 50 pmol each of biotinylated ATP, 2'-Adenosine-PEG-Biotin, and 5'-Adenosine-PEG-Biotin. Then, the BSA-blocked magnetic beads were added to the phage library suspension, and the complex of phage with adenosine and/or ATP was allowed to bind to the magnetic beads at room temperature for 15 minutes. The beads were washed three times with TBST and twice with TBS. Then, the beads were combined with 0.5 ml of 1 mg/ml trypsin solution. Immediately after the beads were suspended at room temperature for 15 minutes, a phage suspension was collected from the beads separated using a magnetic stand. The collected phage suspension was added to 10 ml of *E. coli* cells of strain ER2738 at the logarithmic growth phase (OD600=0.4 to 0.7). The *E. coli* was incubated at 37° C. for one hour with gentle stirring to be infected by phage. The infected E. coli was seeded in a 225 mm×225 mm plate. Then, phages were collected from the culture medium of the seeded E. coli to prepare a liquid stock of phage library.

By the same procedure, panning was performed three times to obtain antibodies that are capable of binding to adenosine and/or ATP. In the fourth round of panning, TBST wash and TBS wash were each performed five times.

(1-3) Assessment of Adenosine- and ATP-Binding Activity by Phage ELISA

From single colonies of E. coli obtained by panning as described in the Example above, culture supernatants containing phages were collected according to a conventional method (Method Mol. Biol. (2002) 178, 133-145). The collected culture supernatants were treated by ultrafiltration using NucleoFast 96 (MACHERY-NAGEL). 100 µl of the culture supernatants were added to each well of NucleoFast 96 and centrifuged at 4500 g for 45 minutes to remove flow through. After addition of 100 µl of $H_2O$, the NucleoFast 96 was washed by centrifugation at 4500 g for 30 minutes. After addition of 100 µl of TBS, the NucleoFast 96 was allowed to stand for five minutes at room temperature. Then, phage suspensions were collected from the supernatants.

Purified phages, to which TBS was added, were subjected to ELISA by the following procedure. A StreptaWell 96 microtiter plate (Roche) was coated at room temperature for one hour with 100 µl of TBS containing biotin-labeled antigens (a mixture of equal amounts of 2'-adenosine-PEG-biotin, 5'-adenosine-PEG-biotin, and ATP-PEG-biotin). After antigens were removed from each well of the plate by washing with TBST (TBS containing 0.1% Tween20), the wells were blocked with 250 µl of 2% skim milk/TBS for one hour or more. 2% skim milk/TBS was removed, and then the prepared, purified phages were added to each well. The plate was allowed to stand at room temperature for one hour to allow the antibody-displaying phage to bind antigens in each well. After washing with TBST, a HRP-conjugated anti-M13 antibody (Amersham Pharmacia Biotech) diluted with TBS was added to each well. The plate was incubated for one hour. Following TBST wash, the TMB single solution (ZYMED) was added to each well. The chromogenic reaction in the solution of each well was terminated by adding sulfuric acid. Then, the developed color was assessed by measuring absorbance at 450 nm.

From the 192 clones subjected to phage ELISA, 106 clones that have the ability to bind to any one or two, or all three of 2'-Adenosine-PEG-biotin, 5'-Adenosine-PEG-biotin, and ATP-PEG-biotin were obtained.

Next, for the purpose of confirming to which antigen of 2'-adenosine-PEG-biotin, 5'-adenosine-PEG-biotin, and ATP-PEG-biotin these clones have binding ability, the purified phages diluted with TBS were subjected to ELISA by the following procedure. A StreptaWell 96 microtiter plate (Roche) was coated at room temperature for one hour with 100 µl of TBS containing a biotin-labeled antigen (2'-adenosine-PEG-biotin, 5'-adenosine-PEG-biotin, or ATP-PEG-biotin). After the antigens were removed by washing each well of the plate with TBST, the wells were blocked with 250 µl of 2% skim milk/TBS for one hour or more. 2% skim milk/TBS was removed, and then the prepared, purified phages were added to each well. The plate was allowed to stand at room temperature for one hour to allow binding of antibody-displaying phages to antigens in each well. After TBST wash, a HRP-conjugated anti-M13 antibody (Amersham Pharmacia Biotech) diluted with TBS was added to each well. The plate was incubated for one hour. Following TBST wash, the TMB single solution (ZYMED) was added to each well. The chromogenic reaction in the solution of each well was terminated by adding sulfuric acid. Then, the developed color was assessed by measuring absorbance at 450 nm. The result of phage ELISA is shown in Table 45 below.

TABLE 45

| Enrichment indicator | | Antigen binding ability (S/N ratio > 1.5) |
|---|---|---|
| Number of panning rounds | | 4 |
| Number of clones subjected to ELISA | | 192 |
| Number of ELISA-positive clones | Combination of 2'-Adenosine-PEG-biotin, 5'-Adenosine-PEG-biotin, ATP-PEG-biotin | 106 |
| | 2'-Adenos me-PEG-blot in | 0 |
| | 5'-Adenosine-PEG-b iot in | 6 |
| | ATP-PEG-biotin | 76 |
| | Bind to two or more of 2'-Adenosine-PEG-biotin, 5'-Adenosine-PEG-biotin, and ATP-PEG-biotin | 1 |

Among the clones subjected to phage ELISA, a clone was demonstrated to bind to two or more types of antigens. The nucleotide sequence of the gene was analyzed using the antibody fragment as a template. This clone had the ability to bind to both 5'-Adenosine-PEG-biotin and ATP-PEG-biotin, and was named ATNLSA1-4_D12. The heavy-chain variable region sequence of antibody ATNLSA1-4_D12 is shown in SEQ ID NO: 48, and its light-chain variable region sequence is shown in SEQ ID NO: 49.

(1-4) Assessment of Adenosine- and ATP-Binding Activity by Competitive Phage ELISA Based on the structures of 5'-Adenosine-PEG-biotin and ATP-PEG-biotin, there remained the possibility that clone ATNLSA1-4_D12 (heavy chain variable region, SEQ ID NO: 48; light chain, SEQ ID NO: 49), which was demonstrated by the result of phage ELISA to have the ability to bind to both 5'-Adenosine-PEG-biotin and ATP-PEG-biotin, recognizes the biotin tag or PEG moiety. Thus, to demonstrate that ATNLSA1-4_D12 is not an antibody that recognizes the biotin tag or PEG, whether the antigen binding is inhibited by adenosine or ATP was tested by phage ELISA using ATNLSA1-4_D12, and hIL-6R-binding clone PF1 (heavy chain, SEQ ID NO: 50; light chain, SEQ ID NO: 51) prepared as a negative control. ATNLSA1-4_D12 and PF1 were each diluted with TBS and subjected to ELISA by the following procedure.

A StreptaWell 96 microtiter plate (Roche) was coated at room temperature for one hour with 100 µl of TBS containing biotin-labeled antigens (a mixture of 5'-adenosine-PEG-biotin and ATP-PEG-biotin). After the antigens were removed by washing each well of the plate with TBST, the wells were blocked with 250 µl of 2% skim milk/TBS for one hour or more. 2% skim milk/TBS was removed, and then the prepared, purified phages were added to each well. The plate was allowed to stand at room temperature for one hour to allow binding of the antibody-displaying phages to the antigens in each well. Then, TBS that does not contain antigen or that contains serial dilutions of ATP from an equal amount up to 10000 times that of the antigen was added to the wells. For the competition of the immobilized antigen with ATP, the plate was allowed to stand at room temperature for one hour. Then, after TBST wash, an HRP-conjugated anti-M13 antibody (Amersham Pharmacia Biotech) diluted with TBS was added to each well. The plate was incubated for one hour. Following TBST wash, the TMB single solution (ZYMED) was added to each well. The chromogenic reaction in the solution of each well was terminated by adding sulfuric acid. Then, the developed color was assessed by measuring absorbance at 450 nm.

The measurement result is shown in FIG. 42. It was demonstrated that the higher the ATP concentration, the smaller the degree of color development for ATNLSA1-4_D12 in the presence of an excess amount of ATP. Thus, the binding between ATNLSA1-4_D12 and its antigen was demonstrated to be inhibited in an ATP concentration-dependent manner. Meanwhile, in a control experiment with PF1 as a negative control, its antigen binding was not detected regardless of the ATP concentration. The above finding demonstrates that ATNLSA1-4_D12 is an antibody that has the ability to bind to ATP but does not recognize the biotin tag or PEG.

(1-5) Expression and Purification of Antibodies that Bind to ATP and Adenosine

The gene encoding the variable region of ATNLSA1-4_D12 was inserted into an animal expression plasmid for human IgG1/Lambda. The antibody was expressed using the method described below. Cells of human fetal kidney cell-derived FreeStyle 293-F (Invitrogen) were suspended at a cell density of $1.33 \times 10^6$ cells/ml in FreeStyle 293 Expression Medium (Invitrogen) and aliquoted at 3 ml into each well of a 6-well plate. The constructed plasmid was introduced into the cells by lipofection. After four days of culture in a CO2 incubator (37° C., 8% CO2, 90 rpm), the antibody was purified from the culture supernatants by a method known to those skilled in the art using rProtein A Sepharose™ Fast Flow (Amersham Biosciences). Absorbance of the purified antibody solutions was measured at 280 nm using a spectrophotometer. From the values obtained by the measurement, the concentration of the purified antibody was calculated using an extinction coefficient determined by the PACE method (Protein Science (1995) 4, 2411-2423).

(1-6) Assessment of the ATP- and Adenosine-Binding Antibody for its ATP and Adenosine Binding by Surface Plasmon Resonance Biacore T200 (GE Healthcare) was used to analyze the interaction of D12, in which the constant region of IgG is linked to the variable region of clone ATNLSA1-4_D12 with ATP- and adenosine-binding activity, in antigen-antibody reaction. Sensor chip CM5 or CM4 (GE Healthcare) was immobilized with an appropriate amount of protein A (Life technologies) by amine coupling. The antibody of interest was captured by the chip to allow interaction with ATP (Wako), adenosine (Wako), or ADP (adenosine diphosphate) (Wako) as an antigen. The running buffer used was 50 mM Tris-HCl (Takara, T903), 500 mM NaCl, 0.01% (w/v) Tween20. The antigen was allowed to interact for 30 seconds at a flow rate of 30 µl/min, and was dissociated for 30 seconds. The interaction with the antigen was assessed at 15° C. The antigen was diluted using the same running buffer.

The dissociation constant $K_D$ (M) was calculated based on the association rate constant ka (1/Ms) and dissociation rate constant kd (1/s), both of which are kinetic parameters calculated from the sensorgram obtained by the measurement. Alternatively, the dissociation constant $K_D$ (M) was calculated using steady state analysis. Each parameter was calculated using the Biacore T200 Evaluation Software (GE Healthcare).

To calculate the $K_D$ for adenosine, the binding response was assessed at various concentrations of adenosine in the presence or absence of 20 µmol/l ADP. In addition, the binding response was separately assessed in the presence of 20 µmol/l ADP. The response (R) for specific adenosine binding was obtained by subtracting the value of binding response in the presence of ADP alone from the binding response to various concentrations of adenosine in the presence of ADP, and then subtracting the resultant value, which is assumed to correspond to the non-specific binding components, from the value of binding response to adenosine in the absence of ADP. From a curve in which adenosine concentration is plotted on the X axis and R calculated according to Formula 2 is plotted on the Y axis, the value of $K_D$ for adenosine was determined by the least squares method using the Solver function of Office Excel 2007 (Microsoft).

$$R = R\text{max} \times \text{conc}/(K_D + \text{conc}) \qquad \text{(Formula 2)}$$

In Formula 2, conc represents adenosine concentration (mol/l) while Rmax represents the value of response expected for the maximal binding of adenosine to antibody. Measured response values were extracted by using Scrubber2 (BioLogics. Inc).

The KD of D12 determined by the measurement described above was 8.5 µmol/l for ATP, 0.25 µmol/l for ADP, or 1100 µmol/l for adenosine. This result demonstrates that D12 has binding activity to ATP, ADP, and adenosine; and it also suggests that D12 has binding activity to AMP (adenosine monophosphate) and cAMP (cyclic adenosine monophosphate).

[Reference Example 2] Design of Library Using Anti-ATP/Adenosine Antibodies to Prepare ATP/Adenosine Switch Antibodies In cancer tissues and inflamed tissues, not only the adenosine but also the ATP concentration is known to be high. Thus, it is beneficial to use antibodies for which both adenosine and ATP (referred to as ATP/adenosine in this Example) can serve as a switch (specifically, antibodies that can bind to antigens when adenosine or ATP is present at a high concentration) as well as antibodies for which either adenosine or ATP alone serves as a switch. ATNLSA1-4_D12 described in Reference Example 1-4 is an antibody that binds to ATP/adenosine. As shown in FIG. 43, ATP/adenosine is thought to be fit between the antibody and its target antigen, and thus the antibody comprises an antibody variable region that comes in contact with the target antigen. Thus, the present inventors conceived that synthetic antibody libraries that can isolate ATP/adenosine switch antibodies whose binding activity to arbitrary antigens is altered depending on the presence of ATP/adenosine could be constructed by collecting, as a library, antibody variable region segments that are capable of establishing contact with a target antigen and maintaining ATP/adenosine binding.

The crystal structure of the complex of ATP and ATP/adenosine antibody ATNLSA1-4_D12 obtained from a human antibody library as described in Reference Example 1-4 was analyzed. The result of crystal structure analysis revealed the mode of adenosine (or ATP) recognition by the antibody as well as identification of amino acid residues that are considered not to be substantially involved in adenosine (or ATP) binding in the antibody variable region. Amino acid residues that have been identified to be closely involved in the adenosine (ATP) binding are Ser52, Ser52a, Arg53, Gly96, Leu100a, and Trp100c (Kabat numbering) in the heavy chain.

In designing such a library, sites that meet at least one of the conditions described below were selected as suitable for the library construction.

Condition 1: sites that are not greatly involved in ATP binding, or if involved in the binding, a position having an amino acid other than the wild-type sequence that does not inhibit the ATP binding;

Condition 2: sites having a certain level of diversity of amino acid occurrence frequency as repertoire of human antibodies; and Condition 3: sites that are not essential for the formation of canonical structure.

In regions contained in both heavy chain and light chain of the ATNLSA1-4_D12 sequence and that meet the conditions described above, amino acids in the CDR1 and CDR2 regions that have an occurrence frequency of 2% or more in the germ line, as well as amino acids in the CDR3 region that have an occurrence frequency of 1% or more in the germ line were comprehensively substituted. These substitutions were combined to construct multiple variants of ATNLSA1-4_D12.

Alteration sites in the heavy chain (in the Table, positions indicated by "Kabat" according to Kabat numbering), as well as amino acids before alteration (in the table, amino acids referred to as "natural sequence") at the sites and amino acids after alteration (in the table, amino acids referred to as "altered amino acids") are shown in Table 46.

Alteration sites in the light chain (in the Table, positions indicated by "Kabat" according to Kabat numbering), as well as amino acids before alteration (in the table, amino acids referred to as "natural sequence") at the sites and amino acids after alteration (in the table, amino acids referred to as "altered amino acids") are shown in Table 47.

TABLE 46

| | | HCDR1 | | | HCDR2 | | | HCDR3 | | | | |
| --- | --- | --- | --- | --- | --- | --- | --- | --- | --- | --- | --- | --- |
| | | | | | Kabat | | | | | | | |
| | | 31 | 32 | 35 | 55 | 57 | 58 | 96 | 97 | 99 | 100 | 100a |
| | | | | | Native sequence | | | | | | | |
| | | T | Y | N | N | I | N | G | R | G | D | L |
| Altered amino acid | A | | A | | A | A | | A | A | A | A | A |
| | C | | | | | | | | | | | |
| | E | | | | | E | | | | | | |
| | D | D | | | | D | | D | D | D | D | |
| | G | G | | | | G | G | | | | | |
| | F | | F | | | | F | | | | | F |
| | I | | | | | | | | | | | I |
| | H | | H | H | | | H | | | | | |
| | K | | | | | K | | | | K | K | K |
| | M | | | | | | | | | | | M |
| | L | | | | | L | | | | | | |
| | N | N | N | | | | | | N | N | N | N |
| | Q | | | | | | | | | | | |
| | P | | | | | | | | | | | |
| | S | S | S | S | S | | S | S | S | S | S | |
| | R | R | | | R | R | | | | | | R |
| | T | | | | T | T | T | T | | | | |
| | W | | | | | | | | | | | W |
| | V | | | | | | | | V | V | V | V |
| | Y | | Y | | | Y | | | Y | Y | Y | Y |

TABLE 47

| | | LCDR1 | | | | | | | | | LCDR2 | | | | | | LCDR3 | | | | | | | | |
| --- | --- | --- | --- | --- | --- | --- | --- | --- | --- | --- | --- | --- | --- | --- | --- | --- | --- | --- | --- | --- | --- | --- | --- | --- |
| | | | | | | | | | | | Kabat | | | | | | | | | | | | | |
| | | 26 | 27 | 27a | 27b | 27c | 28 | 29 | 31 | 32 | 50 | 51 | 52 | 53 | 54 | 55 | 89 | 90 | 91 | 92 | 93 | 94 | 95a | 96 | 97 |
| | | | | | | | | | | | Native sequence | | | | | | | | | | | | | |
| | | T | S | S | D | V | G | G | N | Y | E | V | S | K | R | P | S | S | Y | A | G | S | N | V | V |
| Altered amino acid | A | A | | | | | | | A | A | | | A | | | | A | A | A | | A | A | A | A | A |
| | C | | | | | | | | | | | | | | | | | | | | | | | | |
| | E | | | | | | | E | | | E | | | | | | | E | | | E | | | | |
| | D | | | | D | D | D | D | D | D | D | | | D | | | | | D | D | D | D | D | | |
| | G | | | G | | | | | | | | | G | G | | | G | | | | | G | G | G | G |
| | F | | | | | | F | | | | | | F | | F | | | | F | | | | | F | |
| | I | | | | | I | | | | | | | | | | | | I | I | I | | | | | I |
| | H | | | | | | | | | | | | H | | | | | H | | | | H | H | | |
| | K | | | | | | | | K | K | K | | | K | | | K | | | | | K | K | | |
| | M | | | | | | | | | | | | | | | | | | | | | | | | M |
| | L | | | | | | | | | | | | | L | L | L | | | | | | L | L | L |
| | N | | N | N | | | | | N | N | N | N | | | | | N | | N | | N | N | | N | |
| | Q | | | | | | | | | | Q | | | Q | | | Q | | | | | Q | Q | | |
| | P | | | | | | | | | | | | | | | | | | | | | | P | P | |
| | S | S | | | | | | | S | S | S | | S | | | | S | S | S | | | S | S | S | S |
| | R | | | | | | | | | R | R | | | R | | | | R | R | R | R | | | | |
| | T | | T | T | | | | | T | | T | | T | T | | | T | T | T | T | T | T | T | T | T |
| | W | | | | | | | | | | | | | | | | | W | | | | | | W | |
| | V | | | | | | | | | | | V | V | V | V | | | | | | | | | | |
| | Y | | | | | | | Y | | Y | | | | Y | | | Y | | Y | Y | | | Y | Y | Y |

Each variant expressed and purified by the method described in Reference Example 1-1 was assayed for its ATP and adenosine binding by the same method as described in Reference Example 1-6 using Biacore. Based on the assay result, the affinity of each variant for ATP was calculated as a $K_D$ value. Sites in the heavy chain, where alteration does not reduce the ATP-binding ability to less than 1/5 of the binding ability of ATNLSA1-4_D12 (specifically, where the $K_D$ value is lower than 42.5 μmol/l), and sites in the light chain where the ATP-binding ability is larger than that of ATNLSA1-4_D12 (specifically, where the $K_D$ value is smaller than 8.5 μmol/l), were assessed to be plausible for alteration. Amino acids substituted at those sites were judged to be appropriate for inclusion in the library (flexible residues to be introduced into library).

Based on the assessment result on the ATP-binding ability of each variant, the ATP-binding ability was predicted to be reduced by collecting each site to construct a library. Thus, substitutions were introduced at sites close to positions that are expected to be involved in ATP binding, and various variants resulting from combination of these substitutions were comprehensively assessed to test whether it is possible to identify alterations which are expected to have effect of augmenting the ATP-binding ability. Such alteration sites (positions indicated by "Kabat" according to Kabat numbering in the Table), and amino acids before alteration (amino acids referred to as "wild type sequence" in the table) and amino acids after alteration (amino acids referred to as "altered amino acids" in the table) at the sites are shown in Table 48.

TABLE 48

| | | HCDR1 | HCDR2 | | HCDR3 | | | LCDR3 |
|---|---|---|---|---|---|---|---|---|
| | | | | | Kabat | | | |
| | | 33 | 50 | 56 | 95 | 98 | 100b | 95 |
| | | | | Native sequence | | | | |
| | | T | S | Y | F | K | N | N |
| Altered amino acid | A C E D G F I H K M | A E D G F I H K M | A E D G F I H K M | A E D G F I H K M | A I K M | A E D G F I H M | A E D G F I H K M | A E D G F I H K M |

TABLE 48-continued

| HCDR1 | HCDR2 | | HCDR3 | | | LCDR3 |
|---|---|---|---|---|---|---|
| | | | Kabat | | | |
| 33 | 50 | 56 | 95 | 98 | 100b | 95 |
| | | Native sequence | | | | |
| T | S | Y | F | K | N | N |
| L N Q P S R T W V Y | L N Q P S R W V Y | L N Q P S R T W V Y | L Q P S R W V | L N Q P S R T W V Y | L Q P S R T W V Y | L Q P S R T W V Y | L Q P S R T W V Y |

Each variant expressed and purified by the method described in Reference Example 1-1 was assayed for its ATP and adenosine binding by the same assay method using Biacore as described in Reference Example 1-6. The assay result showed that the ATP and adenosine binding was expected to be augmented by alterations at positions 56 and 100 and such according to Kabat numbering (for example, amino acid alteration such as Tyr56His and Asn100bLeu). It was determined that amino acids substituted at the sites could be included in a library (flexible residues to be introduced into a library).

In the CDR regions of ATNLSA1-4_D12, amino acid repertoires containing amino acids selected by the above-described variant analysis as suitable to be included in a library (flexible amino acid residues to be introduced into a library) and amino acids before alteration of the amino acids (specifically, amino acids included in the natural sequence of ATNLSA1-4_D12), and sites comprising such repertoires were designed to construct a library for preparation of ATP/adenosine switch antibodies. The library was constructed in such a manner that in an amino acid repertoire the amino acid occurrence frequency is the same for every amino acid (for example, when there are ten types of amino acids in an amino acid repertoire, each amino acid occurs at 10%).

Sites comprising amino acid repertoires in the heavy chain (positions indicated by "Kabat" according to Kabat numbering in the Table) and amino acid repertoires at the sites are shown in Table 49. Sites comprising amino acid repertoires in the light chain (positions indicated by "Kabat" according to Kabat numbering in the Table) and amino acid repertoires at the sites are shown in Table 50.

TABLE 49

| | | HCDR1 | | | HCDR2 | | | | | HCDR3 | | | | | |
|---|---|---|---|---|---|---|---|---|---|---|---|---|---|---|---|
| | | | | | | | | Kabat | | | | | | | |
| | | 31 | 32 | 35 | 55 | 56 | 57 | 58 | 59 | 95 | 97 | 98 | 99 | 100 | 100a | 100b |
| | | | | | | | | Native sequence | | | | | | | |
| | | T | Y | N | N | Y | I | N | Y | F | R | K | G | D | L | N |
| Altered amino acid | A | | | 17% | | 25% | | | | | 11% | | | 5% | | |
| | C | | | | | | | | | | | | 9% | 5% | | |
| | E | | | | | | | | | | | | 9% | 5% | | |
| | D | | | | | | 13% | | | | | | 9% | 5% | | |
| | G | 33% | | | 17% | | | 13% | | | 11% | | 9% | 5% | | |
| | F | | 33% | | | | | 13% | | 50% | | | 9% | 5% | | |
| | I | | | | | 25% | | | | | 11% | | | 5% | | |
| | H | | 33% | 50% | | 50% | | 13% | | | 11% | | 9% | 5% | 17% | |
| | K | | | | | | 25% | | | | 11% | 33% | 9% | 5% | | |
| | M | | | | | | | | | | 11% | | | 5% | 17% | |
| | L | | | | | | | | 50% | | 11% | 33% | | 5% | 17% | 50% |

TABLE 49-continued

| | | HCDR1 | | | HCDR2 (Kabat) | | | | | HCDR3 | | | | | |
|---|---|---|---|---|---|---|---|---|---|---|---|---|---|---|---|
| | | 31 | 32 | 35 | 55 | 56 | 57 | 58 | 59 | 95 | 97 | 98 | 99 | 100 | 100a | 100b |
| | | | | | | | | Native sequence | | | | | | | | |
| | | T | Y | N | N | Y | I | N | Y | F | R | K | G | D | L | N |
| | N | | | 50% | 17% | | | 13% | | | | | 9% | 5% | | 50% |
| | O | | | | | | | | | | | | 9% | 5% | | |
| | P | | | | | | | | | | | | | 5% | | |
| | S | 33% | | | 17% | | | 13% | | | | | | 5% | | |
| | R | | | | 17% | 25% | | 13% | | | 11% | 33% | 9% | 5% | 17% | |
| | T | 33% | | | 17% | | | 13% | | | | | | 5% | | |
| | W | | | | | | | | | | | | 9% | 5% | 17% | |
| | V | | | | | | | | | | 11% | | | 5% | | |
| | Y | | 33% | | | 50% | | 13% | 50% | 50% | | | 9% | 5% | 17% | |

TABLE 50

| | | LCDR1 | | LCDR2 | | | LCDR3 (Kabat) | | | | | | | | |
|---|---|---|---|---|---|---|---|---|---|---|---|---|---|---|---|
| | | 27a | 29 | 50 | 51 | 54 | 90 | 91 | 92 | 93 | 94 | 95 | 95a | 96 | 97 |
| | | | | | | | | Native sequence | | | | | | | |
| | | S | S | E | V | R | S | Y | A | G | S | N | N | V | V |
| Altered amino acid | A | | 17% | | | | | | 17% | 14% | 13% | 6% | | | 17% |
| | C | | | | | | | | | | | | | | |
| | E | | | 14% | | | | | 17% | | | 6% | | | |
| | D | | 17% | 14% | | | | | | 14% | 13% | 6% | 11% | | |
| | G | | 17% | 14% | 25% | | | | | 14% | 13% | 6% | 11% | | 17% |
| | F | | 17% | | | | | | | | | 6% | | | |
| | I | | | | | | | | | 14% | 13% | 6% | 11% | | |
| | H | | | | | | | | | | | 6% | 11% | | |
| | K | | 14% | | 50% | | | 14% | | | | 6% | | | |
| | M | | | | | | | | | | | 6% | | | 17% |
| | L | | | | | 25% | | | | | | 6% | 11% | 33% | 17% |
| | N | | | 25% | | | | 14% | | | 13% | 6% | 11% | | |
| | Q | | 14% | | | | | | | | | 6% | 11% | | |
| | P | | | | | | | | | | | 6% | | 33% | |
| | S | 50% | 17% | 14% | | | 25% | | 17% | 14% | 13% | 6% | 11% | | 17% |
| | R | | | | 50% | | 14% | 17% | | | 13% | 6% | | | |
| | T | 50% | 17% | 25% | | 25% | 14% | 17% | 14% | 13% | | 6% | | | |
| | W | | | | | | 14% | | | | | 6% | | | |
| | V | | | | 25% | 25% | 14% | | | | | | | 33% | 17% |
| | Y | | 14% | | | | | 14% | 17% | 14% | | 6% | 11% | | |

The result of sequence analysis suggests that the framework of ATNLSA1-4_D12 was derived from germ line VH3-21. Then, for the purpose of improving antibody stability, the framework sequence of ATNLSA1-4_D12 was restored to the germ line sequence VH3-21 by introducing into the framework sequence of ATNLSA1-4_D12, alterations Gln01Glu, Gln05Val, Asp10Gly, Asn30Ser, Leu48Val, and Asn58Tyr (numerals represent Kabat numbers). ATNLSA1-4_D12 variants expressed and purified by the method described in Reference Example 1-1 were measured for their Tm by DSC. DSC measurement was carried out by a method known to those skilled in the art. Tm of the variant which results from adding these alterations to ATNLSA1-4_D12 was markedly improved from 74.37° C. to 81.44° C., and stabilization of the structure was observed. It is sometimes preferable to use highly stable frameworks for antibody libraries, and thus a framework sequence to which alterations described above had been added was used as the framework sequence of a library. The framework used for the library is shown in Table 51.

TABLE 51

| Framework | SEQ ID NO: | Sequence |
|---|---|---|
| Heavy chain framework 1 | 52 | EVQLVESGGDLVKPGGGLRLSCAASGFTFS |
| Heavy chain framework 2 | 53 | WVRQAPGKGLEWVS |
| Heavy chain framework 3 | 54 | RFTISRDNAKNSLYLQMNSLRAEDTAVYYCAR |
| Heavy chain framework 4 | 55 | WGQGTLVTVSS |
| Light chain framework 1 | 56 | QSALTQPPSASGSPGQTVTISC |

TABLE 51-continued

| Framework | SEQ ID NO: | Sequence |
|---|---|---|
| Light chain framework 2 | 57 | WYQQHPGKAPKLMIY |
| Light chain framework 3 | 58 | GVPDRFSGSKSGNTASLTVSGLQAEDEADYFC |
| Light chain framework 4 | 59 | FGGGTKLTVL |

Genes were synthesized to comprise respective sequences in a library designed as described above (DNA2.0), and the gene library was amplified with primers that are capable of amplifying VH and VL respectively, by using a collection (library) of the respective genes as a template. The sequences of primers used for VL amplification are shown in SEQ ID NOs: 81 and 82, while the sequences of primers used for VH amplification are shown in SEQ ID NOs: 83 and 84. The amplified rationally designed gene library of the heavy-chain and light-chain variable regions of human antibody was inserted into an appropriate phagemid vector carrying both a human IgG-derived CH1 sequence and a human IgG-derived light chain constant region sequence. The phagemid vector was introduced into E. coli by electroporation to construct a rationally designed library which presents Fab domains containing a human antibody variable region-constant region, and from which one can isolate antibodies that are capable of binding to antigens via adenosine or ATP as a switch. Such a rationally designed library which is constituted with various H chains and L chains that have adenosine- or ATP-binding activity is expected to be useful as a library containing human antibodies that, with the adenosine (or ATP) is fit in between antibody and antigen as shown in FIG. 43, can efficiently obtain adenosine/ATP switch antibodies against any arbitrary antigen. Furthermore, as described above, since ATNLSA1-4_D12 binds not only to adenosine and ATP but also to ADP, it was predicted to have binding activity to AMP and cAMP which are structurally similar to ATP, ADP, and adenosine. This suggests that such libraries are useful for isolating switch antibodies whose binding activity to arbitrary target antigens is altered depending on the presence of any one or more small molecules of ATP, ADP, AMP, cAMP, and adenosine.

[Reference Example 3] Acquisition of Antibodies that Bind to Antigens in the Presence of Adenosine and ATP from Antibody Library Using Phage Display Techniques (3-1) Acquisition of Antibodies that Bind to Antigens in the Presence of Small Molecules Using a Mixture of Adenosine and ATP from Library Antibodies that exhibit antigen-binding activity in the presence of adenosine and/or ATP were obtained from the constructed phage-display library of rationally designed antibodies. To obtain antibodies, phages displaying antibodies that exhibit the ability to bind to antigens captured by beads in the presence of adenosine and ATP were collected, and then the phages were collected in eluate from the beads in the absence of adenosine and ATP.

Phages were produced in E. coli containing the phagemid vector constructed for phage display. To the culture medium of E. coli in which phage production was carried out, 2.5 M NaCl/10% PEG was added to precipitate phages. The precipitated phage fraction was diluted with TBS to prepare a library suspension. Then, BSA was added at a final concentration of 4% to the phage library suspension. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin). Biotinylated human IL-6 receptor was used as an antigen.

500 pmol of biotin-labeled antigen and a final concentration of 1 mM ATP-Na and adenosine were each added to the prepared phage library suspension. The phage library suspension was contacted with the antigen, adenosine, and ATP at room temperature for 60 minutes. The BSA-blocked magnetic beads were added to the phage library suspension, and the antigen-phage complex was allowed to bind to the magnetic beads at room temperature for 15 minutes. The beads were washed once with ATP- and adenosine-dissolved TBS. Then, the beads were combined with 0.5 ml of 1 mg/ml trypsin. Immediately after the beads were suspended at room temperature for 15 minutes, a phage suspension was collected from the beads that were separated using a magnetic stand. The collected phage suspension was added to 10 ml of E. coli cells of strain ER2738 at the logarithmic growth phase (OD600=0.4 to 0.7). The E. coli was incubated at 37° C. with gentle stirring for one hour to be infected by phage. The infected E. coli was seeded in a 225 mm×225 mm plate. Then, phages were collected from the culture medium of the seeded E. coli to prepare a liquid stock of phage library.

The first round of panning was carried out to collect phages that are capable of antigen binding in the presence of adenosine and ATP, while the second and subsequent rounds of panning were performed to enrich phages that are capable of antigen binding only in the presence of adenosine and ATP. Specifically, 40 pmol of biotin-labeled antigen and a final concentration of 1 mM adenosine and ATP were each added to the prepared phage library suspension. Thus, the phage library was contacted with antigen, adenosine, and ATP for 60 minutes at room temperature. BSA-blocked magnetic beads were added, and the antigen-phage complex was allowed to bind to the magnetic beads for 15 minutes at room temperature. The beads were washed with 1 ml of adenosine and ATP-dissolved TBST (hereinafter referred to as (adenosine+ATP)/TBST), adenosine, and adenosine and ATP-dissolved TBS (hereinafter referred to as (adenosine+ATP)/TBS). Then, the beads were combined with 0.5 ml of TBS. Immediately after the beads were suspended at room temperature, a phage suspension was collected from the beads separated using a magnetic stand. After this treatment was repeated, the two separately eluted phage suspensions were combined together. The pIII protein (helper phage-derived protein pIII) that does not display Fab was cleaved off from phages by adding 5 µl of 100 mg/ml trypsin to the collected phage suspension to eliminate the ability of phages that do not display Fab to infect E. coli. The phages collected from the trypsinized phage suspension were added to 10 ml of E. coli cells of strain ER2738 at the logarithmic growth phase (OD600=0.4 to 0.7). The *E. coli* was incubated at 37° C. with gentle stirring for one hour to be infected by phage. The infected *E. coli* was seeded in a 225 mm×225 mm plate. Then, phages were collected from the culture medium of the seeded *E. coli* to prepare a phage library suspension. Panning was performed three times to isolate antibodies that have antigen-binding activity in the presence of adenosine and ATP.

(3-2) Acquisition of Antibodies that Bind to Antigens in the Presence of Adenosine and ATP Using a Negative Selection Method from Antibody Library A phage-display library of rationally designed antibodies was screened for antibodies that exhibit antigen-binding activity in the presence of adenosine and/or ATP. As a first step of screening, the phage-display antibody library was contacted with biotin-labeled antigen-streptavidin in the absence of adenosine and ATP to eliminate phages displaying antibodies that have antigen-binding activity even in the absence of adenosine and ATP. Then, panning was performed in the same manner in the presence of adenosine and ATP to screen for antibodies that exhibit antigen-binding activity in the presence of adenosine and ATP.

Phages were produced in *E. coli* containing the constructed phage-display phagemid. To the culture medium of *E. coli* in which phage production took place, 2.5 M NaCl/10% PEG was added to precipitate phages. The precipitated phage fraction was diluted with TBS to prepare a library suspension. Then, BSA was added at a final concentration of 4% to the phage library suspension. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin).

Together with 250 pmol of biotin-labeled antigen, a mixture of adenosine and ATP was added at a final concentration of 1 mM to the prepared phage library suspension. Thus, the phage library suspension was contacted with the antigen, adenosine, and ATP for 60 minutes at room temperature. Then, BSA-blocked magnetic beads were added to the phage library suspension, and allowed to bind to the antigen-phage complex at room temperature for 15 minutes. The beads were washed once with (adenosine+ATP)/TBS. Then, the beads were combined with 0.5 ml of 1 mg/ml trypsin solution. Immediately after the beads were suspended at room temperature for 15 minutes, a phage suspension was collected from the beads that were separated using a magnetic stand. The collected phage suspension was added to 10 ml of *E. coli* cells of strain ER2738 at the logarithmic growth phase (OD600=0.4 to 0.7). The *E. coli* was incubated at 37° C. with gentle stirring for one hour to be infected by phage. The infected *E. coli* was seeded in a 225 mm×225 mm plate. Next, M13KO7 Helper Phage (Takara Bio Inc.) or M13 KO7ΔpIII (called Hyperphage; PROGEN Biotechnik GmbH) was added to the culture solution of the seeded *E. coli* for infection, and after an overnight culture at 30° C., phages were collected from the supernatant to prepare a phage library suspension displaying monovalent antibodies and a phage library suspension displaying multivalent antibodies.

The first round of panning was carried out to collect phages that are capable of binding in the presence of adenosine and ATP, while the second and subsequent rounds of panning were performed to enrich phages that are capable of antigen binding only in the presence of adenosine and ATP. Specifically, 250 pmol of biotinylated antigen was added to BSA-blocked Sera-Mag NeutrAvidin beads, and allowed to bind at room temperature for 15 minutes. The beads were washed three times with TBS. The phage library suspension subjected to BSA blocking was added to the washed beads, and allowed to bind at room temperature for one hour. Phages that did not bind to the antigens or beads were collected by isolating the beads using a magnetic stand. Forty pmol of biotin-labeled antigen, and a final concentration of 1 mM adenosine and ATP were each added to the collected phages. Thus, the phage library was contacted with the antigen, adenosine, and ATP for 60 minutes at room temperature. Then, BSA-blocked magnetic beads were added to the mixture of the labeled antigen, adenosine, ATP, and phage library, and allowed to bind to the antigen-phage complex for 15 minutes at room temperature. The beads were washed with 1 ml of (adenosine+ATP)/TBST and (adenosine+ATP)/TBS. Then, 0.5 ml of 1 mg/ml trypsin solution was added to the mixture. After the mixed suspension was stirred at room temperature for 20 minutes, phages were collected from the beads that had been separated using a magnetic stand. The collected phages were added to 10 ml of *E. coli* cells of strain ER2738 at the logarithmic growth phase (OD600=0.4 to 0.7). The *E. coli* was incubated at 37° C. with gentle stirring for one hour to be infected by phage. The infected *E. coli* was seeded in a 225 mm×225 mm plate. Panning was performed three times to isolate antibodies that have antigen-binding activity in the presence of adenosine and ATP.

(3-3) Assessment of Binding Activity in the Presence or Absence of Adenosine and/or ATP by Phage ELISA Phage-containing culture supernatants were collected according to a conventional method (Methods Mol. Biol. (2002) 178, 133-145) from single colonies of *E. coli* obtained by the method described above. The collected culture supernatants were treated by ultrafiltration using NucleoFast 96 (MACHERY-NAGEL). 100 μl of the culture supernatants were added to each well of NucleoFast 96, and it was centrifuged (4500 g for 45 minutes) to remove flow through. After addition of 100 μl of $H_2O$, the NucleoFast 96 was washed by centrifugation (4500 g for 30 minutes). Finally, 100 μl of TBS was added, and the NucleoFast 96 was allowed to stand for five minutes at room temperature. A phage suspension was collected from the supernatant in each well of the NucleoFast 96.

The purified phages, to which TBS or (adenosine+ATP)/TBS was added, were subjected to ELISA by the following procedure. A StreptaWell 96 microtiter plate (Roche) was coated overnight with 100 μl of TBS containing biotin-labeled antigen. After the antigen was removed by washing each well of the plate with TBST, the wells were blocked with 250 μl of 2% skim milk/TBS for one hour or more. 2% skim milk/TBS was removed, and then the prepared, purified phages were added to each well. The plate was allowed to stand at 37° C. for one hour to allow binding of antibody-displaying phages to the antigen in each well in the presence or absence of adenosine and/or ATP. After washing with TBST or (adenosine+ATP)/TBST, HRP-conjugated anti-M13 antibody (Amersham Pharmacia Biotech) diluted with TBS or (adenosine+ATP)/TBS was added to each well. The plate was incubated for one hour. Following washes with TBST or (adenosine+ATP)/TBST, the TMB single solution (ZYMED) was added to each well. The chromogenic reaction in the solution of each well was terminated by adding sulfuric acid. Then, the developed color was assessed by measuring absorbance at 450 nm. The result revealed multiple types of antibodies that bind human IL-6 receptors in the presence of ATP or adenosine. The result of phage ELISA is shown in Table 52.

TABLE 52

| Number of panning rounds | 3 | 4 |
|---|---|---|
| Number of clones subjected to ELISA | 96 | 96 |
| Number of positive clones (S/N ratio > 10) | 23 | 64 |
| Number of switch clones (SM +/− ratio > 2) | 22 | 64 |
| Number of switch clone sequences | 17 | 35 |

(3-4) Sequence Analysis of Switch Antibodies Whose Antigen-Binding Activity Varies Depending on the Presence or Absence of Adenosine and ATP Using specific primers (SEQ ID NOs: 79 and 80), genes were amplified from clones judged to have antigen-binding activity under the condition where adenosine or ATP is present based on the phage ELISA results described in Reference Example (3-3). The nucleotide sequences were analyzed, and based on the result, following clones were obtained and judged to have binding activity to biotin-labeled hIL-6R in the presence of adenosine or ATP: 6RAD2C1-4_001, 6RAD2C1-4_005, 6RAD2C1-4_011, 6RAD2C1-4_026, 6RAD2C1-4_030, 6RAD2C1-4_042, 6RAD2C1-4_076, 6RDL3C1-4_085, and 6RDL3C5-4_011 (Table 53).

TABLE 53

| Clone name | Heavy chain SEQ ID NO | Light chain SEQ ID NO |
|---|---|---|
| 6RAD2C1-4_001 | SEQ ID NO: 60 | SEQ ID NO: 61 |
| 6RAD2C1-4_005 | SEQ ID NO: 62 | SEQ ID NO: 63 |
| 6RAD2C1-4_011 | SEQ ID NO: 64 | SEQ ID NO: 65 |
| 6RAD2C1-4_026 | SEQ ID NO: 66 | SEQ ID NO: 67 |
| 6RAD2C1-4_030 | SEQ ID NO: 68 | SEQ ID NO: 69 |
| 6RAD2C1-4_042 | SEQ ID NO: 70 | SEQ ID NO: 71 |
| 6RAD2C1-4_076 | SEQ ID NO: 72 | SEQ ID NO: 73 |
| 6RDL3C1-4_085 | SEQ ID NO: 74 | SEQ ID NO: 75 |
| 6RDL3C5-4_011 | SEQ ID NO: 76 | SEQ ID NO: 77 |

[Reference Example 4] Acquisition of Antibodies that Bind to Antigens in the Absence of Adenosine or ATP from Antibody Library Using Phage-Display Techniques (4-1) Acquisition of Antibodies Whose Antigen Binding is Inhibited in the Presence of Small Molecules Using a Mixture of Adenosine and ATP from a Library Antibodies that bind to target antigens in the presence of small molecules serving as a switch were obtained as described in Reference Example 3 above. In this Reference example, the present inventors attempted to obtain antibodies that bind to target antigens in the absence of small molecules.

Antibodies that exhibit antigen-binding activity in the absence of adenosine and/or ATP but whose binding ability is impaired in the presence of adenosine and/or ATP were obtained from a phage-display library of rationally designed antibodies constructed in Reference Example 2. As a first step to isolate antibodies, a phage-display library of antibodies was contacted with biotinylated adenosine and biotinylated ATP to collect a phage-display library of antibodies that bind to adenosine and/or ATP. Then, the phage-display antibody library was contacted with biotinylated antigen-streptavidin in the absence of adenosine and ATP to collect antibodies that bind to antigens in the absence of adenosine and ATP. Panning was performed in the alternating manner described above to screen for antibodies that have binding activity to both antigen and adenosine and/or ATP. In the presence of adenosine and ATP, the antigen binding of antibodies with such properties was expected to be inhibited by binding of adenosine and/or ATP to the antibodies.

Phages were produced in *E. coli* containing the phagemid vector constructed in Reference Example 2 for phage display. To the culture medium of *E. coli* in which phage production was carried out, 2.5 M NaCl/10% PEG was added to precipitate phages. The precipitated phage fraction was diluted with TBS to prepare a phage library suspension. Then, BSA was added at a final concentration of 4% to the phage library suspension. Panning was performed using antigen-immobilized magnetic beads. The magnetic beads used were NeutrAvidin-coated beads (Sera-Mag Speed-Beads NeutrAvidin-coated) and Streptavidin-coated beads (Dynabeads M-280 Streptavidin).

500 pmol of biotinylated ATP, 2'-adenosine-PEG-Biotin, and 5'-adenosine-PEG-Biotin were added to the prepared phage library suspension. Thus, the phage library suspension was contacted with adenosine and ATP for 60 minutes at room temperature. Then, BSA-blocked magnetic beads were added to the phage library suspension and the complex of phage with adenosine and/or ATP was allowed to bind to the magnetic beads at room temperature for 15 minutes. The beads were washed once with TBS, and then 0.5 ml of a 1 mg/ml trypsin solution was added to the beads. Immediately after the beads were suspended at room temperature for 15 minutes, a phage suspension was collected from the beads that were separated using a magnetic stand. The collected phage suspension was added to 10 ml of *E. coli* cells of strain ER2738 at the logarithmic growth phase (OD600=0.4 to 0.7). The *E. coli* was incubated with gentle stirring at 37° C. for one hour to be infected by phage. The infected *E. coli* was seeded in a 225 mm×225 mm plate. Then, phages were collected from the culture medium of the seeded *E. coli* to prepare a phage library suspension.

The second round of panning was performed to enrich phages capable of binding to the biotinylated antigen in the absence of adenosine and ATP. Specifically, 250 pmol of biotinylated antigen was added to the prepared phage library suspension. Thus, the phage library suspension was contacted with the antigen for 60 minutes at room temperature. Then, BSA-blocked magnetic beads were added to the phage library suspension, and the antigen-phage complex was allowed to bind to the magnetic beads at room temperature for 15 minutes. The beads were washed twice with TBST and once with TBS. Then, 0.5 ml of a 1 mg/ml trypsin solution was added to the beads. Immediately after the beads were suspended at room temperature for 15 minutes, a phage suspension was collected from the beads that were separated using a magnetic stand. The collected phage suspension was added to 10 ml of *E. coli* cells of strain ER2738 at the logarithmic growth phase (OD600=0.4 to 0.7). The *E. coli* was incubated with gentle stirring at 37° C. for one hour to be infected by phage. The infected *E. coli* was seeded in a 225 mm×225 mm plate. Then, phages were collected from the culture medium of the seeded *E. coli* to prepare a phage library suspension.

At subsequent odd-numbered rounds, panning was performed in the same manner as the first-round panning. However, the number of bead washes with TBST and TBS was increased to three times and twice, respectively.

At subsequent even-numbered rounds, panning was performed in the same manner as the second-round panning. However, in the fourth and subsequent rounds of panning, the biotinylated antigen was reduced to 40 pmol, and the number of bead washes with TBST and TBS was increased to three times and twice, respectively.

(4-2) Assessment of Binding Activity in the Presence of Small Molecules by Phage ELISA Culture supernatants containing phages were collected according to a conventional method (Methods Mol. Biol. (2002) 178, 133-145) from single colonies of *E. coli* obtained by the method described above. The collected culture supernatants were ultrafiltrated using NucleoFast 96 (MACHEREY-NAGEL). 100 µl of the culture supernatants were added to each well, and the NucleoFast 96 was centrifuged (4500 g for 45 minutes) to remove flow-through. 100 µl of H$_2$O was added to each well, and again the NucleoFast 96 was washed by centrifugation (4500 g for 30 minutes). After 100 µl of TBS was added, the NucleoFast 96 was allowed to stand at room temperature for five minutes. Finally, a phage suspension was collected from the supernatant in each well.

Purified phages, to which TBS, or ATP and adenosine/TBS had been added, were subjected to ELISA by the following procedure. A StreptaWell 96 microtiter plate (Roche) was coated overnight with 100 µl of TBS containing a biotin-labeled antigen. After the antigen not bound to streptavidin was removed from each well of the plate by washing with TBST, the wells were blocked with 250 µl of 2% skim milk/TBS for one hour or more. 2% skim milk/TBS was removed, and then the prepared, purified phages were added to each well. The plate was allowed to stand at 37° C. for one hour to allow binding of antibody-displaying phages to antigens in each well in the presence or absence of 10 mM adenosine and ATP. After washing with TBST or 10 mM (ATP and adenosine)/TBST, an HRP-conjugated anti-M13 antibody (Amersham Pharmacia Biotech) diluted with TBS or 10 mM (ATP and adenosine)/TBS was added to each well. The plate was incubated for one hour. Following wash with TBST or 10 mM (ATP and adenosine)/TBST, the TMB single solution (ZYMED) was added to each well. The chromogenic reaction in the solution of each well was terminated by adding sulfuric acid. Then, the developed color was assessed by measuring absorbance at 450 nm.

Phage ELISA was carried out using 96 isolated clones to obtain from the library of rationally designed antibodies, clone "I6RLSA1-6_011", which had an antigen-binding activity to human IL-6 in the absence of ATP and adenosine, clone "HSADSA1-6_020", which had antigen-binding activity to human serum albumin (HSA) in the absence of ATP and adenosine, as well as clones "6RRLSA1-6_037" and "6RRLSA1-6_045", which had an antigen-binding activity to human IL-6 receptor in the absence of ATP and adenosine (FIGS. 44, 45, and 46).

(4-3) Sequence Analysis of Antibodies for which Adenosine and ATP Serve as a Switch Genes were amplified using specific primers (SEQ ID NOs: 79 and 80) from clones that had been assessed to have antigen-binding activity in the absence of adenosine and ATP based on the result of phage ELISA described in (4-2). The nucleotide sequences of the genes were analyzed. Based on the analysis result, the amino acid sequences are shown in Table 54 below.

TABLE 54

| Clone name | Heavy chain SEQ ID NO | Light chain SEQ ID NO |
|---|---|---|
| I6RLSA1-6_011 | 138 | 139 |
| HSADSA1-6_020 | 140 | 141 |
| 6RRLSA1-6_037 | 142 | 143 |
| 6RRLSA1-6_045 | 144 | 145 |

[Reference Example 5] Preparation of Biotinylated Human IgA-Fc

Among the naturally-occurring human IgA sequence, the Fc portion was used as a human IgA (human IgA-Fc). To attach biotin to the C terminus of human IgA-Fc, a gene fragment encoding a specific sequence (AviTag sequence, SEQ ID NO: 147) for attaching biotin by biotin ligase was linked via a linker. A gene fragment encoding a protein (SEQ ID NO: 146) in which human IgA-Fc is linked to AviTag sequence was inserted into a vector expression in animal cells. The constructed plasmid vector was introduced into FreeStyle293 cells (Invitrogen) using 293Fectin (Invitrogen). In this experiment, genes for expressing EBNA1 (SEQ ID NO: 148) and biotin ligase (BirA, SEQ ID NO: 149) were co-introduced, and biotin was added for biotin-labeling the human IgA-Fc. Cells introduced with the genes by the procedure described above were cultured at 37° C. under 8% CO2 for six days to secrete the protein of interest in the culture supernatant.

The cell culture medium containing the biotinylated human IgA-Fc of interest was filtered through a 0.22-µm bottle-top filter to obtain the culture supernatant. The culture supernatant was diluted with 20 mM Tris-HCl, pH 7.4 and applied to HiTrap Q HP (GE Healthcare) equilibrated with 20 mM Tris-HCl, pH 7.4. The biotinylated human IgA-Fc of interest was eluted with a concentration gradient of NaCl. Then, the HiTrap Q HP eluate was diluted with 50 mM Tris-HCl, pH 8.0, and applied to a SoftLink Avidin column (Promega) equilibrated with 50 mM Tris-HCl, pH 8.0. The biotinylated human IgA-Fc of interest was eluted with 5 mM biotin, 150 mM NaCl, 50 mM Tris-HCl, pH 8.0. Then, aggregates as unintended impurities were removed by gel filtration chromatography using Superdex200 (GE Healthcare), to obtain purified biotinylated human IgA-Fcin which the buffer is replaced with 20 mM Histidine-HCl, 150 mM NaCl, pH 6.0.

INDUSTRIAL APPLICABILITY

Antigen-binding domains or antigen binding molecules comprising antigen binding domains of the present invention whose antigen-binding activity varies depending on the concentration of a small molecule compound, and pharmaceutical compositions containing them, have no systemic effect in normal tissues and blood but act in a reversible manner in cancer or at inflamed sites, which are the sites of pathology in target tissues, exert their medicinal effect while avoiding adverse effects, and enable therapeutic treatment of diseases caused by target tissues. In case an antibody whose antigen binding is regulated depending on an unnatural compound is obtained, such antibody is highly useful because it can be controlled by administration of exogenous compounds that activate the activity or pharmaceutical effect of the antibody or exogenous compounds that can be administered in a non-invasive manner.

Moreover, various antigen-binding molecules useful for treating tissue-specific diseases can be efficiently and rapidly obtained by using a library that contains multiple antigen-binding domains or antigen-binding molecules comprising antigen-binding domains of the present invention whose sequences are different from one another and whose antigen-binding activity varies depending on the concentration of small molecule compounds.

The invention claimed is:

1. A library that comprises:
   (i) a plurality of antigen-binding domains having different amino acid sequences from one another, or
   (ii) a plurality of nucleic acids that encode a plurality of antigen-binding domains having different amino acid sequences from one another, or
   (iii) a plurality of antigen-binding molecules each comprising an antigen-binding domain, which have different amino acid sequences from one another, or
   (iv) a plurality of nucleic acids that encode a plurality of antigen-binding molecules each comprising an antigen-binding domain, which have different amino acid sequences from one another,
   wherein the plurality of antigen-binding domains or antigen-binding domains contained in the plurality of antigen-binding molecules comprises a first antigen-binding domain whose binding affinity for a first antigen varies depending on the concentration of a small molecule compound; and wherein the first antigen is not the small molecule compound.

2. The library of claim 1, wherein the small molecule compound is not a naturally-occurring compound.

3. The library of claim 1, wherein the small molecule compound is a compound naturally found in cancer tissue or inflammatory tissue in vivo.

4. The library of claim 1, wherein the small molecule compound is selected from the group consisting of nucleosides that have a purine ring structure, amino acids and their metabolites, lipids and their metabolites, primary metabolites from sugar metabolism, and nicotinamide and its metabolites.

5. The library of claim 1, wherein the small molecule compound is kynurenine, adenosine, adenosine monophosphate, adenosine diphosphate, or adenosine triphosphate.

6. The library of claim 1, wherein the antigen-binding domains or antigen-binding molecules differ from each other by amino acid substitution at one or more positions that (i) are not involved in binding to the small molecule compound; or (ii) show diversity of amino acid occurrence frequency in the antibody repertoire of an animal species; or (iii) are not important for canonical structure formation; or (i) and (ii); or (i) and (iii); or (ii) and (iii); or (i) and (ii) and (iii).

7. The library of claim 6, wherein the one or more positions that are not involved in binding to the small molecule compound are positions other than any one or more position selected from heavy chain positions 97, 100c, 101, 94, 95, 100d, 100e, 33, 50, 52, 56, 57, 58, 99, 100, 100a, 54, and 55 (Kabat numbering) and light chain positions 49, 55, 95c, 96, 95a, and 95b (Kabat numbering).

8. The library of claim 1, wherein the library comprises a plurality of antigen-binding molecules comprising antibody heavy chains and antibody light chains, wherein the heavy chains and light chains together form the antigen-binding domains.

9. The library of claim 8, wherein the antibody heavy chains and the antibody light chains comprise germline-derived framework sequences.

10. The library of claim 1, wherein the members of the plurality of antigen-binding molecules are fusion polypeptides, each comprising an antigen-binding domain and at least a portion of a virus coat protein.

11. A method of screening a library for an antigen-binding molecule comprising an antigen-binding domain whose binding to an antigen varies depending on the concentration of a small molecule compound that is not the antigen, the method comprising:
   (a) providing the library of claim 1, wherein the library comprises the plurality of antigen-binding domains of (i);
   (b) contacting the plurality of antigen-binding domains with the first antigen in the presence of a first concentration of the small molecule compound; and
   (c) identifying an antigen-binding domain of the plurality that binds to the first antigen in the presence of the small molecule compound at the first concentration but not in the presence of the small molecule compound at a second concentration that is lower than the first concentration.

12. The method of claim 11, wherein the antigen-binding domains of the library comprise antibody heavy chains associated with antibody light chains.

13. The method of claim 11, wherein the antigen-binding domains of the library are in the form of Fab fragments or in the form of Fab fragments fused to a viral coat protein or to a portion of a viral coat protein.

14. The method of claim 11, wherein the antigen-binding domains of the library are in the form of single-chain Fv (scFv) or in the form of scFv fused to a viral coat protein or to a portion of a viral coat protein.

* * * * *

SEQUENCE LISTING

<160> NUMBER OF SEQ ID NOS: 149

<210> SEQ ID NO 1
<211> LENGTH: 468
<212> TYPE: PRT
<213> ORGANISM: Homo sapiens

<400> SEQUENCE: 1

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320
```

```
Pro Pro Ala Glu Asn Glu Val Ser Thr Pro Met Gln Ala Leu Thr Thr
            325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
        370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
        450                 455                 460

Phe Phe Pro Arg
465

<210> SEQ ID NO 2
<211> LENGTH: 1407
<212> TYPE: DNA
<213> ORGANISM: Homo sapiens

<400> SEQUENCE: 2
atgctggccg tcggctgcgc gctgctggct gccctgctgg ccgcgccggg agcggcgctg      60
gccccaaggc gctgccctgc gcaggaggtg gcgagaggcg tgctgaccag tctgccagga     120
gacagcgtga ctctgacctg cccgggggta gagccggaag acaatgccac tgttcactgg     180
gtgctcagga agccggctgc aggctcccac cccagcagat gggctggcat gggaaggagg     240
ctgctgctga ggtcggtgca gctccacgac tctggaaact attcatgcta ccgggccggc     300
cgcccagctg ggactgtgca cttgctggtg gatgttcccc ccgaggagcc ccagctctcc     360
tgcttccgga gagcccccct cagcaatgtt gtttgtgagt ggggtcctcg gagcacccca     420
tccctgacga caaaggctgt gctcttggtg aggaagtttc agaacagtcc ggccgaagac     480
ttccaggagc cgtgccagta ttcccaggag tcccagaagt ctcctgccag gttagcagtc     540
ccggagggag acagctcttt ctacatagtg tccatgtgcg tcgccagtag tgtcgggagc     600
aagttcagca aaactcaaac ctttcagggt tgtggaatct tgcagcctga tccgcctgcc     660
aacatcacag tcactgccgt ggccagaaac ccccgctggc tcagtgtcac ctggcaagac     720
ccccactcct ggaactcatc tttctacaga ctacggtttg agctcagata tcgggctgaa     780
cggtcaaaga cattcacaac atggatggtc aaggacctcc agcatcactg tgtcatccac     840
gacgcctgga gcggcctgag gcacgtggtg cagcttcgtg cccaggagga gttcgggcaa     900
ggcgagtgga gcgagtggag cccggaggcc atgggcacgc cttggacaga atccaggagt     960
cctccagctg agaacgaggt gtccacccccc atgcaggcac ttactactaa taaagacgat    1020
gataatattc tcttcagaga ttctgcaaat gcgacaagcc tcccagtgca agattcttct    1080
tcagtaccac tgcccacatt cctggttgct ggagggagcc tggccttcgg aacgctcctc    1140
tgcattgcca ttgttctgag gttcaagaag acgtggaagc tgcgggctct gaaggaaggc    1200
aagacaagca tgcatccgcc gtactctttg gggcagctgg tcccggagag gcctcgaccc    1260
```

-continued

```
accccagtgc ttgttcctct catctcccca ccggtgtccc ccagcagcct ggggtctgac    1320
aatacctcga gccacaaccg accagatgcc agggacccac ggagcccttta tgacatcagc   1380 aatacagact acttcttccc cagatag                                        1407
```

<210> SEQ ID NO 3
<211> LENGTH: 19
<212> TYPE: PRT
<213> ORGANISM: Artificial sequence
<220> FEATURE:
<223> OTHER INFORMATION: an artificially synthesized sequence

<400> SEQUENCE: 3

Met Gly Trp Ser Cys Ile Ile Leu Phe Leu Val Ala Thr Ala Thr Gly
1               5                   10                  15

Val His Ser

<210> SEQ ID NO 4
<211> LENGTH: 21
<212> TYPE: PRT
<213> ORGANISM: Clostridium sp.

<400> SEQUENCE: 4

Phe Asn Asn Phe Thr Val Ser Phe Trp Leu Arg Val Pro Lys Val Ser
1               5                   10                  15

Ala Ser His Leu Glu
            20

<210> SEQ ID NO 5
<211> LENGTH: 330
<212> TYPE: PRT
<213> ORGANISM: Artificial sequence
<220> FEATURE:
<223> OTHER INFORMATION: an artificially synthesized sequence

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 326
<212> TYPE: PRT
<213> ORGANISM: Artificial sequence
<220> FEATURE:
<223> OTHER INFORMATION: an artificially synthesized sequence

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 377
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

```
Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 8
<211> LENGTH: 327
<212> TYPE: PRT
<213> ORGANISM: Artificial sequence
<220> FEATURE:
<223> OTHER INFORMATION: an artificially synthesized sequence

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 9
<211> LENGTH: 1125
<212> TYPE: DNA
<213> ORGANISM: Homo sapiens
<220> FEATURE:
<221> NAME/KEY: CDS
<222> LOCATION: (1)..(1125)

<400> SEQUENCE: 9
```

| | | | | | | | | | | | | | | | | |
|---|---|---|---|---|---|---|---|---|---|---|---|---|---|---|---|---|
| atg | tgg | ttc | ttg | aca | act | ctg | ctc | ctt | tgg | gtt | cca | gtt | gat | ggg | caa | 48 |
| Met | Trp | Phe | Leu | Thr | Thr | Leu | Leu | Leu | Trp | Val | Pro | Val | Asp | Gly | Gln | |
| 1 | | | | 5 | | | | | 10 | | | | | 15 | | |
| gtg | gac | acc | aca | aag | gca | gtg | atc | act | ttg | cag | cct | cca | tgg | gtc | agc | 96 |
| Val | Asp | Thr | Thr | Lys | Ala | Val | Ile | Thr | Leu | Gln | Pro | Pro | Trp | Val | Ser | |
| | | | 20 | | | | | 25 | | | | | 30 | | | |
| gtg | ttc | caa | gag | gaa | acc | gta | acc | ttg | cac | tgt | gag | gtg | ctc | cat | ctg | 144 |
| Val | Phe | Gln | Glu | Glu | Thr | Val | Thr | Leu | His | Cys | Glu | Val | Leu | His | Leu | |
| | | 35 | | | | | 40 | | | | | 45 | | | | |
| cct | ggg | agc | agc | tct | aca | cag | tgg | ttt | ctc | aat | ggc | aca | gcc | act | cag | 192 |
| Pro | Gly | Ser | Ser | Ser | Thr | Gln | Trp | Phe | Leu | Asn | Gly | Thr | Ala | Thr | Gln | |
| | 50 | | | | | 55 | | | | | 60 | | | | | |
| acc | tcg | acc | ccc | agc | tac | aga | atc | acc | tct | gcc | agt | gtc | aat | gac | agt | 240 |
| Thr | Ser | Thr | Pro | Ser | Tyr | Arg | Ile | Thr | Ser | Ala | Ser | Val | Asn | Asp | Ser | |
| 65 | | | | | 70 | | | | | 75 | | | | | 80 | |
| ggt | gaa | tac | agg | tgc | cag | aga | ggt | ctc | tca | ggg | cga | agt | gac | ccc | ata | 288 |
| Gly | Glu | Tyr | Arg | Cys | Gln | Arg | Gly | Leu | Ser | Gly | Arg | Ser | Asp | Pro | Ile | |
| | | | | 85 | | | | | 90 | | | | | 95 | | |
| cag | ctg | gaa | atc | cac | aga | ggc | tgg | cta | cta | ctg | cag | gtc | tcc | agc | aga | 336 |
| Gln | Leu | Glu | Ile | His | Arg | Gly | Trp | Leu | Leu | Leu | Gln | Val | Ser | Ser | Arg | |
| | | | 100 | | | | | 105 | | | | | 110 | | | |
| gtc | ttc | acg | gaa | gga | gaa | cct | ctg | gcc | ttg | agg | tgt | cat | gcg | tgg | aag | 384 |
| Val | Phe | Thr | Glu | Gly | Glu | Pro | Leu | Ala | Leu | Arg | Cys | His | Ala | Trp | Lys | |
| | | 115 | | | | | 120 | | | | | 125 | | | | |
| gat | aag | ctg | gtg | tac | aat | gtg | ctt | tac | tat | cga | aat | ggc | aaa | gcc | ttt | 432 |
| Asp | Lys | Leu | Val | Tyr | Asn | Val | Leu | Tyr | Tyr | Arg | Asn | Gly | Lys | Ala | Phe | |
| | 130 | | | | | 135 | | | | | 140 | | | | | |
| aag | ttt | ttc | cac | tgg | aat | tct | aac | ctc | acc | att | ctg | aaa | acc | aac | ata | 480 |
| Lys | Phe | Phe | His | Trp | Asn | Ser | Asn | Leu | Thr | Ile | Leu | Lys | Thr | Asn | Ile | |
| 145 | | | | | 150 | | | | | 155 | | | | | 160 | |
| agt | cac | aat | ggc | acc | tac | cat | tgc | tca | ggc | atg | gga | aag | cat | cgc | tac | 528 |
| Ser | His | Asn | Gly | Thr | Tyr | His | Cys | Ser | Gly | Met | Gly | Lys | His | Arg | Tyr | |
| | | | | 165 | | | | | 170 | | | | | 175 | | |
| aca | tca | gca | gga | ata | tct | gtc | act | gtg | aaa | gag | cta | ttt | cca | gct | cca | 576 |
| Thr | Ser | Ala | Gly | Ile | Ser | Val | Thr | Val | Lys | Glu | Leu | Phe | Pro | Ala | Pro | |
| | | | 180 | | | | | 185 | | | | | 190 | | | |
| gtg | ctg | aat | gca | tct | gtg | aca | tcc | cca | ctc | ctg | gag | ggg | aat | ctg | gtc | 624 |

```
                  Val Leu Asn Ala Ser Val Thr Ser Pro Leu Leu Glu Gly Asn Leu Val
                              195                 200                 205 acc ctg agc tgt gaa aca aag ttg ctc ttg cag agg cct ggt ttg cag          672
Thr Leu Ser Cys Glu Thr Lys Leu Leu Leu Gln Arg Pro Gly Leu Gln
210                 215                 220 ctt tac ttc tcc ttc tac atg ggc agc aag acc ctg cga ggc agg aac          720
Leu Tyr Phe Ser Phe Tyr Met Gly Ser Lys Thr Leu Arg Gly Arg Asn
225                 230                 235                 240 aca tcc tct gaa tac caa ata cta act gct aga aga gaa gac tct ggg          768
Thr Ser Ser Glu Tyr Gln Ile Leu Thr Ala Arg Arg Glu Asp Ser Gly
                245                 250                 255 tta tac tgg tgc gag gct gcc aca gag gat gga aat gtc ctt aag cgc          816
Leu Tyr Trp Cys Glu Ala Ala Thr Glu Asp Gly Asn Val Leu Lys Arg
                260                 265                 270 agc cct gag ttg gag ctt caa gtg ctt ggc ctc cag tta cca act cct          864
Ser Pro Glu Leu Glu Leu Gln Val Leu Gly Leu Gln Leu Pro Thr Pro
            275                 280                 285 gtc tgg ttt cat gtc ctt ttc tat ctg gca gtg gga ata atg ttt tta          912
Val Trp Phe His Val Leu Phe Tyr Leu Ala Val Gly Ile Met Phe Leu
        290                 295                 300 gtg aac act gtt ctc tgg gtg aca ata cgt aaa gaa ctg aaa aga aag          960
Val Asn Thr Val Leu Trp Val Thr Ile Arg Lys Glu Leu Lys Arg Lys
305                 310                 315                 320 aaa aag tgg gat tta gaa atc tct ttg gat tct ggt cat gag aag aag         1008
Lys Lys Trp Asp Leu Glu Ile Ser Leu Asp Ser Gly His Glu Lys Lys
                325                 330                 335 gta att tcc agc ctt caa gaa gac aga cat tta gaa gaa gag ctg aaa         1056
Val Ile Ser Ser Leu Gln Glu Asp Arg His Leu Glu Glu Glu Leu Lys
                340                 345                 350 tgt cag gaa caa aaa gaa gaa cag ctg cag gaa ggg gtg cac cgg aag         1104
Cys Gln Glu Gln Lys Glu Glu Gln Leu Gln Glu Gly Val His Arg Lys
            355                 360                 365 gag ccc cag ggg gcc acg tag                                              1125
Glu Pro Gln Gly Ala Thr
        370

<210> SEQ ID NO 10
<211> LENGTH: 374
<212> TYPE: PRT
<213> ORGANISM: Homo sapiens

<400> SEQUENCE: 10

Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
                100                 105                 110

Val Phe Thr Glu Gly Glu Pro Leu Ala Leu Arg Cys His Ala Trp Lys
            115                 120                 125
```

```
Asp Lys Leu Val Tyr Asn Val Leu Tyr Tyr Arg Asn Gly Lys Ala Phe
    130                 135                 140
Lys Phe Phe His Trp Asn Ser Asn Leu Thr Ile Leu Lys Thr Asn Ile
145                 150                 155                 160
Ser His Asn Gly Thr Tyr His Cys Ser Gly Met Gly Lys His Arg Tyr
                165                 170                 175
Thr Ser Ala Gly Ile Ser Val Thr Val Lys Glu Leu Phe Pro Ala Pro
            180                 185                 190
Val Leu Asn Ala Ser Val Thr Ser Pro Leu Leu Glu Gly Asn Leu Val
        195                 200                 205
Thr Leu Ser Cys Glu Thr Lys Leu Leu Leu Gln Arg Pro Gly Leu Gln
    210                 215                 220
Leu Tyr Phe Ser Phe Tyr Met Gly Ser Lys Thr Leu Arg Gly Arg Asn
225                 230                 235                 240
Thr Ser Ser Glu Tyr Gln Ile Leu Thr Ala Arg Arg Glu Asp Ser Gly
                245                 250                 255
Leu Tyr Trp Cys Glu Ala Ala Thr Glu Asp Gly Asn Val Leu Lys Arg
            260                 265                 270
Ser Pro Glu Leu Glu Leu Gln Val Leu Gly Leu Gln Leu Pro Thr Pro
        275                 280                 285
Val Trp Phe His Val Leu Phe Tyr Leu Ala Val Gly Ile Met Phe Leu
    290                 295                 300
Val Asn Thr Val Leu Trp Val Thr Ile Arg Lys Glu Leu Lys Arg Lys
305                 310                 315                 320
Lys Lys Trp Asp Leu Glu Ile Ser Leu Asp Ser Gly His Glu Lys Lys
                325                 330                 335
Val Ile Ser Ser Leu Gln Glu Asp Arg His Leu Glu Glu Glu Leu Lys
            340                 345                 350
Cys Gln Glu Gln Lys Glu Glu Gln Leu Gln Glu Gly Val His Arg Lys
        355                 360                 365
Glu Pro Gln Gly Ala Thr
    370

<210> SEQ ID NO 11
<211> LENGTH: 951
<212> TYPE: DNA
<213> ORGANISM: Homo sapiens
<220> FEATURE:
<221> NAME/KEY: CDS
<222> LOCATION: (1)..(951)

<400> SEQUENCE: 11 atg act atg gag acc caa atg tct cag aat gta tgt ccc aga aac ctg      48
Met Thr Met Glu Thr Gln Met Ser Gln Asn Val Cys Pro Arg Asn Leu
1               5                   10                  15 tgg ctg ctt caa cca ttg aca gtt ttg ctg ctg gct tct gca gac          96
Trp Leu Leu Gln Pro Leu Thr Val Leu Leu Leu Ala Ser Ala Asp
            20                  25                  30 agt caa gct gct ccc cca aag gct gtg ctg aaa ctt gag ccc ccg tgg     144
Ser Gln Ala Ala Pro Pro Lys Ala Val Leu Lys Leu Glu Pro Pro Trp
        35                  40                  45 atc aac gtg ctc cag gag gac tct gtg act ctg aca tgc cag ggg gct    192
Ile Asn Val Leu Gln Glu Asp Ser Val Thr Leu Thr Cys Gln Gly Ala
    50                  55                  60 cgc agc cct gag agc gac tcc att cag tgg ttc cac aat ggg aat ctc    240
Arg Ser Pro Glu Ser Asp Ser Ile Gln Trp Phe His Asn Gly Asn Leu
65                  70                  75                  80
```

| | | |
|---|---|---|
| att ccc acc cac acg cag ccc agc tac agg ttc aag gcc aac aac aat<br>Ile Pro Thr His Thr Gln Pro Ser Tyr Arg Phe Lys Ala Asn Asn Asn<br>                      85                        90                    95 | 288 | |
| gac agc ggg gag tac acg tgc cag act ggc cag acc agc ctc agc gac<br>Asp Ser Gly Glu Tyr Thr Cys Gln Thr Gly Gln Thr Ser Leu Ser Asp<br>                100                      105                    110 | 336 | |
| cct gtg cat ctg act gtg ctt tcc gaa tgg ctg gtg ctc cag acc cct<br>Pro Val His Leu Thr Val Leu Ser Glu Trp Leu Val Leu Gln Thr Pro<br>        115                      120                    125 | 384 | |
| cac ctg gag ttc cag gag gga gaa acc atc atg ctg agg tgc cac agc<br>His Leu Glu Phe Gln Glu Gly Glu Thr Ile Met Leu Arg Cys His Ser<br>130                      135                    140 | 432 | |
| tgg aag gac aag cct ctg gtc aag gtc aca ttc ttc cag aat gga aaa<br>Trp Lys Asp Lys Pro Leu Val Lys Val Thr Phe Phe Gln Asn Gly Lys<br>145                      150                    155                    160 | 480 | |
| tcc cag aaa ttc tcc cat ttg gat ccc acc ttc tcc atc cca caa gca<br>Ser Gln Lys Phe Ser His Leu Asp Pro Thr Phe Ser Ile Pro Gln Ala<br>                      165                    170                    175 | 528 | |
| aac cac agt cac agt ggt gat tac cac tgc aca gga aac ata ggc tac<br>Asn His Ser His Ser Gly Asp Tyr His Cys Thr Gly Asn Ile Gly Tyr<br>        180                      185                    190 | 576 | |
| acg ctg ttc tca tcc aag cct gtg acc atc act gtc caa gtg ccc agc<br>Thr Leu Phe Ser Ser Lys Pro Val Thr Ile Thr Val Gln Val Pro Ser<br>                195                      200                    205 | 624 | |
| atg ggc agc tct tca cca atg ggg gtc att gtg gct gtg gtc att gcg<br>Met Gly Ser Ser Ser Pro Met Gly Val Ile Val Ala Val Val Ile Ala<br>        210                      215                    220 | 672 | |
| act gct gta gca gcc att gtt gct gct gta gtg gcc ttg atc tac tgc<br>Thr Ala Val Ala Ala Ile Val Ala Ala Val Val Ala Leu Ile Tyr Cys<br>225                      230                    235                    240 | 720 | |
| agg aaa aag cgg att tca gcc aat tcc act gat cct gtg aag gct gcc<br>Arg Lys Lys Arg Ile Ser Ala Asn Ser Thr Asp Pro Val Lys Ala Ala<br>                      245                    250                    255 | 768 | |
| caa ttt gag cca cct gga cgt caa atg att gcc atc aga aag aga caa<br>Gln Phe Glu Pro Pro Gly Arg Gln Met Ile Ala Ile Arg Lys Arg Gln<br>        260                      265                    270 | 816 | |
| ctt gaa gaa acc aac aat gac tat gaa aca gct gac ggc ggc tac atg<br>Leu Glu Glu Thr Asn Asn Asp Tyr Glu Thr Ala Asp Gly Gly Tyr Met<br>                275                      280                    285 | 864 | |
| act ctg aac ccc agg gca cct act gac gat gat aaa aac atc tac ctg<br>Thr Leu Asn Pro Arg Ala Pro Thr Asp Asp Asp Lys Asn Ile Tyr Leu<br>        290                      295                    300 | 912 | |
| act ctt cct ccc aac gac cat gtc aac agt aat aac taa<br>Thr Leu Pro Pro Asn Asp His Val Asn Ser Asn Asn<br>305                      310                    315 | 951 | |

<210> SEQ ID NO 12
<211> LENGTH: 316
<212> TYPE: PRT
<213> ORGANISM: Homo sapiens

<400> SEQUENCE: 12

Met Thr Met Glu Thr Gln Met Ser Gln Asn Val Cys Pro Arg Asn Leu
1                  5                    10                    15

Trp Leu Leu Gln Pro Leu Thr Val Leu Leu Leu Leu Ala Ser Ala Asp
                20                      25                    30

Ser Gln Ala Ala Pro Pro Lys Ala Val Leu Lys Leu Glu Pro Pro Trp
        35                      40                    45

Ile Asn Val Leu Gln Glu Asp Ser Val Thr Leu Thr Cys Gln Gly Ala
50                      55                    60

```
Arg Ser Pro Glu Ser Asp Ser Ile Gln Trp Phe His Asn Gly Asn Leu
 65                  70                  75                  80

Ile Pro Thr His Thr Gln Pro Ser Tyr Arg Phe Lys Ala Asn Asn Asn
                 85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Lys Asn Ile Tyr Leu
    290                 295                 300

Thr Leu Pro Pro Asn Asp His Val Asn Ser Asn Asn
305                 310                 315

<210> SEQ ID NO 13
<211> LENGTH: 876
<212> TYPE: DNA
<213> ORGANISM: Homo sapiens
<220> FEATURE:
<221> NAME/KEY: CDS
<222> LOCATION: (1)..(876)

<400> SEQUENCE: 13 atg gga atc ctg tca ttc tta cct gtc ctt gcc act gag agt gac tgg      48
Met Gly Ile Leu Ser Phe Leu Pro Val Leu Ala Thr Glu Ser Asp Trp
  1               5                  10                  15 gct gac tgc aag tcc ccc cag cct tgg ggt cat atg ctt ctg tgg aca      96
Ala Asp Cys Lys Ser Pro Gln Pro Trp Gly His Met Leu Leu Trp Thr
                 20                  25                  30 gct gtg cta ttc ctg gct cct gtt gct ggg aca cct gca gct ccc cca     144
Ala Val Leu Phe Leu Ala Pro Val Ala Gly Thr Pro Ala Ala Pro Pro
             35                  40                  45 aag gct gtg ctg aaa ctc gag ccc cag tgg atc aac gtg ctc cag gag     192
Lys Ala Val Leu Lys Leu Glu Pro Gln Trp Ile Asn Val Leu Gln Glu
         50                  55                  60 gac tct gtg act ctg aca tgc cgg ggg act cac agc cct gag agc gac     240
Asp Ser Val Thr Leu Thr Cys Arg Gly Thr His Ser Pro Glu Ser Asp
 65                  70                  75                  80
```

```
tcc att cag tgg ttc cac aat ggg aat ctc att ccc acc cac acg cag      288
Ser Ile Gln Trp Phe His Asn Gly Asn Leu Ile Pro Thr His Thr Gln
         85                  90                  95 ccc agc tac agg ttc aag gcc aac aac aat gac agc ggg gag tac acg      336
Pro Ser Tyr Arg Phe Lys Ala Asn Asn Asn Asp Ser Gly Glu Tyr Thr
            100                 105                 110 tgc cag act ggc cag acc agc ctc agc gac cct gtg cat ctg act gtg      384
Cys Gln Thr Gly Gln Thr Ser Leu Ser Asp Pro Val His Leu Thr Val
        115                 120                 125 ctt tct gag tgg ctg gtg ctc cag acc cct cac ctg gag ttc cag gag      432
Leu Ser Glu Trp Leu Val Leu Gln Thr Pro His Leu Glu Phe Gln Glu
    130                 135                 140 gga gaa acc atc gtg ctg agg tgc cac agc tgg aag gac aag cct ctg      480
Gly Glu Thr Ile Val Leu Arg Cys His Ser Trp Lys Asp Lys Pro Leu
145                 150                 155                 160 gtc aag gtc aca ttc ttc cag aat gga aaa tcc aag aaa ttt tcc cgt      528
Val Lys Val Thr Phe Phe Gln Asn Gly Lys Ser Lys Lys Phe Ser Arg
                165                 170                 175 tcg gat ccc aac ttc tcc atc cca caa gca aac cac agt cac agt ggt      576
Ser Asp Pro Asn Phe Ser Ile Pro Gln Ala Asn His Ser His Ser Gly
            180                 185                 190 gat tac cac tgc aca gga aac ata ggc tac acg ctg tac tca tcc aag      624
Asp Tyr His Cys Thr Gly Asn Ile Gly Tyr Thr Leu Tyr Ser Ser Lys
        195                 200                 205 cct gtg acc atc act gtc caa gct ccc agc tct tca ccg atg ggg atc      672
Pro Val Thr Ile Thr Val Gln Ala Pro Ser Ser Ser Pro Met Gly Ile
    210                 215                 220 att gtg gct gtg gtc act ggg att gct gta gcg gcc att gtt gct gct      720
Ile Val Ala Val Val Thr Gly Ile Ala Val Ala Ala Ile Val Ala Ala
225                 230                 235                 240 gta gtg gcc ttg atc tac tgc agg aaa aag cgg att tca gcc aat ccc      768
Val Val Ala Leu Ile Tyr Cys Arg Lys Lys Arg Ile Ser Ala Asn Pro
                245                 250                 255 act aat cct gat gag gct gac aaa gtt ggg gct gag aac aca atc acc      816
Thr Asn Pro Asp Glu Ala Asp Lys Val Gly Ala Glu Asn Thr Ile Thr
            260                 265                 270 tat tca ctt ctc atg cac ccg gat gct ctg gaa gag cct gat gac cag      864
Tyr Ser Leu Leu Met His Pro Asp Ala Leu Glu Glu Pro Asp Asp Gln
        275                 280                 285 aac cgt att tag                                                      876
Asn Arg Ile
    290

<210> SEQ ID NO 14
<211> LENGTH: 291
<212> TYPE: PRT
<213> ORGANISM: Homo sapiens

<400> SEQUENCE: 14

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80
```

```
Ser Ile Gln Trp Phe His Asn Gly Asn Leu Ile Pro Thr His Thr Gln
                 85                  90                  95

Pro Ser Tyr Arg Phe Lys Ala Asn Asn Asp Ser Gly Glu Tyr Thr
            100                 105                 110

Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
        130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290

<210> SEQ ID NO 15
<211> LENGTH: 765
<212> TYPE: DNA
<213> ORGANISM: Homo sapiens
<220> FEATURE:
<221> NAME/KEY: CDS
<222> LOCATION: (1)..(765)

<400> SEQUENCE: 15 atg tgg cag ctg ctc ctc cca act gct ctg cta ctt cta gtt tca gct      48
Met Trp Gln Leu Leu Leu Pro Thr Ala Leu Leu Leu Leu Val Ser Ala
1               5                   10                  15 ggc atg cgg act gaa gat ctc cca aag gct gtg gtg ttc ctg gag cct      96
Gly Met Arg Thr Glu Asp Leu Pro Lys Ala Val Val Phe Leu Glu Pro
                20                  25                  30 caa tgg tac agg gtg ctc gag aag gac agt gtg act ctg aag tgc cag     144
Gln Trp Tyr Arg Val Leu Glu Lys Asp Ser Val Thr Leu Lys Cys Gln
            35                  40                  45 gga gcc tac tcc cct gag gac aat tcc aca cag tgg ttt cac aat gag     192
Gly Ala Tyr Ser Pro Glu Asp Asn Ser Thr Gln Trp Phe His Asn Glu
        50                  55                  60 agc ctc atc tca agc cag gcc tcg agc tac ttc att gac gct gcc aca     240
Ser Leu Ile Ser Ser Gln Ala Ser Ser Tyr Phe Ile Asp Ala Ala Thr
65                  70                  75                  80 gtt gac gac agt gga gag tac agg tgc cag aca aac ctc tcc acc ctc     288
Val Asp Asp Ser Gly Glu Tyr Arg Cys Gln Thr Asn Leu Ser Thr Leu
                85                  90                  95 agt gac ccg gtg cag cta gaa gtc cat atc ggc tgg ctg ttg ctc cag     336
```

```
                Ser Asp Pro Val Gln Leu Glu Val His Ile Gly Trp Leu Leu Leu Gln
                                100                 105                 110 gcc cct cgg tgg gtg ttc aag gag gaa gac cct att cac ctg agg tgt          384
Ala Pro Arg Trp Val Phe Lys Glu Glu Asp Pro Ile His Leu Arg Cys
                115                 120                 125 cac agc tgg aag aac act gct ctg cat aag gtc aca tat tta cag aat          432
His Ser Trp Lys Asn Thr Ala Leu His Lys Val Thr Tyr Leu Gln Asn
130                 135                 140 ggc aaa ggc agg aag tat ttt cat cat aat tct gac ttc tac att cca          480
Gly Lys Gly Arg Lys Tyr Phe His His Asn Ser Asp Phe Tyr Ile Pro
145                 150                 155                 160 aaa gcc aca ctc aaa gac agc ggc tcc tac ttc tgc agg ggg ctt gtt          528
Lys Ala Thr Leu Lys Asp Ser Gly Ser Tyr Phe Cys Arg Gly Leu Val
                165                 170                 175 ggg agt aaa aat gtg tct tca gag act gtg aac atc acc atc act caa          576
Gly Ser Lys Asn Val Ser Ser Glu Thr Val Asn Ile Thr Ile Thr Gln
                180                 185                 190 ggt ttg tca gtg tca acc atc tca tca ttc ttt cca cct ggg tac caa          624
Gly Leu Ser Val Ser Thr Ile Ser Ser Phe Phe Pro Pro Gly Tyr Gln
                195                 200                 205 gtc tct ttc tgc ttg gtg atg gta ctc ctt ttt gca gtg gac aca gga          672
Val Ser Phe Cys Leu Val Met Val Leu Leu Phe Ala Val Asp Thr Gly
210                 215                 220 cta tat ttc tct gtg aag aca aac att cga agc tca aca aga gac tgg          720
Leu Tyr Phe Ser Val Lys Thr Asn Ile Arg Ser Ser Thr Arg Asp Trp
225                 230                 235                 240 aag gac cat aaa ttt aaa tgg aga aag gac cct caa gac aaa tga              765
Lys Asp His Lys Phe Lys Trp Arg Lys Asp Pro Gln Asp Lys
                245                 250

<210> SEQ ID NO 16
<211> LENGTH: 254
<212> TYPE: PRT
<213> ORGANISM: Homo sapiens

<400> SEQUENCE: 16

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175
```

```
Gly Ser Lys Asn Val Ser Ser Glu Thr Val Asn Ile Thr Ile Thr Gln
            180                 185                 190

Gly Leu Ser Val Ser Thr Ile Ser Ser Phe Pro Pro Gly Tyr Gln
        195                 200                 205

Val Ser Phe Cys Leu Val Met Val Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 17
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 17
```

| | | | | | | | | | | | | | | | | |
|---|---|---|---|---|---|---|---|---|---|---|---|---|---|---|---|---|
| atg | tgg | cag | ctg | ctc | ctc | cca | act | gct | ctg | cta | ctt | cta | gtt | tca | gct | 48 |
| Met | Trp | Gln | Leu | Leu | Leu | Pro | Thr | Ala | Leu | Leu | Leu | Leu | Val | Ser | Ala | |
| 1 | | | | 5 | | | | | 10 | | | | | 15 | | |
| ggc | atg | cgg | act | gaa | gat | ctc | cca | aag | gct | gtg | gtg | ttc | ctg | gag | cct | 96 |
| Gly | Met | Arg | Thr | Glu | Asp | Leu | Pro | Lys | Ala | Val | Val | Phe | Leu | Glu | Pro | |
| | | | 20 | | | | | 25 | | | | | 30 | | | |
| caa | tgg | tac | agc | gtg | ctt | gag | aag | gac | agt | gtg | act | ctg | aag | tgc | cag | 144 |
| Gln | Trp | Tyr | Ser | Val | Leu | Glu | Lys | Asp | Ser | Val | Thr | Leu | Lys | Cys | Gln | |
| | | 35 | | | | | 40 | | | | | 45 | | | | |
| gga | gcc | tac | tcc | cct | gag | gac | aat | tcc | aca | cag | tgg | ttt | cac | aat | gag | 192 |
| Gly | Ala | Tyr | Ser | Pro | Glu | Asp | Asn | Ser | Thr | Gln | Trp | Phe | His | Asn | Glu | |
| 50 | | | | | 55 | | | | | 60 | | | | | | |
| agc | ctc | atc | tca | agc | cag | gcc | tcg | agc | tac | ttc | att | gac | gct | gcc | aca | 240 |
| Ser | Leu | Ile | Ser | Ser | Gln | Ala | Ser | Ser | Tyr | Phe | Ile | Asp | Ala | Ala | Thr | |
| 65 | | | | | 70 | | | | | 75 | | | | | 80 | |
| gtc | aac | gac | agt | gga | gag | tac | agg | tgc | cag | aca | aac | ctc | tcc | acc | ctc | 288 |
| Val | Asn | Asp | Ser | Gly | Glu | Tyr | Arg | Cys | Gln | Thr | Asn | Leu | Ser | Thr | Leu | |
| | | | | 85 | | | | | 90 | | | | | 95 | | |
| agt | gac | ccg | gtg | cag | cta | gaa | gtc | cat | atc | ggc | tgg | ctg | ttg | ctc | cag | 336 |
| Ser | Asp | Pro | Val | Gln | Leu | Glu | Val | His | Ile | Gly | Trp | Leu | Leu | Leu | Gln | |
| | | | 100 | | | | | 105 | | | | | 110 | | | |
| gcc | cct | cgg | tgg | gtg | ttc | aag | gag | gaa | gac | cct | att | cac | ctg | agg | tgt | 384 |
| Ala | Pro | Arg | Trp | Val | Phe | Lys | Glu | Glu | Asp | Pro | Ile | His | Leu | Arg | Cys | |
| | | 115 | | | | | 120 | | | | | 125 | | | | |
| cac | agc | tgg | aag | aac | act | gct | ctg | cat | aag | gtc | aca | tat | tta | cag | aat | 432 |
| His | Ser | Trp | Lys | Asn | Thr | Ala | Leu | His | Lys | Val | Thr | Tyr | Leu | Gln | Asn | |
| 130 | | | | | 135 | | | | | 140 | | | | | | |
| ggc | aaa | gac | agg | aag | tat | ttt | cat | cat | aat | tct | gac | ttc | cac | att | cca | 480 |
| Gly | Lys | Asp | Arg | Lys | Tyr | Phe | His | His | Asn | Ser | Asp | Phe | His | Ile | Pro | |
| 145 | | | | | 150 | | | | | 155 | | | | | 160 | |
| aaa | gcc | aca | ctc | aaa | gat | agc | ggc | tcc | tac | ttc | tgc | agg | ggg | ctt | gtt | 528 |
| Lys | Ala | Thr | Leu | Lys | Asp | Ser | Gly | Ser | Tyr | Phe | Cys | Arg | Gly | Leu | Val | |
| | | | | 165 | | | | | 170 | | | | | 175 | | |
| ggg | agt | aaa | aat | gtg | tct | tca | gag | act | gtg | aac | atc | acc | atc | act | caa | 576 |
| Gly | Ser | Lys | Asn | Val | Ser | Ser | Glu | Thr | Val | Asn | Ile | Thr | Ile | Thr | Gln | |
| | | | 180 | | | | | 185 | | | | | 190 | | | |
| ggt | ttg | gca | gtg | tca | acc | atc | tca | tca | ttc | tct | cca | cct | ggg | tac | caa | 624 |
| Gly | Leu | Ala | Val | Ser | Thr | Ile | Ser | Ser | Phe | Ser | Pro | Pro | Gly | Tyr | Gln | |
| | | 195 | | | | | 200 | | | | | 205 | | | | |

```
gtc tct ttc tgc ttg gtg atg gta ctc ctt ttt gca gtg gac aca gga    672
Val Ser Phe Cys Leu Val Met Val Leu Leu Phe Ala Val Asp Thr Gly
    210             215                 220 cta tat ttc tct gtg aag aca aac att tga                            702
Leu Tyr Phe Ser Val Lys Thr Asn Ile
225                 230
```

<210> SEQ ID NO 18
<211> LENGTH: 233
<212> TYPE: PRT
<213> ORGANISM: Homo sapiens

<400> SEQUENCE: 18

```
Met Trp Gln Leu Leu Pro Thr Ala Leu Leu Leu Val Ser Ala
1               5                   10                  15

Gly Met Arg Thr Glu Asp Leu Pro Lys Ala Val Phe Leu Glu Pro
            20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

<210> SEQ ID NO 19
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 19

```
Gly Gly Gly Ser
1
```

<210> SEQ ID NO 20
<211> LENGTH: 4
<212> TYPE: PRT
<213> ORGANISM: Artificial sequence

```
<220> FEATURE:
<223> OTHER INFORMATION: an artificially synthesized sequence

<400> SEQUENCE: 20

Ser Gly Gly Gly
1

<210> SEQ ID NO 21
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 21

Gly Gly Gly Gly Ser
1               5

<210> SEQ ID NO 22
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 22

Ser Gly Gly Gly Gly
1               5

<210> SEQ ID NO 23
<211> LENGTH: 6
<212> TYPE: PRT
<213> ORGANISM: Artificial sequence
<220> FEATURE:
<223> OTHER INFORMATION: an artificially synthesized sequence

<400> SEQUENCE: 23

Gly Gly Gly Gly Gly Ser
1               5

<210> SEQ ID NO 24
<211> LENGTH: 6
<212> TYPE: PRT
<213> ORGANISM: Artificial sequence
<220> FEATURE:
<223> OTHER INFORMATION: an artificially synthesized sequence

<400> SEQUENCE: 24

Ser Gly Gly Gly Gly Gly
1               5

<210> SEQ ID NO 25
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 25

Gly Gly Gly Gly Gly Gly Ser
1               5

<210> SEQ ID NO 26
<211> LENGTH: 7
<212> TYPE: PRT
<213> ORGANISM: Artificial sequence
<220> FEATURE:
```

-continued

<223> OTHER INFORMATION: an artificially synthesized sequence

<400> SEQUENCE: 26

Ser Gly Gly Gly Gly Gly
1               5

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 28
<211> LENGTH: 365
<212> TYPE: PRT
<213> ORGANISM: Homo sapiens

<400> SEQUENCE: 28

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

```
Gly Arg Gly Asn Leu Glu Trp Lys Glu Pro Ser Met Arg Leu Lys
            195                 200                 205

Ala Arg Pro Ser Ser Pro Gly Phe Ser Val Leu Thr Cys Ser Ala Phe
210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
            245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
            275                 280                 285

Glu Leu Glu Ser Pro Ala Lys Ser Ser Val Leu Val Val Gly Ile Val
            290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
            325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
            355                 360                 365

<210> SEQ ID NO 29
<211> LENGTH: 119
<212> TYPE: PRT
<213> ORGANISM: Homo sapiens

<400> SEQUENCE: 29

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 30
<211> LENGTH: 118
<212> TYPE: PRT
<213> ORGANISM: Oryctolagus cuniculus

<400> SEQUENCE: 30

Cys Gln Ser Val Glu Glu Ser Gly Gly Arg Leu Val Thr Pro Gly Thr
1               5                   10                  15

Pro Leu Thr Leu Thr Cys Thr Val Ser Gly Ile Asp Leu Ser Asn Tyr
            20                  25                  30
```

Ala Met Gly Trp Val Arg Gln Ala Pro Gly Lys Gly Leu Glu Trp Ile
            35                  40                  45

Gly Ile Ile Gly Ala Asp Ser Ser Thr Trp Tyr Pro Ser Trp Val Lys
 50                  55                  60

Gly Arg Phe Thr Ile Ser Lys Thr Ser Thr Thr Val Asp Leu Lys Met
 65                  70                  75                  80

Thr Ser Leu Thr Thr Glu Asp Thr Ala Thr Tyr Phe Cys Ala Arg Gly
                 85                  90                  95

Arg Phe Val Gly Tyr Thr Asn Ala Phe Asp Pro Trp Gly Pro Gly Thr
            100                 105                 110

Leu Val Thr Val Ser Ser
            115

<210> SEQ ID NO 31
<211> LENGTH: 113
<212> TYPE: PRT
<213> ORGANISM: Oryctolagus cuniculus

<400> SEQUENCE: 31

Ala Gln Val Leu Thr Gln Thr Pro Ser Ser Val Ser Ala Ala Val Gly
 1               5                   10                  15

Gly Thr Val Thr Ile Ser Cys Gln Ser Ser Gln Ser Val Trp Asn Asn
             20                  25                  30

Asn Tyr Leu Ser Trp Tyr Gln Gln Lys Pro Gly Gln Pro Pro Lys Leu
         35                  40                  45

Leu Ile Phe Asp Ala Ser Thr Leu Ala Ser Gly Val Pro Ser Arg Phe
 50                  55                  60

Ser Gly Arg Gly Ser Gly Thr Gln Phe Thr Leu Thr Ile Ser Gly Val
 65                  70                  75                  80

Gln Cys Glu Asp Ala Ala Thr Tyr Tyr Cys His Gly Ser Tyr Ala Asn
                 85                  90                  95

Ser Gly Trp Tyr Asp Asn Ala Phe Gly Gly Thr Glu Val Val Val
            100                 105                 110

Lys

<210> SEQ ID NO 32
<211> LENGTH: 123
<212> TYPE: PRT
<213> ORGANISM: Homo sapiens

<400> SEQUENCE: 32

Gln Val Gln Leu Val Gln Ser Gly Ala Glu Val Lys Lys Pro Gly Ser
 1               5                   10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ala Pro Val Val Ala Arg Pro Arg Gly Ala Phe Asp Ile
            100                 105                 110

Trp Gly Gln Gly Thr Met Val Thr Val Ser Ser
            115                 120

<210> SEQ ID NO 33
<211> LENGTH: 112
<212> TYPE: PRT
<213> ORGANISM: Homo sapiens

<400> SEQUENCE: 33

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile His Glu Ile Ser Asn Arg Phe Ser Gly Val Pro
    50                  55                  60

Asp Arg Phe Ser Gly Ser Gly Ala Gly Thr Asn Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Arg Thr Phe Gly Gln Gly Thr Lys Val Glu Ile Lys
            100                 105                 110

<210> SEQ ID NO 34
<211> LENGTH: 122
<212> TYPE: PRT
<213> ORGANISM: Homo sapiens

<400> SEQUENCE: 34

Glu Val Gln Leu Val Gln Ser Gly Gly Asp Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Val Pro Ser Ser Gly Tyr Pro Gly Arg Phe Asp Pro Trp
            100                 105                 110

Gly Gln Gly Thr Leu Val Thr Val Ser Ser
            115                 120

<210> SEQ ID NO 35
<211> LENGTH: 106
<212> TYPE: PRT
<213> ORGANISM: Homo sapiens

<400> SEQUENCE: 35

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ser
            20                  25                  30

Leu Asn Trp Tyr Gln Gln Ile Pro Gly Lys Ala Pro Lys Leu Leu Ile

```
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Ser Ala Trp Thr
                85                  90                  95

Phe Gly Gln Gly Thr Lys Val Glu Ile Lys
            100                 105

<210> SEQ ID NO 36
<211> LENGTH: 115
<212> TYPE: PRT
<213> ORGANISM: Artificial sequence
<220> FEATURE:
<223> OTHER INFORMATION: an artificially synthesized sequence

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Ile Arg Gln Pro Pro Gly Gln Gly Leu Glu Trp Ile
            35                  40                  45

Gly Ala Ile Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 37
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

```
<210> SEQ ID NO 38
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 38
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Val Val Ala Arg Pro Arg Gly Ala Phe Asp Ile
            100                 105                 110

Trp Gly Gln Gly Thr Met Val Thr Val Ser Ser
        115                 120

```
<210> SEQ ID NO 39
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 39
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Val Val Ala Arg Pro Arg Gly Ala Phe Asp Ile
            100                 105                 110

Trp Gly Gln Gly Thr Met Val Thr Val Ser Ser
        115                 120

```
<210> SEQ ID NO 40
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 40
```

Gln Val Gln Leu Val Gln Ser Gly Ala Glu Val Lys Lys Pro Gly Ser

```
                1               5                  10                  15
Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Val Ala Arg Gly Arg Gly Ala Phe Asp Ile
                100                 105                 110

Trp Gly Gln Gly Thr Met Val Thr Val Ser Ser
            115                 120
```

<210> SEQ ID NO 41
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 41

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Val Ala Arg Pro Ala Gly Ala Phe Asp Ile
                100                 105                 110

Trp Gly Gln Gly Thr Met Val Thr Val Ser Ser
            115                 120
```

<210> SEQ ID NO 42
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 42

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60
```

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Val Ala Arg Pro Arg Ala Ala Phe Asp Ile
            100                 105                 110

Trp Gly Gln Gly Thr Met Val Thr Val Ser Ser
            115                 120
```

```
<210> SEQ ID NO 43
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Val Ala Arg Pro Arg Val Ala Phe Asp Ile
            100                 105                 110

Trp Gly Gln Gly Thr Met Val Thr Val Ser Ser
            115                 120
```

```
<210> SEQ ID NO 44
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Val Ala Arg Pro Arg Gly Ala Phe Ala Ile
            100                 105                 110

Trp Gly Gln Gly Thr Met Val Thr Val Ser Ser
            115                 120
```

<210> SEQ ID NO 45
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 45

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Glu Ile Ser Asn Arg Phe Ser Gly Val Pro
    50                  55                  60

Asp Arg Phe Ser Gly Ser Gly Ala Gly Thr Asn Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Arg Thr Phe Gly Gln Gly Thr Lys Val Glu Ile Lys
            100                 105                 110

<210> SEQ ID NO 46
<211> LENGTH: 328
<212> TYPE: PRT
<213> ORGANISM: Homo sapiens

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 47
<211> LENGTH: 107
<212> TYPE: PRT
<213> ORGANISM: Homo sapiens

<400> SEQUENCE: 47

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 48
<211> LENGTH: 122
<212> TYPE: PRT
<213> ORGANISM: Homo sapiens

<400> SEQUENCE: 48

Gln Val Gln Leu Gln Glu Ser Gly Gly Asp Leu Val Lys Pro Gly Gly
1               5                   10                  15

Phe Leu Arg Leu Ser Cys Ala Ala Ser Gly Phe Thr Phe Asn Thr Tyr
            20                  25                  30

Thr Met Asn Trp Val Arg Gln Ala Pro Gly Lys Gly Leu Glu Trp Leu
        35                  40                  45

Ser Ser Ile Ser Ser Arg Ser Asn Tyr Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Phe Gly Arg Lys Gly Asp Leu Asn Trp Val Phe Asp Tyr Trp
            100                 105                 110

Gly Gln Gly Thr Leu Val Thr Val Ser Ser
        115                 120

<210> SEQ ID NO 49
<211> LENGTH: 110
<212> TYPE: PRT
<213> ORGANISM: Homo sapiens

<400> SEQUENCE: 49

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Ala Gly Ser
                85                  90                  95

Asn Asn Val Val Phe Gly Gly Gly Thr Lys Leu Thr Val Leu
            100                 105                 110

<210> SEQ ID NO 50
<211> LENGTH: 119
<212> TYPE: PRT
<213> ORGANISM: Artificial sequence
<220> FEATURE:
<223> OTHER INFORMATION: an artificially synthesized sequence

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Val Leu Ala Arg Ile Thr Ala Met Asp Tyr Trp Gly Glu Gly
            100                 105                 110

Thr Leu Val Thr Val Ser Ser
        115

<210> SEQ ID NO 51
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 51

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 52
<211> LENGTH: 30
<212> TYPE: PRT
<213> ORGANISM: Homo sapiens

<400> SEQUENCE: 52

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser
            20                  25                  30

<210> SEQ ID NO 53
<211> LENGTH: 14
<212> TYPE: PRT
<213> ORGANISM: Homo sapiens

<400> SEQUENCE: 53

Trp Val Arg Gln Ala Pro Gly Lys Gly Leu Glu Trp Val Ser
1               5                   10

<210> SEQ ID NO 54
<211> LENGTH: 32
<212> TYPE: PRT
<213> ORGANISM: Homo sapiens

<400> SEQUENCE: 54

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 55
<211> LENGTH: 11
<212> TYPE: PRT
<213> ORGANISM: Homo sapiens

<400> SEQUENCE: 55

Trp Gly Gln Gly Thr Leu Val Thr Val Ser Ser
1               5                   10

<210> SEQ ID NO 56
<211> LENGTH: 22
<212> TYPE: PRT
<213> ORGANISM: Homo sapiens

<400> SEQUENCE: 56

```
Gln Ser Ala Leu Thr Gln Pro Pro Ser Ala Ser Gly Ser Pro Gly Gln
1               5                   10                  15

Thr Val Thr Ile Ser Cys
            20
```

<210> SEQ ID NO 57
<211> LENGTH: 15
<212> TYPE: PRT
<213> ORGANISM: Homo sapiens

<400> SEQUENCE: 57

```
Trp Tyr Gln Gln His Pro Gly Lys Ala Pro Lys Leu Met Ile Tyr
1               5                   10                  15
```

<210> SEQ ID NO 58
<211> LENGTH: 32
<212> TYPE: PRT
<213> ORGANISM: Homo sapiens

<400> SEQUENCE: 58

```
Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Phe Cys
            20                  25                  30
```

<210> SEQ ID NO 59
<211> LENGTH: 10
<212> TYPE: PRT
<213> ORGANISM: Homo sapiens

<400> SEQUENCE: 59

```
Phe Gly Gly Gly Thr Lys Leu Thr Val Leu
1               5                   10
```

<210> SEQ ID NO 60
<211> LENGTH: 122
<212> TYPE: PRT
<213> ORGANISM: Homo sapiens

<400> SEQUENCE: 60

```
Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Leu His Asp Arg Asn Trp Val Phe Asp Tyr Trp
            100                 105                 110

Gly Gln Gly Thr Leu Val Thr Val Ser Ser
        115                 120
```

<210> SEQ ID NO 61
<211> LENGTH: 110
<212> TYPE: PRT
<213> ORGANISM: Homo sapiens -continued

<400> SEQUENCE: 61

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Lys Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Arg Ser Tyr Gly
                85                  90                  95

Ala Gly Val Val Phe Gly Gly Gly Thr Lys Leu Thr Val Leu
            100                 105                 110

<210> SEQ ID NO 62
<211> LENGTH: 122
<212> TYPE: PRT
<213> ORGANISM: Homo sapiens

<400> SEQUENCE: 62

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr His
            20                  25                  30

Thr Met Asn Trp Val Arg Gln Ala Pro Gly Lys Gly Leu Glu Trp Val
        35                  40                  45

Ser Ser Ile Ser Ser Arg Ser Ser Tyr Ile His Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Lys Leu Gly Glu Arg Asn Trp Val Phe Asp Tyr Trp
            100                 105                 110

Gly Gln Gly Thr Leu Val Thr Val Ser Ser
        115                 120

<210> SEQ ID NO 63
<211> LENGTH: 110
<212> TYPE: PRT
<213> ORGANISM: Homo sapiens

<400> SEQUENCE: 63

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Lys Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Val Arg Ser Asp Gly
                85                  90                  95

His Gly Pro Met Phe Gly Gly Gly Thr Lys Leu Thr Val Leu
            100                 105                 110

<210> SEQ ID NO 64
<211> LENGTH: 122
<212> TYPE: PRT
<213> ORGANISM: Homo sapiens

<400> SEQUENCE: 64

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met Asn Trp Val Arg Gln Ala Pro Gly Lys Gly Leu Glu Trp Val
        35                  40                  45

Ser Ser Ile Ser Ser Arg Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Leu Gly Met Asn Trp Val Phe Asp Tyr Trp
            100                 105                 110

Gly Gln Gly Thr Leu Val Thr Val Ser Ser
        115                 120

<210> SEQ ID NO 65
<211> LENGTH: 110
<212> TYPE: PRT
<213> ORGANISM: Homo sapiens

<400> SEQUENCE: 65

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Ser Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Arg Ser Ser Ser
                85                  90                  95

Met Asn Val Leu Phe Gly Gly Gly Thr Lys Leu Thr Val Leu
            100                 105                 110

<210> SEQ ID NO 66
<211> LENGTH: 122
<212> TYPE: PRT
<213> ORGANISM: Homo sapiens

<400> SEQUENCE: 66

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr

```
            20                  25                  30
Thr Met Asn Trp Val Arg Gln Ala Pro Gly Lys Gly Leu Glu Trp Val
        35                  40                  45
Ser Ser Ile Ser Ser Arg Ser Asn Tyr Ala His Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Tyr Gly Arg Leu Gly Asp Arg Asn Trp Val Phe Asp Tyr Trp
            100                 105                 110
Gly Gln Gly Thr Leu Val Thr Val Ser Ser
            115                 120
```

<210> SEQ ID NO 67
<211> LENGTH: 110
<212> TYPE: PRT
<213> ORGANISM: Homo sapiens

<400> SEQUENCE: 67

```
Gln Ser Ala Leu Thr Gln Pro Pro Ser Ala Ser Gly Ser Pro Gly Gln
1               5                   10                  15
Thr Val Thr Ile Ser Cys Thr Gly Thr Ser Thr Asp Val Gly Ala Tyr
            20                  25                  30
Asn Tyr Val Ser Trp Tyr Gln Gln His Pro Gly Lys Ala Pro Lys Leu
        35                  40                  45
Met Ile Tyr Lys Val Ser Lys Lys Pro Ser Gly Val Pro Asp Arg Phe
    50                  55                  60
Ser Gly Ser Lys Ser Gly Asn Thr Ala Ser Leu Thr Val Ser Gly Leu
65                  70                  75                  80
Gln Ala Glu Asp Glu Ala Asp Tyr Phe Cys Ser Leu Arg Ala Ala Thr
                85                  90                  95
Thr Gly Val Leu Phe Gly Gly Gly Thr Lys Leu Thr Val Leu
            100                 105                 110
```

<210> SEQ ID NO 68
<211> LENGTH: 122
<212> TYPE: PRT
<213> ORGANISM: Homo sapiens

<400> SEQUENCE: 68

```
Glu Val Gln Leu Val Glu Ser Gly Gly Asp Leu Val Lys Pro Gly Gly
1               5                   10                  15
Gly Leu Arg Leu Ser Cys Ala Ala Ser Gly Phe Thr Phe Ser Ser Tyr
            20                  25                  30
Thr Met Asn Trp Val Arg Gln Ala Pro Gly Lys Gly Leu Glu Trp Val
        35                  40                  45
Ser Ser Ile Ser Ser Arg Ser Gly Tyr Ala Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Phe Gly Ala Leu Asn Thr Leu Asn Trp Val Phe Asp Tyr Trp
            100                 105                 110
Gly Gln Gly Thr Leu Val Thr Val Ser Ser
```

-continued

```
            115                 120

<210> SEQ ID NO 69
<211> LENGTH: 110
<212> TYPE: PRT
<213> ORGANISM: Homo sapiens

<400> SEQUENCE: 69

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Arg Thr Ala Asn
                85                  90                  95

Ala Gly Val Leu Phe Gly Gly Gly Thr Lys Leu Thr Val Leu
            100                 105                 110

<210> SEQ ID NO 70
<211> LENGTH: 122
<212> TYPE: PRT
<213> ORGANISM: Homo sapiens

<400> SEQUENCE: 70

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Ser Tyr Ala Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Leu Asn Ser His Asn Trp Val Phe Asp Tyr Trp
            100                 105                 110

Gly Gln Gly Thr Leu Val Thr Val Ser Ser
        115                 120

<210> SEQ ID NO 71
<211> LENGTH: 110
<212> TYPE: PRT
<213> ORGANISM: Homo sapiens

<400> SEQUENCE: 71

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45
```

```
Met Ile Tyr Gln Gly Ser Lys Pro Ser Gly Val Pro Asp Arg Phe
        50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Thr Arg Ala Thr Thr
                 85                  90                  95

Lys Gly Val Leu Phe Gly Gly Gly Thr Lys Leu Thr Val Leu
            100                 105                 110
```

<210> SEQ ID NO 72
<211> LENGTH: 122
<212> TYPE: PRT
<213> ORGANISM: Homo sapiens

<400> SEQUENCE: 72

```
Glu Val Gln Leu Val Glu Ser Gly Gly Asp Leu Val Lys Pro Gly Gly
 1               5                  10                  15

Gly Leu Arg Leu Ser Cys Ala Ala Ser Gly Phe Thr Phe Ser Gly Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Ser Tyr Ile Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Gly Ala Leu Gly Gln Arg Asn Trp Val Phe Asp Tyr Trp
            100                 105                 110

Gly Gln Gly Thr Leu Val Thr Val Ser Ser
            115                 120
```

<210> SEQ ID NO 73
<211> LENGTH: 109
<212> TYPE: PRT
<213> ORGANISM: Homo sapiens

<400> SEQUENCE: 73

```
Gln Ser Ala Leu Thr Gln Pro Pro Ser Ala Ser Gly Ser Pro Gly Gln
 1               5                  10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Thr Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Ser Arg Ser Ile Lys
                 85                  90                  95

His Pro Val Phe Gly Gly Gly Thr Lys Leu Thr Val Leu
            100                 105
```

<210> SEQ ID NO 74
<211> LENGTH: 122
<212> TYPE: PRT
<213> ORGANISM: Homo sapiens

<400> SEQUENCE: 74

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Leu His Asp Arg Asn Trp Val Phe Asp Tyr Trp
            100                 105                 110

Gly Gln Gly Thr Leu Val Thr Val Ser Ser
        115                 120

<210> SEQ ID NO 75
<211> LENGTH: 110
<212> TYPE: PRT
<213> ORGANISM: Homo sapiens

<400> SEQUENCE: 75

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Arg Ser Tyr Gly
                85                  90                  95

Ala Gly Val Val Phe Gly Gly Gly Thr Lys Leu Thr Val Leu
            100                 105                 110

<210> SEQ ID NO 76
<211> LENGTH: 122
<212> TYPE: PRT
<213> ORGANISM: Homo sapiens

<400> SEQUENCE: 76

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser His
            20                  25                  30

Thr Met Asn Trp Val Arg Gln Ala Pro Gly Lys Gly Leu Glu Trp Val
        35                  40                  45

Ser Ser Ile Ser Ser Arg Ser Gly Tyr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Phe Gly Lys Leu Asn His Met Asn Trp Val Phe Asp Tyr Trp
            100                 105                 110

Gly Gln Gly Thr Leu Val Thr Val Ser Ser
        115                 120

<210> SEQ ID NO 77
<211> LENGTH: 110
<212> TYPE: PRT
<213> ORGANISM: Homo sapiens

<400> SEQUENCE: 77

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Thr Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Arg Ala Ile Thr
                85                  90                  95

Arg Gly Val Ala Phe Gly Gly Gly Thr Lys Leu Thr Val Leu
            100                 105                 110

<210> SEQ ID NO 78
<211> LENGTH: 20
<212> TYPE: DNA
<213> ORGANISM: Artificial sequence
<220> FEATURE:
<223> OTHER INFORMATION: an artificially synthesized primer sequence

<400> SEQUENCE: 78
cgcaacgcaa ttaatgtgag                                            20

<210> SEQ ID NO 79
<211> LENGTH: 18
<212> TYPE: DNA
<213> ORGANISM: Artificial sequence
<220> FEATURE:
<223> OTHER INFORMATION: an artificially synthesized primer sequence

<400> SEQUENCE: 79
gcgtcacact ttgctatg                                              18

<210> SEQ ID NO 80
<211> LENGTH: 21
<212> TYPE: DNA
<213> ORGANISM: Artificial sequence
<220> FEATURE:
<223> OTHER INFORMATION: an artificially synthesized primer sequence

<400> SEQUENCE: 80
tgagttccac gacaccgtca c                                          21

<210> SEQ ID NO 81
<211> LENGTH: 25
<212> TYPE: DNA
<213> ORGANISM: Artificial sequence
<220> FEATURE:
<223> OTHER INFORMATION: an artificially synthesized primer sequence

<400> SEQUENCE: 81
actcgcggcc cagccggcca tggcg                25

<210> SEQ ID NO 82
<211> LENGTH: 27
<212> TYPE: DNA
<213> ORGANISM: Artificial sequence
<220> FEATURE:
<223> OTHER INFORMATION: an artificially synthesized primer sequence

<400> SEQUENCE: 82
taggacggtc agcttggtac ctccgcc              27

<210> SEQ ID NO 83
<211> LENGTH: 18
<212> TYPE: DNA
<213> ORGANISM: Artificial sequence
<220> FEATURE:
<223> OTHER INFORMATION: an artificially synthesized primer sequence

<400> SEQUENCE: 83
gcgcagccgg cgctagcc                        18

<210> SEQ ID NO 84
<211> LENGTH: 18
<212> TYPE: DNA
<213> ORGANISM: Artificial sequence
<220> FEATURE:
<223> OTHER INFORMATION: an artificially synthesized primer sequence

<400> SEQUENCE: 84
tgggcccttg gtcgacgc                        18

<210> SEQ ID NO 85
<211> LENGTH: 120
<212> TYPE: PRT
<213> ORGANISM: Artificial sequence
<220> FEATURE:
<223> OTHER INFORMATION: an artificially synthesized sequence

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Val Ser Gly Ile Asp Leu Thr Asn Tyr
            20                  25                  30

Ala Met Gly Trp Val Arg Gln Pro Pro Gly Lys Gly Leu Glu Trp Ile
        35                  40                  45

Gly Ile Ile Gly Ala Asp Ser Ser Thr Trp Tyr Pro Ser Trp Val Lys
    50                  55                  60

Gly Arg Phe Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Gly Arg Phe Val Gly Tyr Thr Asn Ala Phe Asp Pro Trp Gly Gln
            100                 105                 110

Gly Thr Leu Val Thr Val Ser Ser
        115                 120

<210> SEQ ID NO 86

```
<211> LENGTH: 113
<212> TYPE: PRT
<213> ORGANISM: Artificial sequence
<220> FEATURE:
<223> OTHER INFORMATION: an artificially synthesized sequence

<400> SEQUENCE: 86

Asp Ile Gln Leu Thr Gln Ser Pro Ser Ser Leu Ser Ala Ser Val Gly
1               5                   10                  15

Asp Arg Val Thr Ile Thr Cys Gln Ser Ser Gln Ser Val Trp Asn Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Thr Leu Ala Ser Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys His Gly Ser Tyr Ala Asn
                85                  90                  95

Ser Gly Trp Tyr Asp Asn Ala Phe Gly Gly Gly Thr Glu Val Val Val
            100                 105                 110

Lys

<210> SEQ ID NO 87
<211> LENGTH: 30
<212> TYPE: PRT
<213> ORGANISM: Artificial sequence
<220> FEATURE:
<223> OTHER INFORMATION: an artificially synthesized sequence

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 88
<211> LENGTH: 14
<212> TYPE: PRT
<213> ORGANISM: Artificial sequence
<220> FEATURE:
<223> OTHER INFORMATION: an artificially synthesized sequence

<400> SEQUENCE: 88

Trp Val Arg Gln Ala Pro Gly Gln Gly Leu Glu Trp Met Gly
1               5                   10

<210> SEQ ID NO 89
<211> LENGTH: 32
<212> TYPE: PRT
<213> ORGANISM: Artificial sequence
<220> FEATURE:
<223> OTHER INFORMATION: an artificially synthesized sequence

<400> SEQUENCE: 89

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 90
<211> LENGTH: 11
```

```
<212> TYPE: PRT
<213> ORGANISM: Artificial sequence
<220> FEATURE:
<223> OTHER INFORMATION: an artificially synthesized sequence

<400> SEQUENCE: 90

Trp Gly Gln Gly Thr Leu Val Thr Val Ser Ser
1               5                   10

<210> SEQ ID NO 91
<211> LENGTH: 23
<212> TYPE: PRT
<213> ORGANISM: Artificial sequence
<220> FEATURE:
<223> OTHER INFORMATION: an artificially synthesized sequence

<400> SEQUENCE: 91

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 92
<211> LENGTH: 15
<212> TYPE: PRT
<213> ORGANISM: Artificial sequence
<220> FEATURE:
<223> OTHER INFORMATION: an artificially synthesized sequence

<400> SEQUENCE: 92

Trp Tyr Leu Gln Lys Pro Gly Gln Ser Pro Gln Leu Leu Ile Tyr
1               5                   10                  15

<210> SEQ ID NO 93
<211> LENGTH: 32
<212> TYPE: PRT
<213> ORGANISM: Artificial sequence
<220> FEATURE:
<223> OTHER INFORMATION: an artificially synthesized sequence

<400> SEQUENCE: 93

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 94
<211> LENGTH: 15
<212> TYPE: PRT
<213> ORGANISM: Artificial sequence
<220> FEATURE:
<223> OTHER INFORMATION: an artificially synthesized sequence

<400> SEQUENCE: 94

Trp Tyr Leu Gln Lys Pro Gly Gln Ser Pro Gln Leu Leu Ile Tyr
1               5                   10                  15

<210> SEQ ID NO 95
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 95

Gln Val Gln Leu Val Gln Ser Gly Ala Glu Val Lys Lys Pro Gly Ser
```

-continued

```
                1               5                  10                  15
Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Val Ala Arg Pro Gly Ala Phe Asp Ile
                100                 105                 110

Trp Gly Gln Gly Thr Leu Val Thr Val Ser Ser
            115                 120

<210> SEQ ID NO 96
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 96

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asp Gly Asn Thr Tyr Leu Ser Trp Tyr Leu Gln Lys Pro Gly Gln Ser
            35                  40                  45

Pro Gln Leu Leu Ile Tyr Glu Ile Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Arg Thr Phe Gly Gln Gly Thr Lys Val Glu Ile Lys
                100                 105                 110

<210> SEQ ID NO 97
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 97

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asp Gly Asn Thr Tyr Leu Ser Trp Tyr Leu Gln Lys Pro Gly Gln Ser
            35                  40                  45

Pro Gln Leu Leu Ile Tyr Glu Ile Ser Asn Arg Phe Tyr Gly Val Pro
        50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
         85                  90                  95

Thr Gln Phe Pro Arg Thr Phe Gly Gln Gly Thr Lys Val Glu Ile Lys
    100                 105                 110
```

<210> SEQ ID NO 98
<211> LENGTH: 25
<212> TYPE: DNA
<213> ORGANISM: Artificial sequence
<220> FEATURE:
<223> OTHER INFORMATION: an artificially synthesized sequence

<400> SEQUENCE: 98
tgaagagggg tattaataat gtatc         25

<210> SEQ ID NO 99
<211> LENGTH: 18
<212> TYPE: DNA
<213> ORGANISM: Artificial sequence
<220> FEATURE:
<223> OTHER INFORMATION: an artificially synthesized sequence

<400> SEQUENCE: 99
ccagaggtgc tcttggag         18

<210> SEQ ID NO 100
<211> LENGTH: 106
<212> TYPE: PRT
<213> ORGANISM: Artificial sequence
<220> FEATURE:
<223> OTHER INFORMATION: an artificially synthesized sequence

<400> SEQUENCE: 100

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 101
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 101

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Tyr Phe Ser Pro Tyr
            20                  25                  30

Ala Ile Ser Trp Val Arg Gln Ala Pro Gly Gln Gly Leu Glu Trp Met
        35                  40                  45
```

Gly Ala Ile Leu Pro Ile Leu Ser Ala Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Pro Val Ser Gln Thr Pro His Gly Ala Phe Asp Ile
                100                 105                 110

Trp Gly Gln Gly Thr Leu Val Thr Val Ser Ser
            115                 120

<210> SEQ ID NO 102
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 102

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Pro
                20                  25                  30

Ser Gly Asn Thr Tyr Leu Ser Trp Tyr Leu Gln Lys Pro Gly Gln Ser
            35                  40                  45

Pro Gln Leu Leu Ile Tyr Glu Ile Ser Arg Arg Phe Tyr Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Val Thr Phe Pro Arg Thr Phe Gly Gln Gly Thr Lys Val Glu Ile Lys
                100                 105                 110

<210> SEQ ID NO 103
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Val Ala Arg Pro Arg Gly Ala Phe Asp Ile
                100                 105                 110

Trp Gly Gln Gly Thr Leu Val Thr Val Ser Ser

<210> SEQ ID NO 104
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 104

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Pro Lys
            20                  25                  30

Gly Gly Asn Thr Phe Leu Ser Trp Tyr Leu Gln Lys Pro Gly Gln Ser
        35                  40                  45

Pro Gln Leu Leu Ile Tyr Glu Ile Ala Asn Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gly Val Phe Pro Arg Thr Phe Gly Gln Gly Thr Lys Val Glu Ile Lys
            100                 105                 110

<210> SEQ ID NO 105
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Val Phe Ser Arg Tyr
            20                  25                  30

Gly Ile Ser Trp Val Arg Gln Ala Pro Gly Gln Gly Leu Glu Trp Met
        35                  40                  45

Gly Gly Ile Leu Pro Ile His Gly Ala Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Pro Val Leu Gly Pro Pro His Gly Ala Phe Asp Ile
            100                 105                 110

Trp Gly Gln Gly Thr Leu Val Thr Val Ser Ser
        115                 120

<210> SEQ ID NO 106
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 106

Asp Ile Val Met Thr Gln Ser Pro Leu Ser Leu Pro Val Thr Pro Gly
1               5                   10                  15

```
Glu Pro Ala Ser Ile Ser Cys Arg Ser Ser Gln Ser Leu Val Gly Leu
            20                  25                  30

Gly Pro Asn Thr Phe Leu Ser Trp Tyr Leu Gln Lys Pro Gly Gln Ser
        35                  40                  45

Pro Gln Leu Leu Ile Tyr Glu Ile Ser Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Met Phe Pro Arg Thr Phe Gly Gln Gly Thr Lys Val Glu Ile Lys
            100                 105                 110
```

<210> SEQ ID NO 107
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 107

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Thr Pro Ile Ala Gly Ala Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Gln Ala Asp Pro His Gly Ala Phe Asp Ile
            100                 105                 110

Trp Gly Gln Gly Thr Leu Val Thr Val Ser Ser
        115                 120
```

<210> SEQ ID NO 108
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 108

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Gln Ser
            20                  25                  30

Tyr Gly Asn Thr Phe Leu Ser Trp Tyr Leu Gln Lys Pro Gly Gln Ser
        35                  40                  45

Pro Gln Leu Leu Ile Tyr Glu Ile Arg Arg Lys Phe Tyr Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

```
                      85                  90                  95

Ser Glu Phe Pro Arg Thr Phe Gly Gln Gly Thr Lys Val Glu Ile Lys
                100                 105                 110

<210> SEQ ID NO 109
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Arg Tyr
                20                  25                  30

Ala Ile Ser Trp Val Arg Gln Ala Pro Gly Gln Gly Leu Glu Trp Met
            35                  40                  45

Gly Ala Ile Ser Pro Ile Tyr Gly Ala Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Phe Asp Ser Pro His Gly Ala Phe Asp Ile
                100                 105                 110

Trp Gly Gln Gly Thr Leu Val Thr Val Ser Ser
            115                 120

<210> SEQ ID NO 110
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asp His
                20                  25                  30

Tyr Arg Asn Thr Tyr Val Ser Trp Tyr Leu Gln Lys Pro Gly Gln Ser
            35                  40                  45

Pro Gln Leu Leu Ile Tyr Glu Ile Tyr Lys Arg Phe Tyr Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Asp Phe Pro Arg Thr Phe Gly Gln Gly Thr Lys Val Glu Ile Lys
                100                 105                 110

<210> SEQ ID NO 111
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 111
```

Gln Val Gln Leu Val Gln Ser Gly Ala Glu Lys Lys Pro Gly Ser
1               5                   10                  15

Ser Val Lys Val Ser Cys Lys Ala Ser Gly Gly Arg Phe Ser Asp Tyr
                20                  25                  30

Ala Ile Ser Trp Val Arg Gln Ala Pro Gly Gln Gly Leu Glu Trp Met
            35                  40                  45

Gly Thr Val Leu Pro Ile Glu Ser Ser Ala Ser Tyr Ala Gln Lys Phe
        50                  55                  60

Leu Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Tyr Ala Ser Pro His Gly Ala Phe Asp Ile
                100                 105                 110

Trp Gly Gln Gly Thr Leu Val Thr Val Ser Ser
            115                 120

<210> SEQ ID NO 112
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 112

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Gly Gly
                20                  25                  30

Asp Arg Asn Thr Phe Leu Ser Trp Tyr Leu Gln Arg Pro Gly Gln Ser
            35                  40                  45

Pro Gln Leu Leu Ile Tyr Glu Val Ala Arg Arg Phe Tyr Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Asp Glu Phe Pro Arg Thr Phe Gly Gln Gly Thr Lys Val Glu Ile Lys
                100                 105                 110

<210> SEQ ID NO 113
<211> LENGTH: 328
<212> TYPE: PRT
<213> ORGANISM: Artificial sequence
<220> FEATURE:
<223> OTHER INFORMATION: an artificially synthesized sequence

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr

```
                65                  70                  75                  80
        Tyr Ile Cys Asn Val Asn His Lys Pro Ser Asn Thr Lys Val Asp Lys
                        85                  90                  95

Lys Val Glu Pro Lys Ser Cys Asp Lys Thr His Thr Cys Pro Pro Cys
                        100                 105                 110

Pro Ala Pro Glu Leu Leu Gly Pro Ser Val Phe Leu Phe Pro Pro
                        115                 120                 125

Lys Pro Lys Asp Thr Leu Met Ile Ser Arg Thr Pro Glu Val Thr Cys
                130                 135                 140

Val Val Val Asp Val Ser His Glu Glu Pro Glu Val Lys Phe Asn Trp
        145                 150                 155                 160

Tyr Val Asp Gly Val Glu Val His Asn Ala Lys Thr Lys Pro Arg Glu
                        165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                        195                 200                 205

Asp Ala Leu Pro Met Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
        225                 230                 235                 240

Leu Thr Lys Asn Gln Val Ser Leu Thr Cys Leu Val Lys Gly Phe Tyr
                        245                 250                 255

Pro Ser Asp Ile Ala Val Glu Trp Glu Ser Asn Gly Gln Pro Glu Asn
                        260                 265                 270

Asn Tyr Lys Thr Thr Pro Pro Tyr Leu Asp Ser Asp Gly Ser Phe Phe
                        275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
        305                 310                 315                 320

Gln Glu Ser Leu Ser Leu Ser Pro
                        325

<210> SEQ ID NO 114
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 114

Gln Val Gln Leu Val Gln Ser Gly Ala Glu Val Lys Lys Pro Gly Ser
        1               5                   10                  15

Ser Val Lys Val Ser Cys Lys Ala Ser Gly Gly His Phe Ser Ile Tyr
                        20                  25                  30

Gly Ile Ser Trp Val Arg Gln Ala Pro Gly Gln Gly Leu Glu Trp Met
                        35                  40                  45

Gly Phe Ile Leu Pro Ile Ser Gly Gly Ala Arg Tyr Ala Gln Lys Phe
                50                  55                  60

Gln Gly Arg Val Thr Ile Thr Ala Asp Glu Ser Thr Ser Thr Ala Tyr
        65                  70                  75                  80

Met Glu Leu Ser Ser Leu Arg Ser Glu Asp Thr Ala Val Tyr Tyr Cys
                        85                  90                  95

Ala Arg Asp Ala Pro Val Val Ala Met Pro His Gly Ala Phe Asp Ile
```

```
                    100                 105                 110

Trp Gly Gln Gly Thr Leu Val Thr Val Ser Ser
            115                 120

<210> SEQ ID NO 115
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 115

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Gly Thr
            20                  25                  30

Arg Ala Asn Thr Tyr Leu Ser Trp Tyr Leu Gln Lys Pro Gly Gln Ser
        35                  40                  45

Pro Gln Leu Leu Ile Tyr Glu Ile Ser Arg Lys Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Val Glu Phe Pro Arg Thr Phe Gly Gln Gly Thr Lys Val Glu Ile Lys
            100                 105                 110

<210> SEQ ID NO 116
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Ser Leu Tyr
            20                  25                  30

Arg Ile Ser Trp Val Arg Gln Ala Pro Gly Gln Gly Leu Glu Trp Met
        35                  40                  45

Gly Ala Val Leu Pro Ile Ala Gly Arg Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Leu Met Ser Pro His Gly Ala Phe Asp Ile
            100                 105                 110

Trp Gly Gln Gly Thr Leu Val Thr Val Ser Ser
        115                 120

<210> SEQ ID NO 117
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 117
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ile Asp
            20                  25                  30

Ser Gly Asn Thr Phe Leu Ser Trp Tyr Arg Gln Lys Pro Gly Gln Ser
        35                  40                  45

Pro Gln Leu Leu Ile Tyr Glu Ile Thr Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Lys Thr Phe Pro Arg Thr Phe Gly Gln Gly Thr Lys Val Glu Ile Lys
                100                 105                 110
```

<210> SEQ ID NO 118
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 118

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Ser Leu Tyr
            20                  25                  30

Arg Ile Ser Trp Val Arg Gln Ala Pro Gly Gln Gly Leu Glu Trp Met
        35                  40                  45

Gly Gly Val Leu Pro Ile Thr Gly Arg Ala Trp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Gly Tyr Ala Pro His Gly Ala Phe Asp Ile
                100                 105                 110

Trp Gly Gln Gly Thr Leu Val Thr Val Ser Ser
                115                 120
```

<210> SEQ ID NO 119
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 119

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Thr Gln
            20                  25                  30

Ser Gly Asn Thr Tyr Leu Ser Trp Tyr Leu Gln Lys Pro Gly Gln Ser
        35                  40                  45

Pro Gln Leu Leu Ile Tyr Glu Ile Ser Lys Arg Phe Tyr Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Met Gln Ala
                    85                  90                  95

Leu Val Phe Pro Arg Thr Phe Gly Gln Gly Thr Lys Val Glu Ile Lys
                100                 105                 110
```

<210> SEQ ID NO 120
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 120

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Ser Leu Tyr
                20                  25                  30

Arg Ile Ser Trp Val Arg Gln Ala Pro Gly Gln Gly Leu Glu Trp Met
            35                  40                  45

Gly Ser Val Leu Pro Ile Thr Ser Phe Ala Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Phe Ala Arg Pro His Gly Ala Phe Asp Ile
                100                 105                 110

Trp Gly Gln Gly Thr Leu Val Thr Val Ser Ser
            115                 120
```

<210> SEQ ID NO 121
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 121

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asp Gly
                20                  25                  30

Asn Gly Asn Thr Phe Leu Ser Trp Tyr Leu Gln Lys Pro Gly Gln Ser
            35                  40                  45

Pro Gln Leu Leu Ile Tyr Glu Ile Arg His Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Asn Phe Pro Arg Thr Phe Gly Gln Gly Thr Lys Val Glu Ile Lys
                100                 105                 110
```

<210> SEQ ID NO 122
<211> LENGTH: 123
<212> TYPE: PRT
<213> ORGANISM: Artificial sequence
<220> FEATURE:

<223> OTHER INFORMATION: an artificially synthesized sequence

<400> SEQUENCE: 122

Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Ser Leu Tyr
            20                  25                  30

Gly Ile Ser Trp Val Arg Gln Ala Pro Gly Gln Gly Leu Glu Trp Met
        35                  40                  45

Gly Ser Val Leu Pro Ile Asn Ser Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Val His His Pro His Gly Ala Phe Asp Ile
            100                 105                 110

Trp Gly Gln Gly Thr Leu Val Thr Val Ser Ser
        115                 120

<210> SEQ ID NO 123
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 123

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Ala
            20                  25                  30

Arg Ser Asn Thr Phe Leu Ser Trp Tyr Leu Gln Lys Pro Gly Gln Ser
        35                  40                  45

Pro Gln Leu Leu Ile Tyr Glu Ile His Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Asn Thr Phe Pro Arg Thr Phe Gly Gln Gly Thr Lys Val Glu Ile Lys
            100                 105                 110

<210> SEQ ID NO 124
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Phe Ser Leu Tyr
            20                  25                  30

Arg Ile Ser Trp Val Arg Gln Ala Pro Gly Gln Gly Leu Glu Trp Met
        35                  40                  45

Gly Gly Val Leu Pro Ile Thr Gly His Ala Leu Tyr Ala Gln Lys Phe

```
                 50                   55                   60
Gln Gly Arg Val Thr Ile Thr Ala Asp Glu Ser Thr Ser Thr Ala Tyr
 65                   70                   75                   80

Met Glu Leu Ser Ser Leu Arg Ser Glu Asp Thr Ala Val Tyr Tyr Cys
                     85                   90                   95

Ala Arg Asp Ser Pro Val Val His Pro His Gly Ala Phe Asp Ile
                100                  105                  110

Trp Gly Gln Gly Thr Leu Val Thr Val Ser Ser
            115                  120
```

<210> SEQ ID NO 125
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 125

```
Asp Ile Val Met Thr Gln Ser Pro Leu Ser Leu Pro Val Thr Pro Gly
  1               5                   10                  15

Glu Pro Ala Ser Ile Ser Cys Arg Ser Ser Gln Ser Leu Val Gly Gln
                 20                  25                  30

Gly Glu Asn Thr Phe Leu Ser Trp Tyr Leu Gln Lys Pro Gly Gln Ser
             35                  40                  45

Pro Gln Leu Leu Ile Tyr Glu Val Gly Arg Lys Phe Tyr Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Tyr Gln Phe Pro Arg Thr Phe Gly Gln Gly Thr Lys Val Glu Ile Lys
                100                  105                 110
```

<210> SEQ ID NO 126
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 126

```
Gln Val Gln Leu Val Gln Ser Gly Ala Glu Val Lys Lys Pro Gly Ser
  1               5                   10                  15

Ser Val Lys Val Ser Cys Lys Ala Ser Gly Gly Glu Phe Ser Arg Tyr
                 20                  25                  30

Gly Ile Ser Trp Val Arg Gln Ala Pro Gly Gln Gly Leu Glu Trp Met
             35                  40                  45

Gly Met Val Leu Pro Ile Phe Gly Tyr Ala Trp Tyr Ala Gln Lys Phe
 50                  55                  60

His Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asn Pro Val Tyr Ala Ala Pro His Gly Ala Phe Asp Ile
                100                  105                 110

Trp Gly Gln Gly Thr Leu Val Thr Val Ser Ser
            115                  120
```

<210> SEQ ID NO 127
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 127

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ile Asp
            20                  25                  30

Ser Gly Asn Thr Phe Leu Ser Trp Tyr Arg Gln Lys Pro Gly Gln Ser
        35                  40                  45

Pro Gln Leu Leu Ile Tyr Glu Ile Thr Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Lys Thr Phe Pro Arg Thr Phe Gly Gln Gly Thr Lys Val Glu Ile Lys
            100                 105                 110
```

<210> SEQ ID NO 128
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 128

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Met Phe Ser Ser Tyr
            20                  25                  30

Ala Ile Ser Trp Val Arg Gln Ala Pro Gly Gln Gly Leu Glu Trp Met
        35                  40                  45

Gly Ala Ile Val Pro Ile Thr Gly Leu Ala Leu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Pro Val Tyr Ala Tyr Pro His Gly Ala Phe Asp Ile
            100                 105                 110

Trp Gly Gln Gly Thr Leu Val Thr Val Ser Ser
        115                 120
```

<210> SEQ ID NO 129
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 129

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asp His
```

```
                20                  25                  30
Tyr Arg Asn Thr Tyr Val Ser Trp Tyr Leu Gln Lys Pro Gly Gln Ser
                35                  40                  45

Pro Gln Leu Leu Ile Tyr Glu Ile Tyr Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Asp Phe Pro Arg Thr Phe Gly Gln Gly Thr Lys Val Glu Ile Lys
                100                 105                 110

<210> SEQ ID NO 130
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Gly Tyr
                20                  25                  30

Gly Ile Ser Trp Val Arg Gln Ala Pro Gly Gln Gly Leu Glu Trp Met
                35                  40                  45

Gly Ile Leu Glu Pro Ile Leu Gly Ala Ala Phe Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Pro Val Val Glu Ile Pro His Gly Ala Phe Asp Ile
                100                 105                 110

Trp Gly Gln Gly Thr Leu Val Thr Val Ser Ser
        115                 120

<210> SEQ ID NO 131
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 131

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
                20                  25                  30

Arg Ser Asn Thr Phe Val Ser Trp Tyr Leu Gln Lys Pro Gly Gln Ser
                35                  40                  45

Pro Gln Leu Leu Ile Tyr Glu Ile Phe Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

```
Gln Gln Phe Pro Arg Thr Phe Gly Gln Gly Thr Lys Val Glu Ile Lys
                100                 105                 110
```

<210> SEQ ID NO 132
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 132

```
Gln Val Gln Leu Val Gln Ser Gly Ala Glu Val Lys Lys Pro Gly Ser
1               5                   10                  15

Ser Val Lys Val Ser Cys Lys Ala Ser Gly Ile Phe Ser Glu Tyr
            20                  25                  30

Gly Ile Ser Trp Val Arg Gln Ala Pro Gly Gln Gly Leu Glu Trp Met
        35                  40                  45

Gly Ile Phe Ala Pro Ile Leu Gly Ile Ala Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Met Pro Val Phe Asp Ala Pro His Gly Ala Phe Asp Ile
                100                 105                 110

Trp Gly Gln Gly Thr Leu Val Thr Val Ser Ser
            115                 120
```

<210> SEQ ID NO 133
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 133

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asp Asn
            20                  25                  30

Glu Gly Asn Thr Tyr Leu Ser Trp Tyr Leu Gln Lys Pro Gly Gln Ser
        35                  40                  45

Pro Gln Leu Leu Ile Tyr Glu Ile Gly Ser Leu Phe Tyr Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Lys Glu Phe Pro Arg Thr Phe Gly Gln Gly Thr Lys Val Glu Ile Lys
                100                 105                 110
```

<210> SEQ ID NO 134
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 134

```
Gln Val Gln Leu Val Gln Ser Gly Ala Glu Val Lys Lys Pro Gly Ser
```

```
  1               5                  10                 15
Ser Val Lys Val Ser Cys Lys Ala Ser Gly Gly Arg Phe Ser Tyr
            20                  25                 30
Ala Ile Ser Trp Val Arg Gln Ala Pro Gly Gln Gly Leu Glu Trp Met
            35                  40                 45
Gly Leu Val Glu Pro Ile Trp Gly Ile Ala Ser Tyr Ala Gln Lys Phe
        50                  55                 60
Gln Gly Arg Val Thr Ile Thr Ala Asp Glu Ser Thr Ser Thr Ala Tyr
65                  70                  75                 80
Met Glu Leu Ser Ser Leu Arg Ser Gly Asp Thr Ala Val Tyr Tyr Cys
                85                  90                 95
Ala Arg Asp Ala Pro Val Phe Lys Arg Pro His Gly Ala Phe Asp Ile
            100                 105                110
Trp Gly Gln Gly Thr Leu Val Thr Val Ser Ser
            115                 120
```

<210> SEQ ID NO 135
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 135

```
Asp Ile Val Met Thr Gln Ser Pro Leu Ser Leu Pro Val Thr Pro Gly
1               5                  10                 15
Glu Pro Ala Ser Ile Ser Cys Arg Ser Ser Gln Ser Leu Val Ser Ser
            20                  25                 30
Gly Gly Asn Thr Phe Leu Ser Trp Tyr Leu Gln Lys Pro Gly Gln Ser
        35                  40                 45
Pro Gln Leu Leu Ile Tyr Glu Ile Gln Thr Arg Phe Tyr Gly Val Pro
    50                  55                 60
Asp Arg Phe Ser Gly Ser Gly Ser Gly Thr Asp Phe Thr Leu Lys Ile
65                  70                  75                 80
Ser Arg Val Glu Ala Glu Asp Val Gly Val Tyr Tyr Cys Met Gln Ala
                85                  90                 95
His Gln Phe Pro Arg Thr Phe Gly Gln Gly Thr Lys Val Glu Ile Lys
            100                 105                110
```

<210> SEQ ID NO 136
<211> LENGTH: 123
<212> TYPE: PRT
<213> ORGANISM: Artificial sequence
<220> FEATURE:
<223> OTHER INFORMATION: an artificially synthesized sequence

<400> SEQUENCE: 136

```
Gln Val Gln Leu Val Gln Ser Gly Ala Glu Val Lys Lys Pro Gly Ser
1               5                  10                 15
Ser Val Lys Val Ser Cys Lys Ala Ser Gly Gly Trp Phe Ser Lys Tyr
            20                  25                 30
Gly Ile Ser Trp Val Arg Gln Ala Pro Gly Gln Gly Leu Glu Trp Met
            35                  40                 45
Gly Ile Val Val Pro Ile Glu Gly Ile Ala Leu Tyr Ala Gln Lys Phe
        50                  55                 60
Gln Gly Arg Val Thr Ile Thr Ala Asp Glu Ser Thr Ser Thr Ala Tyr
65                  70                  75                 80
```

```
Met Glu Leu Ser Ser Leu Arg Ser Glu Asp Thr Ala Val Tyr Tyr Cys
                85                  90                  95

Ala Arg Asp Ser Pro Val Thr Tyr Arg Pro His Gly Ala Phe Asp Ile
            100                 105                 110

Trp Gly Gln Gly Thr Leu Val Thr Val Ser Ser
        115                 120

<210> SEQ ID NO 137
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 137

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Ser Gly Asn Thr Phe Leu Ser Trp Tyr Leu Gln Lys Pro Gly Gln Ser
        35                  40                  45

Pro Gln Leu Leu Ile Tyr Glu Ile His Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Phe Trp Phe Pro Arg Thr Phe Gly Gln Gly Thr Lys Val Glu Ile Lys
            100                 105                 110

<210> SEQ ID NO 138
<211> LENGTH: 122
<212> TYPE: PRT
<213> ORGANISM: Artificial sequence
<220> FEATURE:
<223> OTHER INFORMATION: an artificially synthesized sequence

<400> SEQUENCE: 138

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr
            20                  25                  30

Thr Met His Trp Val Arg Gln Ala Pro Gly Lys Gly Leu Glu Trp Val
        35                  40                  45

Ser Ser Ile Ser Ser Arg Ser Ser His Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Arg Lys Tyr Arg Met Asn Trp Val Phe Asp Tyr Trp
            100                 105                 110

Gly Gln Gly Thr Leu Val Thr Val Ser Ser
        115                 120

<210> SEQ ID NO 139
<211> LENGTH: 110
<212> TYPE: PRT
<213> ORGANISM: Artificial sequence
```

```
<220> FEATURE:
<223> OTHER INFORMATION: an artificially synthesized sequence

<400> SEQUENCE: 139

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
                20                  25                  30

Asn Tyr Val Ser Trp Tyr Gln Gln His Pro Gly Lys Ala Pro Lys Leu
            35                  40                  45

Met Ile Tyr Asp Thr Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Val Thr Gly Ile
                85                  90                  95

Trp Ser Val Gly Phe Gly Gly Gly Thr Lys Leu Thr Val Leu
            100                 105                 110

<210> SEQ ID NO 140
<211> LENGTH: 122
<212> TYPE: PRT
<213> ORGANISM: Artificial sequence
<220> FEATURE:
<223> OTHER INFORMATION: an artificially synthesized sequence

<400> SEQUENCE: 140

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser His
                20                  25                  30

Thr Met Asn Trp Val Arg Gln Ala Pro Gly Lys Gly Leu Glu Trp Val
            35                  40                  45

Ser Ser Ile Ser Ser Arg Ser Asn His Ala Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Lys Lys Gly Arg Tyr Leu Trp Val Phe Asp Tyr Trp
            100                 105                 110

Gly Gln Gly Thr Leu Val Thr Val Ser Ser
            115                 120

<210> SEQ ID NO 141
<211> LENGTH: 110
<212> TYPE: PRT
<213> ORGANISM: Artificial sequence
<220> FEATURE:
<223> OTHER INFORMATION: an artificially synthesized sequence

<400> SEQUENCE: 141

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Asp Tyr
                20                  25                  30

Asn Tyr Val Ser Trp Tyr Gln Gln His Pro Gly Lys Ala Pro Lys Leu
            35                  40                  45
```

```
Met Ile Tyr Tyr Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Leu Thr Thr Asp Ser
                 85                  90                  95

Leu Asn Pro Val Phe Gly Gly Gly Thr Lys Leu Thr Val Leu
                100                 105                 110

<210> SEQ ID NO 142
<211> LENGTH: 122
<212> TYPE: PRT
<213> ORGANISM: Artificial sequence
<220> FEATURE:
<223> OTHER INFORMATION: an artificially synthesized sequence

<400> SEQUENCE: 142

Glu Val Gln Leu Val Glu Ser Gly Gly Asp Leu Val Lys Pro Gly Gly
 1               5                  10                  15

Gly Leu Arg Leu Ser Cys Ala Ala Ser Gly Phe Thr Phe Ser Thr Tyr
                 20                  25                  30

Thr Met His Trp Val Arg Gln Ala Pro Gly Lys Gly Leu Glu Trp Val
             35                  40                  45

Ser Ser Ile Ser Ser Arg Ser Gly His Arg His Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Gly Lys Lys Gly Asn Arg Asn Trp Val Phe Asp Tyr Trp
                100                 105                 110

Gly Gln Gly Thr Leu Val Thr Val Ser Ser
            115                 120

<210> SEQ ID NO 143
<211> LENGTH: 110
<212> TYPE: PRT
<213> ORGANISM: Artificial sequence
<220> FEATURE:
<223> OTHER INFORMATION: an artificially synthesized sequence

<400> SEQUENCE: 143

Gln Ser Ala Leu Thr Gln Pro Pro Ser Ala Ser Gly Ser Pro Gly Gln
 1               5                  10                  15

Thr Val Thr Ile Ser Cys Thr Gly Thr Ser Thr Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Ser Thr Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Thr Thr Tyr Tyr Ala
                 85                  90                  95

Lys Asn Pro Val Phe Gly Gly Gly Thr Lys Leu Thr Val Leu
                100                 105                 110

<210> SEQ ID NO 144
```

```
<211> LENGTH: 122
<212> TYPE: PRT
<213> ORGANISM: Artificial sequence
<220> FEATURE:
<223> OTHER INFORMATION: an artificially synthesized sequence

<400> SEQUENCE: 144

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr
            20                  25                  30

Thr Met His Trp Val Arg Gln Ala Pro Gly Lys Gly Leu Glu Trp Val
        35                  40                  45

Ser Ser Ile Ser Ser Arg Ser Asn His Arg Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Lys Arg Phe Asp Arg Asn Trp Val Phe Asp Tyr Trp
            100                 105                 110

Gly Gln Gly Thr Leu Val Thr Val Ser Ser
        115                 120

<210> SEQ ID NO 145
<211> LENGTH: 110
<212> TYPE: PRT
<213> ORGANISM: Artificial sequence
<220> FEATURE:
<223> OTHER INFORMATION: an artificially synthesized sequence

<400> SEQUENCE: 145

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Thr Tyr
            20                  25                  30

Asn Tyr Val Ser Trp Tyr Gln Gln His Pro Gly Lys Ala Pro Lys Leu
        35                  40                  45

Met Ile Tyr Lys Thr Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Arg Arg Tyr Arg
                85                  90                  95

Arg Ser Leu Ser Phe Gly Gly Gly Thr Lys Leu Thr Val Leu
            100                 105                 110

<210> SEQ ID NO 146
<211> LENGTH: 233
<212> TYPE: PRT
<213> ORGANISM: Artificial sequence
<220> FEATURE:
<223> OTHER INFORMATION: an artificially synthesized sequence

<400> SEQUENCE: 146

Cys His Pro Arg Leu Ser Leu His Arg Pro Ala Leu Glu Asp Leu Leu
1               5                   10                  15

Leu Gly Ser Glu Ala Asn Leu Thr Cys Thr Leu Thr Gly Leu Arg Asp
            20                  25                  30
```

Ala Ser Gly Val Thr Phe Thr Trp Thr Pro Ser Ser Gly Lys Ser Ala
            35                  40                  45

Val Gln Gly Pro Pro Glu Arg Asp Leu Cys Gly Cys Tyr Ser Val Ser
 50                  55                  60

Ser Val Leu Pro Gly Cys Ala Glu Pro Trp Asn His Gly Lys Thr Phe
 65                  70                  75                  80

Thr Cys Thr Ala Ala Tyr Pro Glu Ser Lys Thr Pro Leu Thr Ala Thr
                85                  90                  95

Leu Ser Lys Ser Gly Asn Thr Phe Arg Pro Glu Val His Leu Leu Pro
            100                 105                 110

Pro Pro Ser Glu Glu Leu Ala Leu Asn Glu Leu Val Thr Leu Thr Cys
            115                 120                 125

Leu Ala Arg Gly Phe Ser Pro Lys Asp Val Leu Val Arg Trp Leu Gln
130                 135                 140

Gly Ser Gln Glu Leu Pro Arg Glu Lys Tyr Leu Thr Trp Ala Ser Arg
145                 150                 155                 160

Gln Glu Pro Ser Gln Gly Thr Thr Thr Phe Ala Val Thr Ser Ile Leu
                165                 170                 175

Arg Val Ala Ala Glu Asp Trp Lys Lys Gly Asp Thr Phe Ser Cys Met
            180                 185                 190

Val Gly His Glu Ala Leu Pro Leu Ala Phe Thr Gln Lys Thr Ile Asp
            195                 200                 205

Arg Leu Ala Gly Lys Gly Gly Gly Ser Gly Leu Asn Asp Ile Phe
            210                 215                 220

Glu Ala Gln Lys Ile Glu Trp His Glu
225                 230

<210> SEQ ID NO 147
<211> LENGTH: 15
<212> TYPE: PRT
<213> ORGANISM: Artificial sequence
<220> FEATURE:
<223> OTHER INFORMATION: an artificially synthesized sequence

<400> SEQUENCE: 147

Gly Leu Asn Asp Ile Phe Glu Ala Gln Lys Ile Glu Trp His Glu
1               5                   10                  15

<210> SEQ ID NO 148
<211> LENGTH: 641
<212> TYPE: PRT
<213> ORGANISM: Artificial sequence
<220> FEATURE:
<223> OTHER INFORMATION: an artificially synthesized sequence

<400> SEQUENCE: 148

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
            35                  40                  45

Arg Gly Gly Gly Arg Pro Gly Ala Pro Gly Gly Ser Gly Ser Gly Pro
        50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

```
Gly Ala Gly Ala Gly Ala Gly Ala Gly Gly Ala Gly Ala Gly
            100                 105                 110
Gly Gly Ala Gly Gly Ala Gly Ala Gly Gly Ala Gly Ala Gly Gly
            115                 120                 125
Gly Ala Gly Ala Gly Gly Ala Gly Gly Ala Gly Gly Ala Gly Ala
            130                 135                 140
Gly Gly Gly Ala Gly Ala Gly Gly Ala Gly Ala Gly Ala Gly
145                 150                 155                 160
Gly Gly Ala Gly Ala Gly Gly Ala Gly Ala Gly Gly Ala Gly
                165                 170                 175
Ala Gly Gly Gly Ala Gly Gly Ala Gly Ala Gly Gly Ala Gly Gly
            180                 185                 190
Ala Gly Gly Ala Gly Ala Gly Gly Ala Gly Ala Gly Gly Ala Gly
            195                 200                 205
Gly Ala Gly Gly Ala Gly Ala Gly Gly Ala Gly Ala Gly Gly Ala
            210                 215                 220
Gly Gly Ala Gly Gly Ala Gly Ala Gly Gly Ala Gly Ala Gly Ala
225                 230                 235                 240
Gly Ala Gly Gly Ala Gly Ala Gly Gly Ala Gly Ala Gly Ala Gly
            245                 250                 255
Gly Ala Gly Gly Ala Gly Ala Gly Gly Ala Gly Ala Gly Ala Gly
            260                 265                 270
Gly Ala Gly Gly Ala Gly Ala Gly Gly Ala Gly Gly Ala Gly
                275                 280                 285
Ala Gly Gly Ala Gly Ala Gly Ala Gly Gly Ala Gly Gly Ala Gly
            290                 295                 300
Ala Gly Gly Ala Gly Ala Gly Ala Gly Gly Ala Gly Gly Ala Gly
305                 310                 315                 320
Gly Ala Gly Ala Gly Gly Gly Arg Gly Arg Gly Gly Ser Gly Gly
            325                 330                 335
Arg Gly Arg Gly Gly Ser Gly Gly Arg Gly Arg Gly Gly Ser Gly Gly
            340                 345                 350
Arg Arg Gly Arg Gly Arg Glu Arg Ala Arg Gly Gly Ser Arg Glu Arg
            355                 360                 365
Ala Arg Gly Arg Gly Arg Gly Arg Gly Glu Lys Arg Pro Arg Ser Pro
            370                 375                 380
Ser Ser Gln Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
                420                 425                 430
Ala Ile Glu Gln Gly Pro Ala Asp Asp Pro Gly Glu Gly Pro Ser Thr
                435                 440                 445
Gly Pro Arg Gly Gln Gly Asp Gly Gly Arg Arg Lys Lys Gly Gly Trp
            450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
                500                 505                 510
```

Ser Lys Thr Ser Leu Tyr Asn Leu Arg Arg Gly Thr Ala Leu Ala Ile
            515                 520                 525

Pro Gln Cys Arg Leu Thr Pro Leu Ser Arg Leu Pro Phe Gly Met Ala
        530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
                580                 585                 590

Ile Arg Val Thr Val Cys Ser Phe Asp Asp Gly Val Asp Leu Pro Pro
            595                 600                 605

Trp Phe Pro Pro Met Val Glu Gly Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu

<210> SEQ ID NO 149
<211> LENGTH: 321
<212> TYPE: PRT
<213> ORGANISM: Artificial sequence
<220> FEATURE:
<223> OTHER INFORMATION: an artificially synthesized sequence

<400> SEQUENCE: 149

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala

-continued

```
            225                 230                 235                 240
Met Leu Ile Arg Glu Leu Arg Ala Ala Leu Glu Leu Phe Glu Gln Glu
                    245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
            275                 280                 285

Ser Arg Gly Ile Asp Lys Gln Gly Ala Leu Leu Leu Glu Gln Asp Gly
            290                 295                 300

Ile Ile Lys Pro Trp Met Gly Gly Glu Ile Ser Leu Arg Ser Ala Glu
305                 310                 315                 320

Lys
```